(12) United States Patent (10) Patent No.: US 9,029,389 B2
No et al. (45) Date of Patent: May 12, 2015

(54) ANTI-INFLAMMATION COMPOUNDS

(75) Inventors: Zaesung No, Gyeonggi-do (KR); Jaeseung Kim, Seoul (KR); Sung-Jun Han, Seoul (KR); Jung Hwan Kim, Gyeonggi (KR); Young Sam Park, Daejeon (KR); Sangchul Lee, Gyeonggi-do (KR); Kiyean Nam, Seoul (KR); Jeongjun Kim, Seoul (KR); Jinhwa Lee, Gyeonggi-do (KR); Sunhee Kang, Gyeonggi-do (KR); Min Jung Seo, Incheon (KR); Saeyeon Lee, Gyeonggi-do (KR); Gahee Choi, Seoul (KR)

(73) Assignees: Institut Pasteur Korea, Gyeonggi-Do (KR); Qurient Co. Ltd, Gyeonggi-Do (KR)

( * ) Notice: Subject to any disclaimer, the term of this patent is extended or adjusted under 35 U.S.C. 154(b) by 0 days.

(21) Appl. No.: 14/112,933

(22) PCT Filed: Apr. 20, 2012

(86) PCT No.: PCT/IB2012/000991
§ 371 (c)(1),
(2), (4) Date: Feb. 4, 2014

(87) PCT Pub. No.: WO2012/143796
PCT Pub. Date: Oct. 26, 2012

(65) Prior Publication Data
US 2014/0155387 A1 Jun. 5, 2014

Related U.S. Application Data

(60) Provisional application No. 61/477,704, filed on Apr. 21, 2011.

(51) Int. Cl.
*A61K 31/4353* (2006.01)
*C07D 491/113* (2006.01)
(Continued)

(52) U.S. Cl.
CPC ........ *C07D 491/113* (2013.01); *A61K 31/4353* (2013.01);
(Continued)

(58) Field of Classification Search
CPC .................................................. A61K 31/4353
USPC ......................................................... 514/300
See application file for complete search history.

(56) References Cited

U.S. PATENT DOCUMENTS

2006/0264460 A1* 11/2006 Green et al. ................... 514/313
2008/0051409 A1 2/2008 Gmeiner et al.

FOREIGN PATENT DOCUMENTS

EP 2 338 888 A1 6/2011
(Continued)

OTHER PUBLICATIONS

Green et al., Journal of Medicinal Chemistry (2007), 50(19), 4728-4745.*
(Continued)

*Primary Examiner* — Niloofar Rahmani
(74) *Attorney, Agent, or Firm* — Saliwanchik, Lloyd & Eisenschenk

(57) ABSTRACT

The present invention refers to: a compound having the general formula (I), wherein n is 0, 1, 2 or; m is 0, 1, 2 or 3; o is 0, 1, 2 or 3; W, X, Y and Z are independently selected from CH, N or N-oxide; A is $NR^4$, C=O, C=S, OP(O)(O), P=O, $CH_2$, or a heteroaryl selected from the group consisting of (a), (b), (c), (d), (e), (f), (g); V is C=O, O, S, $CH_2$, or $NR^5$; as well as its use in treating inflammatory diseases such as asthma, COPD, inflammation post infection, arthritis, atherosclerosis, pain and dermatitis.

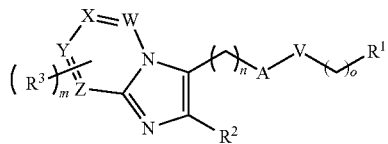

(I)

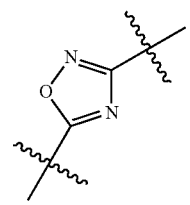

(a)

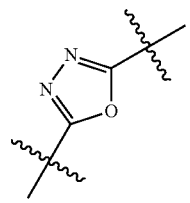

(b)

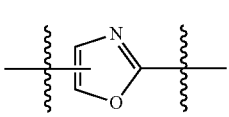

(c)

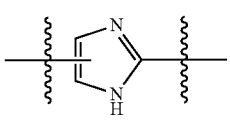

(d)

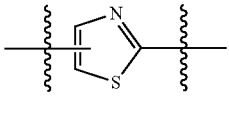

(e)

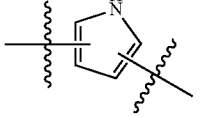

(f)

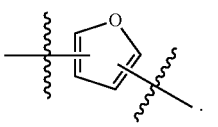

(g)

13 Claims, 1 Drawing Sheet

(51) Int. Cl.
*C07D 471/04* (2006.01)
*C07D 487/04* (2006.01)
*C07D 519/00* (2006.01)

(52) U.S. Cl.
CPC ............ *C07D 471/04* (2013.01); *C07D 487/04* (2013.01); *C07D 519/00* (2013.01)

(56) References Cited

FOREIGN PATENT DOCUMENTS

| WO | WO 2006/015737 A1 | 2/2006 |
| WO | 2008022396 * | 2/2008 |
| WO | WO 2008/047883 A1 | 4/2008 |
| WO | WO 2008/099221 A1 | 8/2008 |
| WO | 2009027077 * | 3/2009 |
| WO | WO 2011/057145 A2 | 5/2011 |
| WO | WO 2011/113606 A1 | 9/2011 |

OTHER PUBLICATIONS

Cheeseright et al., Journal of Medicinal Chemistry (2009), 52(14), 4200-4209.*

* cited by examiner

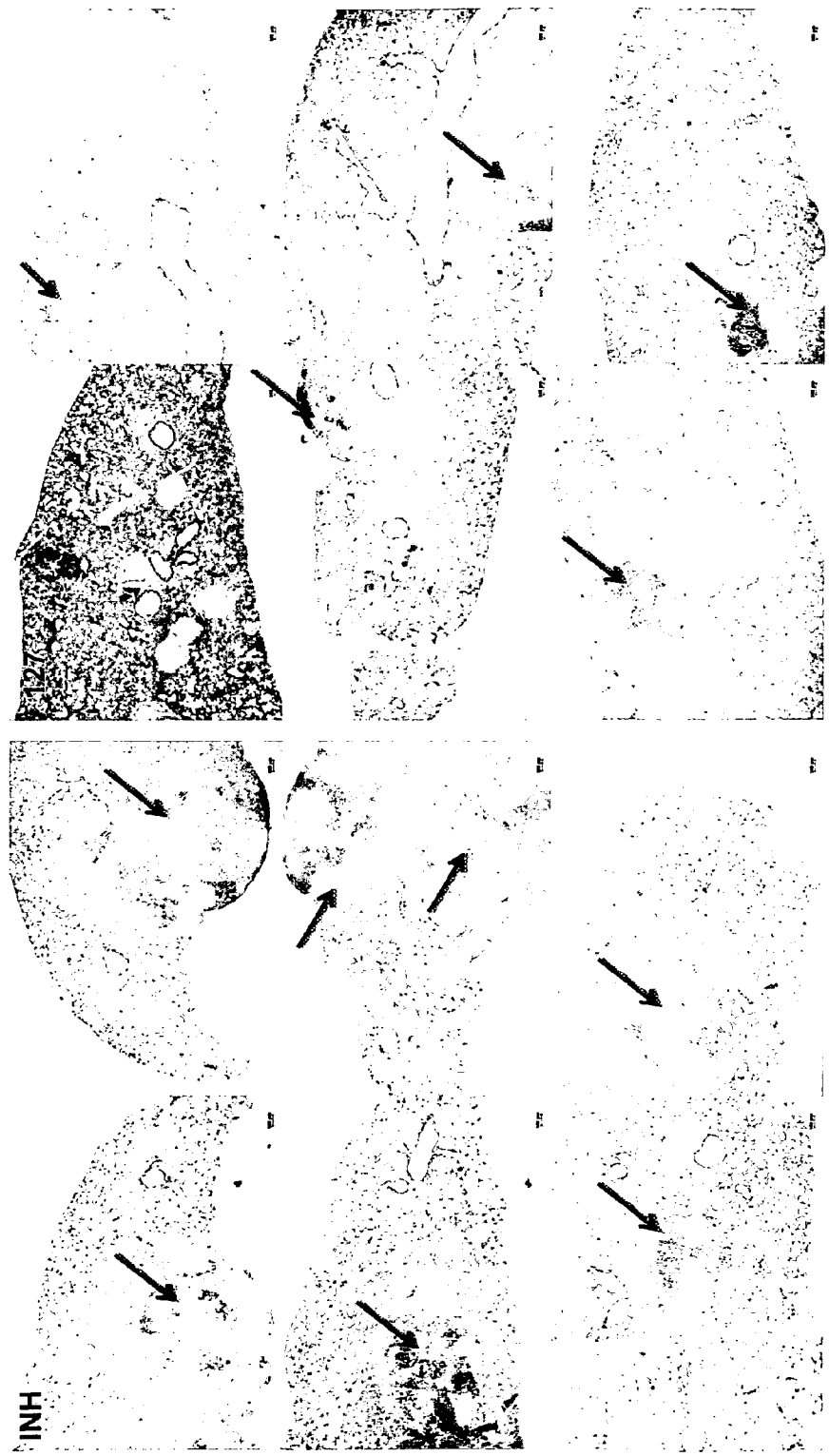

ANTI-INFLAMMATION COMPOUNDS

CROSS REFERENCE TO A RELATED APPLICATION

This application is a National Stage Application of International Application Number PCT/IB2012/000991, filed Apr. 20, 2012; which claims the benefit of U.S. Provisional Application No. 61/477,704, filed Apr. 21, 2011; both of which are incorporated herein by reference in their entirety.

The present invention relates to small molecule compounds and their use in the treatment of inflammatory diseases, in particular asthma, chronic obstructive pulmonary disease (COPD), inflammation post infection, arthritis, atherosclerosis, pain and dermatitis.

BACKGROUND OF THE INVENTION

Inflammation is defined as the response of body tissues to injury or irritation. As such, inflammation is a fundamental, stereotyped complex of cytologic and chemical reactions of affected blood vessels and adjacent tissues in response to an injury or abnormal stimulation caused by a physical, chemical or biological agent. Inflammation usually leads to the accumulation of fluid and blood cells at the site of injury, and is usually a healing process. However, inflammation sometimes causes harm, usually through a dysfunction of the normal progress of inflammation. Inflammatory diseases are those pertaining to, characterized by, causing, resulting from, or becoming affected by inflammation. Examples of inflammatory diseases or disorders include, without limitation, asthma, lung inflammation, COPD, inflammation post infection, atherosclerosis, pain, dermatitis, chronic granulomatous diseases such as tuberculosis, leprosy, sarcoidosis, and silicosis, nephritis, amyloidosis, rheumatoid arthritis, ankylosing spondylitis, chronic bronchitis, scleroderma, lupus, polymyositis, appendicitis, inflammatory bowel disease, ulcers, Sjogren's syndrome, Reiter's syndrome, psoriasis, pelvic inflammatory disease, orbital inflammatory disease, thrombotic disease, and inappropriate allergic responses to environmental stimuli such as poison ivy, pollen, insect stings and certain foods, including atopic dermatitis and contact dermatitis.

There is a need for novel anti-inflammatory agents e.g. drugs that demonstrate improved pharmacokinetics, activity, oral bioavailability, potency or effective half-lives in vivo. Such agents may also have distinct resistance profiles, fewer side effects, less complicated dosing schedules, or have increased oral activity. There is still a need in the art for novel non-steroidal anti-inflammatory drugs (NSAIDs) that do not have the adverse side effects associated with prior art compounds. There is also a need for new and improved treatments of inflammatory diseases states and disorders.

Arachidonate 5-lipoxygenase (5-lipoxygenase, 5-LO or Alox5) is a member of the lipoxygenase family of enzymes. It catalyzes the oxidation of arachidonic acid to yield 5-hydroperoxyeicosatetraenoic acid. 5-LO inhibitors have been developed, mostly unsuccessfully to date, for the treatment of asthma and for rheumatic conditions such as rheumatoid arthritis. There are, however, a few marketed drugs; Zileuton, a 5-LO iron chelating inhibitor, which is an orally active inhibitor that blocks the production of leukotrienes (LTA4, LTB4, LTD4 and LTE4). The product is now marketed in two formulations; the original immediate-release formulation and now the extended-release formulation. The immediate release tablet was withdrawn from the United States market on Feb. 12, 2008. Zileuton's most serious side effect is liver toxicity and hence is not available to patients with liver disease. Montelukast and Zafirlukast are oral leukotriene receptor antagonists (i.e. they block the action of 5-LO enzyme products) used to treat asthma and relieve symptoms of seasonal allergies. Side effects of Montelukast include gastrointestinal disturbances, hypersensitivity reactions, sleep disorders and increased bleeding tendency. Zafirlukast product warning includes notification regarding eosinophilia, vasculitic rash, worsening pulmonary symptoms and/or cardiac complications. There is also some evidence that the use of either Montelukast or Zafirlukas is associated with a higher incidence of Churg-Straus syndrome. Hence improved anti-5-LO enzyme and/or pathway compounds are required for the treatment of inflammationary disorders. Herein are disclosed compounds with anti-inflammatory activity and anti-5-LO activity.

It was an object of the present invention to identify compounds with an inhibitory effect against arachidonate 5-lipoxygenase.

It was an object of the present invention to identify compounds effective against inflammatory disease, in particular asthma, atherosclerosis, pain, COPD, inflammation post infection, arthritis, and dermatitis.

DESCRIPTION OF THE INVENTION

In one aspect, the present invention relates to a compound having the general formula I:

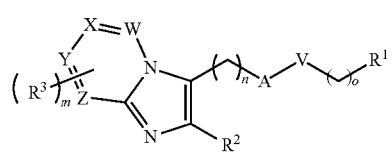

wherein n is 0, 1, 2, or 3;

m is 0, 1, 2, or 3;

o is 0, 1, 2, or 3;

W, X, Y and Z are independently selected from CH, N or N-oxide;

A is $NR^4$, C=O, C=S, OP(O), P=O, $CH_2$, or a heteroaryl selected from the group consisting of

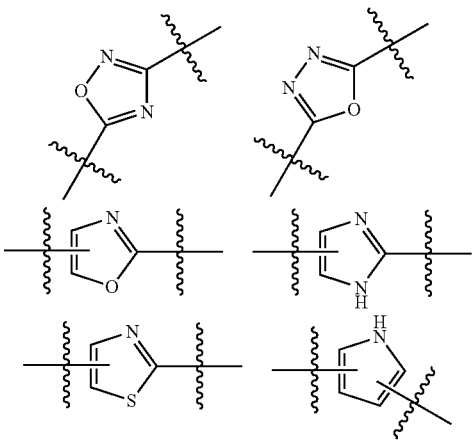

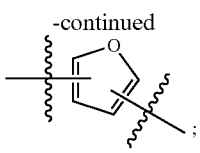

V is C=O, O, S, CH$_2$ or NR$^5$;

R$^1$ is a moiety selected from the group consisting of

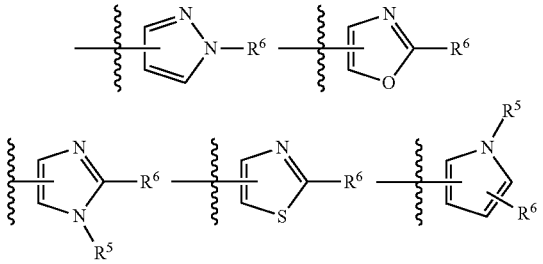

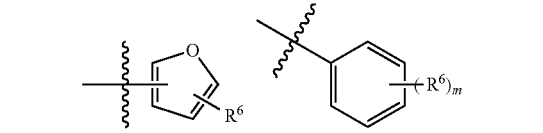

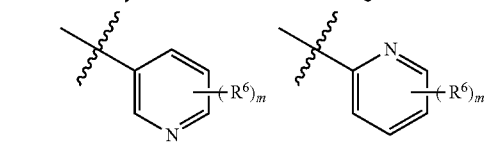

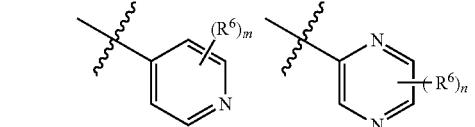

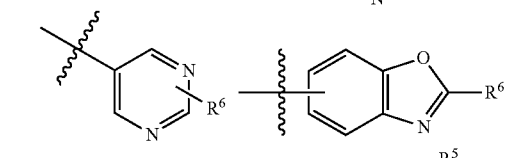

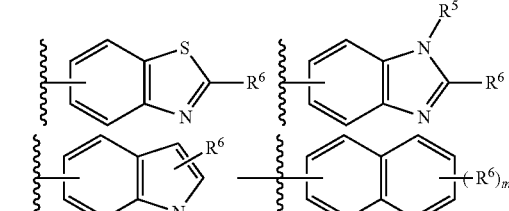

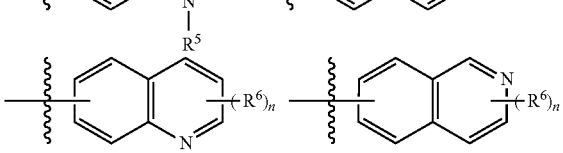

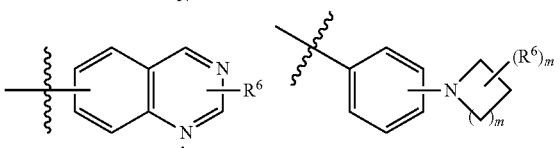

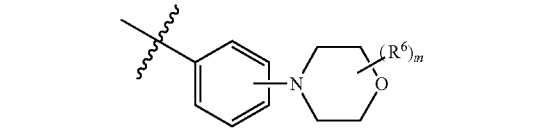

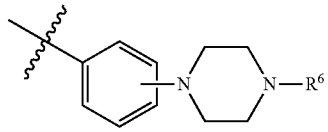

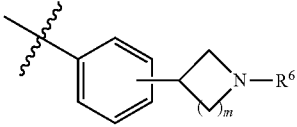

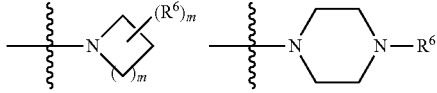

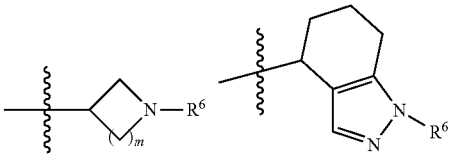

m and n being, independently at each occurrence, selected from 0, 1, 2 or 3;

R$^2$ is, at each occurrence, independently, selected from the group consisting of hydrogen, halogen, C$_1$-C$_{10}$ alkyl, C$_3$-C$_{10}$ cycloalkyl, C$_2$-C$_{10}$ alkenyl, C$_3$-C$_{10}$ cycloalkenyl, C$_2$-C$_{10}$ alkynyl, C$_1$-C$_{10}$ haloalkyl, —OH, —OR$^5$, C$_1$-C$_{10}$ alkoxy, C$_3$-C$_{10}$ cycloalkoxy, C$_3$-C$_{15}$ cycloalkylalkoxy, C$_3$-C$_{15}$ cycloalkylalkyl, —CN, —NO$_2$, —NH$_2$, —N(R$^5$)$_2$, —C(O)R$^5$, —C(O)OR$^5$, —C(O)N(R$^5$)$_2$, —P(O)OR$^5$, —P(O)OR$^5$N(R$^5$)$_2$, —SR$^5$, —S(O)R$^5$, —S(O)$_2$R$^5$, —S(O)$_2$N(R$^5$)$_2$, aryl, e.g. phenyl, benzyl, heteroaryl, and heterocyclyl, any of which is optionally substituted;

R$^3$ is, at each occurrence, independently selected from the group consisting of hydrogen, halogen, C$_1$-C$_{10}$ alkyl, C$_3$-C$_{10}$ cycloalkyl, C$_1$-C$_3$ haloalkyl, hydroxyl, —OR$^6$, —CN, —NO$_2$, —NH$_2$, —N(R$^6$)C(O)R$^6$, —C(O)R$^6$, —C(O)OR$^6$, —C(O)N(R$^6$)$_2$, —S(O)R$^6$, —S(O)$_2$R$^6$, —S(O)$_2$N(R$^6$)$_2$, aryl, e.g. phenyl, benzyl, heteroaryl, heterocyclyl, any of which is optionally substituted, or two groups of R$^3$ are connected to each other to make a five or six membered cyclic or heterocyclic ring, any of which is optionally substituted;

R$^4$ and R$^5$ are, at each occurrence, independently selected from the group consisting of hydrogen, C$_1$-C$_{10}$ alkyl, C$_3$-C$_{10}$ cycloalkyl, C$_2$-C$_{10}$ alkenyl, C$_3$-C$_{10}$ cycloalkenyl, C$_2$-C$_{10}$ alkynyl, C$_1$-C$_{10}$ haloalkyl, —OH, —OR$^7$, C$_1$-C$_{10}$ alkoxy, C$_3$-C$_{10}$ cycloalkoxy, C$_3$-C$_{15}$ cycloalkylalkoxy, C$_3$-C$_{15}$ cycloalkylalkyl, —NH$_2$, —N(R$^7$)$_2$, —C(O)R$^7$, —C(O)OR$^7$, —C(O)N(R$^7$)$_2$, S(O)R$^7$, —S(O)$_2$R$^7$, —S(O)$_2$N(R$^7$)$_2$, aryl, e.g. phenyl, benzyl, heteroaryl, and heterocyclyl, any of which is optionally substituted;

R$^6$ is, at each occurrence, independently selected from the group consisting of hydrogen, C$_1$-C$_{10}$ alkyl, C$_3$-C$_{10}$ cycloalkyl, C$_2$-C$_{10}$ alkenyl, C$_3$-C$_{10}$ cycloalkenyl, C$_2$-C$_{10}$ alkynyl, C$_1$-C$_{10}$ haloalkyl, hydroxyl, —OR$^8$, —C(O)R$^8$, —R$^8$(R$^8$)C(O)R$^8$, —C(O)OR$^8$, —R$^8$(R$^8$)C(O)OR$^8$, —CN, —NO$_2$, —NH$_2$, —N(R$^8$)$_2$, —C(O)N(R$^8$)$_2$, —R$^8$(R$^8$)C(O)N(R$^8$)$_2$, —S(O)R$^8$, —S(O)$_2$R$^8$, —S(O)$_2$N(R$^8$)$_2$, aryl, e.g. phenyl, benzyl, heteroaryl, and heterocyclyl, any of which is optionally substituted;

R$^7$ is, at each occurrence, independently selected from the group consisting of hydrogen, C$_1$-C$_{10}$ alkyl, C$_3$-C$_{10}$ cycloalkyl, C$_2$-C$_{10}$ alkenyl, C$_3$-C$_{10}$ cycloalkenyl, C$_2$-C$_{10}$ alkynyl, C$_1$-C$_{10}$ haloalkyl, aryl, e.g. phenyl, benzyl, heteroaryl, and heterocyclyl, any of which is optionally substituted; and $R^8$ is, at each occurrence, independently selected from the group consisting of hydrogen, $C_1$-$C_8$ alkyl optionally substituted with at least one hydroxyl or halogen; $C_3$-$C_7$ cycloalkyl, $C_2$-$C_{10}$ alkenyl, $C_3$-$C_{10}$ cycloalkenyl, $C_2$-$C_{10}$ alkynyl, $C_1$-$C_{10}$ haloalkyl, aryl, e.g. phenyl, benzyl, heteroaryl and heterocyclyl, any of which is optionally substituted, or a pharmaceutically acceptable salt thereof, for use in the treatment of an inflammatory disease.

The term "optionally substituted" as used herein is meant to indicate that a hydrogen atom attached to a member atom within a group, or several such hydrogen atoms, is replaced by a group, such as halogen including fluorine, chlorine, bromine, $C_1$-$C_{10}$ alkyl, $C_1$-$C_3$ haloalkyl, $C_3$-$C_7$ cycloalkyl, oxo, —OH, —OR$^9$, —OC(O)R$^9$, —CN, NO$_2$, —N(R$^9$)$_2$, —N(R$^9$)C(O)R$^9$, —R$^9$N(R$^9$)C(O)R$^9$, —C(O)R$^9$, —R$^9$C(O)R$^9$, —C(O)OR$^9$, —R$^9$C(O)OR$^9$, —C(O)N(R$^9$)$_2$, —R$^9$C(O)N(R$^9$)$_2$, —S(O)R$^9$, —S(O)$_2$R$^9$, —S(O)$_2$N(R$^9$)$_2$, phenyl, benzyl, aryl, heteroaryl or heterocyclyl, any of which itself is "optionally substituted"; i.e. one or several of the hydrogen atoms may be replaced by one of the aforementioned groups.

$R^9$ is, at each occurrence, independently selected from the group consisting of hydrogen, halogen, $C_1$-$C_{10}$ alkyl, $C_1$-$C_3$ haloalkyl, $C_3$-$C_7$ cycloalkyl, hydroxyl, oxo, —OR$^{10}$, —C(O)OR$^{10}$, —C(O)R$^{10}$, —C(O)N(R$^{10}$)$_2$, —CN, —NO$_2$, —NH$_2$, —N(R$^{10}$)$_2$, —OR$^{10}$HetA, —OR$^{10}$N(R$^{10}$)$_2$, —C(O)N(R$^{10}$)HetA, —C(O)HetA, —C(O)N(R$^{10}$)R$^{10}$S(O)$_2$R$^{10}$; —S(O)$_2$N(R$^{10}$)$_2$, —S(O)$_2$R$^{10}$, —N(R$^{10}$)C(O)R$^{10}$SR$^{10}$, —N(R$^{10}$)R$^{10}$S(O)$_2$R$^{10}$, or —N(R$^{10}$)S(O)$_2$R$^{10}$, aryl, e.g. phenyl, benzyl, heteroaryl, and heterocyclyl, any of which is optionally substituted.

$R^{10}$ is, at each occurrence, independently selected from the group consisting of hydrogen, $C_1$-$C_8$ alkyl optionally substituted with at least one hydroxyl or halogen; $C_3$-$C_7$ cycloalkyl, aryl, e.g. phenyl, benzyl, and heterocyclyl, any of which is optionally substituted.

In one embodiment, the present invention also relates to pharmaceutically acceptable salts of the compounds according to the present invention, for use in the treatment of an inflammatory disease.

The term "alkyl" refers to a monovalent straight or branched chain, saturated aliphatic hydrocarbon radical having a number of carbon atoms in the specified range. Thus, for example, "$C_1$-$C_6$ alkyl" refers to any of the hexyl alkyl and pentyl alkyl isomers as well as n-, iso-, sec-, and t-butyl, n- and isopropyl, ethyl and methyl.

The term "alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—CH$_3$ or OMe), ethoxy (—OCH$_2$CH$_3$ or —OEt), t-butoxy (—O—C(CH$_3$)$_3$ or -OtBu) and the like.

The term "alkenyl" refers to a monovalent straight or branched chain aliphatic hydrocarbon radical containing one carbon-carbon double bond and having a number of carbon atoms in the specified range. Thus, for example, "$C_2$-$C_6$ alkenyl" refers to all of the hexenyl and pentenyl isomers as well as 1-butenyl, 2-butenyl, 3-butenyl, isobutenyl, 1-propenyl, 2-propenyl, and ethenyl (or vinyl).

The term "alkynyl" refers to a monovalent straight or branched chain aliphatic hydrocarbon radical containing one carbon-carbon triple bond and having a number of carbon atoms in the specified range. Thus, for example, "$C_2$-$C_6$ alkynyl" refers to all of the hexynyl and pentynyl isomers as well as 1-butynyl, 2-butynyl, 3-butynyl, 1-propynyl, 2-propynyl, and ethynyl.

The term "alkylene" refers to a saturated, branched or straight chain or cyclic hydrocarbon radical having two monovalent radical centers derived by the removal of two hydrogen atoms from the same or two different carbon atoms, 1 to 10 carbon atoms, or 1 to 6 carbon atoms. Typical alkylene radicals include, but are not limited to, methylene (—CH$_2$—), 1,1-ethyl (—CH(CH$_3$)—), 1,2-ethyl (—CH$_2$CH$_2$—), 1,1-propyl (—CH(CH$_2$CH$_3$)—), 1,2-propyl (—CH$_2$CH(CH$_3$)—), 1,3-propyl (—CH$_2$CH$_2$CH$_2$—), 1,4-butyl (—CH$_2$CH$_2$CH$_2$CH$_2$—), and the like.

The term "alkenylene" refers to an unsaturated, branched or straight chain or cyclic hydrocarbon radical having two monovalent radical centers derived by the removal of two hydrogen atoms from the same or two different carbon atoms of parent alkene. For example, an alkenylene group can have 1 to 20 carbon atoms, 1 to 10 carbon atoms, or 1 to 6 carbon atoms. Typical alkenylene radicals include, but are not limited to, 1,2-ethenyl (—CH=CH—).

The term "alkynylene" refers to an unsaturated, branched or straight chain or cyclic hydrocarbon radical having two monovalent radical centers derived by the removal of two hydrogen atoms from the same or two different carbon atoms of parent alkyne. For example, an alkynylene group can have 1 to 20 carbon atoms, 1 to 10 carbon atoms or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡CH—).

The term "cycloalkyl", alone or in combination with any other term, refers to a group, such as optionally substituted or non-substituted cyclic hydrocarbon, having from three to eight carbon atoms, unless otherwise defined. Thus, for example, "$C_3$-$C_8$ cycloalkyl" refers to cyclopropyl, cyclobutyl, cyclopentyl, cyclohexyl, cycloheptyl, and cyclooctyl.

The term "haloalkyl" refers to an alkyl group, as defined herein that is substituted with at least one halogen. Examples of straight or branched chained "haloalkyl" groups useful in the present invention include, but are not limited to, methyl, ethyl, propyl, isopropyl, n-butyl, and t-butyl substituted independently with one or more halogens. The term "haloalkyl" should be interpreted to include such substituents such as —CHF$_2$, —CF$_3$, —CH$_2$—CH$_2$—F, —CH$_2$—CF$_3$, and the like.

The term "heteroalkyl" refers to an alkyl group where one or more carbon atoms have been replaced with a heteroatom, such as, O, N, or S. For example, if the carbon atom of alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or thioalkyl group (e.g., —SCH$_3$, etc.). If a non-terminal carbon atom of the alkyl group which is not attached to the parent molecule is replaced with a heteroatom (e.g., O, N, or S) and the resulting heteroalkyl groups are, respectively, an alkyl ether (e.g., —CH$_2$CH$_2$—O—CH$_3$, etc.), alkyl amine (e.g., —CH$_2$NHCH$_3$, —CH$_2$N(CH$_3$)$_2$, etc.), or thioalkyl ether (e.g., —CH$_2$—S—CH$_3$).

The term "halogen" refers to fluorine, chlorine, bromine, or iodine.

The term "aryl" refers to (i) optionally substituted phenyl, (ii) optionally substituted 9- or 10 membered bicyclic, fused carbocyclic ring systems in which at least one ring is aromatic, and (iii) optionally substituted 11- to 14-membered tricyclic, fused carbocyclic ring systems in which at least one ring is aromatic. Suitable aryls include, for example, phenyl, biphenyl, naphthyl, tetrahydronaphthyl (tetralinyl), indenyl, anthracenyl, and fluorenyl.

The term "phenyl" as used herein is meant to indicate that optionally substituted or non-substituted phenyl group.

The term "benzyl" as used herein is meant to indicate that optionally substituted or non-substituted benzyl group.

The term "heteroaryl" (herein sometimes also abbreviated as "HetA") refers to (i) optionally substituted 5- and 6-membered heteroaromatic rings and (ii) optionally substituted 9- and 10-membered bicyclic, fused ring systems in which at least one ring is aromatic, wherein the heteroaromatic ring or the bicyclic, fused ring system contains from 1 to 4 heteroatoms independently selected from N, O, and S, where each N is optionally in the form of an oxide and each S in a ring which is not aromatic is optionally $S(O)$ or $S(O)_2$. Suitable 5- and 6-membered heteroaromatic rings include, for example, pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydroquinolinyl, tetrahydroisoquinolinyl, isoindolyl, benzodioxolyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, and 2,3-dihydrobenzo-1,4-dioxinyl.

The term "heterocyclyl" refers to (i) optionally substituted 4- to 8-membered, saturated and unsaturated but non-aromatic monocyclic rings containing at least one carbon atom and from 1 to 4 heteroatoms, (ii) optionally substituted bicyclic ring systems containing from 1 to 6 heteroatoms, and (iii) optionally substituted tricyclic ring systems, wherein each ring in (ii) or (iii) is independent of fused to, or bridged with the other ring or rings and each ring is saturated or unsaturated but nonaromatic, and wherein each heteroatom in (i), (ii), and (iii) is independently selected from N, O, and S, wherein each N is optionally in the form of an oxide and each S is optionally oxidized to $S(O)$ or $S(O)_2$. Suitable 4- to 8-membered saturated heterocyclyls include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, dioxanyl, and azacyclooctyl. Suitable unsaturated heterocyclic rings include those corresponding to the saturated heterocyclic rings listed in the above sentence in which a single bond is replaced with a double bond. It is understood that the specific rings and ring systems suitable for use in the present invention are not limited to those listed in this and the preceding paragraphs. These rings and ring systems are merely representative.

In one embodiment, said compound has an inhibitory activity on an enzyme involved in an inflammatory pathway(s), preferably an arachidonate 5-lipoxygenase (5-lipoxygenase, 5-LO, Alox 5), at a concentration of said compound between 0.01-30 µM, particularly preferably having an $IC_{50}$ on arachidonate 5-lipoxygenase of less than 1 µM and/or having an $EC_{50}$ of less than 1 µM on the production of leukotriene B4 (LTB4) in peripheral blood mononuclear cells (PBMCs).

In one aspect, the present invention relates to compounds for use in the treatment of an inflammatory disease, said compound having one of the formulae 1-403, as shown in Tables 1-3 and/or Example 4, preferably having one of the formulae 58, 70, 85, 86, 100, 103, 110, 123, 124, 126, 127, 128, 130, 143, 157, 161, 164, 174, 175, 181, 189, 190, 193, 194, 197, 207, 208, 209, 211, 217, 219, 223, 224, 225, 227, 228, 231, 232, 243, 260, 265, 266, 295, 296, 298, 299, 304, 311, 312, 313, 314, 324, 347, 375, 376, 380, 393-396 and 398-403 as shown in Table 1 and/or 2, or a pharmaceutically acceptable salt thereof. Particularly preferred compounds are compounds having one of the formulae 127, 128, 189, 219, 224, 225, 232, 243, 265, 266, 299, 311, 312, 313, 314, 380, 393-396 and 398-403 as shown in Tables 2 and/or 3, or a pharmaceutically acceptable salt thereof.

Preferably, the compounds as defined above have an inhibitory activity on an enzyme involved in an inflammatory pathway(s), preferably on arachidonate 5-lipoxygenase (5-lipoxygenase, 5-LO, Alox5), at a concentration of said compound between 0.01-30 M, particularly preferably having an $IC_{50}$ on arachidonate 5-lipoxygenase of less than 1 µM and/or having an $EC_{50}$ of less than 1 µM on the production of leukotriene B4 (LTB4) in peripheral blood mononuclear cells (PBMCs).

In one aspect the present invention relates to a composition comprising a compound according to the present invention and a pharmaceutically acceptable carrier, for use in the treatment of an inflammatory disease, e.g. asthma.

In one embodiment, said inflammatory disease is asthma or arthritis or dermatitis or chronic obstructive pulmonary disease (COPD) or inflammation post infection or atherosclerosis or pain.

In one embodiment, said treatment comprises administering a suitable amount of a compound or of a composition as defined above to a patient in need thereof, suffering from an inflammatory disease.

In a further aspect the present invention relates to a method of treatment of an inflammatory disease, comprising the application of a suitable amount of a compound or composition as defined above to a patient in need thereof, suffering from an inflammatory disease. In one embodiment said inflammatory disease is asthma or arthritis or dermatitis or chronic obstructive pulmonary disease (COPD) or inflammation post infection or atherosclerosis or pain.

In one embodiment, said suitable amount is an amount in the range of 0.01 mg/kg body weight to 1 g/kg body weight of said patient.

In a further aspect the present invention relates to compound that competitively inhibits the specific binding of a compound according to the present invention as defined above to arachidonate 5-lipoxygenase (5-lipoxygenase, 5-LO, Alox5).

In yet a further aspect the present invention relates to method of treatment of an inflammatory disease, in particular asthma, atherosclerosis, pain, COPD, inflammation post infection, arthritis and/or dermatitis comprising the application of a suitable amount of a compound as just defined, i.e. a compound that competitively inhibits the specific binding of a compound according to the present invention to arachidonate 5-lipoxygenase, to a patient in need thereof.

Such compound that competitively inhibits the specific binding of a compound according to the present invention to 5-LO, is herein also sometimes referred to as a "competitively inhibitory compound".

In one embodiment, such patient is a patient suffering from an inflammatory disease, preferably as defined further above.

The terms "$IC_{50}$" and "$EC_{50}$" refer to the half-maximal inhibitory concentration and the half-maximal effective concentration, respectively, of a compound with respect to a given activity, for example an inhibition of an enzyme through a compound, or the production of a substance stimulated by a compound. One example of an $IC_{50}$ is the half-maximum inhibitory concentration of a compound on the activity of arachidonate 5-lipoxygenase. One example for an $EC_{50}$-value is the half maximum effective concentration of a compound on the production and/or secretion of leukotriene B4 (LTB4) in a cell, for example a peripheral blood mononuclear cell (PBMC).

Pharmaceutical Compositions
Pharmaceutically Acceptable Salts

Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enanthate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphthalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt, for use in the treatment of an inflammatory disease.

In another embodiment, the compounds of the invention are used in their respective free base form, for use in the treatment of an inflammatory disease, according to the present invention.

Metal salts of a chemical compound of the invention include alkali metal salts, such as the sodium salt of a chemical compound of the invention containing a carboxy group.

The chemical compounds of the invention may be provided in unsolvated or solvated forms together with a pharmaceutically acceptable solvent(s) such as water, ethanol, and the like. Solvated forms may also include hydrated forms such as the monohydrate, the dihydrate, the hemihydrate, the trihydrate, the tetrahydrate, and the like. In general, solvated forms are considered equivalent to unsolvated forms for the purposes of this invention.

Administration and Formulation

The production of medicaments containing the compounds of the invention, its active metabolites or isomers and salts according to the invention and their application can be performed according to well-known pharmaceutical methods.

While the compounds of the invention, useable according to the invention for use in therapy, may be administered in the form of the raw chemical compound, it is preferred to introduce the active ingredient, optionally in the form of a physiologically acceptable salt in a pharmaceutical composition together with one or more adjuvants, excipients, carriers, buffers, diluents, and/or other customary pharmaceutical auxiliaries. Such salts of the compounds of the invention may be anhydrous or solvated.

In a preferred embodiment, the invention provides medicaments comprising a compound useable according to the invention, or a pharmaceutically acceptable salt or derivative thereof, together with one or more pharmaceutically acceptable carriers therefor, and, optionally, other therapeutic and/or prophylactic ingredients. The carrier(s) must be "acceptable" in the sense of being compatible with the other ingredients of the formulation and not harmful to the recipient thereof.

A medicament of the invention may be those suitable for oral, rectal, bronchial, nasal, topical, buccal, sub-lingual, transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The compounds useable according to the invention, together with a conventional adjuvant, carrier, or diluent, may thus be placed into the form of medicament and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such medicament and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The compounds useable according to the invention can be administered in a wide variety of oral and parenteral dosage forms. It will be obvious to those skilled in the art that the following dosage forms may comprise, as the active component, either a compound(s) useable according to the invention or a pharmaceutically acceptable salt of a compound(s) useable according to the invention.

For preparing a medicament from a compound useable according to the invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify. Compositions suitable for vaginal administration may be presented as pessaries, tampons, creams, gels, pastes, foams or sprays containing in addition to the active ingredient such carriers as are known in the art to be appropriate. Liquid preparations include solutions, suspensions, and emulsions, for example, water or water-propylene glycol solutions. For example, parenteral injection liquid preparations can be formulated as solutions in aqueous polyethylene glycol solution.

The chemical compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

In one embodiment of the present invention, the medicament is applied topically or systemically or via a combination of the two routes.

For administration, the compounds of the present invention may, in one embodiment, be administered in a formulation containing 0.001% to 70% per weight of the compound, preferably between 0.01% to 70% per weight of the compound, even more preferred between 0.1% and 70% per weight of the compound. In one embodiment, a suitable amount of compound administered is in the range of 0.01 mg/kg body weight to 1 g/kg body weight.

Compositions suitable for administration also include lozenges comprising the active agent in a flavoured base, usually sucrose and acacia or tragacanth; pastilles comprising the active ingredient in an inert base such as gelatin and glycerol or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form. Tablets or capsules for oral administration and liquids for intravenous administration and continuous infusion are preferred compositions.

Further details on techniques for formulation and administration may be found in the latest edition of Remington's Pharmaceutical Sciences (Maack Publishing Co. Easton, Pa.).

FIGURES AND TABLES

Reference is now made to the tables and figures, wherein

FIG. 1 illustrates the anti-inflammatory effect of compound 127 in an acute TB mouse model of infection. The arrows indicate inflammatory lesions in the lung.

Table 1 summarizes imidazopyridine derivatives (general scaffold I) with their respective 5-LOinhibitory activities, at 10 uM wherein the compound number refers to the compounds listed in Example 4;

Table 2 summarizes imidazopyridine derivatives (general scaffold I) with their respective 5-LO $IC_{50}$ inhibitory activities (uM);

Table 3 summarizes imidazopyridine derivatives (general scaffold I) with their respective LTB4 secretion $EC_{50}$ effective activities (uM).

Table 4 summarizes the anti-TB effect of compound 127 in an acute TB mouse model of infection. (INH is the control compound isoniazid)

EXAMPLES

The invention is now further described by reference to the following examples which are intended to illustrate, not to limit the scope of the invention.

Example 1

Activity of Compounds Against 5-LO Enzyme

The activity of compounds against 5-LO were determined by measuring $LTB_4$ (leukotriene B4) levels and/or by a fluorescence method. Both approaches are outlined in more detail below;

$LTB_4$ Measurement:

Human 5-lipoxygenase (Cayman, Cat#60402) produced in insect cells was pre-incubated with compound for 15 min at RT in incubation buffer (50 mM Tris-Cl, pH 7.4, 2 mM $CaCl_2$, 0.1 mM ATP, 1% DMSO). The enzymatic reaction was started by adding arachidonic acid to a final concentration of 3 uM. After 5 min of incubation at 37° C., the reaction was stopped by heatinactivation at 80° C. for 5 min. $LTB_4$ levels were quantified by using $LTB_4$ EIA kit (Cayman, Cat#520111) as instructed and/or $LTB_4$ levelswere measured with LC/MS/MS using Quattro Premier™ XE tandem quadrupole mass spectrometer equipped with Acquity UPLC system (Waters, Milford, Mass.). The method was slightly modified as reported previously (Zweifel et al., 2008, Willey et al., 2008, Chappell et al, 2011). Briefly, chromatographic separation was carried out with Acquity UPLC BEH Shield RP18 Column (2.1 mm×50 mm, 1.7 μm particle size, Waters, Milford, Mass.). Sample injection volume was 10 μl, the column temperature was 35° C., the mobile phase A consisted of water with 0.1% formic acid and the mobile phase B consisted of acetonitrile with 0.1% formic acid. Flow rate was 0.4 mL/min and the gradient condition was as follows.

| Time (min) | % Mobile phase A | % Mobile phase B |
| --- | --- | --- |
| 0 | 90 | 10 |
| 1 | 30 | 70 |
| 2.5 | 5 | 95 |
| 3 | 90 | 10 |

Relative quantification of $LTB_4$ and $LTB_4$-d4 (Internal Standard) was done using multi reaction monitoring (MRM) of the transitions of m/z 335→195 for $LTB_4$, 339→197 for $LTB_4$-d4 in electrospray ionization (ESI) negative mode. Desolvation temperature was 400° C., source temperature was 130° C. Capillary voltage, cone voltage, and collision voltage were 3.5 kV, 30V, and 20 eV, respectively. Nitrogen was used for desolvation (750 L/h) and cone (50 L/h) gas. Argon was used for collision gas (0.22 ml/min). The dwell time was 10 ms.

Fluoresence Method:

Besides the two methods quantifying LTB4 level, a fluorescence assay measuring 5-HpETE was introduced for high-throughput screening in a 384 well microplate format (Pufahl et al., 2007). For nonspecific ester cleavage of the acetate groups in H2DCFDA, the insect cell lysate expressing human 5-LO (Cayman Cat#60402) was incubated with H2DCFDA (50 mM Tris-Cl, pH 7.5, 2 mM CaCl2, 20 uM H2DCFDA, 500 mU 5-LO per reaction) for 5 minutes. Compound and enzyme mixture were pre-incubated for 5 minutes, and the enzymatic reaction was initiated by addition of ATP and arachidonic acid to a final concentration of 100 uM and 3 uM, respectively. After 5 minutes of incubation, the fluorescence was measured using Spectramax M5 (Molecular Device, Ex/Em=485 nm/530 nm). All steps were carried out at room temperature.

A total of 378 compounds were initially tested at a single concentration of 10 uM in duplicate with the results summarized in Table 1. From these 378 compounds, 53 compounds plus an additional 25 were selected for confirmation of activity by 6 or 11 point dose response in duplicate with the corresponding $IC_{50}$ values outlined in Table 2. These results demonstrate that the imidazopyridine derivatives are potent inhibitors of the 5-LO enzyme.

Example 2

Activity of Compounds on Production of $LTB_4$ in PBMC

Frozen human PBMC (peripheral blood mononuclear cells, AllCells, Cat#PB006F) was diluted 50 times with fresh culture media (RPMI 1640 supplemented with 10% FBS, 2 mM L-alanyl-L-glutamine). Cells were harvested by centrifugation and resuspended in fresh culture media to a concentration of $5 \times 10^6$ cells per milliliter. 140 ul of cell suspension was then liquated to each well (96-well plate). After incubation at 37° C. for 1 hr under 5% $CO_2$, 10 ul of serially diluted compounds (in 100% DMSO) and 10 ul of arachidonic acid to a final concentration of 30 uM were added and further incubated for 1 hr at 37° C. for 1 hr under 5% $CO_2$. Then, inducers, such as A23187 (Ionophor), sodium arsenite, sodium chloride and/or Anti-DNP IgE, were added in a volume of 40 ul and cells were incubated at 37° C. for 1 hr under 5% $CO_2$ for 30 min. Culture supernatant was harvested by centrifugation and $LTB_4$ levels were quantified using $LTB_4$ EIA kit (Cayman, Cat#520111).

Six of the 378 compounds tested against the 5-LO enzyme in vitro were also selected to be tested for their activity in a human cellular assay. Compounds were tested in a 12 point dose response in duplicate. The $EC_{50}$ results from this assay are summarized in Table 3. These results confirm the findings from Example 1 in that these compounds are inhibitors of the 5-LO enzyme. These findings also demonstrate that the imidazopyridine derivatives are strong inhibitors of the 5-LO enzyme in an in vivo human cellular assay system.

Example 3

In Vivo Anti-Inflammation Activity in a Murine Model

Previously, the imidazopyridine derivatives have demonstrated in vivo activity against *Mycobacterium tuberculosis* (TB). Histopathological evidence demonstrated that these compounds, in addition to having anti-TB activity, also demonstrated anti-inflammatory activity.

The effect of compound 127 on TB-infected mice was compared to that of the reference compound Isoniazid (INH). 8-week old female BalbC mice were infected with 6×10[5] *M. tuberculosis* H37Rv via intranasal instillation. Mice were sacrificed at day 1 to control the number of CFU in the lungs. In the acute model of infection, mice were treated for 4 weeks, starting at day 1. Compounds were freshly dissolved in a 0.5% methylcellulose solution and administered by oral gavage 5 times/week. Bacterial load was assessed in lungs after homogenizing the organs in 1×PBS. Serial dilutions of organ homogenates were spread on Middlebrook 7H11 plates and CFU were determined after 3 weeks incubation at 37° C. under 5% CO2. Histopathological analysis of lung tissue was performed by Hematoxylin and Eosin staining.

In the acute model of infection (after 4 weeks of treatment; Table 4), a reduction of ~1 log CFU compared to untreated mice was observed in the lungs of mice treated with 50 mg/kg of compound 127. In addition, notably, was a significant reduction in the number and size of inflammatory lesions in the lungs (FIG. 1) in mice treated with compound 127 compared with even INH treatment. Overall, compound 127 demonstrated an anti-inflammatory effect in a TB acute mouse model of infection.

Taken together, these data demonstrate that the imidazopyridine derivatives have an anti-inflammation effect and mediate, at least partially, this effect through their activity on the 5-LO enzyme.

Example 4

Derivatization of the Imidazopyridine General Scaffold

The imidazopyridine compounds (scaffold I; see Tables 1 and/or 2) underwent derivatization according to the methods outlined below (Schemes 1-15). Resulting derivatives were examined for inhibitory activity (single point, $IC_{50}$, $EC_{50}$, in vivo) using the assays described above (Examples 1, 2 and 3) and the results are summarized in Tables 1, 2, 3 and 4 and FIG. 1.

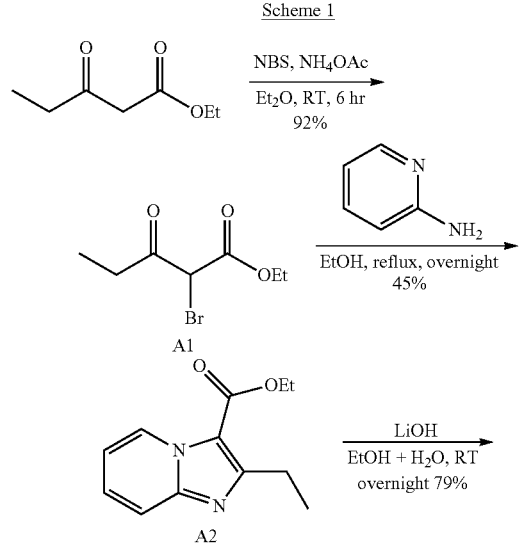

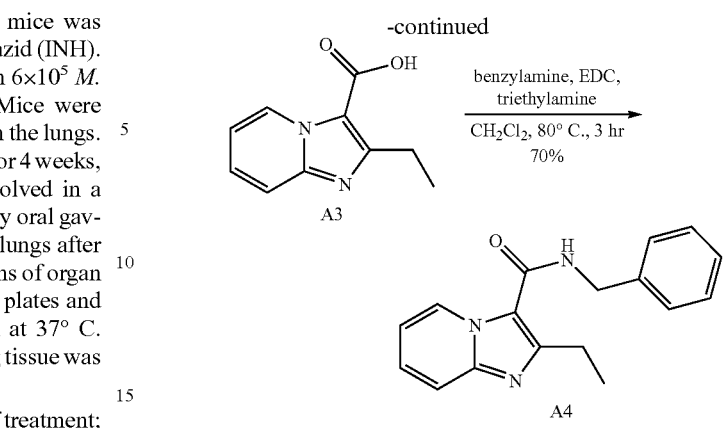

General Procedure for the Synthesis of A1

To a solution of Ethyl propionylacetate (6.9 mmol) in $Et_2O$ (30 mL) was added Ammonium acetate (2.07 mmol) and N-Bromosuccinimide (7.6 mmol). The mixture was stirred at room temperature for 6 hour. After reaction was completed, the reaction mixture was filtered off and washed with $H_2O$ (30 mL). The organic layer was dried over anhydrous $MgSO_4$ and concentrated in vacuo to give A1.

General Procedure for the Synthesis of A2

To a solution of A1 (0.89 mmol) in EtOH (4 mL) was added 2-aminopyridine (0.89 mmol). The mixture was stirred and refluxed for overnight. After cooling, the dark residue was diluted with EtOAc (20 mL) and saturated $NaHCO_3$ solution (30 mL). The organic layer was dried over anhydrous $MgSO_4$ and concentrated in vacuo. The crude product was purified by flash column chromatography to give A2.

Ethyl 2-methylimidazo[1,2-a]pyridine-3-carboxylate (A2)

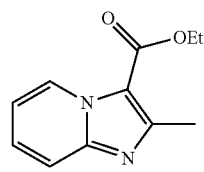

$^1$H NMR (400 MHz, $CDCl_3$) δ 1.28 (t, J=7.2 Hz, 3H), 2.56 (s, 3H), 4.27 (q, J=7.2 Hz, 2H), 6.78 (dd, J=7.2 Hz, 7.2 Hz, 1H), 7.19 (dd, J=6.8 Hz, 6.8 Hz, 1H), 7.42 (dd, J=8.8 Hz, 8.8 Hz, 1H), 9.12 (dd, J=6.8 Hz, 6.8 Hz, 1H); $^{13}$C NMR (100 MHz, $CDCl_3$) δ 14.5, 16.7, 60.3, 112.6, 113.6, 116.9, 127.5, 127.9, 146.9, 152.8, 161.4.

General Procedure for the Synthesis of A3

To a solution of A2 (0.31 mmol) in $H_2O$ (1.0 mL) and EtOH (3.0 mL) was added Lithium hydroxide (0.93 mmol). The mixture was stirred at room temperature for overnight. After reaction was completed, the mixture was evaporated and 1 N HCl (10 ml) was added until pH was 4. The residual pale solid was collected by filtration and washed with $H_2O$ to give A3.

General Procedure for the Synthesis of A4

To a solution of A3 (0.56 mmol) in CH$_2$Cl$_2$ (3 mL) was added triethylamine (1.7 mmol), benzylamine (0.56 mmol) and 1-ethyl-3-(3-dimethylaminopropyl)carbodiimide (0.84 mmol). The reaction mixture was stirred at room temperature for overnight. After reaction was completed, the reaction mixture was diluted with CH$_2$Cl$_2$ (10 mL) washed with 1N HCl (10 ml) and saturated NaHCO$_3$ solution (10 mL). The organic layer was dried over anhydrous MgSO$_4$ and concentrated in vacuo. The crude product was purified by flash column chromatography to give A4.

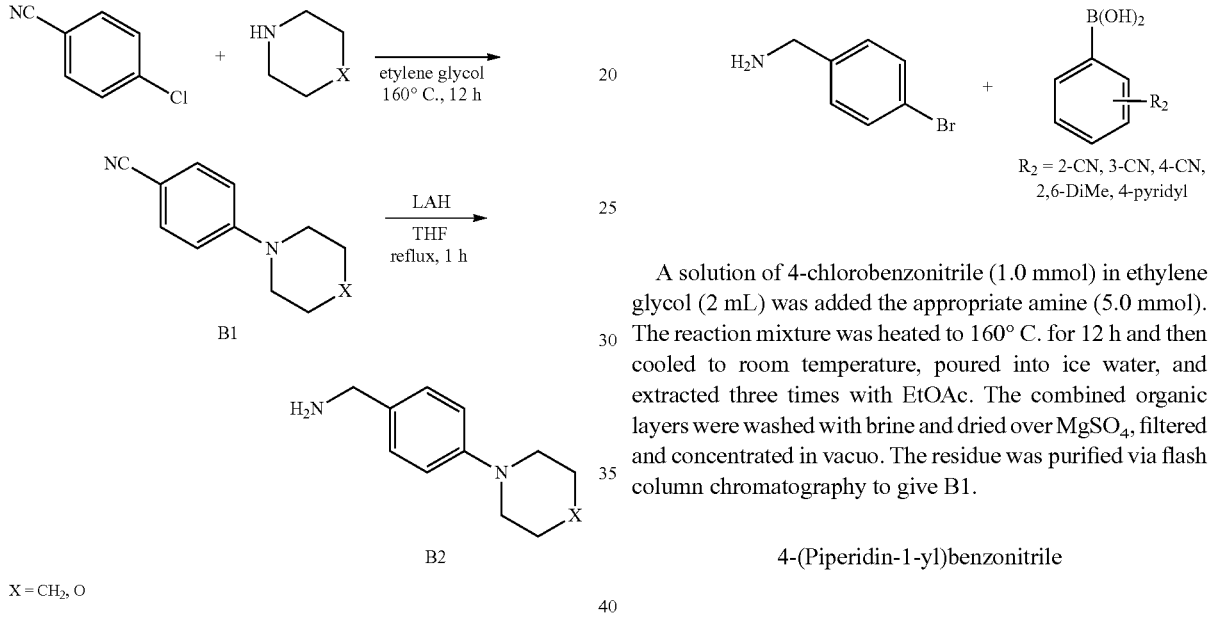

General Procedure of B1

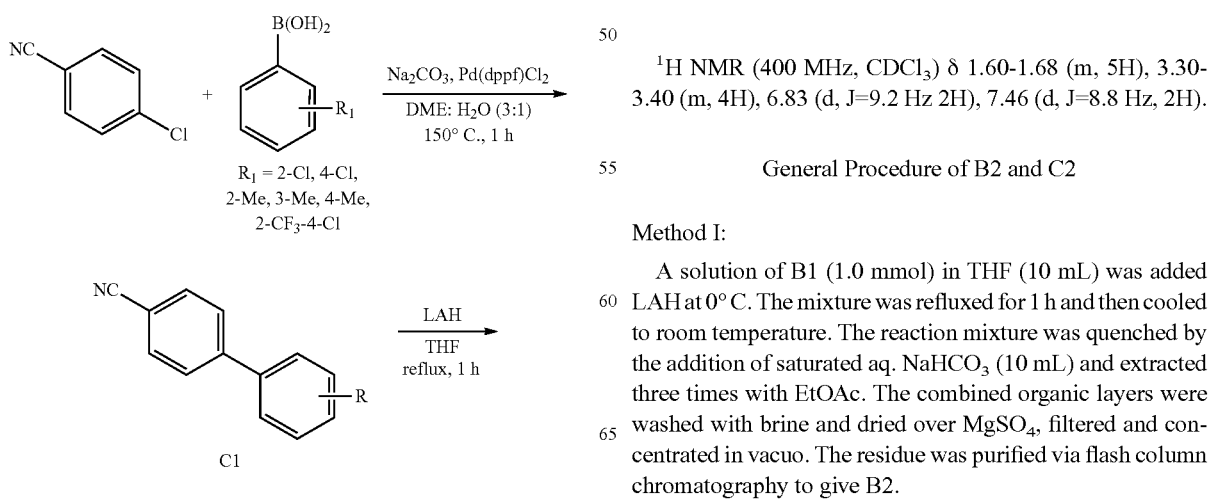

A solution of 4-chlorobenzonitrile (1.0 mmol) in ethylene glycol (2 mL) was added the appropriate amine (5.0 mmol). The reaction mixture was heated to 160° C. for 12 h and then cooled to room temperature, poured into ice water, and extracted three times with EtOAc. The combined organic layers were washed with brine and dried over MgSO$_4$, filtered and concentrated in vacuo. The residue was purified via flash column chromatography to give B1.

4-(Piperidin-1-yl)benzonitrile $^1$H NMR (400 MHz, CDCl$_3$) δ 1.60-1.68 (m, 5H), 3.30-3.40 (m, 4H), 6.83 (d, J=9.2 Hz 2H), 7.46 (d, J=8.8 Hz, 2H).

General Procedure of B2 and C2

Method I:

A solution of B1 (1.0 mmol) in THF (10 mL) was added LAH at 0° C. The mixture was refluxed for 1 h and then cooled to room temperature. The reaction mixture was quenched by the addition of saturated aq. NaHCO$_3$ (10 mL) and extracted three times with EtOAc. The combined organic layers were washed with brine and dried over MgSO$_4$, filtered and concentrated in vacuo. The residue was purified via flash column chromatography to give B2.

(4-(Piperidin-1-yl)phenyl)methanamine

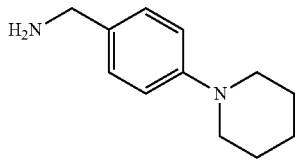 [SMILES: NCc1ccc(N2CCCCC2)cc1]

¹H NMR (400 MHz, CDCl₃) δ 1.55-1.59 (m, 2H), 1.68-1.74 (m, 4H), 3.13 (t, J=5.6 Hz, 4H), 3.77 (s, 2H), 6.92 (d, J=8.4 Hz 2H), 7.19 (d, J=8.8 Hz, 2H).

Method II:

A solution of 4-bromobenzylamine (1.0 mmol) in DME (3 mL) were added the appropriate arylboronic acid (1.0 mmol), 1,1'-bis(diphenylphosphino)ferrocene)-dichloropalladium (II) (0.03 mmol), Na₂CO₃ (aq. 2.0 mmol). The mixture was stirred and heated at reflux under N₂ atmosphere. After 1 h, the mixture was cooled to room temperature, then the mixture was extracted with EtOAc, washed with sat. NaHCO₃ (aq.) brine and dried over MgSO₄ and filtered. After removal of the solvent, the amines were obtained, which were used without purification.

General Procedure of C1

A solution of 4-chlorobenzonitrile (1.0 mmol) in DME (3 mL) were added the appropriatethylboronic acid (1.0 mmol), 1,1'-bis(diphenylphosphino)ferrocene)dichloropalladium (II) (0.03 mmol), Na₂CO₃ (aq. 2.0 mmol). The mixture was stirred and heated at reflux under N₂ atmosphere. After 1 h, the mixture was cooled to room temperature, then filtered and evaporated in vacuo. The residue was extracted with EtOAc, washed with sat. NaHCO₃ (aq.) brine and dried over MgSO₄, filtered and concentrated in vacuo. The residue was purified via flash column chromatography to give C1.

2'-(Trifluoromethyl)biphenyl-4-carbonitrile

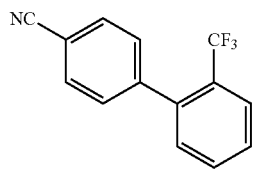 [SMILES: N#Cc1ccc(-c2ccccc2C(F)(F)F)cc1]

¹H NMR (400 MHz, CDCl₃) δ 7.30 (d, J=7.0 Hz, 1H), 7.45 (d, J=8.0 Hz, 2H), 7.54 (dd, J=7.6, 7.6 Hz, 1H), 7.61 (dd, J=7.2, 7.6 Hz, 1H), 7.70 (d, J=8.0 Hz, 2H), 7.76 (d, J=7.6 Hz, 1H).

Scheme 4

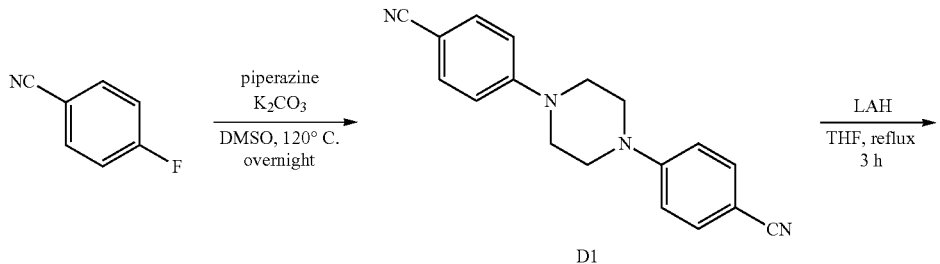

D1

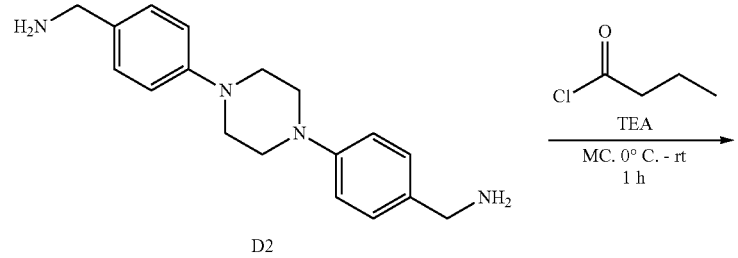

D2

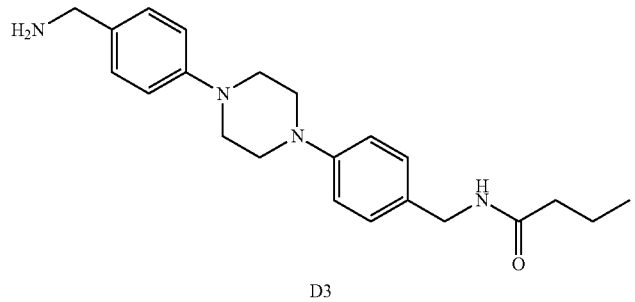

D3

-continued

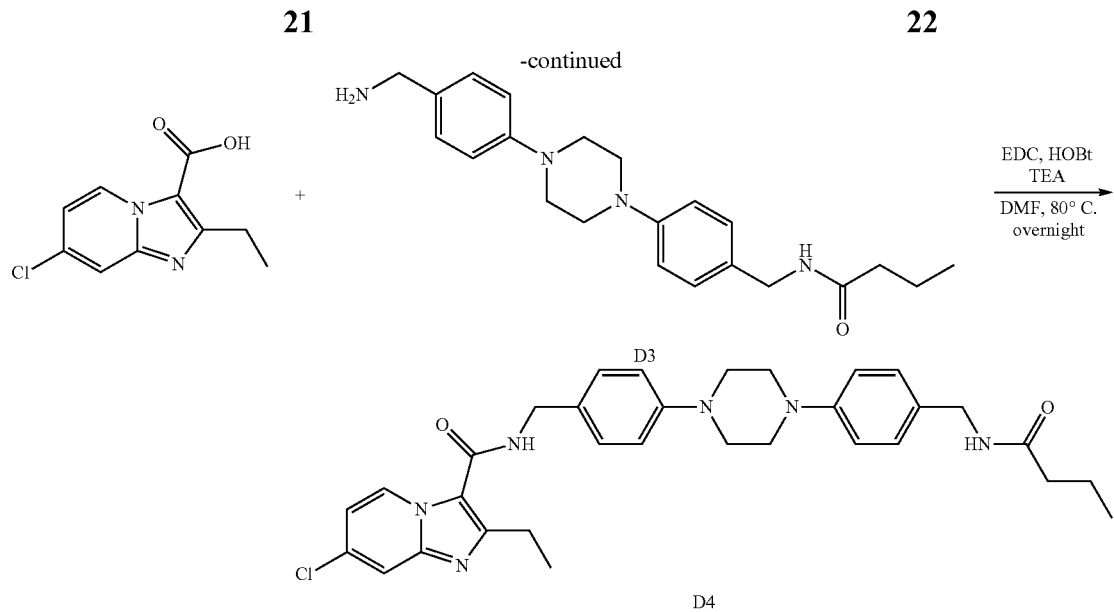

Procedure for the Synthesis of D1

A mixture of 4-fluorobenzonitrile (4.2 g, 35 mmol), piperazine (1.0 g, 12 mmol) and $K_2CO_3$ (4.8 g, 35 mmol) in DMSO (30 mL) was stirred for overnight at 120° C. The reaction mixture was poured on ice and the resulting solid was filtered, washed with methanol and dried in vacuo to give D1 as a white solid; $^1$H NMR (400 MHz, DMSO) δ 3.49 (s, 8H), 7.01 (d, J=9.2 Hz, 4H), 7.57 (d, J=9.2 Hz, 4H); LCMS (electrospray) m/z (M+H) 289.

Procedure for the Synthesis of D2

To a stirred solution of D1 (0.30 g, 1.00 mmol) in THF (5 mL) was added LAH (0.24 g, 6.20 mmol) and the resulting mixture was heated to reflux temperature for 3 h. The reaction mixture was quenched with water and the solid was filtered off. The filtrate was extracted with MC (30 mL×2), the organic layer was washed with saturated aqueous $Na_2CO_3$ (20 mL) and concentrated in vacuo to give D2; $^1$H NMR (400 MHz, CDCl$_3$) δ 3.32 (s, 8H), 3.80 (s, 4H), 6.95 (d, J=8.4 Hz, 4H), 7.25 (d, J=8.4 Hz, 4H); LCMS (electrospray) m/z (M)$^+$ 296.

Procedure for the Synthesis of D3

To a stirred solution of D2 (0.70 g, 2.36 mmol) in MC (25 mL) was added butyryl chloride (25 uL, 0.23 mmol) and the resulting mixture was stirred for 30 min under ice bath. After removal of the ice bath, the reaction mixture was stirred for another 30 min. The reaction mixture was diluted with MC (20 mL), washed with saturated aqueous $Na_2CO_3$ (20 mL) and the organic layer was concentrated under reduced pressure. The crude residue was purified by column chromatography (20% MeOH in MC) to give D3; $^1$H NMR (400 MHz, CDCl$_3$) δ 0.41 (t, J=7.2 Hz, 3H), 1.00 (brs, 2H), 1.12-1.21 (m, 2H), 1.63 (t, J=7.2 Hz, 2H), 2.80 (s, 8H), 3.27 (s, 2H), 3.84 (d, J=5.2 Hz, 2H), 5.16 (brs, 1H), 6.38-6.45 (m, 4H), 6.67-6.74 (m, 4H); LCMS (electrospray) m/z (M+H)$^+$ 367.

Procedure for the Synthesis of D4

To a solution of acid (0.012 g, 0.054 mmol) in DMF (1 mL) was added triethylamine (15 uL, 0.11 mmol), D3 (0.020 g, 0.055 mmol), hydroxybenzotriazole (3.7 mg, 0.027 mmol) and 1-ethyl-3-(3-dimethylaminopropyl)carbodiimide (0.016 g, 0.082 mmol) and the reaction mixture was stirred at 80° C. for overnight. The reaction mixture was cooled to −10° C., the resulting solid was filtered, washed with MC and dried in vacuo to give D4.

Scheme 5

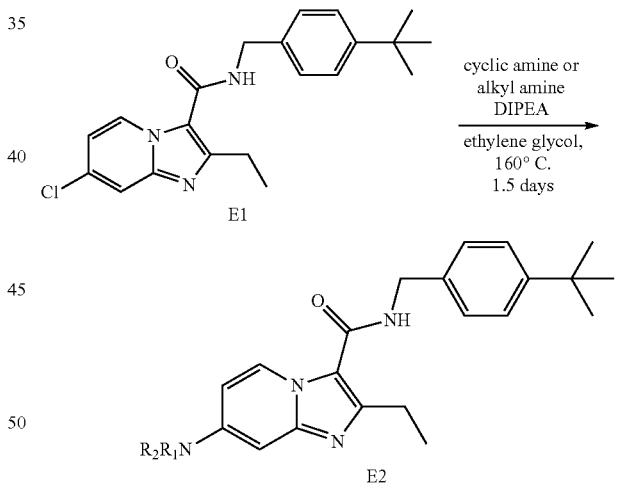

Procedure for the Synthesis of E2

A mixture of E1 (0.32 g, 0.86 mmol), an amine (excess) and DIPEA (0.75 mL, 4.32 mmol) in ethylene glycol (4 mL) was heated to 160° C. for 1.5 days. After reaction completion, the reaction mixture was diluted with water (20 mL) and extracted with ethyl acetate (20 mL×3). The organic layer was dried over anhydrous $MgSO_4$ and concentrated in vacuo. The crude residue was purified by flash column chromatography (20% MeOH in MC) and then precipitated with acetonitrile to give E2 as a white solid.

Scheme 6

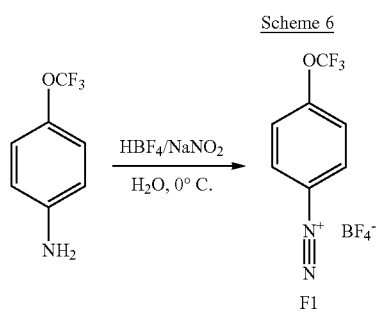

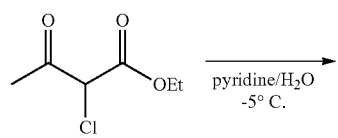

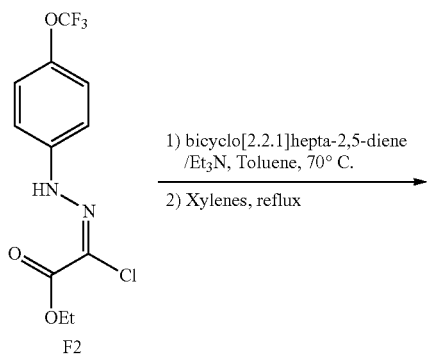

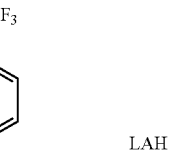

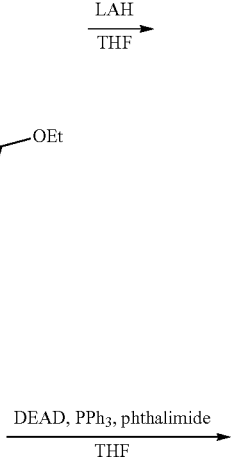

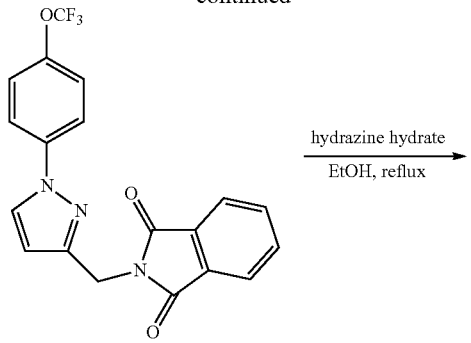

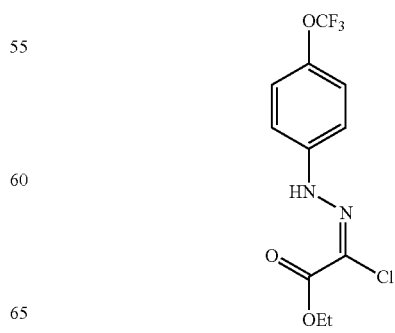

General Procedure for the Synthesis of F1

To an ice-salt-cooled solution of the 4-(trifluoromethoxy) aniline (11.29 mmol) in $HBF_4$ (50%, 22.58 mmol) and water (2 mL) was dropwise added a precooled solution of $NaNO_2$ (12.42 mmol) in water (2 mL). During the addition, the temperature was carefully kept below 5° C. and the resulting mixture was left to stir at 0° C. for 30 min. The diazonium salt (F1) was collected by filtration, washed with $Et_2O$, and extensively dried in vacuo.

General Procedure for the Synthesis of F2

F1 (11.30 mmol) was added to a solution of 2-chloroacetoacetate (11.30 mmol) in pyridine (4 mL) and water (4 mL) at −5° C. The mixture was stirred at −5° C. for 30 min, and the resulting precipitate was filtered and washed with ice cold water. Recrystallization from EtOH/water gave F2.

(E)-Ethyl 2-chloro-2-(2-(4-(trifluoromethoxy)phenyl)hydrazono)acetate (F2)

$^1$H NMR (400 MHz, CDCl$_3$) δ 1.41 (t, J=7.2 Hz, 3H), 4.39 (q, J=7.2 Hz, 2H), 7.20 (d, J=9.6 Hz, 2H), 7.24 (d, J=9.2 Hz, 2H), 8.32 (brs, 1H)

General Procedure for the Synthesis of F3

A mixture of F2 (9.33 mmol), bicyclo[2.2.1]hepta-2,5-diene (46.67 mmol) and Et$_3$N (28.00 mmol) in toluene (10 mL) was stirred at 70° C. for 1 h. The resulting mixture was cooled and filtered, the filter cake was washed with toluene, and the organic fractions were combined and evaporated. The residue was refluxed in xylenes (10 mL) for 2 h. Column chromatography of the cooled reaction mixture, eluting with hexanes, first gave xylenes, and then further elution with ethyl acetate gave F3.

Ethyl 1-(4-(trifluoromethoxy)phenyl)-1H-pyrazole-3-carboxylate (F3)

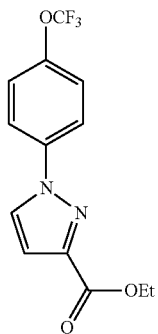 [SMILES: CCOC(=O)c1ccn(-c2ccc(OC(F)(F)F)cc2)n1]

$^1$H NMR (400 MHz, CDCl$_3$) δ 1.42 (t, J=7.2 Hz, 3H), 4.44 (q, J=7.2 Hz, 2H), 7.00 (d, J=2.4 Hz, 1H), 7.33 (d, J=8.8 Hz, 2H), 7.79 (d, J=9.2 Hz, 2H), 7.91 (d, J=2.4 Hz, 1H)

General Procedure for the Synthesis of F4

LiAlH$_4$ (0.67 mmol) was added to a stirred solution of F3 (0.67 mmol) in THF (5 mL) at 0° C., and the mixture was warmed to room temperature for 1 hr, then cooled to 0° C. and quenched with ice. The resulting mixture was diluted with ethyl acetate (10 mL) washed with water (10 mL) and brine (10 mL). The organic layer was dried over anhydrous MgSO$_4$, filtered and concentrated in vacuo. The crude product was purified by flash column chromatography to give F4.

General Procedure for the Synthesis of F5

DEAD (0.84 mmol) was added dropwise to a stirred and cooled (0° C.) solution of phthalimide (0.83 mmol), Ph$_3$P (0.84 mmol) and F4 (0.69 mmol) in dry THF. The cooling bath was removed and stirring was continued at room temperature for 4 hr, then water (1 mL) was added and the reaction mixture was filtered through a column of silica, eluting with CH$_2$Cl$_2$. The eluate was concentrated in vacuo and the residue was purified by flash column chromatography to give F5.

General Procedure for the Synthesis of F6

To a solution of F5 (0.69 mmol) in EtOH (5 mL) was added hydrazine hydrate (1.38 mmol). The reaction mixture was stirred and refluxed for 4 hr. After cooling, the reaction mixture was evaporated and diluted with EtOAc (10 mL) and saturated NaHCO$_3$ solution (10 mL), then washed with brine (10 mL). The organic layer was dried over anhydrous MgSO$_4$, filtered and concentrated in vacuo to give F6.

Scheme 7

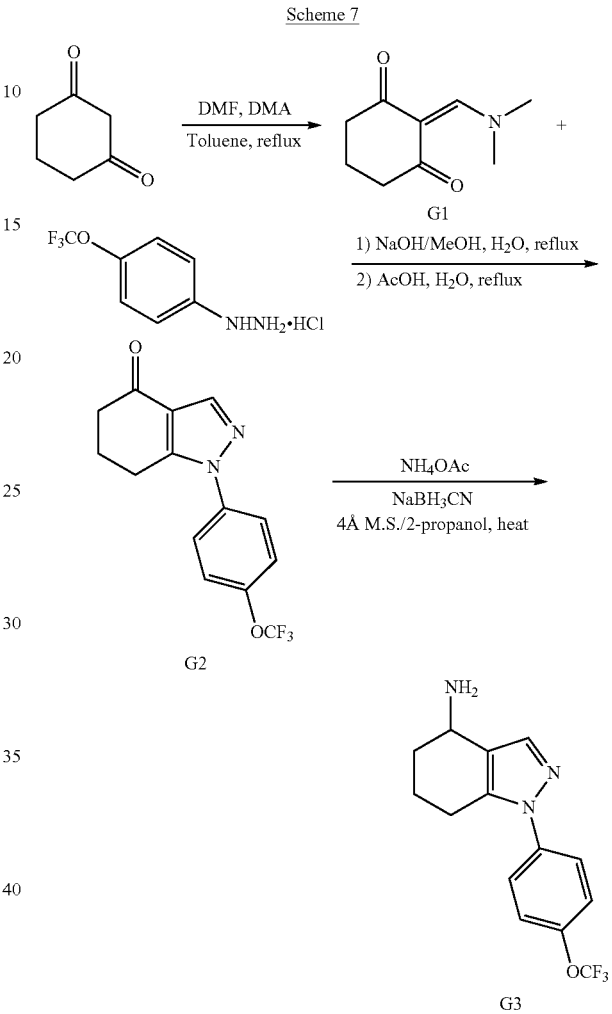

General Procedure for the Synthesis of G1

To a solution of cyclohexane-1,3-dione (17.84 mmol) in toluene (20 mL) was added DMF.DMA (26.75 mmol). The reaction mixture was stirred and refluxed for overnight. After cooling, the reaction mixture was concentrated in vacuo. The crude product G1 was used for the next step without further purification.

General Procedure for the Synthesis of G2

To a solution of G1 (8.98 mmol) in methanol (20 mL) and water (3 mL) was added (4-(trifluoromethoxy)phenyl)hydrazine hydrochloride (8.98 mmol) and sodium hydroxide (8.98 mmol). The reaction mixture was heated at reflux for 2 h and concentrated in vacuo. Then to the residue were added AcOH (20 mL) and water (10 mL), and the reaction mixture was heated to 110° C. for 2 h. On completion of the reaction, the solution was concentrated in vacuo, the residue was diluted with EtOAc (20 mL) and saturated NaHCO$_3$ solution (20 mL), then washed with brine (20 mL). The organic layer was dried over anhydrous MgSO$_4$, filtered and concentrated in vacuo. The residue was purified by flash column chromatography to give G2.

General Procedure for the Synthesis of G3

To a solution of G2 (2.36 mmol) in 2-propanol (5 mL) was added ammonium acetate (23.65 mmol). After complete dissolution, molecular sieves (4 Å, 1.0 g) and NaBH$_3$CN (11.82 mmol) were added and the reaction mixture was stirred and refluxed for overnight. After cooling, the reaction mixture was evaporated and diluted with EtOAc (10 mL) and saturated NaHCO$_3$ solution (10 mL), then washed with brine (10 mL). The organic layer was dried over anhydrous MgSO$_4$, filtered and concentrated in vacuo to give G3.

crude product H2 was used in the next reaction (amide coupling) without further purification.

General Procedure for the Synthesis of H4

To a solution of an acid (H3 in scheme 8, 114 mg, 0.506 mmol) in dry DMF were added 1-ethyl-3-(3-dimethylaminopropyl)carbodiimide (97 mg, 0.506 mmol), 1-hydroxybenzotriazole (68 mg, 0.506 mmol). The mixture was stirred for 30 min at room temperature. Then to the reaction mixture was added a solution of C2 (108 mg, 0.46 mmol) in dry DMF. The reaction mixture was stirred at 140° C. for 2 h. After cooling, the reaction mixture was diluted with ethyl acetate (10 mL), washed with saturated NaHCO$_3$ solution (10 mL) and brine (10 mL). The organic layer was dried over anhydrous MgSO$_4$ and concentrated in vacuo. The crude product was purified by flash column chromatography to give H4.

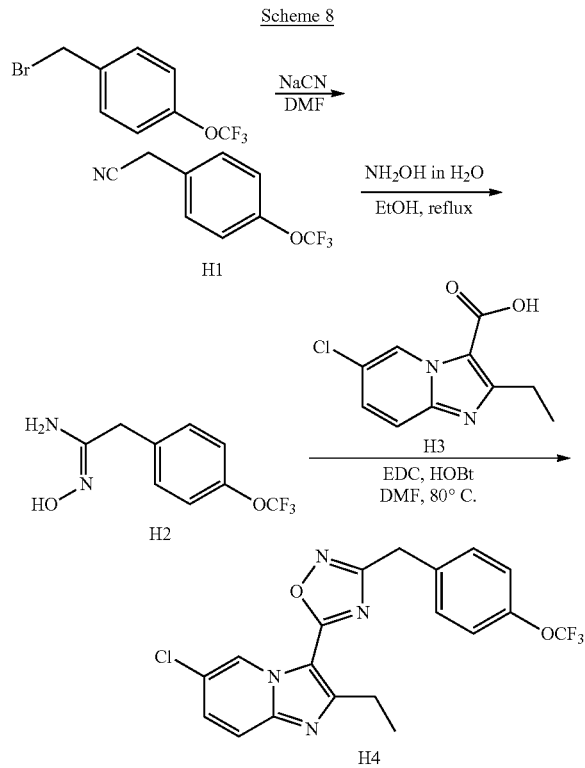

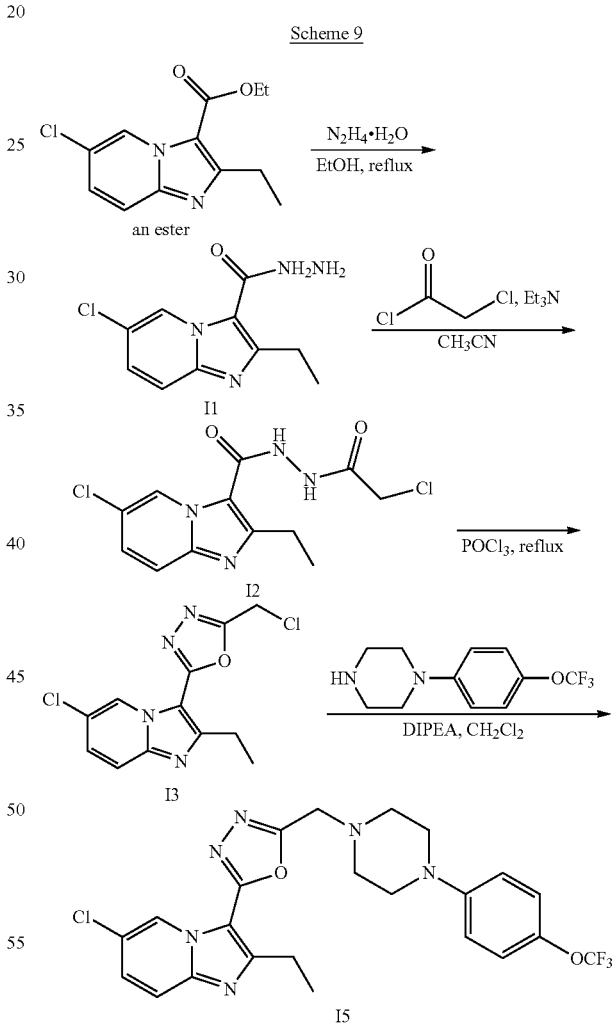

General Procedure for the Synthesis of H1

To a solution of 4-trifluoromethoxybenzyl bromide (1.05 g, 4.09 mmol) in 5 mL dry DMF was added sodium cyanide (220 mg, 4.50 mmol). The reaction was stirred for 1 h at room temperature, poured into water and extracted with ethyl acetate (2×20 mL). The combined layer was dried over anhydrous MgSO$_4$, filtered and concentrated in vacuo. The crude product H1 was used in the next reaction without further purification.

General Procedure for the Synthesis of H2

To a solution of H1 (93 mg, 0.46 mmol) in EtOH was added a solution of hydroxylamine 50 wt % in water (0.12 mL, 1.84 mmol). The reaction mixture was refluxed for overnight. After cooling, the mixture was concentrated in vacuo. The General Procedure for the Synthesis of I1

To a solution of an ester (253 mg, 1.0 mmol) in EtOH was added hydrazine hydrate (0.75 mL, mmol). The reaction mixture was refluxed for 12 h. After cooling, the resulting precipitate (I1) was filtered, washed with EtOH and dried.

General Procedure for the Synthesis of I2

To a solution of I1 (96 mg, 0.402 mmol) in CH$_2$Cl$_2$ was added Et$_3$N (0.057 mL, 0.406 mmol). The reaction mixture was cooled to 0° C. and to the mixture was added dropwise a solution of chloroacetyl chloride (0.035 mL, 0.442 mmol) in CH$_2$Cl$_2$. The reaction mixture was stirred at 0° C., the reaction temperature was raised to room temperature and the resultant mixture was further stirred for 30 min. To the mixture was added water and then the solution was extracted with CH$_2$Cl$_2$ and washed with brine. The organic layer was dried over anhydrous MgSO$_4$ and concentrated in vacuo. The crude product (I2) was used in the next reaction without further purification.

General Procedure for the Synthesis of I3

I2 (0.402 mmol) was placed under nitrogen and POCl$_3$ (2 mL) was added. The reaction mixture was refluxed for 2 h. The mixture was cooled to room temperature, poured into water and extracted with ethylacetate (×2). The combined organic layers were washed with brine, dried over anhydrous MgSO$_4$ and concentrated in vacuo. The crude product was purified by flash column chromatography to give I3.

General Procedure for the Synthesis of I5

To a solution of I3 (50 mg, 0.17 mmol) in CH$_2$Cl$_2$ were added an amine (50 mg, 0.20 mmol) and DIPEA (0.035 mL, 0.20 mmol). The reaction mixture was stirred for overnight. The mixture was extracted with CH$_2$Cl$_2$ and water and then washed with brine. The organic layer was dried over anhydrous MgSO$_4$ and concentrated in vacuo. The crude product was purified by flash column chromatography to give I5.

Scheme 10

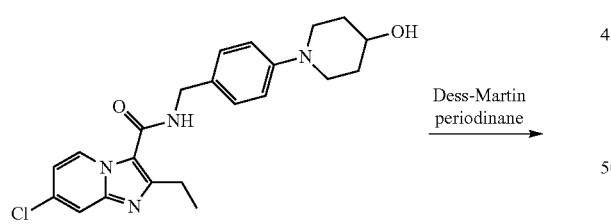

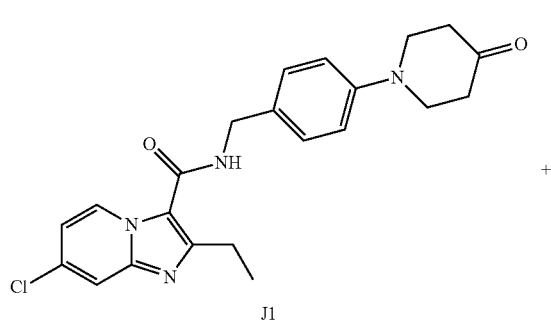

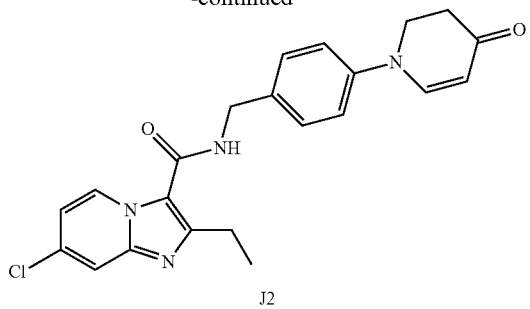

To a stirred suspension of an alcohol (0.050 g, 0.12 mmol) and NaHCO$_3$ (0.051 g, 0.60 mmol) in methylene chloride (2.0 mL) was added dess-martin periodinane (0.10 g, 0.24 mmol) under ice-bath. After 5-minutes, the reaction temperature was raised to room temperature and the resulting solution was stirred for 2 h. The reaction mixture was diluted with methylene chloride (10 mL) and washed with saturated aqueous NaHCO$_3$ solution (10 mL) and brine (10 mL). The organic layer was dried over anhydrous MgSO$_4$ and concentrated in vacuo. The resulting crude residue was purified by flash column chromatography (methylene chloride:methanol=50:1 ratio) to give J1 and J2.

Scheme 11

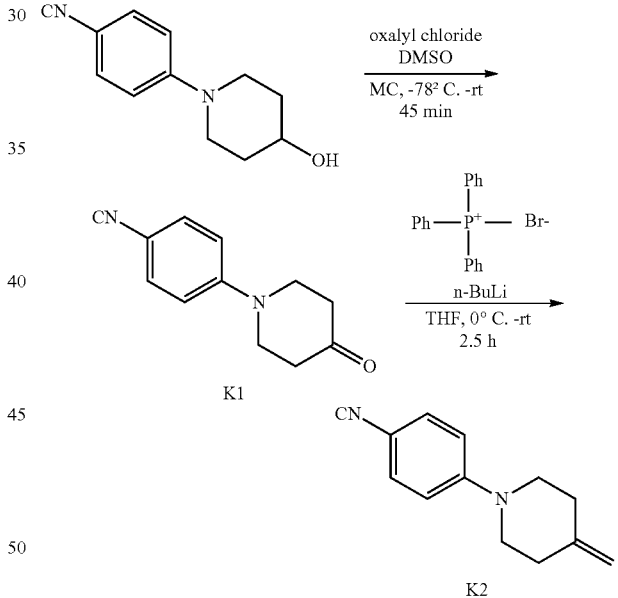

A solution of oxalyl chloride (0.43 mL, 4.94 mmol) in methylene chloride (5 mL) was cooled to −78° C. and DMSO (0.70 mL, 9.88 mmol) was added slowly. After 10 minutes, a solution of an alcohol (0.50 g, 2.47 mmol) in methylene chloride (3 mL) was added over 10 min, and the mixture was further stirred for 15 min at −78° C. Triethylamine (1.4 mL, 9.88 mmol) was added to the solution and the mixture was stirred for 15 min and allowed to warm up to 0° C. After reaction completion, the reaction mixture was diluted with methylene chloride (15 mL) and washed with aqueous Na$_2$CO$_3$ (15 mL). The organic layer was dried over MgSO$_4$ and concentrated in vacuo. The resulting crude residue was purified by flash column chromatography (n-hexane:ethyl acetate=5:1 ratio) to give K1.

To a suspension of methyltriphenylphosphonium bromide (0.43 g, 1.20 mmol) in THF (5 mL) was added nBuLi (2.5 M in n-hexane, 0.48 mL, 1.20 mmol) under ice-bath and the mixture was stirred for 30 min. A solution of ketone compound K1 in THF (3 mL) was added dropwise and the resulting mixture was allowed to warm up to room temperature over 2 h. After reaction completion, solution was diluted with methylene chloride (10 mL) and washed with aqueous NaHCO₃ (15 mL). The organic layer was dried over MgSO₄ and concentrated in vacuo. The resulting crude residue was purified by flash column chromatography (n-hexane:ethyl acetate=15:1 ratio) to give K2.

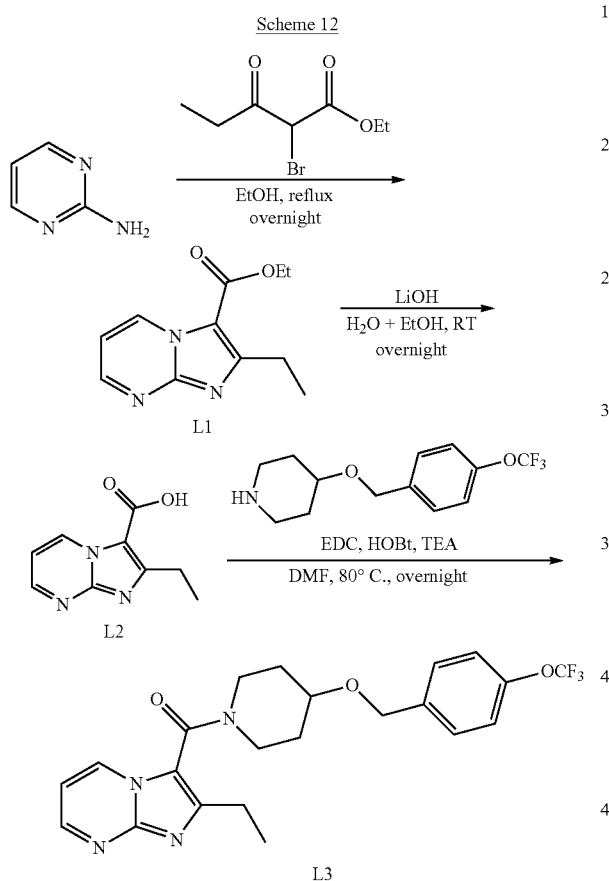

General Procedure for the Synthesis of L1

To a stirred solution of 2-Aminopyrimidine (10.5 mmol) in Ethanol (50.0 mL) was added ethyl 2-bromo-3-oxopentanoate (12.6 mmol). The mixture was stirred at reflux for overnight. After the reaction was completed, the mixture was evaporated, diluted with EtOAc (50.0 mL) and washed with saturated NaHCO₃ solution (50.0 mL). The organic layer was dried over anhydrous MgSO₄ and concentrated in vacuo. The crude product was purified by flash column chromatography to give L1.

General Procedure for the Synthesis of L2

To a stirred solution of L1 (1.82 mmol) in H₂O (3.0 mL) and EtOH (9.0 mL) was added Lithium hydroxide (5.5 mmol). The mixture was stirred at room temperature for overnight. After the reaction was completed, the mixture was evaporated and 1 N HCl (10.0 ml) was added until pH was 4. The residual pale solid was collected by filtration and washed with H₂O to give L2.

General Procedure for the Synthesis of L3

To a stirred solution of L2 (0.56 mmol) in DMF (3.0 mL) was added triethylamine (1.7 mmol), 4-((4-(trifluoromethoxy)benzyl)oxy)piperidine hydrochloride (0.56 mmol), 1-Hydroxy benzotriazole (0.17 mmol) and 1-ethyl-3-(3-dimethylaminopropyl)carbodiimide (0.84 mmol). The reaction mixture was stirred at 80° C. for overnight. After the reaction was completed, the reaction mixture was diluted with CH₂Cl₂ (10.0 mL), washed with 1N HCl (10.0 ml) and saturated NaHCO₃ solution (10.0 mL). The organic layer was dried over anhydrous MgSO₄ and concentrated in vacuo. The crude product was purified by flash column chromatography to give L3.

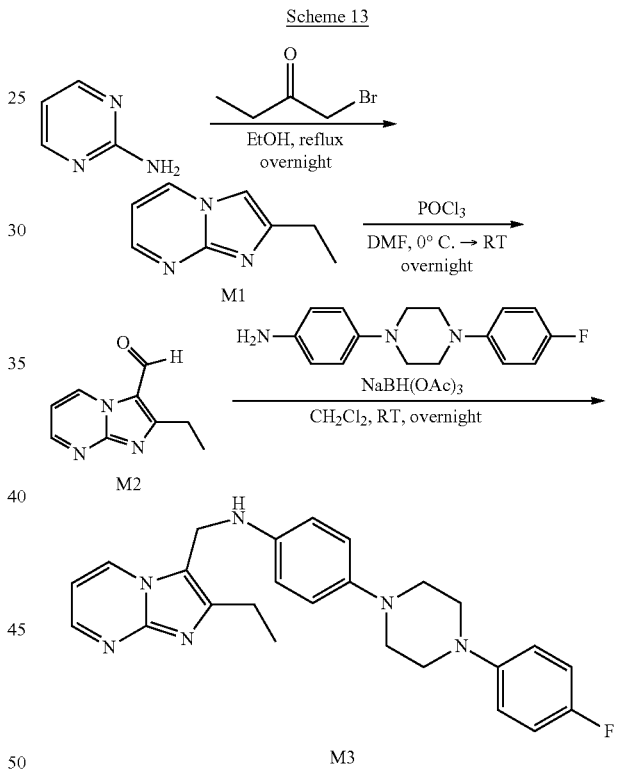

General Procedure for the Synthesis of M1

To a stirred solution of 2-Aminopyrimidine (5.25 mmol) in Ethanol (25.0 mL) was added 1-bromobutan-2-one (7.9 mmol). The mixture was stirred at reflux for overnight. After the reaction was completed, the mixture was evaporated, diluted with EtOAc (50.0 mL) and washed with 1N NaOH solution (50.0 mL). The organic layer was dried over anhydrous MgSO₄ and concentrated in vacuo. The crude product was purified by flash column chromatography to give M1.

General Procedure for the Synthesis of M2

To a stirred solution of M1 (2.0 mmol) in DMF (3.0 mL) was added POCl₃ (7.1 mmol) at 0° C. The mixture was stirred at room temperature for overnight. After the reaction was completed, the mixture was evaporated, diluted with CH₂Cl₂ (20.0 mL) and washed with 1N NaOH solution (20.0 mL). The organic layer was dried over anhydrous MgSO₄ and concentrated in vacuo. The crude product was purified by flash column chromatography to give M2.

General Procedure for the Synthesis of M3

To a stirred solution of M2 (0.57 mmol) in CH₂Cl₂ (3.0 mL) was added 4-(4-(4-fluorophenyl)piperazin-1-yl)aniline (0.68 mmol) and Sodium triacetoxyborohydride (1.14 mmol). The reaction mixture was stirred at room temperature for overnight. After the reaction was completed, the reaction mixture was washed with brine (5.0 ml). The organic layer was dried over anhydrous MgSO₄ and concentrated in vacuo. The crude product was purified by flash column chromatography to give M3.

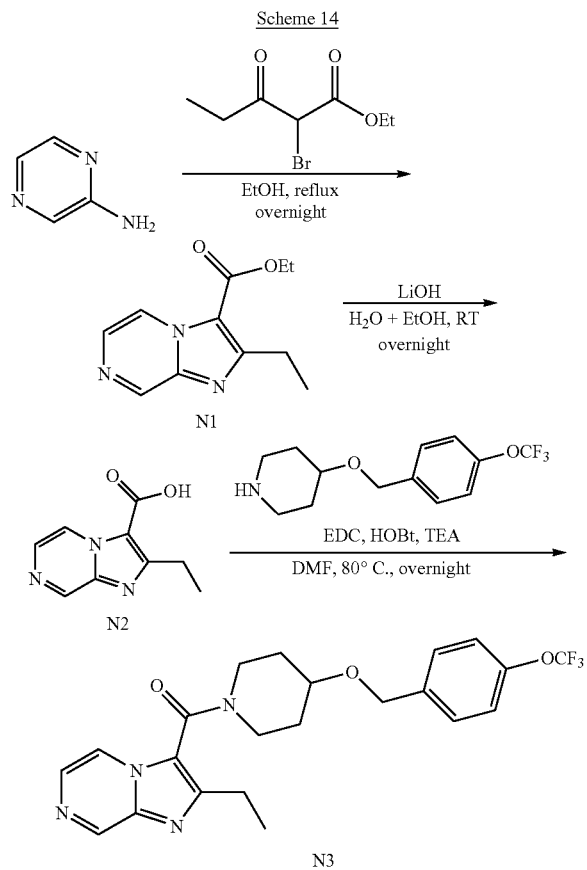

General Procedure for the Synthesis of N1

To a stirred solution of aminopyrazine (10.5 mmol) in ethanol (50.0 mL) was added ethyl 2-bromo-3-oxopentanoate (12.6 mmol). The mixture was stirred at reflux for overnight. After the reaction was completed, the mixture was evaporated, diluted with EtOAc (50.0 mL) and washed with saturated NaHCO₃ solution (50.0 mL). The organic layer was dried over anhydrous MgSO₄ and concentrated in vacuo. The crude product was purified by flash column chromatography to give N1.

General Procedure for the Synthesis of N2

To a stirred solution of N1 (1.82 mmol) in H₂O (3.0 mL) and EtOH (9.0 mL) was added lithium hydroxide (5.5 mmol). The mixture was stirred at room temperature for overnight. After the reaction was completed, the mixture was evaporated and 1 N HCl (10.0 ml) was added until pH was 4. The residual pale solid was collected by filtration and washed with H₂O to give N2.

General Procedure for the Synthesis of N3

To a stirred solution of N2 (0.56 mmol) in DMF (3.0 mL) was added triethylamine (1.7 mmol), 4-((4-(trifluoromethoxy)benzyl)oxy)piperidine hydrochloride (0.56 mmol), 1-Hydroxy benzotriazole (0.17 mmol) and 1-ethyl-3-(3-dimethylaminopropyl)carbodiimide (0.84 mmol). The reaction mixture was stirred at 80° C. for overnight. After the reaction was completed, the reaction mixture was diluted with CH₂Cl₂ (10.0 mL), washed with 1N HCl (10.0 ml) and saturated NaHCO₃ solution (10.0 mL). The organic layer was dried over anhydrous MgSO₄ and concentrated in vacuo. The crude product was purified by flash column chromatography to give N3.

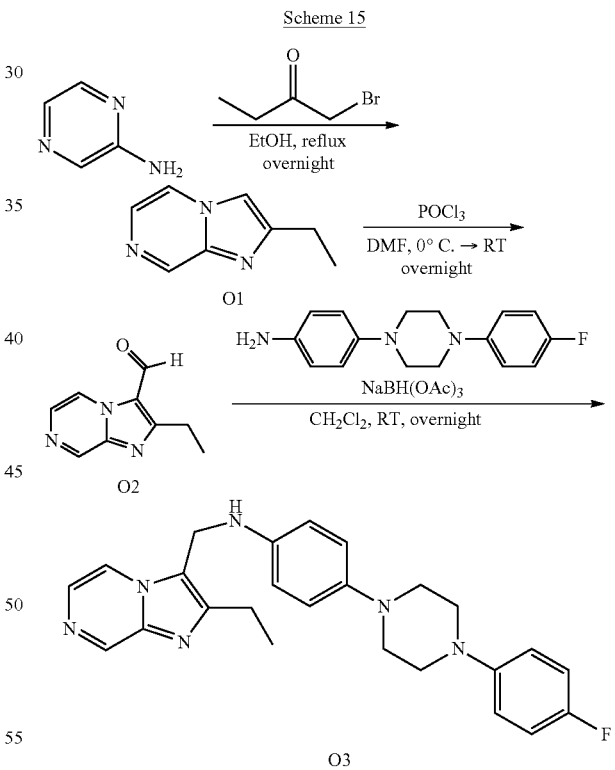

General Procedure for the Synthesis of O1

To a stirred solution of aminopyrazine (5.25 mmol) in ethanol (25.0 mL) was added 1-bromobutan-2-one (7.9 mmol). The mixture was stirred at reflux for overnight. After the reaction was completed, the mixture was evaporated, diluted with EtOAc (50.0 mL) and washed with 1N NaOH solution (50.0 mL). The organic layer was dried over anhydrous MgSO₄ and concentrated in vacuo. The crude product was purified by flash column chromatography to give O1.

General Procedure for the Synthesis of O2

To a stirred solution of O1 (2.0 mmol) in DMF (3.0 mL) was added POCl₃ (7.1 mmol) at 0° C. The mixture was stirred at room temperature for overnight. After the reaction was completed, the mixture was evaporated, diluted with CH₂Cl₂ (20.0 mL) and washed with 1N NaOH solution (20.0 mL). The organic layer was dried over anhydrous MgSO₄ and concentrated in vacuo. The crude product was purified by flash column chromatography to give O2.

General Procedure for the Synthesis of O3

To a stirred solution of O2 (0.57 mmol) in CH₂Cl₂ (3.0 mL) was added 4-(4-(4-fluorophenyl)piperazin-1-yl)aniline (0.68 mmol) and Sodium triacetoxyborohydride (1.14 mmol). The reaction mixture was stirred at room temperature for overnight. After the reaction was completed, the reaction mixture was washed with brine (5.0 ml). The organic layer was dried over anhydrous MgSO₄ and concentrated in vacuo. The crude product was purified by flash column chromatography to give O3.

Ethyl 2-methylimidazo[1,2-a]pyridine-3-carboxylate (1)

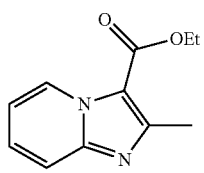

¹H NMR (400 MHz, CDCl₃) δ 1.28 (t, J=7.2 Hz, 3H), 2.56 (s, 3H), 4.27 (q, J=7.2 Hz, 2H), 6.78 (dd, J=7.2 Hz, 7.2 Hz, 1H), 7.19 (dd, J=6.8 Hz, 6.8 Hz, 1H), 7.42 (dd, J=8.8 Hz, 8.8 Hz, 1H), 9.12 (dd, J=6.8 Hz, 6.8 Hz, 1H); ¹³C NMR (100 MHz, CDCl₃) δ 14.5, 16.7, 60.3, 112.6, 113.6, 116.9, 127.5, 127.9, 146.9, 152.8, 161.4.

2-Methylimidazo[1,2-a]pyridine-3-carboxylic acid (2)

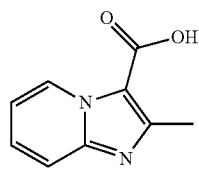

¹H NMR (400 MHz, CD₃OD) δ 2.84 (s, 3H), 7.04 (dd, J=1.2 Hz, 7.2 Hz, 1H), 7.96 (d, J=8.8 Hz, 1H), 8.07 (dd, J=1.2 Hz, 7.2 Hz, 1H), 9.65 (d, J=7.2 Hz, 1H).

N-Benzyl-2-methylimidazo[1,2-a]pyridine-3-carboxamide (3)

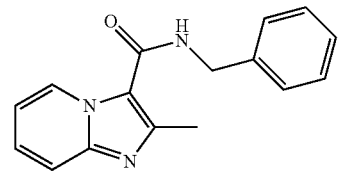 [SMILES: Cc1nc2ccccn2c1C(=O)NCc1ccccc1]

¹H NMR (400 MHz, CDCl₃) δ 2.68 (s, 3H), 4.70 (d, J=5.6 Hz, 2H), 6.13 (brs, 1H), 6.91 (dd, J=1.2 Hz, 7.2 Hz, 1H), 7.29-7.39 (m, 6H), 7.56 (d, J=9.2 Hz, 1H), 9.42 (d, J=7.2 Hz, 1H).

N-(4-Fluorobenzyl)-2-methylimidazo[1,2-a]pyridine-3-carboxamide (4)

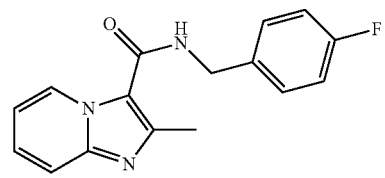 [SMILES: Cc1nc2ccccn2c1C(=O)NCc1ccc(F)cc1]

¹H NMR (400 MHz, CDCl₃) δ 2.67 (s, 3H), 4.66 (d, J=6.0 Hz, 2H), 6.11 (brs, 1H), 6.91 (d, J=6.8 Hz, 1H), 7.02-7.06 (m, 2H), 7.30-7.36 (m, 3H), 7.56 (d, J=8.8 Hz, 1H), 9.41 (d, J=6.8 Hz, 1H).

2-Methyl-N-(pyridin-3-ylmethyl)imidazo[1,2-a]pyridine-3-carboxamide (5)

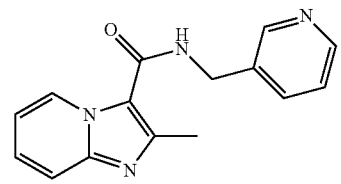 [SMILES: Cc1nc2ccccn2c1C(=O)NCc1cccnc1]

¹H NMR (400 MHz, CDCl₃) δ 2.68 (s, 3H), 4.70 (d, J=6.0 Hz, 2H), 6.30 (brs, 1H), 6.89-6.93 (m, 1H), 7.26-7.35 (m, 2H), 7.55 (d, J=8.8 Hz, 1H), 7.72 (d, J=8.0 Hz, 1H), 8.53 (d, J=3.6 Hz, 1H), 8.62 (s, 1H), 9.38 (d, J=7.2 Hz, 1H).

2-Methyl-N-(4-phenoxybenzyl)imidazo[1,2-a]pyridine-3-carboxamide (6)

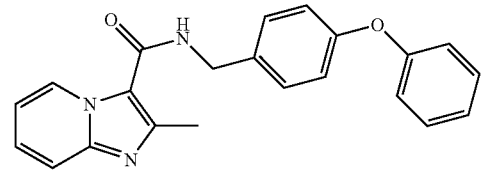

1H NMR (400 MHz, CDCl₃) δ 2.70 (s, 3H), 4.67 (d, J=5.6 Hz, 2H), 6.14 (brs, 1H), 6.92-6.96 (m, 1H), 6.99-7.08 (m, 4H), 7.12 (dd, J=6.4 Hz, 6.4 Hz, 1H), 7.31-7.37 (m, 5H), 7.59 (d, J=8.8 Hz, 1H), 9.43 (d, J=6.8 Hz, 1H).

N-(4-Methoxybenzyl)-2-methylimidazo[1,2-a]pyridine-3-carboxamide (7)

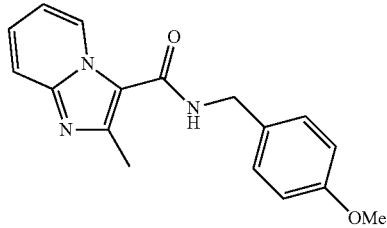 [SMILES: COc1ccc(CNC(=O)c2c(C)nc3ccccn23)cc1]

¹H NMR (400 MHz, CDCl₃) δ 2.67 (s, 3H), 3.810 (s, 3H), 4.63 (d, J=5.2 Hz, 2H), 6.01 (m, 1H), 6.89-6.94 (m, 3H), 7.30-7.35 (m, 3H), 7.56-7.58 (m, 1H), 9.43 (dd, J=0.8, 6.8 Hz, 1H).

N-(4-Methoxyphenethyl)-2-methylimidazo[1,2-a]pyridine-3-carboxamide (8)

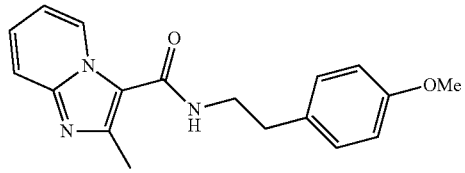 [SMILES: COc1ccc(CCNC(=O)c2c(C)nc3ccccn23)cc1]

¹H NMR (400 MHz, CDCl₃) δ 2.46 (s, 3H), 2.92 (t, J=6.6 Hz, 2H), 3.74 (q, J=6.4 Hz, 2H), 3.80 (s, 3H), 6.87-6.92 (m, 3H), 7.18 (d, J=8.4 Hz, 2H), 7.29-7.33 (m, 1H), 7.55 (d, J=8.8 Hz, 1H), 9.41 (d, J=7.2 Hz, 1H); LCMS (electrospray) m/z (M+H)⁺ 310.25

N-(Cyclohexylmethyl)-2-methylimidazo[1,2-a]pyridine-3-carboxamide (9)

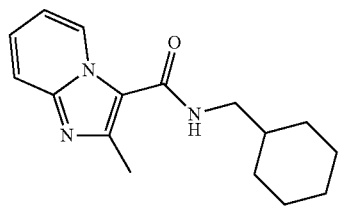 [SMILES: Cc1nc2ccccn2c1C(=O)NCC1CCCCC1]

¹H NMR (400 MHz, CDCl₃) δ 0.94-1.27 (m, 5H), 1.54-1.78 (m, 6H), 2.67 (s, 3H), 3.31 (t, J=6.2 Hz, 2H), 5.91 (m 1H), 6.64 (t, J=6.8 Hz, 1H), 7.24-7.28 (m, 1H), 7.50 (d, J=9.2 Hz, 1H), 9.32 (d, J=6.8 Hz, 1H).

tert-Butyl 4-((2-methylimidazo[1,2-a]pyridine-3-carboxamido)methyl)piperidine-1-carboxylate (10)

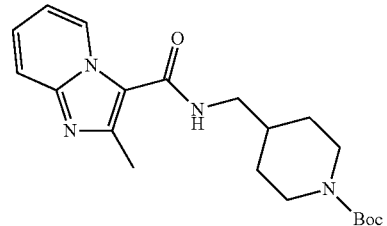 [SMILES: Cc1nc2ccccn2c1C(=O)NCC1CCN(C(=O)OC(C)(C)C)CC1]

¹H NMR (400 MHz, CDCl₃) δ 1.87-1.25 (m, 2H), 1.44 (s, 9H), 1.73-1.82 (m, 3H), 1.97 (m, 2H), 2.70 (s, 3H), 3.40 (m, 2H), 5.92 (t, J=5.6 Hz, 1H), 6.90 (t, J=6.8 Hz, 1H), 7.29-7.33 (m, 1H), 7.55 (d, J=8.8 Hz, 1H), 9.36 (d, J=6.8 Hz, 1H).

2-Methyl-N-(pyridin-4-yl)imidazo[1,2-a]pyridine-3-carboxamide (11)

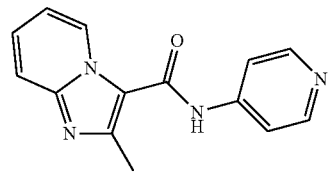 [SMILES: Cc1nc2ccccn2c1C(=O)Nc1ccncc1]

¹H NMR (400 MHz, CDCl₃+DMSO-d₆) δ 2.72 (s, 3H), 6.89 (dd, J=1.2, 7.2 Hz, 1H), 7.28-7.33 (m, 1H), 7.52 (d, J=9.2 Hz, 1H), 7.57 (dd, J=1.6, 4.8 Hz, 2H), 8.43 (dd, J=1.6, 4.8 Hz, 1H), 8.92 (br s, 1H), 9.11 (d, J=6.8 Hz, 1H); LCMS (electrospray) m/z (M+H)⁺ 253.18

2-Methyl-N-phenethylimidazo[1,2-a]pyridine-3-carboxamide (12)

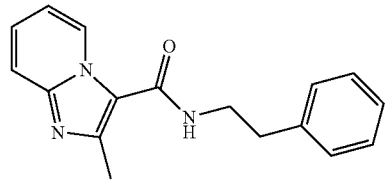 [SMILES: Cc1nc2ccccn2c1C(=O)NCCc1ccccc1]

¹H NMR (400 MHz, CDCl₃) δ2.28 (s, 3H), 2.82 (t, J=7.2 Hz, 2H), 3.56 (t, J=6.8 Hz, 2H), 6.79 (t, J=6.8 Hz, 1H), 7.06 (t, J=6.8 Hz, 1H), 7.14 (d, J=7.2 Hz, 3H), 7.30 (t, J=7.2 Hz, 2H), 7.33 (d, J=6.8 Hz, 1H), 8.74 (d, J=5.6 Hz, 1H).

2-Methyl-N-(4-phenoxyphenyl)imidazo[1,2-a]pyridine-3-carboxamide (13)

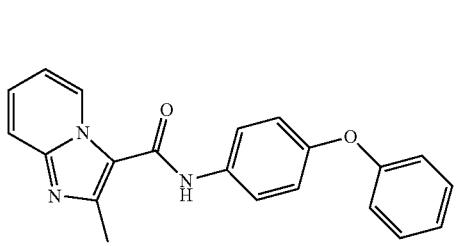 [SMILES: Cc1nc2ccccn2c1C(=O)Nc1ccc(Oc2ccccc2)cc1]

$^1$H NMR (400 MHz, CDCl$_3$) δ2.60 (s, 3H), 6.89 (t, J=8.0 Hz, 3H), 6.96 (d, J=6.8 Hz, 2H), 7.02 (t, J=7.6 Hz, 1H), 7.27 (t, J=7.6 Hz, 2H), 7.38 (t, J=6.8 Hz, 1H), 7.47 (d, J=8.8 Hz, 1H), 7.57 (d, J=6.8 Hz, 2H), 8.89 (d, J=6.8 Hz, 1H).

N-(4-(Benzyloxy)phenyl)-2-methylimidazo[1,2-a]pyridine-3-carboxamide (14)

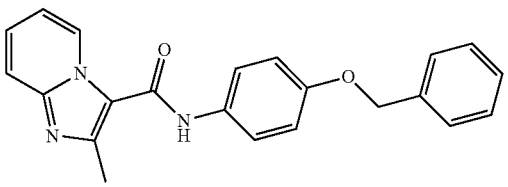 [SMILES: Cc1nc2ccccn2c1C(=O)Nc1ccc(OCc2ccccc2)cc1]

$^1$H NMR (400 MHz, CDCl$_3$) δ2.57 (s, 3H), 4.97 (s, 2H), 6.88-6.91 (m, 3H), 7.19 (t, J=7.2 Hz, 1H), 7.28 (t, J=8.4 Hz, 2H), 7.32 (t, J=6.8 Hz, 3H), 7.43-7.46 (m, 3H), 8.85 (d, J=5.6 Hz, 1H).

N-Benzyl-8-chloro-2-methylimidazo[1,2-a]pyridine-3-carboxamide (15)

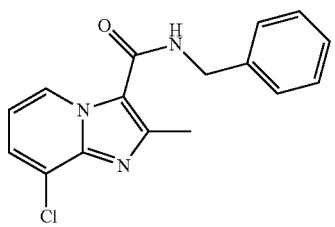 [SMILES: Cc1nc2c(Cl)cccn2c1C(=O)NCc1ccccc1]

$^1$H NMR (400 MHz, CDCl$_3$) δ2.72 (s, 3H), 4.71 (d, J=6.0 Hz, 2H), 6.14 (brs, 1H), 6.87 (dd, J=7.2 Hz, 7.2 Hz, 1H), 7.32 (dd, J=4.4 Hz, 4.4 Hz, 1H), 7.34-7.42 (m, 5H), 9.38 (d, J=7.2 Hz, 1H); $^{13}$C NMR (100 MHz, CDCl$_3$) 16.9, 29.9, 43.8, 113.1, 122.4, 126.2, 127.1, 127.9, 128.0, 129.1, 138.1, 141.8, 145.9, 161.3.

N-Benzyl-7-chloro-2-methylimidazo[1,2-a]pyridine-3-carboxamide (16)

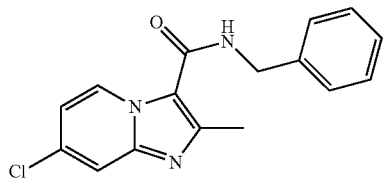 [SMILES: Cc1nc2cc(Cl)ccn2c1C(=O)NCc1ccccc1]

$^1$H NMR (400 MHz, CDCl$_3$) δ2.66 (s, 3H), 4.69 (d, J=5.6 Hz, 2H), 6.13 (brs, 1H), 6.89-6.91 (m, 1H), 7.29-7.37 (m, 5H), 7.55 (d, J=1.6 Hz, 1H), 9.37 (d, J=7.6 Hz, 1H).

N-Benzyl-6-chloro-2-methylimidazo[1,2-a]pyridine-3-carboxamide (17)

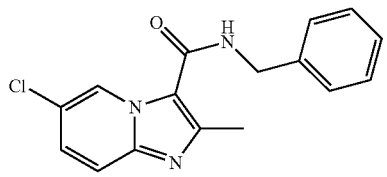 [SMILES: Cc1nc2ccc(Cl)cn2c1C(=O)NCc1ccccc1]

$^1$H NMR (400 MHz, CDCl$_3$) δ 2.68 (s, 3H), 4.70 (d, J=5.6 Hz, 2H), 6.16 (brs, 1H), 7.30-7.35 (m, 3H), 7.37-7.38 (m, 3H), 7.53 (d, J=9.2 Hz, 1H), 9.56 (d, J=1.6 Hz, 1H).

Ethyl 2-methyl-7-phenylimidazo[1,2-a]pyridine-3-carboxylate (18)

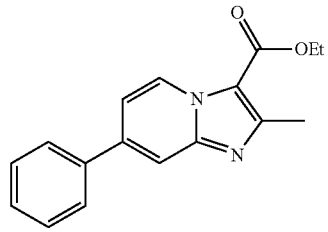 [SMILES: CCOC(=O)c1c(C)nc2cc(-c3ccccc3)ccn12]

$^1$H NMR (400 MHz, CDCl$_3$) δ 1.45 (t, J=7.2 Hz, 3H), 2.73 (s, 3H), 4.44 (q, J=7.2 Hz, 2H), 7.25 (dd, J=1.6 Hz, 7.2 Hz, 1H), 7.42-7.51 (m, 3H), 7.68 (d, J=7.6 Hz, 2H), 7.80 (s, 1H), 9.32 (d, J=7.2 Hz, 1H).

2-Methyl-7-phenylimidazo[1,2-a]pyridine-3-carboxylic acid (19)

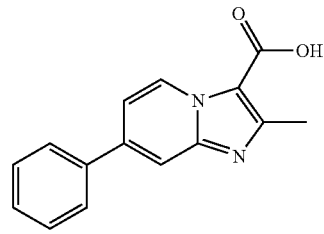 [SMILES: Cc1nc2cc(-c3ccccc3)ccn2c1C(=O)O]

$^1$H NMR (400 MHz, DMSO d-6) δ 2.60 (s, 3H), 7.43-7.52 (m, 5H), 7.83 (s, 1H), 7.85 (s, 1H), 7.94 (s, 1H), 9.26 (d, J=7.6 Hz, 1H)

N-(Biphenyl-4-ylmethyl)-2-methylimidazo[1,2-a]pyridine-3-carboxamide (20)

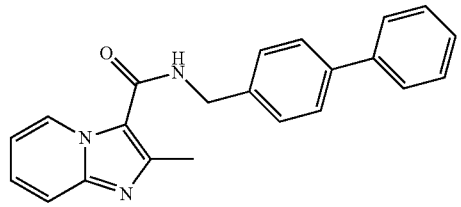 [SMILES: Cc1nc2ccccn2c1C(=O)NCc1ccc(-c2ccccc2)cc1]

$^1$H NMR (400 MHz, CDCl$_3$) δ 2.70 (s, 3H), 4.74 (d, J=4.0 Hz, 2H), 6.19 (brs, 1H), 6.91 (dd, J=6.0 Hz, 6.0 Hz, 1H), 7.30-7.36 (m, 2H), 7.41-7.45 (m, 5H), 7.58 (m, 4H), 9.43 (d, J=6.8 Hz, 1H).

N-((1H-Indol-5-yl)methyl)-2-methylimidazo[1,2-a]pyridine-3-carboxamide (21)

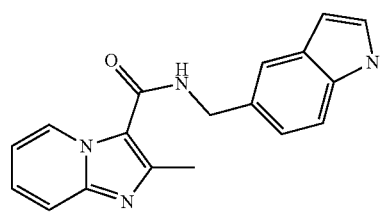 [SMILES: Cc1nc2ccccn2c1C(=O)NCc1ccc2[nH]ccc2c1]

$^1$H NMR (400 MHz, CDCl$_3$) δ 2.68 (s, 3H), 4.78 (d, J=5.2 Hz, 2H), 6.18 (brs, 1H), 6.55 (s, 1H), 6.98-7.02 (m, 1H), 7.22-7.24 (m, 2H), 7.40 (s, 1H), 7.42 (s, 1H), 7.66-7.68 (m, 2H), 8.24 (brs, 1H), 9.47 (d, J=7.2 Hz, 1H).

N-Benzyl-2-methyl-7-phenylimidazo[1,2-a]pyridine-3-carboxamide (22)

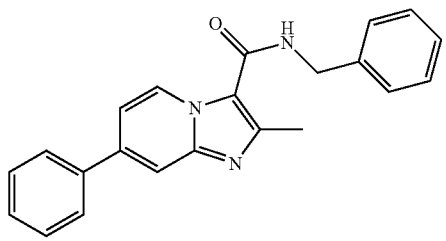 [SMILES: Cc1nc2cc(-c3ccccc3)ccn2c1C(=O)NCc1ccccc1]

$^1$H NMR (400 MHz, CDCl$_3$) δ 2.70 (s, 3H), 4.71 (d, J=5.6 Hz, 2H), 6.15 (brs, 1H), 7.22 (dd, J=2.0 Hz, 7.2 Hz, 1H), 7.29-7.33 (m, 1H), 7.36-7.44 (m, 5H), 7.47-7.51 (m, 2H), 7.66 (s, 1H), 7.68 (d, J=1.2 Hz, 1H), 7.78 (s, 1H), 9.47 (d, J=7.2 Hz, 1H).

(S)-Methyl 2-(2-methylimidazo[1,2-a]pyridine-3-carboxamido)-3-phenylpropanoate (23)

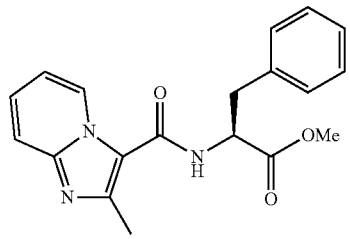 [SMILES: COC(=O)[C@H](Cc1ccccc1)NC(=O)c1c(C)nc2ccccn12]

$^1$H NMR (400 MHz, CDCl$_3$) δ 2.50 (s, 3H), 3.25 (dd, J=5.6, 14.0 Hz, 1H), 3.33 (dd, J=5.6, 14.0 Hz, 1H), 5.08-5.13 (m, 1H), 6.23 (d, J=7.2 Hz, 1H), 6.91 (dd, J=1.2, 6.8 Hz, 1H), 7.14-7.16 (m, 2H), 7.27-7.35 (m, 4H), 7.57 (d, J=8.8 Hz, 1H), 9.39 (d, J=7.2 Hz, 1H); LCMS (electrospray) m/z (M+H)$^+$ 338.28

2-Methyl-N-(piperidin-4-ylmethyl)imidazo[1,2-a]pyridine-3-carboxamide (24)

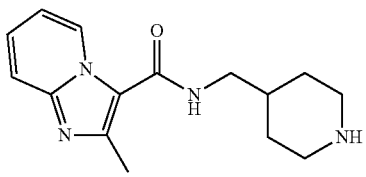 [SMILES: Cc1nc2ccccn2c1C(=O)NCC1CCNCC1]

$^1$H NMR (400 MHz, CDCl$_3$) δ 1.20-1.77 (m, 6H), 2.58-2.64 (m, 1H), 2.65 (s, 3H), 3.13 (d, J=11.6 Hz, 2H), 3.34 (t, J=12.0 Hz, 2H), 3.68 (br s, 1H), 6.71 (m, 1H), 6.84 (t, J=6.8 Hz, 1H), 7.26 (t, J=7.6 Hz, 1H), 7.49 (d, J=8.8 Hz, 1H), 9.28 (d, J=6.8 Hz, 1H).

Methyl 4-((2-methylimidazo[1,2-a]pyridine-3-carboxamido)methyl)benzoate (25)

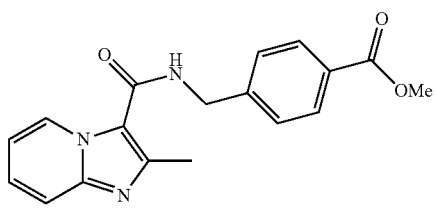 [SMILES: COC(=O)c1ccc(CNC(=O)c2c(C)nc3ccccn23)cc1]

$^1$H NMR (400 MHz, CDCl$_3$) δ 2.70 (s, 3H), 3.90 (s, 3H), 4.76 (d, J=6.0 Hz, 2H), 6.24 (brs, 1H), 6.91-6.95 (m, 1H), 7.32-7.36 (m, 1H), 7.44 (d, J=8.4 Hz, 2H), 7.56 (d, J=9.2 Hz, 1H), 8.02 (d, J=8.4 Hz, 2H), 9.41 (d, J=6.8 Hz, 1H).

4-((2-Methylimidazo[1,2-a]pyridine-3-carboxamido)methyl)benzoic acid (26)

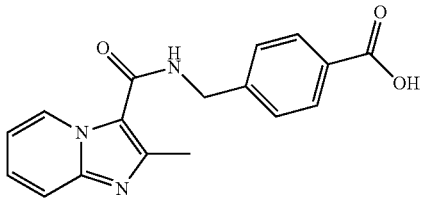 [SMILES: Cc1nc2ccccn2c1C(=O)NCc1ccc(C(=O)O)cc1]

¹H NMR (400 MHz, CD₃OD) δ 2.64 (s, 3H), 4.69 (s, 2H), 7.03 (dd, J=6.8 Hz, 6.8 Hz, 1H), 7.43-7.47 (m, 1H), 7.50 (d, J=8.4 Hz, 2H), 7.53-7.55 (m, 1H), 8.01 (d, J=8.4 Hz, 2H), 9.04 (d, J=7.2 Hz, 1H).

Ethyl 2-methyl-6-phenylimidazo[1,2-a]pyridine-3-carboxylate (27)

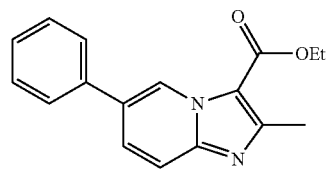 [SMILES: CCOC(=O)c1c(C)nc2ccc(-c3ccccc3)cn12]

¹H NMR (400 MHz, CDCl₃) δ 1.41 (t, J=7.2 Hz, 3H), 2.70 (s, 3H), 4.40 (q, J=7.2 Hz, 2H), 7.33-7.36 (m, 1H), 7.42 (t, J=7.4 Hz, 2H), 7.56 (d, J=7.2 Hz, 2H), 7.60-7.61 (m, 1H), 9.52 (s, 1H).

2-Methyl-N-(2-phenoxyethyl)imidazo[1,2-a]pyridine-3-carboxamide (28)

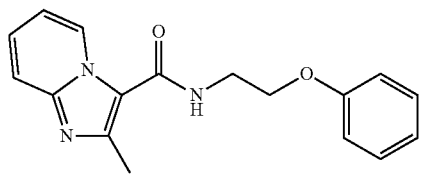 [SMILES: Cc1nc2ccccn2c1C(=O)NCCOc1ccccc1]

¹H NMR (400 MHz, CDCl₃) δ 2.72 (s, 3H), 3.93 (q, J=4.8 Hz, 2H), 4.19 (t, J=5.0 Hz, 2H), 6.33 (m, 1H), 6.90-9.94 (m, 3H), 6.98 (d, J=7.4 Hz, 1H), 7.28-7.34 (m, 3H), 7.57 (d, J=9.2 Hz, 1H), 9.40 (d, J=7.2 Hz, 1H).

N-(2-(Benzyloxy)ethyl)-2-methylimidazo[1,2-a]pyridine-3-carboxamide (29)

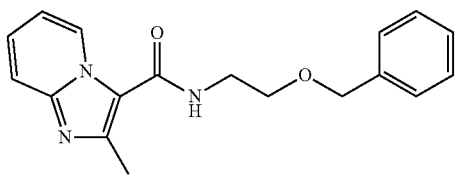 [SMILES: Cc1nc2ccccn2c1C(=O)NCCOCc1ccccc1]

¹H NMR (400 MHz, CDCl₃) δ 2.66 (s, 3H), 3.68-3.75 (m, 4H), 4.57 (s, 2H), 6.90 (dd, J=1.2, 6.8 Hz, 1H), 7.27-7.34 (m, 6H), 7.57 (dd, J=1.2, 9.2 Hz, 1H), 9.37 (dd, J=2.0, 6.8 Hz, 1H).

N-Benzyl-6-cyano-2-methylimidazo[1,2-a]pyridine-3-carboxamide (30)

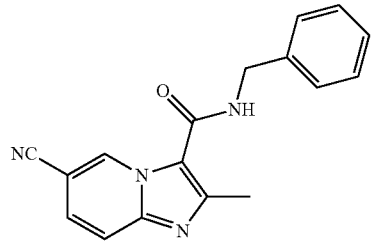 [SMILES: Cc1nc2ccc(C#N)cn2c1C(=O)NCc1ccccc1]

¹H NMR (400 MHz, CD₃OD) δ 2.63 (s, 3H), 4.65 (s, 2H), 7.27 (t, J=7.4 Hz, 1H), 7.35 (t, J=7.6 Hz, 2H), 7.42 (d, J=7.6 Hz, 2H), 7.57 (dd, J=0.8, 9.2 Hz, 1H), 7.85 (dd, J=1.6, 9.2 Hz, 1H), 9.58 (m, 1H).

N-Benzyl-2,8-dimethylimidazo[1,2-a]pyridine-3-carboxamide (31)

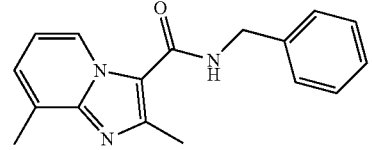 [SMILES: Cc1nc2c(C)cccn2c1C(=O)NCc1ccccc1]

¹H NMR (400 MHz, MeOH-d₄) δ 2.55 (s, 3H), 2.63 (s, 3H), 4.63 (s, 2H), 6.95 (t, J=6.8 Hz, 1H), 7.25 (d, J=6.8 Hz, 1H), 7.28 (d, J=7.2 Hz, 1H), 7.37 (t, J=7.2 Hz, 2H), 7.42 (d, J=7.6 Hz, 2H), 8.87 (d, J=6.8 Hz, 1H).

N-Benzyl-2,7-dimethylimidazo[1,2-a]pyridine-3-carboxamide (32)

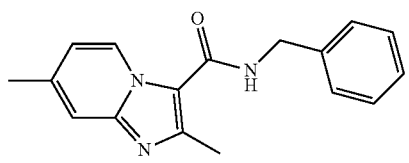 [SMILES: Cc1ccn2c(C(=O)NCc3ccccc3)c(C)nc2c1]

¹H NMR (400 MHz, MeOH-d₄) δ 2.44 (s, 3H), 2.59 (s, 3H), 4.63 (s, 2H), 6.91 (d, J=7.2 Hz, 1H), 7.28 (t, J=7.2 Hz, 1H), 7.33 (d, J=6.4 Hz, 2H), 7.37 (t, J=7.2 Hz, 2H), 7.42 (d, J=7.6 Hz, 2H), 8.92 (d, J=7.2 Hz, 1H).

N-Benzyl-2,6-dimethylimidazo[1,2-a]pyridine-3-carboxamide (33)

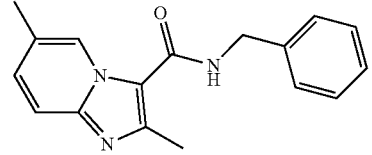 [SMILES: Cc1ccc2nc(C)c(C(=O)NCc3ccccc3)n2c1]

¹H NMR (400 MHz, MeOH-d₄) δ2.36 (s, 3H), 2.59 (s, 3H), 4.63 (s, 2H), 7.29 (d, J=7.6 Hz, 1H), 7.31 (d, J=1.6 Hz, 1H), 7.37 (t, J=7.2 Hz, 3H), 7.43 (t, J=4.8 Hz, 2H), 7.46 (s, L H), 8.83 (s, 1H).

N-Benzyl-2,5-dimethylimidazo[1,2-a]pyridine-3-carboxamide (34)

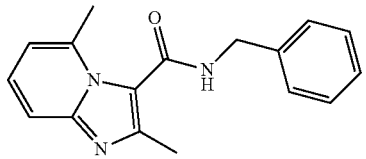 [SMILES: Cc1nc2cccc(C)n2c1C(=O)NCc1ccccc1]

¹H NMR (400 MHz, MeOH-d₄) δ2.44 (s, 3H), 2.59 (s, 3H), 4.29 (s, 2H), 6.75 (d, J=7.2 Hz, 1H), 7.21-7.27 (m, 3H), 7.33 (t, J=6.4 Hz, 2H), 7.41 (t, J=8.8 Hz, 1H), 7.49 (s, 1H).

N-Benzyl-8-fluoro-2-methylimidazo[1,2-a]pyridine-3-carboxamide (35)

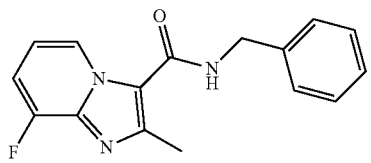 [SMILES: Cc1nc2c(F)cccn2c1C(=O)NCc1ccccc1]

¹H NMR (400 MHz, MeOH-d₄) δ2.63 (s, 3H), 4.64 (s, 2H), 6.96-7.01 (m, 1H), 7.21 (t, J=6.8 Hz, 1H), 7.25-7.29 (m, 2H), 7.37 (t, J=7.2 Hz, 2H), 7.41 (t, J=7.6 Hz, 2H), 8.84 (d, J=6.8 Hz, 1H).

N-Benzyl-2-methyl-8-(trifluoromethyl)imidazo[1,2-a]pyridine-3-carboxamide (36)

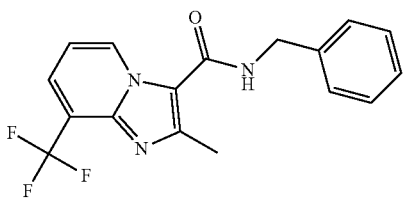 [SMILES: Cc1nc2c(C(F)(F)F)cccn2c1C(=O)NCc1ccccc1]

¹H NMR (400 MHz, MeOH-d₄) δ2.66 (s, 3H), 4.63 (s, 2H), 7.15 (t, J=6.8 Hz, 1H), 7.25-7.28 (m, 1H), 7.37 (t, J=8.0 Hz, 2H), 7.43 (d, J=7.6 Hz, 2H), 7.82 (d, J=7.2 Hz, 1H), 9.21 (d, J=6.8 Hz, 1H).

N-Benzyl-2-propylimidazo[1,2-a]pyridine-3-carboxamide (37)

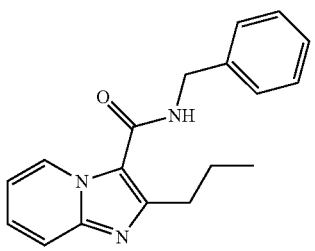 [SMILES: CCCc1nc2ccccn2c1C(=O)NCc1ccccc1]

¹H NMR (400 MHz, CD₃OD) δ 0.93 (t, J=7.4 Hz, 3H), 1.75-1.85 (m, 2H), 2.89 (t, J=7.8 Hz, 2H), 4.67 (d, J=5.6 Hz, 2H), 6.24 (m, 1H), 6.86 (t, J=6.8 Hz, 1H), 7.26-7.36 (m, 6H), 7.54 (d, J=8.8 Hz, 1H), 9.31 (d, J=6.8 Hz, 1H).

N-Benzyl-2-cyclopropylimidazo[1,2-a]pyridine-3-carboxamide (38)

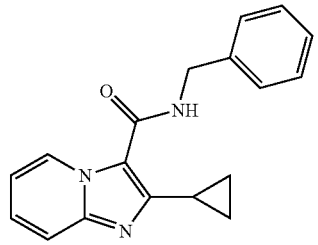 [SMILES: O=C(NCc1ccccc1)c1c(C2CC2)nc2ccccn12]

¹H NMR (400 MHz, CD₃OD) δ 1.00-1.03 (m, 2H), 1.14-1.18 (m, 2H), 2.11-2.15 (m, 1H), 6.91 (dd, J=1.2, 6.8 Hz, 1H), 7.29-7.38 (m, 5H), 7.57 (dd, J=0.8, 8.8 Hz, 1H), 9.49-9.51 (m, 1H); LCMS (electrospray) m/z (M+H)⁺ 292.23

N-Benzyl-2-methyl-6-phenylimidazo[1,2-a]pyridine-3-carboxamide (39)

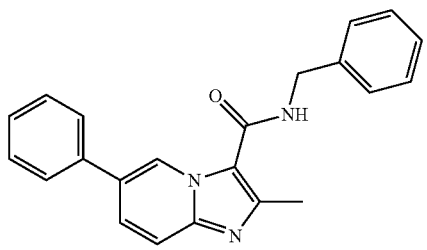 [SMILES: Cc1nc2ccc(-c3ccccc3)cn2c1C(=O)NCc1ccccc1]

¹H NMR (400 MHz, CDCl₃) δ 2.71 (s, 3H), 4.73 (d, J=5.6 Hz, 2H), 6.12 (m, 1H), 7.30-7.34 (m, 1H), 7.36-7.40 (m, 7H), 7.60-7.66 (m, 4H), 9.71 (s, 1H).

N-Benzyl-6-fluoro-2-methylimidazo[1,2-a]pyridine-3-carboxamide (40)

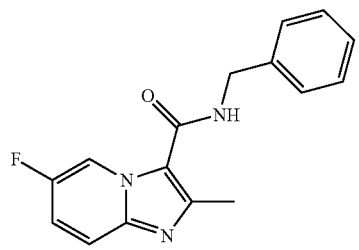 [SMILES: Cc1nc2ccc(F)cn2c1C(=O)NCc1ccccc1]

¹H NMR (400 MHz, CD₃OD) δ 2.68 (s, 3H), 4.71 (d, J=6.0 Hz, 2H), 7.24-7.39 (m 6H), 7.52-7.56 (m, 1H), 9.48-9.49 (m, 1H); LCMS (electrospray) m/z (M+H)⁺ 284.27

N-(2-Methylimidazo[1,2-a]pyridin-3-yl)-2-phenylacetamide (41)

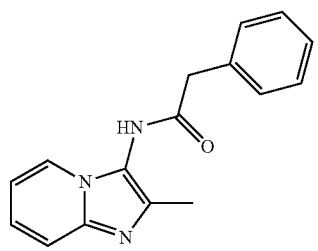 [SMILES: Cc1nc2ccccn2c1NC(=O)Cc1ccccc1]

¹H NMR (400 MHz, CD₃OD) δ 2.26 (s, 3H), 3.82 (s, 2H), 7.24-7.31 (m, 2H), 7.36-7.41 (m, 2H), 7.43-7.44 (m, 3H), 7.76 (d, J=6.8 Hz, 1H).

N-Benzyl-7-cyano-2-methylimidazo[1,2-a]pyridine-3-carboxamide (42)

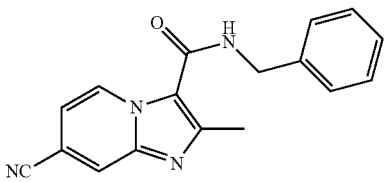

¹H NMR (400 MHz, CDCl₃) δ 1.64 (s, 3H), 4.61 (d, J=6.0 Hz, 2H), 6.39 (brs, 1H), 6.85 (dd, J=1.2 Hz, 5.2 Hz, 1H), 6.89 (s, 1H), 7.29-7.38 (m, 5H), 8.13 (d, J=5.6 Hz, 1H)

N-(Biphenyl-4-ylmethyl)-6-chloro-2-methylimidazo[1,2-a]pyridine-3-carboxamide (43)

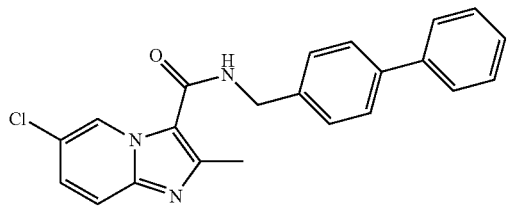 [SMILES: Cc1nc2ccc(Cl)cn2c1C(=O)NCc1ccc(-c2ccccc2)cc1]

¹H NMR (400 MHz, CDCl₃) δ 2.69 (s, 3H), 4.73 (d, J=5.2 Hz, 2H), 6.18 (brs, 1H), 6.92 (d, J=6.4 Hz, 1H), 7.36 (d, J=7.2 Hz, 1H), 7.44-7.45 (m, 4H), 7.57-7.60 (m, 5H), 9.39 (d, J=7.6 Hz, 1H).

N-(Biphenyl-4-ylmethyl)-7-chloro-2-methylimidazo[2-a]pyridine-3-carboxamide (44)

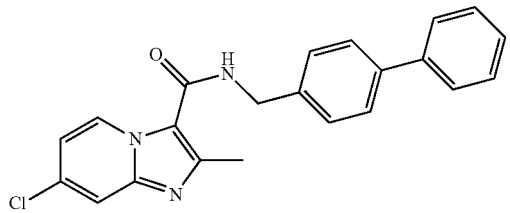 [SMILES: Cc1nc2cc(Cl)ccn2c1C(=O)NCc1ccc(-c2ccccc2)cc1]

¹H NMR (400 MHz, CDCl₃) δ 2.70 (s, 3H), 4.73 (d, J=5.2 Hz, 2H), 6.20 (brs, 1H), 7.29-7.36 (m, 4H), 7.45 (d, J=8.0 Hz, 1H), 7.51 (d, J=9.6 Hz, 1H), 7.57 (m, 5H), 9.56 (s, 1H)

2-Ethyl-N-(4-phenoxybenzyl)imidazo[1,2-a]pyridine-3-carboxamide (45)

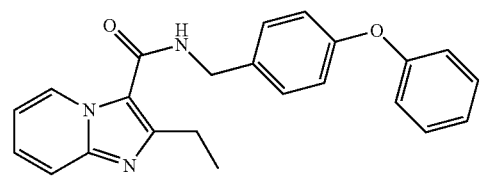 [SMILES: CCc1nc2ccccn2c1C(=O)NCc1ccc(Oc2ccccc2)cc1]

¹H NMR (400 MHz, CDCl₃) δ 1.41 (t, J=7.6 Hz, 3H), 2.99 (q, J=7.6 Hz, 2H), 4.67 (d, J=5.6 Hz, 2H), 6.08 (brs, 1H), 6.89-6.93 (m, 1H), 7.00 (dd, J=2.0 Hz, 8.8 Hz, 4H), 7.08-7.12 (m, 1H), 7.30-7.35 (m, 5H), 7.60 (d, J=9.2 Hz, 1H), 9.39 (d, J=7.2 Hz, 1H).

N-(Biphenyl-4-ylmethyl)-2-propylimidazo[1,2-a]pyridine-3-carboxamide (46)

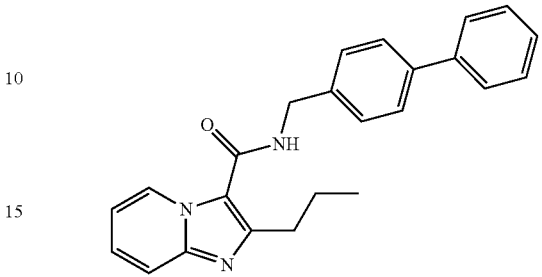

¹H NMR (400 MHz, CDCl₃) δ 0.98 (t, J=7.4 Hz, 3H), 1.80-1.89 (m, 2H), 2.93 (t, J=7.8 Hz, 2H), 4.73 (d, J=5.6 Hz, 2H), 6.29 (t, J=5.2 Hz, 1H), 6.89 (dd, J=1.2, 6.8 Hz, 1H), 7.27-7.37 (m, 2H), 7.42-7.46 (m, 4H), 7.56-7.61 (m, 5H), 9.35 (d, J=6.8 Hz, 1H); LCMS (electrospray) m/z (M+H)⁺ 370.32

N-Benzyl-8-cyano-2-methylimidazo[1,2-a]pyridine-3-carboxamide (47)

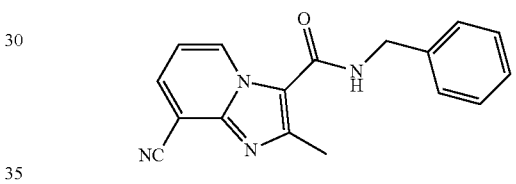

¹H NMR (400 MHz, MeOH-d₄) δ2.67 (s, 3H), 4.65 (s, 2H), 7.17 (t, J=7.2 Hz, 1H), 7.26-7.31 (m, 2H), 7.38 (t, J=7.2 Hz, 2H), 7.44 (d, J=8.0 Hz, 2H), 8.21 (d, J=7.2 Hz, 1H), 9.19 (d, J=6.8 Hz, 1H).

N-Benzyl-8-hydroxy-2-methylimidazo[1,2-a]pyridine-3-carboxamide (48)

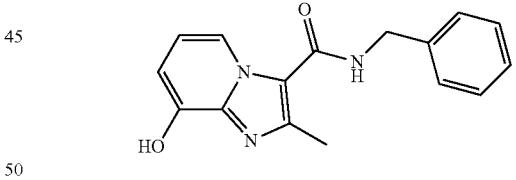

¹H NMR (400 MHz, MeOH-d₄) δ2.60 (s, 3H), 4.63 (s, 2H), 6.70 (d, J=7.6 Hz, 1H), 6.83 (t, J=6.8 Hz, 1H), 7.28 (t, J=7.2 Hz, 1H), 7.40 (t, J=8.0 Hz, 3H), 7.42 (d, J=7.2 Hz, 2H), 8.53 (d, J=6.0 Hz, 1H).

N-(4-tert-Butylbenzyl)-2-ethylimidazo[1,2-a]pyridine-3-carboxamide (49)

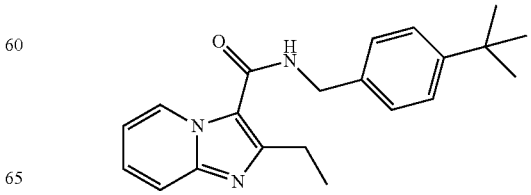

¹H NMR (400 MHz, CDCl₃) δ 1.32 (s, 9H), 1.41 (t, J=7.6 Hz, 3H), 2.99 (q, J=7.6 Hz, 2H), 4.68 (d, J=5.6 Hz, 2H), 6.12 (brs, 1H), 6.93 (dd, J=6.8 Hz, 6.8 Hz, 1H), 7.32 (d, J=8.4 Hz, 2H), 7.34-7.36 (m, 1H), 7.40 (d, J=8.4 Hz, 2H), 7.63 (d, J=8.8 Hz, 1H), 9.40 (d, J=7.2 Hz, 1H).

2-Ethyl-N-((1-methyl-1H-indol-5-yl)methyl)imidazo[1,2-a]pyridine-3-carboxamide (50)

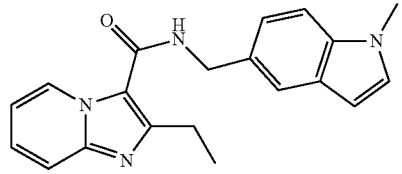 [SMILES: CCc1nc2ccccn2c1C(=O)NCc1ccc2c(ccn2C)c1]

¹H NMR (400 MHz, CDCl₃) δ 1.37 (t, J=7.6 Hz, 3H), 2.95 (q, J=7.6 Hz, 2H), 3.81 (s, 3H), 4.79 (d, J=5.6 Hz, 2H), 6.08 (brs, 1H), 6.48 (s, 1H), 6.92 (dd, J=6.8 Hz, 6.8 Hz, 1H), 7.08 (s, 1H), 7.25 (s, 1H), 7.26-7.34 (m, 2H), 7.60 (d, J=8.8 Hz, 1H), 7.63 (s, 1H), 9.43 (d, J=7.2 Hz, 1H).

2-Ethyl-N-(4-(trifluoromethoxy)benzyl)imidazo[1,2-a]pyridine-3-carboxamide (51)

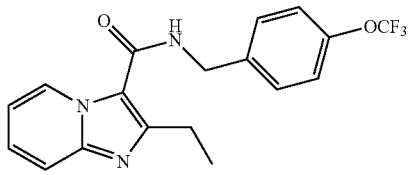 [SMILES: CCc1nc2ccccn2c1C(=O)NCc1ccc(OC(F)(F)F)cc1]

¹H NMR (400 MHz, CDCl₃) δ 1.41 (t, J=7.6 Hz, 3H), 3.00 (q, J=7.6 Hz, 2H), 4.69 (d, J=6.0 Hz, 2H), 6.21 (brs, 1H), 6.91 (dd, J=6.8 Hz, 6.8 Hz, 1H), 7.19 (s, 1H), 7.21 (s, 1H), 7.30-7.34 (m, 1H), 7.39 (s, 1H), 7.41 (s, 1H), 7.60 (d, J=9.2 Hz, 1H), 9.37 (d, J=7.2 Hz, 1H); ¹³C NMR (100 MHz, CDCl₃) δ 13.5, 23.7, 42.9, 113.5, 114.7, 119.3, 121.5, 121.9, 127.3, 128.3, 129.2, 137.3, 146.4, 148.8, 151.1, 161.7.

2-Ethyl-N-(4-(trifluoromethoxy)benzyl)imidazo[1,2-a]pyridine-3-carboxamide (52)

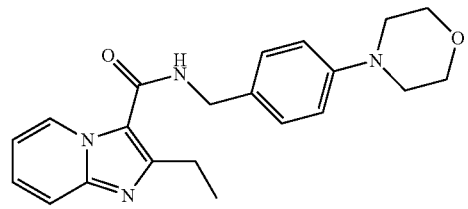 [SMILES: CCc1nc2ccccn2c1C(=O)NCc1ccc(N2CCOCC2)cc1]

¹H NMR (400 MHz, CDCl₃) δ 1.37 (t, J=7.6 Hz, 3H), 2.96 (q, J=7.6 Hz, 2H), 3.14 (t, J=4.8 Hz, 4H), 3.85 (t, J=4.8 Hz, 4H), 4.61 (d, J=5.6 Hz, 2H), 6.05 (brs, 1H), 6.88-6.92 (m, 3H), 7.27-7.33 (m, 3H), 7.59 (d, J=8.8 Hz, 1H), 9.39 (d, J=7.2 Hz, 1H).

2-Ethyl-N-(4-isopropoxybenzyl)imidazo[1,2-a]pyridine-3-carboxamide (53)

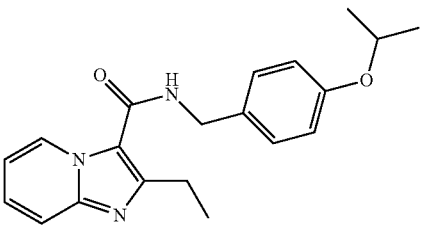 [SMILES: CCc1nc2ccccn2c1C(=O)NCc1ccc(OC(C)C)cc1]

¹H NMR (400 MHz, CDCl₃) δ 1.32 (d, J=5.6 Hz, 6H), 1.38 (t, J=7.6 Hz, 3H), 2.96 (q, J=7.6 Hz, 2H), 4.52-4.56 (m, 1H), 4.61 (d, J=4.8 Hz, 2H), 6.05 (brs, 1H), 6.86-6.92 (m, 3H), 7.26-7.33 (m, 3H), 7.59 (d, J=8.8 Hz, 1H), 9.38 (d, J=6.4 Hz, 1H).

2-Ethyl-N-(4-isobutoxybenzyl)imidazo[1,2-a]pyridine-3-carboxamide (54)

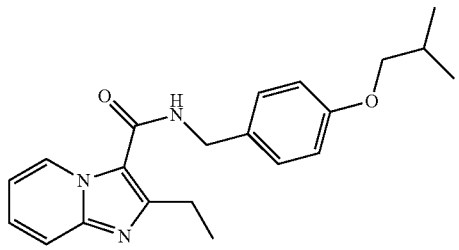 [SMILES: CCc1nc2ccccn2c1C(=O)NCc1ccc(OCC(C)C)cc1]

¹H NMR (400 MHz, CDCl₃) δ 1.01 (d, J=6.8 Hz, 6H), 1.37 (t, J=7.6 Hz, 3H), 2.05-2.09 (m, 1H), 2.96 (q, J=7.6 Hz, 2H), 3.71 (d, J=6.8 Hz, 2H), 4.62 (d, J=5.2 Hz, 2H), 6.06 (brs, 1H), 6.89 (dd, J=2.4 Hz, 2H), 6.92 (dd, J=1.2 Hz, 6.8 Hz, 1H), 7.27-7.34 (m, 3H), 7.59 (d, J=8.0 Hz, 1H), 9.37 (dd, J=2.4 Hz, 6.8 Hz, 1H); ¹³C NMR (100 MHz, CDCl₃) δ 13.6, 19.4, 23.5, 28.4, 43.3, 53.1, 74.7, 113.4, 115.0, 116.7, 124.2, 127.2, 128.3, 129.2, 130.0, 146.2, 150.7, 159.0, 161.5.

6-Chloro-2-ethyl-N-(4-(trifluoromethoxy)benzyl)imidazo[1,2-a]pyridine-3-carboxamide

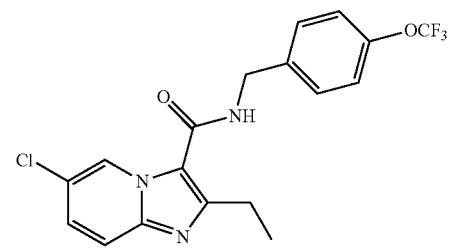 [SMILES: CCc1nc2ccc(Cl)cn2c1C(=O)NCc1ccc(OC(F)(F)F)cc1]

¹H NMR (400 MHz, CDCl₃) δ 1.43 (t, J=7.6 Hz, 3H), 3.00 (q, J=7.6 Hz, 2H), 4.71 (d, J=6.0 Hz, 2H), 6.15 (m, 1H), 7.23 (d, J=8.4 Hz, 2H), 7.31 (dd, J=2.0, 9.6 Hz, 1H), 7.42 (d, J=8.8 Hz, 2H), 7.55 (d, J=9.6 Hz, 1H), 9.54 (d, J=2.0 Hz, 1H)); LCMS (electrospray) m/z (M+H)⁺ 398.21

7-Chloro-2-ethyl-N-((4'-fluorobiphenyl-4-yl)methyl) imidazo[1,2-a]pyridine-3-carboxamide (56)

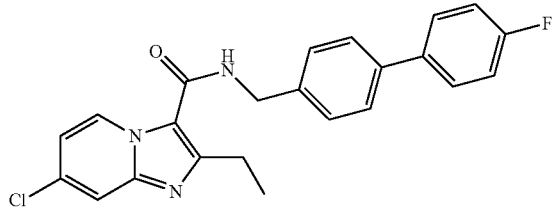 [SMILES: CCc1nc2cc(Cl)ccn2c1C(=O)NCc1ccc(-c2ccc(F)cc2)cc1]

$^1$H NMR (400 MHz, CDCl$_3$) δ 1.42 (t, J=7.6 Hz, 3H), 2.99 (q, J=7.6 Hz, 2H), 4.73 (d, J=5.6 Hz, 2H), 6.14 (brs, 1H), 6.91 (dd, J=7.2, 2.0 Hz, 1H), 7.13 (t, J=8.4 Hz, 2H), 7.44 (d, J=8.4 Hz, 2H), 7.52-7.56 (m, 4H), 7.60 (d, J=2.0 Hz, 1H), 9.38 (d, J=7.2 Hz, 1H); LCMS (electrospray) m/z (M+H)$^+$ 408.21

N-(Biphenyl-4-ylmethyl)-2-ethyl-6-methylimidazo[1,2-a]pyridine-3-carboxamide (57)

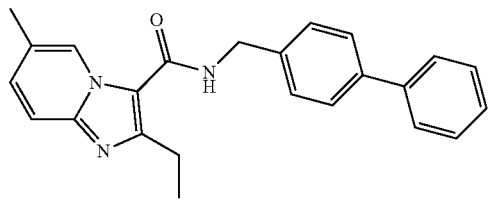 [SMILES: CCc1nc2ccc(C)cn2c1C(=O)NCc1ccc(-c2ccccc2)cc1]

$^1$H NMR (400 MHz, MeOH-d$_4$) δ1.34 (t, J=7.6 Hz, 3H), 2.37 (s, 3H), 3.02 (q, J=7.6 Hz, 2H), 4.68 (s, 2H), 7.31-7.34 (m, 2H), 7.43 (d, J=8.0 Hz, 2H), 7.46 (d, J=4.8 Hz, 1H), 7.51 (d, J=8.8 Hz, 3H), 7.64 (t, J=4.4 Hz, 4H), 8.78 (s, 1H).

2-Ethyl-6-methyl-N-(4-phenoxybenzyl)imidazo[1,2-a]pyridine-3-carboxamide (58)

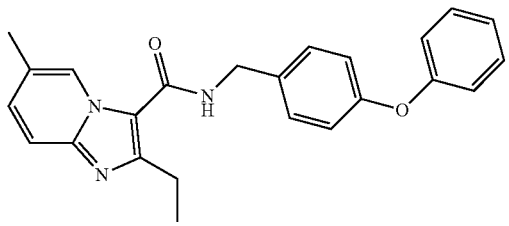 [SMILES: CCc1nc2ccc(C)cn2c1C(=O)NCc1ccc(Oc2ccccc2)cc1]

$^1$H NMR (400 MHz, MeOH-d$_4$) δ1.35 (t, J=8.0 Hz, 3H), 2.37 (s, 3H), 2.99 (q, J=7.2 Hz, 2H), 4.61 (s, 2H), 6.99 (d, J=8.8 Hz, 4H), 7.12 (t, J=7.2 Hz, 1H), 7.31-7.36 (m, 3H), 7.42 (d, J=8.8 Hz, 2H), 7.48 (d, J=9.2 Hz, 1H), 8.76 (s, 1H).

2-Ethyl-6-methyl-N-(4-(trifluoromethoxy)benzyl)imidazo[1,2-a]pyridine-3-carboxamide (59)

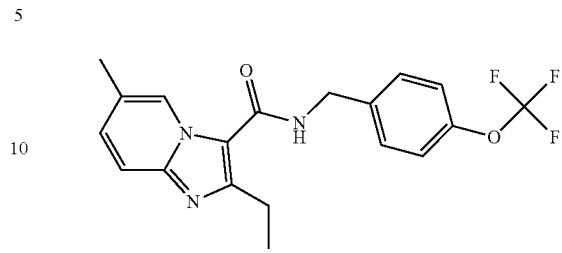

$^1$H NMR (400 MHz, MeOH-d$_4$) δ1.33 (t, J=8.0 Hz, 3H), 2.36 (s, 3H), 3.00 (q, J=7.6 Hz, 2H), 4.65 (s, 2H), 7.28 (d, J=8.0 Hz, 2H), 7.34 (d, J=9.2 Hz, 1H), 7.48 (d, J=9.2 Hz, 1H), 7.52 (d, J=8.4 Hz, 2H), 8.77 (s, 1H).

2-Ethyl-6-methyl-N-((1-methyl-1H-indol-6-yl)methyl)imidazo[1,2-a]pyridine-3-carboxamide (60)

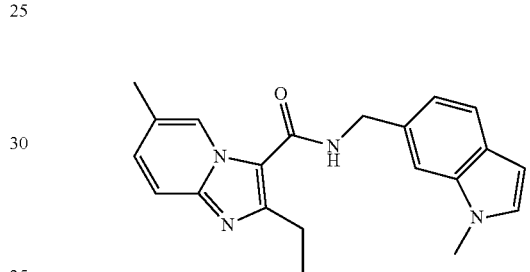

$^1$H NMR (400 MHz, MeOH-d$_4$) δ 1.30 (t, J=7.6 Hz, 3H), 2.35 (s, 3H), 3.0 (q, J=7.6 Hz, 2H), 3.80 (s, 3H), 4.75 (s, 2H), 6.41 (d, J=3.2 Hz, 1H), 7.11-7.14 (m, 2H), 7.32 (d, J=9.2 Hz, 1H), 7.46 (d, J=9.2 Hz, 2H), 7.55 (d, J=8.0 Hz, 1H), 8.74 (s, 1H).

N-(Biphenyl-4-ylmethyl)-6-chloro-2-methylimidazo[1,2-a]pyridine-3-carboxamide (61)

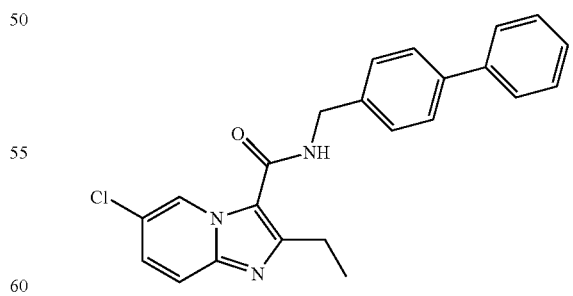

$^1$H NMR (400 MHz, CDCl$_3$) δ 1.43 (t, J=7.6 Hz, 3H), 3.01 (q, J=7.6 Hz, 2H), 4.75 (d, J=5.6 Hz, 2H), 6.15 (m, 1H), 7.31 (dd, J=2.0, 9.6 Hz, 1H), 7.43-7.47 (m, 4H), 7.55 (d, J=9.2 Hz, 1H), 7.58-7.62 (m, 4H), 9.56 (d, J=2.0 Hz, 1H); LCMS (electrospray) m/z (M+H)$^+$ 390.25

6-Chloro-2-methyl-N-(4-phenoxybenzyl)imidazo[1,2-a]pyridine-3-carboxamide (62)

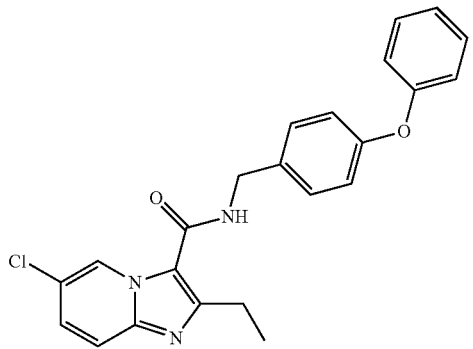 [SMILES: CCc1nc2ccc(Cl)cn2c1C(=O)NCc1ccc(Oc2ccccc2)cc1]

$^1$H NMR (400 MHz, CDCl$_3$) δ 1.41 (t, J=7.6 Hz, 3H), 2.99 (q, J=7.6 Hz, 2H), 4.67 (d, J=5.6 Hz, 2H), 7.01 (d, J=8.4 Hz, 4H), 7.09-7.13 (m, 1H), 7.30 (dd, J=2.0, 9.6 Hz, 1H), 7.32-7.36 (m, 4H), 7.54 (d, J=9.6 Hz, 1H), 9.54 (d, J=2.0 Hz, 1H); LCMS (electrospray) m/z (M+H)$^+$ 406.23

N-(4-tert-Butylbenzyl)-6-chloro-2-methylimidazo[1,2-a]pyridine-3-carboxamide (63)

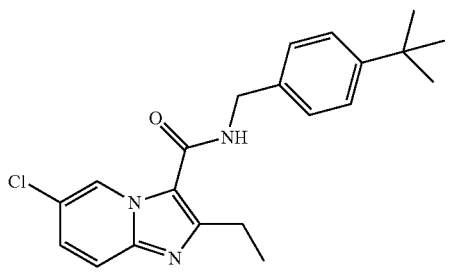 [SMILES: CCc1nc2ccc(Cl)cn2c1C(=O)NCc1ccc(C(C)(C)C)cc1]

$^1$H NMR (400 MHz, CDCl$_3$) δ 1.41 (t, J=7.6 Hz, 3H), 2.98 (q, J=7.6 Hz, 2H), 4.68 (d, J=6.0 Hz, 2H), 6.09 (m, 1H), 7.28-7.31 (m, 1H), 7.32 (d, J=8.0 Hz, 2H), 7.41 (d, J=8.0 Hz, 2H), 7.54 (d, J=9.6 Hz, 1H), 9.54 (d, J=2.0 Hz, 1H); LCMS (electrospray) m/z (M+H)$^+$ 370.25

6-Chloro-2-methyl-N-(4-morpholinobenzyl)imidazo[1,2-a]pyridine-3-carboxamide (64)

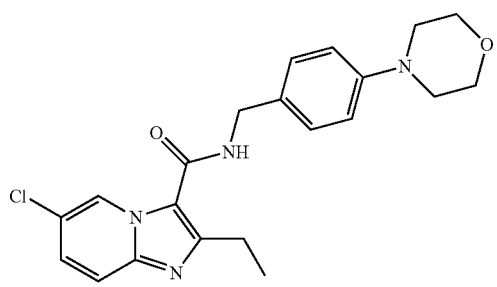 [SMILES: CCc1nc2ccc(Cl)cn2c1C(=O)NCc1ccc(N2CCOCC2)cc1]

$^1$H NMR (400 MHz, CDCl$_3$) δ 1.39 (t, J=7.6 Hz, 3H), 2.95 (q, J=7.6 Hz, 2H), 3.16 (t, J=4.8 Hz, 4H), 3.96 (t, J=4.8 Hz, 4H), 4.61 (d, J=5.6 Hz, 2H), 6.92 (d, J=8.8 Hz, 2H), 7.26-7.30 (m, 3H), 7.54 (d, J=9.6 Hz, 1H), 9.52 (d, J=1.2 Hz, 1H); LCMS (electrospray) m/z (M+H)$^+$ 399.30

6-Chloro-N-(4-isopropoxybenzyl)-2-methylimidazo[1,2-a]pyridine-3-carboxamide

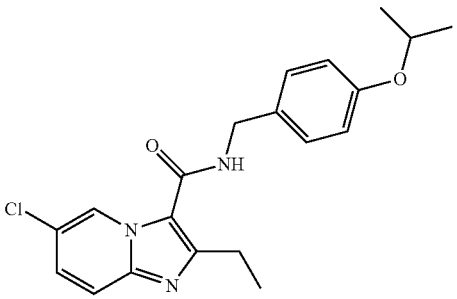 [SMILES: CCc1nc2ccc(Cl)cn2c1C(=O)NCc1ccc(OC(C)C)cc1]

$^1$H NMR (400 MHz, CDCl$_3$) δ 1.34 (d, J=6.0 Hz, 6H), 1.39 (t, J=7.6 Hz, 3H), 2.96 (q, J=7.6 Hz, 2H), 4.52-4.58 (m, 1H), 4.62 (d, J=5.6 Hz, 2H), 6.03 (m, 1H), 6.89 (d, J=8.8 Hz, 2H), 7.27-7.31 (m, 3H), 7.54 (d, J=9.6 Hz, 1H), 9.53 (d, J=1.2 Hz, 1H); LCMS (electrospray) m/z (M+H)$^+$ 372.22

6-Chloro-N-(4-isobutoxybenzyl)-2-methylimidazo[1,2-a]pyridine-3-carboxamide (66)

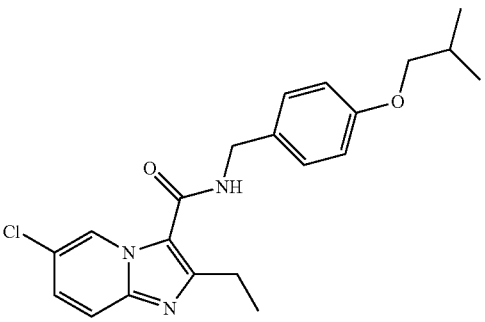 [SMILES: CCc1nc2ccc(Cl)cn2c1C(=O)NCc1ccc(OCC(C)C)cc1]

$^1$H NMR (400 MHz, CDCl$_3$) δ 1.00 (d, J=6.8 Hz, 6H), 1.36 (t, J=7.6 Hz, 3H), 2.03-2.09 (m, 1H), 2.93 (q, J=7.6 Hz, 2H), 3.69 (d, J=6.8 Hz, 2H), 4.59 (d, J=5.6 Hz, 2H), 6.13 (t, J=4.8 Hz, 1H), 6.87 (d, J=8.4 Hz, 2H), 7.24-7.27 (m, 3H), 7.49 (d, J=9.6 Hz, 1H), 9.47 (d, J=1.2 Hz, 1H)); LCMS (electrospray) m/z (M+H)$^+$ 386.30

6-Chloro-2-methyl-N-((1-methyl-1H-indol-5-yl)methyl)imidazo[1,2-a]pyridine-3-carboxamide (67)

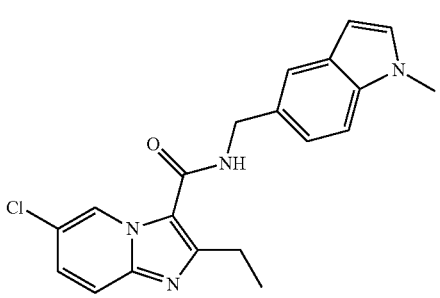 [SMILES: CCc1nc2ccc(Cl)cn2c1C(=O)NCc1ccc2c(ccn2C)c1]

¹H NMR (400 MHz, CDCl₃) δ 1.37 (t, J=7.6 Hz, 3H), 2.94 (q, J=7.6 Hz, 2H), 3.81 (s, 3H), 4.78 (d, J=5.6 Hz, 2H), 6.07 (m, 1H), 6.48 (d, J=3.2 Hz, 1H), 7.09 (d, J=2.8 Hz, 1H), 7.24-7.26 (m, 1H), 7.29 (dd, J=2.0, 9.6 Hz, 1H), 7.34 (d, J=8.4 Hz, 1H), 7.53 (d, J=9.6 Hz, 1H), 7.63 (s, 1H), 9.54 (d, J=1.2 Hz, 1H); LCMS (electrospray) m/z (M+H)⁺ 367.19

6-Chloro-2-methyl-N-((1-methyl-1H-indol-6-yl)methyl)imidazo[1,2-a]pyridine-3-carboxamide (68)

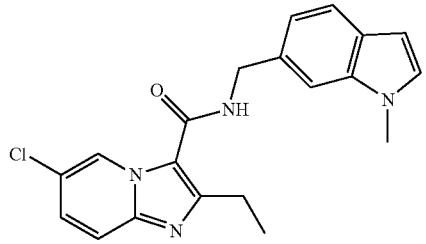 [SMILES: CCc1nc2ccc(Cl)cn2c1C(=O)NCc1ccc2ccn(C)c2c1]

¹H NMR (400 MHz, CDCl₃) δ 1.36 (t, J=7.6 Hz, 3H), 2.95 (q, J=7.6 Hz, 2H), 3.80 (s, 3H), 4.82 (d, J=5.6 Hz, 2H), 6.13 (m, 1H), 6.49 (d, J=3.2 Hz, 1H), 7.08 (d, J=2.8 Hz, 1H), 7.12 (dd, J=1.2, 8.0 Hz, 1H), 7.30 (dd, J=2.0, 9.6 Hz, 1H), 7.34 (s, 1H), 7.55 (d, J=9.6 Hz, 1H), 7.63 (d, J=8.0 Hz, 1H), 9.54 (d, J=1.2 Hz, 1H); LCMS (electrospray) m/z (M+H)⁺ 367.26

2-Ethyl-6-nitro-N-(4-(trifluoromethoxy)benzyl)imidazo[1,2-a]pyridine-3-carboxamide (69)

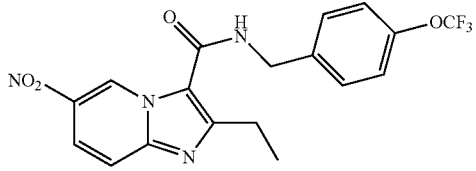 [SMILES: CCc1nc2ccc([N+](=O)[O-])cn2c1C(=O)NCc1ccc(OC(F)(F)F)cc1]

¹H NMR (400 MHz, CDCl₃) δ 1.37 (t, J=7.6 Hz, 3H), 3.49 (q, J=7.6 Hz, 2H), 4.66 (d, J=6.0 Hz, 2H), 7.19 (d, J=7.6 Hz, 2H), 7.41 (d, J=8.4 Hz, 2H), 7.60 (d, J=10.0 Hz, 1H), 7.82 (brs, 1H), 7.99 (dd, J=10.0, 2.0 Hz, 1H), 9.11 (d, J=1.6 Hz, 1H); LCMS (electrospray) m/z (M+H)⁺ 409.23

7-Chloro-2-ethyl-N-(4-(4-(4-fluorophenoxy)piperidin-1-yl)benzyl)imidazo[1,2-a]pyridine-3-carboxamide (70)

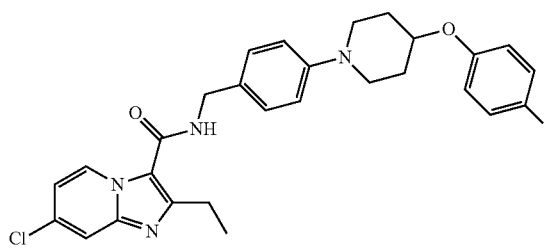

White solid; mp=138-139° C.; ¹H NMR (400 MHz, CDCl₃) δ 1.38 (t, J=7.6 Hz, 3H), 1.88-1.96 (m, 2H), 2.05-2.12 (m, 2H), 2.95 (q, J=7.6 Hz, 2H), 3.08-3.14 (m, 2H), 3.48-3.54 (m, 2H), 4.35-4.41 (m, 2H), 4.60 (d, J=5.6 Hz, 2H), 5.99-6.01 (m, 1H), 6.86-6.91 (m, 3H), 6.91-7.00 (m, 4H), 7.27 (d, J=8.4 Hz, 2H), 7.59 (d, J=2.0 Hz, 1H), 9.36 (d, J=7.6 Hz, 1H)); LCMS (electrospray) m/z (M+H)⁺ 507.31

N-((4'-Chlorobiphenyl-4-yl)methyl)-2-ethylimidazo[1,2-a]pyrazine-3-carboxamide (71)

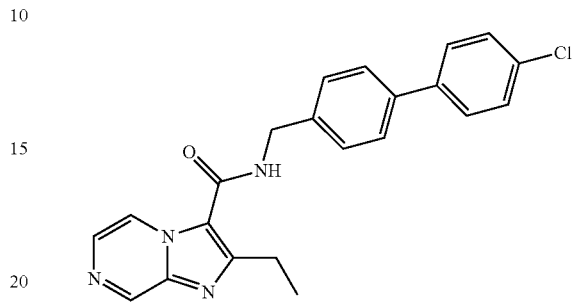

¹H NMR (400 MHz, DMSO-d₆) δ 1.46 (t, J=7.6 Hz, 3H), 3.06 (q, J=7.6 Hz, 2H), 4.76 (d, J=5.6 Hz, 2H), 6.23-6.25 (m, 1H), 7.41 (d, J=8.4 Hz, 2H), 7.45 (d, J=8.0 Hz, 2H), 7.51 (d, J=8.4 Hz, 2H), 7.57 (d, J=8.0 Hz, 2H), 8.03 (d, J=4.4 Hz, 1H), 9.11 (s, 1H), 9.28 (d, J=4.8 Hz, 1H).

6-Chloro-N-((2'-chlorobiphenyl-4-yl)methyl)-2-ethylimidazo[1,2-a]pyridine-3-carboxamide (72)

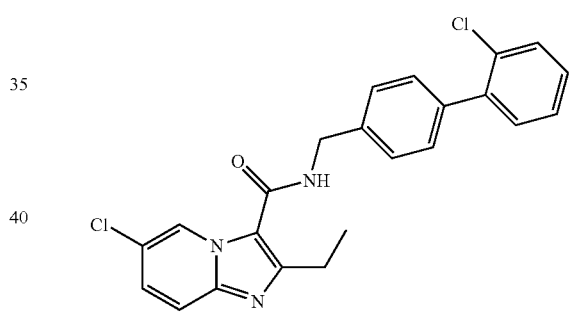

¹H NMR (400 MHz, CDCl₃) δ 1.44 (t, J=7.6 Hz, 3H), 3.02 (q, J=7.6 Hz, 2H), 4.77 (d, J=6.0 Hz, 2H), 6.18 (m, 1H), 7.27-7.35 (m, 4H), 7.43-7.48 (m, 5H), 7.56 (d, J=9.6 Hz, 1H), 9.56 (d, J=2.0 Hz, 1H); LCMS (electrospray) m/z (M+H)⁺ 404.26

6-Chloro-N-((4'-chlorobiphenyl-4-yl)methyl)-2-ethylimidazo[1,2-a]pyridine-3-carboxamide (73)

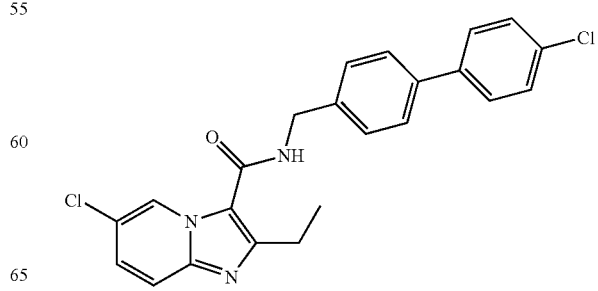

¹H NMR (400 MHz, CDCl₃) δ 1.43 (t, J=7.6 Hz, 3H), 3.01 (q, J=7.6 Hz, 2H), 4.71 (d, J=6.0 Hz, 2H), 6.13 (m, 1H), 7.31 (dd, J=2.0, 9.6 Hz, 1H), 7.41 (d, J=8.8 Hz, 2H), 7.45 (d, J=8.0 Hz, 2H), 7.51 (d, J=8.4 Hz, 2H), 7.54-7.58 (m, 3H), 9.55 (d, J=2.0 Hz, 1H); LCMS (electrospray) m/z (M+H)⁺ 424.26

6-Chloro-2-ethyl-N-(4-(piperidin-1-yl)benzyl)imidazo[1,2-a]pyridine-3-carboxamide (74)

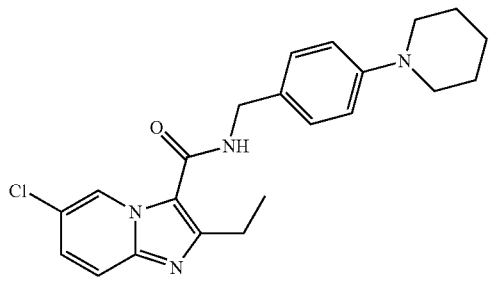 [SMILES: CCc1nc2ccc(Cl)cn2c1C(=O)NCc1ccc(N2CCCCC2)cc1]

¹H NMR (400 MHz, CDCl₃) δ 1.38 (t, J=7.6 Hz, 3H), 1.54-1.60 (m, 2H), 1.69-1.73 (m, 4H), 2.94 (q, J=7.6 Hz, 2H), 3.16 (t, J=5.14 Hz, 4H), 4.59 (d, J=5.6 Hz, 2H), 6.00 (m, 1H), 6.93 (d, J=8.8 Hz, 2H), 7.25 (d, J=8.0 Hz, 2H), 7.29 (dd, J=2.0, 9.6 Hz, 1H), 7.53 (d, J=9.6 Hz, 1H), 9.52 (d, J=2.0 Hz, 1H); LCMS (electrospray) m/z (M+H)⁺ 397.32

6-Chloro-2-ethyl-N-((2'-methylbiphenyl-4-yl)methyl)imidazo[1,2-a]pyridine-3-carboxamide (75)

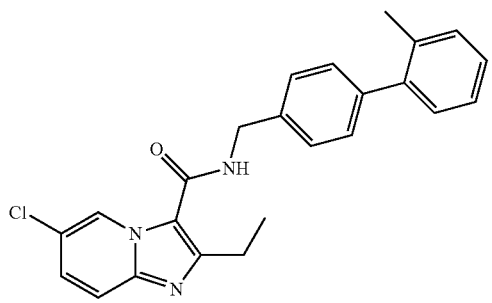 [SMILES: CCc1nc2ccc(Cl)cn2c1C(=O)NCc1ccc(-c2ccccc2C)cc1]

¹H NMR (400 MHz, CDCl₃) δ 1.43 (t, J=7.6 Hz, 3H), 2.27 (s, 3H), 3.02 (q, J=7.6 Hz, 2H), 4.76 (d, J=5.6 Hz, 2H), 6.21 (t, J=5.2 Hz, 1H), 7.20-7.28 (m, 4H), 7.30 (dd, J=2.0, 9.6 Hz, 1H), 7.34 (d, J=8.0 Hz, 2H), 7.42 (d, J=8.0 Hz, 2H), 7.54 (d, J=9.6 Hz, 1H), 9.55 (d, J=2.0 Hz, 1H); LCMS (electrospray) m/z (M+H)⁺ 404.26

6-Chloro-2-ethyl-N-((3'-methylbiphenyl-4-yl)methyl)imidazo[1,2-a]pyridine-3-carboxamide (76)

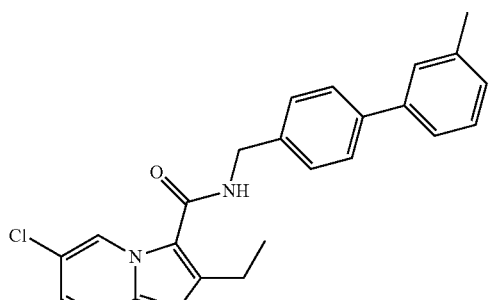

¹H NMR (400 MHz, CDCl₃) δ 1.43 (t, J=7.6 Hz, 3H), 2.42 (s, 3H), 3.00 (q, J=7.6 Hz, 2H), 4.75 (d, J=5.6 Hz, 2H), 6.14 (m, 1H), 7.18 (d, J=7.2 Hz, 1H), 7.31 (dd, J=2.0, 9.6 Hz, 1H), 7.34 (d, J=7.2 Hz, 1H), 7.39 (d, J=8.0 Hz, 2H), 7.44 (d, J=8.4 Hz, 2H), 7.55 (d, J=9.6 Hz, 1H), 7.60 (d, J=8.0 Hz, 2H), 9.56 (d, J=2.0 Hz, 1H); LCMS (electrospray) m/z (M+H)⁺ 404.26

6-Chloro-2-ethyl-N-((4'-methylbiphenyl-4-yl)methyl)imidazo[1,2-a]pyridine-3-carboxamide (77)

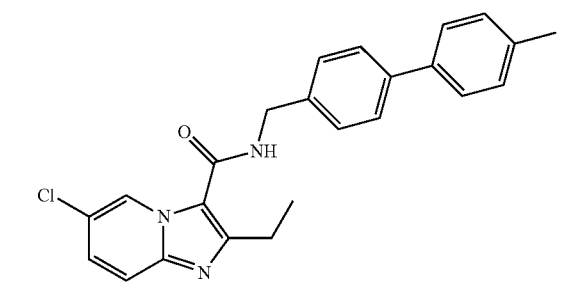 [SMILES: CCc1nc2ccc(Cl)cn2c1C(=O)NCc1ccc(-c2ccc(C)cc2)cc1]

¹H NMR (400 MHz, CDCl₃) δ 1.42 (t, J=7.6 Hz, 3H), 3.00 (q, J=7.6 Hz, 2H), 2.40 (s, 3H), 4.74 (d, J=5.6 Hz, 2H), 6.16 (m, 1H), 7.25 (d, J=7.2 Hz, 2H), 7.30 (dd, J=2.0, 9.6 Hz, 1H), 7.44 (d, J=8.0 Hz, 2H), 7.49 (d, J=8.0 Hz, 2H), 7.54 (d, J=9.6 Hz, 1H), 7.59 (d, J=8.4 Hz, 2H), 9.55 (d, J=2.0 Hz, 1H); LCMS (electrospray) m/z (M+H)⁺ 404.26

6-Chloro-N-(4-chlorobenzyl)-2-ethylimidazo[1,2-a]pyridine-3-carboxamide

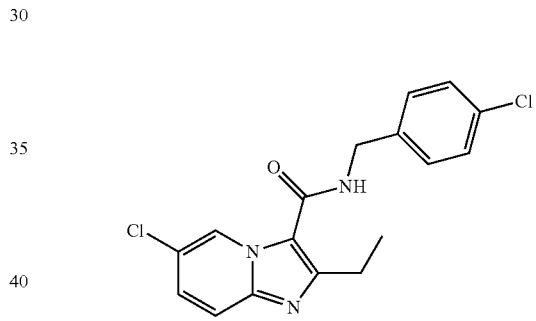

¹H NMR (400 MHz, CDCl₃) δ 1.41 (t, J=7.6 Hz, 3H), 2.98 (q, J=7.6 Hz, 2H), 4.66 (d, J=5.6 Hz, 2H), 6.14 (m, 1H), 7.29-7.35 (m, 5H), 7.54 (dd, J=0.8, 9.6 Hz, 1H), 9.51 (dd, J=0.8, 2.0 Hz, 1H); LCMS (electrospray) m/z (M+H)⁺ 348.14

6-Chloro-2-ethyl-N-(naphthalen-2-ylmethyl)imidazo[1,2-a]pyridine-3-carboxamide

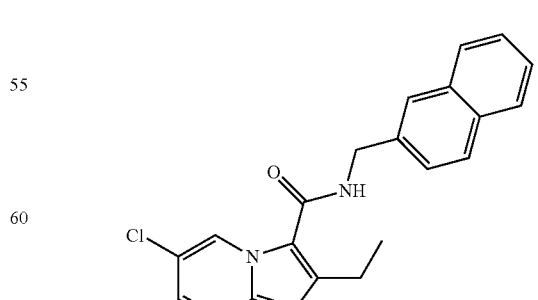

¹H NMR (400 MHz, CDCl₃) 1.40 (t, J=7.4 Hz, 3H), 2.98 (q, J=7.6 Hz, 2H), 4.87 (q, J=5.6 Hz, 2H), 6.19 (m, 1H), 7.31

(dd, J=2.0, 9.6 Hz, 1H), 7.47-7.51 (m, 3H), 7.55 (d, J=9.6 Hz, 1H), 7.82-7.85 (m, 3H), 7.87 (d, J=8.4 Hz, 1H), 9.57 (d, J=2.0 Hz, 1H); LCMS (electrospray) m/z (M+H)+ 364.20

N-(Biphenyl-4-ylmethyl)-6-chloro-2-(trifluoromethyl)imidazo[1,2-a]pyridine-3-carboxamide (80)

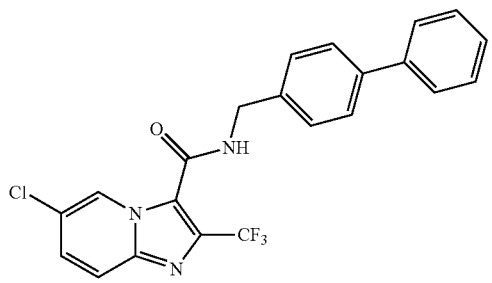 [SMILES: O=C(NCc1ccc(-c2ccccc2)cc1)c1c(C(F)(F)F)nc2ccc(Cl)cn12]

¹H NMR (400 MHz, CDCl₃) δ 4.74 (d, J=5.6 Hz, 2H), 6.69 (m, 1H), 7.36 (dd, J=7.2, 7.2 Hz, 1H), 7.43-7.47 (m, 5H), 7.56 (dd, J=8.0, 8.4 Hz, 4H), 7.71 (d, J=9.6 Hz, 1H), 9.45 (s, 1H)); LCMS (electrospray) m/z (M+H)+ 430.18

N-(4-tert-Butylbenzyl)-6-chloro-2-(trifluoromethyl)imidazo[1,2-a]pyridine-3-carboxamide (81)

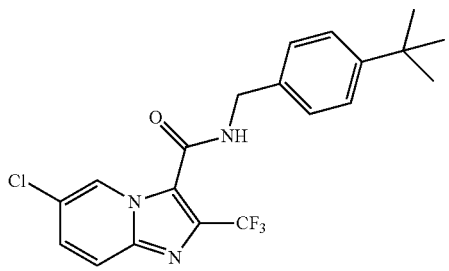 [SMILES: CC(C)(C)c1ccc(CNC(=O)c2c(C(F)(F)F)nc3ccc(Cl)cn23)cc1]

¹H NMR (400 MHz, CDCl₃) δ 1.32 (s, 9H), 4.67 (d, J=6.0 Hz, 2H), 6.63 (m, 1H), 7.30 (d, J=8.0 Hz, 2H), 7.41 (d, J=8.4 Hz, 2H), 7.41-7.45 (m, 1H), 7.69 (d, J=9.6 Hz, 1H), 9.42 (d, J=1.2 Hz, 1H); LCMS (electrospray) m/z (M+H)+ 410.25

7-Chloro-N-((2'-chlorobiphenyl-4-yl)methyl)-2-ethylimidazo[1,2-a]pyridine-3-carboxamide (82)

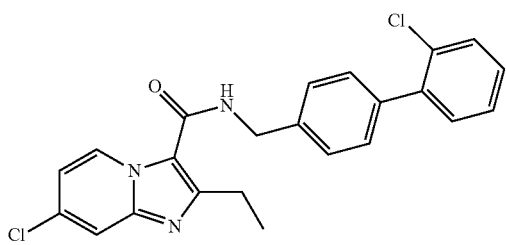 [SMILES: CCc1nc2cc(Cl)ccn2c1C(=O)NCc1ccc(-c2ccccc2Cl)cc1]

¹H NMR (400 MHz, MeOH-d₄) δ 1.32 (t, J=7.6 Hz, 3H), 3.01 (q, J=7.6 Hz, 2H), 4.68 (s, 2H), 7.03 (dd, J=7.6, 2.0 Hz, 1H), 7.29-7.57 (m, 9H), 8.94 (d, J=7.6 Hz, 1H); LCMS (electrospray) m/z (M+H)+ 424.26

7-Chloro-N-((4'-chlorobiphenyl-4-yl)methyl)-2-ethyl-2-ethlimidazo[1,2-a]pyridine-3-carboxamide (83)

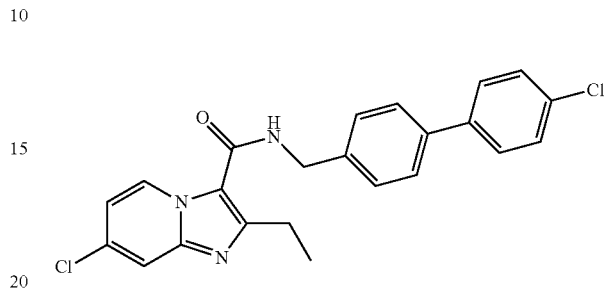

¹H NMR (400 MHz, CDCl₃) δ 1.42 (t, J=7.6 Hz, 3H), 2.99 (q, J=7.6 Hz, 2H), 4.73 (s, 2H), 6.15 (brs, 1H), 6.91 (dd, J=7.6, 2.0 Hz, 1H), 7.40 (d, J=8.4 Hz, 2H), 7.44 (d, J=8.0 Hz, 2H), 7.51 (d, J=8.4 Hz, 2H), 7.56 (d, J=8.0 Hz, 2H), 7.60 (d, J=1.6 Hz, 1H), 9.38 (d, J=7.2 Hz, 1H); LCMS (electrospray) m/z (M+H)+ 424.26

7-Chloro-N-(4-chlorobenzyl)-2-ethylimidazo[1,2-a]pyridine-3-carboxamide (84)

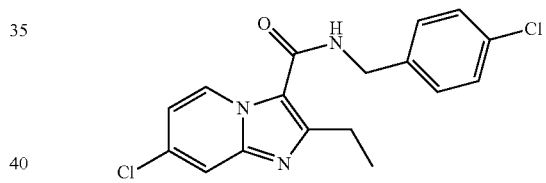

¹H NMR (400 MHz, CDCl₃) δ 1.40 (t, J=7.6 Hz, 3H), 2.96 (q, J=7.6 Hz, 2H), 4.65 (d, J=5.6 Hz, 2H), 6.12 (brs, 1H), 6.90 (dd, J=7.6, 2.4 Hz, 1H), 7.30 (d, J=8.4 Hz, 2H), 7.34 (d, J=8.4 Hz, 2H), 7.58 (d, 1H), 9.34 (d, J=7.6 Hz, 1H); LCMS (electrospray) m/z (M+H)+ 348.21

7-Chloro-2-ethyl-N-((2'-methylbiphenyl-4-yl)methyl)imidazo[1,2-a]pyridine-3-carboxamide (85)

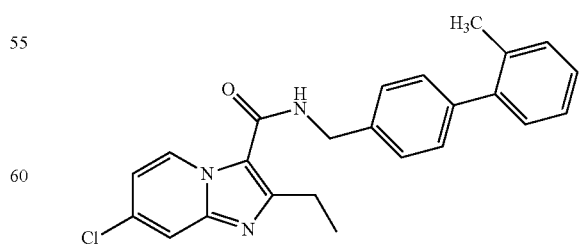

¹H NMR (400 MHz, CDCl₃) δ 1.46 (t, J=7.6 Hz, 3H), 2.31 (s, 3H), 3.05 (q, J=7.6 Hz, 2H), 4.79 (d, J=5.6 Hz, 2H), 6.22 (brs, 1H), 6.95 (dd, J=7.6, 1.6 Hz, 1H), 7.24-7.36 (m, 4H), 7.39 (d, J=7.6 Hz, 2H), 7.45 (d, J=7.6 Hz, 2H), 7.63 (d, 1H), 9.42 (d, J=7.2 Hz, 1H); LCMS (electrospray) m/z (M+H)+ 404.26

7-Chloro-2-ethyl-N-((3'-methylbiphenyl-4-yl)methyl)imidazo[1,2-a]pyridine-3-carboxamide (86)

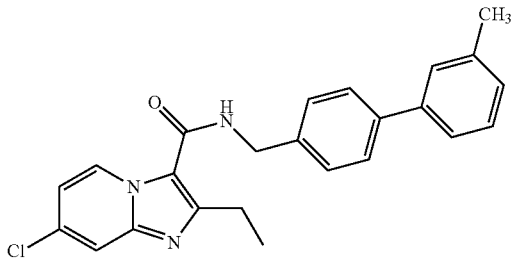 [SMILES: CCc1nc2cc(Cl)ccn2c1C(=O)NCc1ccc(-c2cccc(C)c2)cc1]

$^1$H NMR (400 MHz, CDCl$_3$) δ 1.41 (t, J=7.6 Hz, 3H), 2.42 (s, 3H), 2.99 (q, J=7.6 Hz, 2H), 4.74 (d, J=5.6 Hz, 2H), 6.13 (brs, 1H), 6.91 (dd, J=7.6, 2.0 Hz, 1H), 7.18 (d, J=8.4 Hz, 1H), 7.33-7.40 (m, 3H), 7.43 (d, J=8.4 Hz, 2H), 7.58-7.61 (m, 3H), 9.38 (d, J=7.6 Hz, 1H); LCMS (electrospray) m/z (M+H)+ 404.33

7-Chloro-2-ethyl-N-((4'-methylbiphenyl-4-yl)methyl)imidazo[1,2-a]pyridine-3-carboxamide (87)

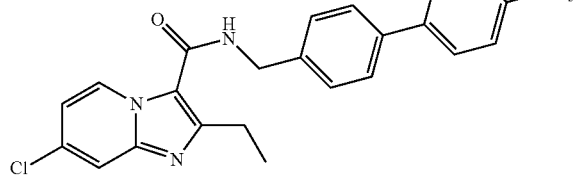

$^1$H NMR (400 MHz, CDCl$_3$) δ 1.41 (t, J=7.6 Hz, 3H), 2.40 (s, 3H), 2.99 (q, J=7.6 Hz, 2H), 4.73 (s, 2H), 6.91 (dd, J=7.6, 2.0 Hz, 1H), 7.25 (d, J=8.4 Hz, 2H), 7.43 (d, J=8.0 Hz, 2H), 7.48 (d, J=8.0 Hz, 2H), 7.58-7.60 (m, 3H), 9.38 (d, J=7.2 Hz, 1H); LCMS (electrospray) m/z (M+H)+ 404.26

7-Chloro-2-ethyl-N-(4-hydroxybenzyl)imidazo[1,2-a]pyridine-3-carboxamide (88)

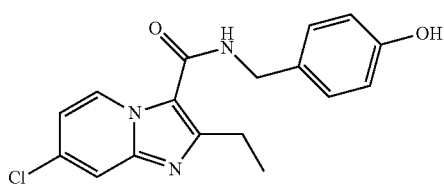 [SMILES: CCc1nc2cc(Cl)ccn2c1C(=O)NCc1ccc(O)cc1]

$^1$H NMR (400 MHz, MeOH-d$_4$) δ 1.29 (t, J=7.6 Hz, 3H), 2.96 (q, J=7.6 Hz, 2H), 3.12-3.15 (m, 4H), 4.52 (s, 2H), 6.76 (d, J=8.4 Hz, 2H), 7.06 (dd, J=7.6, 2.0 Hz, 1H), 7.23 (d, J=8.4 Hz, 2H), 7.58 (d, J=1.6 Hz, 1H), 8.91 (d, J=7.6 Hz, 1H); LCMS (electrospray) m/z (M+H)+ 330.25

7-Chloro-2-ethyl-N-(4-(piperidin-1-yl)benzyl)imidazo[1,2-a]pyridine-3-carboxamide (89)

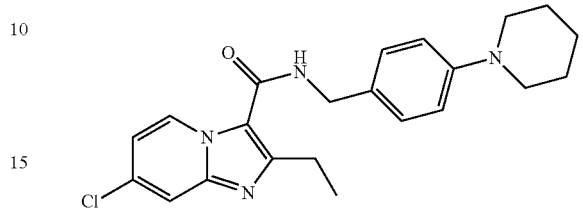

$^1$H NMR (400 MHz, CDCl$_3$) δ 1.35 (t, J=7.6 Hz, 3H), 1.55-1.57 (m, 2H), 1.66-1.70 (m, 4H), 2.91 (q, J=7.6 Hz, 2H), 3.12-3.15 (m, 4H), 4.56 (d, J=5.6 Hz, 2H), 6.07 (brs, 1H), 6.86 (dd, J=7.6, 2.0 Hz, 1H), 6.90 (d, J=8.4 Hz, 2H), 7.22 (d, J=8.4 Hz, 2H), 7.54 (d, J=2.0 Hz, 1H), 9.30 (d, J=7.6 Hz, 1H); LCMS (electrospray) m/z (M+H)+ 397.32

7-Chloro-2-ethyl-N-(naphthalen-2-ylmethyl)imidazo[1,2-a]pyridine-3-carboxamide (90)

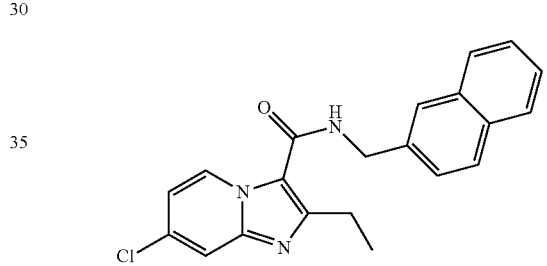

$^1$H NMR (400 MHz, MeOH-d$_4$) δ 1.32 (t, J=7.6 Hz, 3H), 3.02 (q, J=7.6 Hz, 2H), 4.79 (s, 2H), 7.06 (dd, J=7.6, 2.0 Hz, 1H), 7.45-7.48 (m, 2H), 7.54 (d, J=8.4 Hz, 1H), 7.59 (d, J=2.0 Hz, 1H), 7.82-7.88 (m, 4H), 8.96 (d, J=7.6 Hz, 1H); LCMS (electrospray) m/z (M+H)+ 364.20

N-(Biphenyl-4-ylmethyl)-7-chloro-2-ethylimidazo[1,2-a]pyridine-3-carboxamide (91)

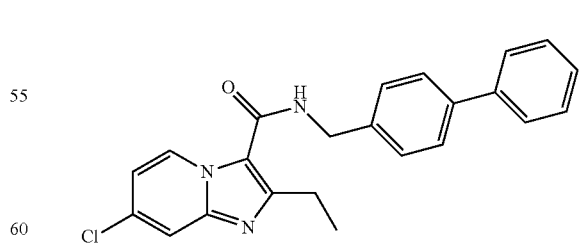

$^1$H NMR (400 MHz, CDCl$_3$) δ 1.42 (t, J=7.6 Hz, 3H), 3.00 (q, J=7.6 Hz, 2H), 4.74 (d, J=5.6 Hz, 2H), 6.14 (brs, 1H), 6.91 (dd, J=7.6, 2.4 Hz, 1H), 7.35 (m, 1H), 7.42-7.46 (m, 4H), 7.57-7.62 (m, 5H), 9.38 (d, J=7.6 Hz, 1H); $^{13}$C NMR (100 MHz, CDCl$_3$) δ 13.4, 23.6, 31.5, 34.7, 43.4, 114.7, 115.8, 126.0, 127.5, 128.6, 133.6, 135.0, 146.2, 150.9, 151.6, 161.3; LCMS (electrospray) m/z (M+H)+ 390.25

N-(4-tert-Butylbenzyl)-7-chloro-2-ethylimidazo[1,2-a]pyridine-3-carboxamide (92)

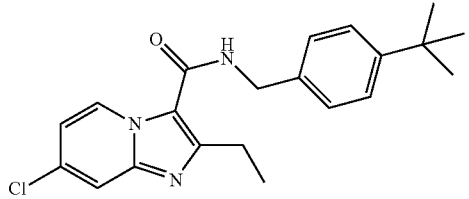 [SMILES: CCc1nc2cc(Cl)ccn2c1C(=O)NCc1ccc(C(C)(C)C)cc1]

$^1$H NMR (400 MHz, CDCl$_3$) δ 1.32 (s, 9H), 1.40 (t, J=7.6 Hz, 3H), 2.96 (q, J=7.6 Hz, 2H), 4.67 (d, J=5.6 Hz, 2H), 6.13 (brs, 1H), 6.90 (dd, J=7.2, 2.4 Hz, 1H), 7.31 (d, J=8.0 Hz, 2H), 7.40 (d, J=8.0 Hz, 2H), 7.59 (d, J=1.6 Hz, 1H), 9.36 (d, J=7.2 Hz, 1H); LCMS (electrospray) m/z (M+H)+ 370.25

7-Chloro-2-ethyl-N-(4-morpholinobenzyl)imidazo[1,2-a]pyridine-3-carboxamide (93)

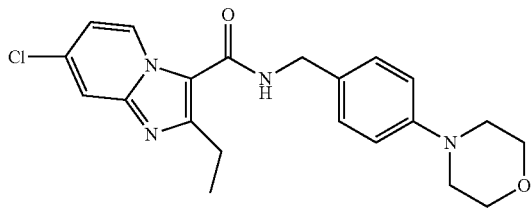 [SMILES: CCc1nc2cc(Cl)ccn2c1C(=O)NCc1ccc(N2CCOCC2)cc1]

White solid, mp 195° C.; $^1$H NMR (400 MHz, MeOH-d$_4$) δ1.31 (t, J=7.6 Hz, 3H), 3.00 (q, J=7.6 Hz, 2H), 3.14 (t, J=4.8 Hz, 4H), 3.84 (t, J=4.8 Hz, 4H), 4.54 (s, 2H), 6.97 (d, J=6.8 Hz, 2H), 7.07 (d, J=7.6 Hz, 1H), 7.32 (d, J=8.8 Hz, 2H), 7.59 (s, 1H), 8.93 (d, J=7.2 Hz, 1H).

2-Ethyl-7-methyl-N-(4-morpholinobenzyl)imidazo[1,2-a]pyridine-3-carboxamide (94)

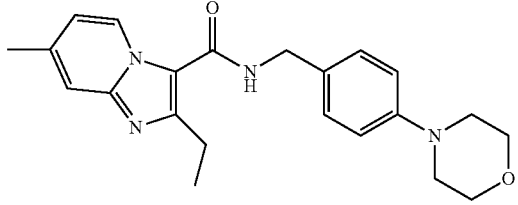 [SMILES: CCc1nc2cc(C)ccn2c1C(=O)NCc1ccc(N2CCOCC2)cc1]

White solid, mp 190° C.; $^1$H NMR (400 MHz, MeOH-d4) δ1.31 (t, J=7.6 Hz, 3H), 2.43 (s, 3H), 2.98 (q, J=7.6 Hz, 2H), 3.14 (t, J=4.8 Hz, 4H), 3.35 (s, 1H), 3.85 (t, J=4.8 Hz, 4H), 4.53 (s, 2H), 6.90 (d, J=7.2 Hz, 1H), 6.98 (d, J=8.8 Hz, 2H), 7.32 (d, J=8.8 Hz, 3H), 8.83 (d, J=7.2 Hz, 1H).

2-Ethyl-7-methyl-N-(naphthalen-2-ylmethyl)imidazo[1,2-a]pyridine-3-carboxamide (95)

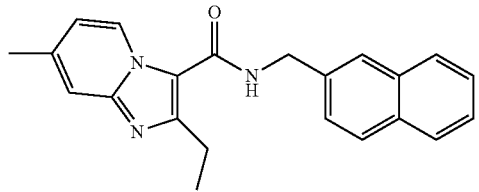 [SMILES: CCc1nc2cc(C)ccn2c1C(=O)NCc1ccc2ccccc2c1]

White solid, mp 192° C.; $^1$H NMR (400 MHz, MeOH-d4) δ1.33 (t, J=7.6 Hz, 3H), 2.45 (s, 3H), 3.02 (q, J=7.6 Hz, 2H), 4.79 (s, 2H), 6.9 (d, J=7.2 Hz, 1H), 7.33 (s, 1H), 7.45-7.48 (m, 2H), 7.56 (d, J=8.8 Hz, 1H), 7.82-7.88 (m, 4H), 8.87 (d, J=7.2 Hz, 1H).

N-(4-Bromobenzyl)-7-chloro-2-ethylimidazo[1,2-a]pyridine-3-carboxamide (96)

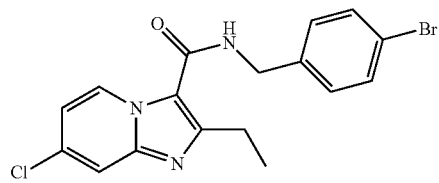 [SMILES: CCc1nc2cc(Cl)ccn2c1C(=O)NCc1ccc(Br)cc1]

$^1$H NMR (400 MHz, CDCl$_3$) δ 1.41 (t, J=7.6 Hz, 3H), 2.97 (q, J=7.6 Hz, 2H), 4.65 (d, J=5.6 Hz, 2H), 6.09 (brs, 1H), 6.91 (dd, J=7.6, 2.0 Hz, 1H), 7.25 (d, J=8.4 Hz, 2H), 7.50 (d, J=8.4 Hz, 2H), 7.60 (d, J=2.0 Hz, 1H), 9.35 (d, J=7.6 Hz, 1H); LCMS (electrospray) m/z (M+H)+ 394.13

6-Chloro-N-((4'-cyanobiphenyl-4-yl)methyl)-2-ethylimidazo[1,2-a]pyridine-3-carboxamide (97)

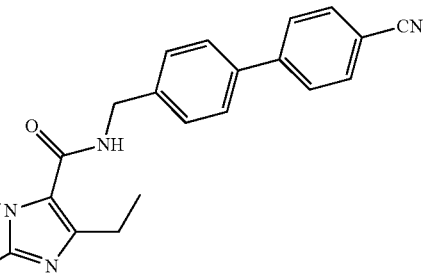

$^1$H NMR (400 MHz, CDCl$_3$) δ 1.44 (t, J=7.6 Hz, 3H), 3.02 (q, J=7.2 Hz, 2H), 4.77 (d, J=5.6 Hz, 2H), 6.19 (m, 1H), 7.32 (dd, J=2.0, 9.6 Hz, 1H), 7.50 (d, J=8.0 Hz, 2H), 7.56 (d, J=9.6 Hz, 1H), 7.68 (d, J=8.4 Hz, 2H), 7.73 (d, J=8.4 Hz, 2H), 9.55 (d, J=2.0 Hz, 1H).

6-Chloro-2-ethyl-N-((2'-(trifluoromethyl)biphenyl-4-yl)methyl)imidazo[1,2-a]pyridine-3-carboxamide (98)

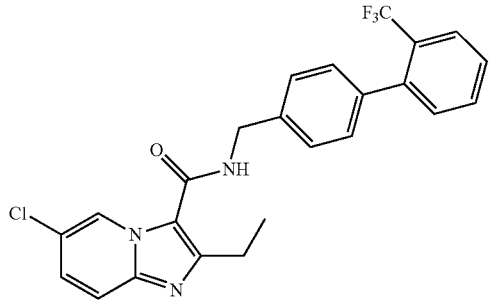 [SMILES: CCc1nc2ccc(Cl)cn2c1C(=O)NCc1ccc(-c2ccccc2C(F)(F)F)cc1]

$^1$H NMR (400 MHz, CDCl$_3$) δ 1.43 (t, J=7.6 Hz, 3H), 3.02 (q, J=7.2 Hz, 2H), 4.78 (d, J=5.6 Hz, 2H), 6.17 (m, 1H), 7.30-7.35 (m, 4H), 7.42 (d, J=8.0 Hz, 2H), 7.48 (t, J=8.0 Hz, 1H), 7.55 (d, J=8.8 Hz, 2H), 7.75 (d, J=7.6 Hz, 1H), 7.73 (d, J=8.4 Hz, 2H), 9.56 (d, J=1.2 Hz, 1H).

6-Chloro-N-((3'-cyanobiphenyl-4-yl)methyl)-2-ethylimidazo[1,2-a]pyridine-3-carboxamide (99)

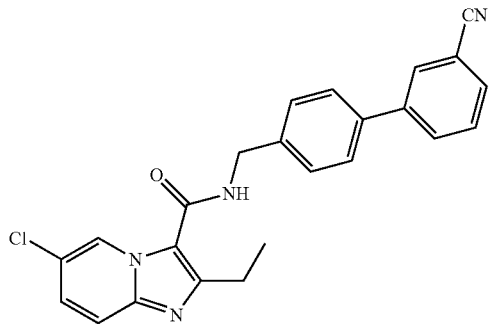 [SMILES: CCc1nc2ccc(Cl)cn2c1C(=O)NCc1ccc(-c2cccc(C#N)c2)cc1]

$^1$H NMR (400 MHz, CDCl$_3$) δ 1.44 (t, J=7.6 Hz, 3H), 3.02 (q, J=7.6 Hz, 2H), 4.77 (d, J=5.6 Hz, 2H), 6.19 (m, 1H), 7.32 (dd, J=2.0, 9.2 Hz, 1H), 7.50 (d, J=8.4 Hz, 2H), 7.55-7.59 (m, 3H), 7.64 (d, J=7.6 Hz, 1H), 7.81 (d, J=8.0 Hz, 1H), 7.86 (s, 1H), 9.56 (d, J=1.6 Hz, 1H).

6-Chloro-N-((4'-chloro-2'-(trifluoromethyl)biphenyl-4-yl)methyl)-2-ethylimidazo[1,2-a]pyridine-3-carboxamide (100)

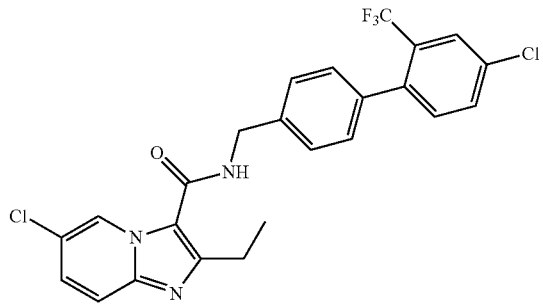 [SMILES: CCc1nc2ccc(Cl)cn2c1C(=O)NCc1ccc(-c2ccc(Cl)cc2C(F)(F)F)cc1]

$^1$H NMR (400 MHz, CDCl$_3$) δ 1.44 (t, J=7.6 Hz, 3H), 3.02 (q, J=7.6 Hz, 2H), 4.77 (d, J=5.6 Hz, 2H), 6.18 (m, 1H), 7.27 (d, J=7.6 Hz, 2H), 7.31 (d, J=7.6 Hz, 2H), 7.42 (d, J=8.0 Hz, 2H), 7.52-7.56 (m, 2H), 7.73 (d, J=2.0 Hz, 1H), 7.86 (s, 1H), 9.55 (d, J=1.2 Hz, 1H).

7-Chloro-N-((3'-cyanobiphenyl-4-yl)methyl)-2-ethylimidazo[1,2-a]pyridine-3-carboxamide (101)

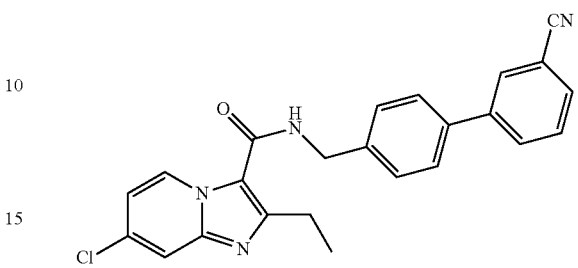

$^1$H NMR (400 MHz, CDCl$_3$) δ 1.42 (t, J=7.6 Hz, 3H), 3.01 (q, J=7.6 Hz, 2H), 4.76 (d, J=6.0 Hz, 2H), 6.17 (brs, 1H), 6.92 (dd, J=7.2, 2.0 Hz, 1H), 7.49 (d, J=8.4 Hz, 1H), 7.55-7.63 (m, 5H), 7.80 (d, J=8.0 Hz, 1H), 7.85 (d, J=1.6 Hz, 1H), 9.38 (d, J=7.2 Hz, 1H); LCMS (electrospray) m/z (M+H)$^+$ 415.28

7-Chloro-2-ethyl-N-((2'-(trifluoromethyl)biphenyl-4-yl)methyl)imidazo[1,2-a]pyridine-3-carboxamide (102)

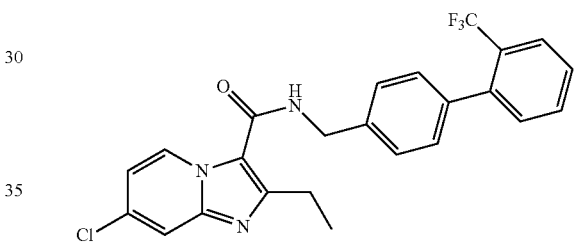

$^1$H NMR (400 MHz, CDCl$_3$) δ 1.41 (t, J=7.6 Hz, 3H), 3.01 (q, J=7.6 Hz, 2H), 4.77 (d, J=5.6 Hz, 2H), 6.16 (brs, 1H), 6.92 (dd, J=7.2, 2.4 Hz, 1H), 7.32 (d, J=7.6 Hz, 1H), 7.34 (d, J=8.4 Hz, 2H), 7.41 (d, J=8.4 Hz, 2H), 7.47 (t, J=7.6 Hz, 1H), 7.56 (t, J=7.6 Hz, 1H), 7.60 (d, J=2.4 Hz, 1H), 7.75 (d, J=8.0 Hz, 1H), 9.38 (d, J=7.2 Hz, 1H); LCMS (electrospray) m/z (M+H)$^+$ 458.27

7-Chloro-N-((4'-chloro-2'-(trifluoromethyl)biphenyl-4-yl)methyl)-2-ethylimidazo[1,2-a]pyridine-3-carboxamide (103)

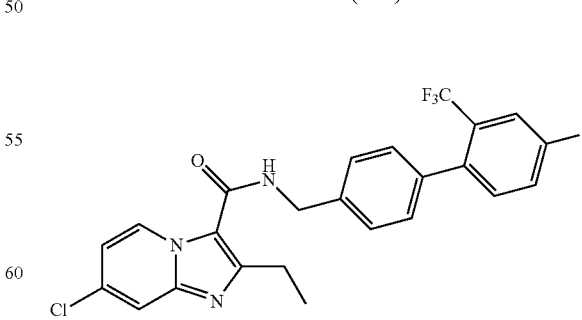

$^1$H NMR (400 MHz, CDCl$_3$) δ 1.41 (t, J=7.6 Hz, 3H), 3.01 (q, J=7.6 Hz, 2H), 4.76 (d, J=6.0 Hz, 2H), 6.16 (brs, 1H), 6.92 (dd, J=7.2, 2.0 Hz, 1H), 7.28 (d, J=8.0 Hz, 1H), 7.30 (d, J=8.0 Hz, 2H), 7.41 (d, J=8.0 Hz, 2H), 7.53 (dd, J=8.0, 1.6 Hz, 1H), 7.60 (d, J=2.0 Hz, 1H), 7.73 (d, J=2.0 Hz, 1H), 9.38 (d, J=7.6 Hz, 1H); LCMS (electrospray) m/z (M+H)+ 492.21

6-Chloro-N-((4'-cyano-2'-methylbiphenyl-4-yl)methyl)-2-ethylimidazo[1,2-a]pyridine-3-carboxamide (104)

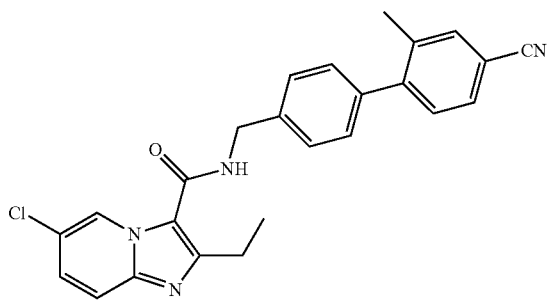 [SMILES: CCc1nc2ccc(Cl)cn2c1C(=O)NCc1ccc(-c2ccc(C#N)cc2C)cc1]

$^1$H NMR (400 MHz, CDCl$_3$) δ 1.44 (t, J=7.6 Hz, 3H), 2.30 (s, 3H), 3.03 (q, J=7.6 Hz, 2H), 4.77 (d, J=5.6 Hz, 2H), 6.21 (t, J=5.2 Hz, 1H), 7.30-7.33 (m, 4H), 7.31 (d, J=7.6 Hz, 2H), 7.46 (d, J=8.0 Hz, 2H), 7.52-7.56 (m, 2H), 7.52-7.57 (m, 3H), 9.56 (d, J=2.0 Hz, 1H).

6-Chloro-2-ethyl-N-(4-(4-methylpiperazin-1-yl)benzyl)imidazo[1,2-a]pyridine-3-carboxamide (105)

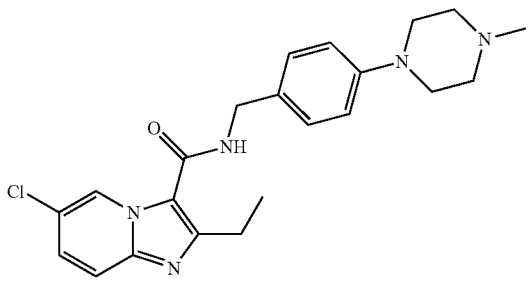 [SMILES: CCc1nc2ccc(Cl)cn2c1C(=O)NCc1ccc(N2CCN(C)CC2)cc1]

$^1$H NMR (400 MHz, CDCl$_3$) δ 1.39 (t, J=7.6 Hz, 3H), 2.36 (s, 3H), 2.58 (t, J=5.0 Hz, 4H), 2.95 (q, J=7.6 Hz, 2H), 3.22 (t, J=4.8 Hz, 4H), 4.60 (d, J=5.6 Hz, 2H), 6.93 (d, J=8.8 Hz, 2H), 7.26-7.30 (m, 3H), 7.53 (d, J=5.6 Hz, 1H), 9.53 (d, J=1.6 Hz, 1H).

7-Chloro-N-((2'-cyanobiphenyl-4-yl)methyl)-2-ethylimidazo[1,2-a]pyridine-3-carboxamide (106)

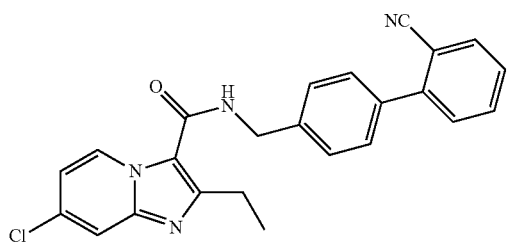

$^1$H NMR (400 MHz, CDCl$_3$) δ 1.44 (t, J=7.6 Hz, 3H), 3.02 (q, J=7.6 Hz, 2H), 4.77 (d, J=5.6 Hz, 2H), 6.18 (brs, 1H), 6.92 (dd, J=7.6, 2.0 Hz, 1H), 7.47-7.60 (m, 4H), 7.63-7.65 (m, 4H), 7.77 (d, J=7.6 Hz, 1H), 9.38 (d, J=7.6 Hz, 1H); LCMS (electrospray) m/z (M+H)+ 415.28

7-Chloro-2-ethyl-N-(4-(trifluoromethoxy)benzyl)imidazo[1,2-a]pyridine-3-carboxamide (107)

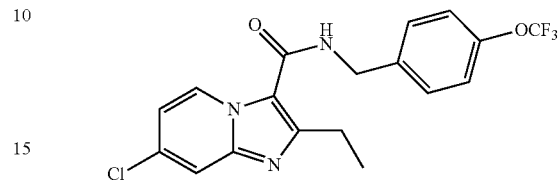

$^1$H NMR (400 MHz, CDCl$_3$) δ 1.41 (t, J=7.6 Hz, 3H), 2.98 (q, J=7.6 Hz, 2H), 4.70 (d, J=5.6 Hz, 2H), 6.09 (brs, 1H), 6.91 (dd, J=7.6, 2.0 Hz, 1H), 7.22 (d, J=8.4 Hz, 2H), 7.40 (d, J=8.4 Hz, 2H), 7.60 (d, J=2.0 Hz, 1H), 9.36 (d, J=7.6 Hz, 1H); LCMS (electrospray) m/z (M+H)+ 398.28

7-Chloro-2-ethyl-N-(4-(4-methylpiperazin-1-yl)benzyl)imidazo[1,2-a]pyridine-3-carboxamide (108)

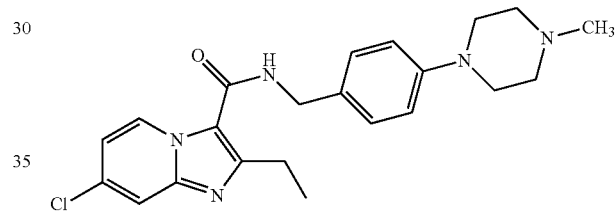

$^1$H NMR (400 MHz, CDCl$_3$) δ 1.37 (t, J=7.6 Hz, 3H), 2.35 (s, 3H), 2.57-2.59 (m, 4H), 2.94 (q, J=7.6 Hz, 2H), 3.20-3.23 (m, 4H), 4.59 (d, J=5.2 Hz, 2H), 6.00 (brs, 1H), 6.88-6.94 (m, 3H), 7.27 (d, J=8.4 Hz, 2H), 7.58 (d, J=2.0 Hz, 1H), 9.35 (d, J=7.6 Hz, 1H); LCMS (electrospray) m/z (M+H)+ 412.29

7-Chloro-N-((4'-cyano-2'-methylbiphenyl-4-yl)methyl)-2-ethylimidazo[1,2-a]pyridine-3-carboxamide (109)

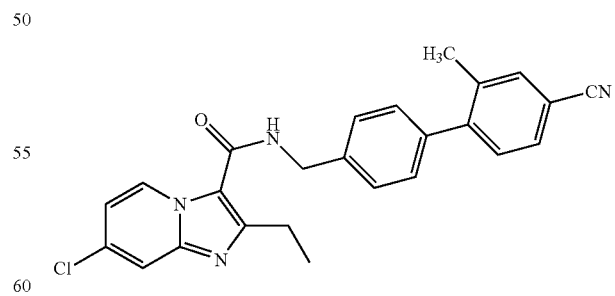

$^1$H NMR (400 MHz, CDCl$_3$) δ 1.43 (t, J=7.6 Hz, 3H), 2.29 (s, 3H), 3.02 (q, J=7.6 Hz, 2H), 4.77 (d, J=6.0 Hz, 2H), 6.18 (brs, 1H), 6.92 (dd, J=7.6, 2.0 Hz, 1H), 7.30 (d, J=8.0 Hz, 3H), 7.45 (d, J=8.0 Hz, 2H), 7.52 (d, J=7.6 Hz, 1H), 7.56 (s, 1H), 7.60 (d, J=2.4 Hz, 1H), 9.39 (d, J=7.2 Hz, 1H); LCMS (electrospray) m/z (M+H)+ 429.29

7-Chloro-2-ethyl-N-(4-(pentylamino)benzyl)imidazo[1,2-a]pyridine-3-carboxamide (110)

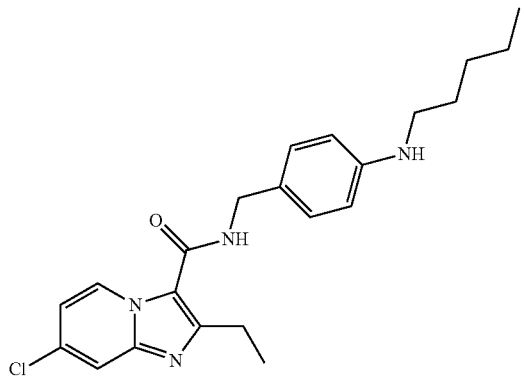 [SMILES: CCCCCNc1ccc(CNC(=O)c2c(CC)nc3cc(Cl)ccn23)cc1]

¹H NMR (400 MHz, CDCl₃) δ 0.92 (t, J=7.0 Hz, 3H), 1.25-1.42 (m, 8H), 1.58-1.66 (m, 2H), 2.93 (q, J=7.6 Hz, 2H), 3.10 (t, J=7.2 Hz, 2H), 3.66 (brs, 1H), 4.55 (d, J=5.2 Hz, 2H), 5.95 (m, 1H), 6.60 (d, J=8.4 Hz, 2H), 6.89 (dd, J=2.0, 7.2 Hz, 1H), 7.18 (d, J=8.0 Hz, 2H), 7.58 (d, J=1.2 Hz, 1H), 9.36 (d, J=7.6 Hz, 1H).

7-Chloro-2-ethyl-N-((4'-(trifluoromethyl)biphenyl-4-yl)methyl)imidazo[1,2-a]pyridine-3-carboxamide (111)

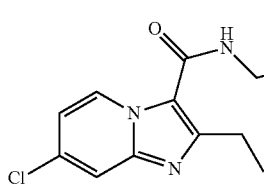

¹H NMR (400 MHz, CDCl₃) δ 1.42 (t, J=7.6 Hz, 3H), 3.01 (q, J=7.6 Hz, 2H), 4.76 (d, J=6.0 Hz, 2H), 6.16 (brs, 1H), 6.92 (dd, J=7.2, 2.0 Hz, 1H), 7.48 (d, J=8.4 Hz, 2H), 7.60 (m, 3H), 7.70 (m, 3H), 9.38 (d, J=7.2 Hz, 1H); LCMS (electrospray) m/z (M+H)⁺ 458.20

7-Chloro-2-ethyl-N-((4'-(trifluoromethoxy)biphenyl-4-yl)methyl)imidazo[1,2-a]pyridine-3-carboxamide (112)

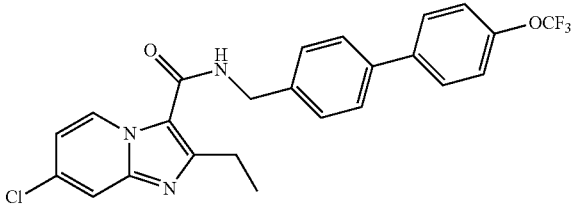 [SMILES: CCc1nc2cc(Cl)ccn2c1C(=O)NCc1ccc(-c2ccc(OC(F)(F)F)cc2)cc1]

¹H NMR (400 MHz, CDCl₃) δ 1.42 (t, J=7.6 Hz, 3H), 3.00 (q, J=7.6 Hz, 2H), 4.75 (d, J=6.0 Hz, 2H), 6.15 (brs, 1H), 6.91 (dd, J=7.6, 2.0 Hz, 1H), 7.28 (d, J=8.4 Hz, 2H), 7.46 (d, J=8.4 Hz, 2H), 7.54-7.60 (m, 5H), 9.38 (d, J=7.6 Hz, 1H); LCMS (electrospray) m/z (M+H)⁺ 474.18

7-Chloro-2-ethyl-N-((4'-methoxybiphenyl-4-yl)methyl)imidazo[1,2-a]pyridine-3-carboxamide (113)

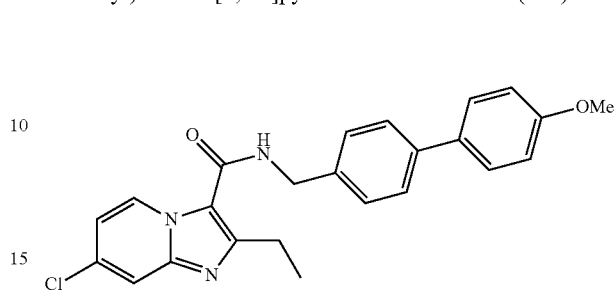

¹H NMR (400 MHz, CDCl₃) δ 1.41 (t, J=7.6 Hz, 3H), 2.99 (q, J=7.6 Hz, 2H), 3.85 (s, 3H), 4.72 (d, J=6.0 Hz, 2H), 6.12 (brs, 1H), 6.91 (dd, J=7.2, 2.0 Hz, 1H), 6.98 (d, J=8.8 Hz, 2H), 7.42 (d, J=8.0 Hz, 2H), 7.52 (d, J=8.8 Hz, 2H), 7.56 (d, J=8.0 Hz, 2H), 7.59 (d, J=1.6 Hz, 1H), 9.38 (d, J=7.6 Hz, 1H); LCMS (electrospray) m/z (M+H)⁺ 420.18

N-((4'-tert-Butylbiphenyl-4-yl)methyl)-7-chloro-2-ethylimidazo[1,2-a]pyridine-3-carboxamide (114)

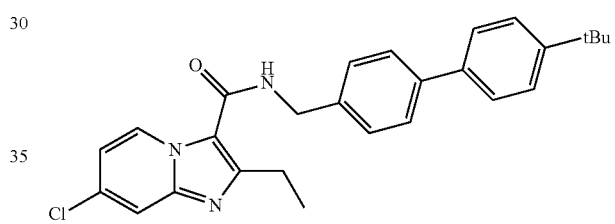

¹H NMR (400 MHz, CDCl₃) δ 1.36 (s, 9H), 1.41 (t, J=7.6 Hz, 3H), 2.99 (q, J=7.6 Hz, 2H), 4.73 (d, J=5.6 Hz, 2H), 6.13 (brs, 1H), 6.91 (dd, J=7.2, 2.0 Hz, 1H), 7.43 (d, J=8.0 Hz, 2H), 7.47 (d, J=8.4 Hz, 2H), 7.53 (d, J=8.4 Hz, 2H), 7.59-7.61 (m, 3H), 9.38 (d, J=7.2 Hz, 1H); LCMS (electrospray) m/z (M+H)⁺ 446.30

N-(7-Chloro-2-ethylimidazo[1,2-a]pyridin-3-yl)biphenyl-4-carboxamide (115)

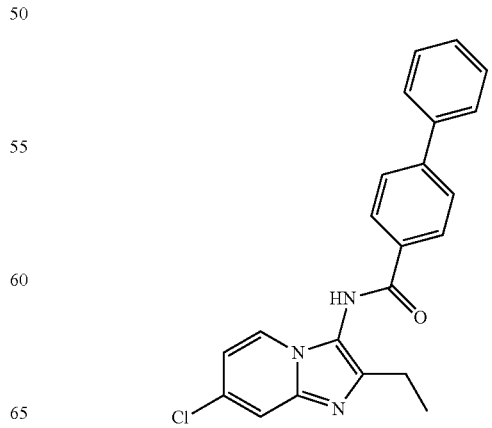

¹H NMR (400 MHz, CDCl₃) δ 1.33 (t, J=7.6 Hz, 3H), 2.75 (q, J=7.2 Hz, 2H), 6.78 (dd, J=1.2, 7.2, 1H), 6.89 (dd, J=1.2, 7.2 Hz, 1H), 7.44 (d, J=8.0 Hz, 2H), 7.48-7.53 (m, 3H), 7.58 (d, J=8.0 Hz, 1H), 7.65 (d, J=7.6 Hz, 2H), 7.72 (d, J=7.6 Hz, 1H), 7.76 (d, J=8.0 Hz, 2H), 8.02 (brs, 1H), 8.07 (d, J=8.0 Hz, 2H).

2-(Biphenyl-4-yl)-N-(7-chloro-2-ethylimidazo[1,2-a]pyridin-3-yl)acetamide (116)

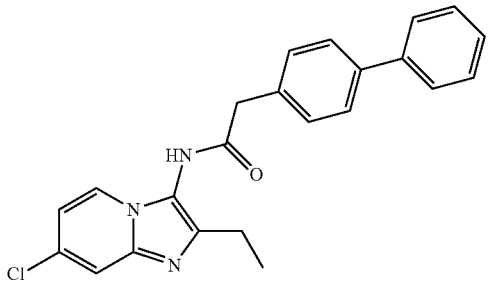 [SMILES: CCc1nc2cc(Cl)ccn2c1NC(=O)Cc1ccc(-c2ccccc2)cc1]

¹H NMR (400 MHz, DMSO-d₆) δ 1.25 (t, J=7.6 Hz, 3H), 2.62 (q, J=7.6 Hz, 2H), 3.89 (s, 2H), 6.74 (dd, J=2.0, 7.2 Hz, 1H), 7.00 (brs, 1H), 7.44-7.53 (m, 5H), 7.61 (d, J=7.2 Hz, 2H), 7.68 (d, J=8.4 Hz, 2H).

N-(4-(1H-Pyrrol-1-yl)benzyl)-7-chloro-2-ethylimidazo[1,2-a]pyridine-3-carboxamide (117)

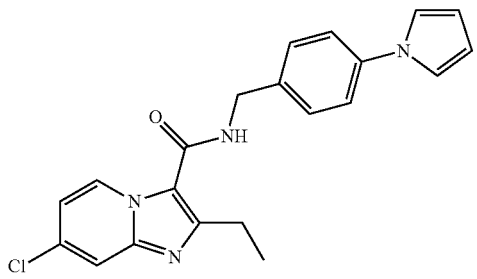 [SMILES: CCc1nc2cc(Cl)ccn2c1C(=O)NCc1ccc(-n2cccc2)cc1]

¹H NMR (400 MHz, CDCl₃) δ 1.41 (t, J=7.6 Hz, 3H), 2.99 (q, J=7.6 Hz, 2H), 4.71 (d, J=6.0 Hz, 2H), 6.12-6.14 (m, 1H), 6.34-6.36 (m, 2H), 6.92 (dd, J=2.0, 7.6 Hz, 1H), 7.08-7.09 (m, 2H), 7.40 (d, J=8.8 Hz, 2H), 7.44 (d, J=8.8 Hz, 21H), 7.60 (d, J=2.0 Hz, 1H), 7.68 (d, J=8.0 Hz, 2H), 9.38 (d, J=7.6 Hz, 1H).

2-Ethyl-7-methoxy-N-(4-(trifluoromethoxy)benzyl)imidazo[1,2-a]pyridine-3-carboxamide (118)

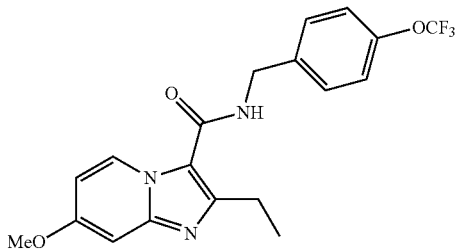 [SMILES: CCc1nc2cc(OC)ccn2c1C(=O)NCc1ccc(OC(F)(F)F)cc1]

¹H NMR (400 MHz, CDCl₃) δ 1.39 (t, J=7.6 Hz, 3H), 2.95 (q, J=7.6 Hz, 2H), 3.87 (s, 3H), 6.06 (m, 1H), 6.61 (dd, J=2.8, 7.6, 1H), 6.89 (d, J=2.4 Hz, 1H), 7.21 (d, J=8.8 Hz, 2H), 7.41 (d, J=8.4 Hz, 2H), 9.24 (d, J=7.6 Hz, 1H).

7-Chloro-2-ethyl-N-(4-(5-methoxypyridin-2-yl)benzyl)imidazo[1,2-a]pyridine-3-carboxamide (119)

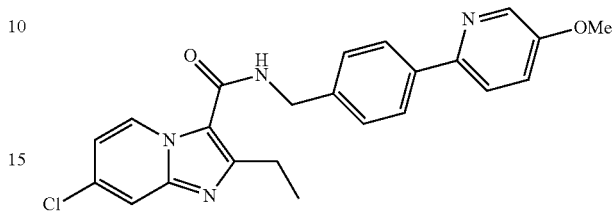

¹H NMR (400 MHz, CDCl₃) δ 1.40 (t, J=7.6 Hz, 3H), 2.97 (q, J=7.6 Hz, 2H), 3.91 (s, 3H), 4.74 (d, J=5.6 Hz, 2H), 6.11 (brs, 1H), 6.91 (dd, J=7.6, 2.0 Hz, 1H), 7.28 (d, J=8.8 Hz, 1H), 7.45 (d, J=8.4 Hz, 2H), 7.60 (d, J=2.0 Hz, 1H), 7.67 (d, J=8.8 Hz, 1H), 7.67 (d, J=8.8 Hz, 1H), 7.94 (d, J=8.4 Hz, 2H), 8.39 (d, J=2.8 Hz, 1H), 9.38 (d, J=7.2 Hz, 1H); LCMS (electrospray) m/z (M+H)⁺ 421.20

2-Ethyl-6-fluoro-N-(4-(trifluoromethoxy)benzyl)imidazo[1,2-a]pyridine-3-carboxamide (120)

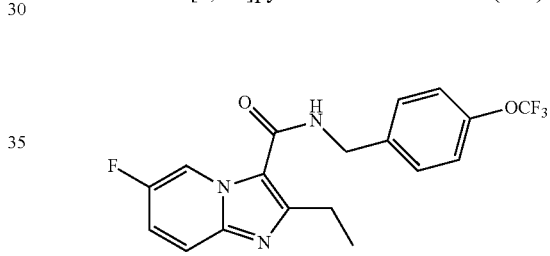

¹H NMR (400 MHz, CDCl₃) δ 1.42 (t, J=7.6 Hz, 3H), 3.00 (q, J=7.6 Hz, 2H), 4.71 (d, J=6.0 Hz, 2H), 6.14 (brs, 1H), 6.91 (dd, J=7.6, 2.0 Hz, 1H), 7.20 (d, J=8.0 Hz, 1H), 7.26 (m, 1H), 7.57 (d, J=5.2 Hz, 1H), 7.59 (d, J=5.2 Hz, 1H), 9.45 (dd, J=5.2, 2.4 Hz, 1H); LCMS (electrospray) m/z (M+H)⁺ 382.15

2-Ethyl-N-(4-(trifluoromethoxy)benzyl)-6-(trifluoromethyl)imidazo[1,2-a]pyridine-3-carboxamide (121)

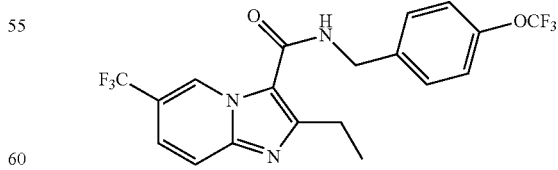

¹H NMR (400 MHz, CDCl₃) δ 1.43 (t, J=7.6 Hz, 3H), 3.02 (q, J=7.6 Hz, 2H), 4.71 (d, J=5.6 Hz, 2H), 6.21 (brs, 1H), 7.22 (d, J=8.4 Hz, 2H), 7.41 (d, J=8.4 Hz, 2H), 7.48 (dd, J=9.2, 1.2 Hz, 1H), 7.69 (d, J=9.2 Hz, 1H), 9.84 (d, J=1.2 Hz, 1H); LCMS (electrospray) m/z (M+H)⁺ 432.42

6-Chloro-2-ethyl-N-(4-(4-(4-(trifluoromethoxy)phenoxy)piperidin-1-yl)benzyl)imidazo[1,2-a]pyridine-3-carboxamide (122)

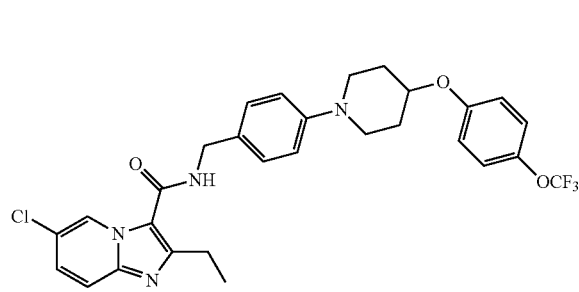

¹H NMR (400 MHz, CDCl₃) δ 1.38 (t, J=7.6 Hz, 3H), 1.90-1.98 (m, 2H), 2.07-2.13 (m, 2H), 2.96 (q, J=7.6 Hz, 2H), 3.10-3.16 (m, 2H), 3.48-3.54 (m, 2H), 4.42-4.48 (m, 1H), 3.22 (t, J=4.8 Hz, 4H), 4.61 (d, J=5.6 Hz, 2H), 6.00-6.20 (m, 1H), 6.91 (d, J=7.2 Hz, 2H), 6.96 (d, J=8.8 Hz, 2H), 7.14 (d, J=8.4 Hz, 1H), 7.26-7.31 (m, 3H), 7.54 (d, J=9.6 Hz, 1H), 9.53 (d, J=1.6 Hz, 1H).

7-Chloro-2-ethyl-N-(4-(4-(4-(trifluoromethoxy)phenoxy)piperidin-1-yl)benzyl)imidazo[1,2-a]pyridine-3-carboxamide (123)

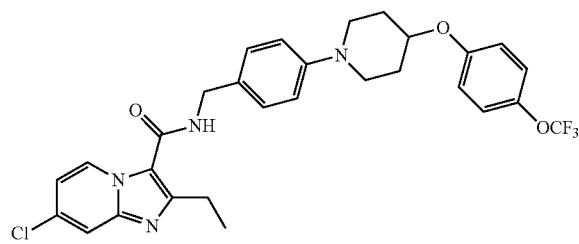

¹H NMR (400 MHz, CDCl₃) δ 1.38 (t, J=7.6 Hz, 3H), 1.89-1.98 (m, 2H), 2.07-2.13 (m, 2H), 2.95 (q, J=7.6 Hz, 2H), 3.09-3.16 (m, 2H), 3.47-3.53 (m, 2H), 4.42-4.48 (m, 1H), 3.22 (t, J=4.8 Hz, 4H), 4.60 (d, J=5.6 Hz, 2H), 5.99-6.01 (m, 1H), 6.88-6.93 (m, 3H), 6.96 (d, J=8.4 Hz, 2H), 7.14 (d, J=8.8 Hz, 2H), 7.26-7.29 (m, 2H), 7.59 (d, J=2.0 Hz, 1H), 9.36 (d, J=7.6 Hz, 1H).

2-Ethyl-N-(4-(4-(4-(trifluoromethoxy)phenoxy)piperidin-1-yl)benzyl)-6-(trifluoromethyl)imidazo[1,2-a]pyridine-3-carboxamide (124)

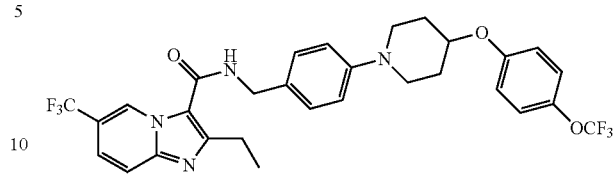

¹H NMR (400 MHz, CDCl₃) δ 1.41 (t, J=7.6 Hz, 3H), 1.90-1.98 (m, 2H), 2.08-2.13 (m, 2H), 2.99 (q, J=7.6 Hz, 2H), 3.10-3.15 (m, 2H), 3.47-3.54 (m, 2H), 4.43-4.46 (m, 1H), 4.62 (d, J=5.6 Hz, 2H), 6.05 (brs, 1H), 6.91 (d, J=8.4 Hz, 2H), 6.96 (d, J=8.4 Hz, 2H), 7.14 (d, J=8.4 Hz, 2H), 7.28 (d, J=8.4 Hz, 2H), 7.46 (dd, J=9.2, 2.0 Hz, 1H), 7.69 (d, J=9.2 Hz, 1H), 9.85 (d, J=2.0 Hz, 1H); LCMS (electrospray) m/z (M+H)⁺ 607.56

N-(4-(4-(4-(Butyramidomethyl)phenyl)piperazin-1-yl)benzyl)-7-chloro-2-ethylimidazo[1,2-a]pyridine-3-carboxamide (125)

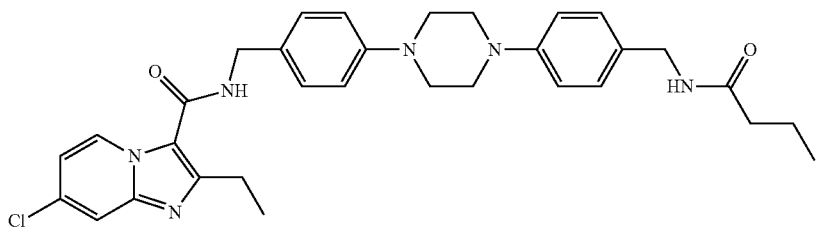

White solid; mp=238.0-239.2° C.; ¹H NMR (400 MHz, CDCl₃); δ 0.93 (t, J=6.4 Hz, 3H), 1.37 (t, J=6.0 Hz, 3H), 1.65-1.71 (m, 2H), 2.15 (t, J=6.4 Hz, 2H), 2.94 (q, J=6.0 Hz, 2H), 3.33 (s, 8H), 4.36 (d, J=4.4 Hz, 2H), 4.61 (d, J=4.0 Hz, 2H), 5.59 (brs, 1H), 6.01 (brs, 1H), 6.88-6.98 (m, 5H), 7.19 (d, J=7.2 Hz, 2H), 7.29 (d, J=7.2 Hz, 2H), 7.58 (s, 1H), 9.35 (d, J=7.2 Hz, 1H); LCMS (electrospray) m/z (M+H)⁺ 573.

7-Chloro-2-ethyl-N-(4-(4-(4-fluorobenzyl)piperazin-1-yl)benzyl)imidazo[1,2-a]pyridine-3-carboxamide (126)

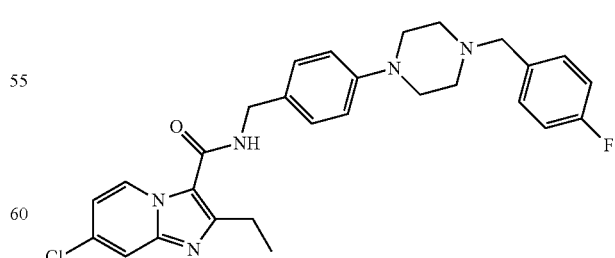

White solid; mp=141-142° C.; ¹H NMR (400 MHz, CDCl₃) δ 1.37 (t, J=7.8 Hz, 3H), 2.59 (t, J=4.8 Hz, 4H), 2.94 (q, J=7.2 Hz, 2H), 3.20 (t, J=5.0 Hz, 4H), 3.53 (s, 2H), 4.59 (d, J=5.2 Hz, 2H), 5.98-6.00 (m, 1H), 6.88-6.92 (m, 3H), 7.01 (dd, J=8.8, 8.8 Hz, 2H), 7.25-7.27 (m, 4H), 7.31 (dd, J=5.6, 8.0 Hz, 2H), 7.58 (d, J=2.0 Hz, 1H), 9.36 (d, J=7.6 Hz, 1H)); LCMS (electrospray) m/z (M+H)+ 506.36

7-Chloro-2-ethyl-N-(4-(4-(4-fluorophenyl)piperazin-1-yl)benzyl)imidazo[1,2-a]pyridine-3-carboxamide (127)

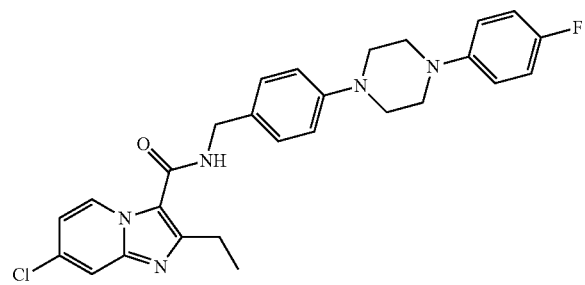 [SMILES: CCc1nc2cc(Cl)ccn2c1C(=O)NCc1ccc(N2CCN(c3ccc(F)cc3)CC2)cc1]

White solid; mp=212-213° C. ¹H NMR (400 MHz, CDCl₃) δ 1.39 (t, J=7.6 Hz, 3H), 2.95 (q, J=7.6 Hz, 2H), 3.26 (t, J=4.8 Hz, 4H), 3.35 (t, J=4.8 Hz, 4H), 4.62 (d, J=5.6 Hz, 2H), 6.01-6.03 (m, 1H), 6.89-7.02 (m, 7H), 7.30 (d, J=8.4 Hz, 2H), 7.59 (d, J=2.0 Hz, 1H), 9.37 (d, J=7.2 Hz, 1H)); LCMS (electrospray) m/z (M+H)+ 492.28

7-Chloro-2-ethyl-N-(4-(4-(trifluoromethoxy)phenoxy)benzyl)imidazo[1,2-a]pyridine-3-carboxamide (128)

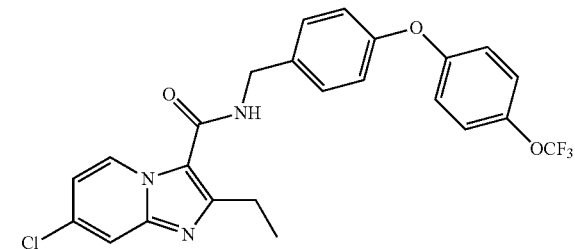 [SMILES: CCc1nc2cc(Cl)ccn2c1C(=O)NCc1ccc(Oc2ccc(OC(F)(F)F)cc2)cc1]

White solid; mp=141-142° C.; ¹H NMR (400 MHz, CDCl₃) δ 1.41 (t, J=7.6 Hz, 3H), 2.98 (q, J=7.6 Hz, 2H), 4.68 (d, J=5.6 Hz, 2H), 6.09-6.11 (m, 1H), 6.91 (dd, J=2.0, 7.6 Hz, 1H), 6.98-7.02 (m, 4H), 7.18 (d, J=8.8 Hz, 2H), 7.37 (d, J=8.4 Hz, 2H), 7.60 (d, J=2.0 Hz, 1H), 9.37 (d, J=7.2 Hz, 1H)); LCMS (electrospray) m/z (M+H)+ 490.24

7-Chloro-2-ethyl-N-(4-(4-fluorophenoxy)benzyl)imidazo[1,2-a]pyridine-3-carboxamide (129)

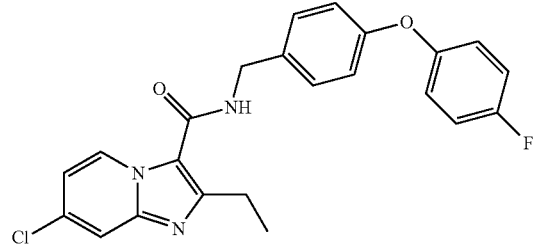 [SMILES: CCc1nc2cc(Cl)ccn2c1C(=O)NCc1ccc(Oc2ccc(F)cc2)cc1]

White solid; mp=146-147° C.; ¹H NMR (400 MHz, CDCl₃) δ 1.40 (t, J=7.6 Hz, 3H), 2.97 (q, J=7.6 Hz, 2H), 4.66 (d, J=5.6 Hz, 2H), 6.07-6.09 (m, 1H), 6.91 (dd, J=2.2, 7.4 Hz, 1H), 6.95-7.06 (m, 6H), 7.33 (d, J=8.4 Hz, 2H), 7.59 (d, J=2.2 Hz, 1H), 9.37 (d, J=7.2 Hz, 1H)); LCMS (electrospray) m/z (M+H)+ 424.26

6-Chloro-2-ethyl-N-(4-(4-(4-fluorobenzyl)piperazin-1-yl)benzyl)imidazo[1,2-a]pyridine-3-carboxamide (130)

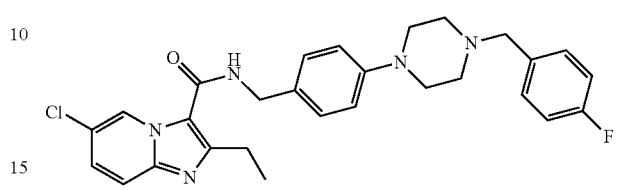

¹H NMR (400 MHz, CDCl₃) δ 1.38 (t, J=7.6 Hz, 3H), 2.59 (m, 4H), 2.95 (q, J=7.6 Hz, 2H), 3.20 (m, 4H), 3.52 (s, 2H), 4.60 (d, J=5.6 Hz, 2H), 6.00 (brs, 1H), 6.91 (d, J=8.4 Hz, 2H), 7.01 (t, J=8.4 Hz, 2H), 7.26-7.32 (m, 5H), 7.53 (d, J=9.6 Hz, 1H), 9.52 (d, J=1.2 Hz, 1H); LCMS (electrospray) m/z (M+H)+ 506.29

6-Chloro-2-ethyl-N-(4-(4-(trifluoromethoxy)phenoxy)benzyl)imidazo[1,2-a]pyridine-3-carboxamide (131)

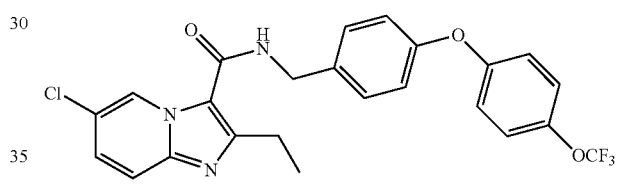

¹H NMR (400 MHz, CDCl₃) δ 1.42 (t, J=7.6 Hz, 3H), 2.99 (q, J=7.6 Hz, 2H), 4.68 (d, J=6.0 Hz, 2H), 6.11 (brs, 1H), 7.00 (d, J=8.8 Hz, 2H), 7.01 (d, J=8.4 Hz, 2H), 7.18 (d, J=8.8 Hz, 2H), 7.30 (dd, J=9.6, 2.0 Hz, 1H), 7.37 (d, J=8.8 Hz, 2H), 7.54 (d, J=9.2 Hz, 1H), 9.53 (d, J=1.6 Hz, 1H); LCMS (electrospray) m/z (M+H)+ 490.17

6-Chloro-2-ethyl-N-((1-(4-(trifluoromethoxy)phenyl)-1H-pyrazol-3-yl)methyl)imidazo[1,2-a]pyridine-3-carboxamide (132)

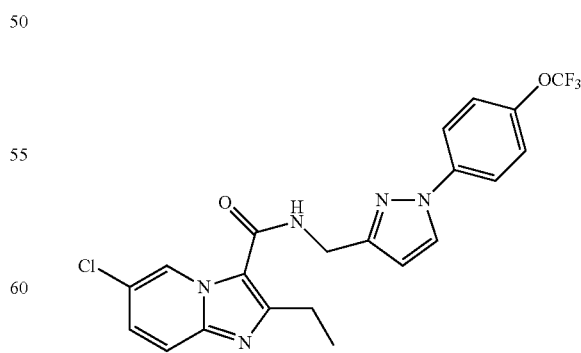

¹H NMR (400 MHz, CDCl₃) δ 1.48 (t, J=7.6 Hz, 3H), 3.12 (q, J=7.6 Hz, 2H), 4.80 (d, J=4.8 Hz, 2H), 6.49 (d, J=2.4 Hz, 2H), 6.69 (brs, 1H), 7.29-7.33 (m, 3H), 7.55 (d, J=9.2 Hz, 1H), 7.70 (d, J=9.2 Hz, 2H), 7.90 (d, J=2.4 Hz, 1H), 9.56 (d, J=2.0 Hz, 1H); LCMS (electrospray) m/z (M+H)⁺ 464.19

7-Chloro-2-ethyl-N-((1-(4-(trifluoromethoxy)phenyl)-1H-pyrazol-3-yl)methyl)imidazo[1,2-a]pyridine-3-carboxamide (133)

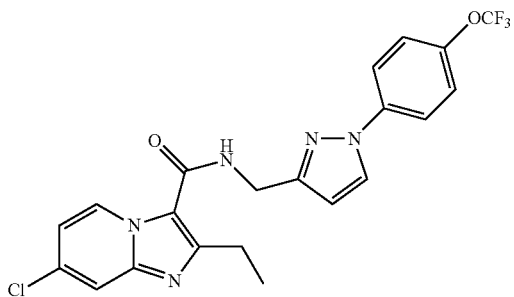 [SMILES: CCc1nc2cc(Cl)ccn2c1C(=O)NCc1ccn(-c2ccc(OC(F)(F)F)cc2)n1]

¹H NMR (400 MHz, CDCl₃) δ 1.47 (t, J=7.6 Hz, 3H), 3.11 (q, J=7.6 Hz, 2H), 4.79 (d, J=5.2 Hz, 2H), 6.48 (d, J=2.4 Hz, 2H), 6.68 (brs, 1H), 6.91 (dd, J=7.6, 2.0 Hz, 1H), 7.32 (d, J=8.4 Hz, 2H), 7.60 (d, J=2.0 Hz, 1H), 7.70 (d, J=6.8 Hz, 2H), 7.90 (d, J=2.0 Hz, 1H), 9.39 (d, J=7.6 Hz, 1H); LCMS (electrospray) m/z (M+H)⁺ 464.19

6-Chloro-N-(4-cyanobenzyl)-2-ethylimidazo[1,2-a]pyridine-3-carboxamide (134)

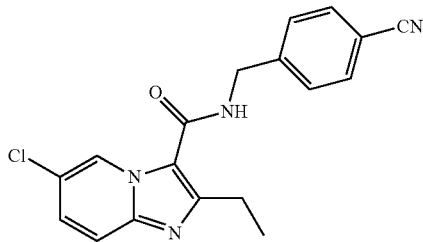 [SMILES: CCc1nc2ccc(Cl)cn2c1C(=O)NCc1ccc(C#N)cc1]

White solid; mp=223-224° C.; ¹H NMR (400 MHz, CDCl₃) δ 1.45 (t, J=7.6 Hz, 3H), 3.02 (q, J=7.2 Hz, 2H), 4.76 (d, J=6.0 Hz, 2H), 6.21-6.23 (m, 1H), 7.33 (dd, J=2.0, 9.6 Hz, 1H), 7.49 (d, J=8.0 Hz, 2H), 7.56 (d, J=9.2 Hz, 1H), 7.67 (d, J=8.0 Hz, 2H), 9.53 (d, J=2.0 Hz, 1H); LCMS (electrospray) m/z (M+H)⁺ 339.16

6-Chloro-2-ethyl-N-(4-(trifluoromethyl)benzyl)imidazo[1,2-a]pyridine-3-carboxamide (135)

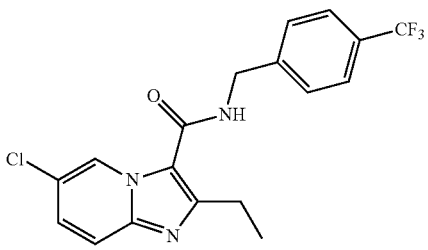 [SMILES: CCc1nc2ccc(Cl)cn2c1C(=O)NCc1ccc(C(F)(F)F)cc1]

White solid; mp=179-180° C.; ¹H NMR (400 MHz, CDCl₃) δ 1.44 (t, J=7.6 Hz, 3H), 3.01 (q, J=7.6 Hz, 2H), 4.77 (d, J=6.0 Hz, 2H), 6.19-6.21 (m, 1H), 7.32 (dd, J=2.0, 9.2 Hz, 1H), 7.50 (d, J=8.4 Hz, 2H), 7.56 (d, J=9.6 Hz, 1H), 7.64 (d, J=8.4 Hz, 2H), 9.54 (d, J=2.0 Hz, 1H)); LCMS (electrospray) m/z (M+H)⁺ 382.15

6-Chloro-2-ethyl-N-(4-methoxyphenethyl)imidazo[1,2-a]pyridine-3-carboxamide (136)

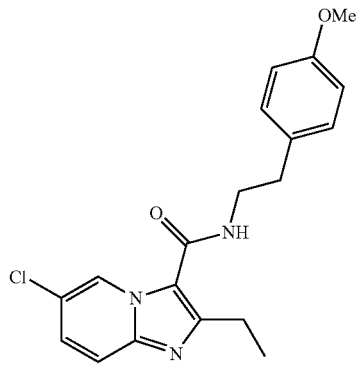 [SMILES: CCc1nc2ccc(Cl)cn2c1C(=O)NCCc1ccc(OC)cc1]

White solid; mp=129-130° C.; ¹H NMR (400 MHz, CDCl₃) δ 1.25 (t, J=7.4 Hz, 3H), 2.72 (q, J=7.6 Hz, 2H), 2.92 (t, J=6.8 Hz, 2H), 3.77 (q, J=5.6 Hz, 2H), 3.80 (s, 3H), 5.73-5.74 (m, 1H), 6.89 (d, J=8.4 Hz, 2H), 7.18 (d, J=8.8 Hz, 2H), 7.28 (d, J=2.0 Hz, 1H), 7.51 (dd, J=0.8, 9.6 Hz, 1H), 9.49 (d, J=2.0 Hz, 1H)); LCMS (electrospray) m/z (M+H)⁺ 358.21

6-Chloro-N-(4-chlorophenethyl)-2-ethylimidazo[1,2-a]pyridine-3-carboxamide (137)

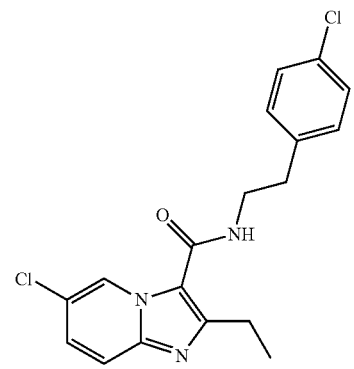 [SMILES: CCc1nc2ccc(Cl)cn2c1C(=O)NCCc1ccc(Cl)cc1]

White solid; mp=158-159° C.; ¹H NMR (400 MHz, CDCl₃) δ 1.28 (t, J=7.4 Hz, 3H), 2.76 (q, J=7.6 Hz, 2H), 2.96 (t, J=6.6 Hz, 2H), 3.78 (q, J=6.0 Hz, 2H), 5.73-5.74 (m, 1H), 7.20 (d, J=8.4 Hz, 2H), 7.29 (d, J=2.0 Hz, 1H), 7.32 (d, J=8.4 Hz, 1H), 7.52 (dd, J=2.0, 9.6 Hz, 1H), 9.48 (d, J=1.6 Hz, 1H)); LCMS (electrospray) m/z (M+H)⁺ 362.16

6-Chloro-2-ethyl-N-((1-(4-(trifluoromethoxy)benzyl)piperidin-4-yl)methyl)imidazo[1,2-a]pyridine-3-carboxamide (138)

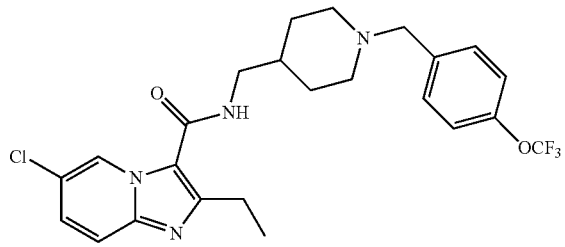 [SMILES: CCc1nc2ccc(Cl)cn2c1C(=O)NCC1CCN(Cc2ccc(OC(F)(F)F)cc2)CC1]

White solid; mp=171-172° C.; ¹H NMR (400 MHz, CDCl₃) δ 1.35-1.41 (m, 2H), 1.44 (t, J=7.6 Hz, 3H), 1.63-1.72 (m, 1H), 1.74-1.77 (m, 2H), 1.99-2.05 (m, 2H), 2.90-2.93 (m, 2H), 3.00 (q, J=7.6 Hz, 2H), 3.41 (t, J=6.2 Hz, 2H), 3.51 (s, 2H), 5.89 (t, J=5.4 Hz, 1H), 7.15 (d, J=8.0 Hz, 2H), 7.28 (dd, J=2.4, 9.6 Hz, 1H), 7.34 (d, J=8.4 Hz, 2H), 7.53 (d, J=9.6 Hz, 1H), 9.49 (d, J=1.6 Hz, 1H)); LCMS (electrospray) m/z (M+H)⁺ 495.34

6-Chloro-2-ethyl-N-((1-(4-fluorobenzyl)piperidin-4-yl)methyl)imidazo[1,2-a]pyridine-3-carboxamide (139)

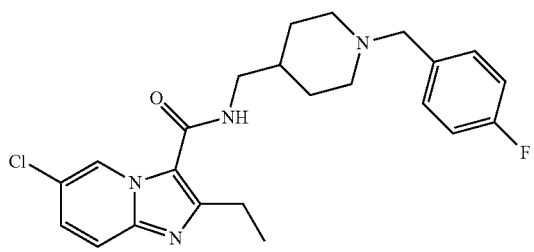 [SMILES: CCc1nc2ccc(Cl)cn2c1C(=O)NCC1CCN(Cc2ccc(F)cc2)CC1]

White solid; mp=176-177° C.; ¹H NMR (400 MHz, CDCl₃) δ 1.33-1.39 (m, 2H), 1.44 (t, J=7.6 Hz, 3H), 1.62-1.70 (m, 1H), 1.72-1.76 (m, 2H), 1.95-2.00 (m, 2H), 2.88-2.91 (m, 2H), 2.99 (q, J=7.6 Hz, 2H), 3.05 (t, J=6.4 Hz, 2H), 3.46 (s, 2H), 5.87-5.89 (m, 1H), 6.99 (dd, J=8.4, 8.8 Hz, 2H), 7.25-7.30 (m, 3H), 7.53 (d, J=9.6 Hz, 1H), 9.48 (d, J=1.6 Hz, 1H)); LCMS (electrospray) m/z (M+H)⁺ 429.29

7-Chloro-2-ethyl-N-((1-(4-(trifluoromethoxy)benzyl)piperidin-4-yl)methyl)imidazo[1,2-a]pyridine-3-carboxamide (140)

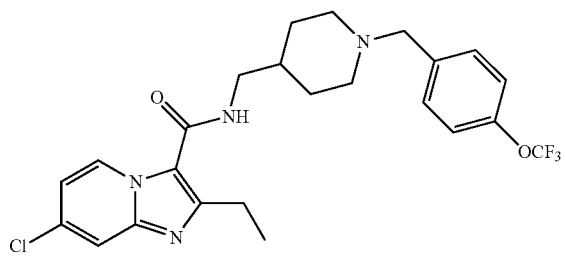 [SMILES: CCc1nc2cc(Cl)ccn2c1C(=O)NCC1CCN(Cc2ccc(OC(F)(F)F)cc2)CC1]

White solid; mp=145-146° C.; ¹H NMR (400 MHz, CDCl₃) δ 1.33-1.39 (m, 2H), 1.44 (t, J=7.6 Hz, 3H), 1.62-1.69 (m, 1H), 1.72-1.76 (m, 2H), 1.96-2.02 (m, 2H), 2.88-2.91 (m, 2H), 2.99 (q, J=7.6 Hz, 2H), 3.41 (t, J=6.4 Hz, 2H), 3.48 (s, 2H), 5.87 (t, J=5.4 Hz, 1H), 6.88 (dd, J=2.0, 7.6 Hz, 1H), 7.15 (d, J=8.0 Hz, 2H), 7.33 (d, J=8.4 Hz, 2H), 7.58 (d, J=2.4 Hz, 1H), 9.31 (d, J=7.2 Hz, 1H)); LCMS (electrospray) m/z (M+H)⁺ 495.20

2-Ethyl-N-(4-(trifluoromethoxy)benzyl)imidazo[1,2-a]pyrazine-3-carboxamide (141)

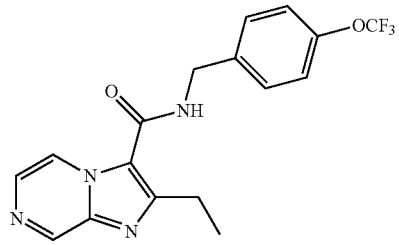 [SMILES: CCc1nc2cnccn2c1C(=O)NCc1ccc(OC(F)(F)F)cc1]

White solid; mp=176-177° C.; ¹H NMR (400 MHz, CDCl₃) δ 1.48 (t, J=7.6 Hz, 3H), 3.04 (q, J=7.6 Hz, 2H), 4.71 (d, J=5.6 Hz, 2H), 6.26-6.27 (m, 1H), 7.22 (d, J=8.0 Hz, 2H), 7.41 (d, J=8.8 Hz, 2H), 8.02 (d, J=4.8 Hz, 1H), 9.10 (d, J=1.2 Hz, 1H), 9.25 (dd, J=1.2, 4.8 Hz, 1H)); LCMS (electrospray) m/z (M+H)⁺ 365.12

2-Ethyl-3-((4-(trifluoromethoxy)benzyl)carbamoyl)imidazo[1,2-a]pyrazine 7-oxide (142)

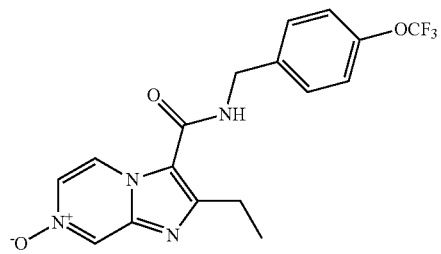

White solid; mp=215-216° C.; ¹H NMR (400 MHz, CDCl₃) δ 1.43 (t, J=7.6 Hz, 3H), 2.99 (q, J=7.6 Hz, 2H), 4.70 (d, J=6.0 Hz, 2H), 6.19-6.20 (m, 1H), 7.23 (d, J=8.0 Hz, 2H), 7.40 (d, J=8.4 Hz, 2H), 7.69 (dd, J=1.6, 5.6 Hz, 1H). 8.57 (d, J=2.0 Hz, 1H), 9.29 (d, J=6.0 Hz, 1H)); LCMS (electrospray) m/z (M+H)⁺ 381.13

6-Chloro-2-ethyl-3-((4-(trifluoromethoxy)phenoxy)methyl)imidazo[1,2-a]pyridine (143)

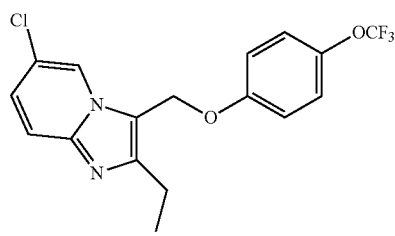 [SMILES: CCc1nc2ccc(Cl)cn2c1COc1ccc(OC(F)(F)F)cc1]

White solid; mp=127-128° C.; $^1$H NMR (400 MHz, CDCl$_3$) δ 1.34 (t, J=7.6 Hz, 3H), 2.82 (q, J=7.6 Hz, 2H), 5.27 (s, 2H), 7.00 (d, J=9.2 Hz, 2H), 7.19 (d, J=9.2 Hz, 2H), 7.53 (dd, J=0.8, 9.2 Hz, 1H), 8.12 (dd, J=0.8, 2.0 Hz, 1H); LCMS (electrospray) m/z (M+H)$^+$ 371.07

N-((6-Chloro-2-ethylimidazo[1,2-a]pyridin-3-yl)methyl)-4-(trifluoromethoxy)aniline (144)

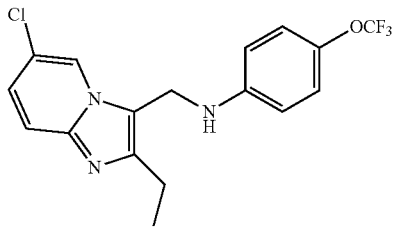 [SMILES: CCc1nc2ccc(Cl)cn2c1CNc1ccc(OC(F)(F)F)cc1]

White solid; $^1$H NMR (400 MHz, CDCl$_3$) δ 1.35 (J=7.6 Hz, 3H), 2.82 (q, J=7.2 Hz, 2H), 3.67 (t, J=4.6 Hz, 1H), 4.50 (d, J=5.2 Hz, 2H), 6.72 (d, J=8.8 Hz, 2H), 7.13 (d, J=8.8 Hz, 2H), 7.51 (dd, J=2.0, 9.6 Hz, 1H), 7.51 (d, J=9.6 Hz, 1H), 8.10 (d, J=1.2 Hz, 1H); LCMS (electrospray) m/z (M+H)$^{30}$ 370.11

6-Chloro-2-ethylimidazo[1,2-a]pyridine-3-carbaldehyde (145)

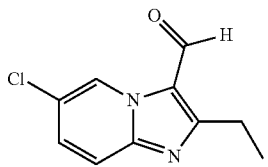

White solid; mp=115-116° C.; $^1$H NMR (400 MHz, CDCl$_3$) δ 1.44 (t, J=7.6 Hz, 3H), 3.07 (q, J=7.6 Hz, 2H), 7.49 (dd, J=2.0, 9.2 Hz, 1H), 7.64 (d, J=9.2 Hz, 1H), 9.62 (d, J=2.0 Hz, 1H), 10.03 (s, 1H); LCMS (electrospray) m/z (M+H)$^+$ 209.09

(6-Chloro-2-ethylimidazo[1,2-a]pyridin-3-yl)methanol (146)

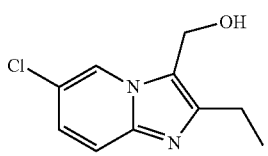

White solid; mp=173.2-174.2° C.; $^1$H NMR (400 MHz, CDCl$_3$) δ 1.29 (t, J=7.6 Hz, 3H), 2.72 (q, J=7.6 Hz, 2H), 4.93 (s, 2H), 7.13 (dd, J=2.0, 9.6 Hz, 1H), 7.43 (d, J=9.6 Hz, 1H), 8.26 (d, J=2.0 Hz, 1H); LCMS (electrospray) m/z (M+H)$^+$ 211.07

6-Chloro-2-ethyl-N-((1-(4-(trifluoromethoxy)phenyl)-4,5,6,7-tetrahydro-1H-indazol-4-yl)methyl)imidazo[1,2-a]pyridine-3-carboxamide (147)

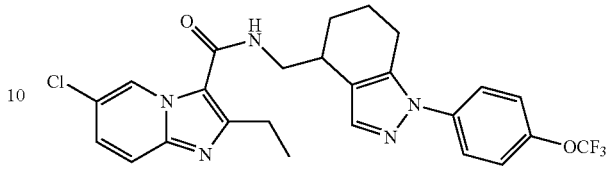

$^1$H NMR (400 MHz, CDCl$_3$) δ 1.41 (t, J=7.6 Hz, 3H), 1.89-1.98 (m, 3H), 2.27 (m, 1H), 2.77-2.84 (m, 2H), 2.96 (q, J=7.6 Hz, 2H), 5.40 (m, 1H), 5.96 (d, J=8.0 Hz, 1H), 7.29-7.34 (m, 3H), 7.54-7.58 (m, 3H), 7.70 (s, 1H), 9.54 (d, J=1.2 Hz, 1H); LCMS (electrospray) m/z (M+H)$^+$ 504.25

6-Chloro-2-ethyl-N-(4-(4-(4-fluorophenyl)piperazin-1-yl)benzyl)imidazo[1,2-a]pyridine-3-carboxamide (148)

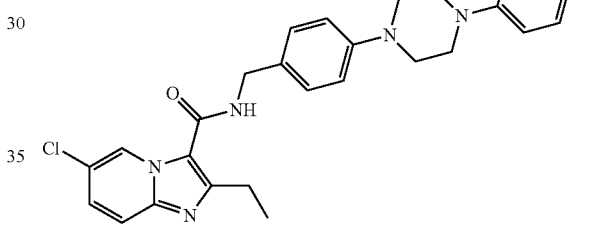

$^1$H NMR (400 MHz, CDCl$_3$) δ 1.40 (t, J=7.6 Hz, 3H), 2.96 (q, J=7.6 Hz 2H), 3.25-3.27 (m, 4H), 3.34-3.36 (m, 4H), 4.62 (d, J=5.6 Hz, 2H), 6.02-6.64 (m, 1H), 6.92-6.95 (m, 3H), 6.97-7.01 (m, 3H), 7.29 (dd, J=2.4, 9.6 Hz, 1H), 7.31 (d, J=8.8 Hz, 2H), 7.54 (d, J=9.6 Hz, 2H), 9.54 (d, J=1.2 Hz, 2H); LCMS (electrospray) m/z (M+H)$^+$ 492.28

6-Chloro-2-ethyl-N-((1-(4-fluorophenyl)-4,5,6,7-tetrahydro-1H-indazol-4-yl)methyl)imidazo[1,2-a]pyridine-3-carboxamide (149)

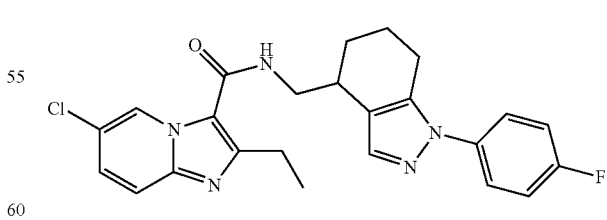

$^1$H NMR (400 MHz, CDCl$_3$) δ 1.42 (t, J=7.6 Hz, 3H), 1.88-1.97 (m, 3H), 2.26 (m, 1H), 2.74-2.78 (m, 2H), 2.96 (q, J=7.6 Hz, 2H), 5.40 (m, 1H), 5.96 (d, J=7.6 Hz, 1H), 7.17 (dd, J=8.0, 8.8 Hz, 2H), 7.31 (dd, J=9.2, 2.0 Hz, 1H), 7.48-7.50 (m, 2H), 7.55 (d, J=9.2 Hz, 1H), 7.68 (s, 1H), 9.54 (d, J=2.0 Hz, 1H); LCMS (electrospray) m/z (M+H)$^+$ 438.40

2-Ethyl-7-nitro-N-(4-(trifluoromethoxy)benzyl)imi-
dazo[1,2-a]pyridine-3-carboxamide (150)

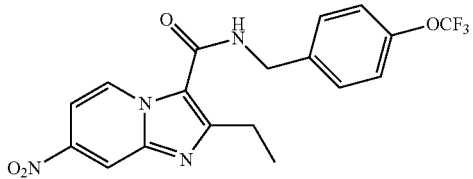 [SMILES: CCc1nc2cc([N+](=O)[O-])ccn2c1C(=O)NCc1ccc(OC(F)(F)F)cc1]

$^1$H NMR (400 MHz, DMSO-d$_6$) δ 1.29 (t, J=7.6 Hz, 3H), 3.05 (q, J=7.6 Hz, 2H), 4.57 (d, J=5.6 Hz, 2H), 7.35 (d, J=8.4 Hz, 2H), 7.50 (d, J=8.4 Hz, 2H), 7.76 (dd, J=7.6, 2.4 Hz, 1H), 8.56 (d, J=2.4 Hz, 1H), 8.79 (brs, 1H), 9.06 (d, J=8.0 Hz, 1H); LCMS (electrospray) m/z (M+H)$^+$ 409.35

6-Chloro-2-ethyl-N-((1-(4-(trifluoromethyl)phenyl)-1H-pyrazol-3-yl)methyl)imidazo[1,2-a]pyridine-3-carboxamide (151)

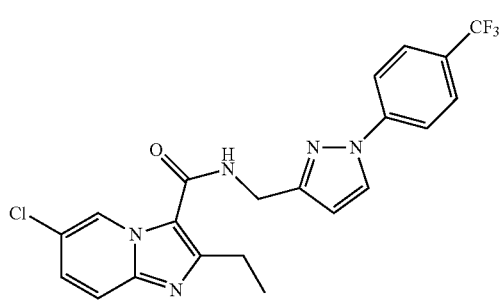 [SMILES: CCc1nc2ccc(Cl)cn2c1C(=O)NCc1ccn(-c2ccc(C(F)(F)F)cc2)n1]

$^1$H NMR (400 MHz, DMSO-d$_6$) δ 1.29 (t, J=7.6 Hz, 3H), 3.02 (q, J=7.6 Hz, 2H), 4.62 (d, J=5.6 Hz, 2H), 6.59 (d, J=2.8 Hz, 1H), 7.46 (dd, J=9.2, 1.6 Hz, 1H), 7.67 (d, J=9.2 Hz, 1H), 7.87 (d, J=8.8 Hz, 2H), 8.06 (d, J=8.4 Hz, 2H), 8.55 (t, J=5.6 Hz, 1H), 8.62 (d, J=2.4 Hz, 1H), 9.10 (d, J=2.0 Hz, 2H); LCMS (electrospray) m/z (M+H)$^+$ 448.37

7-Chloro-2-ethyl-N-((1-(4-(trifluoromethyl)phenyl)-1H-pyrazol-3-yl)methyl)imidazo[1,2-a]pyridine-3-carboxamide (152)

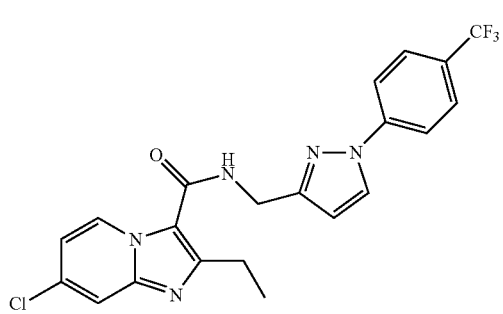 [SMILES: CCc1nc2cc(Cl)ccn2c1C(=O)NCc1ccn(-c2ccc(C(F)(F)F)cc2)n1]

$^1$H NMR (400 MHz, DMSO-d$_6$) δ 1.28 (t, J=7.6 Hz, 3H), 3.02 (q, J=7.6 Hz, 2H), 4.61 (d, J=5.6 Hz, 2H), 6.58 (d, J=2.8 Hz, 1H), 7.11 (dd, J=7.6, 2.0 Hz, 1H), 7.80 (d, J=2.0 Hz, 1H), 7.87 (d, J=8.8 Hz, 2H), 8.06 (d, J=8.8 Hz, 2H), 8.52 (t, J=5.6 Hz, 1H), 8.61 (d, J=2.4 Hz, 1H), 8.97 (d, J=7.6 Hz, 1H); LCMS (electrospray) m/z (M+H)$^+$ 448.13

6-Chloro-2-ethyl-N-((1-(4-fluorophenyl)-1H-pyrazol-3-yl)methyl)imidazo[1,2-a]pyridine-3-carboxamide (153)

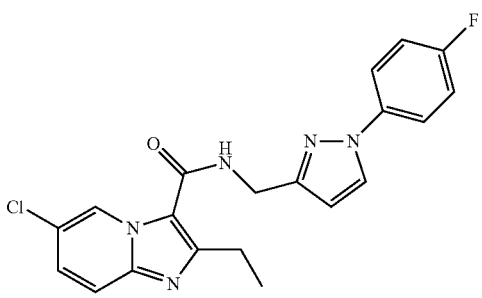 [SMILES: CCc1nc2ccc(Cl)cn2c1C(=O)NCc1ccn(-c2ccc(F)cc2)n1]

$^1$H NMR (400 MHz, CDCl$_3$) δ 1.47 (t, J=7.6 Hz, 3H), 3.11 (q, J=7.6 Hz, 2H), 4.79 (d, J=4.8 Hz, 2H), 6.46 (d, J=2.0 Hz, 1H), 6.70 (brs, 1H), 7.16 (dd, J=8.8 Hz, 2H), 7.30 (dd, J=9.2, 2.0 Hz, 1H), 7.55 (d, J=9.6 Hz, 1H), 7.61-7.64 (m, 2H), 7.85 (d, J=2.4 Hz, 1H), 9.56 (d, J=2.0 Hz, 1H); LCMS (electrospray) m/z (M+H)$^+$ 398.32

7-Chloro-2-ethyl-N-((1-(4-fluorophenyl)-1H-pyrazol-3-yl)methyl)imidazo[1,2-a]pyridine-3-carboxamide (154)

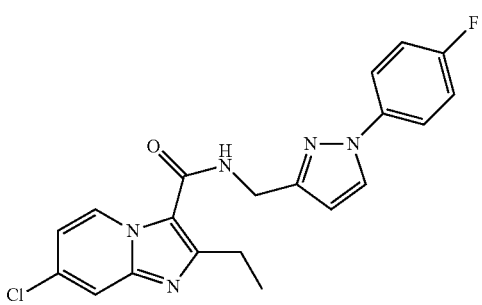 [SMILES: CCc1nc2cc(Cl)ccn2c1C(=O)NCc1ccn(-c2ccc(F)cc2)n1]

$^1$H NMR (400 MHz, CDCl$_3$) δ 1.46 (t, J=7.6 Hz, 3H), 3.11 (q, J=7.6 Hz, 2H), 4.78 (d, J=4.8 Hz, 2H), 6.46 (d, J=2.0 Hz, 1H), 6.69 (brs, 1H), 6.91 (dd, J=7.6, 2.4 Hz, 1H), 7.16 (dd, J=8.8 Hz, 2H), 7.59-7.64 (m, 3H), 7.85 (d, J=2.4 Hz, 1H), 9.39 (d, J=7.6 Hz, 1H); LCMS (electrospray) m/z (M+H)$^+$ 398.14

7-Chloro-2-ethyl-N-(4-(trifluoromethyl)benzyl)imi-
dazo[1,2-a]pyridine-3-carboxamide (155)

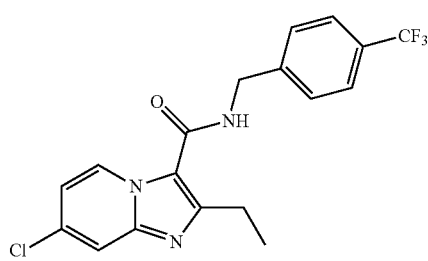 [SMILES: CCc1nc2cc(Cl)ccn2c1C(=O)NCc1ccc(C(F)(F)F)cc1]

White solid; mp=196.2-196.9° C.; ¹H NMR (400 MHz, CDCl₃) δ 1.43 (t, J=7.4 Hz, 3H), 3.00 (q, J=7.6 Hz, 2H), 4.76 (d, J=6.4 Hz, 2H), 6.92 (dd, J=2.0, 7.2 Hz, 1H), 7.49 (d, J=8.4 Hz, 2H), 7.60 (d, J=2.0 Hz, 1H), 7.63 (d, J=8.0 Hz, 2H), 9.36 (d, J=7.6 Hz, 1H); LCMS (electrospray) m/z (M+H)⁺ 382.15

6-Chloro-2-ethyl-N-(4-(4-(4-(trifluoromethoxy)benzyl)piperazin-1-yl)benzyl)imidazo[1,2-a]pyridine-3-carboxamide (156)

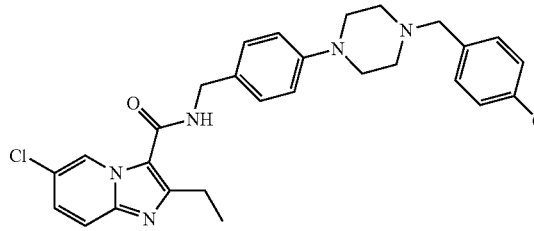

White solid; mp=138.1-138.7° C.; ¹H NMR (400 MHz, CDCl₃) δ 1.39 (t, J=7.6 Hz, 3H), 2.60 (t, J=5.0 Hz, 4H), 2.95 (q, J=7.6 Hz, 2H), 3.21 (t, J=5.0 Hz, 4H), 3.56 (s, 2H), 4.60 (d, J=5.6 Hz, 2H), 6.00-6.02 (m, 1H), 6.92 (d, J=8.8 Hz, 2H), 7.18 (d, J=8.0 Hz, 2H), 7.26-7.30 (m, 3H), 7.38 (d, J=8.4 Hz, 2H), 7.53 (d, J=9.2 Hz, 1H), 9.53 (d, J=2.0 Hz, 1H); LCMS (electrospray) m/z (M+H)⁺ 572.40

7-Chloro-2-ethyl-N-(4-(4-(4-(trifluoromethoxy)benzyl)piperazin-1-yl)benzyl)imidazo[1,2-a]pyridine-3-carboxamide (157)

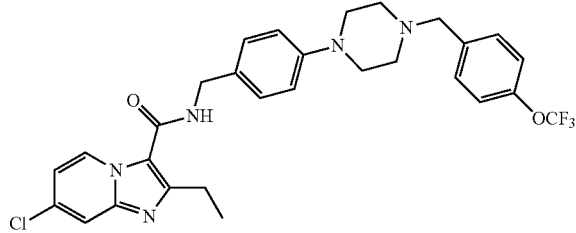

White solid; mp=137.1-137.6° C.; ¹H NMR (400 MHz, CDCl₃) δ 1.37 (t, J=7.6 Hz, 3H), 2.60 (t, J=4.8 Hz, 4H), 2.94 (q, J=7.6 Hz, 2H), 3.21 (t, J=4.8 Hz, 4H), 3.56 (s, 2H), 4.60 (d, J=5.6 Hz, 2H), 5.99-6.00 (m, 1H), 6.88-6.93 (m, 3H), 7.18 (d, J=8.0 Hz, 2H), 7.26 (d, J=8.0 Hz, 2H), 7.38 (d, J=8.4 Hz, 2H), 7.58 (d, J=1.6 Hz, 1H), 9.36 (d, J=7.6 Hz, 1H); LCMS (electrospray) m/z (M+H)⁺ 572.40

6-Chloro-2-ethyl-N-(4-(4-(4-(trifluoromethoxy)phenyl)piperazin-1-yl)benzyl)imidazo[1,2-a]pyridine-3-carboxamide (158)

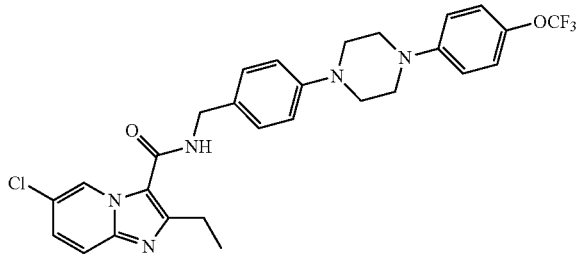 [SMILES: CCc1nc2ccc(Cl)cn2c1C(=O)NCc1ccc(N2CCN(c3ccc(OC(F)(F)F)cc3)CC2)cc1]

White solid; mp=206.5-207.0° C.; ¹H NMR (400 MHz, CDCl₃) δ 1.40 (t, J=7.6 Hz, 3H), 2.96 (q, J=7.6 Hz, 2H), 3.30-3.40 (m, 8H), 4.63 (d, J=5.2 Hz, 2H), 6.03-6.04 (m, 1H), 6.95 (d, J=9.2 Hz, 2H), 6.98 (d, J=8.4 Hz, 2H), 7.14 (d, J=8.0 Hz, 2H), 7.27-7.32 (m, 3H), 7.54 (d, J=9.6 Hz, 1H), 9.53-9.34 (m, 1H); LCMS (electrospray) m/z (M+H)⁺ 558.32

7-Chloro-2-ethyl-N-(4-(4-(4-(trifluoromethoxy)phenyl)piperazin-1-yl)benzyl)imidazo[1,2-a]pyridine-3-carboxamide (159)

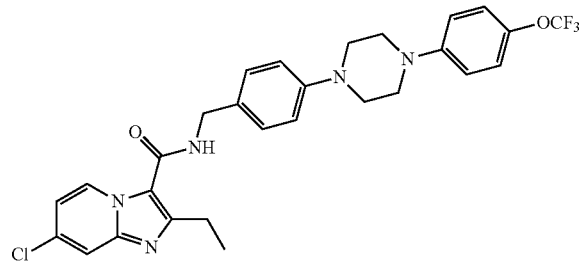 [SMILES: CCc1nc2cc(Cl)ccn2c1C(=O)NCc1ccc(N2CCN(c3ccc(OC(F)(F)F)cc3)CC2)cc1]

White solid; mp=216.3-217.0° C.; ¹H NMR (400 MHz, CDCl₃) δ 1.39 (t, J=7.6 Hz, 3H), 2.95 (q, J=7.6 Hz, 2H), 3.30-3.40 (m, 8H), 4.62 (d, J=5.6 Hz, 2H), 6.01-6.02 (m, 1H), 6.90 (dd, J=2.0, 7.2 Hz, 1H), 6.94 (d, J=9.2 Hz, 2H), 6.98 (d, J=8.8 Hz, 2H), 7.14 (d, J=8.8 Hz, 2H), 7.31 (d, J=8.8 Hz, 2H), 7.59 (d, J=1.6 Hz, 1H), 9.37 (d, J=7.6 Hz, 1H); LCMS (electrospray) m/z (M+H)⁺ 558.32

6-Chloro-N-(4-(4-chlorophenoxy)benzyl)-2-ethylimidazo[1,2-a]pyridine-3-carboxamide (160)

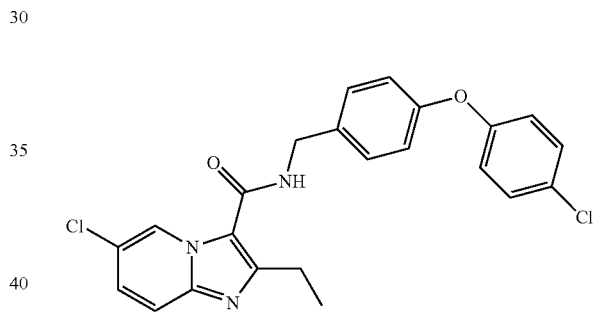

White solid; mp=159-160.7° C.; ¹H NMR (400 MHz, CDCl₃) δ 1.42 (t, J=7.6 Hz, 3H), 2.99 (q, J=7.2 Hz, 2H), 4.68 (d, J=5.6 Hz, 2H), 6.10-6.11 (m, 1H), 6.94 (d, J=9.2 Hz, 2H), 7.00 (d, J=8.8 Hz, 2H), 7.27-7.32 (m, 3H), 7.36 (d, J=8.4 Hz, 2H), 7.55 (d, J=9.6 Hz, 1H), 9.54 (d, J=2.0 Hz, 1H); LCMS (electrospray) m/z (M+H)⁺ 440.18

7-Chloro-N-(4-(4-chlorophenoxy)benzyl)-2-ethylimidazo[1,2-a]pyridine-3-carboxamide (161)

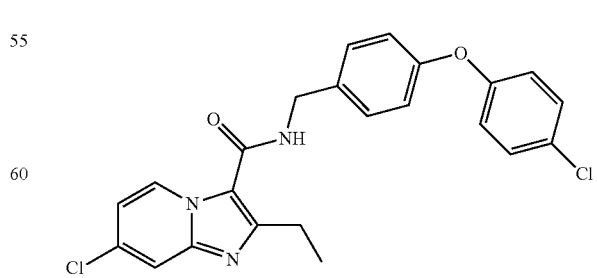

White solid; mp=167.1-167.9° C.; ¹H NMR (400 MHz, CDCl₃) δ 1.41 (t, J=7.6 Hz, 3H), 2.98 (q, J=7.6 Hz, 2H), 4.67

(d, J=5.6 Hz, 2H), 6.08-6.10 (m, 1H), 6.91 (dd, J=2.4, 7.6 Hz, 1H), 6.94 (d, J=8.8 Hz, 2H), 7.00 (d, J=8.8 Hz, 2H), 7.29 (d, J=9.2 Hz, 2H), 7.35 (d, J=8.8 Hz, 2H), 7.60 (d, J=2.0 Hz, 1H), 9.37 (d, J=7.6 Hz, 1H); LCMS (electrospray) m/z (M+H)⁺ 440.18

[1,1'-Biphenyl]-4-ylmethyl 6-chloro-2-ethylimidazo[1,2-a]pyridine-3-carboxylate (162)

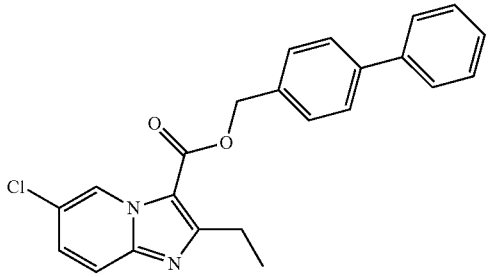 [SMILES: CCc1nc2ccc(Cl)cn2c1C(=O)OCc1ccc(-c2ccccc2)cc1]

White solid; mp=122.3-123.0° C.; ¹H NMR (400 MHz, CDCl₃) δ 1.34 (t, J=7.6 Hz, 3H), 3.13 (q, J=7.6 Hz, 2H), 5.48 (s, 2H), 7.34-7.38 (m, 2H), 7.45 (dd, J=7.2, 8.0 Hz, 2H), 7.54 (d, J=8.4 Hz, 2H), 7.57-7.65 (m, 5H), 9.45 (d, J=2.0 Hz, 1H); LCMS (electrospray) m/z (M+H)⁺ 390.20

4-Phenoxybenzyl 6-chloro-2-ethylimidazo[1,2-a]pyridine-3-carboxylate (163)

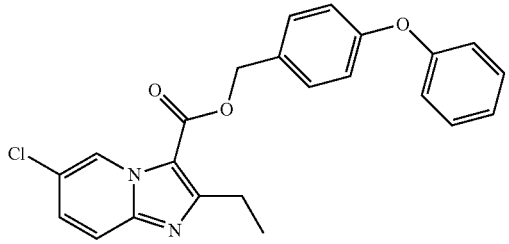 [SMILES: CCc1nc2ccc(Cl)cn2c1C(=O)OCc1ccc(Oc2ccccc2)cc1]

White solid; mp=123.3-123.8° C.; ¹H NMR (400 MHz, CDCl₃) δ 1.31 (t, J=7.4 Hz, 3H), 3.10 (q, J=7.6 Hz, 2H), 4.67 (s, 2H), 7.02 (d, J=8.4 Hz, 4H), 7.12 (dd, J=7.2, 7.6 Hz, 1H), 7.34 (dd, J=7.2, 7.6 Hz, 3H), 7.43 (d, J=8.8 Hz, 2H), 7.58 (d, J=9.6 Hz, 1H), 9.42 (d, J=2.0 Hz, 1H); LCMS (electrospray) m/z (M+H)⁺ 407.12

6-Chloro-2-ethyl-N-(4-(4-fluorophenoxy)benzyl)-N-methylimidazo[1,2-a]pyridine-3-carboxamide (164)

White solid; ¹H NMR (400 MHz, CDCl₃) δ 1.37 (t, J=7.4 Hz, 3H), 2.78 (q, J=7.6 Hz, 2H), 3.01 (s, 3H), 4.70 (s, 2H), 6.94-7.06 (m, 6H), 7.21-7.26 (m, 3H), 8.47 (d, J=9.2 Hz, 1H), 8.47 (d, J=1.6 Hz, 1H); LCMS (electrospray) m/z (M+H)⁺ 438.20

5-(6-Chloro-2-ethylimidazo[1,2-a]pyridin-3-yl)-3-(4-(trifluoromethoxy)benzyl)-1,2,4-oxadiazole (165)

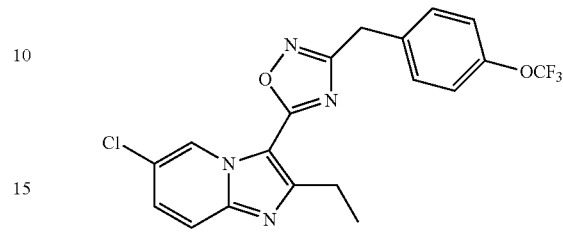

Pale yellow solid; mp=146.4-146.9° C.; ¹H NMR (400 MHz, CDCl₃) δ 1.42 (t, J=7.6 Hz, 3H), 3.22 (q, J=7.2 Hz, 2H), 4.20 (s, 2H), 7.21 (d, J=8.0 Hz, 2H), 7.40 (dd, J=2.0, 9.6 Hz, 1H), 7.46 (d, J=8.8 Hz, 2H), 7.65 (d, J=9.6 Hz, 1H), 8.47 (d, J=1.2 Hz, 1H); LCMS (electrospray) m/z (M+H)⁺ 423.10

6-Chloro-N-(4-(4-(4-chlorophenoxy)piperidin-1-yl)benzyl)-2-ethylimidazo[1,2-a]pyridine-3-carboxamide (166)

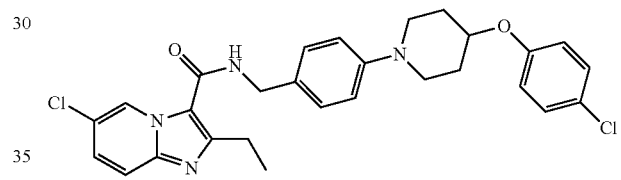

¹H NMR (400 MHz, CDCl₃) δ 1.39 (t, J=7.6 Hz, 3H), 1.94 (m, 2H), 2.06-2.10 (m, 2H), 2.96 (q, J=7.6 Hz, 2H), 3.09-3.14 (m, 2H), 3.15-3.52 (m, 2H), 4.43 (m, 1H), 4.61 (d, J=5.6 Hz, 2H), 6.01 (brs, 1H), 6.85 (d, J=9.2 Hz, 2H), 6.95 (d, J=8.8 Hz, 2H), 7.20-7.31 (m, 5H), 7.53 (d, J=10.4 Hz, 1H), 9.53 (d, J=1.2 Hz, 1H); LCMS (electrospray) m/z (M+H)⁺ 523.29

7-Chloro-N-(4-(4-(4-chlorophenoxy)piperidin-1-yl)benzyl)-2-ethylimidazo[1,2-a]pyridine-3-carboxamide (167)

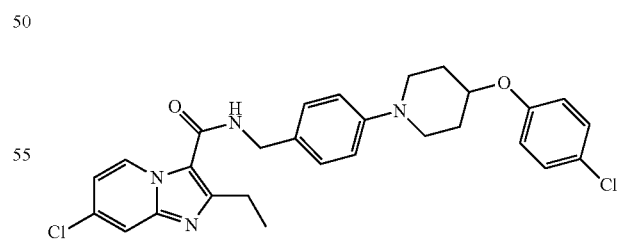

¹H NMR (400 MHz, CDCl₃) δ 1.21 (t, J=7.2 Hz, 3H), 1.91-1.96 (m, 2H), 2.06-2.11 (m, 2H), 2.96 (q, J=7.6 Hz, 2H), 2.97-3.15 (m, 2H), 3.47-3.52 (m, 2H), 4.43 (m, 1H), 4.60 (d, J=5.6 Hz, 2H), 6.00 (brs, 1H), 6.86 (d, J=8.8 Hz, 2H), 6.90 (dd, J=7.6, 2.4 Hz, 1H), 6.95 (d, J=8.8 Hz, 2H), 7.21-7.28 (m, 4H), 7.58 (d, J=1.6 Hz, 1H), 9.36 (d, J=7.6 Hz, 1H); LCMS (electrospray) m/z (M+H)⁺ 523.29

89

6-Chloro-2-ethyl-N-(4-(4-(4-(trifluoromethyl)phenoxy)piperidin-1-yl)benzyl)imidazo[1,2-a]pyridine-3-carboxamide (168)

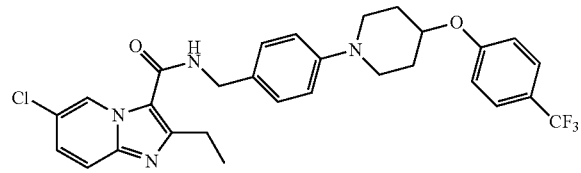 [SMILES: CCc1nc2ccc(Cl)cn2c1C(=O)NCc1ccc(N2CCC(Oc3ccc(C(F)(F)F)cc3)CC2)cc1]

$^1$H NMR (400 MHz, CDCl$_3$) δ 1.40 (t, J=7.6 Hz, 3H), 1.94-1.99 (m, 2H), 2.10-2.15 (m, 2H), 2.96 (q, J=7.6 Hz, 2H), 3.12-3.18 (m, 2H), 3.47-3.53 (m, 2H), 4.53-4.57 (m, 1H), 4.61 (d, J=5.2 Hz, 2H), 6.02 (brs, 1H), 6.96 (d, J=8.4 Hz, 2H), 6.98 (d, J=8.4 Hz, 2H), 7.27-7.31 (m, 3H), 7.51-7.55 (m, 3H), 9.53 (d, J=2.0 Hz, 1H); LCMS (electrospray) m/z (M+H)$^+$ 557.37

7-Chloro-2-ethyl-N-(4-(4-(4-(trifluoromethyl)phenoxy)piperidin-1-yl)benzyl)imidazo[1,2-a]pyridine-3-carboxamide (169)

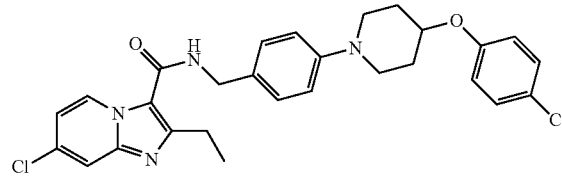

$^1$H NMR (400 MHz, CDCl$_3$) δ 1.39 (t, J=7.6 Hz, 3H), 1.94-1.98 (m, 2H), 2.09-2.11 (m, 2H), 2.95 (q, J=7.6 Hz, 2H), 3.12-3.18 (m, 2H), 3.47-3.53 (m, 2H), 4.55 (m, 1H), 4.60 (d, J=5.6 Hz, 2H), 6.00 (brs, 1H), 6.90 (dd, J=7.6, 2.0 Hz, 1H), 6.96 (d, J=8.8 Hz, 2H), 6.98 (d, J=8.4 Hz, 2H), 7.28 (d, J=8.8 Hz, 2H), 7.54 (d, J=8.4 Hz, 2H), 7.58 (d, J=2.0 Hz, 1H), 9.36 (d, J=8.0 Hz, 1H); LCMS (electrospray) m/z (M+H)$^+$ 557.37

6-Chloro-2-ethyl-N-(4-(4-(trifluoromethyl)benzyloxy)benzyl)imidazo[1,2-a]pyridine-3-carboxamide (170)

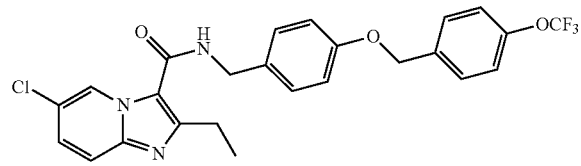 [SMILES: CCc1nc2ccc(Cl)cn2c1C(=O)NCc1ccc(OCc2ccc(OC(F)(F)F)cc2)cc1]

$^1$H NMR (400 MHz, CDCl$_3$) δ 1.40 (t, J=7.6 Hz, 3H), 2.96 (q, J=7.6 Hz, 2H), 4.64 (d, J=5.6 Hz, 2H), 5.06 (s, 2H), 6.05 (brs, 1H), 6.97 (d, J=8.4 Hz, 2H), 7.20-7.33 (m, 5H), 7.46 (d, J=8.8 Hz, 2H), 7.54 (d, J=9.2 Hz, 2H), 9.53 (d, J=1.2 Hz, 1H); LCMS (electrospray) m/z (M+H)$^+$ 504.25

90

7-Chloro-2-ethyl-N-(4-(4-(trifluoromethyl)benzyloxy)benzyl)imidazo[1,2-a]pyridine-3-carboxamide (171)

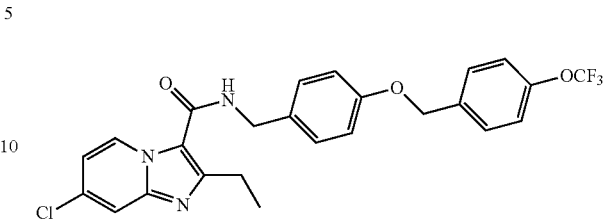

$^1$H NMR (400 MHz, CDCl$_3$) δ 1.39 (t, J=7.6 Hz, 3H), 2.95 (q, J=7.6 Hz, 2H), 4.63 (d, J=5.6 Hz, 2H), 5.06 (s, 2H), 6.03 (brs, 1H), 6.90 (dd, J=7.6, 2.0 Hz, 1H), 6.97 (d, J=8.8 Hz, 2H), 7.23 (d, J=8.0 Hz, 2H), 7.28 (d, J=8.8 Hz, 2H), 7.31 (d, J=8.8 Hz, 2H), 7.46 (d, J=8.8 Hz, 2H), 7.59 (d, J=2.0 Hz, 1H), 9.36 (d, J=7.6 Hz, 1H); LCMS (electrospray) m/z (M+H)$^+$ 504.25

6-Chloro-2-ethyl-N-(4-(4-fluorobenzyloxy)benzyl)imidazo[1,2-a]pyridine-3-carboxamide (172)

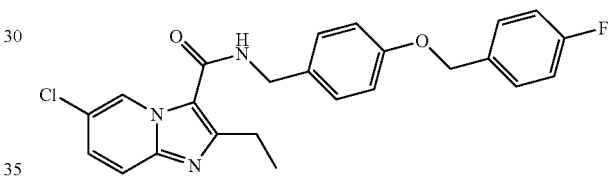

$^1$H NMR (400 MHz, CDCl$_3$) δ 1.40 (t, J=7.6 Hz, 3H), 2.96 (q, J=7.6 Hz, 2H), 4.63 (d, J=5.6 Hz, 2H), 5.03 (s, 2H), 6.04 (brs, 1H), 6.96 (d, J=8.8 Hz, 2H), 7.06 (d, J=8.8 Hz, 1H), 7.08 (d, J=8.4 Hz, 1H), 7.28-7.32 (m, 3H), 7.40 (dd, J=8.8 Hz, 2H), 7.53 (d, J=9.2 Hz, 1H), 9.53 (d, J=1.6 Hz, 1H); LCMS (electrospray) m/z (M+H)$^+$ 438.20

7-Chloro-2-ethyl-N-(4-(4-fluorobenzyloxy)benzyl)imidazo[1,2-a]pyridine-3-carboxamide (173)

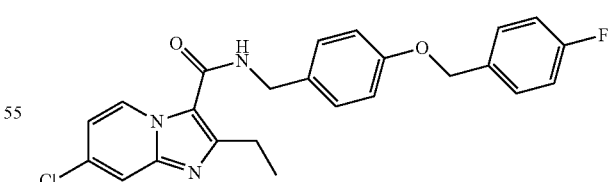

$^1$H NMR (400 MHz, CDCl$_3$) δ 1.38 (t, J=7.6 Hz, 3H), 2.95 (q, J=7.6 Hz, 2H), 4.62 (d, J=5.6 Hz, 2H), 5.03 (s, 2H), 6.02 (brs, 1H), 6.90 (dd, J=7.6, 2.4 Hz, 1H), 6.96 (d, J=8.8 Hz, 2H), 7.07 (dd, J=8.8 Hz, 2H), 7.30 (d, J=8.8 Hz, 2H), 7.40 (dd, J=8.8 Hz, 2H), 7.58 (d, J=1.6 Hz, 1H), 9.36 (d, J=7.6 Hz, 1H); LCMS (electrospray) m/z (M+H)$^+$ 438.20

6-Chloro-2-ethyl-N-(4-(4-(trifluoromethoxy)phenylamino)benzyl)imidazo[1,2-a]pyridine-3-carboxamide (174)

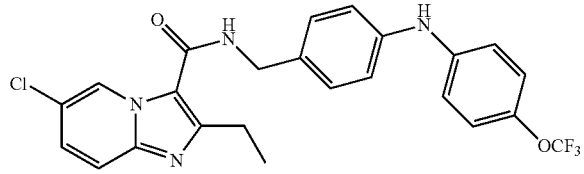 [SMILES: CCc1nc2ccc(Cl)cn2c1C(=O)NCc1ccc(Nc2ccc(OC(F)(F)F)cc2)cc1]

$^1$H NMR (400 MHz, CDCl$_3$) δ 1.41 (t, J=7.6 Hz, 3H), 2.98 (q, J=7.6 Hz, 2H), 4.64 (d, J=5.6 Hz, 2H), 5.74 (s, 1H), 6.07 (brs, 1H), 7.04 (d, J=7.2 Hz, 2H), 7.06 (d, J=7.2 Hz, 2H), 7.12 (d, J=8.4 Hz, 2H), 7.28-7.32 (m, 3H), 7.54 (d, J=9.2 Hz, 1H), 9.54 (d, J=1.2 Hz, 1H); LCMS (electrospray) m/z (M+H)$^+$ 489.22

7-Chloro-2-ethyl-N-(4-(4-(trifluoromethoxy)phenylamino)benzyl)imidazo[1,2-a]pyridine-3-carboxamide (175)

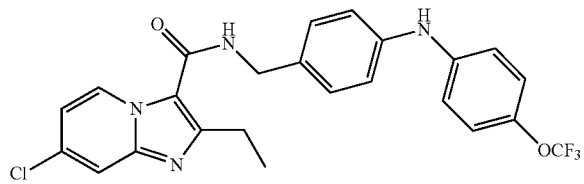 [SMILES: CCc1nc2cc(Cl)ccn2c1C(=O)NCc1ccc(Nc2ccc(OC(F)(F)F)cc2)cc1]

$^1$H NMR (400 MHz, CDCl$_3$) δ 1.40 (t, J=7.6 Hz, 3H), 2.98 (q, J=7.6 Hz, 2H), 4.63 (d, J=5.6 Hz, 2H), 5.74 (s, 1H), 6.05 (brs, 1H), 6.91 (dd, J=7.6, 2.0 Hz, 1H), 7.04 (d, J=9.2 Hz, 2H), 7.06 (d, J=8.8 Hz, 2H), 7.12 (d, J=9.2 Hz, 2H), 7.29 (d, J=8.8 Hz, 2H), 7.59 (d, J=1.6 Hz, 1H), 9.36 (d, J=7.6 Hz, 1H); LCMS (electrospray) m/z (M+H)$^+$ 489.22

6-Bromo-2-ethyl-N-(4-(trifluoromethoxy)benzyl)imidazo[1,2-a]pyridine-3-carboxamide (176)

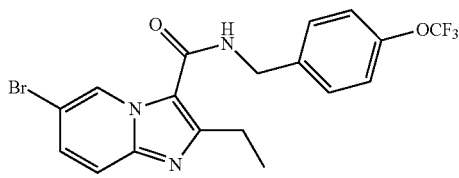 [SMILES: CCc1nc2ccc(Br)cn2c1C(=O)NCc1ccc(OC(F)(F)F)cc1]

$^1$H NMR (400 MHz, CDCl$_3$) δ 1.43 (t, J=7.6 Hz, 3H), 2.99 (q, J=7.6 Hz, 2H), 4.71 (d, J=5.6 Hz, 2H), 6.14 (brs, 1H), 7.23 (d, J=8.4 Hz, 2H), 7.39-7.42 (m, 3H), 7.51 (d, J=9.2 Hz, 1H), 9.63 (d, J=2.0 Hz, 1H); LCMS (electrospray) m/z (M+H)$^+$ 444.12

6-Bromo-2-ethyl-N-(4-(4-fluorophenoxy)benzyl)imidazo[1,2-a]pyridine-3-carboxamide (177)

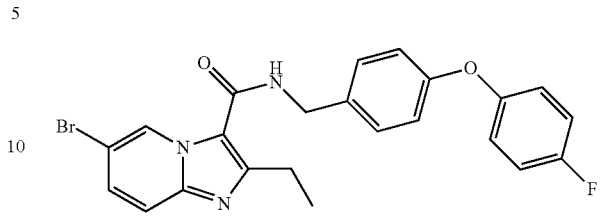

$^1$H NMR (400 MHz, CDCl$_3$) δ 1.41 (t, J=7.6 Hz, 3H), 2.98 (q, J=7.6 Hz, 2H), 4.66 (d, J=5.6 Hz, 2H), 6.09 (brs, 1H), 6.95-7.06 (m, 6H), 7.34 (d, J=8.8 Hz, 2H), 7.40 (dd, J=9.6, 1.6 Hz, 1H), 7.49 (d, J=9.6 Hz, 1H), 9.63 (d, J=1.2 Hz, 1H); LCMS (electrospray) m/z (M+H)$^+$ 470.10

6,7-Dichloro-2-ethyl-N-(4-(trifluoromethoxy)benzyl)imidazo[1,2-a]pyridine-3-carboxamide (178)

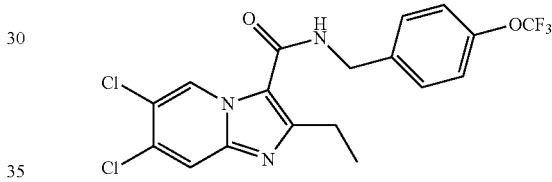

$^1$H NMR (400 MHz, CDCl$_3$) δ 1.42 (t, J=7.6 Hz, 3H), 2.99 (q, J=7.6 Hz, 2H), 4.70 (d, J=6.0 Hz, 2H), 6.14 (brs, 1H), 7.23 (d, J=8.0 Hz, 2H), 7.41 (d, J=8.8 Hz, 2H), 7.72 (s, 1H), 9.66 (s, 1H); LCMS (electrospray) m/z (M+H)$^+$ 432.15

6,7-Dichloro-2-ethyl-N-(4-(4-(4-fluorobenzyl)piperazin-1-yl)benzyl)imidazo1,2-a]pyridine-3-carboxamide (179)

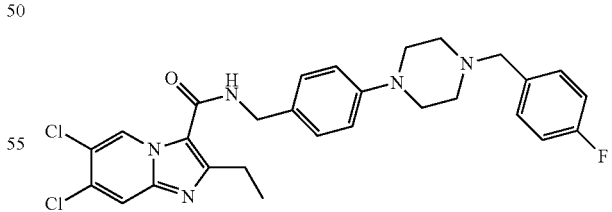

$^1$H NMR (400 MHz, DMSO-d$_6$) δ 1.24 (t, J=7.6 Hz, 3H), 2.50 (m, 4H), 2.95 (q, J=7.6 Hz, 2H), 3.08 (m, 4H), 3.48 (s, 2H), 4.41 (d, J=6.0 Hz, 2H), 6.89 (d, J=8.8 Hz, 2H), 7.14 (dd, J=9.2 Hz, 2H), 7.20 (d, J=8.4 Hz, 2H), 7.33-7.36 (m, 2H), 8.06 (s, 1H), 8.44 (t, 1H), 9.20 (s, 1H); LCMS (electrospray) m/z (M+H)$^+$ 540.36

6,7-Dichloro-2-ethyl-N-(4-(4-(4-fluorophenyl)piperazin-1-yl)benzyl)imidazo[1,2-a]pyridine-3-carboxamide (180)

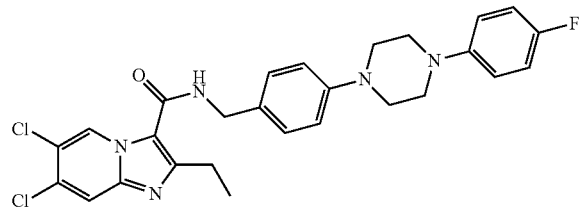 [SMILES: CCc1nc2cc(Cl)c(Cl)cn2c1C(=O)NCc1ccc(N2CCN(c3ccc(F)cc3)CC2)cc1]

¹H NMR (400 MHz, CDCl₃) δ 1.39 (t, J=7.6 Hz, 3H), 2.95 (q, J=7.6 Hz, 2H), 3.24-3.27 (m, 4H), 3.34-3.36 (m, 4H), 4.62 (d, J=5.6 Hz, 2H), 6.03 (brs, 1H), 6.91-7.02 (m, 6H), 7.30 (d, J=8.8 Hz, 2H), 7.71 (s, 1H), 9.67 (s, 1H); LCMS (electrospray) m/z (M+H)⁺ 526.35

2-Ethyl-N-(4-(4-(4-(trifluoromethoxy)phenyl)piperazin-1-yl)benzyl)imidazo[1,2-a]pyridine-3-carboxamide (181)

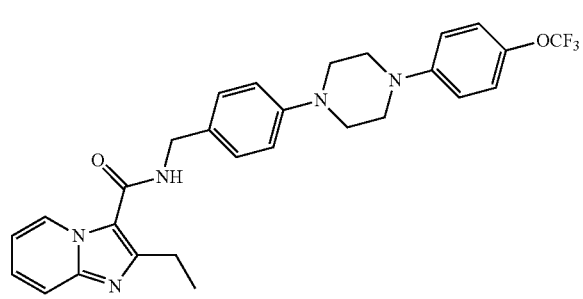

White solid; mp=178-179° C.; ¹H NMR (400 MHz, CDCl₃) δ 1.40 (t, J=7.6 Hz, 3H), 2.97 (q, J=7.2 Hz, 2H), 3.31-3.38 (m, 8H), 4.63 (d, J=5.6 Hz, 2H), 6.05 (t, J=5.0 Hz, 1H), 6.89-6.99 (m, 5H), 7.14 (d, J=8.8 Hz, 2H), 7.29-7.32 (m, 3H), 7.60 (d, J=9.2 Hz, 1H), 9.40 (d, J=6.8 Hz, 1H); LCMS (electrospray) m/z (M+H)⁺ 524.45

6-Chloro-N-(4-(2,6-dimethylmorpholino)benzyl)-2-ethylimidazo[1,2-a]pyridine-3-carboxamide (182)

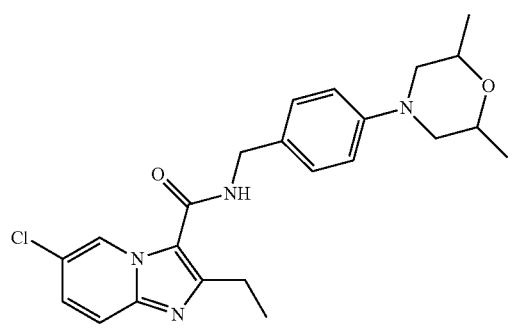 [SMILES: CCc1nc2ccc(Cl)cn2c1C(=O)NCc1ccc(N2CC(C)OC(C)C2)cc1]

White solid; mp=176-177° C.; ¹H NMR (400 MHz, CDCl₃) δ 1.25 (s, 3H), 1.27 (s, 3H), 1.39 (t, J=7.6 Hz, 3H), 2.42 (t, J=11.2 Hz, 2H), 2.95 (q, J=7.2 Hz, 2H), 3.46 (d, J=10.4 Hz, 2H), 3.78-3.82 (m, 2H), 4.61 (d, J=5.6 Hz, 2H), 6.00-6.02 (m, 1H), 6.91 (d, J=8.8 Hz, 1H), 7.26-7.31 (m, 3H), 7.54 (d, J=9.2 Hz, 1H), 9.53 (d, J=2.2 Hz, 1H); LCMS (electrospray) m/z (M+H)⁺ 427.32

7-Chloro-N-(4-(2,6-dimethylmorpholino)benzyl)-2-ethylimidazo[1,2-a]pyridine-3-carboxamide (183)

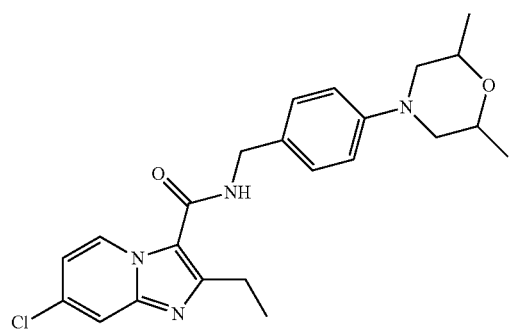 [SMILES: CCc1nc2cc(Cl)ccn2c1C(=O)NCc1ccc(N2CC(C)OC(C)C2)cc1]

White solid; mp=165-166° C.; ¹H NMR (400 MHz, CDCl₃) δ 1.25 (s, 3H), 1.27 (s, 3H), 1.38 (t, J=7.6 Hz, 3H), 2.42 (t, J=11.2 Hz, 2H), 2.94 (q, J=7.6 Hz, 2H), 3.45 (d, J=10.4 Hz, 2H), 3.76-3.84 (m, 2H), 4.60 (d, J=5.6 Hz, 2H), 5.99-6.01 (m, 1H), 6.89-6.92 (m, 3H), 7.28 (d, J=8.4 Hz, 2H), 7.58 (d, J=2.0 Hz, 1H), 9.35 (d, J=7.2 Hz, 1H); LCMS (electrospray) m/z (M+H)⁺ 427.32

6-Chloro-2-methyl-N-(4-(trifluoromethoxy)benzyl)imidazo[1,2-a]pyridine-3-carboxamide (184)

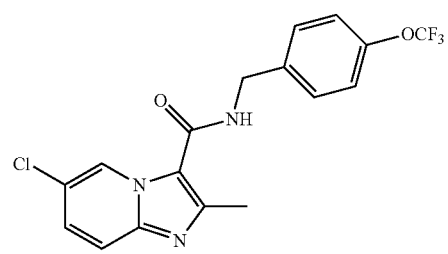 [SMILES: Cc1nc2ccc(Cl)cn2c1C(=O)NCc1ccc(OC(F)(F)F)cc1]

White solid; mp=192-193° C.; ¹H NMR (400 MHz, CDCl₃) δ 2.70 (s, 3H), 4.71 (d, J=6.0 Hz, 2H), 6.12-6.14 (m, 1H), 7.22 (d, J=8.4 Hz, 2H), 7.32 (dd, J=2.0, 9.6 Hz, 1H), 7.42 (d, J=8.8 Hz, 2H), 7.52 (d, J=9.6 Hz, 1H), 9.65 (d, J=2.0 Hz, 1H); LCMS (electrospray) m/z (M+H)⁺ 384.20

6-Chloro-2-ethyl-N-((2-(4-(trifluoromethoxy)phenyl)-1H-benzo[d]imidazol-5-yl)methyl)imidazo[1,2-a]pyridine-3-carboxamide (185)

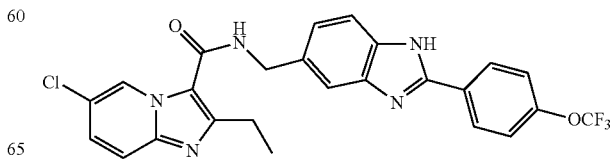

¹H NMR (400 MHz, DMSO-d₆) 1.26 (m, 3H), 2.97-3.03 (m, 2H), 4.65 (t, J=6.4 Hz, 2H), 7.24 (dd, J=18.4, 8.0 Hz, 1H), 7.45 (d, J=9.6, 2.4 Hz, 1H), 7.51-7.56 (m, 3H), 7.65-7.68 (m, 2H), 8.24-8.28 (m, 1H), 8.52-8.56 (m, 1H), 9.09-7.10 (m, 1H), 12.96 (ss, 1H); LCMS (electrospray) m/z (M+H)⁺ 514.38

7-Chloro-2-ethyl-N-((2-(4-(trifluoromethoxy)phenyl)-1H-benzo[d]imidazol-5-yl)methyl)imidazo[1,2-a]pyridine-3-carboxamide (186)

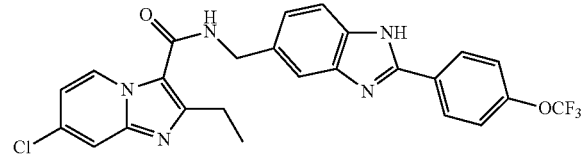 [SMILES: CCc1nc2cc(Cl)ccn2c1C(=O)NCc1ccc2[nH]c(-c3ccc(OC(F)(F)F)cc3)nc2c1]

¹H NMR (400 MHz, CDCl₃) δ 1.38 (t, J=7.6 Hz, 3H), 2.97 (q, J=7.6 Hz, 2H), 4.82 (d, J=5.6 Hz, 2H), 6.19 (brs, 1H), 6.90 (dd, J=7.6, 2.0 Hz, 1H), 7.30 (m, 1H), 7.35 (d, J=8.0 Hz, 2H), 7.50-7.52 (m, 1H), 7.59 (d, J=2.0 Hz, 1H), 7.81 (m, 1H), 8.07 (d, J=8.8 Hz, 2H), 9.37 (d, J=7.6 Hz, 1H); LCMS (electrospray) m/z (M+H)⁺ 514.31

7-Chloro-2-ethyl-N-((2-(4-(trifluoromethoxy)phenyl)benzo[d]oxazol-5-yl)methyl)imidazo[1,2-a]pyridine-3-carboxamide (187)

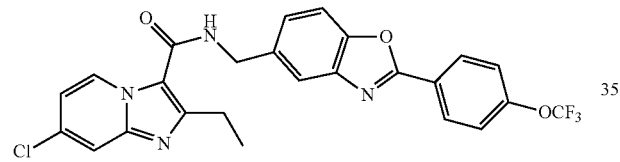

White solid; ¹H NMR (400 MHz, CDCl₃); δ 1.40 (t, J=7.6 Hz, 3H), 2.98 (q, J=7.6 Hz, 2H), 4.82 (d, J=6.0 Hz, 2H), 6.19 (brs, 1H), 6.92 (dd, J=2.0, 7.6 Hz, 1H), 7.36 (d, J=8.0 Hz, 2H), 7.41 (dd, J=2.0, 8.4 Hz, 1H), 7.59 (d, J=8.8 Hz, 2H), 7.77 (s, 1H), 8.28 (d, J=8.8 Hz, 2H), 9.38 (d, J=7.6 Hz, 1H); LCMS (electrospray) m/z (M+H)⁺ 515, 517 (Cl⁻ isotope pattern).

7-Chloro-2-ethyl-N-((6-(4-fluorophenoxy)pyridin-3-yl)methyl)imidazo[1,2-a]pyridine-3-carboxamide (188)

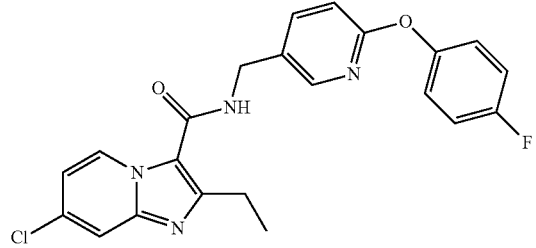 [SMILES: CCc1nc2cc(Cl)ccn2c1C(=O)NCc1ccc(Oc2ccc(F)cc2)nc1]

White solid; mp=167.0-167.6° C.; ¹H NMR (400 MHz, CDCl₃) δ 1.41 (t, J=7.6 Hz, 3H), 2.97 (q, J=7.6 Hz, 2H), 4.64 (d, J=6.0 Hz, 2H), 6.09 (t, J=5.6 Hz, 1H), 6.90-6.93 (m, 2H), 7.06-7.11 (m, 4H), 7.58 (d, J=2.0 Hz, 1H), 7.80 (dd, J=2.8, 8.8 Hz, 1H), 8.20 (d, J=2.0 Hz, 1H), 9.34 (d, J=7.6 Hz, 1H); LCMS (electrospray) m/z (M+H)⁺ 425.28

6-Chloro-2-ethyl-N-((6-(4-(trifluoromethoxy)phenoxy)pyridin-3-yl)methyl)imidazo[1,2-a]pyridine-3-carboxamide (189)

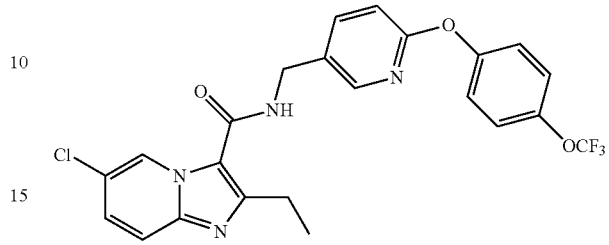

White solid; mp=154-155° C.; ¹H NMR (400 MHz, CDCl₃) δ 1.42 (t, J=7.8 Hz, 3H), 2.98 (q, J=7.6 Hz, 2H), 4.66 (d, J=6.0 Hz, 2H), 6.14 (t, J=5.6 Hz, 1H), 6.96 (d, J=8.4 Hz, 1H), 7.16 (d, J=9.2 Hz, 2H), 7.24 (d, J=9.2 Hz, 2H), 7.32 (dd, J=2.0, 9.6 Hz, 1H), 7.54 (d, J=9.2 Hz, 1H), 7.80 (dd, J=2.4, 8.4 Hz, 1H), 8.20 (d, J=2.4 Hz, 1H), 9.51 (d, J=2.0 Hz, 1H); LCMS (electrospray) m/z (M+H)⁺ 491.26

7-Chloro-2-ethyl-N-((6-(4-(trifluoromethoxy)phenoxy)pyridin-3-yl)methy)imidazo[1,2-a]pyridine-3-carboxamide (190)

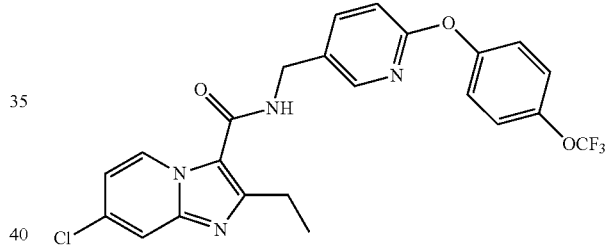

White solid; ¹H NMR (400 MHz, CDCl₃) δ 1.41 (t, J=7.4 Hz, 3H), 2.97 (q, J=7.6 Hz, 2H), 4.66 (d, J=6.0 Hz, 2H), 6.14 (t, J=5.4 Hz, 1H), 6.92 (dd, J=2.0, 7.6 Hz, 1H), 6.96 (d, J=8.8 Hz, 1H), 7.16 (d, J=9.2 Hz, 2H), 7.24 (d, J=9.2 Hz, 2H), 7.60 (d, J=1.6 Hz, 1H), 7.79 (dd, J=2.4, 8.4 Hz, 1H), 8.20 (d, J=2.0 Hz, 1H), 9.35 (d, J=7.6 Hz, 1H).

6-Chloro-2-ethyl-N-(4-(pyrrolidin-1-yl)benzyl)imidazo[1,2-a]pyridine-3-carboxamide (191)

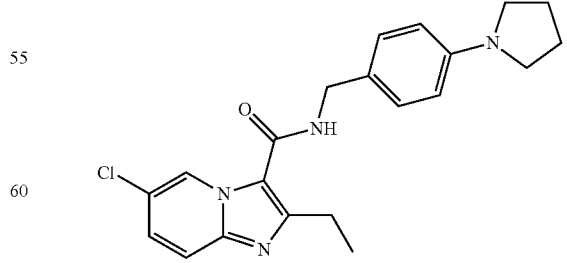

White solid; mp=222-223° C.; ¹H NMR (400 MHz, CDCl₃) δ 1.38 (t, J=7.4 Hz, 3H), 1.99-2.03 (m, 4H), 2.94 (q, J=7.6 Hz, 2H), 3.29 (t, J=6.6 Hz, 4H), 4.57 (d, J=5.6 Hz, 2H), 5.95-5.97 (m, 1H), 6.56 (d, J=8.4 Hz, 2H), 7.22-7.30 (m, 6H), 7.53 (d, J=9.6 Hz, 1H), 9.53 (d, J=1.6 Hz, 1H); LCMS (electrospray) m/z (M+H)+ 383.24

N-(4-(Azepan-1-yl)benzyl)-6-chloro-2-ethylimidazo[1,2-a]pyridine-3-carboxamide (192)

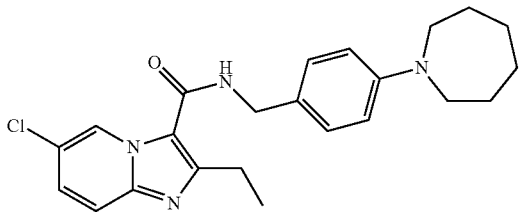 [SMILES: CCc1nc2ccc(Cl)cn2c1C(=O)NCc1ccc(N2CCCCCC2)cc1]

¹H NMR (400 MHz, CDCl₃) δ 1.26 (t, J=7.2 Hz, 3H), 1.38 (m, 4H), 1.53-1.56 (m, 4H), 2.95 (q, J=7.6 Hz, 2H), 3.45 (t, J=5.6 Hz, 4H), 4.56 (d, J=5.6 Hz, 2H), 5.97 (brs, 1H), 6.68 (d, J=8.8 Hz, 2H), 7.21 (d, J=8.8 Hz, 2H), 7.28 (dd, J=9.6, 2.0 Hz, 2H), 7.53 (d, J=9.6 Hz, 1H), 9.53 (d, J=2.4 Hz, 1H); LCMS (electrospray) m/z (M+H)+ 411.40

N-(4-(Azepan-1-yl)benzyl)-7-chloro-2-ethylimidazo[1,2-a]pyridine-3-carboxamide (193)

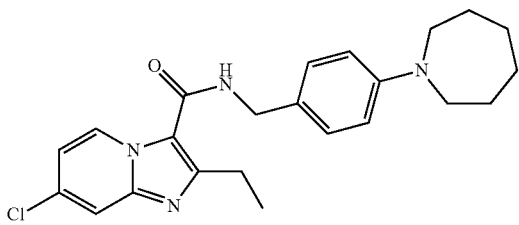 [SMILES: CCc1nc2cc(Cl)ccn2c1C(=O)NCc1ccc(N2CCCCCC2)cc1]

¹H NMR (400 MHz, CDCl₃) δ 1.38 (t, J=7.6 Hz, 3H), 1.52-1.55 (m, 4H), 1.78 (m, 4H), 2.94 (q, J=7.6 Hz, 2H), 3.45 (t, J=6.0 Hz, 4H), 4.56 (d, J=5.2 Hz, 2H), 5.95 (brs, 1H), 6.67 (d, J=8.8 Hz, 2H), 6.89 (dd, J=7.6, 2.4 Hz, 1H), 7.20 (d, J=8.8 Hz, 2H), 7.57 (d, J=2.4 Hz, 1H), 9.36 (d, J=7.6 Hz, 1H); LCMS (electrospray) m/z (M+H)+ 411.40

7-Chloro-N-(4-(5,6-dihydropyridin-1(2H)-yl)benzyl)-2-ethylimidazo[1,2-a]pyridine-3-carboxamide (194)

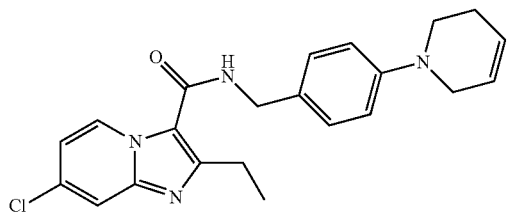

¹H NMR (400 MHz, CDCl₃) δ 1.38 (t, J=7.6 Hz, 3H), 2.29-2.32 (m, 2H), 2.94 (q, J=7.6 Hz, 2H), 3.38 (t, J=5.6 Hz, 2H), 3.68-3.72 (m, 2H), 4.59 (d, J=5.6 Hz, 2H), 5.79-5.82 (m, 1H), 5.88-5.91 (m, 1H), 5.99 (brs, 1H), 6.88-6.93 (m, 3H), 7.27 (d, J=8.0 Hz, 2H), 7.58 (d, J=1.6 Hz, 1H), 9.36 (d, J=7.6 Hz, 1H); LCMS (electrospray) m/z (M+H)+ 395.35

7-Chloro-2-ethyl-N-(4-(4-methylpiperidin-1-yl)benzyl)imidazo[1,2-a]pyridine-3-carboxamide (195)

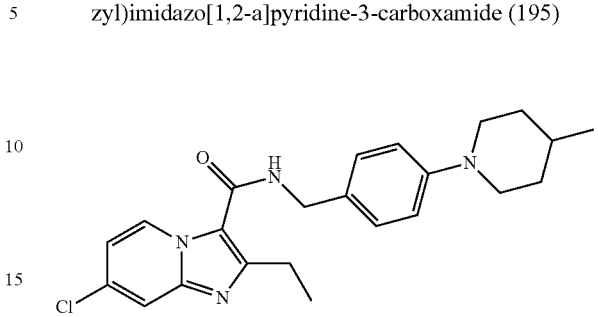

¹H NMR (400 MHz, CDCl₃) δ 0.97 (d, J=6.8 Hz, 3H), 1.35 (m, 2H), 1.37 (t, J=7.6 Hz, 3H), 1.51-1.53 (m, 1H), 1.72-1.75 (m, 2H), 2.66-2.73 (m, 2H), 2.94 (q, J=7.6 Hz, 2H), 3.64-3.67 (m, 2H), 4.59 (d, J=5.6 Hz, 2H), 5.98 (brs, 1H), 6.90 (dd, J=7.6, 2.4 Hz, 1H), 6.93 (d, J=8.4 Hz, 2H), 7.25 (d, J=8.4 Hz, 2H), 7.58 (d, J=2.4 Hz, 1H), 9.36 (d, J=7.6 Hz, 1H); LCMS (electrospray) m/z (M+H)+ 411.40

7-Chloro-2-ethyl-N-((2-(morpholinomethyl)-1H-benzo[d]imidazol-5-yl)methyl)imidazo[1,2-a]pyridine-3-carboxamide (196)

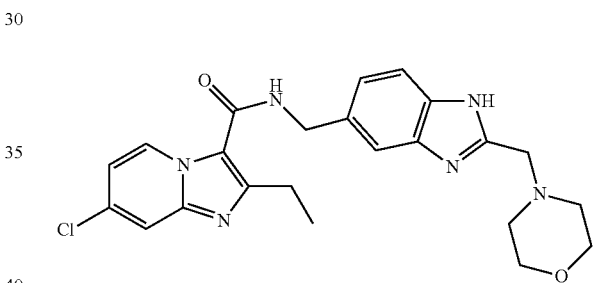

¹H NMR (400 MHz, DMSO-d₆) δ 1.23-1.28 (m, 3H), 2.44 (m, 4H), 2.98 (q, J=7.6 Hz, 2H), 3.59 (m, 4H), 3.69 (s, 2H), 4.61 (m, 2H), 6.19 (brs, 1H), 7.09 (dd, J=9.6, 2.0 Hz, 1H), 7.18 (dd, J=9.6, 7.2 Hz, 1H), 7.41 (m, 1H), 7.51 (m, 1H), 7.79 (d, J=2.0 Hz, 1H), 8.52 (m, 1H), 8.96 (d, J=7.6 Hz, 1H), 9.37 (d, J=7.6 Hz, 1H), 12.27 (m, 1H); LCMS (electrospray) m/z (M+H)+ 453.39

6-Chloro-N-(4-(3,5-dimethylpiperidin-1-yl)benzyl)-2-ethylimidazo[1,2-a]pyridine-3-carboxamide (197)

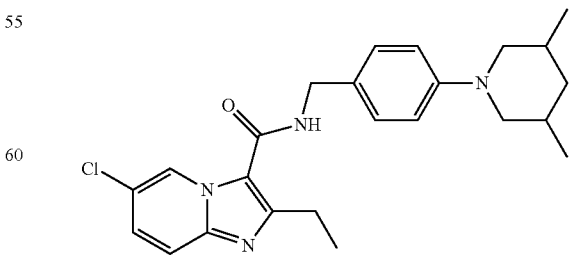

Pale yellow solid; mp=157.2-158.0° C.; ¹H NMR (400 MHz, CDCl₃); δ 0.91 (d, J=6.4 Hz, 6H), 1.35 (t, J=7.6 Hz, 3H), 1.73-1.81 (m, 4H), 2.16 (dd, J=11.6, 11.6 Hz, 2H), 2.90 (q, 7.6 Hz, 2H), 3.58-3.61 (m, 2H), 4.56 (d, J=5.6 Hz, 2H), 6.01 (brs, 1H), 6.90 (d, J=8.8 Hz, 2H), 7.22 (d, J=8.8 Hz, 2H), 7.26 (dd, J=2.0, 9.6 Hz, 1H), 7.49 (d, J=9.6 Hz, 1H), 9.49 (d, J=2.0 Hz, 1H); $^{13}$C NMR (100 MHz, CDCl$_3$); δ 13.3, 19.6, 23.6, 30.9, 42.2, 43.4, 57.2, 115.4, 116.6, 117.0, 121.5, 126.3, 127.8, 128.2, 128.9, 144.5, 151.3, 151.4, 161.1; LCMS (electrospray) m/z (M+H)$^+$ 425, 427 (Cl$^-$ isotope pattern).

7-Chloro-N-(4-(3,5-dimethylpiperidin-1-yl)benzyl)-2-ethylimidazo[1,2-a]pyridine-3-carboxamide (198)

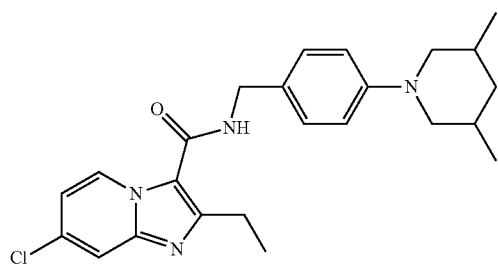 [SMILES: CCc1nc2cc(Cl)ccn2c1C(=O)NCc1ccc(N2CC(C)CC(C)C2)cc1]

Pale yellow solid; mp=181.5-182.8° C.; $^1$H NMR (400 MHz, CDCl$_3$); δ 0.92 (d, J=6.8 Hz, 6H), 1.35 (t, J=7.6 Hz, 3H), 1.74-1.82 (m, 4H), 2.17 (dd, J=11.6, 11.6 Hz, 2H), 2.90 (q, 7.6 Hz, 2H), 3.59-3.62 (m, 2H), 4.57 (d, J=5.2 Hz, 2H), 6.01 (brs, 1H), 6.87 (dd, J=2.0, 7.6 Hz, 1H), 6.91 (d, J=8.8 Hz, 2H), 7.23 (d, J=8.8 Hz, 2H), 7.57 (d, J=2.0 Hz, 1H), 9.33 (d, J=7.6 Hz, 1H); $^{13}$C NMR (100 MHz, CDCl$_3$); δ 13.4, 19.6, 23.6, 30.9, 42.2, 43.4, 57.2, 114.7, 115.1, 115.7, 116.6, 127.8, 128.6, 128.9, 133.6, 146.1, 151.3, 151.6, 161.1; LCMS (electrospray) m/z (M+H)$^{425}$, 427 (Cl$^-$ isotope pattern).

7-Chloro-2-ethyl-N-(4-(4-hydroxypiperidin-1-yl)benzyl)imidazo[1,2-a]pyridine-3-carboxamide (199)

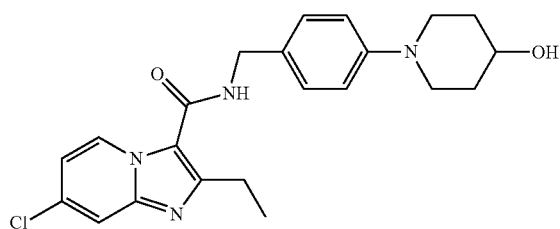 [SMILES: CCc1nc2cc(Cl)ccn2c1C(=O)NCc1ccc(N2CCC(O)CC2)cc1]

Pale yellow solid; mp=179.1-180.0° C.; $^1$H NMR (400 MHz, DMSO-d6); δ 1.22 (t, J=7.2 Hz, 3H), 1.39-1.48 (m, 2H), 1.76-1.81 (m, 2H), 2.76-2.82 (m, 2H), 2.92 (q, J=7.2 Hz, 2H), 3.46-3.51 (m, 2H), 3.57-3.62 (m, 1H), 4.39 (d, J=5.6 Hz, 2H), 4.64 (d, J=4.0 Hz, 1H), 6.88 (d, J=8.4 Hz, 2H), 7.07 (dd, J=2.0, 7.2 Hz, 1H), 7.18 (d, J=8.4 Hz, 2H), 7.77 (d, J=2.0 Hz, 1H), 8.37 (t, J=5.6 Hz, 1H), 8.93 (d, J=7.2 Hz, 1H); LCMS (electrospray) m/z (M+H)$^+$ 413, 415 (Cl$^-$ isotope pattern).

7-Chloro-2-ethyl-N-(4-(4-oxopiperidin-1-yl)benzyl)imidazo[1,2-a]pyridine-3-carboxamide (200)

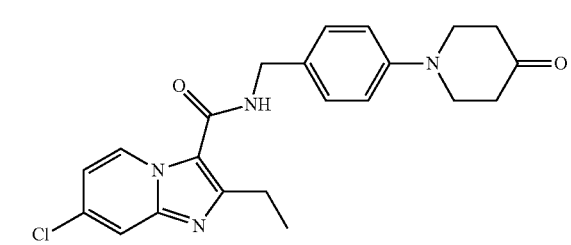 [SMILES: CCc1nc2cc(Cl)ccn2c1C(=O)NCc1ccc(N2CCC(=O)CC2)cc1]

Pale yellow solid; $^1$H NMR (400 MHz, CDCl$_3$); δ 1.37 (t, J=7.2 Hz, 3H), 2.54 (t, J=6.6 Hz, 4H), 2.93 (q, J=7.2 Hz, 2H), 3.60 (t, J=6.0 Hz, 4H), 4.61 (d, J=5.6 Hz, 2H), 6.04 (brt, J=5.6 Hz, 1H), 6.89 (dd, J=2.4, 7.6 Hz, 1H), 6.96 (d, J=8.4 Hz, 2H), 7.29 (d, J=8.4 Hz, 2H), 7.58 (d, J=2.4 Hz, 1H), 9.35 (d, J=7.6 Hz, 1H); LCMS (electrospray) m/z (M+H)$^+$ 411, 413 (Cl$^-$ isotope pattern).

7-Chloro-2-ethyl-N-(4-(4-oxo-3,4-dihydropyridin-1(2H)-yl)benzyl)imidazo[1,2-a]pyridine-3-carboxamide (201)

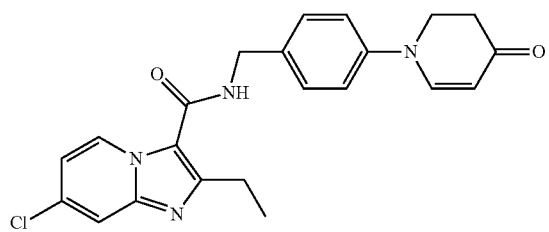 [SMILES: CCc1nc2cc(Cl)ccn2c1C(=O)NCc1ccc(N2C=CC(=O)CC2)cc1]

Pale yellow solid; mp=201.3-202.8° C.; $^1$H NMR (400 MHz, CDCl$_3$); δ 1.38 (t, J=7.6 Hz, 3H), 2.64 (t, J=7.6 Hz, 2H), 2.95 (q, J=7.6 Hz, 2H), 3.98 (t, J=7.2 Hz, 2H), 4.66 (d, J=5.6 Hz, 2H), 5.23 (d, J=8.0 Hz, 1H), 6.13 (t, J=5.6 Hz, 1H), 6.89 (dd, J=2.4, 7.6 Hz, 1H), 7.08 (d, J=8.4 Hz, 2H), 7.38 (d, J=8.4 Hz, 2H), 7.41 (d, J=8.0 Hz, 1H), 7.60 (d, J=2.4 Hz, 1H), 9.34 (d, J=7.2 Hz, 1H); LCMS (electrospray) m/z (M+H)$^+$ 409, 411 (Cl$^-$ isotope pattern).

7-Chloro-N-(4-(3a,4-dihydro-1H-isoindol-2(3H7H, 7aH)-yl)benzyl)-2-ethylimidazo[1,2-a]pyridine-3-carboxamide (202)

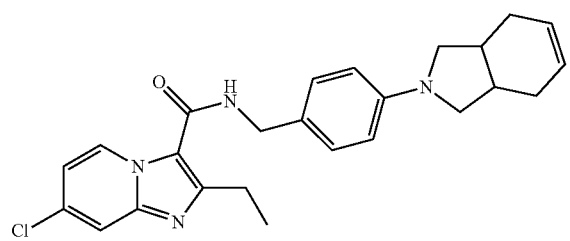 [SMILES: CCc1nc2cc(Cl)ccn2c1C(=O)NCc1ccc(N2CC3CC=CCC3C2)cc1]

White solid; $^1$H NMR (400 MHz, CDCl$_3$); δ 1.36 (t, J=7.6 Hz, 3H), 1.96 (dd, J=4.0 Hz, 16.4 Hz, 2H), 2.25-2.31 (m, 2H), 2.45 (dd, J=5.2 Hz, 8.8 Hz, 2H), 2.92 (q, J=7.6 Hz, 2H), 3.11

(dd, J=5.2 Hz, 8.8 Hz, 2H), 3.39 (dd, J=6.4 Hz, 8.8 Hz, 2H), 4.55 (d, J=5.2 Hz, 2H), 5.67 (s, 2H), 5.94 (brs, 1H), 6.51 (d, J=8.8 Hz, 2H), 6.89 (dd, J=2.0 Hz, 7.6 Hz, 1H), 7.22 (d, J=8.8 Hz, 2H), 7.57 (d, J=2.0 Hz, 1H), 9.35 (d, J=7.6 Hz, 1H); LCMS (electrospray) m/z (M+H)+ 435, 437 (Cl− isotope pattern).

7-Chloro-2-ethyl-N-(4-(4-fluorophenoxy)benzyl)imidazo[1,2-a]pyridine-3-carboxamide (203)

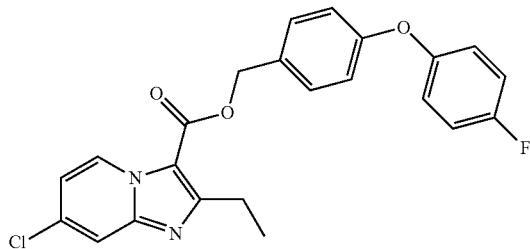 [SMILES: CCc1nc2cc(Cl)ccn2c1C(=O)OCc1ccc(Oc2ccc(F)cc2)cc1]

White solid; mp=89.7° C.; $^1$H NMR (400 MHz, CDCl$_3$) δ 1.298 (t, J=7.6 Hz, 3H), 3.07 (q, J=7.6 Hz, 2H), 5.37 (s, 2H), 6.93-7.05 (m, 7H), 7.41 (d, J=8.8 Hz, 2H), 7.62 (d, J=2.0 Hz, 1H), 9.24 (d, J=7.6 Hz, 1H); LCMS (electrospray) m/z (M+H)+ 425.

7-Chloro-2-ethyl-N-((4'-(trifluoromethoxy)biphenyl-3-yl)methyl)imidazo[1,2-a]pyridine-3-carboxamide (204)

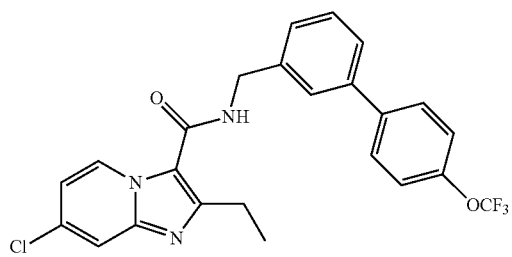 [SMILES: CCc1nc2cc(Cl)ccn2c1C(=O)NCc1cccc(-c2ccc(OC(F)(F)F)cc2)c1]

White solid; mp=192.6° C.; $^1$H NMR (400 MHz, CDCl$_3$); δ 1.37 (t, J=7.2 Hz, 3H), 2.95 (q, J=7.2 Hz, 2H), 4.75 (d, J=6.0 Hz, 2H), 6.19 (brt, J=6.0 Hz, 1H), 6.88 (dd, J=2.0, 7.6 Hz, 1H), 7.26 (d, J=8.8 Hz, 2H), 7.36 (d, J=7.6 Hz, 1H), 7.43 (dd, J=7.2, 7.6 Hz, 1H), 7.48-7.59 (m, 5H), 9.33 (d, J=7.6 Hz, 1H); LCMS (electrospray) m/z 474, 476 (M+H)+ (Cl− isotope pattern).

2-Ethyl-6-fluoro-N-(4-(4-(trifluoromethoxy)benzyloxy)benzyl)imidazo[1,2-a]pyridine-3-carboxamide (205)

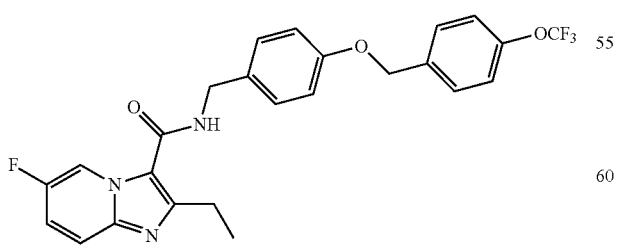

White solid; $^1$H NMR (400 MHz, CDCl$_3$); δ 1.37 (t, J=7.2 Hz, 3H), 2.93 (q, J=7.2 Hz, 2H), 4.62 (d, J=5.6 Hz, 2H), 5.06 (s, 2H), 6.06 (brt, J=5.6 Hz, 1H), 6.95 (d, J=8.8 Hz, 2H), 7.22-7.26 (m, 3H), 7.29 (d, J=8.4 Hz, 2H), 7.45 (d, J=8.8 Hz, 2H), 7.47-7.58 (m, 1H), 9.43-9.45 (m, 1H); LCMS (electrospray) m/z 488 (M+H)+.

6-Bromo-2-ethyl-N-(4-(4-(trifluoromethoxy)benzyloxy)benzyl)imidazo[1,2-a]pyridine-3-carboxamide (206)

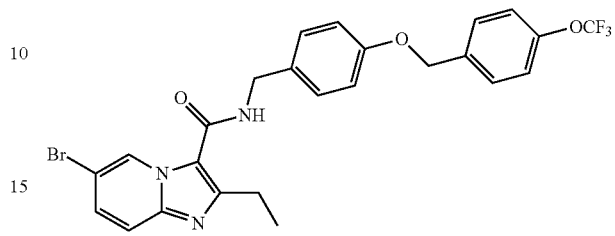

Pale yellow solid; mp=189.7° C.; $^1$H NMR (400 MHz, CDCl$_3$); δ 1.36 (t, J=7.6 Hz, 3H), 2.92 (q, J=7.6 Hz, 2H), 4.62 (d, J=5.6 Hz, 2H), 5.05 (s, 2H), 6.06 (brt, J=5.6 Hz, 1H), 6.95 (d, J=8.4 Hz, 2H), 7.21 (d, J=8.4 Hz, 2H), 7.29 (d, J=8.8 Hz, 2H), 7.36 (dd, J=2.0, 9.2 Hz, 1H), 7.43-7.49 (m, 3H), 9.60 (d, J=2.0 Hz, 1H); LCMS (electrospray) m/z 548, 550 (M+H)+ (Br− isotope pattern).

2-Ethyl-N-(4-(4-(trifluoromethoxy)benzyloxy)benzyl)imidazo[1,2-a]pyridine-3-carboxamide (207)

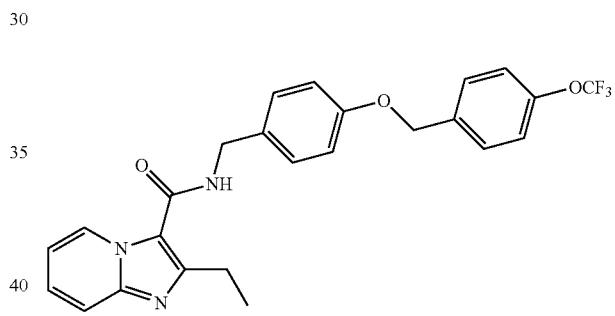

White solid; mp=138.7° C.; $^1$H NMR (400 MHz, CDCl$_3$); δ 1.35 (t, J=7.6 Hz, 3H), 2.91 (q, J=7.6 Hz, 2H), 4.60 (d, J=5.6 Hz, 2H), 5.03 (s, 2H), 6.14 (brt, J=5.6 Hz, 1H), 6.85 (ddd, J=1.2, 7.2, 7.2 Hz, 1H), 6.92 (d, J=8.0 Hz, 2H), 7.20 (d, J=8.0 Hz, 2H), 7.26-7.30 (m, 3H), 7.42 (d, J=8.8 Hz, 2H), 7.55 (d, J=9.2 Hz, 1H), 9.33 (d, J=7.2 Hz, 1H); LCMS (electrospray) m/z 470 (M+H)+.

N-(4-(4-Benzylpiperidin-1-yl)benzyl)-7-chloro-2-ethylimidazo[1,2-a]pyridine-3-carboxamide (208)

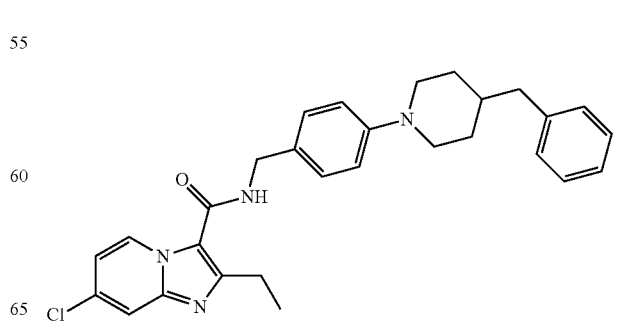

White solid; mp=63.8° C.; $^1$H NMR (400 MHz, CDCl$_3$); δ 1.33 (t, J=7.6 Hz, 3H), 1.37-1.44 (m, 2H), 1.63-1.70 (m, 1H), 1.72-1.76 (m, 2H), 2.56 (d, J=6.8 Hz, 2H), 2.61-2.67 (m, 2H), 2.89 (q, J=7.6 Hz, 2H), 3.63-3.66 (m, 2H), 4.56 (d, J=5.2 Hz, 2H), 6.08 (brs, 1H), 6.84-6.87 (m, 1H), 6.89 (d, J=8.0 Hz, 2H), 7.14 (d, J=7.2 Hz, 2H), 7.19-7.30 (m, 5H), 7.54 (d, J=1.6 Hz, 1H), 9.29-9.32 (m, 1H); $^{13}$C NMR (100 MHz, CDCl$_3$) δ 13.3, 23.5, 32.0, 37.9, 43.2, 43.3, 49.9, 114.6, 115.1, 115.7, 116.7, 126.0, 128.2, 128.3, 128.5, 128.8, 129.2, 133.5, 140.5, 146.0, 151.5, 151.6, 161.1; LCMS (electrospray) m/z 487, 489 (M+H)$^+$ (Cl$^-$ isotope pattern).

7-Chloro-2-ethyl-N-(4-(4-phenylpiperidin-1-yl)benzyl)imidazo[1,2-a]pyridine-3-carboxamide (209)

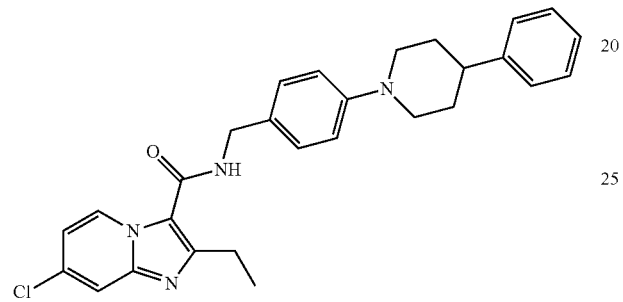

White solid; mp=164.5° C.; $^1$H NMR (400 MHz, CDCl$_3$); δ 1.36 (t, J=7.6 Hz, 3H), 1.87-1.98 (m, 4H), 2.67-2.68 (m, 1H), 2.80-2.85 (m, 2H), 2.91 (q, J=7.6 Hz, 2H), 3.80-3.83 (m, 2H), 4.59 (d, J=5.6 Hz, 2H), 6.01 (brt, J=5.6 Hz, 1H), 6.87 (d, J=7.6 Hz, 1H), 6.97 (d, J=8.4 Hz, 2H), 7.19-7.33 (m, 7H), 7.57 (s, 1H), 9.34 (d, J=7.6 Hz, 1H); $^{13}$C NMR (100 MHz, CDCl$_3$)$_8$. 13.4, 23.6, 33.3, 42.6, 43.4, 50.5, 114.7, 115.1, 115.8, 116.9, 126.5, 127.0, 128.5, 128.6, 128.7, 128.9, 133.6, 146.1, 146.2, 151.5, 151.6, 161.2; LCMS (electrospray) m/z 473, 475 (M+H)$^+$ (Cl$^-$ isotope pattern).

6-Chloro-2-ethyl-N-(4-(4-phenylpiperidin-1-yl)benzyl)imidazo[1,2-a]pyridine-3-carboxamide (210)

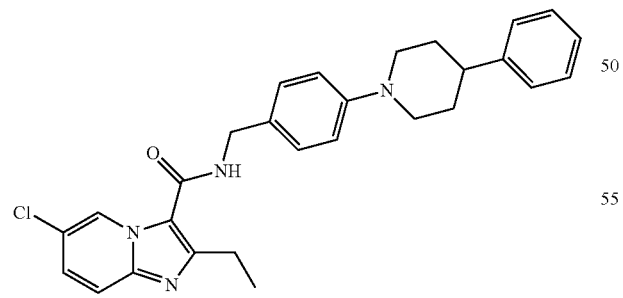

Pale yellow solid; mp=138.2° C.; $^1$H NMR (400 MHz, CDCl$_3$); δ 1.36 (t, J=7.6 Hz, 3H), 1.84-1.97 (m, 4H), 2.62-2.69 (m, 1H), 2.79-2.86 (m, 2H), 2.92 (q, J=7.6 Hz, 2H), 3.80-3.83 (m, 2H), 4.60 (d, J=5.2 Hz, 2H), 6.07 (brt, J=5.2 Hz, 1H), 6.97 (d, J=8.8 Hz, 2H), 7.19-7.33 (m, 8H), 7.50 (d, J=9.6 Hz, 1H), 9.50 (d, J=2.0 Hz, 1H); $^{13}$C NMR (100 MHz, CDCl$_3$) δ 13.3, 23.5, 33.3, 42.5, 43.3, 50.5, 115.4, 116.9, 117.0, 121.6, 126.3, 126.4, 126.9, 128.2, 128.4, 128.6, 128.9, 144.4, 146.0, 151.3, 151.4, 161.1; LCMS (electrospray) m/z 473, 475 (M+H)$^+$ (Cl$^-$ isotope pattern).

7-Chloro-N-(4-(4,4-dimethylpiperidin-1-yl)benzyl)-2-ethyl-1,8a-dihydroimidazo[1,2-a]pyridine-3-carboxamide (211)

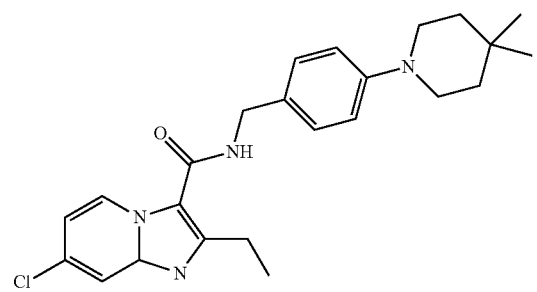 [SMILES: CCC1=C(C(=O)NCc2ccc(N3CCC(C)(C)CC3)cc2)N2C=CC(Cl)=CC2N1]

White solid; mp=121.3° C.; $^1$H NMR (400 MHz, CDCl$_3$); δ 0.97 (s, 6H), 1.34 (t, J=7.2 Hz, 3H), 1.49-1.52 (m, 4H), 2.89 (q, J=7.2 Hz, 2H), 3.15-3.17 (m, 4H), 4.57 (d, J=5.2 Hz, 2H), 6.00 (brt, J=5.2 Hz, 1H), 6.86 (dd, J=2.0, 7.6 Hz, 1H), 6.91 (d, J=8.4 Hz, 2H), 7.22 (d, J=8.4 Hz, 2H), 7.56 (d, J=2.0 Hz, 1H), 9.32 (d, J=7.6 Hz, 1H); $^{13}$C NMR (100 MHz, CDCl$_3$) δ 13.4, 23.5, 28.0, 29.8, 38.5, 43.4, 45.9, 114.7, 115.7, 116.4, 127.9, 128.6, 128.9, 129.0, 133.6, 146.1, 151.5, 151.6, 161.2; LCMS (electrospray) m/z 425, 427 (M+H)$^+$ (Cl$^-$ isotope pattern).

7-Chloro-2-ethyl-N-(4-(4-(hydroxymethyl)piperidin-1-yl)benzyl)imidazo[1,2-a]pyridine-3-carboxamide (212)

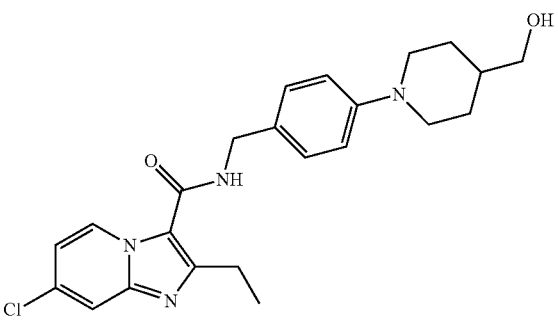 [SMILES: CCc1nc2cc(Cl)ccn2c1C(=O)NCc1ccc(N2CCC(CO)CC2)cc1]

White solid; mp=179.8° C.; $^1$H NMR (400 MHz, CDCl$_3$); δ 1.33 (t, J=7.6 Hz, 3H), 1.35-1.42 (m, 2H), 1.60-1.67 (m, 1H), 1.82-1.85 (m, 2H), 1.98 (brs, 1H), 2.66-2.73 (m, 2H), 2.91 (q, J=7.6 Hz, 2H), 3.52 (d, J=6.4 Hz, 2H), 3.68-3.71 (m, 2H), 4.56 (d, J=5.6 Hz, 2H), 6.04 (brt, J=5.6 Hz, 1H), 6.86 (dd, J=2.0, 7.6 Hz, 1H), 6.91 (d, J=8.8 Hz, 2H), 7.22 (d, J=8.8 Hz, 2H), 7.55 (d, J=2.0 Hz, 1H), 9.30 (d, J=7.6 Hz, 1H); $^{13}$C NMR (100 MHz, CDCl$_3$) δ 13.4, 23.5, 28.7, 38.6, 43.3, 49.7, 67.7, 114.7, 115.1, 115.7, 116.8, 128.3, 128.6, 128.8, 133.6, 146.1, 151.5, 151.6, 161.1; LCMS (electrospray) m/z 427, 429 (M+H)$^+$ (Cl$^-$ isotope pattern).

6-chloro-2-ethyl-N-(4-(4-((4-(trifluoromethoxy)phenoxy)methyl)piperidin-1-yl)benzyl)imidazo[1,2-a]pyridine-3-carboxamide (213)

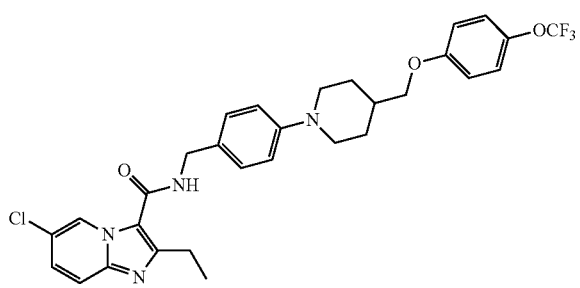 [SMILES: CCc1nc2ccc(Cl)cn2c1C(=O)NCc1ccc(N2CCC(COc3ccc(OC(F)(F)F)cc3)CC2)cc1]

Pale yellow solid; mp=183.6° C.; ¹H NMR (400 MHz, CDCl₃); δ 1.35 (t, J=7.6 Hz, 3H), 1.46-1.57 (m, 2H), 1.93-1.96 (m, 3H), 2.72-2.78 (m, 2H), 2.91 (q, J=7.6 Hz, 2H), 3.71-3.74 (m, 2H), 3.81 (d, J=6.0 Hz, 2H), 4.58 (d, J=5.6 Hz, 2H), 6.05 (brt, J=5.6 Hz, 1H), 6.85 (d, J=8.8 Hz, 2H), 6.93 (d, J=8.8 Hz, 2H), 7.11 (d, J=8.8 Hz, 2H), 7.24-7.28 (m, 3H), 7.50 (d, J=9.6 Hz, 1H), 9.50 (d, J=1.2 Hz, 1H); LCMS (electrospray) m/z 587, 589 (M+H)⁺ (Cl⁻ isotope pattern).

7-Chloro-2-ethyl-N-(4-(4-((4-(trifluoromethoxy)phenoxy)methyl)piperidin-1-yl)benzyl)imidazo[1,2-a]pyridine-3-carboxamide (214)

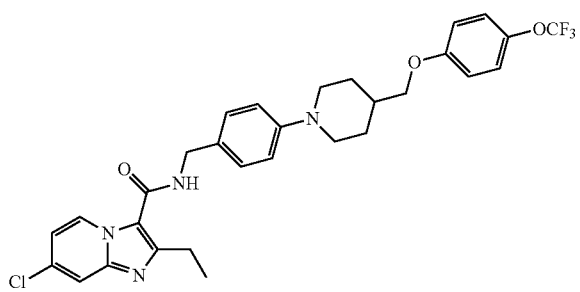 [SMILES: CCc1nc2cc(Cl)ccn2c1C(=O)NCc1ccc(N2CCC(COc3ccc(OC(F)(F)F)cc3)CC2)cc1]

White solid; mp=189.5° C.; ¹H NMR (400 MHz, CDCl₃); δ 1.34 (t, J=7.6 Hz, 3H), 1.46-1.56 (m, 2H), 1.93-2.02 (m, 3H), 2.71-2.78 (m, 2H), 2.90 (q, J=7.6 Hz, 2H), 3.71-3.74 (m, 2H), 3.81 (d, J=6.0 Hz, 2H), 4.57 (d, J=5.2 Hz, 2H), 6.05 (brt, J=5.2 Hz, 1H), 6.84-6.87 (m, 3H), 6.93 (d, J=8.8 Hz, 2H), 7.11 (d, J=8.8 Hz, 2H), 7.24 (d, J=8.8 Hz, 2H), 7.55 (d, J=2.0 Hz, 1H), 9.31 (d, J=7.2 Hz, 1H); LCMS (electrospray) m/z 587, 589 (M+H)⁺ (Cl⁻ isotope pattern).

7-Chloro-2-ethyl-N-(4-(((4-(trifluoromethoxy)benzyl)amino)benzyl)imidazo[1,2-a]pyridine-3-carboxamide (215)

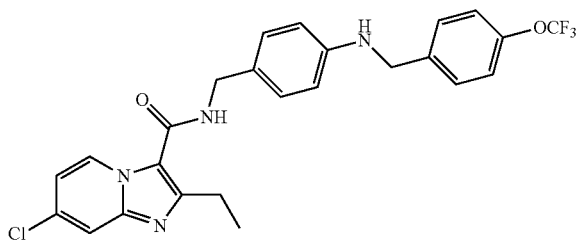 [SMILES: CCc1nc2cc(Cl)ccn2c1C(=O)NCc1ccc(NCc2ccc(OC(F)(F)F)cc2)cc1]

White solid; mp=169.6° C.; ¹H NMR (400 MHz, CDCl₃) δ 1.36 (t, J=7.6 Hz, 3H), 2.05-2.12 (m, 2H), 2.93 (q, J=7.2 Hz, 2H), 4.18 (br s, 1H), 4.55 (d, J=5.2 Hz, 2H), 5.99-6.01 (m, 1H), 6.60 (d, J=8.4 Hz, 2H), 6.87 (d, J=7.6 Hz, 1H), 7.17 (d, J=8.0 Hz, 4H), 7.38 (d, J=8.0 Hz, 2H), 7.56 (s, 1H), 9.33 (d, J=7.2 Hz, 1H); LCMS (electrospray) m/z (M+H)⁺ 503.

N-(4-(1H-isoindol-2(3H,3aH,4H,5H,6H,7H,7aH)-yl)benzyl)-7-chloro-2-ethylimidazo[1,2-a]pyridine-3-carboxamide (216)

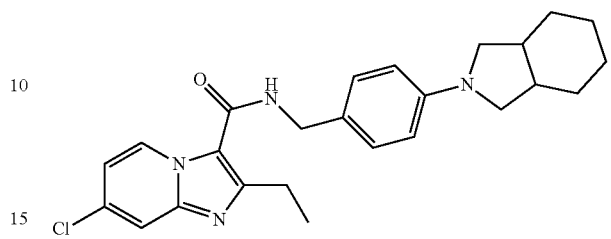

White solid; ¹H NMR (400 MHz, CDCl₃); δ 1.36 (t, J=7.6 Hz, 3H), 1.40-2.03 (m, 8H), 2.29-2.34 (m, 2H), 2.92 (q, J=7.2 Hz, 2H), 3.16 (dd, J=5.2 Hz, 9.2 Hz, 2H), 3.29 (dd, J=6.8 Hz, 8.8 Hz, 2H), 4.55 (d, J=5.2 Hz, 2H), 5.97 (brs, 1H), 6.49 (d, J=8.4 Hz, 2H), 6.88 (dd, J=2.4 Hz, 7.6 Hz, 1H), 7.21 (d, J=8.4 Hz, 2H), 7.56 (d, J=2.4 Hz, 1H), 9.33 (d, J=7.6 Hz, 1H); LCMS (electrospray) m/z (M+H)⁺ 437, 439 (Cl⁻ isotope pattern)

7-Chloro-2-ethyl-N-(4-(4,5,6,7-tetrahydro-2H-isoindol-2-yl)benzyl)imidazo[1,2-a]pyridine-3-carboxamide (217)

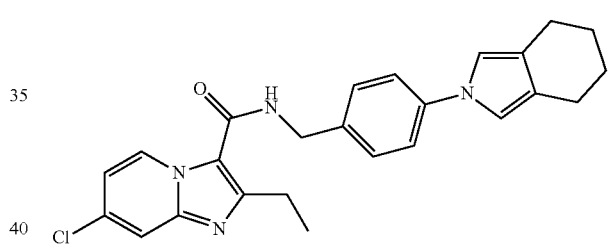

White solid; ¹H NMR (400 MHz, CDCl₃); δ 1.39 (t, J=7.6 Hz, 3H), 1.74-1.77 (m, 4H), 2.63 (m, 4H), 2.97 (q, J=7.6 Hz, 2H), 4.68 (d, J=6.0 Hz, 2H), 6.14 (brs, 1H), 6.78 (s, 2H), 6.91 (dd, J=2.0 Hz, 7.6 Hz, 1H), 7.32 (d, J=8.4 Hz, 2H), 7.38 (d, J=8.4 Hz, 2H), 7.59 (d, J=2.0 Hz, 1H), 9.36 (d, J=7.2 Hz, 1H); LCMS (electrospray) m/z (M+H)⁺ 433, 435 (Cl⁻ isotope pattern).

7-Chloro-2-ethyl-N-(4-(4-methylenepiperidin-1-yl)benzyl)imidazo[1,2-a]pyridine-3-carboxamide (218)

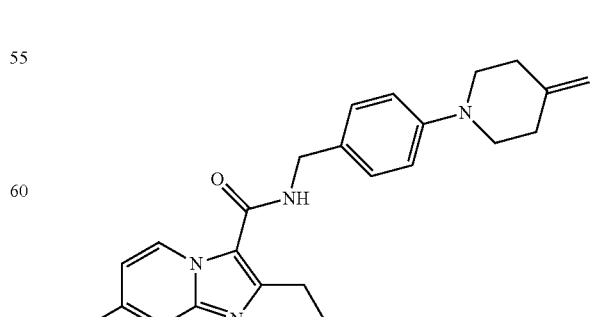

White solid; mp=168.3° C.; ¹H NMR (400 MHz, CDCl₃); δ 1.33 (t, J=7.2 Hz, 3H), 2.32-2.34 (m, 4H), 2.89 (q, J=7.2 Hz, 2H), 3.23-3.25 (m, 4H), 4.56 (d, J=5.2 Hz, 2H), 4.73 (s, 2H), 6.07 (brs, 1H), 6.84 (d, J=7.2 Hz, 1H), 6.90 (d, J=8.4 Hz, 2H), 7.22 (d, J=8.4 Hz, 2H), 7.54 (s, 1H), 9.29 (d, J=7.2 Hz, 1H); ¹³C NMR (100 MHz, CDCl₃) δ 13.4, 23.5, 34.2, 43.3, 51.2, 108.5, 114.6, 115.1, 115.7, 116.7, 128.3, 128.5, 128.9, 133.5, 145.8, 146.0, 150.8, 151.5, 161.1; LCMS (electrospray) m/z 409, 411 (M+H)⁺ (Cl⁻ isotope pattern).

2-Ethyl-7-methyl-N-(4-(4-(trifluoromethoxy)phenoxy)benzyl)imidazo[1,2-a]pyridine-3-carboxamide (219)

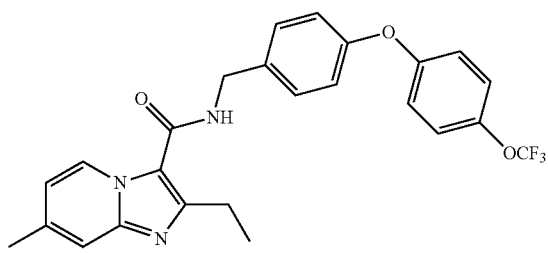 [SMILES: CCc1nc2cc(C)ccn2c1C(=O)NCc1ccc(Oc2ccc(OC(F)(F)F)cc2)cc1]

Pale yellow solid; mp=133.6° C.; ¹H NMR (400 MHz, CDCl₃); δ 1.36 (t, J=7.6 Hz, 3H), 2.39 (s, 3H), 2.93 (q, J=7.6 Hz, 2H), 4.65 (d, J=5.6 Hz, 2H), 6.13 (brt, J=5.6 Hz, 1H), 6.71 (dd, J=1.6, 7.2 Hz, 1H), 6.96-7.00 (m, 4H), 7.15 (d, J=8.4 Hz, 2H), 7.32-7.37 (m, 3H), 9.23 (d, J=7.2 Hz, 1H); LCMS (electrospray) m/z 470 (M+H)⁺.

2-Ethyl-N-(4-(4-(4-fluorophenyl)piperazin-1-yl)benzyl)-7-methylimidazo[1,2-a]pyridine-3-carboxamide (220)

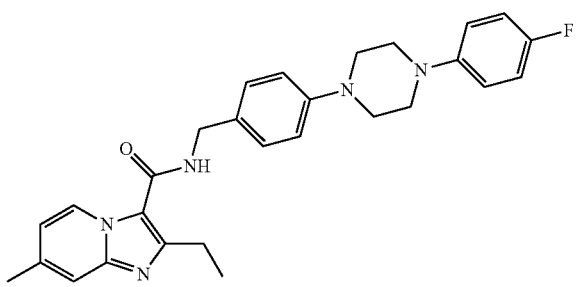 [SMILES: CCc1nc2cc(C)ccn2c1C(=O)NCc1ccc(N2CCN(c3ccc(F)cc3)CC2)cc1]

White solid; mp=203.7° C.; ¹H NMR (400 MHz, CDCl₃); δ 1.35 (t, J=7.6 Hz, 3H), 2.40 (s, 3H), 2.91 (q, J=7.6 Hz, 2H), 3.23-3.26 (m, 4H), 3.32-3.34 (m, 4H), 4.60 (d, J=5.6 Hz, 2H), 6.02 (brt, J=5.6 Hz, 1H), 6.72-6.74 (m, 1H), 6.91-7.00 (m, 6H), 7.29-7.33 (m, 3H), 9.25 (d, J=7.2 Hz, 1H); LCMS (electrospray) m/z 472 (M+H)⁺.

6-Chloro-2-ethyl-N-(4-(octahydroisoquinolin-2(1H)-yl)benzyl)imidazo[1,2-a]pyridine-3-carboxamide (221)

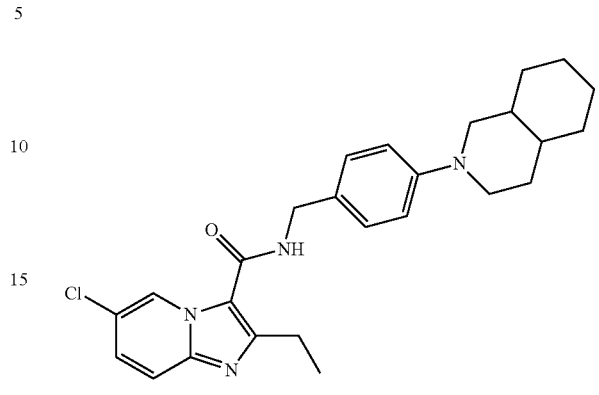

White solid; mp=141.7° C.; ¹H NMR (400 MHz, CDCl₃); δ 0.94-1.03 (m, 3H), 1.24-1.42 (m, 4H), 1.34 (t, J=7.2 Hz, 3H), 1.57-1.66 (m, 3H), 1.73-1.74 (m, 2H), 2.30-2.35 (m, 1H), 2.65-2.72 (m, 1H), 2.89 (q, J=7.2 Hz, 2H), 3.48-3.53 (m, 1H), 3.67-3.71 (m, 1H), 4.56 (d, J=5.6 Hz, 2H), 6.03 (brt, J=5.6 Hz, 1H), 6.89 (d, J=8.4 Hz, 2H), 7.21 (d, J=8.4 Hz, 2H) 7.24 (dd, J=2.0, 9.2 Hz, 1H), 7.48 (d, J=9.2 Hz, 1H), 9.48 (d, J=2.0 Hz, 1H); ¹³C NMR (100 MHz, CDCl₃) δ 13.3, 23.5, 26.1, 26.5, 30.5, 32.8, 33.0, 41.6, 41.8, 43.3, 50.3, 56.2, 115.4, 116.5, 116.9, 121.5, 126.3, 127.8, 128.2, 128.8, 144.5, 151.3, 151.5, 161.1; LCMS (electrospray) m/z 451, 453 (M+H)⁺ (Cl⁻ isotope pattern).

7-Chloro-2-ethyl-N-(4-(octahydroisoquinolin-2(1H)-yl)benzyl)imidazo[1,2-a]pyridine-3-carboxamide (222)

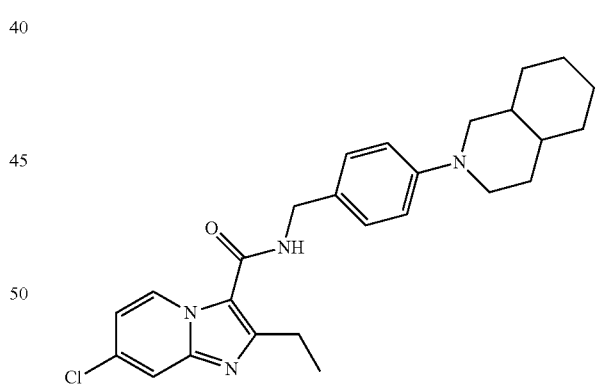

White solid; mp=174.2° C.; ¹H NMR (400 MHz, CDCl₃); δ 0.93-1.01 (m, 3H), 1.24-1.40 (m, 4H), 1.30 (t, J=7.6 Hz, 3H), 1.56-1.64 (m, 3H), 1.71-1.72 (m, 2H), 2.27-2.33 (m, 1H), 2.63-2.69 (m, 1H), 2.86 (q, J=7.6 Hz, 2H), 3.48-3.50 (m, 1H), 3.65-3.68 (m, 1H), 4.53 (d, J=5.2 Hz, 2H), 6.10 (brt, J=5.2 Hz, 1H), 6.81 (d, J=7.2 Hz, 1H), 6.87 (d, J=8.0 Hz, 2H), 7.18 (d, J=8.0 Hz, 2H), 7.51 (s, 1H), 9.25 (d, J=7.2 Hz, 1H); ¹³C NMR (100 MHz, CDCl₃) δ 13.3, 23.4, 26.1, 26.4, 30.5, 32.8, 33.0, 41.6, 41.7, 43.3, 50.2, 56.1, 114.5, 115.1, 115.6, 116.4, 127.8, 128.4, 128.7, 133.4, 145.9, 151.4, 151.5, 161.1; LCMS (electrospray) m/z 451, 453 (M+H)⁺ (Cl⁻ isotope pattern).

2-Ethyl-8-fluoro-N-(4-(4-(4-fluorophenyl)piperazin-1-yl)benzyl)imidazo[1,2-a]pyridine-3-carboxamide (223)

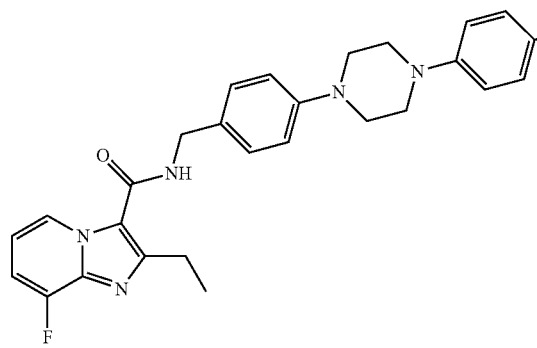

Pale yellow solid; mp=204.1° C.; ¹H NMR (400 MHz, CDCl₃+CD₃OD); δ 1.34 (t, J=7.6 Hz, 3H), 2.94 (q, J=7.6 Hz, 2H), 3.24-3.26 (m, 4H), 3.33-3.35 (m, 4H), 4.60 (d, J=5.6 Hz, 2H), 6.44 (brt, J=5.6 Hz, 1H), 6.81-6.86 (m, 1H), 6.92-7.06 (m, 7H), 7.29 (d, J=8.8 Hz, 2H), 9.08 (d, J=6.8 Hz, 1H); LCMS (electrospray) m/z 476 (M+H)⁺.

2-Ethyl-8-fluoro-N-(4-(4-(trifluoromethoxy)phenoxy)benzyl)imidazo[1,2-a]pyridine-3-carboxamide (224)

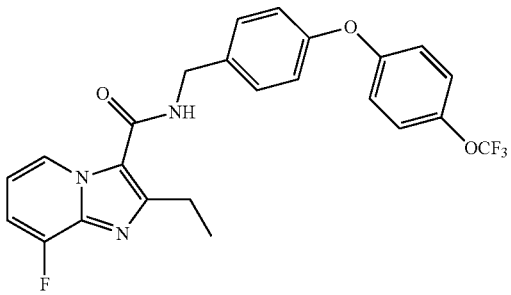 [SMILES: CCc1nc2c(F)cccn2c1C(=O)NCc1ccc(Oc2ccc(OC(F)(F)F)cc2)cc1]

Pale yellow solid; mp=105.6° C.; ¹H NMR (400 MHz, CDCl₃); δ 1.35 (t, J=7.6 Hz, 3H), 2.96 (q, J=7.6 Hz, 2H), 4.65 (d, J=5.6 Hz, 2H), 6.29 (brt, J=5.6 Hz, 1H), 6.77-6.82 (m, 1H), 6.96-7.02 (m, 5H), 7.13-7.17 (m, 2H), 7.32-7.35 (m, 2H), 9.12 (dd, J=0.8, 7.2 Hz, 1H); LCMS (electrospray) m/z 474 (M+H)⁺.

2-Ethyl-6-fluoro-N-(4-(4-(trifluoromethoxy)phenoxy)benzyl)imidazo[1,2-a]pyridine-3-carboxamide (225)

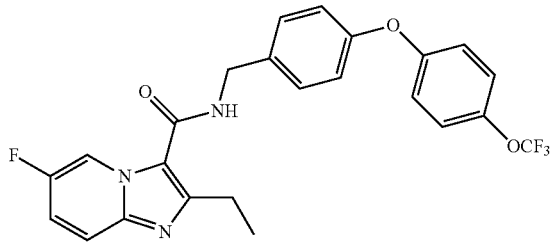 [SMILES: CCc1nc2ccc(F)cn2c1C(=O)NCc1ccc(Oc2ccc(OC(F)(F)F)cc2)cc1]

White solid; mp=133.4° C.; ¹H NMR (400 MHz, CDCl₃) δ 1.42 (t, J=7.6 Hz, 3H), 3.00 (q, J=7.6 Hz, 2H), 4.68 (d, J=5.6 Hz, 2H), 6.12-6.14 (m, 1H), 6.98-7.03 (m, 4H), 7.18 (d, J=8.8 Hz, 2H), 7.23-7.28 (m, 1H), 7.58 (dd, J=5.2, 9.6 Hz, 1H), 9.44-9.46 (m, 1H); LCMS (electrospray) m/z (M+H)⁺ 474.

6-Bromo-2-ethyl-N-(4-(4-(trifluoromethoxy)phenoxy)benzyl)imidazo[1,2-a]pyridine-3-carboxamide (226)

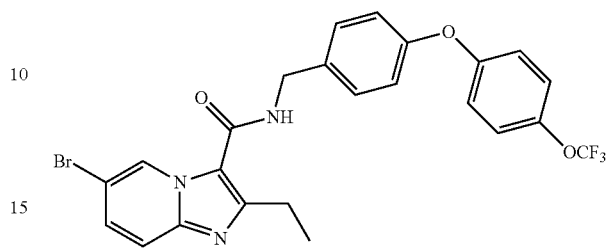

White solid; mp=152.9° C.; ¹H NMR (400 MHz, CDCl₃) δ 1.42 (t, J=7.4 Hz, 3H), 2.99 (q, J=7.6 Hz, 2H), 4.68 (d, J=5.6 Hz, 2H), 6.12-6.14 (m, 1H), 6.98-6.03 (m, 4H), 7.18 (d, J=8.8 Hz, 2H), 7.37 (d, J=8.4 Hz, 1H), 7.40 (dd, J=2.0, 9.6 Hz, 1H), 7.50 (d, J=9.2 Hz, 1H), 9.63 (d, J=1.2 Hz, 1H)); LCMS (electrospray) m/z (M+H)⁺ 534, 536 (Br⁻ isotope pattern).

2-Ethyl-N-(4-(4-(4-fluorophenyl)piperazin-1-yl)benzyl)imidazo[1,2-a]pyridine-3-carboxamide (227)

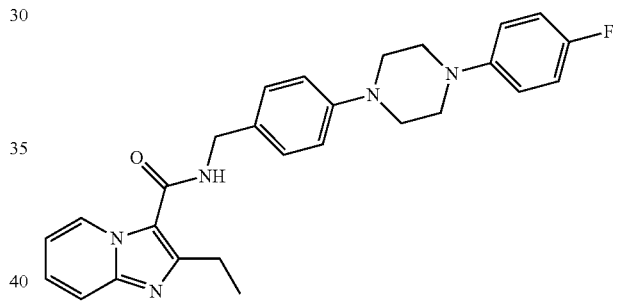

White solid; mp=189.2° C.; ¹H NMR (400 MHz, CDCl₃) δ 1.40 (t, J=7.8 Hz, 3H), 2.96 (q, J=7.6 Hz, 2H), 3.24-3.29 (m, 2H), 3.32-3.36 (m, 2H), 4.63 (d, J=5.6 Hz, 2H), 6.02-6.04 (m, 1H), 6.90-7.01 (m, 7H), 7.30-7.34 (m, 2H), 7.60 (d, J=9.2 Hz, 1H), 9.41 (d, J=7.2 Hz, 1H); LCMS (electrospray) m/z (M+H)⁺ 458.

2-Ethyl-6-fluoro-N-(4-(4-(4-fluorophenyl)piperazin-1-yl)benzyl)imidazo[1,2-a]pyridine-3-carboxamide (228)

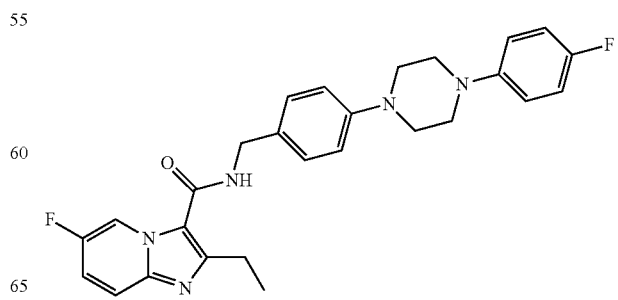

White solid; mp=200.9° C.; ¹H NMR (400 MHz, CDCl₃) δ 1.40 (t, J=7.8 Hz, 3H), 2.96 (q, J=7.6 Hz, 2H), 3.24-3.29 (m, 2H), 3.32-3.36 (m, 2H), 4.62 (d, J=5.6 Hz, 2H), 6.03-6.05 (m, 1H), 6.92-7.01 (m, 6H), 7.22-7.27 (m, 2H), 7.31 (d, J=8.4 Hz, 2H), 7.56 (dd, J=5.0, 9.8 Hz, 1H), 9.44-9.46 (m, 1H); LCMS (electrospray) m/z (M+H)⁺ 476.

6-Bromo-2-ethyl-N-(4-(4-(4-fluorophenyl)piperazin-1-yl)benzyl)imidazo[1,2-a]pyridine-3-carboxamide (229)

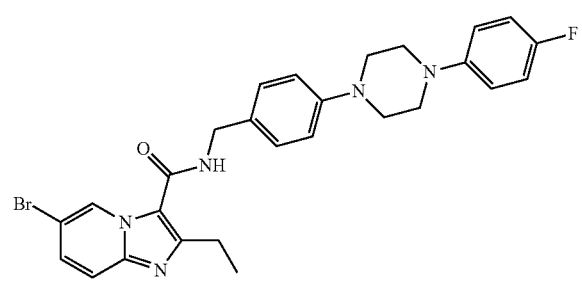

White solid; mp=218.1° C.; ¹H NMR (400 MHz, CDCl₃) δ 1.40 (t, J=7.6 Hz, 3H), 2.95 (q, J=7.6 Hz, 2H), 3.24-3.29 (m, 2H), 3.31-3.36 (m, 2H), 4.62 (d, J=5.6 Hz, 2H), 6.04 (t, J=5.0 Hz, 1H), 6.92-7.01 (m, 6H), 7.31 (d, J=8.8 Hz, 2H), 7.39 (dd, J=2.0, 9.2 Hz, 1H), 7.49 (d, J=9.6 Hz, 1H), 9.63 (d, J=1.6 Hz, 1H); LCMS (electrospray) m/z (M+H)⁺ 536, 538 (Br⁻ isotope pattern).

6-Chloro-2-ethyl-N-(4-(4-(hydroxymethyl)piperidin-1-yl)benzyl)imidazo[1,2-a]pyridine-3-carboxamide (230)

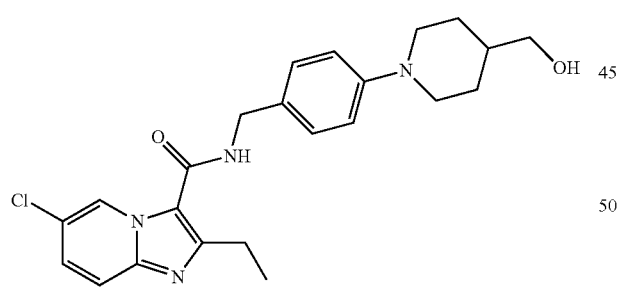

Pale yellow solid; mp=161.1° C.; ¹H NMR (400 MHz, CDCl₃); δ 1.23-1.41 (m, 2H), 1.33 (t, J=7.6 Hz, 3H), 1.59-1.65 (m, 1H), 1.80-1.84 (m, 2H), 2.64-2.71 (m, 2H), 2.89 (q, J=7.6 Hz, 2H), 3.50 (d, J=6.4 Hz, 2H), 3.66-3.69 (m, 2H), 4.55 (d, J=5.2 Hz, 2H), 6.09 (brt, J=5.2 Hz, 1H), 6.89 (d, J=8.4 Hz, 2H), 7.21 (d, J=8.4 Hz, 2H), 7.23 (dd, J=2.0, 9.2 Hz, 1H), 7.47 (d, J=9.2 Hz, 1H), 9.45 (d, J=2.0 Hz, 1H); ¹³C NMR (100 MHz, CDCl₃) δ 13.3, 23.4, 28.7, 38.6, 43.3, 49.6, 67.6, 115.3, 116.8, 116.9, 121.5, 126.2, 128.2, 128.3, 128.8, 144.4, 151.3, 151.4, 161.1; LCMS (electrospray) m/z 427, 429 (M+H)⁺ (Cl⁻ isotope pattern).

2-Ethyl-N-(4-(4-(4-fluorophenyl)piperazin-1-yl)benzyl)-6-methylimidazo[1,2-a]pyridine-3-carboxamide (231)

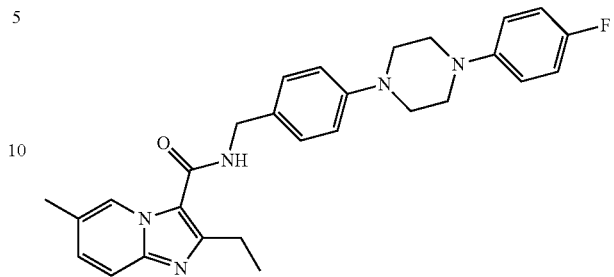

White solid; mp=187.6° C.; ¹H NMR (400 MHz, CDCl₃); δ 1.35 (t, J=7.6 Hz, 3H), 2.89 (s, 3H), 2.91 (q, J=7.6 Hz, 2H), 3.22-3.24 (m, 4H), 3.31-3.33 (m, 4H), 4.60 (d, J=5.2 Hz, 2H), 6.04 (brt, J=5.2 Hz, 1H), 6.89-6.99 (m, 6H), 7.13 (dd, J=1.6, 9.2 Hz, 1H), 7.28 (d, J=8.4 Hz, 2H), 7.46 (d, J=9.2 Hz, 1H), 9.18 (s, 1H); LCMS (electrospray) m/z 472 (M+H)⁺.

2-Ethyl-6-methyl-N-(4-(4-(trifluoromethoxy)phenoxy)benzyl)imidazo[1,2-a]pyridine-3-carboxamide (232)

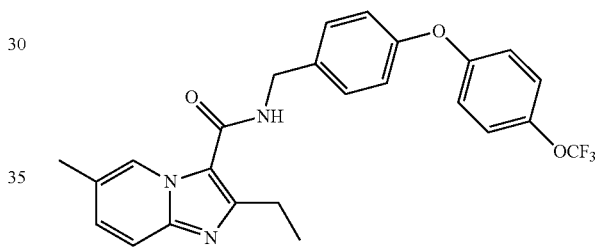

Pale yellow solid; ¹H NMR (400 MHz, CDCl₃); δ 1.31 (t, J=7.6 Hz, 3H), 2.30 (s, 3H), 2.90 (q, J=7.6 Hz, 2H), 4.62 (d, J=5.6 Hz, 2H), 6.32 (brt, J=5.6 Hz, 1H), 6.93-6.96 (m, 4H), 7.11-7.14 (m, 3H), 7.31 (d, J=8.4 Hz, 2H), 7.42 (d, J=8.4 Hz, 1H), 9.11 (s, 1H); LCMS (electrospray) m/z 470 (M+H)⁺.

6-Chloro-2-ethyl-N-(4-(4-(trifluoromethyl)piperidin-1-yl)benzyl)imidazo[1,2-a]pyridine-3-carboxamide (233)

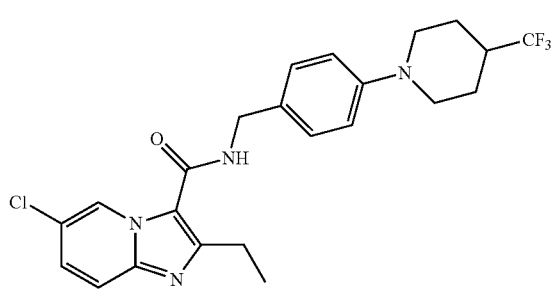 [SMILES: CCc1nc2ccc(Cl)cn2c1C(=O)NCc1ccc(N2CCC(C(F)(F)F)CC2)cc1]

White solid; mp=197.9° C.; ¹H NMR (400 MHz, CDCl₃); δ 1.35 (t, J=7.6 Hz, 3H), 1.68-1.82 (m, 2H), 1.94-1.97 (m, 2H), 2.12-2.18 (m, 1H), 2.66-2.73 (m, 2H), 2.91 (q, J=7.6 Hz, 2H), 3.73-3.77 (m, 2H), 4.58 (d, J=5.6 Hz, 2H), 6.04 (brt, J=5.2 Hz, 1H), 6.91 (d, J=8.8 Hz, 2H), 7.25-7.29 (m, 3H), 7.50 (d, J=9.2 Hz, 1H), 9.50 (d, J=1.2 Hz, 1H); LCMS (electrospray) m/z 465, 467 (M+H)+ (Cl− isotope pattern).

7-Chloro-2-ethyl-N-(4-(4-(trifluoromethyl)piperidin-1-yl)benzyl)imidazo[1,2-a]pyridine-3-carboxamide (234)

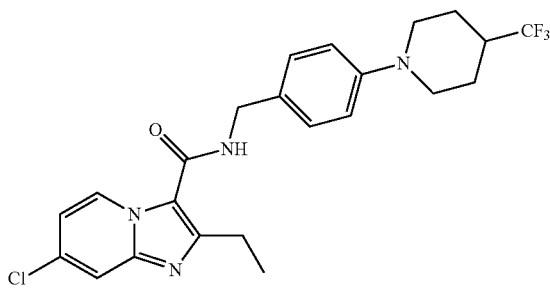 [SMILES: CCc1nc2cc(Cl)ccn2c1C(=O)NCc1ccc(N2CCC(C(F)(F)F)CC2)cc1]

White solid; mp=209.4° C.; 1H NMR (400 MHz, CDCl3); δ 1.34 (t, J=7.6 Hz, 3H), 1.68-1.78 (m, 2H), 1.94-1.98 (m, 2H), 2.11-2.20 (m, 1H), 2.66-2.73 (m, 2H), 2.90 (q, J=7.6 Hz, 2H), 3.73-3.77 (m, 2H), 4.58 (d, J=5.2 Hz, 2H), 6.03 (brt, J=5.2 Hz, 1H), 6.86 (dd, J=2.4, 7.6 Hz, 1H), 6.91 (d, J=8.8 Hz, 2H), 7.25 (d, J=8.8 Hz, 2H), 7.56 (d, J=2.4 Hz, 1H), 9.32 (d, J=7.6 Hz, 1H); LCMS (electrospray) m/z 465, 467 (M+H)+ (Cl− isotope pattern).

6-chloro-N-(4-(4,4-difluoropiperidin-1-yl)benzyl)-2-ethylimidazo[1,2-a]pyridine-3-carboxamide (235)

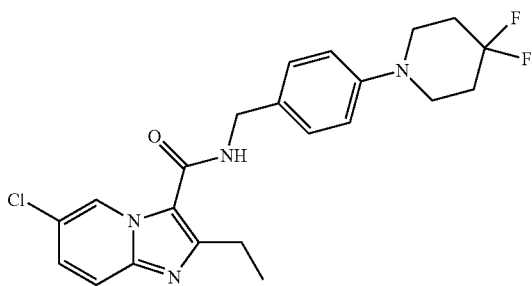 [SMILES: CCc1nc2ccc(Cl)cn2c1C(=O)NCc1ccc(N2CCC(F)(F)CC2)cc1]

White solid; mp=194.2° C.; 1H NMR (400 MHz, CDCl3); δ 1.36 (t, J=7.6 Hz, 3H), 1.98-2.13 (m, 4H), 2.92 (q, J=7.6 Hz, 2H), 3.33-3.36 (m, 4H), 4.59 (d, J=5.6 Hz, 2H), 6.04 (brt, J=5.6 Hz, 1H), 6.91-6.95 (m, 2H), 7.25-7.30 (m, 3H), 7.52 (d, J=9.6 Hz, 1H), 9.51 (d, J=2.0 Hz, 1H); LCMS (electrospray) m/z 433, 435 (M+H)+ (Cl− isotope pattern).

7-Chloro-N-(4-(4,4-difluoropiperidin-1-yl)benzyl)-2-ethylimidazo[1,2-a]pyridine-3-carboxamide (236)

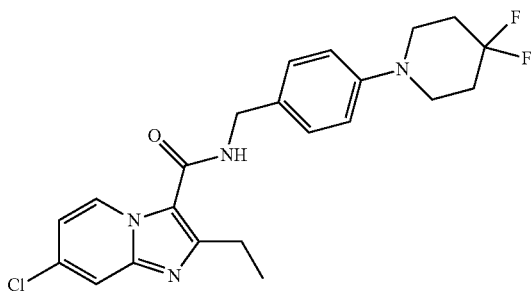 [SMILES: CCc1nc2cc(Cl)ccn2c1C(=O)NCc1ccc(N2CCC(F)(F)CC2)cc1]

White solid; mp=166.3° C.; 1H NMR (400 MHz, CDCl3); δ 1.34 (t, J=7.2 Hz, 3H), 2.03-2.12 (m, 4H), 2.90 (q, J=7.2 Hz, 2H), 3.32-3.35 (m, 4H), 4.58 (d, J=5.2 Hz, 2H), 6.06 (brt, J=5.2 Hz, 1H), 6.86 (dd, J=2.0, 7.6 Hz, 1H), 6.91 (d, J=8.4 Hz, 2H), 7.25 (d, J=8.4 Hz, 2H), 7.55 (d, J=2.0 Hz, 1H), 9.31 (d, J=7.6 Hz, 1H); LCMS (electrospray) m/z 433, 435 (M+H)+ (Cl− isotope pattern).

6-Chloro-2-ethyl-N-(4-(hexahydropyrrolo[1,2-a]pyrazin-2(1H)-yl)benzyl)imidazo[1,2-a]pyridine-3-carboxamide (237)

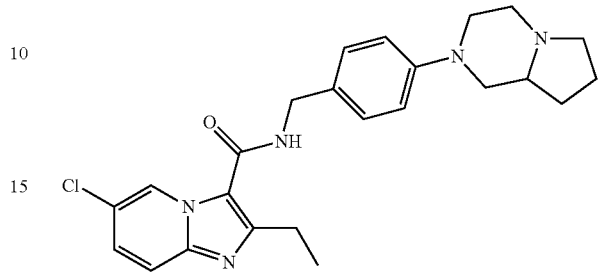

White solid; mp=163.0° C.; 1H NMR (400 MHz, CDCl3); δ1.38 (t, J=7.6 Hz, 3H), 1.47-1.53 (m, 2H), 1.65-1.85 (m, 2H), 2.17 (t, J=8.8 Hz, 2H), 2.34-2.40 (m, 1H), 2.54 (t, J=10.8 Hz, 1H), 2.89-2.97 (m, 3H), 3.13 (m, 2H), 3.61 (d, J=12.4 Hz, 1H), 3.76 (d, J=10.4 Hz, 1H), 4.60 (d, J=5.6 Hz, 2H), 6.01 (brs, 1H), 6.93 (d, J=8.4 Hz, 2H), 7.25-7.29 (m, 3H), 7.52 (d, J=9.6 Hz, 1H), 9.51 (s, 1H); LCMS (electrospray) m/z (M+H)+ 438.

6-Chloro-N,2-diethylimidazo[1,2-a]pyridine-3-carboxamide (238)

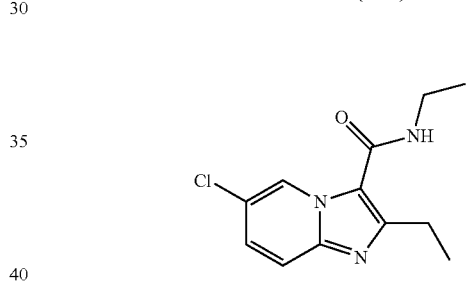

White solid; mp=176.7° C.; 1H NMR (400 MHz, CDCl3); δ 1.29 (t, J=7.2 Hz, 3H), 1.43 (t, J=7.6 Hz, 3H), 2.99 (q, J=7.2 Hz, 2H), 3.51-3.57 (m, 2H), 5.79 (brs, 1H), 7.27 (dd, J=2.4 Hz, 9.6 Hz, 1H), 7.51 (d, J=9.6 Hz, 1H), 9.45 (d, J=2.4 Hz, 1H); LCMS (electrospray) m/z (M+H)+ 252.

6-Chloro-2-ethyl-N-isobutylimidazo[1,2-a]pyridine-3-carboxamide (239)

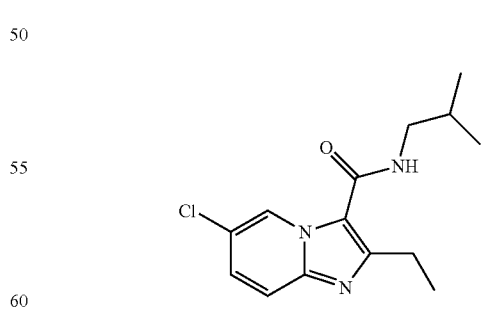

White solid; mp=162.2° C.; 1H NMR (400 MHz, CDCl3); δ 1.01 (d, J=6.8 Hz, 6H), 1.45 (t, J=7.6 Hz, 3H), 1.90-1.97 (m, 1H), 3.01 (q, J=7.6 Hz, 2H), 3.34 (t, J=6.8 Hz, 2H), 5.86 (brs, 1H), 7.28 (dd, J=2.0 Hz, 9.6 Hz, 1H), 7.53 (d, J=9.6 Hz, 1H), 9.47 (d, J=2.0 Hz, 1H); LCMS (electrospray) m/z (M+H)+ 280.

6-Bromo-2-ethyl-N-(4-morpholinobenzyl)imidazo[1,2-a]pyridine-3-carboxamide (240)

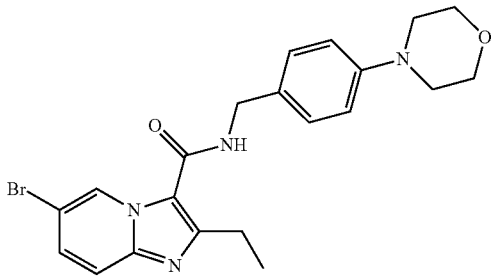

White solid; mp=228.2° C.; ¹H NMR (400 MHz, CDCl₃); δ 1.38 (t, J=7.6 Hz, 3H), 2.95 (q, J=7.6 Hz, 2H), 3.16 (t, J=4.8 Hz, 4H), 3.86 (t, J=4.8 Hz, 4H), 4.61 (d, J=5.6 Hz, 2H), 6.02 (brs, 1H), 6.91 (d, J=8.8 Hz, 2H), 7.29 (d, J=8.8 Hz, 2H), 7.38 (dd, J=1.6 Hz, 9.6 Hz, 1H), 7.48 (d, J=9.6 Hz, 1H), 9.61 (d, J=0.8 Hz, 1H); LCMS (electrospray) m/z (M+H)⁺ 443.

2-Ethyl-6-fluoro-N-(4-morpholinobenzyl)imidazo[1,2-a]pyridine-3-carboxamide (241)

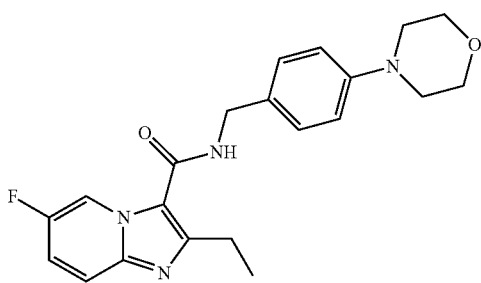 [SMILES: CCc1nc2ccc(F)cn2c1C(=O)NCc1ccc(N2CCOCC2)cc1]

White solid; mp=181.7° C.; ¹H NMR (400 MHz, CDCl₃); δ1.42 (t, J=7.6 Hz, 3H), 2.99 (q, J=7.6 Hz, 2H), 3.19 (t, J=4.8 Hz, 4H), 3.89 (t, J=4.8 Hz, 4H), 4.64 (d, J=5.2 Hz, 2H), 6.02 (brs, 1H), 6.91 (d, J=8.4 Hz, 2H), 7.26-7.33 (m, 3H), 7.60 (dd, J=5.2 Hz, 5.4 Hz, 1H), 9.48 (dd, J=2.4 Hz, 5.2 Hz, 1H); LCMS (electrospray) m/z (M+H)⁺ 383.

2-Ethyl-8-fluoro-N-(4-morpholinobenzyl)imidazo[1,2-a]pyridine-3-carboxamide (242)

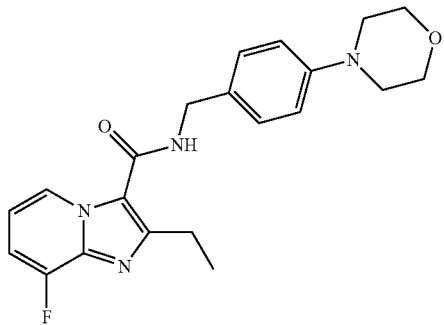 [SMILES: CCc1nc2c(F)cccn2c1C(=O)NCc1ccc(N2CCOCC2)cc1]

White solid; mp=197.3° C.; ¹H NMR (400 MHz, CDCl₃); δ1.39 (t, J=7.6 Hz, 3H), 2.98 (q, J=7.6 Hz, 2H), 3.15-3.17 (m, 4H), 3.85-3.87 (m, 4H), 4.61 (d, J=5.6 Hz, 2H), 6.05 (brs, 1H), 6.80-6.85 (m, 1H), 6.92 (d, J=8.8 Hz, 2H), 7.00-7.05 (m, 1H), 7.29 (d, J=8.8 Hz, 2H), 9.19 (dd, J=0.8 Hz, 7.2 Hz, 1H); LCMS (electrospray) m/z (M+H)⁺ 383.

2-Ethyl-N-(4-(4-((4-fluorophenoxy)methyl)piperidin-1-yl)benzyl)imidazo[1,2-a]pyridine-3-carboxamide (243)

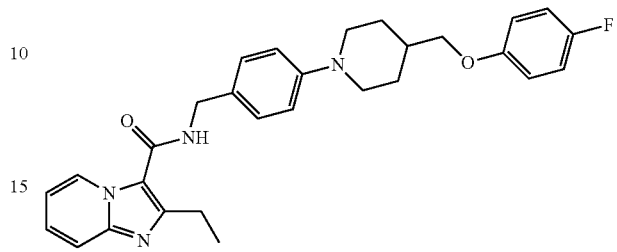

White solid; mp=144.2° C.; ¹H NMR (400 MHz, CDCl₃); δ 1.39 (t, J=7.2 Hz, 3H), 1.46-1.60 (m, 3H), 1.94-1.96 (m, 2H), 2.73-2.78 (m, 2H), 2.96 (q, J=7.2 Hz, 2H), 3.73 (d, J=12.0, 2H), 3.80 (d, J=6.0 Hz, 2H), 4.61 (d, J=5.2 Hz, 2H), 5.99 (brs, 1H), 6.82-6.84 (m, 1H), 6.89-6.92 (m, 2H), 6.94-6.98 (m, 4H), 7.25-7.29 (m, 2H), 7.32 (d, J=8.4 Hz, 1H), 7.59 (d, J=8.4 Hz, 1H), 8.40 (d, J=7.2 Hz, 1H); LCMS (electrospray) m/z (M+H)⁺ 487.

6-Chloro-2-ethyl-N-(4-(4-((4-fluorophenoxy)methyl)piperidin-1-yl)benzyl)imidazo[1,2-a]pyridine-3-carboxamide (244)

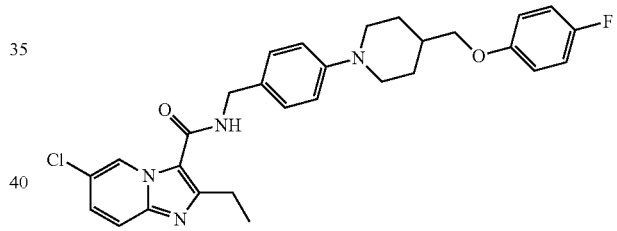

White solid; mp=171.0° C.; ¹H NMR (400 MHz, CDCl₃); δ 1.38 (t, J=7.6 Hz, 3H), 1.50-1.56 (m, 2H), 1.94-1.96 (m, 3H), 2.72-2.79 (m, 2H), 2.95 (q, J=7.6 Hz, 2H), 3.74 (d, J=12.4 Hz, 2H), 3.80 (d, J=5.6 Hz, 2H), 4.60 (d, J=5.6 Hz, 2H), 6.01 (brs, 1H), 6.81-6.84 (m, 2H), 6.94-6.98 (m, 4H), 7.27-7.29 (m, 3H), 7.53 (d, J=9.6 Hz, 1H), 9.52 (d, J=2.0 Hz, 1H); LCMS (electrospray) m/z (M+H)⁺ 521.

7-Chloro-2-ethyl-N-(4-(4-((4-fluorophenoxy)methyl)piperidin-1-yl)benzyl)imidazo[1,2-a]pyridine-3-carboxamide (245)

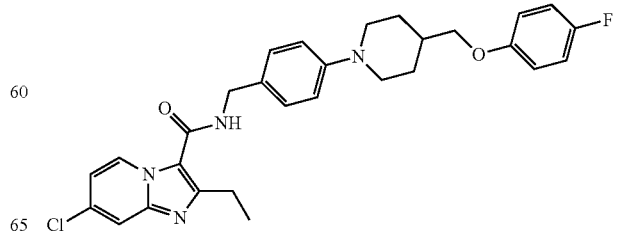

White solid; mp=186.5° C.; ¹H NMR (400 MHz, CDCl₃); δ 1.37 (t, J=7.6 Hz, 3H), 1.50-1.61 (m, 2H), 1.94-1.96 (m, 3H), 2.76 (t, J=10.8 Hz, 2H), 2.93 (q, J=7.6 Hz, 2H), 3.74 (d, J=12.0 Hz, 2H), 3.80 (d, J=5.6 Hz, 2H), 4.59 (d, J=5.6 Hz, 2H), 6.00 (brs, 1H), 6.80-6.84 (m, 2H), 6.88-6.90 (m, 1H), 6.94-6.98 (m, 4H), 7.25-7.27 (m, 2H), 7.58 (d, J=1.6 Hz, 1H), 9.34 (d, J=8.0 Hz, 1H); LCMS (electrospray) m/z (M+H)⁺ 521.

2-Ethyl-7-(4-phenylpiperazin-1-yl)-N-(4-(trifluoromethyl)benzyl)imidazo[1,2-a]pyridine-3-carboxamide (246)

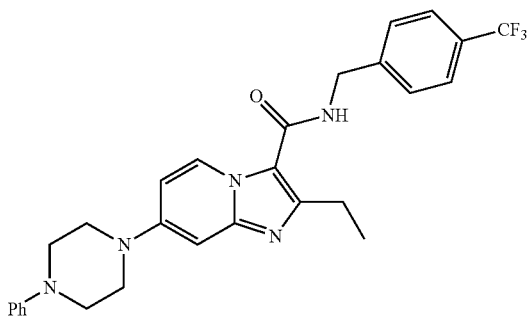 [SMILES: CCc1nc2cc(N3CCN(c4ccccc4)CC3)ccn2c1C(=O)NCc1ccc(C(F)(F)F)cc1]

Pale yellow solid; mp=235.2° C.; ¹H NMR (400 MHz, CDCl₃); δ 1.40 (t, J=7.2 Hz, 3H), 2.93 (q, J=7.2 Hz, 2H), 3.34-3.36 (m, 4H), 3.44-3.48 (m, 4H), 4.74 (d, J=6.0 Hz, H), 6.07 (brt, J=6.0 Hz, 1H), 6.70 (dd, J=2.4, 7.6 Hz, 1H), 6.84 (d, J=2.4 Hz, 1H), 6.90 (dd, J=7.2, 7.6 Hz, 1H), 6.97 (d, J=8.4 Hz, 2H), 7.28-7.32 (m, 2H), 7.48 (d, J=8.0 Hz, 2H), 7.61 (d, J=8.4 Hz, 2H), 9.22 (d, J=7.6 Hz, 1H); LCMS (electrospray) m/z 508 (M+H)⁺.

6-Chloro-2-ethyl-N-(4-(4-(methoxymethyl)piperidin-1-yl)benzyl)imidazo[1,2-a]pyridine-3-carboxamide (247)

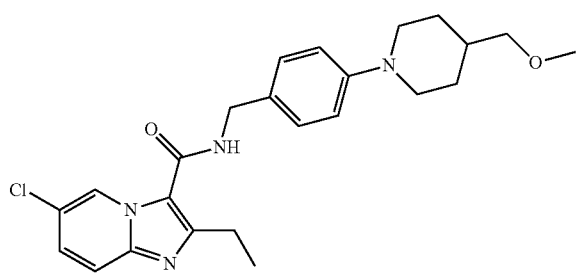 [SMILES: CCc1nc2ccc(Cl)cn2c1C(=O)NCc1ccc(N2CCC(COC)CC2)cc1]

White solid; mp=162.1° C.; ¹H NMR (400 MHz, CDCl₃); δ 1.34-1.57 (m, 2H), 1.36 (t, J=7.6 Hz, 3H), 1.70-1.85 (m, 3H), 2.68-2.74 (m, 2H), 2.88 (q, J=7.6 Hz, 2H), 3.25 (d, J=6.4 Hz, 2H), 3.53 (s, 3H), 3.68-3.71 (m, 2H), 4.58 (d, J=5.6 Hz, 2H), 5.98 (brt, J=5.6 Hz, 1H), 6.92 (d, J=8.4 Hz, 2H), 7.24-7.30 (m, 3H), 7.51 (d, J=10.0 Hz, 1H), 9.52 (d, J=1.6 Hz, 1H); LCMS (electrospray) m/z 441, 443 (M+H)⁺ (Cl⁻ isotope pattern).

7-Chloro-2-ethyl-N-(4-(4-(methoxymethyl)piperidin-1-yl)benzyl)imidazo[1,2-a]pyridine-3-carboxamide (248)

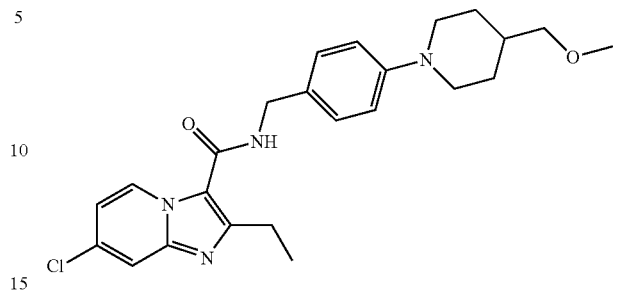

White solid; mp=172.5° C.; ¹H NMR (400 MHz, CDCl₃); δ 1.33-1.43 (m, 2H), 1.35 (t, J=7.6 Hz, 3H), 0.72-1.85 (m, 3H), 2.67-2.74 (m, 2H), 2.90 (q, J=7.6 Hz, 2H), 3.25 (d, J=6.4 Hz, 2H), 3.35 (s, 3H), 3.68-3.71 (m, 2H), 4.58 (d, J=5.2 Hz, 2H), 5.97 (brt, J=5.2 Hz, 1H), 6.88 (dd, J=2.4, 7.6 Hz, 1H), 6.92 (d, J=8.8 Hz, 2H), 7.23 (d, J=8.8 Hz, 2H), 7.57 (d, J=2.4 Hz, 1H), 9.34 (d, J=7.6 Hz, 1H); LCMS (electrospray) m/z 441, 443 (M+H)⁺ (Cl⁻ isotope pattern).

6-Chloro-2-ethyl-N-(4-(4-(4-fluorophenyl)piperidin-1-yl)benzyl)imidazo[1,2-a]pyridine-3-carboxamide (249)

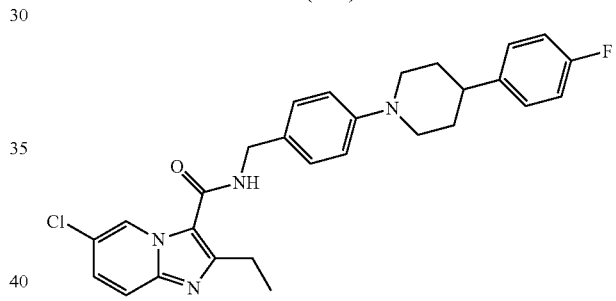

White solid; mp=164.0° C.; ¹H NMR (400 MHz, CDCl₃); δ 1.35 (t, J=7.6 Hz, 3H), 1.76-1.95 (m, 4H), 2.60-2.66 (m, 1H), 2.78-2.85 (m, 2H), 2.92 (q, J=7.6 Hz, 2H), 3.79-3.82 (m, 2H), 4.60 (d, J=5.2 Hz, 2H), 6.03 (brt, J=5.2 Hz, 1H), 6.96-7.01 (m, 4H), 7.17-7.21 (m, 2H), 7.26-7.29 (m, 3H), 7.51 (d, J=9.6 Hz, 1H), 9.52 (d, J=1.6 Hz, 1H); LCMS (electrospray) m/z 491 (M+H)⁺.

7-Chloro-2-ethyl-N-(4-(4-(4-fluorophenyl)piperidin-1-yl)benzyl)imidazo[1,2-a]pyridine-3-carboxamide (250)

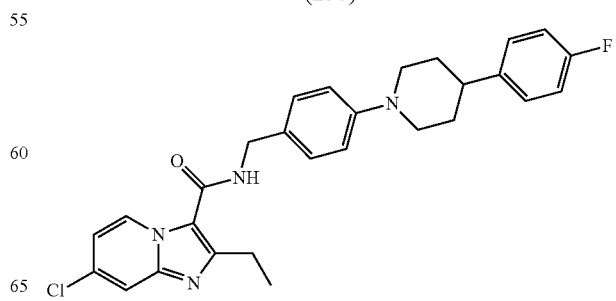

White solid; mp=182.7° C.; $^1$H NMR (400 MHz, CDCl$_3$); δ 1.35 (t, J=7.6 Hz, 3H), 1.79-1.95 (m, 4H), 2.59-2.67 (m, 1H), 2.78-2.85 (m, 2H), 2.91 (q, J=7.6 Hz, 2H), 3.79-3.82 (m, 2H), 4.59 (d, J=5.6 Hz, 2H), 6.03 (brt, J=5.6 Hz, 1H), 6.87 (dd, J=2.4, 7.6 Hz, 1H), 6.96-7.01 (m, 4H), 7.17-7.21 (m, 2H), 7.26 (d, J=8.8 Hz, 2H), 7.57 (d, J=2.4 Hz, 1H), 9.33 (d, J=7.6 Hz, 1H); LCMS (electrospray) m/z 491 (M+H)$^+$.

6-chloro-2-ethyl-N-(4-(2-methylpiperidin-1-yl)benzyl)imidazo[1,2-a]pyridine-3-carboxamide (251)

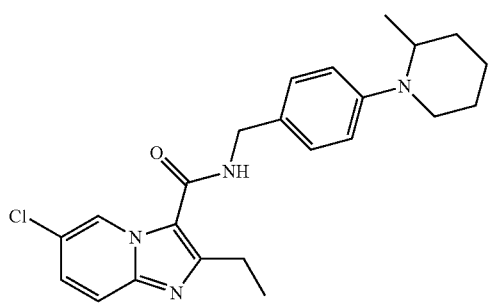 [SMILES: CCc1nc2ccc(Cl)cn2c1C(=O)NCc1ccc(N2CCCCC2C)cc1]

Sticky pale yellow solid; $^1$H NMR (400 MHz, CDCl$_3$); δ 0.99 (d, J=6.4 Hz, 3H), 1.32 (t, J=7.6 Hz, 3H), 1.55-1.70 (m, 4H), 1.81-1.88 (m, 2H), 2.91 (q, J=7.6 Hz, 2H), 2.92-2.98 (m, 1H), 3.21-3.26 (m, 1H), 3.93-3.96 (m, 1H), 4.58 (d, J=5.2 Hz, 2H), 6.01 (brt, J=5.2 Hz, 1H), 6.90 (d, J=8.8 Hz, 2H), 7.22 (d, J=8.8 Hz, 2H), 7.26 (dd, J=2.0, 9.2 Hz, 1H), 7.50 (d, J=9.2 Hz, 1H), 9.50 (d, J=2.0 Hz, 1H); $^{13}$C NMR (100 MHz, CDCl$_3$) δ 13.3, 13.7, 19.6, 23.6, 26.2, 31.6, 43.4, 44.6, 51.2, 115.4, 117.0, 117.5, 121.6, 126.3, 127.9, 128.2, 128.8, 144.5, 151.1, 151.4, 161.1; LCMS (electrospray) m/z 411, 413 (M+H)$^+$ (Cl$^-$ isotope pattern).

7-chloro-2-ethyl-N-(4-(2-methylpiperidin-1-yl)benzyl)imidazo[1,2-a]pyridine-3-carboxamide (252)

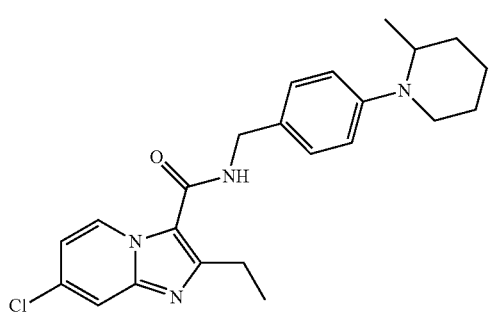 [SMILES: CCc1nc2cc(Cl)ccn2c1C(=O)NCc1ccc(N2CCCCC2C)cc1]

White solid; mp=117.9° C.; $^1$H NMR (400 MHz, CDCl$_3$); δ 1.00 (d, J=6.4 Hz, 3H), 1.35 (t, J=7.6 Hz, 3H), 1.56-1.69 (m, 4H), 1.75-1.90 (m, 2H), 2.92 (q, J=7.6 Hz, 2H), 2.96-2.99 (m, 1H), 3.23-3.28 (m, 1H), 3.95-3.98 (m, 1H), 4.59 (d, J=5.6 Hz, 2H), 6.08 (brt, J=5.6 Hz, 1H), 6.87 (dd, J=2.0, 7.6 Hz, 1H), 6.91 (d, J=8.8 Hz, 2H), 7.23 (d, J=8.8 Hz, 2H), 7.57 (d, J=2.0 Hz, 1H), 9.32 (d, J=7.6 Hz, 1H); $^{13}$C NMR (100 MHz, CDCl$_3$) δ 13.4, 13.7, 19.5, 23.5, 26.1, 31.6, 43.3, 44.5, 51.2, 114.6, 115.1, 115.7, 117.4, 127.8, 128.5, 128.8, 133.5, 146.0, 151.0, 151.5, 161.1; LCMS (electrospray) m/z 411, 413 (M+H)$^+$ (Cl$^-$ isotope pattern).

7-Bromo-2-ethyl-N-(4-morpholinobenzyl)imidazo[1,2-a]pyridine-3-carboxamide (253)

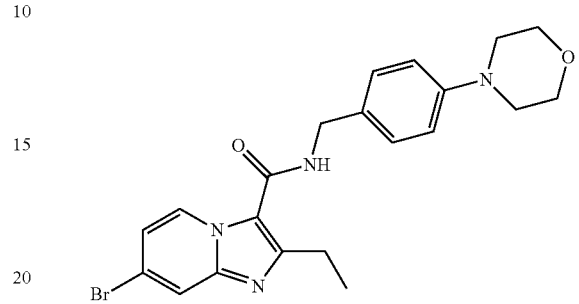

Pale gray solid; mp=202.6° C.; $^1$H NMR (400 MHz, CDCl$_3$); δ 1.34 (t, J=7.6 Hz, 3H), 2.90 (q, J=7.6 Hz, 2H), 3.13-3.15 (m, 4H), 3.83-3.86 (m, 4H), 4.58 (d, J=5.6 Hz, 2H), 6.05 (brt, J=5.6 Hz, 1H), 6.88 (d, J=8.8 Hz, 2H), 6.97 (dd, J=2.0, 7.2 Hz, 1H), 7.26 (d, J=8.8 Hz, 2H), 7.74 (d, J=2.0 Hz, 1H), 9.25 (d, J=7.2 Hz, 1H); $^{13}$C NMR (100 MHz, CDCl$_3$) δ 13.4, 23.5, 43.2, 49.3, 67.0, 115.1, 116.0, 117.0, 119.1, 121.1, 128.5, 128.9, 129.2, 143.6, 151.0, 151.4, 161.2; LCMS (electrospray) m/z 443, 445 (M+H)$^+$ (Br$^-$ isotope pattern).

2-Ethyl-7-(4-methylpiperazin-1-yl)-N-(4-morpholinobenzyl)imidazo[1,2-a]pyridine-3-carboxamide (254)

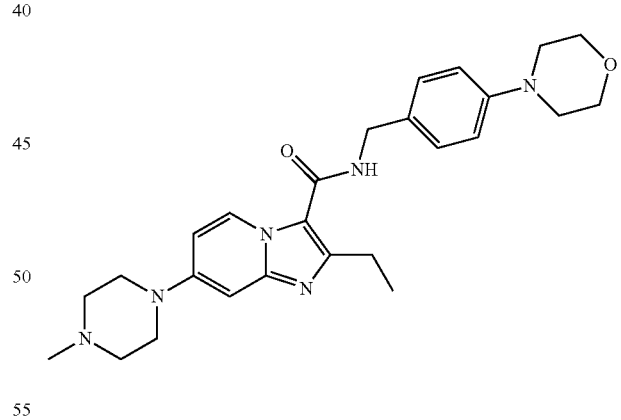

White solid; mp=204.8° C.; $^1$H NMR (400 MHz, CDCl$_3$); δ 1.33 (t, J=7.6 Hz, 3H), 2.33 (s, 3H), 2.54-2.56 (m, 4H), 2.85 (q, J=7.6 Hz, 2H), 3.12-3.15 (m, 4H), 3.27-3.30 (m, 4H), 3.83-3.85 (m, 4H), 4.57 (d, J=5.6 Hz, 2H), 5.91 (brt, J=5.6 Hz, 1H), 6.62 (dd, J=2.4, 8.0 Hz, 1H), 6.5 (d, J=2.4 Hz, 1H), 6.88 (d, J=8.4 Hz, 2H), 7.26 (d, J=8.4 Hz, 2H), 9.16 (d, J=8.0 Hz, 1H); $^{13}$C NMR (100 MHz, CDCl$_3$) δ 13.4, 23.6, 43.1, 46.2, 47.8, 49.4, 54.7, 67.0, 96.4, 105.9, 113.2, 116.0, 128.3, 128.8, 129.8, 148.5, 150.0, 150.9, 151.2, 161.7; LCMS (electrospray) m/z 463 (M+H)$^+$.

2-Ethyl-N-(4-morpholinobenzyl)-7-(pyridin-4-yl) imidazo[1,2-a]pyridine-3-carboxamide (255)

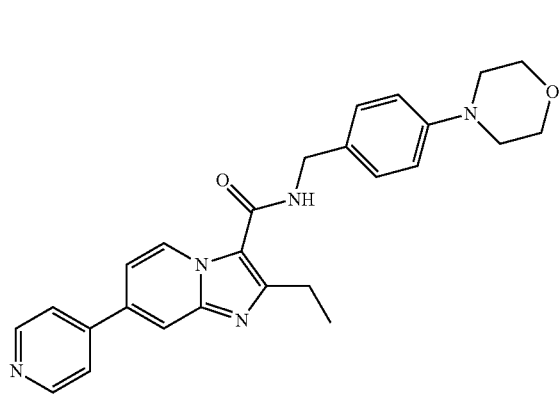 [SMILES: CCc1nc2cc(-c3ccncc3)ccn2c1C(=O)NCc1ccc(N2CCOCC2)cc1]

Yellow solid; mp=210.1° C.; $^1$H NMR (400 MHz, CDCl$_3$); δ 1.37 (t, J=7.6 Hz, 3H), 2.94 (q, J=7.6 Hz, 2H), 3.12-3.15 (m, 4H), 3.82-3.85 (m, 4H), 4.60 (d, J=5.2 Hz, 2H), 6.16 (brt, J=5.2 Hz, 1H), 6.88 (d, J=8.8 Hz, 2H), 7.16 (dd, J=2.0, 7.2 Hz, 1H), 7.27 (d, J=8.8 Hz, 2H), 7.53 (d, J=6.0 Hz, 2H), 7.85 (d, J=2.0 Hz, 1H), 8.68 (d, J=6.0 Hz, 2H), 9.44 (d, J=7.2 Hz, 1H); $^{13}$C NMR (100 MHz, CDCl$_3$) δ 13.3, 23.6, 43.2, 49.3, 66.9, 111.8, 114.3, 115.3, 116.0, 121.2, 128.6, 128.9, 129.2, 136.3, 145.5, 146.1, 150.7, 151.0, 151.9, 161.2; LCMS (electrospray) m/z 442 (M+H)$^+$.

2-Ethyl-7-(4-(4-fluorophenyl)piperazin-1-yl)-N-(4-morpholinobenzyl)imidazo[1,2-a]pyridine-3-carboxamide (256)

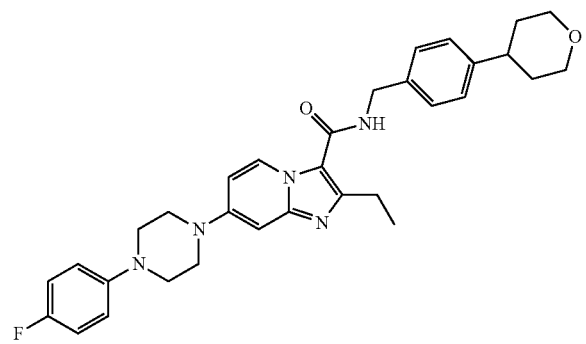

White solid; $^1$H NMR (400 MHz, CDCl$_3$); δ 1.34 (t, J=7.6 Hz, 3H), 2.87 (q, J=7.6 Hz, 2H), 3.13-3.15 (m, 4H), 3.22-3.25 (m, 4H), 3.41-3.43 (m, 4H), 3.83-3.86 (m, 4H), 4.58 (d, J=5.2 Hz, 2H), 5.99 (brt, J=5.2 Hz, 1H), 6.67 (dd, J=2.4, 8.0 Hz, 1H), 6.81 (d, J=2.4 Hz, 1H), 6.88-6.93 (m, 4H), 6.96 (dd, J=8.4, 8.8 Hz, 2H), 7.27 (d, J=8.4 Hz, 2H), 9.19 (d, J=8.0 Hz, 1H); LCMS (electrospray) m/z 543 (M+H)$^+$.

2-Ethyl-7-(4-(4-fluorobenzyl)piperazin-1-yl)-N-(4-morpholinobenzyl)imidazo[1,2-a]pyridine-3-carboxamide (257)

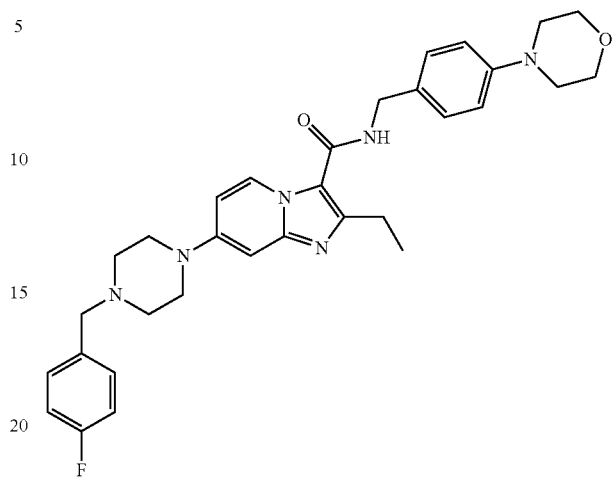

White solid; mp=212.5° C.; $^1$H NMR (400 MHz, CDCl$_3$); δ 1.33 (t, J=7.6 Hz, 3H), 2.56-2.58 (m, 4H), 2.85 (q, J=7.6 Hz, 2H), 3.13-3.15 (m, 4H), 3.26-3.29 (m, 4H), 3.51 (s, 2H), 3.83-3.86 (m, 4H), 4.57 (d, J=5.6 Hz, 2H), 5.93 (brt, J=5.6 Hz, 1H), 6.62 (dd, J=2.4, 7.6 Hz, 1H), 6.75 (d, J=2.4 Hz, 1H), 6.88 (d, J=8.8 Hz, 2H), 6.98-7.03 (m, 2H), 7.26-7.31 (m, 4H), 9.15 (d, J=7.6 Hz, 1H).

6-Chloro-2-ethyl-N-((2-(4-fluorophenyl)benzo[d]oxazol-5-yl)methyl)imidazo[1,2-a]pyridine-3-carboxamide (258)

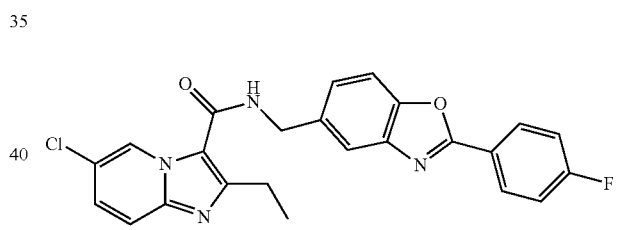

White solid; $^1$H NMR (400 MHz, DMSO-d$_6$) δ1.25 (t, J=7.6 Hz, 3H), 2.99 (q, J=7.6 Hz, 2H), 4.65 (d, J=5.6 Hz, 2H), 7.41-7.46 (m, 4H), 7.64 (d, J=9.6 Hz, 1H), 7.74 (d, J=8.4 Hz, 1H), 7.78 (s, 1H), 8.21-8.25 (m, 2H), 8.54 (t, J=5.6 Hz, 1H), 9.08 (d, J=2.0 Hz, 1H); LCMS (electrospray) m/z (M+H)$^+$ 449.

7-Chloro-2-ethyl-N-((2-(4-fluorophenyl)benzo[d]oxazol-5-yl)methyl)imidazo[1,2-a]pyridine-3-carboxamide (259)

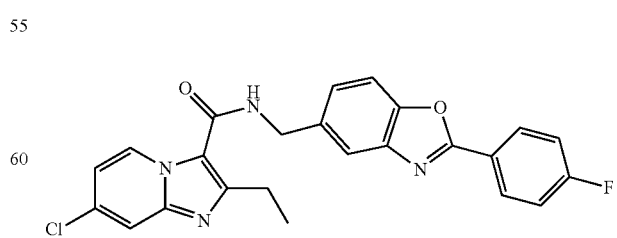

White solid; $^1$H NMR (400 MHz, DMSO-d$_6$) δ1.25 (t, J=7.2 Hz, 3H), 2.98 (q, J=7.2 Hz, 2H), 4.64 (d, J=5.6 Hz, 2H), 7.07 (d, J=7.6 Hz, 1H), 7.42-7.46 (m, 3H), 7.75 (d, J=8.4 Hz, 2H), 7.77 (s, 1H), 8.23 (d, J=8.4 Hz, 2H), 8.55 (brs, 1H), 8.96 (d, J=7.2 Hz, 1H); LCMS (electrospray) m/z (M+H)+ 449.

8-Bromo-2-ethyl-N-(4-(4-(4-fluorophenyl)piperazin-1-yl)benzyl)imidazo[1,2-a]pyridine-3-carboxamide (260)

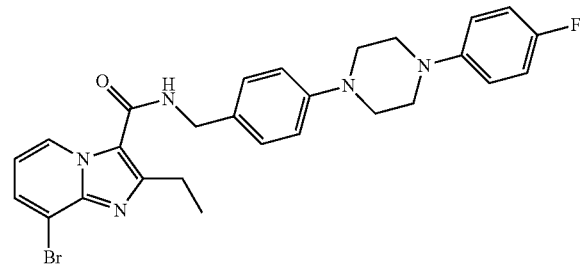 [SMILES: CCc1nc2c(Br)cccn2c1C(=O)NCc1ccc(N2CCN(c3ccc(F)cc3)CC2)cc1]

White solid; $^1$H NMR (400 MHz, CDCl$_3$) δ1.37 (t, J=7.6 Hz, 3H), 3.00 (q, J=7.6 Hz, 2H), 3.23-3.35 (m, 8H), 4.61 (d, J=5.6 Hz, 2H), 6.08 (brs, 1H), 6.77 (dd, J=6.8 Hz, 6.8 Hz, 1H), 6.90-7.00 (m, 6H), 7.29 (d, J=8.4 Hz, 2H), 7.56 (d, J=7.2 Hz, 1H), 9.38 (d, J=7.2 Hz, 1H); $^{13}$C NMR (100 MHz, CDCl$_3$) δ14.1, 23.7, 43.4, 49.5, 50.6, 110.7, 113.3, 115.7, 115.9, 116.7, 118.4, 127.6, 129.0, 129.2, 129.4, 144.1, 148.0, 151.0, 151.5, 158.8, 161.3; LCMS (electrospray) m/z (M+H)+ 538.

2-Ethyl-7-methoxy-N-(4-morpholinobenzyl)imidazo[1,2-a]pyridine-3-carboxamide (261)

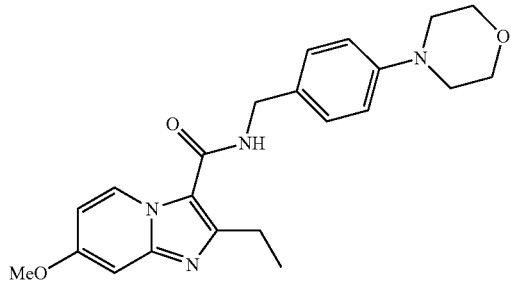 [SMILES: CCc1nc2cc(OC)ccn2c1C(=O)NCc1ccc(N2CCOCC2)cc1]

White solid; $^1$H NMR (400 MHz, CDCl$_3$); δ 1.33 (t, J=7.6 Hz, 3H), 2.86 (q, J=7.6 Hz, 2H), 3.12-3.14 (m, 4H), 3.80-3.88 (m, 4H), 3.83 (s, 3H), 4.56 (d, J=5.6 Hz, 2H), 5.98 (brt, J=5.6 Hz, 1H), 6.56 (dd, J=2.4, 7.6 Hz, 1H), 6.84 (d, J=2.4 Hz, 1H), 6.87 (d, J=8.8 Hz, 2H), 7.25 (d, J=8.8 Hz, 2H), 9.19 (d, J=7.6 Hz, 1H); $^{13}$C NMR (100 MHz, CDCl$_3$) δ 13.4, 23.5, 43.1, 49.4, 55.6, 67.0, 94.5, 107.4, 113.9, 116.0, 128.8, 128.9, 129.6, 148.1, 150.9, 151.0, 159.4, 161.5.

2-Ethyl-8-methoxy-N-(4-morpholinobenzyl)imidazo[1,2-a]pyridine-3-carboxamide (262)

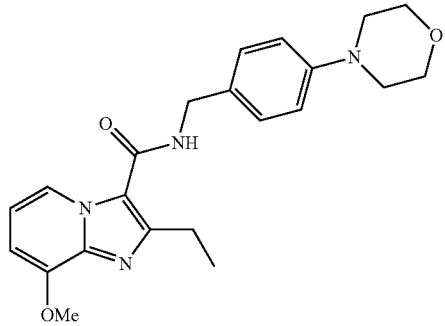 [SMILES: CCc1nc2c(OC)cccn2c1C(=O)NCc1ccc(N2CCOCC2)cc1]

Pale yellow solid; $^1$H NMR (400 MHz, CDCl$_3$); δ 1.33 (t, J=7.6 Hz, 3H), 2.92 (q, J=7.6 Hz, 2H), 3.12-3.14 (m, 4H), 3.82-3.84 (m, 4H), 3.98 (s, 3H), 4.58 (d, J=5.6 Hz, 1H), 6.08 (brs, 1H), 6.57 (d, J=7.2 Hz, 1H), 6.75 (dd, J=7.2, 7.2 Hz, 1H), 6.87 (d, J=8.8 Hz, 2H), 7.26 (d, J=8.8 Hz, 2H), 8.93 (d, J=7.2 Hz, 1H); $^{13}$C NMR (100 MHz, CDCl$_3$) δ 13.9, 23.6, 43.2, 49.3, 56.0, 67.0, 103.1, 113.0, 116.0, 120.9, 124.8, 128.9, 129.4, 140.4, 148.2, 149.9, 150.9, 161.5.

2-Ethyl-N-(4-(4-(4-fluorophenyl)piperazin-1-yl)benzyl)-8-methoxyimidazo[1,2-a]pyridine-3-carboxamide (263)

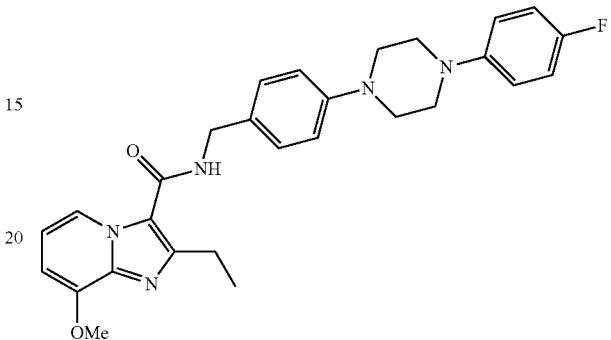

Pale yellow solid; $^1$H NMR (400 MHz, CDCl$_3$); δ 1.34 (t, J=7.6 Hz, 3H), 2.93 (q, J=7.6 Hz, 2H), 3.22-3.27 (m, 4H), 3.29-3.34 (m, 4H), 3.99 (s, 3H), 4.60 (d, J=5.6 Hz, 2H), 6.08 (brs, 1H), 6.58 (d, J=7.6 Hz, 1H), 6.76 (dd, J=7.2, 7.6 Hz, 1H), 6.89-6.99 (m, 6H), 7.28 (d, J=8.4 Hz, 2H), 8.95 (d, J=7.2 Hz, 1H).

2-Ethyl-N-(4-(4-(4-fluorophenyl)piperazin-1-yl)benzyl)-7-methoxyimidazo[1,2-a]pyridine-3-carboxamide (264)

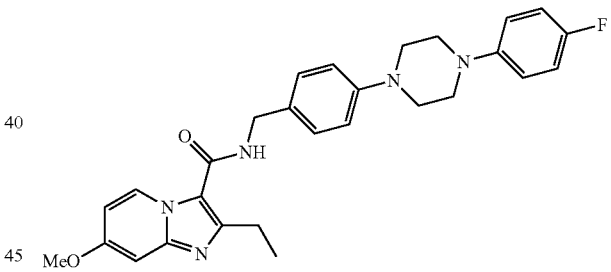

White solid; $^1$H NMR (400 MHz, CDCl$_3$); δ 1.30 (t, J=7.6 Hz, 3H), 2.84 (q, J=7.6 Hz, 2H), 3.18-3.19 (m, 4H), 3.26-3.27 (m, 4H), 3.78 (s, 3H), 4.54 (d, J=5.6 Hz, 2H), 6.15 (brs, 1H), 6.51-6.53 (m, 1H), 6.79 (s, 1H), 6.85-6.95 (m, 6H), 7.24 (d, J=8.0 Hz, 2H), 9.12 (d, J=8.0 Hz, 1H).

2-Ethyl-N-(4-(4-(4-fluorophenyl)piperidin-1-yl)benzyl)imidazo[1,2-a]pyridine-3-carboxamide (265)

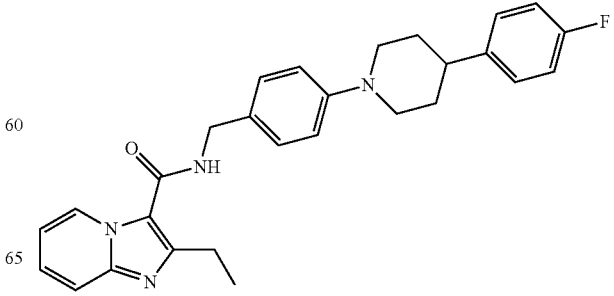

125

Pale yellow solid; ¹H NMR (400 MHz, CDCl₃); δ 1.37 (t, J=7.6 Hz, 3H), 1.81-1.95 (m, 4H), 2.60-2.67 (m, 1H), 2.77-2.85 (m, 2H), 2.94 (q, J=7.6 Hz, 2H), 3.79-3.82 (m, 2H), 4.61 (d, J=5.6 Hz, 2H), 6.02 (brs, 1H), 6.89 (ddd, J=1.2, 6.8, 6.8 Hz, 1H), 6.96-7.02 (m, 4H), 7.17-7.23 (m, 2H), 7.25-7.33 (m, 3H), 7.8 (d, J=8.8 Hz, 1H), 9.39 (d, J=6.8 Hz, 1H).

2-Ethyl-N-(4-(4-(4-(trifluoromethoxy)phenyl)piperidin-1-yl)benzyl)imidazo[1,2-a]pyridine-3-carboxamide (266)

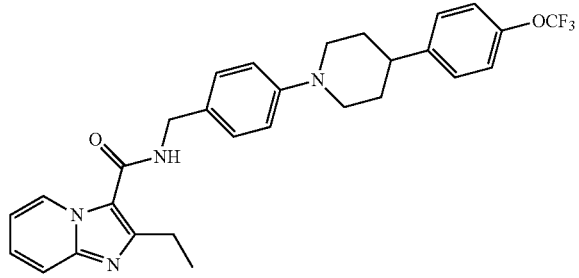 [SMILES: CCc1nc2ccccn2c1C(=O)NCc1ccc(N2CCC(c3ccc(OC(F)(F)F)cc3)CC2)cc1]

Pale yellow solid; mp=146.0° C.; ¹H NMR (400 MHz, CDCl₃); δ 1.37 (t, J=7.6 Hz, 3H), 1.81-1.96 (m, 4H), 2.63-2.69 (m, 1H), 2.79-2.86 (m, 2H), 2.94 (q, J=7.6 Hz, 2H), 3.80-3.83 (m, 2H), 4.61 (d, J=5.6 Hz, 2H), 6.01 (brt, J=5.6 Hz, 1H), 6.88 (ddd, J=0.8, 6.8, 6.8 Hz, 1H), 6.97 (d, J=8.8 Hz, 2H), 7.14 (d, J=8.4 Hz, 2H), 7.24-7.33 (m, 5H), 7.58 (d, J=8.8 Hz, 1H), 9.39 (d, J=6.8 Hz, 1H).

6-Chloro-2-ethyl-N-(4-(4-(4-(trifluoromethoxy)phenyl)piperidin-1-yl)benzyl)imidazo[1,2-a]pyridine-3-carboxamide (267)

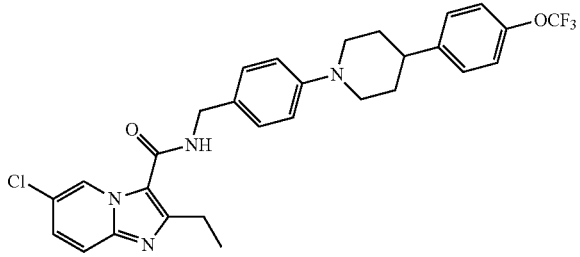 [SMILES: CCc1nc2ccc(Cl)cn2c1C(=O)NCc1ccc(N2CCC(c3ccc(OC(F)(F)F)cc3)CC2)cc1]

White solid; mp=164.0° C.; ¹H NMR (400 MHz, CDCl₃); δ 1.37 (t, J=7.6 Hz, 3H), 1.81-1.96 (m, 4H), 2.63-2.70 (m, 1H), 2.79-2.86 (m, 2H), 2.92 (q, J=7.6 Hz, 2H), 3.80-3.83 (m, 2H), 4.60 (d, J=5.2 Hz, 2H), 6.04 (brt, J=5.2 Hz, 1H), 6.96 (d, J=8.4 Hz, 2H), 7.14 (d, J=8.4 Hz, 2H), 7.24-7.29 (m, 5H), 7.51 (d, J=9.6 Hz, 1H), 9.51 (d, J=1.6 Hz, 1H).

126

7-Chloro-2-ethyl-N-(4-(4-(4-(trifluoromethoxy)phenyl)piperidin-1-yl)benzyl)imidazo[1,2-a]pyridine-3-carboxamide (268)

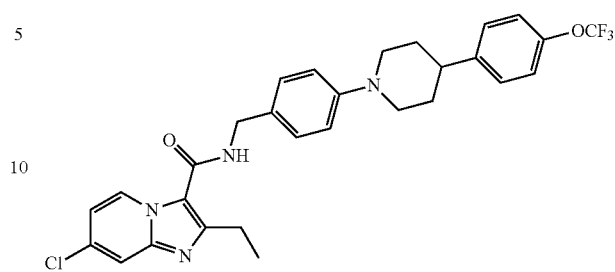

White solid; ¹H NMR (400 MHz, CDCl₃); δ 1.36 (t, J=7.6 Hz, 3H), 1.82-1.96 (m, 4H), 2.64-2.70 (m, 1H), 2.79-2.86 (m, 2H), 2.91 (q, J=7.6 Hz, 2H), 3.80-3.83 (m, 2H), 4.59 (d, J=5.36 Hz, 2H), 6.04 (brs, 1H), 6.87 (dd, J=1.6, 7.2 Hz, 1H), 6.97 (d, J=8.4 Hz, 2H), 7.14 (d, J=8.4 Hz, 2H), 7.24-7.28 (m, 4H), 7.57 (d, J=1.6 Hz, 1H), 9.34 (d, J=7.2 Hz, 1H).

Ethyl 1-(4-((6-chloro-2-ethylimidazo[1,2-a]pyridine-3-carboxamido)methyl)phenyl)piperidine-4-carboxylate (269)

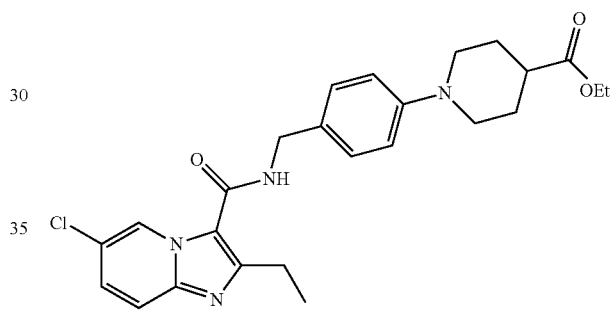

White solid; ¹H NMR (400 MHz, CDCl₃); δ 1.23 (t, J=7.2 Hz, 3H), 1.35 (t, J=7.2 Hz, 3H), 1.80-1.90 (m, 2H), 1.98-2.02 (m, 2H), 2.38-2.46 (m, 1H), 2.75-2.82 (m, 2H), 2.91 (q, J=7.6 Hz, 2H), 3.61-3.65 (m, 2H), 4.11 (q, J=7.2 Hz, 2H), 4.57 (d, J=5.6 Hz, 2H), 6.03 (brt, J=5.6 Hz, 1H), 6.90 (d, J=8.8 Hz, 2H), 7.23-7.28 (m, 3H), 7.49 (d, J=9.6 Hz, 1H), 9.49 (d, J=1.6 Hz, 1H); ¹³C NMR (100 MHz, CDCl₃) δ 13.3, 14.4, 23.6, 28.1, 41.6, 43.3, 49.2, 60.6, 115.4, 116.9, 117.0, 121.5, 126.3, 128.2, 128.6, 128.9, 144.5, 151.2, 151.4, 161.1, 174.9.

Ethyl 1-(4-((7-chloro-2-ethylimidazo[1,2-a]pyridine-3-carboxamido)methyl)phenyl)piperidine-4-carboxylate (270)

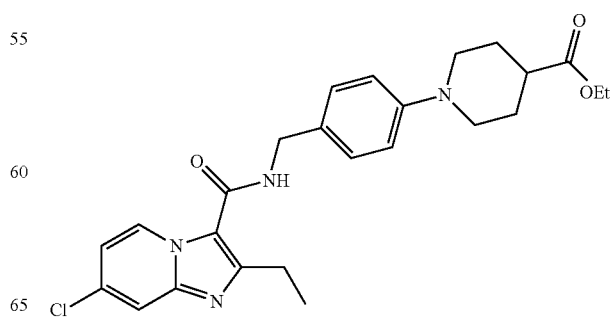

White solid; ¹H NMR (400 MHz, CDCl₃); δ 1.21 (t, J=7.2 Hz, 3H), 1.31 (t, J=7.2 Hz, 3H), 1.77-1.87 (m, 2H), 1.96-2.00 (m, 2H), 2.36-2.42 (m, 1H), 2.72-2.79 (m, 2H), 2.87 (q, J=7.2 Hz, 2H), 3.58-3.63 (m, 2H), 4.09 (q, J=7.2 Hz, 2H), 4.53 (d, J=5.6 Hz, 2H), 6.12 (brt, J=5.6 Hz, 1H), 6.81 (dd, J=2.0, 7.2 Hz, 1H), 6.87 (d, J=8.8 Hz, 2H), 7.20 (d, J=8.8 Hz, 2H), 7.51 (d, J=2.0, 1H), 9.25 (d, J=7.2 Hz, 1H); ¹³C NMR (100 MHz, CDCl₃) δ 13.3, 14.3, 23.4, 28.0, 41.0, 43.2, 49.1, 60.5, 114.5, 115.1, 115.6, 116.7, 128.4, 128.6, 128.8, 133.4, 146.0, 151.1, 151.5, 161.1, 174.8.

2-Ethyl-N-(4-(4-(4-fluorophenyl)piperazin-1-yl)benzyl)-6-methoxyimidazo[1,2-a]pyridine-3-carboxamide (271)

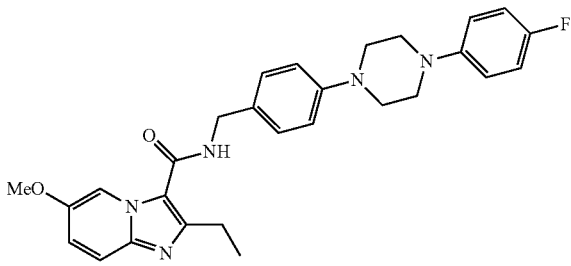 [SMILES: CCc1nc2ccc(OC)cn2c1C(=O)NCc1ccc(N2CCN(c3ccc(F)cc3)CC2)cc1]

White solid; mp=173.8° C.; ¹H NMR (400 MHz, CDCl₃) δ 1.39 (t, J=7.6 Hz, 3H), 2.95 (q, J=7.2 Hz, 2H), 3.24-3.27 (m, 4H), 3.33-3.36 (m, 4H), 3.87 (s, 3H), 4.63 (d, J=5.6 Hz, 2H), 6.03 (t, J=5.0 Hz, 1H), 6.91-7.01 (m, 6H), 7.31 (d, J=8.8 Hz, 2H), 7.48 (d, J=9.6 Hz, 1H), 9.11 (d, J=2.4 Hz, 1H); LCMS (electrospray) m/z (M+H)⁺ 488

2-Ethyl-6-fluoro-N-(4-morpholinobenzyl)imidazo[1,2-a]pyridine-3-carboxamide (272)

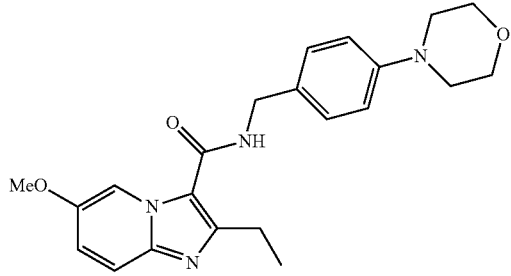 [SMILES: CCc1nc2ccc(OC)cn2c1C(=O)NCc1ccc(N2CCOCC2)cc1]

White solid; mp=193.4° C.; ¹H NMR (400 MHz, CDCl₃) δ 1.38 (t, J=7.4 Hz, 3H), 2.94 (q, J=7.6 Hz, 2H), 3.15-3.17 (m, 4H), 3.85-3.87 (m, 7H), 4.62 (d, J=52 Hz, 2H), 6.00-6.02 (m, 1H), 6.92 (d, J=9.6 Hz, 2H), 7.11 (dd, J=2.4, 9.6 Hz, 1H), 7.30 (d, J=8.8 Hz, 2H), 7.48 (d, J=9.6 Hz, 1H), 9.10 (d, J=2.4 Hz, 1H); LCMS (electrospray) m/z (M+H)⁺ 395

2-Ethyl-N-(4-morpholinobenzyl)-6-(trifluoromethyl)imidazo[1,2-a]pyridine-3-carboxamide (273)

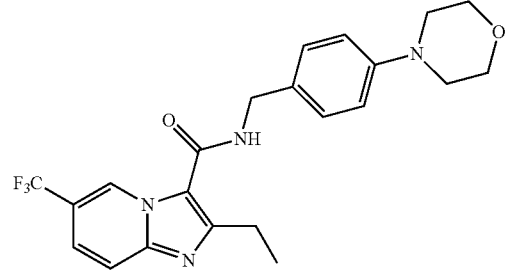 [SMILES: CCc1nc2ccc(C(F)(F)F)cn2c1C(=O)NCc1ccc(N2CCOCC2)cc1]

White solid; mp=207.6° C.; ¹H NMR (400 MHz, CDCl₃); δ 1.37 (t, J=7.2 Hz, 3H), 2.94 (q, J=7.2 Hz, 2H), 3.13-3.15 (m, 4H), 3.83-3.85 (m, 4H), 4.60 (d, J=5.2 Hz, 2H), 6.10 (brs, 1H), 6.89 (d, J=8.0 Hz, 2H), 7.27 (d, J=8.0 Hz, 2H), 7.44 (d, J=9.2 Hz, 1H), 7.65 (d, J=9.2 Hz, 1H), 9.82 (s, 1H).

2-Ethyl-N-(4-morpholinobenzyl)-8-(trifluoromethyl)imidazo[1,2-a]pyridine-3-carboxamide (274)

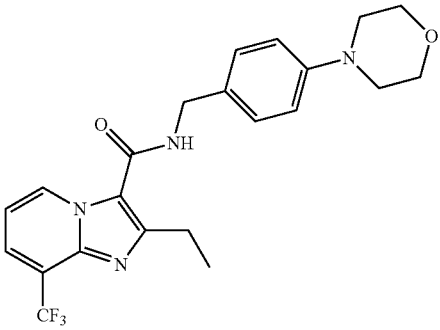 [SMILES: CCc1nc2c(C(F)(F)F)cccn2c1C(=O)NCc1ccc(N2CCOCC2)cc1]

White solid; mp=200.6° C.; ¹H NMR (400 MHz, CDCl₃); δ 1.34 (t, J=7.6 Hz, 3H), 2.98 (q, J=7.6 Hz, 2H), 3.14-3.16 (m, 4H), 3.83-3.86 (m, 4H), 4.60 (d, J=5.6 Hz, 2H), 6.11 (brt, J=5.6 Hz, 1H), 6.89 (d, J=8.8 Hz, 2H), 6.93 (dd, J=6.8, 6.8 Hz, 1H), 7.26 (d, J=8.8 Hz, 2H), 7.62 (d, J=6.8 Hz, 1H), 9.54 (d, J=6.8 Hz, 1H).

1-(4-((7-Chloro-2-ethylimidazo[1,2-a]pyridine-3-carboxamido)methyl)phenyl)piperidine-4-carboxylic acid (275)

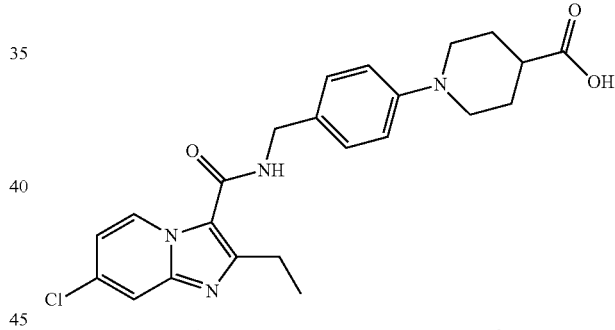

White solid; ¹H NMR (400 MHz, DMSO-d⁶); δ 1.22 (t, J=7.6 Hz, 3H), 1.57-1.66 (m, 2H), 1.84-1.88 (m, 2H), 2.29-2.34 (m, 1H), 2.67-2.73 (m, 2H), 2.92 (q, J=7.6 Hz, 2H), 3.57-3.60 (m, 2H), 4.40 (d, J=5.6 Hz, 2H), 5.75 (s, 1H), 6.89 (d, J=8.4 Hz, 2H), 7.06 (dd, J=1.6, 7.6 Hz, 1H), 7.19 (d, J=8.4 Hz, 2H), 7.77 (d, J=1.6 Hz, 1H), 8.37 (brt, J=5.6 Hz, 1H), 8.93 (d, J=7.6 Hz, 1H).

6-Chloro-2-ethyl-N-(4-(4-(isopropoxymethyl)piperidin-1-yl)benzyl)imidazo[1,2-a]pyridine-3-carboxamide (276)

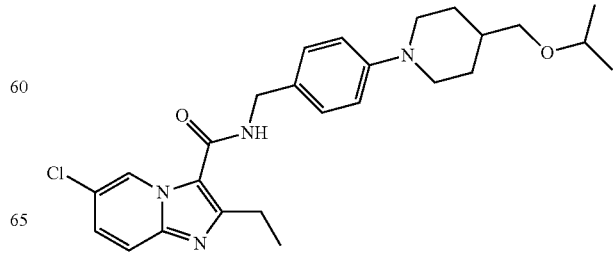

White solid; ¹H NMR (400 MHz, CDCl₃); δ 1.29 (d, J=6.0 Hz, 6H), 1.46-1.56 (m, 2H), 1.50 (t, J=7.6 Hz, 3H), 1.81-1.89 (m, 1H), 1.99-2.02 (m, 2H), 2.82-2.89 (m, 2H), 3.06 (q, J=7.6 Hz, 2H), 3.43 (d, J=6.4 Hz, 2H), 3.66-3.72 (m, 1H), 3.82-3.85 (m, 2H), 4.73 (d, J=5.6 Hz, 2H), 6.17 (brt, J=5.6 Hz, 1H), 7.06 (d, J=8.4 Hz, 2H), 7.38 (d, J=8.4 Hz, 2H), 7.40 (dd, J=2.0, 9.2 Hz, 1H), 7.65 (d, J=9.2 Hz, 1H), 9.65 (d, J=2.0 Hz, 1H); ¹³C NMR (100 MHz, CDCl₃) δ 13.3, 22.2, 23.6, 29.4, 36.6, 43.4, 49.7, 71.8, 73.3, 115.4, 116.8, 117.0, 121.5, 126.3, 128.2, 128.8, 144.5, 151.4, 151.6, 161.1 (hidden 1 aromatic carbon).

7-Chloro-2-ethyl-N-(4-(4-(isopropoxymethyl)piperidin-1-yl)benzyl)imidazo[1,2-a]pyridine-3-carboxamide (277)

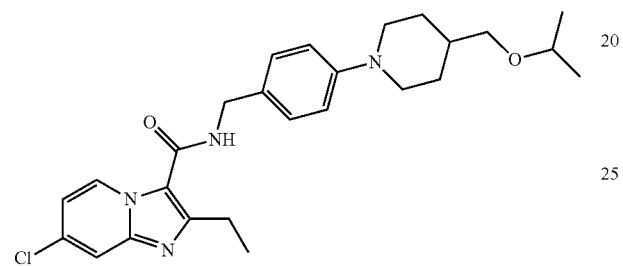

White solid; ¹H NMR (400 MHz, CDCl₃); δ 1.14 (d, J=6.0 Hz, 6H), 1.31-1.41 (m, 2H), 1.34 (t, J=7.6 Hz, 3H), 1.66-1.73 (m, 1H), 1.84-1.87 (m, 2H), 2.67-2.74 (m, 2H), 2.90 (q, J=7.6 Hz, 2H), 3.27 (d, J=6.8 Hz, 2H), 3.50-3.56 (m, 1H), 3.67-3.70 (m, 2H), 4.57 (d, J=5.6 Hz, 2H), 5.99 (brt, J=5.6 Hz, 1H), 6.86 (dd, J=2.0, 7.2 Hz, 1H), 6.91 (d, J=8.4 Hz, 2H), 7.22 (d, J=8.4 Hz, 2H), 7.56 (d, J=1.6 Hz, 1H), 9.33 (d, J=7.2 Hz, 1H); ¹³C NMR (100 MHz, CDCl₃) δ 13.4, 22.2, 23.6, 29.4, 36.6, 43.4, 49.7, 71.8, 73.3, 114.7, 115.2, 115.8, 116.8, 128.2, 128.6, 128.8, 133.6, 146.1, 151.6, 151.7, 161.2.

8-(Difluoromethoxy)-2-ethyl-N-(4-(4-(4-fluorophenyl)piperazin-1-yl)benzyl)imidazo[1,2-a]pyridine-3-carboxamide (278)

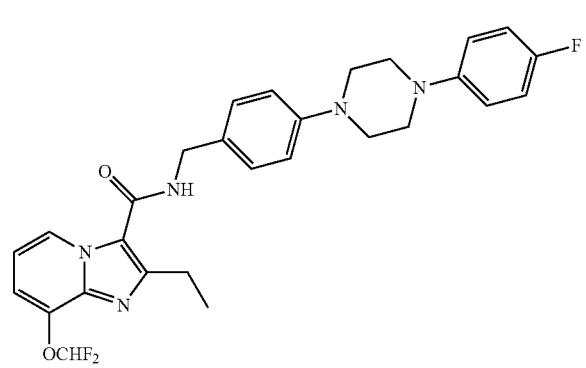 [SMILES: CCc1nc2c(OC(F)F)cccn2c1C(=O)NCc1ccc(N2CCN(c3ccc(F)cc3)CC2)cc1]

Pale yellow; mp=186.3° C.; ¹H NMR (400 MHz, CDCl₃) δ 1.38 (t, J=7.6 Hz, 3H), 2.98 (q, J=7.6 Hz, 2H), 3.24-3.27 (m, 4H), 3.34-3.36 (m, 4H), 4.63 (d, J=5.6 Hz, 2H), 6.05-6.07 (m, 1H), 6.85 (dd, J=7.2 Hz, 1H), 6.91-7.01 (m, 6H), 7.10 (d, J=7.6 Hz, 2H), 7.26 (t, J=74.2 Hz, 1H due to F₂), 9.24 (d, J=6.8 Hz, 1H); LCMS (electrospray) m/z (M+H)⁺ 524

8-(Difluoromethoxy)-2-ethyl-N-(4-morpholinobenzyl)imidazo[1,2-a]pyridine-3-carboxamide (279)

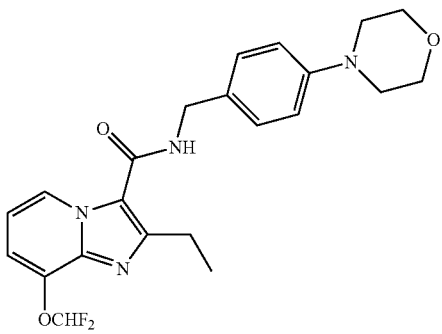 [SMILES: CCc1nc2c(OC(F)F)cccn2c1C(=O)NCc1ccc(N2CCOCC2)cc1]

Off-white solid; mp=163.0° C.; ¹H NMR (400 MHz, CDCl₃) δ 1.38 (t, J=7.6 Hz, 3H), 2.97 (q, J=7.6 Hz, 2H), 3.16 (t, J=5.0 Hz, 4H), 3.86 (t, J=4.8 Hz, 4H), 4.62 (d, J=5.6 Hz, 2H), 6.03-6.05 (m, 1H), 6.85 (dd, J=7.6 Hz, 2H), 6.92 (d, J=6.8 Hz, 2H), 7.11 (d, J=7.6 Hz, 1H), 7.26 (t, J=74.2 Hz, 1H due to F₂), 7.29 (d, J=8.4 Hz, 2H), 9.25 (d, J=7.2 Hz, 1H); LCMS (electrospray) m/z (M+H)⁺ 431

2-Ethyl-7-methyl-N-(4-(trifluoromethoxy)benzyl)imidazo[1,2-a]pyridine-3-carboxamide (280)

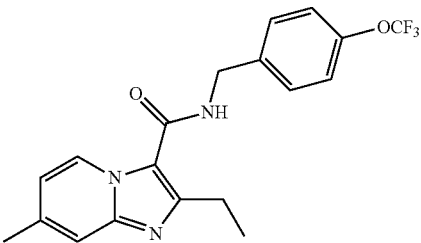 [SMILES: CCc1nc2cc(C)ccn2c1C(=O)NCc1ccc(OC(F)(F)F)cc1]

Pale yellow solid; ¹H NMR (400 MHz, CDCl₃); δ 1.33 (t, J=7.6 Hz, 3H), 2.91 (q, J=7.6 Hz, 2H), 4.64 (d, J=5.2 Hz, 2H), 6.25 (brt, J=5.2 Hz, 1H), 6.69 (dd, J=1.6, 7.2 Hz, 1H), 7.16 (d, J=8.4 Hz, 2H), 7.30 (s, 1H), 7.35 (d, J=8.4 Hz, 2H), 9.19 (d, J=7.2 Hz, 1H).

7-Bromo-2-ethyl-N-(4-(trifluoromethoxy)benzyl)imidazo[1,2-a]pyridine-3-carboxamide (281)

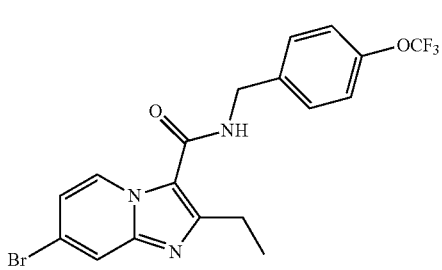 [SMILES: CCc1nc2cc(Br)ccn2c1C(=O)NCc1ccc(OC(F)(F)F)cc1]

White solid; ¹H NMR (400 MHz, CDCl₃); δ 1.37 (t, J=7.6 Hz, 3H), 2.94 (q, J=7.6 Hz, 2H), 4.67 (d, J=5.6 Hz, 2H), 6.18 (brt, J=5.6 Hz, 1H), 6.99 (dd, J=1.6, 7.2 Hz, 1H), 7.19 (d, J=8.4 Hz, 2H), 7.38 (d, J=8.4 Hz, 2H), 7.75 (d, J=1.6 Hz, 1H), 9.25 (d, J=7.2 Hz, 1H).

2-Ethyl-8-fluoro-N-(4-(trifluoromethoxy)benzyl)imidazo[1,2-a]pyridine-3-carboxamide (282)

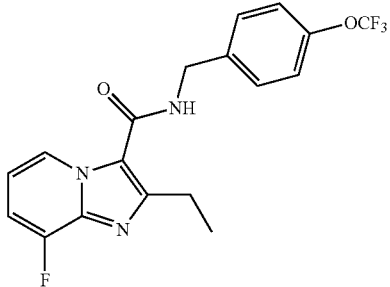 [SMILES: CCc1nc2c(F)cccn2c1C(=O)NCc1ccc(OC(F)(F)F)cc1]

White solid; ¹H NMR (400 MHz, CDCl₃); δ 1.38 (t, J=7.6 Hz, 3H), 2.97 (q, J=7.6 Hz, 2H), 4.68 (d, J=6.0 Hz, 2H), 6.25 (brs, 1H), 6.79-6.84 (m, 1H), 7.00 (dd, J=8.0, 9.6 Hz, 1H), 7.19 (d, J=8.4 Hz, 2H), 7.38 (d, J=8.4 Hz, 2H), 9.16 (d, J=6.8 Hz, 1H).

2-Ethyl-N-(4-(4-(4-fluorophenyl)piperazin-1-yl)benzyl)-8-(pyridin-4-yl)imidazo[1,2-a]pyridine-3-carboxamide (283)

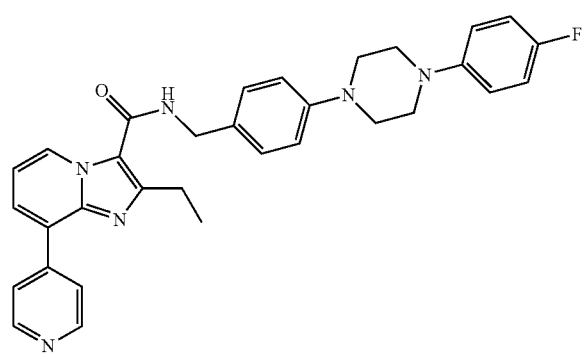 [SMILES: CCc1nc2c(-c3ccncc3)cccn2c1C(=O)NCc1ccc(N2CCN(c3ccc(F)cc3)CC2)cc1]

White solid; ¹H NMR (400 MHz, CDCl₃) δ 1.40 (t, J=7.6 Hz, 3H), 2.99 (q, J=7.6 Hz, 2H), 3.25 (t, J=5.2 Hz, 4H), 3.34 (t, J=5.2 Hz, 4H), 4.64 (d, J=5.6 Hz, 2H), 6.10 (brs, 1H), 6.91-7.04 (m, 7H), 7.32 (d, J=8.4 Hz, 2H), 7.53 (d, J=7.2 Hz, 1H), 7.99 (d, J=5.2 Hz, 2H), 8.72 (d, J=4.4 Hz, 2H), 9.47 (d, J=6.8 Hz, 1H); LCMS (electrospray) m/z (M+H)⁺ 535.

2-Ethyl-N-(4-morpholinobenzyl)-8-(pyridin-4-yl)imidazo[1,2-a]pyridine-3-carboxamide (284)

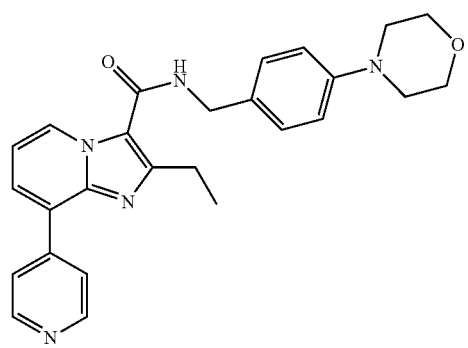 [SMILES: CCc1nc2c(-c3ccncc3)cccn2c1C(=O)NCc1ccc(N2CCOCC2)cc1]

White solid; ¹H NMR (400 MHz, CDCl₃) δ1.40 (t, J=7.6 Hz, 3H), 2.99 (q, J=7.6 Hz, 2H), 3.16 (t, J=4.8 Hz, 4H), 3.86 (t, J=4.8 Hz, 4H), 4.63 (d, J=5.6 Hz, 2H), 6.07 (brs, 1H), 6.92 (d, J=8.8 Hz, 2H), 7.02 (dd, J=6.8, 6.8 Hz, 1H), 7.31 (d, J=8.8 Hz, 2H), 7.54 (dd, J=1.2 Hz, 7.2 Hz, 1H), 7.99 (d, J=6.0 Hz, 2H), 8.72 (d, J=5.2 Hz, 2H), 9.47 (dd, J=1.2 Hz, 5.6 Hz, 1H); LCMS (electrospray) m/z (M+H)⁺ 442.

6-Chloro-N-(4-(4-(cyclopentyloxymethyl)piperidin-1-yl)benzyl)-2-ethylimidazo[1,2-a]pyridine-3-carboxamide (285)

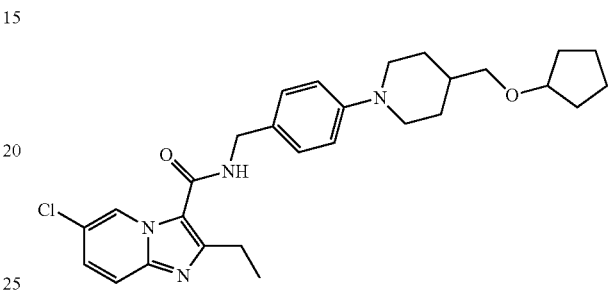

White solid; ¹H NMR (400 MHz, CDCl₃); δ 1.28-1.38 (m, 2H), 1.32 (t, J=7.6 Hz, 3H), 1.46-1.51 (m, 2H), 1.58-1.66 (m, 7H), 1.79-1.83 (m, 2H), 2.63-2.70 (m, 2H), 2.87 (q, J=7.6 Hz, 2H), 3.21 (d, J=6.4 Hz, 2H), 3.63-3.66 (m, 2H), 3.82-3.83 (m, 1H), 4.54 (d, J=5.2 Hz, 2H), 6.08 (brt, J=5.2 Hz, 1H), 6.87 (d, J=8.4 Hz, 2H), 7.19-7.25 (m, 3H), 7.45 (d, J=9.2 Hz, 1H), 9.44 (d, J=1.6 Hz, 1H); ¹³C NMR (100 MHz, CDCl₃) δ 13.2, 23.4, 23.6, 29.3, 32.3, 36.4, 43.3, 49.6, 73.7, 81.5, 115.3, 116.6, 116.8, 121.4, 126.2, 128.0, 128.1, 128.7, 144.4, 151.3, 151.5, 161.0.

7-Chloro-N-(4-(4-(cyclopentyloxymethyl)piperidin-1-yl)benzyl)-2-ethylimidazo[1,2-a]pyridine-3-carboxamide (286)

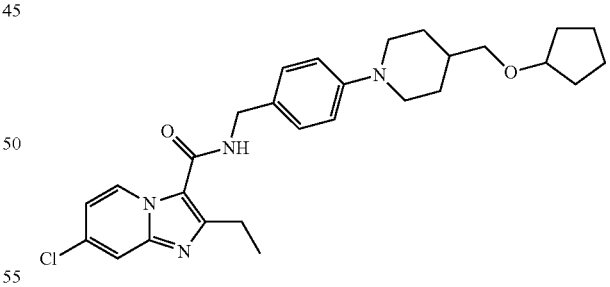

White solid; ¹H NMR (400 MHz, CDCl₃); δ 1.23-1.38 (m, 2H), 1.31 (t, J=7.6 Hz, 3H), 1.47-1.52 (m, 2H), 1.56-1.70 (m, 7H), 1.80-1.83 (m, 2H), 2.64-2.70 (m, 2H), 2.87 (q, J=7.6 Hz, 2H), 3.21 (d, J=6.8 Hz, 2H), 3.63-3.66 (m, 2H), 3.81-3.86 (m, 1H), 4.53 (d, J=5.2 Hz, 2H), 6.07 (brt, J=5.2 Hz, 1H), 6.82 (dd, J=1.6, 7.2 Hz, 1H), 6.88 (d, J=8.4 Hz, 2H), 7.19 (d, J=8.4 Hz, 2H), 7.52 (d, J=1.6 Hz, 1H), 9.26 (d, J=7.2 Hz, 1H); ¹³C NMR (100 MHz, CDCl₃) δ 13.3, 23.4, 23.6, 29.3, 32.3, 36.4, 43.3, 49.6, 73.7, 81.5, 114.5, 115.1, 115.6, 116.7, 128.1, 128.5, 128.7, 128.8, 133.4, 146.0, 151.5, 161.1.

7-Chloro-2-ethyl-N-((4'-formylbiphenyl-4-yl)methyl)imidazo[1,2-a]pyridine-3-carboxamide (287)

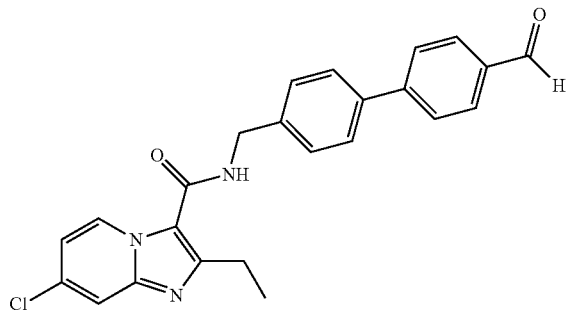 [SMILES: CCc1nc2cc(Cl)ccn2c1C(=O)NCc1ccc(-c2ccc(C=O)cc2)cc1]

White solid; ¹H NMR (400 MHz, CDCl₃); δ 1.40 (t, J=7.6 Hz, 3H), 2.97 (q, J=7.6 Hz, 2H), 4.75 (d, J=6.0 Hz, 2H), 6.18 (brt, J=6.0 Hz, 1H), 6.89 (dd, J=2.4, 7.6 Hz, 1H), 7.47 (d, J=8.4 Hz, 2H), 7.59 (d, J=2.4 Hz, 1H), 7.63 (d, J=8.0 Hz, 2H), 7.73 (d, J=8.0 Hz, 2H), 7.93 (d, J=8.4 Hz, 2H), 9.36 (d, J=7.6 Hz, 1H), 10.05 (s, 1H); ¹³C NMR (100 MHz, CDCl₃) δ 13.4, 23.8, 43.4, 114.9, 115.9, 127.8, 128.0, 128.4, 128.7, 130.5, 133.8, 135.5, 138.7, 139.3, 146.3, 146.7, 151.9, 161.4, 192.0 (hidden 1 aromatic carbon).

7-Chloro-2-ethyl-N-(4-(morpholine-4-carbonyl)benzyl)imidazo[1,2-a]pyridine-3-carboxamide (288)

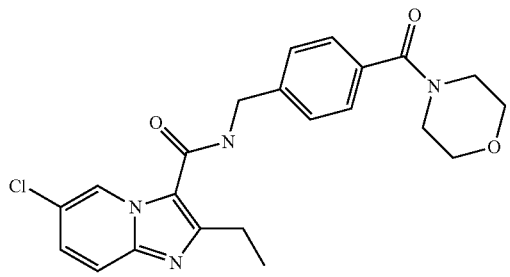 [SMILES: CCc1nc2ccc(Cl)cn2c1C(=O)NCc1ccc(C(=O)N2CCOCC2)cc1]

White solid; ¹H NMR (400 MHz, CDCl₃) δ1.42 (t, J=7.6 Hz, 3H), 2.99 (q, J=7.6 Hz, 2H), 3.70-3.71 (m, 8H), 4.72 (d, J=6.0 Hz, 2H), 6.17 (brs, 1H), 7.31 (dd, J=2.0 Hz, 9.2 Hz, 1H), 7.42 (s, 4H), 7.55 (dd, J=0.8 Hz, 9.6 Hz, 1H), 9.53 (dd, J=0.8 Hz, 2.0 Hz, 1H); LCMS (electrospray) m/z (M+H)⁺ 427.

5-(6-Chloro-2-ethylimidazo[1,2-a]pyridin-3-yl)-3-(4-(4-fluorophenoxy)benzyl)-1,2,4-oxadiazole (289)

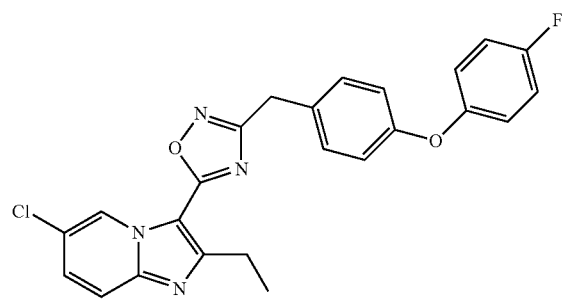 [SMILES: CCc1nc2ccc(Cl)cn2c1-c1nc(Cc2ccc(Oc3ccc(F)cc3)cc2)no1]

Yellow solid; mp=129.9° C.; ¹H NMR (400 MHz, CDCl₃) δ 1.41 (t, J=7.8 Hz, 3H), 3.22 (q, J=7.2 Hz, 2H), 4.16 (s, 2H), 6.93-7.04 (m, 6H), 7.36-7.39 (m, 3H), 7.63 (d, J=9.6 Hz, 1H), 9.48 (d, J=2.0 Hz, 1H); LCMS (electrospray) m/z (M+H)⁺ 449

2-Ethyl-N-(4-morpholinobenzyl)-7-(trifluoromethyl)imidazo[1,2-a]pyridine-3-carboxamide (290)

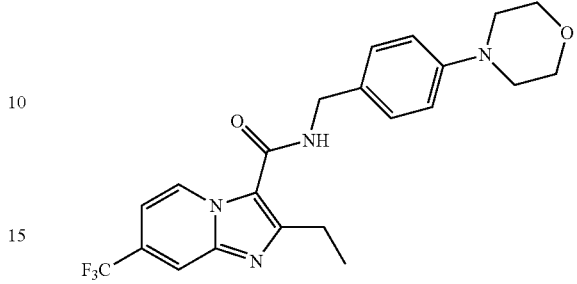

White solid; mp=174.1° C.; ¹H NMR (400 MHz, CDCl₃) δ 1.40 (t, J=7.6 Hz, 3H), 2.98 (q, J=7.6 Hz, 2H), 3.16 (t, J=4.8 Hz, 4H), 3.86 (t, J=4.8 Hz, 4H), 4.62 (d, J=5.6 Hz, 2H), 6.09-6.11 (m, 1H), 6.91 (d, J=8.8 Hz, 2H), 7.07 (dd, J=2.0, 7.6 Hz, 1H), 7.29 (d, J=8.4 Hz, 2H), 7.88-7.90 (m, 1H), 9.50 (d, J=7.2 Hz, 1H); LCMS (electrospray) m/z (M+H)⁺ 433

N-(4-(4-Carbamoylpiperidin-1-yl)benzyl)-6-chloro-2-ethylimidazo[1,2-a]pyridine-3-carboxamide (291)

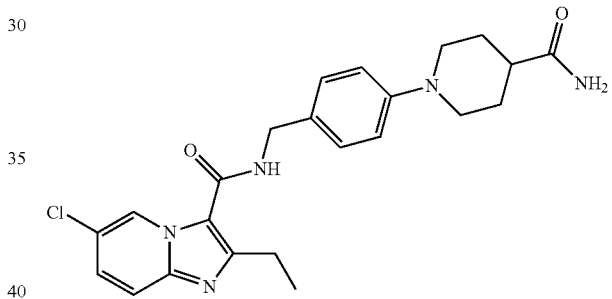

White solid; mp=257.5° C.; ¹H NMR (400 MHz, DMSO-d⁶); δ 1.23 (t, J=7.2 Hz, 3H), 1.57-1.66 (m, 2H), 1.74-1.76 (m, 2H), 2.19-2.45 (m, 1H), 2.59-2.66 (m, 2H), 2.94 (q, J=7.2 Hz, 2H), 3.65-3.69 (m, 2H), 4.41 (d, J=6.0 Hz, 2H), 6.75 (brs, 1H), 6.90 (d, J=8.4 Hz, 2H), 7.20 (d, J=8.4 Hz, 2H), 7.26 (brs, 1H), 7.43 (d, J=2.4, 9.6 Hz, 1H), 7.67 (d, J=9.6 Hz, 1H), 8.38 (brt, J=6.0 Hz, 1H), 9.06 (d, J=2.4 Hz, 1H); LCMS (electrospray) m/z 440 (M+H).

N-(4-(4-Carbamoylpiperidin-1-yl)benzyl)-7-chloro-2-ethylimidazo[1,2-a]pyridine-3-carboxamide (292)

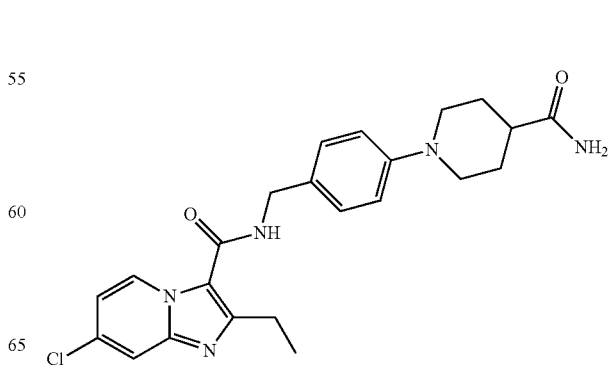

White solid; mp=244° C.; $^1$H NMR (400 MHz, DMSO-d$^6$); δ 1.23 (t, J=7.2 Hz, 3H), 1.56-1.66 (m, 2H), 1.74-1.76 (m, 2H), 2.18-2.24 (m, 1H), 2.59-2.66 (m, 2H), 2.92 (q, J=7.2 Hz, 2H), 3.65-3.68 (m, 2H), 4.40 (d, J=5.6 Hz, 2H), 6.75 (brs, 1H), 6.89 (d, J=8.8 Hz, 2H), 7.07 (dd, J=2.0, 7.6 Hz, 1H), 7.19 (d, J=8.8 Hz, 2H), 7.25 (brs, 1H), 7.77 (d, J=2.0 Hz, 1H), 8.36 (brt, J=5.6 Hz, 1H), 8.93 (d, J=7.6 Hz, 1H); LCMS (electrospray) m/z 440 (M+H)$^+$.

6-Chloro-N-(4-(4-(dimethylcarbamoyl)piperidin-1-yl)benzyl)-2-ethylimidazo[1,2-a]pyridine-3-carboxamide (293)

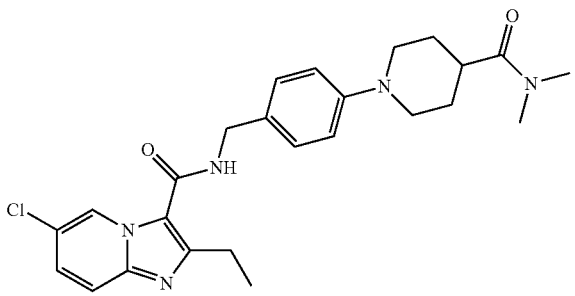 [SMILES: CCc1nc2ccc(Cl)cn2c1C(=O)NCc1ccc(N2CCC(C(=O)N(C)C)CC2)cc1]

White solid; $^1$H NMR (400 MHz, CDCl$_3$); δ 1.35 (t, J=7.6 Hz, 3H), 1.78-1.81 (m, 2H), 1.90-2.00 (m, 2H), 2.59-2.67 (m, 1H), 2.71-7.78 (m, 2H), 2.91-2.97 (m, 5H), 3.07 (s, 3H), 3.73-3.76 (m, 2H), 4.57 (d, J=5.2 Hz, 2H), 6.03 (brt, J=5.2 Hz, 1H), 6.90 (d, J=8.4 Hz, 2H), 7.23-7.28 (m, 3H), 7.50 (d, J=9.6 Hz, 1H), 9.50 (d, J=1.2 Hz, 1H); $^{13}$C NMR (100 MHz, CDCl$_3$) δ 13.3, 23.6, 28.4, 35.8, 37.2, 38.7, 43.3, 49.3, 115.4, 116.7, 117.0, 121.5, 126.3, 128.2, 128.5, 128.9, 144.5, 151.3, 151.4, 161.1, 174.7; LCMS (electrospray) m/z 468 (M+H)$^+$.

7-Chloro-N-(4-(4-(dimethylcarbamoyl)piperidin-1-yl)benzyl)-2-ethylimidazo[1,2-a]pyridine-3-carboxamide (294)

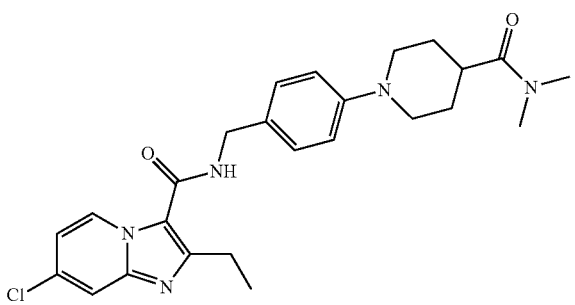 [SMILES: CCc1nc2cc(Cl)ccn2c1C(=O)NCc1ccc(N2CCC(C(=O)N(C)C)CC2)cc1]

Pale yellow solid; $^1$H NMR (400 MHz, CDCl$_3$); δ 1.33 (t, J=7.2 Hz, 3H), 1.77-1.80 (m, 2H), 1.88-1.99 (m, 2H), 2.58-2.66 (m, 1H), 2.70-2.77 (m, 2H), 2.89-2.95 (m, 5H), 3.06 (s, 3H), 3.71-3.74 (m, 2H), 4.56 (d, J=5.2 Hz, 2H), 6.07 (brs, 1H), 6.84 (dd, J=1.6, 7.2 Hz, 1H), 6.89 (d, J=8.4 Hz, 2H), 7.22 (d, J=8.4 Hz, 2H), 7.54 (d, J=1.6 Hz, 1H), 9.30 (d, J=7.2 Hz, 1H); $^{13}$C NMR (100 MHz, CDCl$_3$) δ 13.4, 23.5, 28.4, 35.8, 37.2, 38.7, 43.3, 49.3, 114.6, 115.1, 115.7, 116.7, 128.5, 128.6, 128.8, 133.5, 146.1, 151.2, 151.6, 161.2, 174.7; LCMS (electrospray) m/z 468 (M+H)$^+$.

7-Chloro-N-(4-(4-((difluoromethoxy)methyl)piperidin-1-yl)benzyl)-2-ethylimidazo[1,2-a]pyridine-3-carboxamide (295)

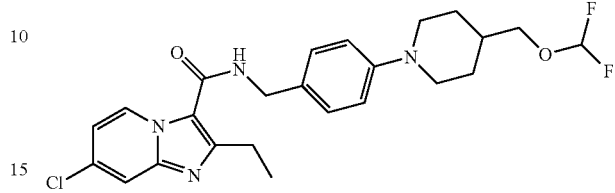

White solid; $^1$H NMR (400 MHz, CDCl$_3$) δ1.37 (t, J=7.6 Hz, 3H), 1.41-1.48 (m, 2H), 1.70-1.86 (m, 3H), 2.72 (t, J=12.4 Hz, 2H), 2.93 (q, J=7.6 Hz, 2H), 3.69-3.73 (m, 4H), 4.58 (d, J=5.6 Hz, 2H), 6.00 (brs, 1H), 6.20 (t, J=75.2 Hz, due to F2), 6.88 (dd, J=1.6, 7.6 Hz, 1H), 6.92 (d, J=8.4 Hz, 2H), 7.25 (d, J=8.4 Hz, 2H), 7.56 (d, J=1.6 Hz, 1H), 9.34 (d, J=7.6 Hz, 1H); LCMS (electrospray) m/z (M+H)$^+$ 477.

6-Chloro-N-(4-(4-(4-chlorophenyl)piperidin-1-yl)benzyl)-2-ethylimidazo[1,2-a]pyridine-3-carboxamide (296)

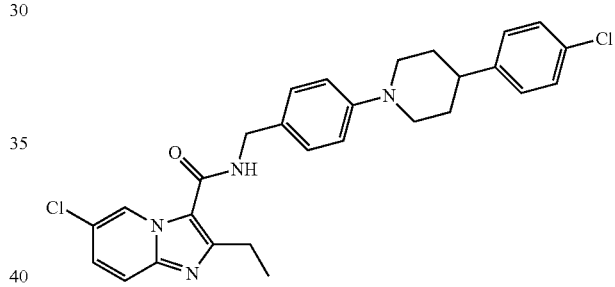

Pale yellow solid; $^1$H NMR (400 MHz, CDCl$_3$) δ 1.39 (t, J=7.6 Hz, 3H), 1.80-1.96 (m, 4H), 2.60-2.68 (m, 1H), 2.92-2.98 (m, 4H), 2.95 (q, J=7.6 Hz, 2H), 3.79-3.83 (m, 2H), 4.61 (q, J=5.2 Hz, 2H), 5.99-6.01 (m, 1H), 6.90 (dd, J=2.2, 7.4 Hz, 1H), 6.98 (d, J=8.4 Hz, 2H), 7.18 (d, J=8.4 Hz, 2H), 7.26-7.29 (m, 4H), 7.59 (d, J=2.0 Hz, 1H), 9.30 (d, J=7.6 Hz, 1H); LCMS (electrospray) m/z (M+H)$^+$ 507

7-Chloro-N-(4-(4-(4-chlorophenyl)piperidin-1-yl)benzyl)-2-ethylimidazo[1,2-a]pyridine-3-carboxamide (297)

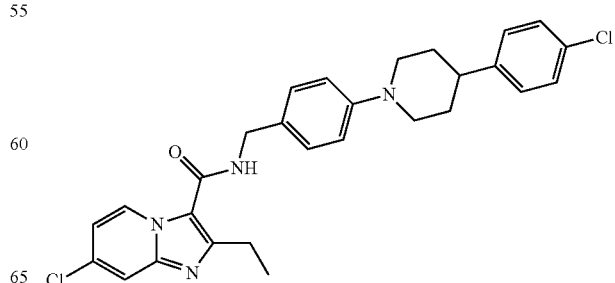

Pale yellow solid; mp=177.0° C.; ¹H NMR (400 MHz, CDCl₃) δ 1.40 (t, J=7.4 Hz, 3H), 1.80-1.96 (m, 4H), 2.60-2.67 (m, 1H), 2.79-2.86 (m, 4H), 2.96 (q, J=7.4 Hz, 2H), 3.80-3.83 (m, 2H), 4.62 (q, J=5.2 Hz, 2H), 6.00-6.02 (m, 1H), 6.98 (dd, J=8.8 Hz, 2H), 7.18 (d, J=8.4 Hz, 2H), 7.26-7.31 (m, 4H), 7.54 (d, J=9.6 Hz, 2H), 9.30 (d, J=7.6 Hz, 1H).

6-Chloro-N-((2-cyclohexylbenzo[d]oxazol-5-yl)methyl)-2-ethylimidazo[1,2-a]pyridine-3-carboxamide (298)

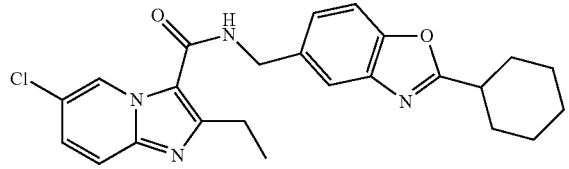 [SMILES: CCc1nc2ccc(Cl)cn2c1C(=O)NCc1ccc2oc(C3CCCCC3)nc2c1]

White solid; mp=169.7° C.; ¹H NMR (400 MHz, CDCl₃) δ 1.30-1.44 (m, 4H), 1.59-1.88 (m, 8H), 2.16 (d, J=10.8 Hz, 2H), 2.96 (q, J=7.6 Hz, 2H), 4.78 (d, J=5.6 Hz, 2H), 6.19 (brs, 1H), 7.28 (d, J=1.6 Hz, 1H), 7.30-7.34 (m, 1H), 7.46 (d, J=8.0 Hz, 1H), 7.53 (d, J=9.2 Hz, 1H), 7.67 (s, 1H), 9.53 (d, J=2.4 Hz, 1H); LCMS (electrospray) m/z (M+H)⁺ 437.

7-Chloro-N-((2-cyclohexylbenzo[d]oxazol-5-yl)methyl)-2-ethylimidazo[1,2-a]pyridine-3-carboxamide (299)

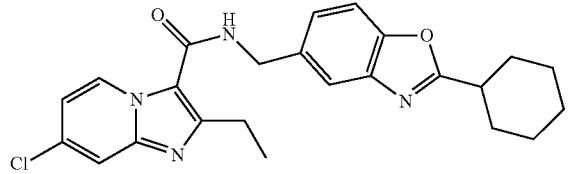 [SMILES: CCc1nc2cc(Cl)ccn2c1C(=O)NCc1ccc2oc(C3CCCCC3)nc2c1]

White solid; mp=163.0° C.; ¹H NMR (400 MHz, CDCl₃) δ 1.30-1.46 (m, 6H), 1.60-1.73 (m, 4H), 1.86 (d, J=13.2 Hz, 2H), 2.15 (d, J=13.2 Hz, 2H), 2.95 (q, J=7.2 Hz, 2H), 4.77 (d, J=5.6 Hz, 2H), 6.12 (brs, 1H), 6.89 (d, J=7.2 Hz, 1H), 7.31 (d, J=8.0 Hz, 1H), 7.46 (d, J=8.0 Hz, 1H), 7.58 (s, 1H), 7.67 (s, 1H), 9.36 (d, J=7.2 Hz, 1H); LCMS (electrospray) m/z (M+H)⁺ 437.

6-Chloro-2-ethyl-N-(4-(4-(4-fluorobenzyloxy)piperidin-1-yl)benzyl)imidazo[1,2-a]pyridine-3-carboxamide (300)

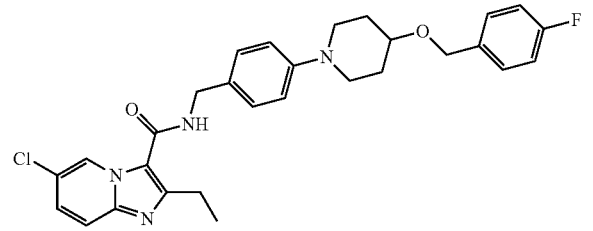 [SMILES: CCc1nc2ccc(Cl)cn2c1C(=O)NCc1ccc(N2CCC(OCc3ccc(F)cc3)CC2)cc1]

Pale pink solid; ¹H NMR (400 MHz, CDCl₃); δ 1.35 (t, J=7.6 Hz, 3H), 1.73-1.82 (m, 2H), 2.00-2.04 (m, 2H), 2.91-2.98 (m, 4H), 3.50-3.59 (m, 3H), 4.53 (s, 2H), 4.58 (d, J=5.2 Hz, 2H), 6.00 (brt, J=5.2 Hz, 1H), 6.91 (d, J=8.8 Hz, 2H), 6.99-7.04 (m, 2H), 7.23-7.35 (m, 5H), 7.50 (d, J=9.6 Hz, 1H), 9.51 (d, J=2.0 Hz, 1H); LCMS (electrospray) m/z 521 (M+H)⁺.

7-Chloro-2-ethyl-N-(4-(4-(4-fluorobenzyloxy)piperidin-1-yl)benzyl)imidazo[1,2-a]pyridine-3-carboxamide (301)

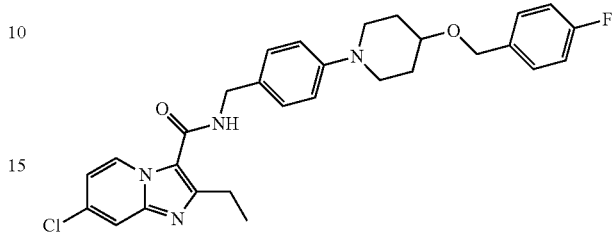

Pale pink solid; ¹H NMR (400 MHz, CDCl₃); δ 1.34 (t, J=7.2 Hz, 3H), 1.73-1.82 (m, 2H), 1.96-2.07 (m, 2H), 2.91-2.95 (m, 4H), 3.49-3.59 (m, 3H), 4.52 (s, 2H), 4.56 (d, J=5.6 Hz, 2H), 5.99 (brt, J=5.6 Hz, 1H), 6.86-6.92 (m, 3H), 6.99-7.03 (m, 2H), 7.22-7.32 (m, 4H), 7.55 (d, J=1.6 Hz, 1H), 9.32 (d, J=7.2 Hz, 1H); LCMS (electrospray) m/z 521 (M+H)⁺.

6-Chloro-N-(3-chloro-4-morpholinobenzyl)-2-ethylimidazo[1,2-a]pyridine-3-carboxamide (302)

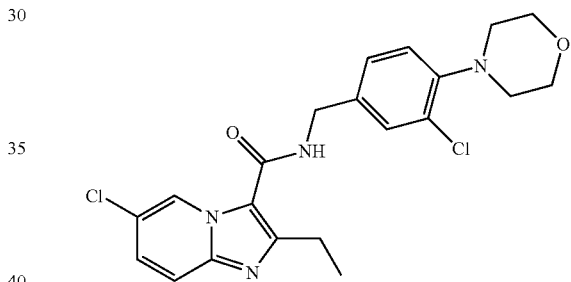

White solid; mp=175.5° C.; ¹H NMR (400 MHz, CDCl₃); δ 1.37 (t, J=7.6 Hz, 3H), 2.94 (q, J=7.6 Hz, 2H), 2.99-3.03 (m, 4H), 3.83-3.85 (m, 4H), 4.58 (d, J=6.0 Hz, 2H), 6.15 (brt, J=6.0 Hz, 1H), 6.99 (d, J=8.0 Hz, 1H), 7.21 (dd, J=1.6, 8.0 Hz, 1H), 7.26-7.28 (m, 1H), 7.36 (d, J=1.6 Hz, 1H), 7.49 (d, J=9.2 Hz, 1H), 9.47 (d, J=0.8 Hz, 1H); ¹³C NMR (100 MHz, CDCl₃) δ 13.3, 23.7, 42.7, 51.8, 67.2, 115.1, 117.0, 120.7, 121.7, 126.3, 127.0, 128.4, 129.2, 130.1, 134.0, 144.6, 148.6, 151.6, 161.2; LCMS (electrospray) m/z 433 (M+H)⁺.

7-Chloro-N-(3-chloro-4-morpholinobenzyl)-2-ethylimidazo[1,2-a]pyridine-3-carboxamide (303)

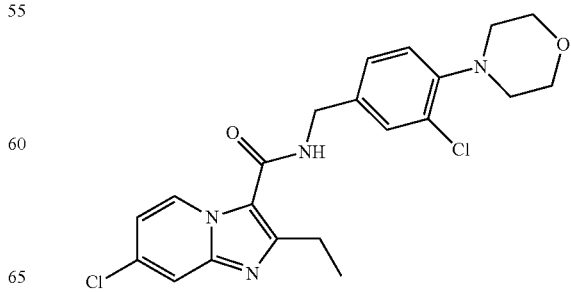

Pale yellow solid; $^1$H NMR (400 MHz, CDCl$_3$); δ 1.38 (t, J=7.6 Hz, 3H), 2.94 (q, J=7.6 Hz, 2H), 3.02-3.05 (m, 4H), 3.85-3.87 (m, 4H), 4.59 (d, J=5.6 Hz, 2H), 6.09 (brt, J=5.6 Hz, 1H), 6.88 (dd, J=2.0, 7.2 Hz, 1H), 7.00 (d, J=8.0 Hz, 1H), 7.22 (dd, J=1.6, 8.0 Hz, 1H), 7.37 (d, J=1.6 Hz, 1H), 7.57 (d, J=2.0 Hz, 1H), 9.32 (d, J=7.2 Hz, 1H); $^{13}$C NMR (100 MHz, CDCl$_3$) δ 13.4, 23.7, 42.7, 51.8, 67.3, 114.9, 115.8, 120.7, 127.1, 128.6, 129.2, 130.1, 133.8, 134.0, 146.3, 148.7, 151.9, 161.3 (hidden 1 carbon); LCMS (electrospray) m/z 433 (M+H)$^+$.

7-Bromo-2-ethyl-N-(4-(4-(4-fluorophenyl)piperazin-1-yl)benzyl)imidazo[1,2-a]pyridine-3-carboxamide (304)

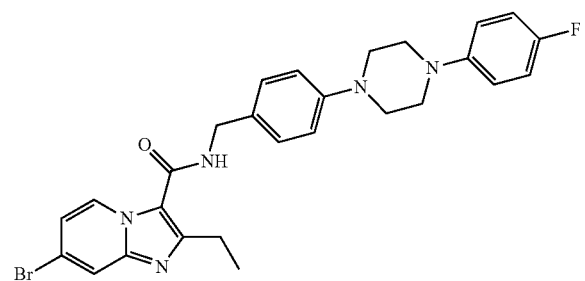

White solid; mp=214.6° C.; $^1$H NMR (400 MHz, CDCl$_3$); δ 1.36 (t, J=7.6 Hz, 3H), 2.92 (q, J=7.6 Hz, 2H), 3.24-3.28 (m, 4H), 3.33-3.35 (m, 4H), 4.60 (d, J=5.2 Hz, 2H), 6.02 (brt, J=5.2 Hz, 1H), 6.91-7.02 (m, 7H), 7.28 (d, J=8.8 Hz, 2H), 7.76 (d, J=1.6 Hz, 1H), 9.28 (d, J=7.6 Hz, 1H); LCMS (electrospray) m/z 536, 538 (M+H)$^+$ (Br isotope pattern).

2-Ethyl-N-(4-morpholinobenzyl)-7-(pyridin-3-yl)imidazo[1,2-a]pyridine-3-carboxamide (305)

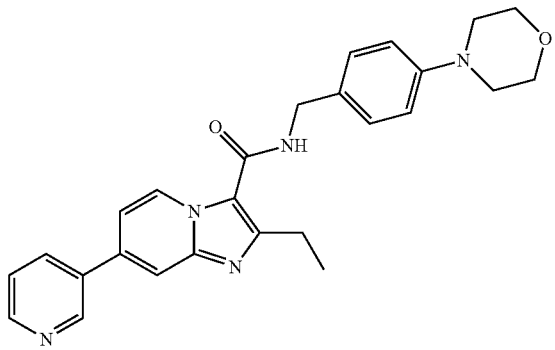 [SMILES: CCc1nc2cc(-c3cccnc3)ccn2c1C(=O)NCc1ccc(N2CCOCC2)cc1]

Yellow solid; mp=208.5° C.; $^1$H NMR (400 MHz, CDCl$_3$); δ 1.36 (t, J=7.2 Hz, 3H), 2.93 (q, J=7.2 Hz, 2H), 3.12-3.15 (m, 4H), 3.82-3.85 (m, 4H), 4.59 (d, J=4.8 Hz, 2H), 6.21 (brs, 1H), 6.87 (d, J=8.4 Hz, 2H), 7.12 (d, J=6.0 Hz, 1H), 7.26 (d, J=8.4 Hz, 2H), 7.37 (dd, J=5.6, 6.0 Hz, 1H), 7.77 (brs, 1H), 7.90 (d, J=7.2 Hz, 1H), 8.60 (brs, 1H), 8.88 (brs, 1H), 9.41 (d, J=7.2 Hz, 1H); $^{13}$C NMR (100 MHz, CDCl$_3$) δ 13.3, 23.5, 43.2, 49.3, 66.9, 112.2, 113.8, 115.0, 116.0, 123.9, 128.5, 128.9, 129.3, 134.0, 134.2, 136.2, 146.3, 148.0, 149.6, 150.9, 151.7, 161.3; LCMS (electrospray) m/z 442 (M+H)$^+$.

6-Chloro-2-ethyl-N-(4-(4-(4-fluorophenyl)-4-hydroxypiperidin-1-yl)benzyl)imidazo[1,2-a]pyridine-3-carboxamide (306)

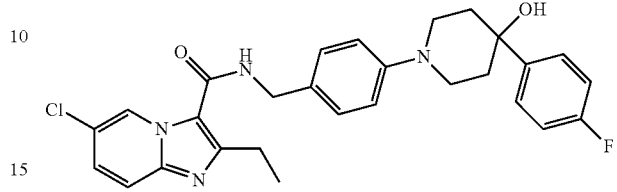

White solid; mp=173.5° C.; $^1$H NMR (400 MHz, CDCl$_3$) δ1.35 (t, J=7.6 Hz, 3H), 1.66 (s, 1H), 1.85 (d, J=12.0 Hz, 2H), 2.18-2.26 (m, 2H), 2.91 (q, J=7.6 Hz, 2H), 3.21-3.26 (dd, J=10.4 Hz, 12.0 Hz, 2H), 3.58 (d, J=11.6 Hz, 2H), 4.60 (d, J=5.6 Hz, 2H), 6.00 (brs, 1H), 6.89 (dd, J=1.6, 7.6 Hz, 1H), 6.99 (d, J=8.4 Hz, 2H), 7.04 (dd, J=8.8 Hz, 2H), 7.26 (d, J=8.4 Hz, 2H), 7.48 (dd, J=5.2 Hz, 8.8 Hz, 2H), 7.56 (d, J=2.0 Hz, 1H), 9.35 (d, J=7.6 Hz, 1H); LCMS (electrospray) m/z (M+H)$^+$ 507.

1-(4-((6-Chloro-2-ethylimidazo[1,2-a]pyridine-3-carboxamido)methyl)phenyl)piperidine-4-carboxylic acid (307)

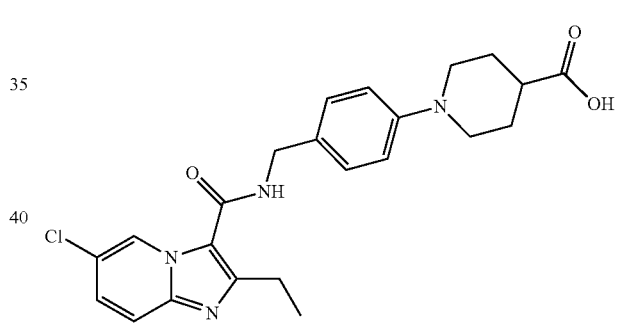

White solid; $^1$H NMR (400 MHz, DMSO-d$^6$); δ 1.23 (t, J=7.6 Hz, 3H), 1.57-1.67 (m, 2H), 1.85-1.89 (m, 2H), 2.34-2.41 (m, 1H), 2.68-2.74 (m, 2H), 2.94 (q, J=7.6 Hz, 2H), 3.58-3.61 (m, 2H), 4.41 (d, J=5.6 Hz, 2H), 6.90 (d, J=8.8 Hz, 2H), 7.20 (d, J=8.8 Hz, 2H), 7.43 (dd, J=2.0, 9.6 Hz, 1H), 7.64 (d, J=9.6 Hz, 1H), 8.38 (brt, J=5.6 Hz, 1H), 9.05 (d, J=2.0 Hz, 1H); LCMS (electrospray) m/z 441 (M+H)$^+$.

6-Chloro-2-ethyl-N-(4-(4-(4-fluorophenoxy)piperidin-1-yl)benzyl)imidazo[1,2-a]pyridine-3-carboxamide (308)

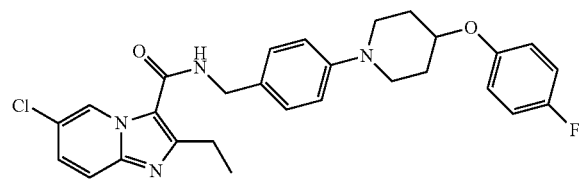 [SMILES: CCc1nc2ccc(Cl)cn2c1C(=O)NCc1ccc(N2CCC(Oc3ccc(F)cc3)CC2)cc1]

¹H NMR (400 MHz, CDCl₃) δ 1.39 (t, J=7.6 Hz, 3H), 1.91-1.94 (m, 2H), 2.06-2.11 (m, 2H), 2.96 (q, J=7.6 Hz, 2H), 3.08-3.14 (m, 2H), 3.47-3.54 (m, 2H), 4.37-4.39 (m, 1H), 4.61 (d, J=5.6 Hz, 2H), 6.01 (brs, 1H), 6.86-6.89 (m, 2H), 6.95-7.00 (m, 4H), 7.26-7.30 (m, 3H), 7.53 (d, J=8.8 Hz, 1H), 9.53 (d, J=1.6 Hz, 1H); LCMS (electrospray) m/z (M+H)⁺ 507.31

6-Chloro-2-ethyl-N-(1-(4-(trifluoromethoxy)benzyl)piperidin-4-yl)imidazo[1,2-a]pyridine-3-carboxamide (309)

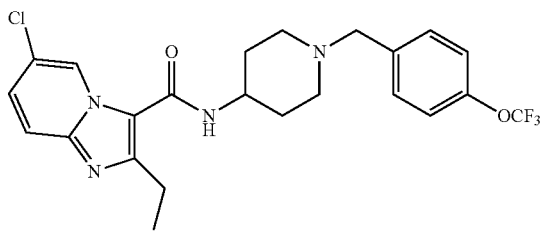 [SMILES: CCc1nc2ccc(Cl)cn2c1C(=O)NC1CCN(Cc2ccc(OC(F)(F)F)cc2)CC1]

White solid; mp=157-158° C.; ¹H NMR (400 MHz, CDCl₃) δ 1.43 (t, J=7.6 Hz, 3H), 1.56-1.66 (m, 2H), 2.05-2.10 (m, 1H), 2.22-2.27 (m, 2H), 2.81-2.84 (m, 2H), 2.98 (q, J=7.6 Hz, 2H), 3.53 (s, 2H), 4.08-4.11 (m, 1H), 5.69-5.71 (m, 1H), 7.17 (d, J=8.0 Hz, 2H), 7.29 (dd, J=2.0, 9.6 Hz, 1H), 7.36 (d, J=8.4 Hz, 2H), 7.53 (d, J=9.2 Hz, 1H), 9.46 (d, J=1.6 Hz, 1H)); LCMS (electrospray) m/z (M+H)⁺ 481.26

3-(((4'-Chloro-[1,1'-biphenyl]-4-yl)methyl)carbamoyl)-2-ethylimidazo[1,2-a]pyrazine 7-oxide (310)

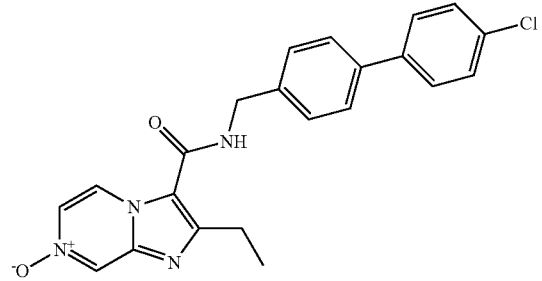

White solid; mp=238° C.; ¹H NMR (400 MHz, CDCl₃) δ 1.43 (t, J=7.6 Hz, 3H), 3.00 (q, J=7.6 Hz, 2H), 4.73 (d, J=6.0 Hz, 2H), 6.21 (t, J=4.8 Hz, 1H), 7.41 (d, J=8.8 Hz, 2H), 7.44 (d, J=8.0 Hz, 2H), 7.51 (d, J=8.4 Hz, 2H), 7.57 (d, J=8.4 Hz, 2H), 7.69 (dd, J=2.0, 6.4 Hz, 1H). 8.56-8.57 (m, 1H), 9.31 (d, J=6.0 Hz, 1H); LCMS (electrospray) m/z (M+H)⁺407.12

N-((6-Chloro-2-ethylimidazo[1,2-a]pyridin-3-yl)methyl)-4-(4-(4-fluorophenyl)piperazin-1-yl)aniline (311)

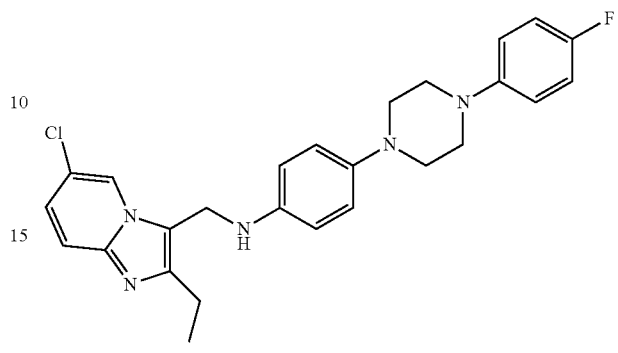

White solid; mp=191-192° C.; ¹H NMR (400 MHz, CDCl₃) δ 1.35 (J=7.6 Hz, 3H), 2.82 (q, J=7.2 Hz, 2H), 3.22-3.24 (m, 4H), 3.26-3.28 (m, 4H), 3.40 (br s, 1H), 4.50 (s, 2H), 6.75 (d, J=8.8 Hz, 2H), 6.92-7.01 (m, 6H), 7.14 (dd, J=1.6, 9.2 Hz, 1H), 7.51 (d, J=9.6 Hz, 1H), 8.18 (d, J=1.2 Hz, 1H); LCMS (electrospray) m/z (M+H)⁺ 464.32

2-Ethyl-7-nitro-N-(4-(4-(4-(trifluoromethoxy)phenoxy)piperidin-1-yl)benzyl)imidazo[1,2-a]pyridine-3-carboxamide (312)

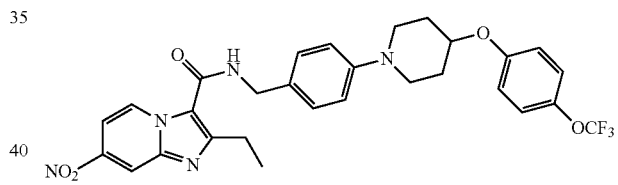

¹H NMR (400 MHz, CDCl₃) δ 1.43 (t, J=7.6 Hz, 3H), 1.95 (m, 2H), 2.10 (m, 2H), 3.01 (q, J=7.6 Hz, 2H), 3.11-3.16 (m, 2H), 3.49-3.53 (m, 2H), 4.45 (m, 1H), 4.63 (d, J=5.2 Hz, 2H), 6.11 (brs, 1H), 6.91 (d, J=9.2 Hz, 2H), 6.96 (d, J=8.8 Hz, 2H), 7.14 (d, J=8.8 Hz, 2H), 7.28 (d, J=8.8 Hz, 2H), 7.72 (d, J=7.6 Hz, 1H), 8.53 (s, 1H), 9.54 (d, J=7.6 Hz, 1H); LCMS (electrospray) m/z (M+H)⁺ 584.58

(6-Chloro-2-ethylimidazo[1,2-a]pyridin-3-yl)(4-(4-(trifluoromethoxy)benzyloxy)piperidin-1-yl)methanone (313)

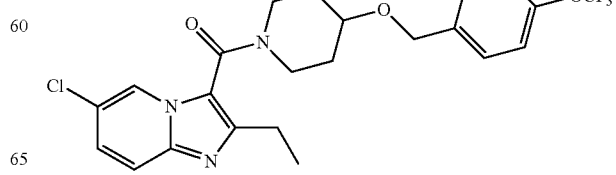

¹H NMR (400 MHz, CDCl₃) δ 1.38 (t, J=7.2 Hz, 3H), 1.71-1.78 (m, 2H), 1.94 (m, 2H), 2.78 (q, J=7.6 Hz, 2H), 3.51 (m, 2H), 3.74 (m, 1H), 3.89 (m, 2H), 4.58 (s, 2H), 7.19-7.23 (m, 3H), 7.38 (d, J=8.4 Hz, 2H), 7.51 (d, J=9.6 Hz, 1H), 8.48 (s, 1H); LCMS (electrospray) m/z (M+H)⁺ 481.26

6-Chloro-2-ethyl-N-(4-(4-(4-fluorophenyl)piperazin-1-yl)benzyl)-N-methylimidazo[1,2-a]pyridine-3-carboxamide (314)

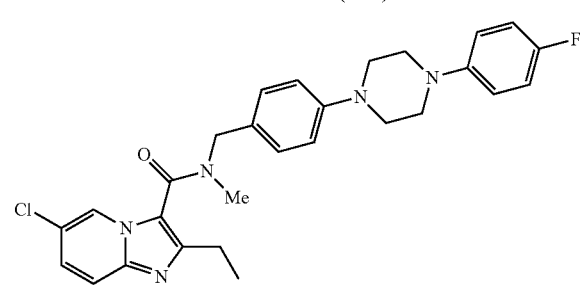

White solid; mp=148-149° C.; ¹H NMR (400 MHz, CDCl₃) δ 1.37 (t, J=7.4 Hz, 3H), 2.78 (q, J=7.6 Hz, 2H), 2.99 (s, 3H), 3.24-3.27 (m, 4H), 3.33-3.36 (m, 4H), 4.66 (s, 2H), 6.92-7.02 (m, 6H), 7.12-7.20 (m, 2H), 7.21 (dd, J=2.0, 9.6 Hz, 1H), 7.52 (d, J=9.6 Hz, 1H), 8.46 (d, J=1.6 Hz, 1H); LCMS (electrospray) m/z (M+H)⁺ 506.36

2-ethyl-6-methyl-N-(4-morpholinobenzyl)imidazo[1,2-a]pyridine-3-carboxamide (315)

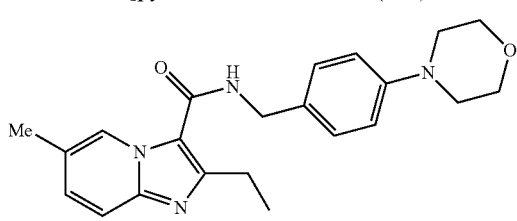

White solid; ¹H NMR (400 MHz, CDCl₃) δ1.38 (t, J=7.2 Hz, 3H), 2.35 (s, 3H), 2.94 (q, J=7.6 Hz, 2H), 3.15 (t, J=4.8 Hz, 4H), 3.86 (t, J=4. Hz, 4H), 4.61 (d, J=5.2 Hz, 2H), 6.00 (brs, 1H), 6.91 (d, J=8.8 Hz, 2H), 7.16 (dd, J=2.0 Hz, 9.2 Hz, 1H), 7.29 (d, J=8.8 Hz, 2H), 7.49 (d, J=9.2 Hz, 1H), 9.20 (s, 1H); LCMS (electrospray) m/z (M+H)⁺ 379.

6-chloro-2-ethyl-N-(4-(4-(2-(4-fluorophenyl)acetamido)piperidin-1-yl)benzyl)imidazo[1,2-a]pyridine-3-carboxamide (316)

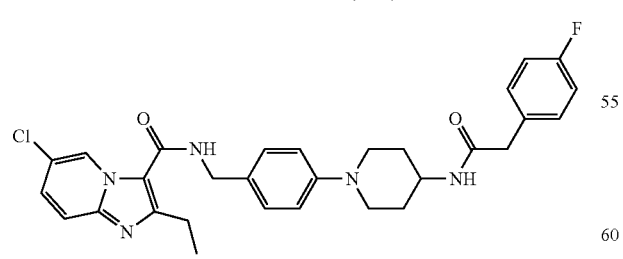

white solid; ¹H-NMR (DMSO-d6, 400 MHz): δ 1.26 (3H, t, J=7.6 Hz), 1.65-1.63 (2H, m), 1.92-1.89 (2H, m), 3.01 (2H, q, J=7.6 Hz), 3.17 (1H, brs), 3.39 (2H, s), 3.62-3.59 (2H, m), 3.82 (1H, m), 4.49 (2H, d, J=5.6 Hz), 7.10 (2H, d, J=8.8 Hz), 7.29-7.25 (4H, m), 7.38-7.36 (2H, m), 7.65 (1H, dd, J=9.2, 1.6 Hz), 7.78 (1H, d, J=9.6 Hz), 8.19 (1H, d, J=7.2 Hz), 8.70 (1H, t, J=5.6 Hz), 9.11 (1H, s); LCMS: 99.7%, MS (ESI): m/z 548.2[M+H]+.

N-(4-(4-(benzyloxy)piperidin-1-yl)benzyl)-6-chloro-2-ethylimidazo[1,2-a]pyridine-3-carboxamide (317)

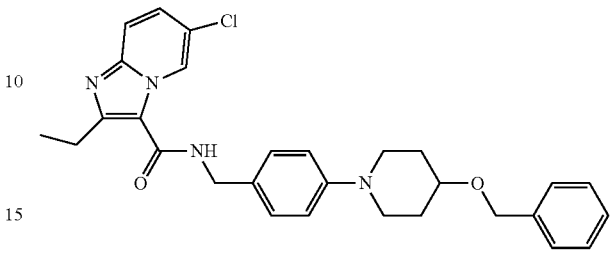

yellow solid; ¹H-NMR (MeOD, 300 MHz): δ1.37 (3H, t, J=7.5 Hz), 2.15-2.23 (4H, m), 3.10 (2H, q, J=7.5 Hz), 3.51-3.57 (2H, m), 3.77-3.87 (3H, m), 4.63 (2H, s), 4.68 (2H, s), 7.29-7.41 (5H, m), 7.57-7.64 (4H, m), 7.76-7.81 (2H, m), 9.22 (1H, d, J=9.0 Hz); LCMS: 98.9%, MS (ESI): m/z 503.2 [M+H]+.

6-chloro-2-ethyl-N-(4-(4-(4-fluorobenzamido)piperidin-1-yl)benzyl)imidazo[1,2-a]pyridine-3-carboxamide (318)

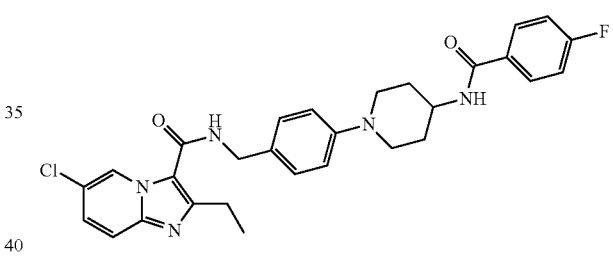

white solid; ¹H NMR (DMSO-d6, 400 MHz): δ1.29 (3H, t, J=7.6 Hz), 1.79-1.81 (2H, m), 1.97-1.99 (2H, m), 3.02 (2H, q, J=7.6 Hz), 3.15 (1H, m), 3.70-3.73 (2H, m), 4.05 (1H, m), 4.50 (2H, d, J=5.6 Hz), 7.25-7.33 (4H, m), 7.36-7.38 (2H, m), 7.64 (1H, dd, J=1.6 Hz, 9.6 Hz), 7.78 (1H, d, J=9.6 Hz), 7.92-7.96 (2H, m), 8.42 (1H, d, J=7.2 Hz), 8.65 (1H, t, J=5.6 Hz), 9.12 (1H, d, J=1.6 Hz); LCMS: 100%, MS (ESI): m/z 534.1[M+H]+.

6-chloro-2-ethyl-N-(4-(4-(4-fluorobenzoyl)piperazin-1-yl)benzyl)imidazo[1,2-a]pyridine-3-carboxamide (319)

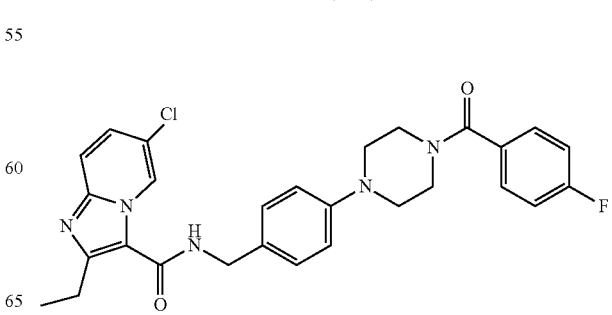

white solid; ¹H NMR (DMSO-d6, Bruker Avance 300 MHz) δ 1.25 (3H, t, J=7.5 Hz), 3.00 (2H, q, J=7.5 Hz), 3.08-3.28 (4H, m), 3.31-3.91 (4H, m), 4.43 (2H, d, J=5.7 Hz), 6.95 (2H, d, J=8.7 Hz), 7.20-7.33 (4H, m), 7.49 (2H, dd, J=8.4, 5.4 Hz), 7.70 (1H, dd, J=9.2, 1.8 Hz), 7.80 (1H, d, J=9.2 Hz), 8.70 (1H, t, J=5.7 Hz), 9.10 (1H, s); LCMS: 100%, MS (ESI): m/z 520.0 [M+H]+.

6-chloro-2-ethyl-N-(4-(4-(2-(4-fluorophenyl)acetyl) piperazin-1-yl)benzyl)imidazo[1,2-a]pyridine-3-carboxamide (320)

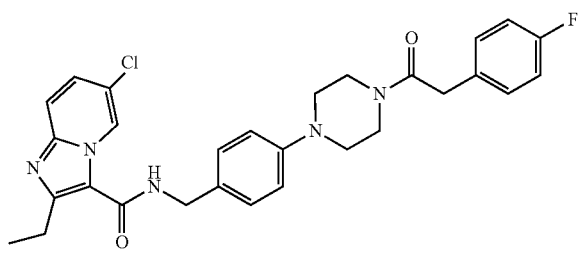 [SMILES: CCc1nc2ccc(Cl)cn2c1C(=O)NCc1ccc(N2CCN(C(=O)Cc3ccc(F)cc3)CC2)cc1]

white solid; ¹H NMR (DMSO-d6, Bruker Advance 300 MHz) δ 1.24 (3H, t, J=7.5 Hz), 2.91-3.12 (6H, m), 3.51-3.65 (4H, m), 3.74 (2H, s), 4.42-4.44 (2H, m), 6.92 (2H, d, J=8.7 Hz), 7.10 (2H, t, J=8.8 Hz), 7.19-7.31 (4H, m), 7.69 (1H, dd, J=9.6, 1.8 Hz), 7.78 (1H, d, J=9.6 Hz), 8.66 (1H, t, J=5.7 Hz), 9.10 (1H, s). LCMS: 100%, MS (ESI): m/z 534.0 [M+H]+.

6-chloro-2-ethyl-N-(4-(4-hydroxy-4-methylpiperidin-1-yl)benzyl)imidazo[1,2-a]pyridine-3-carboxamide (321)

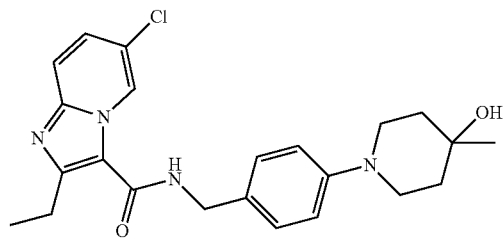 [SMILES: CCc1nc2ccc(Cl)cn2c1C(=O)NCc1ccc(N2CCC(C)(O)CC2)cc1]

pale yellow oil; ¹H-NMR (CD3OD, 300 MHz): δ1.32-1.41 (6H, m), 1.91-1.96 (2H, m), 2.02-2.13 (2H, m), 3.12 (2H, q, J=7.5 Hz), 3.51-3.55 (2H, m), 3.82-3.91 (2H, m), 4.70 (2H, s), 7.66 (4H, s), 7.80-7.90 (2H, m), 9.24 (1H, s); LCMS: 98.4%, MS (ESI): m/z 427.1[M+H]+.

N-(4-(4-(tert-butyl)-4-hydroxypiperidin-1-yl)benzyl)-6-chloro-2-ethylimidazo[1,2-a]pyridine-3-carboxamide (322)

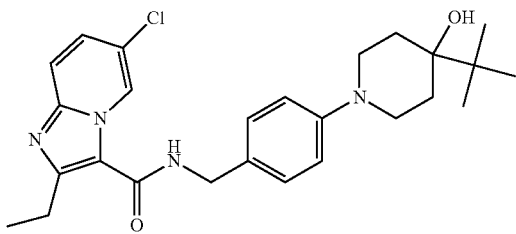 [SMILES: CCc1nc2ccc(Cl)cn2c1C(=O)NCc1ccc(N2CCC(O)(C(C)(C)C)CC2)cc1]

white solid; ¹H-NMR (CD3OD, 400 MHz): δ1.40 (2H, t, J=7.6 Hz), 2.11 (2H, d, J=13.6 Hz), 2.50-2.61 (2H, m), 3.13 (2H, q, J=7.6 Hz), 3.67 (2H, d, J=12.4 Hz), 4.02-4.09 (2H, m), 4.72 (2H, s), 7.29 (1H, d, J=7.6 Hz), 7.39 (2H, t, J=8.0 Hz), 7.57 (2H, d, J=7.2 Hz), 7.67-7.73 (4H, m), 7.81-7.89 (2H, m), 9.26 (1H, d, J=0.8 Hz); LCMS: 99.9%, MS (ESI): m/z 489.2 [M+H]+.

6-chloro-2-ethyl-N-(4-(4-(4-fluorobenzoyl)piperidin-1-yl)benzyl)imidazo[1,2-a]pyridine-3-carboxamide (323)

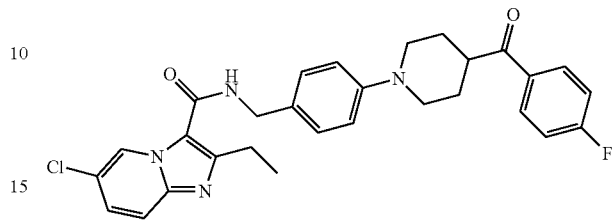

white amorphous (powder); ¹H-NMR (DMSO-d6, Bruker Avance 400 MHz) δ 1.33 (3H, t, J=7.2 Hz), 2.00-2.12 (2H, m), 2.13-2.30 (2H, m), 3.11 (2H, q, J=7.6 Hz), 3.55-3.70 (5H, m), 4.59 (2H, d, J=5.6 Hz), 7.43 (2H, t, J=8.8 Hz), 7.57 (2H, d, J=7.6 Hz), 7.65-7.78 (2H, m), 7.88-7.95 (2H, m), 8.12 (2H, dd, J=8.8, 5.6 Hz), 9.11 (1H, brs), 9.19 (1H, s); LCMS: 100%, MS (ESI): m/z 519 [M+H]+.

6-chloro-2-ethyl-N-(4-(4-(4-(trifluoromethoxy)benzoyl)piperidin-1-yl)benzyl)imidazo[1,2-a]pyridine-3-carboxamide (324)

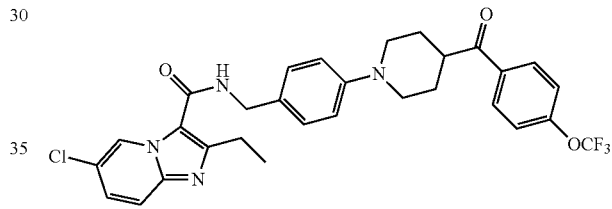

white amorphous (powder); ¹H-NMR (MeOD, Bruker Avance 400 MHz) δ 1.43 (3H, t, J=7.6 Hz), 2.16-2.38 (4H, m), 3.17 (2H, q, J=7.6 Hz), 3.75-3.88 (4H, m), 3.90-4.01 (1H, m), 4.74 (2H, d, J=4.4 Hz), 7.48 (2H, d, J=8.4 Hz), 7.70 (4H, s), 7.89 (1H, d, J=9.6 Hz), 8.00 (1H, dd, J=9.6, 2.0 Hz), 8.22 (2H, d, J=8.8 Hz), 8.95 (1H, t, J=5.6 Hz), 9.31 (1H, s); LCMS: 100%, MS (ESI): m/z 584.8 [M+H]+.

6-chloro-2-ethyl-N-(4-(4-(2-(4-fluorophenyl)acetyl) piperidin-1-yl)benzyl)imidazo[1,2-a]pyridine-3-carboxamide (325)

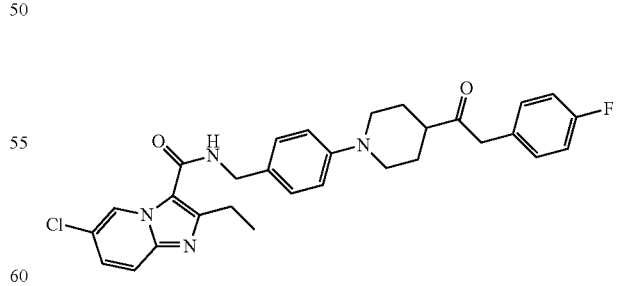

white amorphous (powder); ¹H-NMR (MeOD, Bruker Avance 400 MHz) δ 1.42 (3H, t, J=7.6 Hz), 2.03-2.18 (2H, m), 2.25-2.35 (2H, m), 3.04-3.12 (1H, m), 3.18 (2H, q, J=7.6 Hz), 3.68-3.70 (4H, m), 3.93 (2H, s), 4.72 (2H, d, J=2.8 Hz), 7.06 (2H, t, J=8.8 Hz), 7.23-7.30 (2H, dd, J=8.4, 5.2 Hz), 7.67 (4H, s), 7.93 (1H, d, J=9.6 Hz), 8.08 (1H, dd, J=9.6, 2.0 Hz), 9.05 (1H, t, J=6.0 Hz), 9.32 (1H, d, J=1.2 Hz); LCMS: 100%, MS (ESI): m/z 533.0 [M+H]+.

6-chloro-2-ethyl-N-(4-(1-(4-fluorobenzoyl)piperidin-4-yl)benzyl)imidazo[1,2-a]pyridine-3-carboxamide (326)

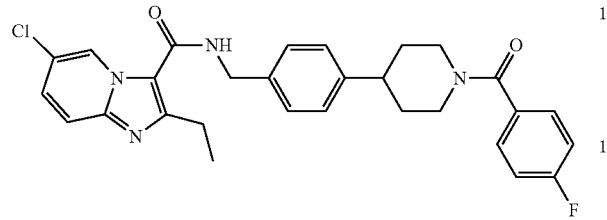

white amorphous (gum); ¹H-NMR (DMSO-d6, Bruker Avance 400 MHz) δ 1.32 (3H, t, J=7.6 Hz), 1.52-1.91 (4H, m), 2.75-2.92 (2H, m), 3.08 (2H, q, J=7.6 Hz), 3.10-3.25 (1H, m), 3.58-3.72 (1H, m), 4.53 (2H, d, J=1.6 Hz), 7.26-7.38 (6H, m), 7.51 (2H, dd, J=8.4, 5.6 Hz), 7.95 (2H, s), 9.09 (1H, t, J=5.6 Hz), 9.19 (1H, s); LC-MS purity: 100%. MS (ESI): m/z 519.1 [M+H]+.

6-chloro-2-ethyl-N-(4-(1-(2-(4-fluorophenyl)acetyl)piperidin-4-yl)benzyl)imidazo[1,2-a]pyridine-3-carboxamide (327)

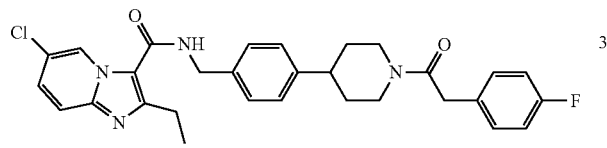

white solid (sticky powder); mp=216.2-220.7° C.; ¹H-NMR (DMSO-d6, Bruker Avance 400 MHz) δ 1.32 (3H, t, J=7.2 Hz), 1.37-1.50 (2H, m), 1.68-1.81 (2H, m), 2.58-2.82 (2H, m), 3.01-3.15 (3H, m), 3.74 (2H, s), 4.03-4.08 (1H, m), 4.51 (2H, d, J=5.6 Hz), 4.54-4.58 (1H, m), 7.11-7.20 (4H, m), 7.24-7.40 (4H, m), 7.950 (2H, s), 9.06 (1H, brs), 9.19 (1H, s); LC-MS purity: 100%. MS (ESI): m/z 533.0 [M+H]+.

6-chloro-2-ethyl-N-(4-(4-hydroxy-4-phenylpiperidin-1-yl)benzyl)imidazo[1,2-a]pyridine-3-carboxamide (328)

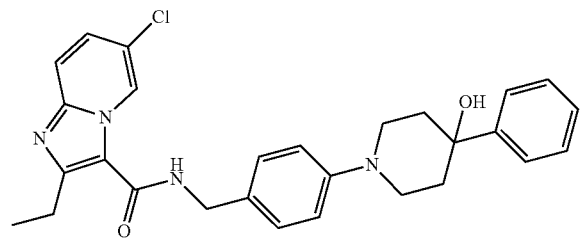 [SMILES: CCc1nc2ccc(Cl)cn2c1C(=O)NCc1ccc(N2CCC(O)(c3ccccc3)CC2)cc1]

white solid (powder); mp=221.5-221.8° C.; ¹H-NMR (DMSO-d6, 400 MHz): δ 0.85 (9H, s). 1.23 (3H, t, J=7.6 Hz), 1.50 (2H, d, J=12.4 Hz), 1.61-1.69 (2H, m), 2.86-2.98 (4H, m), 3.45 (2H, d, J=9.6 Hz), 3.92 (1H, s), 4.40 (2H, d, J=5.6 Hz), 6.89 (2H, d, J=8.8 Hz), 7.19 (2H, d, J=8.4 Hz), 7.44 (1H, dd, J=2.0 Hz, 9.2 Hz), 7.65 (1H, d, J=9.6 Hz), 8.39 (1H, t, J=5.6 Hz), 9.05 (1H, s); LCMS: 97.4%, MS (ESI): m/z 440.2 [M+H]+.

(E)-6-chloro-2-ethyl-N-(4-(4-fluorostyryl)benzyl)imidazo[1,2-a]pyridine-3-carboxamide (329)

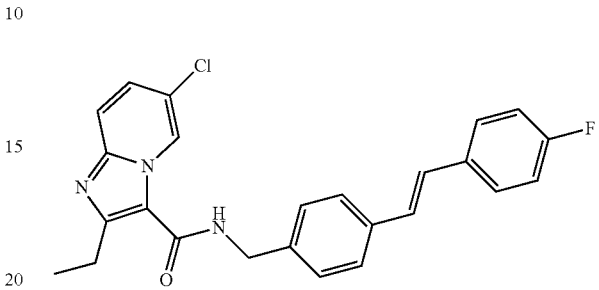

white amorphous (powder); ¹H-NMR (DMSO-d6, 300 MHz): δ 1.23 (3H, t, J=7.5 Hz), 2.97 (2H, q, J=7.5 Hz), 4.50 (2H, d, J=5.7 Hz), 7.10-7.23 (4H, m), 7.34 (2H, d, J=8.1 Hz), 7.43 (1H, dd, J=9.6, 1.5 Hz), 7.50-7.70 (5H, m), 8.48 (1H, t, J=5.7 Hz), 9.04 (1H, s); LCMS: 98.7%, MS (ESI): m/z 433.9 [M+H]+.

(4-(benzyloxy)piperidin-1-yl)(6-chloro-2-ethylimidazo[1,2-a]pyridin-3-yl)methanone

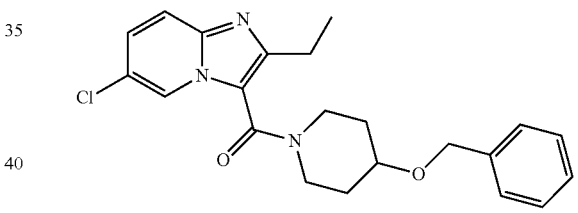

¹H-NMR (CDCl₃, 300 MHz): δ 1.35 (3H, t, J=7.5 Hz), 1.70-1.85 (2H, m), 1.85-2.03 (2H, m), 2.76 (2H, q, J=7.5 Hz), 3.35-3.62 (2H, m), 3.68-3.80 (1H, m), 3.80-4.07 (2H, m), 4.58 (2H, s), 7.20 (1H, dd, J=9.6, 2.1 Hz), 7.28-7.42 (5H, m), 7.51 (1H, d, J=9.6 Hz), 8.47 (1H, s). LCMS: 100%, MS (ESI): m/z 397.8 [M+H]+.

(6-chloro-2-ethylimidazo[1,2-a]pyridin-3-yl)(4-((4-methylbenzyl)oxy)piperidin-1-yl)methanone (331)

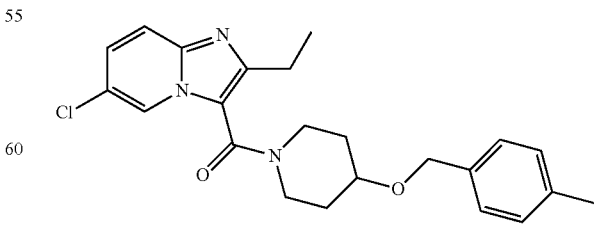

¹H-NMR (CDCl₃, 400 MHz): δ 1.36 (3H, t, J=7.6 Hz), 1.68-2.03 (4H, m), 2.34 (3H, s), 2.76 (2H, q, J=7.6 Hz), 3.32-3.65 (2H, m), 3.65-3.80 (1H, m), 3.80-4.07 (2H, m), 4.54 (2H, s), 7.11-7.35 (5H, m), 7.51 (1H, d, J=9.2 Hz), 8.47 (1H, s). LCMS: 100%, MS (ESI): m/z 411.9 [M+H].

(6-chloro-2-ethylimidazo[1,2-a]pyridin-3-yl)(4-((4-chlorobenzyl)oxy)piperidin-1-yl)methanone (332)

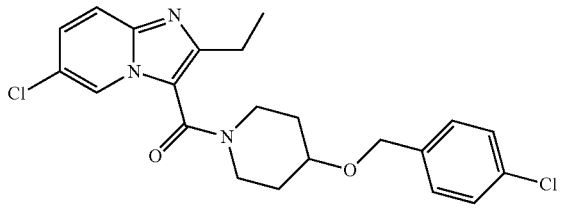 [SMILES: CCc1nc2ccc(Cl)cn2c1C(=O)N1CCC(OCc2ccc(Cl)cc2)CC1]

¹H-NMR (CDCl₃, 400 MHz): δ 1.36 (3H, t, J=7.2 Hz), 1.62-2.08 (4H, m), 2.77 (2H, q, J=7.6 Hz), 3.30-3.65 (2H, m), 3.65-3.80 (1H, m), 3.80-4.08 (2H, m), 4.55 (2H, s), 7.21 (1H, dd, J=9.6, 1.6 Hz), 7.25-7.40 (4H, m), 7.51 (1H, d, J=9.2 Hz), 8.48 (1H, s). LCMS: 100%, MS (ESI): m/z 432.0 [M+H]⁺.

(6-chloro-2-ethylimidazo[1,2-a]pyridin-3-yl)(4-((4-fluorobenzyl)oxy)piperidin-1-yl)methanone (333)

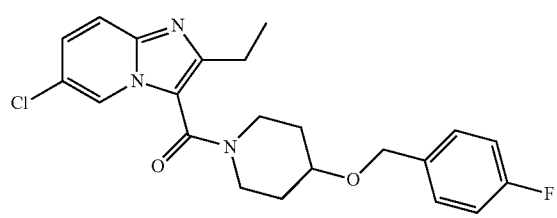 [SMILES: CCc1nc2ccc(Cl)cn2c1C(=O)N1CCC(OCc2ccc(F)cc2)CC1]

¹H-NMR (CDCl₃, 400 MHz): 1.36 (3H, t, J=7.6 Hz), 1.71-1.99 (4H, m), 2.77 (2H, q, J=7.6 Hz), 3.46-3.62 (2H, m), 3.68-3.76 (1H, m), 3.78-4.04 (2H, m), 4.56 (2H, s), 7.05 (2H, t, J=8.8 Hz), 7.22 (1H, dd, J=9.6, 1.6 Hz), 7.31-7.35 (2H, m), 7.51 (1H, d, J=9.2 Hz), 8.48 (1H, s). LCMS: 94.3%, MS (ESI): m/z 415.8 [M+H]⁺.

(6-chloro-2-ethylimidazo[1,2-a]pyridin-3-yl)(4-((4-(trifluoromethyl)benzyl)oxy)piperidin-1-yl)methanone (334)

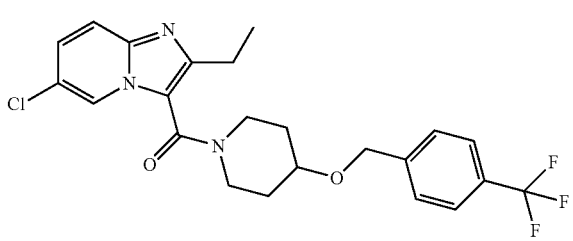 [SMILES: CCc1nc2ccc(Cl)cn2c1C(=O)N1CCC(OCc2ccc(C(F)(F)F)cc2)CC1]

¹H-NMR (CDCl3, 400 MHz): 1.35 (3H, t, J=7.6 Hz), 1.70-2.01 (4H, m), 2.77 (2H, q, J=7.6 Hz), 3.36-3.68 (2H, m), 3.70-3.79 (1H, m), 3.81-4.06 (2H, m), 4.63 (2H, s), 7.21 (1H, dd, J=9.6, 2.0 Hz), 7.42-7.53 (3H, m), 7.60 (2H, d, J=8.0 Hz), 8.48 (1H, s). LCMS: 100%, MS (ESI): m/z 465.9 [M+H]+.

(6-chloro-2-ethylimidazo[1,2-a]pyridin-3-yl)(4-((4-methoxybenzyl)oxy)piperidin-1-yl)methanone (335)

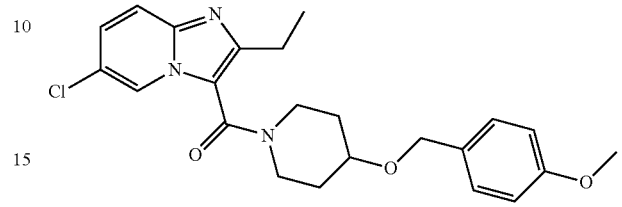

¹H-NMR (CDCl₃, 400 MHz): 1.36 (3H, t, J=7.6 Hz), 1.72-2.05 (4H, m), 2.77 (2H, q, J=7.6 Hz), 3.36-3.62 (2H, m), 3.70-3.79 (1H, m), 3.81 (3H, s), 3.84-4.10 (2H, m), 4.52 (2H, s), 6.89 (2H, d, J=8.4 Hz), 7.19-7.26 (1H, m), 7.28-7.34 (2H, m), 7.52 (1H, d, J=9.6 Hz), 8.48 (1H, s). LCMS: 100%, MS (ESI): m/z 427.9 [M+H]⁺.

(6-chloro-2-ethylimidazo[1,2-a]pyridin-3-yl)(4-((3-fluorobenzyl)oxy)piperidin-1-yl)methanone (336)

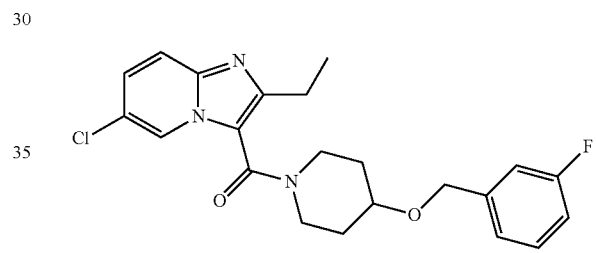

¹H-NMR (CDCl₃, 300 MHz): 1.36 (3H, t, J=7.5 Hz), 1.70-2.10 (4H, m), 2.75 (2H, q, J=7.5 Hz), 3.38-3.63 (2H, m), 3.70-3.80 (1H, m), 3.82-4.02 (2H, m), 4.59 (2H, s), 6.95-7.01 (1H, m), 7.05-7.20 (2H, m), 7.20-7.28 (2H, m), 7.41-7.58 (1H, m), 8.48 (1H, s). LCMS: 100%, MS (ESI): m/z 415.7 [M+H]⁺.

(6-chloro-2-ethylimidazo[1,2-a]pyridin-3-yl)(4-((2-fluorobenzyl)oxy)piperidin-1-yl)methanone (337)

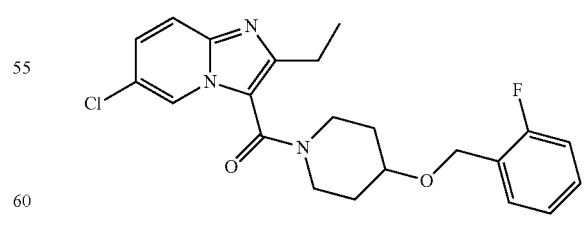

¹H-NMR (CDCl₃, 300 MHz): 1.38 (3H, t, J=7.5 Hz), 1.55-2.10 (4H, m), 2.76 (2H, q, J=7.8 Hz), 3.35-3.68 (2H, m), 3.70-3.78 (1H, m), 3.78-4.10 (2H, m), 4.60 (2H, s), 7.00-7.25 (4H, m), 7.40-7.55 (2H, m), 8.48 (1H, s). LCMS: 100%, MS (ESI): m/z 415.8 [M+H]⁺.

151

1-(6-chloro-2-ethylimidazo[1,2-a]pyridin-3-yl)-N-(4-fluorobenzyl)methanamine (338)

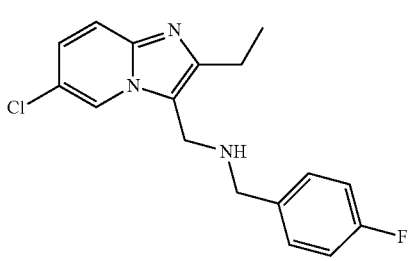 [SMILES: CCc1nc2ccc(Cl)cn2c1CNCc1ccc(F)cc1]

$^1$H-NMR (MeOD, 400 MHz): 1.28 (3H, t, J=7.6 Hz), 2.72 (2H, q, J=7.6 Hz), 3.76 (2H, s), 4.07 (2H, s), 7.02 (2H, t, J=8.8 Hz), 7.23-7.35 (3H, m), 7.44 (1H, d, J=9.2 Hz), 8.43 (1H, d, J=1.2 Hz). LCMS: 99.6%, MS (ESI): m/z 317.9[M+H]$^+$.

4-((((6-chloro-2-ethylimidazo[1,2-a]pyridin-3-yl)methyl)amino)methyl)-N,N-dimethylaniline (339)

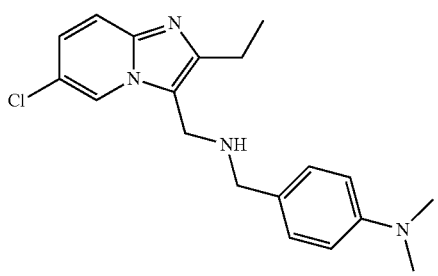 [SMILES: CCc1nc2ccc(Cl)cn2c1CNCc1ccc(N(C)C)cc1]

$^1$H-NMR (DMSO-d$_6$, 400 MHz): 1.32 (3H, t, J=6.8 Hz), 2.90-3.05 (8H, m), 4.24 (2H, s), 4.73 (2H, s), 6.80-7.15 (1H, m), 7.40-7.60 (2H, m), 7.90-8.10 (2H, m), 9.45 (1H, s), 9.70-10.0 (2H, m). LCMS: 98.1%, MS (ESI): m/z 342.9[M+H]$^+$.

1-(4-(((((6-chloro-2-ethylimidazo[1,2-a]pyridin-3-yl)methyl)amino)methyl)phenyl)piperidin-4-ol (340)

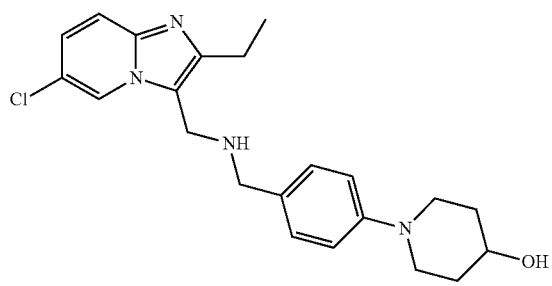 [SMILES: CCc1nc2ccc(Cl)cn2c1CNCc1ccc(N2CCC(O)CC2)cc1]

$^1$H-NMR (MeOD, 400 MHz): 1.29 (3H, t, J=7.6 Hz), 1.61-1.72 (2H, m), 1.94-2.02 (2H, m), 2.73 (2H, q, J=7.6 Hz), 2.85-2.94 (2H, m), 3.53-3.62 (2H, m), 3.72-3.80 (3H, m), 4.12 (2H, s), 6.98 (2H, d, J=8.4 Hz), 7.22 (2H, d, J=8.8 Hz), 7.30 (1H, dd, J=9.6, 2.0 Hz), 7.46 (1H, d, J=9.6 Hz), 8.35 (1H, d, J=1.2 Hz). LCMS: 100%, MS (ESI): m/z 398.9[M+H]$^+$.

152

N-(4-(4-(benzyloxy)piperidin-1-yl)benzyl)-1-(6-chloro-2-ethylimidazo[1,2-a]pyridin-3-yl)methanamine (341)

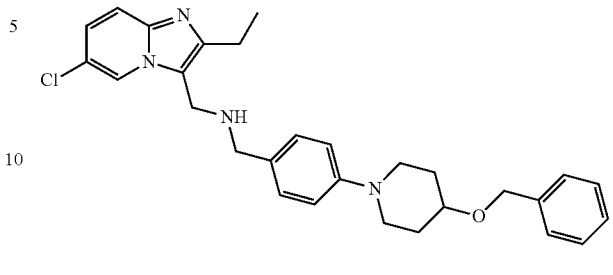

$^1$H-NMR (DMSO-d$_6$, 400 MHz): 1.30 (3H, t, J=7.2 Hz), 1.58-1.70 (2H, m), 1.94-2.10 (2H, m), 2.90-2.99 (2H, q, J=7.2 Hz), 3.00-3.15 (2H, m), 3.68-3.72 (1H, m), 4.23 (2H, s), 4.55 (2H, s), 4.71 (2H, s), 7.06-7.18 (1H, m), 7.25-7.31 (1H, m), 7.32-7.40 (4H, m), 7.40-7.55 (2H, m), 7.86-7.97 (2H, m), 9.35 (1H, s), 9.66 (1H, s). LCMS: 99.7%, MS (ESI): m/z 489.1[M+H]$^+$.

N-((6-chloro-2-ethylimidazo[1,2-a]pyridin-3-yl)methyl)-2-(pyridin-2-yl)ethanamine (342)

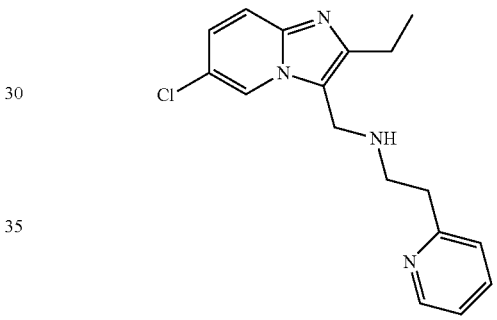

$^1$H-NMR (DMSO-d$_6$, 400 MHz): 1.33 (3H, t, J=7.6 Hz), 3.04 (2H, q, J=7.6 Hz), 3.45-3.52 (2H, m), 3.55-3.60 (2H, m), 4.79 (2H, s), 7.71 (1H, t, J=6.0 Hz), 7.82 (1H, d, J=8.4 Hz), 7.97 (1H, d, J=9.2 Hz), 8.03 (2H, d, J=9.6 Hz), 8.26 (1H, t, J=7.6 Hz), 8.71 (1H, d, J=5.2 Hz), 9.57 (1H, s), 10.14 (2H, brs). LCMS: 100%, MS (ESI): m/z 315.2[M+H]$^+$.

N-((6-chloro-2-ethylimidazo[1,2-a]pyridin-3-yl)methyl)-2-(pyridin-3-yl)ethanamine (343)

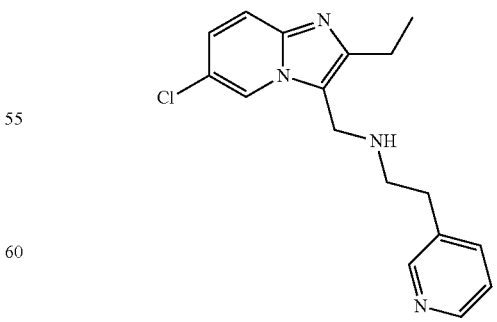

$^1$H-NMR (DMSO-d6, 400 MHz): 1.31 (3H, t, J=7.6 Hz), 2.98-3.18 (2H, q, J=7.6 Hz), 3.28-3.35 (2H, m), 3.42-3.50 (2H, m), 4.73 (2H, s), 7.89-8.11 (3H, m), 8.51 (1H, d, J=7.6

Hz), 8.81 (1H, d, J=5.2 Hz), 8.90 (1H, s), 10.11 (2H, brs). LCMS: 100%, MS (ESI): m/z 315.1[M+H]+.

N-((6-chloro-2-ethylimidazo[1,2-a]pyridin-3-yl)methyl)-2-(pyridin-4-yl)ethanamine (344)

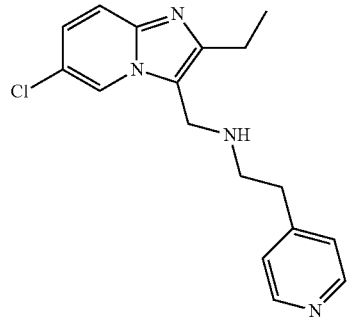 [SMILES: CCc1nc2ccc(Cl)cn2c1CNCCc1ccncc1]

$^{1}$H-NMR (DMSO-d$_{6}$, 400 MHz): 1.32 (3H, t, J=7.6 Hz), 3.04 (2H, q, J=7.6 Hz), 3.36-3.45 (2H, m), 3.46-3.56 (2H, m), 4.75 (2H, s), 7.92-8.08 (4H, m), 8.88 (2H, d, J=6.0 Hz), 9.58 (1H, s), 10.24 (2H, brs). LCMS: 100%, MS (ESI): m/z 315.2 [M+H]$^{+}$.

1-Benzyl-N-((6-chloro-2-ethylimidazo[1,2-a]pyridin-3-yl)methyl)pyrrolidin-3-amine (345)

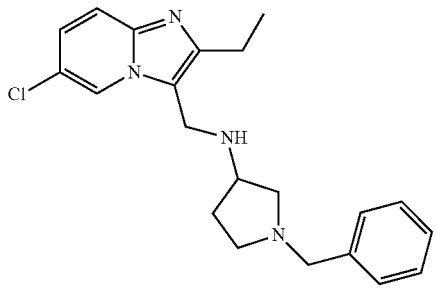 [SMILES: CCc1nc2ccc(Cl)cn2c1CNC1CCN(Cc2ccccc2)C1]

$^{1}$H-NMR (DMSO-d$_{6}$, 400 MHz): 1.24 (3H, t, J=7.6 Hz), 2.73-2.81 (2H, m), 3.51-3.63 (2H, m), 3.65-3.90 (2H, m), 3.99-4.31 (2H, m), 4.38-4.70 (3H, m), 7.30-7.70 (7H, m), 8.80-9.05 (1H, m), 9.35-10.15 (1H, m), 10.90-11.70 (1H, m). LCMS: 100%, MS (ESI): m/z 369.0[M+H]$^{+}$.

N-(4-(1,4-dioxa-8-azaspiro[4.5]decan-8-yl)benzyl)-1-(6-chloro-2-ethylimidazo[1,2-a]pyridin-3-yl)methanamine (346)

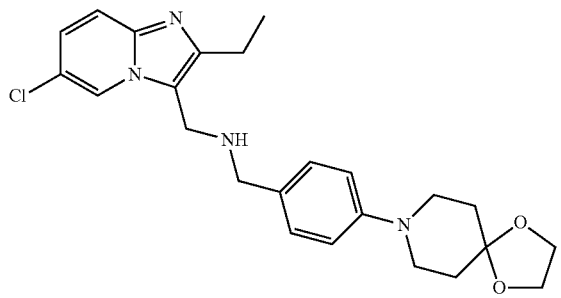 [SMILES: CCc1nc2ccc(Cl)cn2c1CNCc1ccc(N2CCC3(CC2)OCCO3)cc1]

$^{1}$H-NMR (DMSO-d6, 400 MHz): 1.30 (3H, t, J=7.6 Hz), 1.60-1.88 (4H, m), 2.97 (2H, q, J=7.6 Hz), 3.30-3.40 (4H, m), 3.90 (4H, s), 4.22 (2H, s), 4.71 (2H, s), 7.00-7.26 (2H, m), 7.49 (2H, d, J=7.6 Hz), 7.90-8.15 (2H, m), 9.46 (1H, s), 9.84 (2H, brs). LCMS: 99.6%, MS (ESI): m/z 441.0[M+H]+.

6-chloro-2-ethyl-3-((4-((4-(trifluoromethoxy)benzyl)oxy)piperidin-1-yl)methyl)imidazo[1,2-a]pyridine (347)

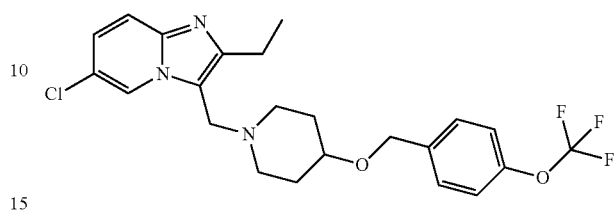

$^{1}$H-NMR (DMSO-d$_{6}$, 400 MHz): δ1.30 (3H, t, J=7.6 Hz), 1.75-1.90 (1H, m), 1.98-2.10 (2H, m), 2.12-2.18 (1H, m), 2.99 (2H, q, J=7.6 Hz), 3.06-3.21 (2H, m), 3.22-3.28 (2H, m), 3.74-3.81 (1H, m), 4.55 (2H, s), 4.70-4.84 (2H, m), 7.32-7.37 (2H, m), 7.44 (1H, d, J=8.0 Hz), 7.53 (1H, d, J=8.4 Hz), 7.90 (2H, s), 9.48 (1H, s), 11.10 (1H, brs). LCMS: 100%, MS (ESI): m/z 468.0 [M+H]$^{+}$.

2-(7-chloro-2-ethylimidazo[1,2-a]pyridin-3-yl)-5-(4-fluorobenzyl)-1,3,4-oxadiazole (348)

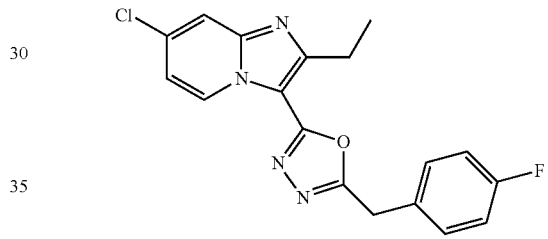

$^{1}$H-NMR (DMSO-d$_{6}$, Bruker Avance 400 MHz): δ 1.22 (3H, t, J=7.6 Hz), 2.97 (2H, q, J=7.6 Hz), 4.42 (2H, s), 7.21 (2H, t, J=8.8 Hz), 7.45 (2H, dd, J=8.4, 5.6 Hz), 7.60 (1H, dd, J 9.6, 2.0 Hz), 7.80 (1H, d, J=9.6 Hz), 7.28 (1H, d, J=1.6 Hz). LCMS: 99.1%, MS (ESI): m/z 482.9 [M+Na]$^{+}$.

6-chloro-2-ethyl-3-((4-(4-fluorophenethyl)piperidin-1-yl)methyl)imidazo[1,2-a]pyridine (349)

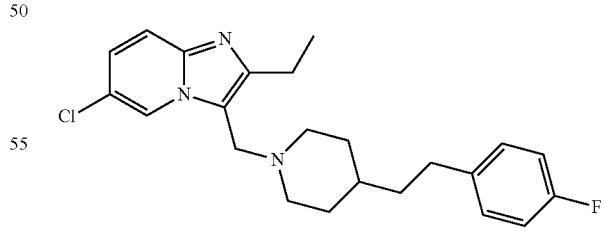

$^{1}$H-NMR (DMSO-d$_{6}$, 400 MHz): 1.34 (3H, t, J=7.6 Hz), 1.45-1.60 (5H, m), 1.87 (2H, d, J=12.8 Hz), 2.59 (2H, t, J=7.6 Hz), 3.00-3.09 (4H, m), 3.55 (2H, d, J=11.2 Hz), 4.81 (2H, d, J=4.8 Hz), 7.09 (2H, t, J=9.2 Hz), 7.23-7.27 (2H, dd, J=6.0 Hz, J=8.8 Hz), 7.98 (1H, d, J=9.2 Hz), 8.03 (1H, d, J=9.6 Hz), 9.60 (1H, s), 11.04 (1H, s). LCMS: 98.1%, MS (ESI): m/z 399.9[M+H]$^{+}$.

(6-chloro-2-ethylimidazo[1,2-a]pyridin-3-yl)(4-((4-(1,1,1-trifluoro-2-hydroxybutan-2-yl)-1H-1,2,3-triazol-1-yl)methyl)piperidin-1-yl)methanone (350)

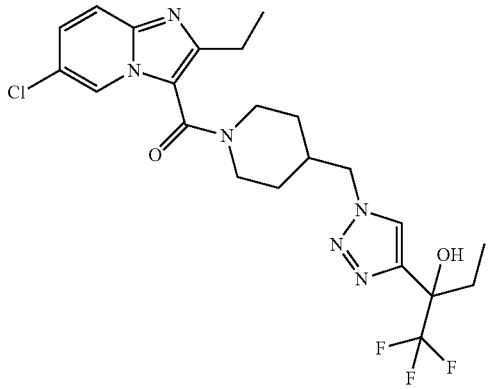 [SMILES: CCc1nc2ccc(Cl)cn2c1C(=O)N1CCC(Cn2cc(C(O)(CC)C(F)(F)F)nn2)CC1]

¹H-NMR (CDCl₃, Bruker Avance 400 MHz): δ 0.85 (3H, t, J=7.2 Hz), 1.20-1.30 (2H, m), 1.37 (3H, t, J=7.2 Hz), 1.68-1.70 (2H, m), 1.95-2.20 (2H, m), 2.25-2.40 (1H, m), 2.76 (2H, q, J=7.6 Hz), 2.85-3.15 (2H, m), 3.82-3.96 (1H, m), 4.20-4.40 (4H, m), 7.20-7.27 (1H, m), 7.45-7.55 (2H, m), 8.40-8.60 (1H, m). LCMS: 100%, MS (ESI): m/z 499.0 [M+H]+.

2-(1-((1-((2-ethylimidazo[1,2-a]pyridin-3-yl)methyl)piperidin-4-yl)methyl)-1H-1,2,3-triazol-4-yl)-1,1,1-trifluorobutan-2-ol (351)

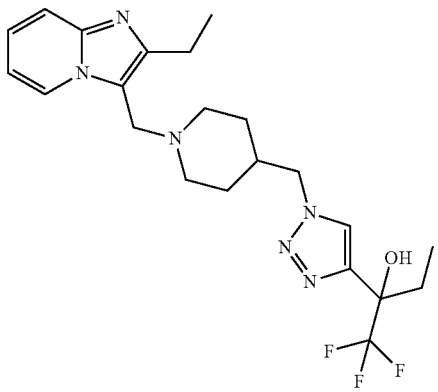 [SMILES: CCc1nc2ccccn2c1CN1CCC(Cn2cc(C(O)(CC)C(F)(F)F)nn2)CC1]

¹H-NMR (CDCl₃, Bruker Avance 400 MHz): δ 0.83 (3H, t, J=7.2 Hz), 1.30-1.39 (2H, m), 1.39 (3H, t, J=7.6 Hz), 1.56-1.62 (2H, m), 1.98-2.15 (5H, m), 2.81-2.90 (4H, m), 3.82 (2H, s), 3.90-4.10 (1H, m), 4.26 (2H, d, J=7.6 Hz), 7.08 (1H, t, J=6.0 Hz), 7.49 (1H, s), 7.49-7.56 (1H, m), 8.00 (1H, d, J=8.4 Hz), 8.43 (1H, d, J=6.8 Hz). LCMS: 100%, MS (ESI): m/z 451.0 [M+H]⁺.

6-chloro-2-ethyl-N-(3-(methyl(4-(trifluoromethoxy)benz)amino)benzyl)imidazo[1,2-a]pyridine-3-carboxamide (352)

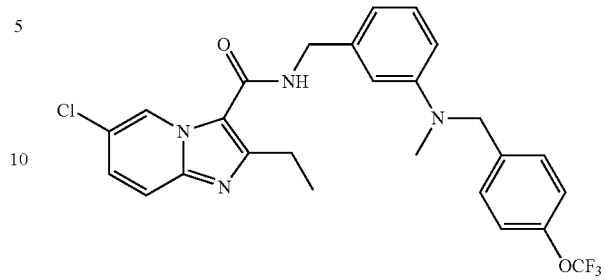

white power; mp>142.3° C., decomposed; ¹H-NMR (DMSO-d6, 400 MHz): 1.23 (3H, t, J=7.6 Hz), 2.94 (2H, q, J=7.6 Hz), 2.97 (3H, s), 4.45 (2H, d, J=6.0 Hz), 4.59 (2H, s), 6.60-6.70 (2H, m), 6.76 (1H, s), 7.12 (1H, t, J=8.0 Hz), 7.24 (2H, d, J=8.4 Hz), 7.29 (2H, d, J=8.8 Hz), 7.45 (1H, dd, J=9.2, 2.0 Hz), 7.66 (1H, d, J=9.6 Hz), 8.43 (1H, t, J=6.0 Hz), 9.04 (1H, d, J=1.2 Hz); LCMS: 98.6%, MS (ESI): m/z 517.0 [M+H]⁺.

6-chloro-2-ethyl-N-(3-((4-(trifluoromethoxy)benzyl)oxy)benzyl)imidazo[1,2-a]pyridine-3-carboxamide (353)

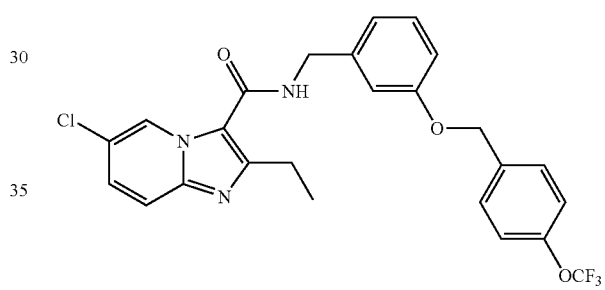

white powder; mp>142.7° C., decomposed; ¹H-NMR (DMSO-d6, 400 MHz): 1.26 (3H, t, J=7.6 Hz), 2.99 (2H, q, J=7.6 Hz), 4.51 (2H, d, J=5.6 Hz), 5.14 (2H, s), 6.90 (1H, dd, J=8.4, 2.0 Hz), 6.94 (1H, d, J=7.6 Hz), 7.03 (1H, s), 7.27 (1H, t, J=8.0 Hz), 7.35 (2H, d, J=8.0 Hz), 7.45 (1H, dd, J=9.2, 2.0 Hz), 7.56 (2H, d, J=8.8 Hz), 7.67 (1H, d, J=9.6 Hz), 8.47 (1H, t, J=5.6 Hz), 9.07 (1H, d, J=1.2 Hz); LCMS: 96.1%, MS (ESI): m/z 504.1[M+H]+.

6-chloro-2-ethyl-N-(3-(4-(4-(trifluoromethoxy)phenyl)piperidin-1-yl)benzyl)imidazo[1,2-a]pyridine-3-carboxamide (354)

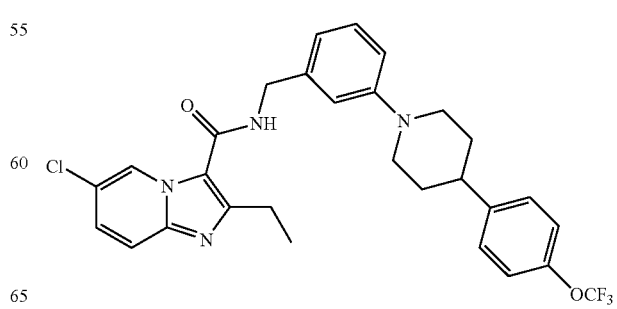

white solid; mp=135.5-136.4° C.; $^1$H-NMR (DMSO-d6, 400 MHz): 1.26 (3H, t, J=7.6 Hz), 1.69-1.79 (2H, m), 1.80-1.90 (2H, m), 2.70-2.80 (3H, m), 2.99 (2H, q, J=7.6 Hz), 3.75-3.85 (2H, m), 4.49 (2H, d, J=6.0 Hz), 6.78 (1H, d, J=7.6 Hz), 6.88 (1H, d, J=8.0 Hz), 7.01 (1H, s), 7.19 (1H, t, J=8.0 Hz), 7.28 (2H, d, J=8.0 Hz), 7.39-7.47 (3H, m), 7.66 (1H, d, J=9.6 Hz), 8.51 (1H, t, J=6.0 Hz), 9.03 (1H, d, J=1.2 Hz); LCMS: 100%, MS (ESI): m/z 557.0 [M+H]+.

6-chloro-2-ethyl-N-(3-(2-((4-fluorophenyl)amino)-2-oxoethyl)benzyl)imidazo[1,2-a]pyridine-3-carboxamide (355)

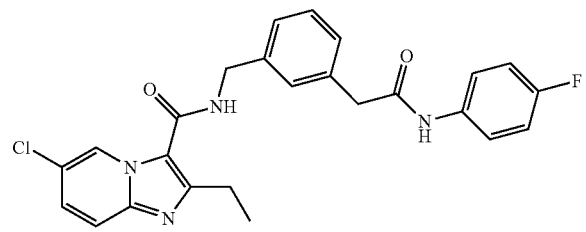 [SMILES: CCc1nc2ccc(Cl)cn2c1C(=O)NCc1cccc(CC(=O)Nc2ccc(F)cc2)c1]

white amorphous; mp>198.8° C., decomposed; $^1$H-NMR (DMSO-d6, 400 MHz): 1.24 (3H, t, J=7.2 Hz), 2.98 (2H, q, J=7.6 Hz), 3.62 (2H, s), 4.53 (2H, d, J=6.0 Hz), 7.09 (2H, t, J=9.2 Hz), 7.10~7.35 (4H, m), 7.46 (1H, dd, J=9.2, 2.0 Hz), 7.58 (2H, dd, J=9.5, 5.2 Hz), 7.66 (1H, d, J=9.2 Hz), 8.50 (1H, brs, J=6.0 Hz), 9.07 (1H, d, J=1.6 Hz), 10.21 (1H, brs); LCMS: 99%, MS (ESI): m/z 465.1 [M+H]+.

6-chloro-2-ethyl-N-(3-(4-(4-(trifluoromethoxy)phenyl)piperazin-1-yl)benzyl)imidazo[1,2-a]pyridine-3-carboxamide (356)

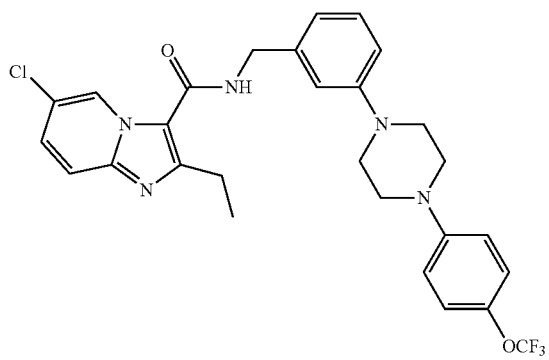 [SMILES: CCc1nc2ccc(Cl)cn2c1C(=O)NCc1cccc(N2CCN(c3ccc(OC(F)(F)F)cc3)CC2)c1]

white amorphous; mp>168.0° C., decomposed; $^1$H-NMR (DMSO-d6, 400 MHz): 1.27 (3H, t, J=7.6 Hz), 3.00 (2H, q, J=7.2 Hz), 3.20-3.30 (8H, m), 4.50 (2H, d, J=6.0 Hz), 4.50 (2H, d, J=6.0 Hz), 6.83 (1H, d, J=7.6 Hz), 6.91 (1H, d, J=8.4 Hz), 7.02 (1H, s), 7.07 (2H, d, J=8.8 Hz), 7.20-7.26 (3H, m), 7.45 (1H, dd, J=9.6, 2.0 Hz), 8.50 (1H, t, J=6.0 Hz), 9.04 (1H, d, J=1.6 Hz); LCMS: 95.2%, MS (ESI): m/z 580.1 [M+Na]+.

2-ethyl-N-(4-((tetrahydro-2H-pyran-4-yl)methyl)benzyl)imidazo[1,2-a]pyridine-3-carboxamide (357)

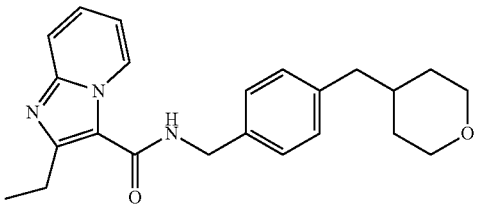 [SMILES: CCc1nc2ccccn2c1C(=O)NCc1ccc(CC2CCOCC2)cc1]

Gum; $^1$H-NMR (CDCl$_3$, 400 MHz): 1.20-1.40 (2H, m), 1.41 (3H, t, J=7.2 Hz), 1.50-1.59 (2H, m), 1.68-1.82 (1H, m), 2.55 (2H, d, J=6.8 Hz), 2.99 (2H, q, J=7.6 Hz), 3.28-3.38 (2H, m), 3.90-4.00 (2H, m), 4.68 (2H, d, J=5.2 Hz), 6.08 (1H, brs), 6.92 (1H, t, J=6.8 Hz), 7.15 (2H, d, J=8.0 Hz), 7.26-7.40 (3H, m), 7.61 (1H, d, J=8.8 Hz), 9.41 (1H, d, J=6.8 Hz); LCMS: 98.96%, MS (ESI): m/z 377.8 [M+H]+.

6-chloro-2-ethyl-N-(4-((tetrahydro-2H-pyran-4-yl)methyl)benzyl)imidazo[1,2-a]pyridine-3-carboxamide (358)

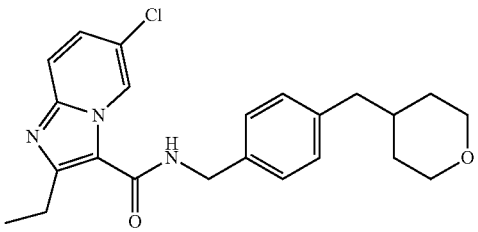 [SMILES: CCc1nc2ccc(Cl)cn2c1C(=O)NCc1ccc(CC2CCOCC2)cc1]

white solid; mp=132.2-133.0° C.; $^1$H-NMR (CDCl3, 400 MHz): 1.25-1.40 (2H, m), 1.44 (3H, t, J=7.6 Hz), 1.52-1.59 (2H, m), 1.70-1.85 (1H, m), 2.57 (2H, d, J=7.2 Hz), 3.00 (2H, q, J=7.6 Hz), 3.30-3.40 (2H, m), 3.90-4.00 (2H, m), 4.69 (2H, d, J=5.6 Hz), 6.11 (1H, brs), 7.18 (2H, d, J=8.0 Hz), 7.30-7.40 (3H, m), 7.57 (1H, d, J=9.6 Hz), 9.56 (1H, d, J=1.6 Hz); LCMS: 100%, MS (ESI): m/z 411.8 [M+H]+.

7-chloro-2-ethyl-N-(4-((tetrahydro-2H-pyran-4-yl)methyl)benzyl)imidazo[1,2-a]pyridine-3-carboxamide (359)

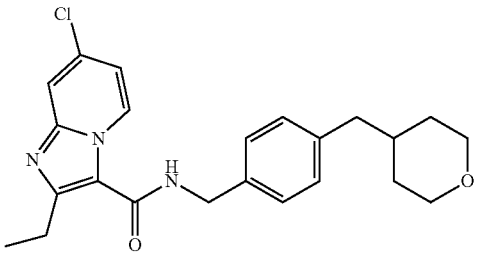 [SMILES: CCc1nc2cc(Cl)ccn2c1C(=O)NCc1ccc(CC2CCOCC2)cc1]

white amorphous; mp>125.9° C., decomposed; $^1$H-NMR (CDCl3, 400 MHz): 1.20-1.40 (2H, m), 1.40 (3H, t, J=7.2 Hz), 1.50-1.60 (2H, m), 1.68-1.83 (1H, m), 2.56 (2H, d, J=7.2 Hz), 2.97 (2H, q, J=7.6 Hz), 3.28-3.40 (2H, m), 3.90-4.00

(2H, m), 4.67 (2H, d, J=5.6 Hz), 6.08 (1H, brs), 6.91 (1H, dd, J=7.6, 2.0 Hz), 7.15 (2H, d, J=8.0 Hz), 7.26-7.38 (2H, m), 7.59 (1H, d, J=1.6 Hz), 9.36 (1H, d, J=7.2 Hz); LCMS: 99.86%, MS (ESI): m/z 411.7 [M+H]+.

6-chloro-2-ethyl-N-(3-(4-(4-(trifluoromethoxy)phenoxy)piperidin-1-yl)benzyl)imidazo[1,2-a]pyridine-3-carboxamide (360)

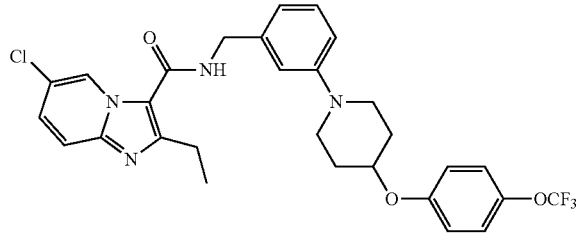 [SMILES: CCc1nc2ccc(Cl)cn2c1C(=O)NCc1cccc(N2CCC(Oc3ccc(OC(F)(F)F)cc3)CC2)c1]

yellow solid; mp=126.3-127.2° C.; ¹H-NMR (DMSO-d6, 400 MHz): 1.24 (3H, t, J=7.6 Hz), 1.65-1.73 (2H, m), 1.95-2.05 (2H, m), 2.97 (2H, t, J=7.2 Hz), 3.00-3.07 (2H, m), 3.45-3.55 (2H, m), 4.47 (2H, d, J=6.0 Hz), 4.55-4.59 (1H, m), 6.76 (1H, d, J=7.2 Hz), 6.84-6.86 (1H, m), 6.97 (1H, s), 7.06 (2H, d, J=9.2 Hz), 7.17 (1H, t, J=8.0 Hz), 7.26 (2H, d, J=8.8 Hz), 7.41-7.44 (1H, dd, J=9.6, 2.0 Hz), 7.64 (1H, d, J=9.2 Hz), 8.49 (1H, t, J=5.6 Hz), 9.01 (1H, d, J=1.6 Hz); LCMS: 96.4%, MS (ESI): m/z 573.1 [M+H]+.

6-chloro-N-((5-chlorobenzo[b]thiophen-2-yl)methyl)-2-ethylimidazo[1,2-a]pyridine-3-carboxamide (361)

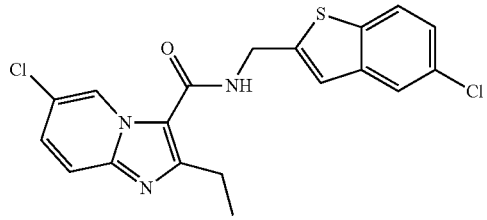 [SMILES: CCc1nc2ccc(Cl)cn2c1C(=O)NCc1cc2cc(Cl)ccc2s1]

white solid; mp>220° C.; ¹H-NMR (DMSO-d6, 400 MHz): 1.28 (3H, t, J=7.6 Hz), 3.00 (2H, q, J=7.6 Hz), 4.79 (2H, d, J=5.6 Hz), 7.33 (1H, dd, J=8.4, 2.0 Hz), 7.37 (1H, s), 7.48 (1H, dd, J=9.6, 2.0 Hz), 7.68 (1H, d, J=9.2 Hz), 7.90 (1H, d, J=2.0 Hz), 7.96 (1H, d, J=8.4 Hz), 8.70 (1H, t, J=5.6 Hz), 9.12 (1H, d, J=1.6 Hz); LCMS: 95.4%, MS (ESI): m/z 404.0 [M+H]+.

2-ethyl-N-(4-(tetrahydro-2H-pyran-4-yl)benzyl)imidazo[1,2-a]pyridine-3-carboxamide (362)

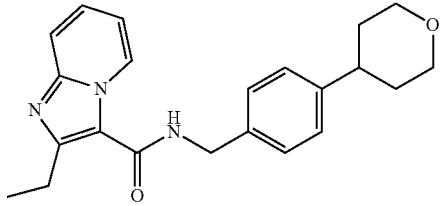 [SMILES: CCc1nc2ccccn2c1C(=O)NCc1ccc(C2CCOCC2)cc1]

White amorphous; mp>133.7° C., decomposed; ¹H-NMR (CDCl3, 400 MHz): 1.42 (3H, t, J=7.6 Hz), 1.72-1.90 (4H, m), 2.70-2.82 (1H, m), 3.00 (2H, q, J=7.6 Hz), 3.53 (2H, td, J=11.6, 2.8 Hz), 3.93 (2H, dd, J=10.8, 2.8 Hz), 4.68 (2H, d, J=6.0 Hz), 6.09 (1H, brs), 6.90-6.95 (1H, m), 7.21-7.30 (2H, m), 7.30-7.40 (3H, m), 7.61 (1H, d, J=9.2 Hz), 9.41 (1H, d, J=7.2 Hz); LCMS: 99.27%, MS (ESI): m/z 364.1 [M+H]+.

6-chloro-2-ethyl-N-(4-(tetrahydro-2H-pyran-4-yl)benzyl)imidazo[1,2-a]pyridine-3-carboxamide (363)

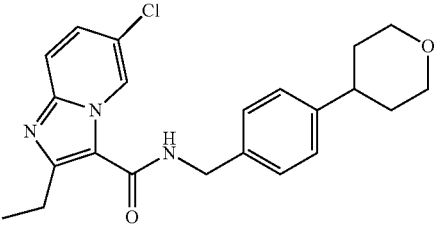 [SMILES: CCc1nc2ccc(Cl)cn2c1C(=O)NCc1ccc(C2CCOCC2)cc1]

White amorphous; mp>195.5° C., decomposed; ¹H-NMR (CDCl3, 400 MHz): 1.41 (3H, t, J=7.6 Hz), 1.71-1.90 (4H, m), 2.72-2.84 (1H, m), 2.98 (2H, q, J=7.2 Hz), 3.53 (2H, td, J=11.6, 2.8 Hz), 4.08 (2H, dd, J=11.2, 3.6 Hz), 4.68 (2H, d, J=5.6 Hz), 6.10 (1H, brs), 7.20-7.28 (2H, m), 7.28-7.49 (3H, m), 7.54 (1H, d, J=9.6 Hz), 9.54 (1H, d, J=1.6 Hz); LCMS: 100%, MS (ESI): m/z 398.1 [M+H]+.

7-chloro-2-ethyl-N-(4-(tetrahydro-2H-pyran-4-yl)benzyl)imidazo[1,2-a]pyridine-3-carboxamide (364)

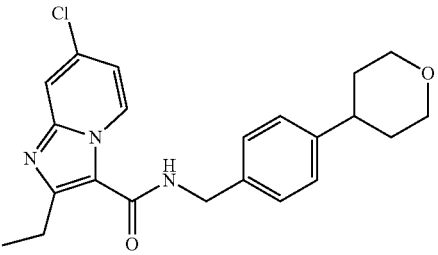 [SMILES: CCc1nc2cc(Cl)ccn2c1C(=O)NCc1ccc(C2CCOCC2)cc1]

White amorphous; mp>156.6° C., decomposed; ¹H-NMR (CDCl3, 400 MHz): 1.40 (3H, t, J=7.6 Hz), 1.71-1.90 (4H, m), 2.72-2.84 (1H, m), 2.97 (2H, q, J=7.6 Hz), 3.53 (2H, td, J=11.6, 2.8 Hz), 4.05-4.15 (2H, m), 4.67 (2H, d, J=6.0 Hz), 6.09 (1H, brs), 6.91 (1H, dd, J=7.6, 2.4 Hz), 7.23-7.26 (2H, m), 7.33 (2H, d, J=8.0 Hz), 7.59 (1H, d, J=2.0 Hz), 9.36 (1H, d, J=7.2 Hz); LCMS: 100%, MS (ESI): m/z 398.1 [M+H]+.

6-chloro-N-((6-chloro-1H-benzo[d]imidazol-2-yl)methyl)-2-ethylimidazo[1,2-a]pyridine-3-carboxamide (365)

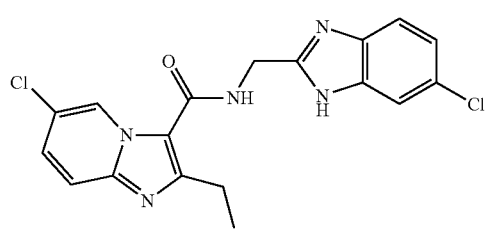 [SMILES: CCc1nc2ccc(Cl)cn2c1C(=O)NCc1nc2ccc(Cl)cc2[nH]1]

yellow amorphous; ¹H-NMR (DMSO-d6, 400 MHz): 1.31 (3H, t, J=7.6 Hz), 3.03 (2H, q, J=7.6 Hz), 4.76 (2H, s), 7.18 (1H, dd, J=8.4, 2.0 Hz), 7.45-7.55 (2H, m), 7.56 (1H, d, J=2.0

Hz), 7.68-7.70 (1H, m), 8.57 (1H, brs), 9.24 (1H, d, J=1.6 Hz); LCMS: 100%, MS (ESI): m/z 388.1[M+H]+.

6-chloro-N-((5-chlorobenzofuran-2-yl)methyl)-2-ethylimidazo[1,2-a]pyridine-3-carboxamide (366)

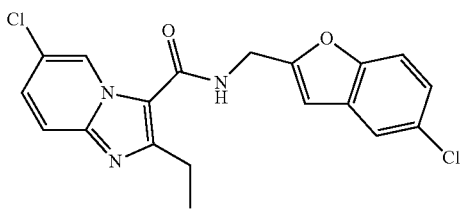 [SMILES: CCc1nc2ccc(Cl)cn2c1C(=O)NCc1cc2cc(Cl)ccc2o1]

white solid; mp=223.5-225.6° C.; ¹H-NMR (DMSO-d6, 400 MHz): 1.27 (3H, t, J=7.6 Hz), 3.00 (2H, q, J=7.2 Hz), 4.70 (2H, d, J=5.6 Hz), 6.81 (1H, s), 7.29 (1H, dd, J=8.8, 2.4 Hz), 7.47 (1H, dd, J=9.6, 2.0 Hz), 7.58 (1H, d, J=8.4 Hz), 7.68 (2H, dd, J=5.6, 3.6 Hz), 8.59 (1H, t, J=5.2 Hz), 9.08 (1H, d, J=1.6 Hz); LCMS: 99.3%, MS (ESI): m/z 387.8 [M+H]+.

6-chloro-N-((6-chloro-1-methyl-1H-benzo[d]imidazol-2-yl)methyl)-2-ethylimidazo[1,2-a]pyridine-3-carboxamide (367)

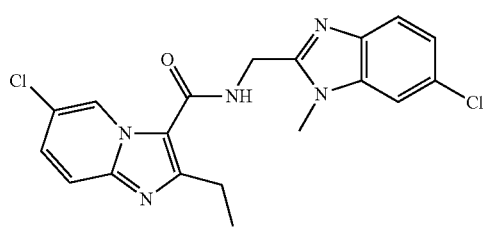 [SMILES: CCc1nc2ccc(Cl)cn2c1C(=O)NCc1nc2ccc(Cl)cc2n1C]

white solid; mp>220° C.; ¹H-NMR (DMSO-d6, 400 MHz): 1.29 (3H, t, J=7.6 Hz), 3.00 (2H, q, J=7.6 Hz), 3.85 (3H, s), 4.84 (2H, d, J=5.6 Hz), 7.21 (1H, dd, J=8.4, 2.0 Hz), 7.47 (1H, dd, J=9.2, 2.0 Hz), 7.59 (1H, d, J=8.8 Hz), 7.68 (1H, d, J=9.6 Hz), 7.74 (1H, d, J=2.0 Hz), 8.65 (1H, t, J=5.6 Hz), 9.26 (1H, d, J=1.6 Hz); LCMS: 100%, MS (ESI): m/z 402.0 [M+H]+.

6-chloro-N-((5-chloro-1-methyl-1H-benzo[d]imidazol-2-yl)methyl)-2-ethylimidazo[1,2-a]pyridine-3-carboxamide (368)

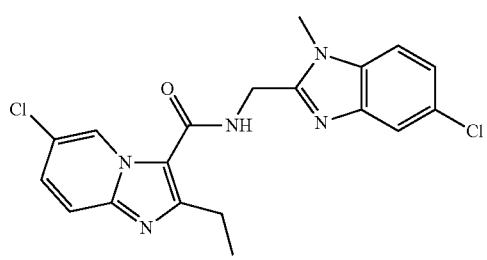 [SMILES: CCc1nc2ccc(Cl)cn2c1C(=O)NCc1nc2cc(Cl)ccc2n1C]

white solid; mp>220° C.; ¹H-NMR (DMSO-d6, 400 MHz): 1.28 (3H, t, J=7.6 Hz), 3.01 (2H, q, J=7.6 Hz), 3.86 (3H, s), 4.84 (2H, d, J=5.6 Hz), 7.28 (1H, dd, J=8.4, 2.0 Hz), 7.47 (1H, dd, J=9.2, 2.0 Hz), 7.59-7.71 (3H, m), 8.66 (1H, t, J=5.6 Hz), 9.24 (1H, d, J=1.6 Hz); LCMS: 98.7%, MS (ESI): m/z 401.9[M+H]+.

6-chloro-N-((6-chlorobenzo[d]oxazol-2-yl)methyl)-2-ethylimidazo[1,2-a]pyridine-3-carboxamide (369)

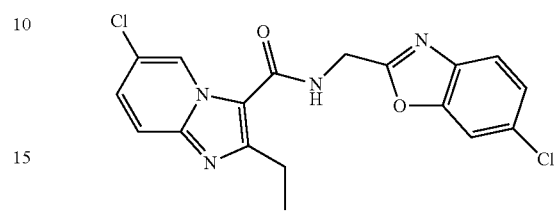

white solid; mp=201.1-201.8° C.; ¹H-NMR (DMSO-d6, 400 MHz): 1.31 (3H, t, J=7.2 Hz), 3.05 (2H, q, J=7.2 Hz), 4.84 (2H, d, J=5.6 Hz), 7.43 (1H, dd, J=8.4, 2.0 Hz), 7.49 (1H, dd, J=9.6, 2.0 Hz), 7.69 (1H, d, J=5.6 Hz), 7.71 (1H, d, J=9.6 Hz), 7.74 (1H, d, J=8.8 Hz), 7.95 (1H, d, J=2.0 Hz), 8.68 (1H, t, J=5.6 Hz), 9.13 (1H, d, J=1.6 Hz); LCMS: 98.6%, MS (ESI): m/z 389.0[M+H]+.

7-chloro-2-ethyl-N-((5-(4-(trifluoromethoxy)phenyl)benzo[d]oxazol-2-yl)methyl)imidazo[1,2-a]pyridine-3-carboxamide (370)

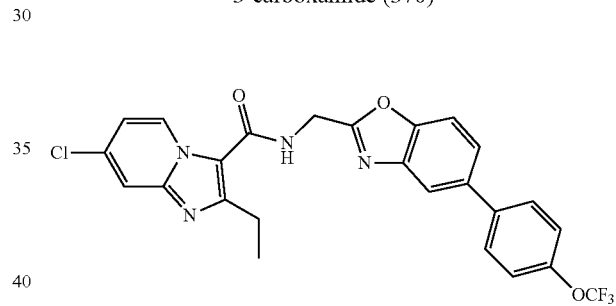

white solid; mp>220° C.; ¹H-NMR (DMSO-d6, 400 MHz): 1.32 (3H, t, J=7.6 Hz), 3.06 (2H, q, J=7.6 Hz), 4.86 (2H, d, J=4.4 Hz), 7.12 (1H, dd, J=7.6, 2.4 Hz), 7.46 (2H, d, J=8.4 Hz), 7.69 (1H, dd, J=8.4, 1.6 Hz), 7.79-7.86 (4H, m), 8.02 (1H, d, J=1.2 Hz), 8.70 (1H, brs), 9.01 (1H, d, J=7.6 Hz); LCMS: 98.2%, MS (ESI): m/z 515.1[M+H]+.

6-chloro-N-((6-chlorobenzo[d]thiazol-2-yl)methyl)-2-ethylimidazo[1,2-a]pyridine-3-carboxamide (371)

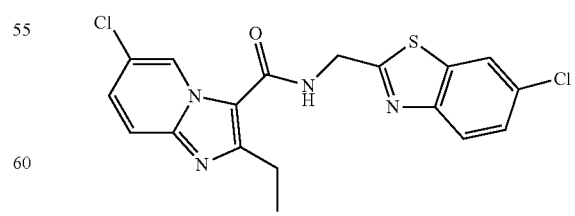

white solid; mp>220° C.; ¹H-NMR (DMSO-d6, 400 MHz): 1.33 (3H, t, J=7.6 Hz), 3.07 (2H, q, J=7.6 Hz), 4.93 (2H, d, J=6.0 Hz), 7.50 (1H, dd, J=9.6, 2.0 Hz), 7.55 (1H, dd, J=8.8, 2.4 Hz), 7.70 (1H, dd, J=9.6, 0.8 Hz), 7.97 (1H, d, J=8.8 Hz), 8.24 (1H, d, J=2.0 Hz), 8.88 (1H, t, J=6.0 Hz), 9.15 (1H, dd, J=2.4, 0.8 Hz); LCMS: 100%, MS (ESI): m/z 405.0 [M+H]+.

2-ethyl-6-fluoro-N-(4-(4-(4-(trifluoromethoxy)phenyl)piperidin-1-yl)benzyl)imidazo[1,2-a]pyridine-3-carboxamide (372)

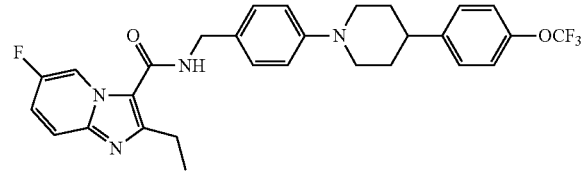 [SMILES: CCc1nc2ccc(F)cn2c1C(=O)NCc1ccc(N2CCC(c3ccc(OC(F)(F)F)cc3)CC2)cc1]

yellow amorphous; mp>167.9° C., decomposed; ¹H-NMR (CDCl₃, 400 MHz): δ1.40 (3H, t, J=7.6 Hz), 1.80-1.99 (4H, m), 2.65-2.72 (1H, m), 2.75-2.87 (2H, m), 2.97 (2H, q, J=7.6 Hz), 3.75-3.85 (2H, m), 4.62 (2H, d, J=5.2 Hz), 6.03 (1H, brs), 6.99 (2H, d, J=8.8 Hz), 7.16 (2H, d, J=8.4 Hz), 7.25-7.32 (5H, m), 7.56 (1H, dd, J=10.0, 5.2 Hz), 9.46 (1H, dd, J=5.2, 2.4 Hz); LCMS: 98.7%, MS (ESI): m/z 541.3 [M+H]+.

2-ethyl-8-fluoro-N-(4-(4-(4-(trifluoromethoxy)phenyl)piperidin-1-yl)benzyl)imidazo[1,2-a]pyridine-3-carboxamide (373)

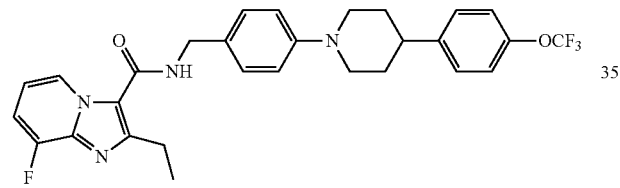

white amorphous; mp>177.7° C., decomposed; ¹H-NMR (CDCl3, 400 MHz): δ1.39 (3H, t, J=7.6 Hz), 1.83-1.96 (4H, m), 2.63-2.69 (1H, m), 2.70-2.90 (2H, m), 2.97 (2H, q, J=7.6 Hz), 3.75-3.85 (2H, m), 4.60 (2H, d, J=5.2 Hz), 6.04 (1H, brs), 6.78-6.84 (1H, m), 6.95-6.99 (3H, m), 7.14 (2H, d, J=8.8 Hz), 7.23-7.29 (4H, m), 9.18 (1H, dd, J=6.8, 0.8 Hz); LCMS: 99.5%, MS (ESI): m/z 541.3 [M+H]+.

7-chloro-2-ethyl-N-((6-(4-(trifluoromethoxy)phenyl)benzo[d]oxazol-2-yl)methyl)imidazo[1,2-a]pyridine-3-carboxamide (374)

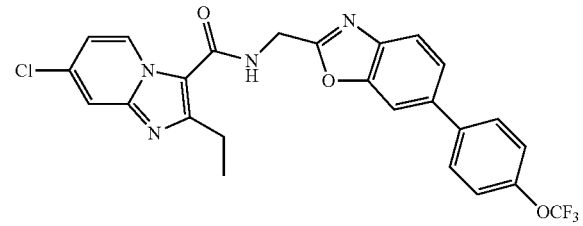 [SMILES: CCc1nc2cc(Cl)ccn2c1C(=O)NCc1nc2ccc(-c3ccc(OC(F)(F)F)cc3)cc2o1]

white solid; mp>220° C.; ¹H-NMR (DMSO-d6, 400 MHz): 1.32 (3H, t, J=7.2 Hz), 3.07 (2H, q, J=7.2 Hz), 4.86 (2H, d, J=5.6 Hz), 7.12 (1H, dd, J=7.6, 2.4 Hz), 7.46-7.50 (2H, m), 7.69 (1H, dd, J=8.4, 0.8 Hz), 7.79-7.80 (4H, m), 8.06 (1H, d, J=1.2 Hz), 8.69 (1H, t, J=6.0 Hz), 9.01 (1H, dd, J=7.6, 0.8 Hz); LCMS: 99.4%, MS (ESI): m/z 515.2 [M+H]+.

N1-((7-chloro-2-ethylimidazo[1,2-a]pyridin-3-yl)methyl)-N4-(1-(4-fluorophenyl)piperidin-4-yl)benzene-1,4-diamine (375)

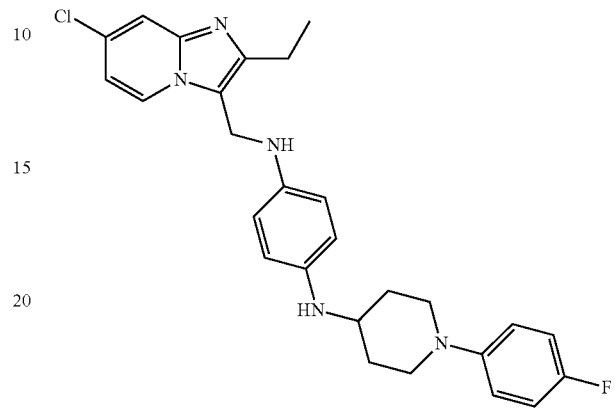

¹H-NMR (CDCl₃, Bruker Avance 400 MHz): δ 1.33 (3H, t, J=7.6 Hz), 1.50-1.63 (2H, m), 2.13-2.19 (2H, m), 2.72-2.90 (4H, m), 3.30-3.40 (1H, m), 3.47-3.60 (2H, m), 4.47 (2H, s), 6.60-6.70 (4H, m), 6.75 (1H, dd, J=7.2, 2.0 Hz), 6.87-7.00 (4H, m), 7.56 (1H, dd, J=2.0, 0.8 Hz), 8.08 (1H, dd, J=7.6, 0.8 Hz). LCMS: 100%, MS (ESI): m/z 478.3 [M+H]⁺.

N-((7-chloro-2-ethylimidazo[1,2-a]pyridin-3-yl)methyl)-4-(4-(4-(trifluoromethoxy)phenyl)piperidin-1-yl)aniline (376)

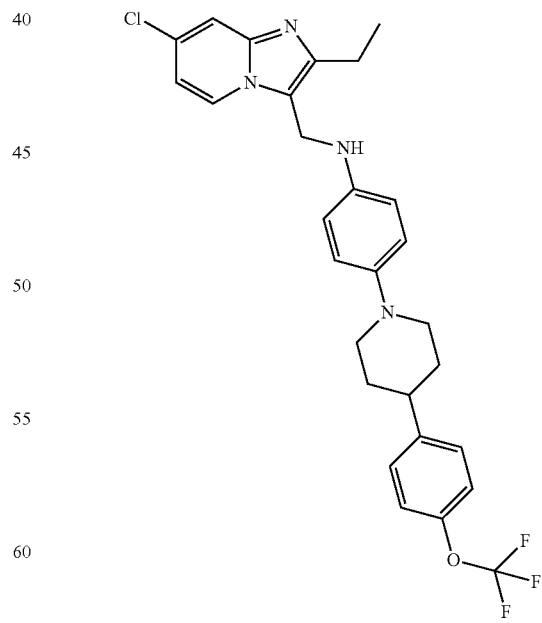

¹H-NMR (CDCl₃, 400 MHz): 1.34 (3H, t, J=7.6 Hz), 1.85-2.01 (4H, m), 2.56-2.70 (1H, m), 2.70-2.86 (4H, m), 3.34 (1H, s), 3.55-3.65 (2H, m), 4.50 (2H, s), 6.68-6.81 (3H, m), 6.95-

7.05 (2H, m), 7.17 (2H, d, J=8.0 Hz), 7.28 (2H, d, J=8.4 Hz), 7.57 (1H, d, J=1.6 Hz), 8.06 (1H, d, J=7.2 Hz), LCMS: 100%, MS (ESI): m/z 529.2[M+H]+.

7-chloro-2-ethyl-N-(4-(5-(4-fluorobenzyl)-2-oxooxazolidin-3-yl)benzyl)imidazo[1,2-a]pyridine-3-carboxamide (377)

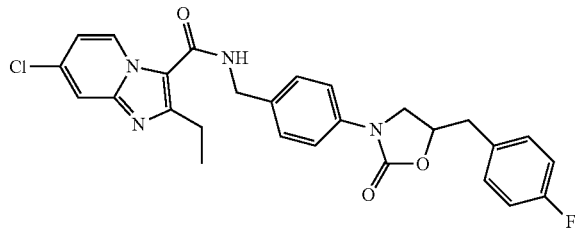 [SMILES: CCc1nc2cc(Cl)ccn2c1C(=O)NCc1ccc(N2CC(Cc3ccc(F)cc3)OC2=O)cc1]

white amorphous; mp>96.9° C., decomposed; ¹H-NMR (CDCl₃, 400 MHz): 1.38 (3H, t, J=7.6 Hz), 2.95 (2H, q, J=7.6 Hz), 3.02 (1H, dd, J=14.4, 6.4 Hz), 3.15 (1H, dd, J=14.0, 6.0 Hz), 3.70 (1H, dd, J=8.8, 6.8 Hz), 4.02 (1H, t, J=8.8 Hz), 4.65 (2H, d, J=5.6 Hz), 4.82-4.90 (1H, m), 6.05 (1H, t, J=2.8 Hz), 6.89 (1H, dd, J=7.6, 2.4 Hz), 6.99-7.05 (2H, m), 7.21-7.26 (2H, m), 7.36 (2H, dd, J=6.8, 2.0 Hz), 7.46 (2H, dd, J=6.4, 2.0 Hz), 7.58 (1H, dd, J=2.0, 0.8 Hz), 9.36 (1H, d, J=0.8 Hz); LCMS: 100%, MS (ESI): m/z 507.0 [M+H]+.

7-chloro-2-ethyl-N-(4-(5-((4-fluorophenoxy)methyl)-2-oxooxazolidin-3-yl)benzyl)imidazo[1,2-a]pyridine-3-carboxamide (378)

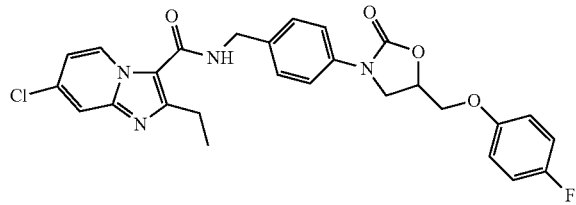 [SMILES: CCc1nc2cc(Cl)ccn2c1C(=O)NCc1ccc(N2CC(COc3ccc(F)cc3)OC2=O)cc1]

white amorphous; mp>97.10° C.; ¹H-NMR (CDCl₃, 400 MHz): 1.27 (3H, t, J=7.6 Hz), 3.00 (2H, q, J=7.6 Hz), 3.89-3.94 (1H, m), 4.19-4.30 (3H, m), 4.51 (2H, d, J=6.0 Hz), 5.01-0.06 (1H, m), 6.95-7.00 (2H, m), 7.08-7.22 (3H, m), 7.40 (2H, d, J=8.8 Hz), 7.56 (2H, d, J=8.8 Hz), 7.85 (1H, s), 8.58 (1H, t, J=7.2 Hz), 8.97 (1H, dd, J=7.2, 0.4 Hz); LCMS: 97.1%, MS (ESI): m/z 523.3 [M+H]+.

N-((6-Chloro-2-ethylimidazo[1,2-a]pyridin-3-yl)methyl)-4-(4-fluorophenoxy)aniline (379)

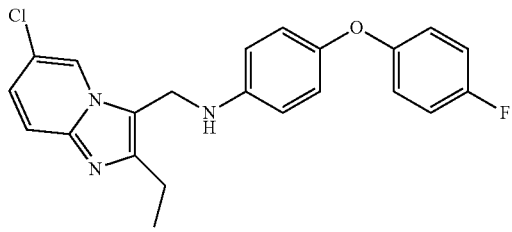 [SMILES: CCc1nc2ccc(Cl)cn2c1CNc1ccc(Oc2ccc(F)cc2)cc1]

White solid; mp=148.6-148.8° C.; ¹H NMR (400 MHz, CDCl₃) δ 1.35 (t, J=7.4 Hz, 3H), 2.82 (q, J=7.6 Hz, 2H), 4.50 (s, 2H), 6.74 (d, J=8.8 Hz, 2H), 6.90-7.01 (m, 6H), 7.15 (dd, J=2.0, 9.6 Hz, 1H), 7.52 (d, J=9.2 Hz, 1H), 8.16 (d, J=1.2 Hz, 1H); LCMS (electrospray) m/z (M+H)+ 396.17

(7-Chloro-2-ethylimidazo[1,2-a]pyridin-3-yl)(4-(4-(trifluoromethoxy)phenoxy)piperidin-1-yl)methanone (380)

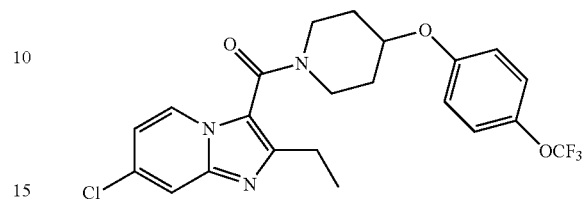

Yellow oil; ¹H NMR (400 MHz, CD₃OD) δ8.40 (dd, J=7.4, 0.6 Hz, 1H), 7.59 (dd, J=2.0, 0.4 Hz, 1H), 7.19 (d, J=8.4 Hz, 2H), 7.04 (m, 3H), 4.70 (m, 1H), 4.10-3.65 (m, 4H), 2.81 (q, J=7.6 Hz, 2H), 2.05 (m, 2H), 1.85 (m, 2H), 1.34 (t, J=7.6 Hz, 3H); LRMS (electrospray) m/z (M+H)+ 468.

1-(6-chloro-2-ethylimidazo[1,2-a]pyridin-3-yl)-N-(4-(4-(4-fluorophenyl)piperazin-1-yl)benzyl)methanamine (381)

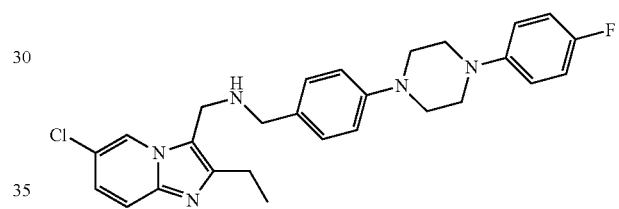

Colorless oil; ¹H NMR (400 MHz, CDCl₃); δ 8.07 (d, J=1.2 Hz, 1H), 7.45 (d, J=9.6 Hz, 1H), 7.24 (d, J=8.4 Hz, 2H), 7.06 (dd, J=9.6, 1.6, Hz 1H), 6.92-7.01 (m, 6H), 7.03 (s, 2H), 3.74 (s, 2H), 3.31-3.35 (m, 4H), 3.24-3.28 (m, 4H), 2.74 (q, J=7.6 Hz, 2H), 1.83 (br s, 1H), 1.31 (t, J=7.6 Hz, 3H); LCMS (electrospray) m/z 478 (M+H)+.

(6-chloro-2-ethylimidazo[1,2-a]pyridin-3-yl)(3-(4-(trifluoromethoxy)benzyloxy)-piperidin-1-yl)methanone (382)

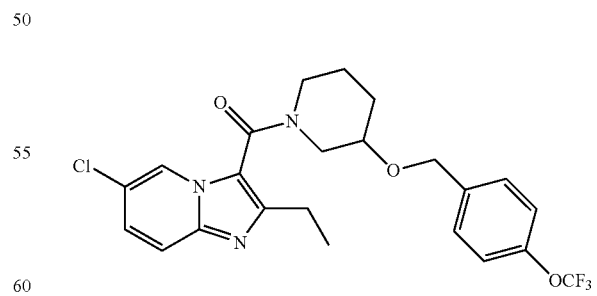

Yellow oil; ¹H NMR (400 MHz, CDCl₃); δ 8.35 (s, 1H), 7.52 (d, J=9.6 Hz, 1H), 7.13-7.25 (m, 5H), 4.42 (br s, 2H), 3.99 (br s, 2H), 3.56 (br s, 1H), 3.25 (br s, 2H), 2.77 (q, J=7.6 Hz, 2H), 1.57-2.21 (m, 3H), 1.55 (br s, 1H), 1.35 (t, J=7.6 Hz, 3H); LCMS (electrospray) m/z 482 (M+H)+.

N-((6-chloro-2-ethylimidazo[1,2-a]pyridin-3-yl)methyl)-4'-(trifluoromethoxy)biphenyl-4-amine (383)

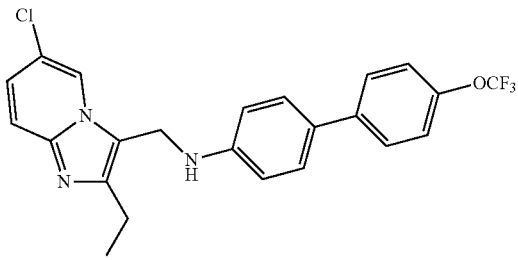 [SMILES: CCc1nc2ccc(Cl)cn2c1CNc1ccc(-c2ccc(OC(F)(F)F)cc2)cc1]

Yellow solid; mp=102.0° C.; ¹H NMR (400 MHz, CD₃OD) δ8.43 (s, 1H), 7.61 (d, J=6.4 Hz, 1H), 7.50 (m, 3H), 7.31 (m, 3H), 6.81 (d, J=6.8 Hz, 2H), 4.64 (s, 2H), 2.87 (q, 2H), 1.35 (t, J=7.6 Hz, 3H); LRMS (electrospray) m/z (M+H)⁺ 446.

(6-Chloro-2-ethylimidazo[1,2-a]pyridin-3-yl)(4-(4-(trifluoromethoxy)phenoxy)piperidin-1-yl)methanone (384)

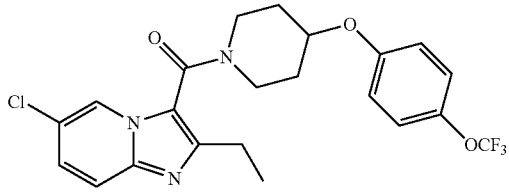 [SMILES: CCc1nc2ccc(Cl)cn2c1C(=O)N1CCC(Oc2ccc(OC(F)(F)F)cc2)CC1]

Yellow solid; mp=80.7° C.; ¹H NMR (400 MHz, CD₃OD) δ8.54 (s, 1H), 7.56 (d, J=9.6 Hz, 1H), 7.43 (d, J=9.6 Hz, 1H), 7.19 (d, J=8.4 Hz, 2H), 7.05 (d, J=6.8 Hz, 2H), 6.69 (m, 1H), 3.88 (m, 2H), 3.35 (m, 2H), 2.81 (q, J=7.6 Hz, 2H), 2.06 (m, 2H), 1.97 (m, 3H), 1.34 (t, J=4.2 Hz, 2H); LRMS (electrospray) m/z (M+H)⁺ 468.

(2-Ethylimidazo[1,2-a]pyrimidin-3-yl)(4-((4-(trifluoromethoxy)benzyl)oxy)piperidin-1-yl)methanone (385)

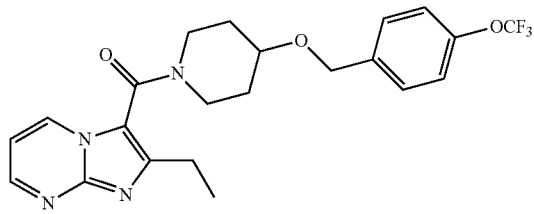 [SMILES: CCc1nc2ncccn2c1C(=O)N1CCC(OCc2ccc(OC(F)(F)F)cc2)CC1]

Colorless oil; ¹H NMR (400 MHz, CDCl₃) δ 8.76 (dd, J=6.8 Hz, 2.0 Hz, 1H), 8.56 (dd, J=4.4 Hz, 2.0 Hz, 1H), 7.37 (d, J=8.4 Hz, 2H), 7.20 (d, J=8.4 Hz, 2H), 6.90 (dd, J=6.8 Hz, 4.4 Hz, 1H), 4.57 (s, 2H), 3.90 (brs, 2H), 3.75-3.71 (m, 1H), 3.50 (brs, 2H), 2.82 (q, J=7.6 Hz, 2H), 1.94 (brs, 2H), 1.75 (brs, 2H), 1.40 (t, J=7.6 Hz, 3H); LCMS (electrospray) m/z (M+H)⁺ 449.

N-((4'-Chloro-[1,1'-biphenyl]-4-yl)methyl)-2-ethylimidazo[1,2-a]pyrimidine-3-carboxamide (386)

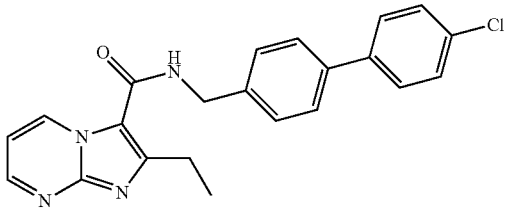 [SMILES: CCc1nc2ncccn2c1C(=O)NCc1ccc(-c2ccc(Cl)cc2)cc1]

Pale yellow solid; mp=184.8° C.; ¹H NMR (400 MHz, CDCl₃) δ 8.60 (dd, J=4.0 Hz, 1.6 Hz, 1H), 8.31 (dd, J=6.8 Hz, 2.0 Hz, 1H), 8.02 (brs, 1H), 7.66-7.34 (m, 8H), 6.95-6.92 (m, 1H), 4.69 (d, J=6.4 Hz, 2H), 3.43 (q, J=7.6 Hz, 2H), 1.32 (t, J=7.6 Hz, 3H); LCMS (electrospray) m/z (M+H)⁺ 391.

(2-Ethylimidazo[1,2-b]pyridazin-3-yl)(4-((4-(trifluoromethoxy)benzyl)oxy)piperidin-1-yl)methanone (387)

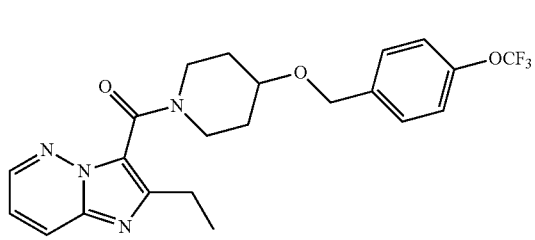 [SMILES: CCc1nc2cccnn2c1C(=O)N1CCC(OCc2ccc(OC(F)(F)F)cc2)CC1]

Yellow oil; ¹H NMR (400 MHz, CDCl₃) δ 8.32 (dd, J=4.4 Hz, 1.6 Hz, 1H), 7.91 (dd, J=9.2 Hz, 1.6 Hz, 1H), 7.37 (d, J=8.0 Hz, 2H), 7.19 (d, J=8.0 Hz, 2H), 7.06 (dd, J=9.2 Hz, 4.4 Hz, 1H), 4.55 (s, 2H), 4.14 (brs, 1H), 3.74-3.69 (m, 2H), 3.53 (brs, 1H), 3.18 (brs, 1H), 2.89 (q, J=7.6 Hz, 2H), 2.03-1.84 (m, 4H), 1.37 (t, J=7.6 Hz, 3H); LCMS (electrospray) m/z (M+H)⁺ 449.

N-((4'-Chloro-[1,1'-biphenyl]-4-yl)methyl)-2-ethylimidazo[1,2-b]pyridazine-3-carboxamide (388)

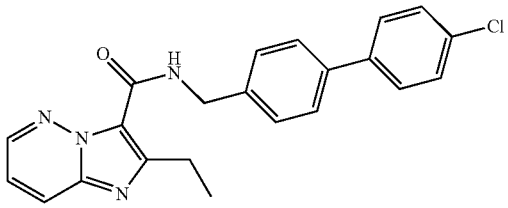 [SMILES: CCc1nc2cccnn2c1C(=O)NCc1ccc(-c2ccc(Cl)cc2)cc1]

Yellow oil; ¹H NMR (400 MHz, CDCl₃) δ 9.19 (brs, 1H), 8.39 (dd, J=4.4 Hz, 1.6 Hz, 1H), 8.03 (d, J=9.2 Hz, 1H), 7.59-7.34 (m, 8H), 7.18 (dd, J=9.2 Hz, 4.4 Hz, 1H), 4.80 (d, J=6.0 Hz, 2H), 3.38 (q, J=7.6 Hz, 2H), 1.42 (t, J=7.6 Hz, 3H); LCMS (electrospray) m/z (M+H)+ 391.

(2-Ethylimidazo[1,2-a]pyrazin-3-yl)(4-((4-(trifluoromethoxy)benzyl)oxy)piperidin-1-yl)methanone (389)

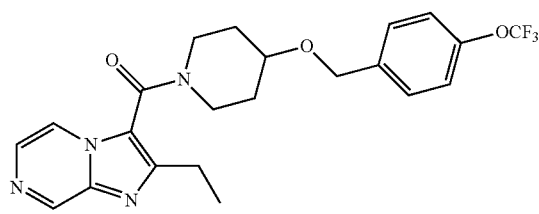 [SMILES: CCc1nc2cnccn2c1C(=O)N1CCC(OCc2ccc(OC(F)(F)F)cc2)CC1]

Yellow oil; ¹H NMR (400 MHz, CDCl₃) δ 9.07 (d, J=1.2 Hz, 1H), 8.28 (dd, J=4.8, 1.2 Hz, 1H), 7.94 (d, J=4.8 Hz, 1H), 7.38 (d, J=8.8 Hz, 2H), 7.21 (d, J=8.0 Hz, 2H), 4.58 (s, 2H), 3.78-3.94 (m, 2H), 3.74-3.77 (m, 1H), 3.45-3.60 (m, 2H), 2.84 (q, J=7.6 Hz, 2H), 1.80-2.00 (m, 2H), 1.39 (t, J=7.6 Hz, 3H).

(S)-(6-chloro-2-ethylimidazo[1,2-a]pyridin-3-yl)(3-(4-(trifluoromethoxy)benzyloxy)-pyrrolidin-1-yl)methanone (390)

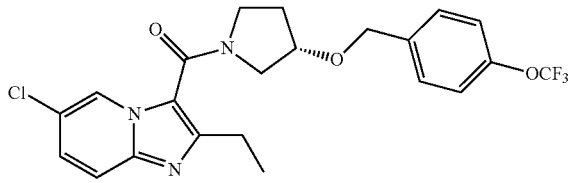 [SMILES: CCc1nc2ccc(Cl)cn2c1C(=O)N1CC[C@H](OCc2ccc(OC(F)(F)F)cc2)C1]

Yellow oil; ¹H NMR (400 MHz, CDCl₃); δ 8.52 (s, 1H), 7.51 (d, J=9.6 Hz, 1H), 7.33 (d, J=8.0 Hz, 2H), 7.18-7.23 (m, 3H), 4.52 (s, 2H), 4.23 (br s, 1H), 3.40-4.01 (m, 4H), 2.80 (q, J=7.6 Hz, 2H), 2.16-2.21 (m, 1H), 2.03-2.05 (m, 1H), 1.34 (t, J=7.6 Hz, 3H); LCMS (electrospray) m/z 468 (M+H)+.

(R)-(6-chloro-2-ethylimidazo[1,2-a]pyridin-3-yl)(3-(4-(trifluoromethoxy)benzyloxy)-pyrrolidin-1-yl)methanone (391)

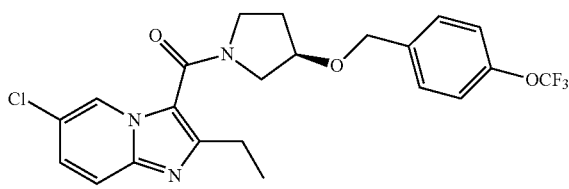 [SMILES: CCc1nc2ccc(Cl)cn2c1C(=O)N1CC[C@@H](OCc2ccc(OC(F)(F)F)cc2)C1]

Yellow oil; ¹H NMR (400 MHz, CDCl₃); 88.51 (d, J=1.2 Hz, 1H), 7.51 (d, J=9.2 Hz, 1H), 7.32 (d, J=8.0 Hz, 2H), 7.18-7.22 (m, 3H), 4.70 (s, 2H), 4.23 (br s, 1H), 3.40-4.01 (m, 4H), 2.71 (q, J=7.6 Hz, 2H), 2.16-2.21 (m, 1H), 2.03-2.08 (m, 1H), 1.67 (t, J=7.6 Hz, 3H); LCMS (electrospray) m/z 468 (M+H)+.

N-((6-chloro-2-ethylimidazo[1,2-a]pyridin-3-yl)methyl)-4-(4-(4-chlorophenyl)piperidin-1-yl)aniline (392)

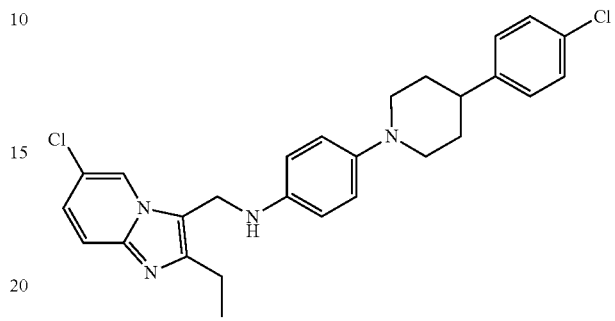

White solid; mp=159.5° C.; ¹H NMR (400 MHz, CDCl₃) δ8.19 (s, 1H), 7.52 (d, J=9.6 Hz, 1H), 7.30 (d, J=2.4 Hz, 2H), 7.21 (d, J=2.0 Hz, 2H), 7.16 (d, J=9.2 Hz, 1H), 7.00 (d, J=8.4 Hz, 2H), 6.76 (d, J=4.4 Hz, 2H), 4.50 (s, 2H), 3.62 (d, J=12 Hz, 2H), 2.79 (m, 4H), 2.60 (m, 1H), 1.94 (m, 4H), 1.34 (t, J=7.6 Hz, 3H); LRMS (electrospray) m/z (M+H)+ 479.29.

(7-chloro-2-ethylimidazo[1,2-a]pyridin-3-yl)(4-(4-(trifluoromethoxy)benzyloxy)piperidin-1-yl)methanone (393)

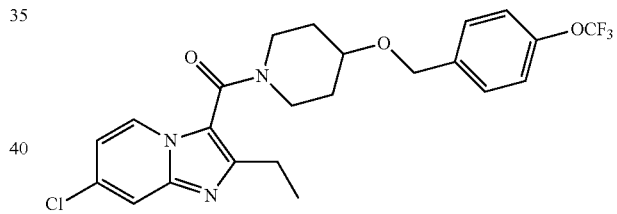

Yellow oil; NMR (400 MHz, CDCl₃); δ 8.34 (d, J=PG 7.2 Hz, 1H), 7.57 (d439, J=2.0 Hz, 1H),Yellow oil; ¹H NMR (400 MHz, CDCl₃); δ 8.34 (d, J=7.2 Hz, 1H), 7.57 (d, J=2.0 Hz, 1H), 7.38 (d, J=8.4 Hz, 2H), 7.21 (d, J=8.0 Hz, 2H), 6.82 (dd, J=7.2, 2.0 Hz, 1H), 4.57 (s, 2H), 3.89 (br s, 2H), 3.73 (septet, J=3.6 Hz, 1H), 2.77 (q, J=7.6 Hz, 2H), 1.94 (br s, 2H), 1.76 (br s, 2H), 1.36 (t, J=7.6 Hz, 3H); LCMS (electrospray) m/z 482 (M+H)+.

N-((6-chloro-2-ethylimidazo[1,2-a]pyridin-3-yl)methyl)-4-(4-(trifluoromethoxy)-phenoxy)aniline (394)

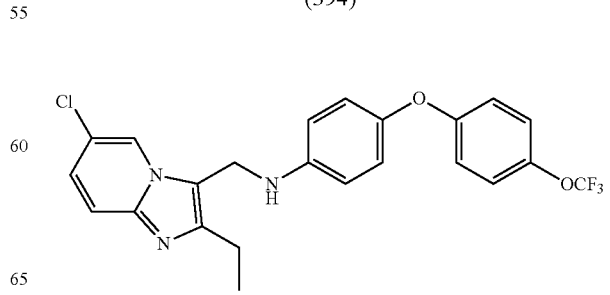

Oil; ¹H NMR (400 MHz, CDCl₃) δ8.18 (d, J=1.2 Hz, 1H), 7.56 (d, J=9.6 Hz, 1H), 7.17 (m, 3H), 6.99 (m, 4H), 6.79 (d, J=5.6 Hz, 2H), 4.51 (s, 2H), 2.86 (q, J=7.6 Hz 2H), 1.32 (t, J=7.6 Hz, 3H); LRMS (electrospray) m/z (M+H)⁺ 462.35.

N-((2-Ethylimidazo[1,2-a]pyrimidin-3-yl)methyl)-4-(4-(4-fluorophenyl)piperazin-1-yl)aniline (395)

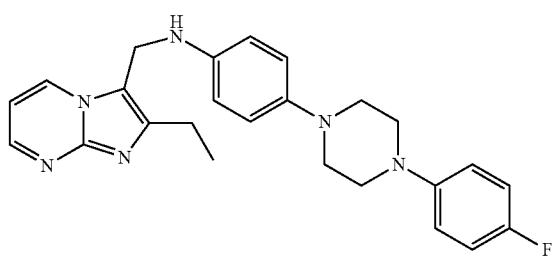 [SMILES: CCc1nc2ncccn2c1CNc1ccc(N2CCN(c3ccc(F)cc3)CC2)cc1]

Yellow solid; mp=210.7° C.; ¹H NMR (400 MHz, CDCl₃) δ 8.51 (dd, J=4.0 Hz, 2.0 Hz, 1H), 8.46 (dd, J=6.8 Hz, 2.0 Hz, 1H), 7.01-6.92 (m, 6H), 6.82 (dd, J=6.8 Hz, 4.0 Hz, 1H), 6.74 (d, J=8.8 Hz, 2H), 4.54 (s, 2H), 3.27-3.22 (m, 8H), 2.87 (q, J=7.6 Hz, 2H), 1.38 (t, J=7.6 Hz, 3H); LCMS (electrospray) m/z (M+H)⁺ 431.

N-((2-Ethylimidazo[1,2-b]pyridazin-3-yl)methyl)-4-(4-(4-fluorophenyl)piperazin-1-yl)aniline (396)

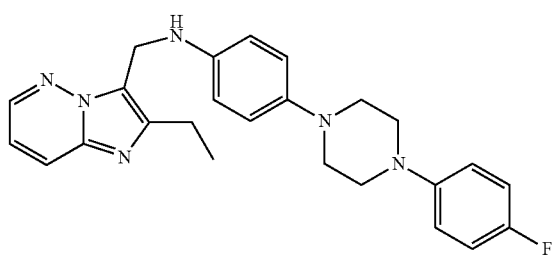 [SMILES: CCc1nc2cccnn2c1CNc1ccc(N2CCN(c3ccc(F)cc3)CC2)cc1]

Pale yellow solid; mp=192.7° C.; ¹H NMR (400 MHz, CDCl₃) δ 8.31 (dd, J=4.4 Hz, 1.6 Hz, 1H), 7.87 (dd, J=9.2 Hz, 1.6 Hz, 1H), 7.01-6.87 (m, 7H), 6.72 (d, J=8.8 Hz, 2H), 4.66 (s, 2H), 3.25-3.16 (m, 8H), 2.89 (q, J=7.6 Hz, 2H), 1.36 (t, J=7.6 Hz, 3H); LCMS (electrospray) m/z (M+H)⁺ 431.

6-chloro-2-ethyl-3-((4-(4-(4-fluorophenyl)piperazin-1-yl)methyl)imidazo[1,2-a]pyridine (397)

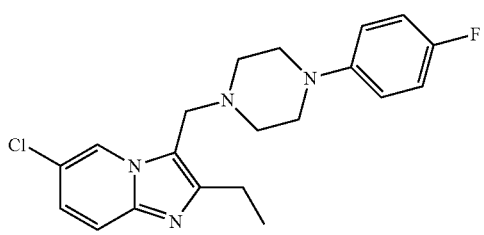

Ivory solid; ¹H NMR (400 MHz, CDCl₃) δ 8.48 (s, 1H), 7.77 (d, J=8.4 Hz, 1H), 7.34 (d, J=8.4 Hz, 1H), 7.01-6.94 (m, 2H), 6.93-6.87 (m, 2H), 3.86 (s, 2H), 3.13 (brs, 4H), 2.89-2.84 (m, 2H), 2.65 (brs, 4H), 1.35 (t, 3H); LCMS (electrospray) m/z (M+H)⁺ 373.

N-((2-Ethylimidazo[1,2-a]pyrazin-3-yl)methyl)-4-(4-(4-fluorophenyl)piperazin-1-yl)aniline (398)

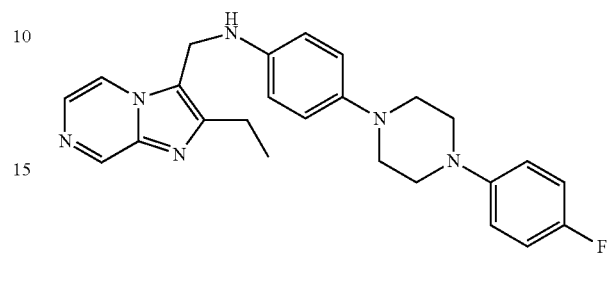

White solid; ¹H NMR (400 MHz, CDCl₃) δ 9.04 (d, J=1.2 Hz, 1H), 8.10 (dd, J=4.8, 1.6 Hz, 1H), 7.86 (d, J=4.8 Hz, 1H), 6.92-7.01 (m, 6H), 6.73 (d, J=8.8 Hz, 2H), 4.57 (s, 2H), 3.26-3.29 (m, 4H), 3.21-3.25 (m, 4H), 2.89 (q, J=7.6 Hz, 2H), 1.38 (t, J=7.6 Hz, 3H).

6-chloro-2-ethyl-3-((4-(4-(4-fluorophenyl)piperazin-1-yl)phenoxy)methyl)imidazo[1,2-a]pyridine (399)

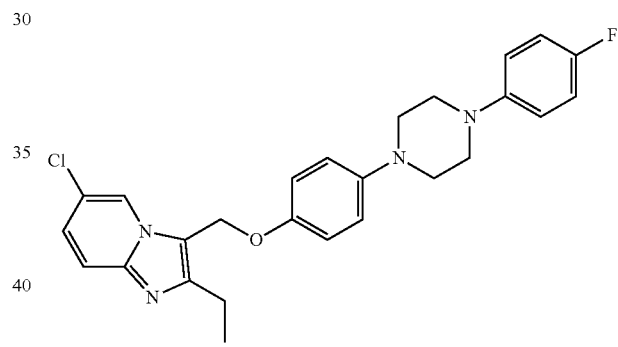

White solid; mp=161.3° C.; ¹H NMR (400 MHz, CDCl₃) δ8.15 (d, J=1.2 Hz, 1H), 7.51 (d, J=9.6 Hz, 1H), 7.16 (d, J=2.0 Hz, 1H), 6.95 (m, 8H), 5.25 (d, J=5.8 Hz, 2H), 3.23 (m, 8H), 2.81 (q, J=7.6 Hz 2H), 1.32 (t, J=7.6 Hz, 3H); LRMS (electrospray) m/z (M+H)⁺ 465.27.

7-chloro-2-ethyl-3-((4-(4-(4-fluorophenyl)piperazin-1-yl)phenoxy)methyl)imidazo[1,2-a]pyridine (400)

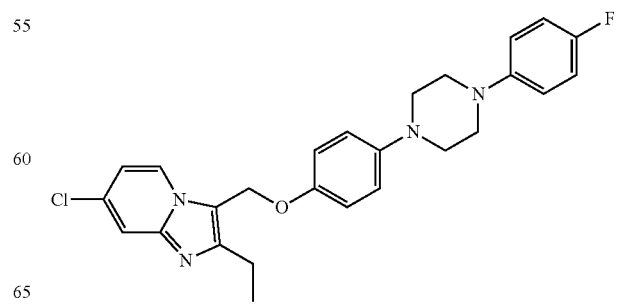

White solid; mp=167.5° C.; ¹H NMR (400 MHz, CDCl₃) δ8.03 (d, J=7.2 Hz, 1H), 7.56 (d, J=1.6 Hz, 1H), 6.91 (m, 8H), 6.80 (d, J=5.2 Hz, 1H), 5.24 (s, 2H), 3.25 (m, 8H), 2.79 (q, J=7.6 Hz 2H), 1.30 (t, J=7.6 Hz, 3H); LRMS (electrospray) m/z (M+H)⁺ 465.34.

N-((2,5-dimethylimidazo[1,2-a]pyridin-3-yl)methyl)-4-(4-(4-fluorophenyl)piperidin-1-yl)aniline (401)

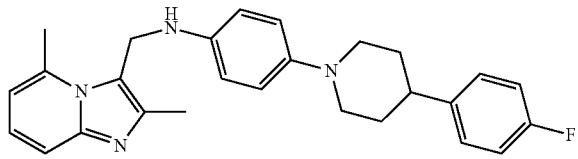 [SMILES: Cc1nc2cccc(C)n2c1CNc1ccc(N2CCC(c3ccc(F)cc3)CC2)cc1]

White solid; mp=228.8° C.; ¹H NMR (400 MHz, DMSO-d₆) δ 7.12-7.32 (m, 3H), 7.04-7.12 (m, 3H), 6.83 (d, J=8.0 Hz, 2H), 6.65 (d, J=8.0 Hz, 2H), 6.59 (d, J=6.4 Hz, 1H), 5.37 (t, J=4.4 Hz, 1H, NH), 4.40 (d, J=4.4 Hz, 2H), 3.46-3.50 (m, 2H), 2.82 (s, 3H), 2.56-2.63 (m, 3H), 2.31 (s, 3H), 1.72-1.83 (m, 4H); LCMS (electrospray) m/z (M+H)⁺ 429.

N-((2,5-dimethylimidazo[1,2-a]pyridin-3-yl)methyl)-4-(4-(4-fluorophenyl)piperazin-1-yl)aniline (402)

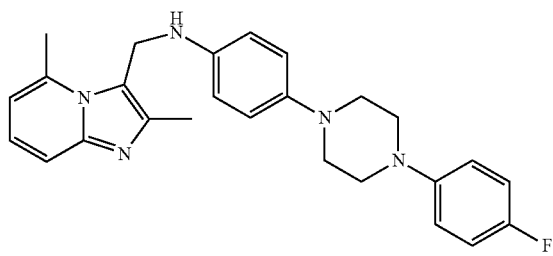 [SMILES: Cc1nc2cccc(C)n2c1CNc1ccc(N2CCN(c3ccc(F)cc3)CC2)cc1]

White solid; mp=196.4° C.; ¹H NMR (400 MHz, DMSO-d₆) δ 7.29 (d, J=9.2 Hz, 1H), 7.08-6.96 (m, 5H), 6.84 (d, J=8.8 Hz, 2H), 6.65 (d, J=9.2 Hz. 2H), 6.59 (d, J=6.8 Hz, 1H), 5.41 (t, J=4.8 Hz, 1H), 4.40 (d, J=4.8 Hz, 2H), 3.19-3.18 (m, 4H), 3.07-3.05 (m, 4H), 2.82 (s, 3H), 2.32 (s, 3H); LCMS (electrospray) m/z (M+H)⁺ 430.

2-Ethyl-6-fluoro-N-(1-(4-(phenylamino)phenyl)pyrrolidin-3-yl)imidazo[1,2-a]pyridine-3-carboxamide (403)

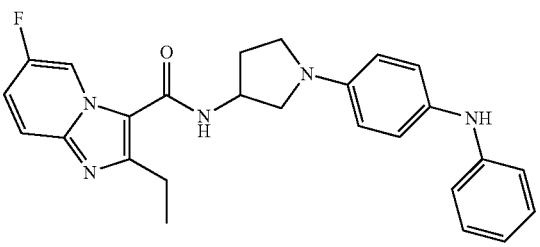 [SMILES: CCc1nc2ccc(F)cn2c1C(=O)NC1CCN(c2ccc(Nc3ccccc3)cc2)C1]

Pale blue solid; mp=224.7° C.; ¹H NMR (400 MHz, acetone-d⁶); Two conformational isomer (3:1 ratio) δ 9.34-9.36 &9.19-9.21 (m, 1H), 7.96 & 7.23 (brs, 1H), 7.81-7.85 & 7.57-7.60 (m, 1H), 7.69-7.74 & 7.36-7.41 (m, 1H), 7.22 & 6.82 (s, 1H), 7.09 (dd, J=8.0, 7.6 Hz, 2H), 7.050 (d, J=8.4 Hz, 2H), 6.861 (d, J=8.0 Hz, 2H), 6.64 (dd, J=7.6, 7.6 Hz, 1H), 6.59 (d, J=8.4 Hz, 2H), 4.82-4.86 (m, 1H), 3.63-3.70 (m, 1H), 3.48-3.54 (m, 1H), 3.34-3.40 (m, 2H), 3.12 & 3.00 (q, J=7.6 Hz, 2H), 2.40-2.49 (m, 1H), 2.18-2.26 (m, 1H), 1.27-1.36 (m, 3H); LCMS (electrospray) m/z 443 (M)⁺.

REFERENCES

Gloria Paola Chappell, Xiaoyao Xiao, Arnaldo Pica-Mendez, Tracey Varnell, Stuart Green, Wesley K. Tanaka, Omar Laterza. (2011) Quantitative measurement of cysteinyl leukotrienes and leukotriene B4 in human sputum using ultra high pressure liquid chromatography-tandem mass spectrometry. Journal of Chromatography B. 879:277-284

Robert A. Pufahl, Thomas P. Kasten, Rob Hills, James K. Gierse, Beverly A. Reitz, Robin A. Weinberg, Jaime L. Masferrer. (2007) Development of a fluorescence-based enzyme assay of human 5-lipoxygenase. Analytical Biochemistry 364:204-212.

Mark B. Willey, William E. Alborn, Barry S. Lutzke, Richard M. LeLacheur, Robert J. White, George Stavrakis, Robert J. Konrad, Bradley L. Ackermann. (2008) The development of methodology for clinical measurement of 5-lipoxygenase pathway intermediates from human peripheral blood mononuclear cells. Journal of Pharmaceutical and Biomedical Analysis 48: 1397-1403.

Ben S. Zweifel, Medora M. Hardy, Gary D. Anderson, Dawn R. Dufield, Robert A. Pufahl, Jaime L. Masferrer. (2008) A rat air pouch model for evaluation the efficacy and selectivity of 5-lipoxygenase inhibitors. European Journal of Pharmacology 584:166-174

TABLE 1

| compounds | % inhibition at 10 uM |
|---|---|
| 1 | + |
| 2 | + |
| 3 | + |
| 4 | + |
| 5 | + |
| 6 | + |
| 7 | + |
| 8 | + |
| 9 | + |
| 10 | + |
| 11 | + |
| 12 | + |
| 13 | + |
| 14 | + |
| 15 | + |
| 16 | + |
| 17 | + |
| 18 | ++ |
| 19 | + |
| 20 | ++ |
| 21 | + |
| 22 | ++ |
| 23 | + |
| 24 | + |
| 25 | + |
| 26 | + |
| 27 | ++ |
| 28 | + |
| 29 | + |
| 30 | + |
| 31 | + |

TABLE 1-continued

| compounds | % inhibition at 10 uM |
|---|---|
| 32 | + |
| 33 | + |
| 34 | ++ |
| 35 | + |
| 36 | + |
| 37 | + |
| 38 | + |
| 39 | + |
| 40 | + |
| 41 | + |
| 42 | + |
| 43 | + |
| 44 | + |
| 45 | + |
| 46 | ++ |
| 47 | + |
| 48 | + |
| 49 | + |
| 50 | + |
| 51 | + |
| 52 | + |
| 53 | + |
| 54 | + |
| 55 | ++ |
| 56 | + |
| 57 | ++ |
| 58 | +++ |
| 59 | ++ |
| 60 | ++ |
| 61 | + |
| 62 | + |
| 63 | ++ |
| 64 | + |
| 65 | + |
| 66 | + |
| 67 | + |
| 68 | + |
| 69 | ++ |
| 70 | +++ |
| 71 | + |
| 72 | ++ |
| 73 | + |
| 74 | + |
| 75 | ++ |
| 76 | ++ |
| 77 | + |
| 78 | + |
| 79 | + |
| 80 | + |
| 81 | + |
| 82 | ++ |
| 83 | ++ |
| 84 | ++ |
| 85 | +++ |
| 86 | +++ |
| 87 | ++ |
| 88 | + |
| 89 | + |
| 90 | ++ |
| 91 | ++ |
| 92 | ++ |
| 93 | + |
| 94 | + |
| 95 | ++ |
| 96 | ++ |
| 97 | + |
| 98 | ++ |
| 99 | + |
| 100 | +++ |
| 101 | ++ |
| 102 | ++ |
| 103 | +++ |
| 104 | ++ |
| 105 | + |
| 106 | ++ |
| 107 | ++ |
| 108 | + |

TABLE 1-continued

| compounds | % inhibition at 10 uM |
|---|---|
| 109 | ++ |
| 110 | +++ |
| 111 | + |
| 112 | ++ |
| 113 | ++ |
| 114 | ++ |
| 115 | ++ |
| 116 | ++ |
| 117 | + |
| 118 | + |
| 119 | ++ |
| 120 | ++ |
| 121 | ++ |
| 122 | ++ |
| 123 | +++ |
| 124 | +++ |
| 125 | ++ |
| 126 | +++ |
| 127 | +++ |
| 128 | +++ |
| 129 | ++ |
| 130 | +++ |
| 131 | ++ |
| 132 | ++ |
| 133 | ++ |
| 134 | + |
| 135 | + |
| 136 | + |
| 137 | ++ |
| 138 | ++ |
| 139 | + |
| 140 | ++ |
| 141 | + |
| 142 | ++ |
| 143 | +++ |
| 144 | ++ |
| 145 | + |
| 146 | + |
| 147 | ++ |
| 148 | ++ |
| 149 | ++ |
| 150 | ++ |
| 151 | + |
| 152 | ++ |
| 153 | + |
| 154 | + |
| 155 | + |
| 156 | + |
| 157 | +++ |
| 158 | ++ |
| 159 | ++ |
| 160 | ++ |
| 161 | +++ |
| 162 | ++ |
| 163 | ++ |
| 164 | +++ |
| 165 | + |
| 166 | ++ |
| 167 | ++ |
| 168 | ++ |
| 169 | ++ |
| 170 | + |
| 171 | + |
| 172 | + |
| 173 | ++ |
| 174 | +++ |
| 175 | +++ |
| 176 | ++ |
| 177 | + |
| 178 | + |
| 179 | ++ |
| 180 | + |
| 181 | +++ |
| 182 | + |
| 183 | + |
| 184 | + |
| 185 | ++ |

TABLE 1-continued

| compounds | % inhibition at 10 uM |
|---|---|
| 186 | ++ |
| 187 | + |
| 188 | ++ |
| 189 | +++ |
| 190 | +++ |
| 191 | + |
| 192 | ++ |
| 193 | +++ |
| 194 | +++ |
| 195 | ++ |
| 196 | + |
| 197 | +++ |
| 198 | ++ |
| 199 | + |
| 200 | ++ |
| 201 | + |
| 202 | ++ |
| 203 | + |
| 204 | + |
| 205 | ++ |
| 206 | + |
| 207 | +++ |
| 208 | +++ |
| 209 | +++ |
| 210 | ++ |
| 211 | +++ |
| 212 | + |
| 213 | + |
| 214 | + |
| 215 | ++ |
| 216 | ++ |
| 217 | +++ |
| 218 | ++ |
| 219 | +++ |
| 220 | ++ |
| 221 | + |
| 222 | + |
| 223 | +++ |
| 224 | +++ |
| 225 | +++ |
| 226 | + |
| 227 | +++ |
| 228 | +++ |
| 229 | + |
| 230 | + |
| 231 | +++ |
| 232 | +++ |
| 233 | ++ |
| 234 | + |
| 235 | + |
| 236 | ++ |
| 237 | + |
| 238 | + |
| 239 | + |
| 240 | + |
| 241 | + |
| 242 | + |
| 243 | +++ |
| 244 | ++ |
| 245 | + |
| 246 | + |
| 247 | ++ |
| 248 | + |
| 249 | ++ |
| 250 | ++ |
| 251 | + |
| 252 | + |
| 253 | + |
| 254 | + |
| 255 | + |
| 256 | + |
| 257 | ++ |
| 258 | + |
| 259 | + |
| 260 | +++ |
| 261 | + |
| 262 | + |
| 263 | ++ |
| 264 | + |
| 265 | +++ |
| 266 | +++ |
| 267 | + |
| 268 | ++ |
| 269 | ++ |
| 270 | ++ |
| 271 | ++ |
| 272 | + |
| 273 | + |
| 274 | + |
| 275 | + |
| 276 | + |
| 277 | + |
| 278 | ++ |
| 279 | + |
| 280 | + |
| 281 | ++ |
| 282 | + |
| 283 | + |
| 284 | + |
| 285 | + |
| 286 | ++ |
| 287 | ++ |
| 288 | + |
| 289 | + |
| 290 | + |
| 291 | + |
| 292 | + |
| 293 | + |
| 294 | + |
| 295 | +++ |
| 296 | +++ |
| 297 | ++ |
| 298 | +++ |
| 299 | +++ |
| 300 | + |
| 301 | ++ |
| 302 | + |
| 303 | + |
| 304 | +++ |
| 305 | + |
| 306 | ++ |
| 307 | + |
| 308 | ++ |
| 309 | ++ |
| 310 | ++ |
| 311 | +++ |
| 312 | +++ |
| 313 | +++ |
| 314 | +++ |
| 315 | + |
| 316 | + |
| 317 | + |
| 318 | + |
| 319 | + |
| 320 | + |
| 321 | + |
| 322 | + |
| 323 | + |
| 324 | +++ |
| 325 | + |
| 326 | + |
| 327 | ++ |
| 328 | + |
| 329 | + |
| 331 | + |
| 332 | + |
| 333 | + |
| 334 | + |
| 335 | + |
| 336 | + |
| 337 | + |
| 338 | + |
| 339 | + |
| 340 | + |

TABLE 1-continued

| compounds | % inhibition at 10 uM |
|---|---|
| 341 | ++ |
| 342 | + |
| 343 | + |
| 344 | + |
| 345 | + |
| 346 | + |
| 347 | +++ |
| 348 | + |
| 349 | ++ |
| 350 | + |
| 351 | + |
| 352 | + |
| 353 | + |
| 354 | + |
| 355 | + |
| 356 | ++ |
| 357 | + |
| 358 | + |
| 359 | + |
| 360 | ++ |
| 361 | + |
| 362 | + |
| 363 | + |
| 364 | + |
| 365 | + |
| 366 | + |
| 367 | + |
| 368 | + |
| 369 | + |
| 370 | + |
| 371 | + |
| 372 | + |
| 373 | ++ |
| 374 | + |
| 375 | +++ |
| 376 | +++ |
| 377 | + |
| 378 | + |

Activity range:
+++ indicates >69%,
++ indicates between 40-69%,
+ indicates <40%

TABLE 2

| # cpds | 5-LO(IC$_{50}$, uM) |
|---|---|
| 55 | ++ |
| 58 | ++ |
| 70 | ++ |
| 75 | ++ |
| 86 | ++ |
| 100 | ++ |
| 103 | ++ |
| 110 | + |
| 123 | + |
| 124 | ++ |
| 126 | ++ |
| 127 | + |
| 128 | +++ |
| 130 | ++ |
| 148 | ++ |
| 157 | ++ |
| 161 | ++ |
| 164 | ++ |
| 174 | ++ |
| 175 | ++ |
| 181 | ++ |
| 189 | +++ |
| 190 | ++ |
| 193 | + |
| 194 | + |
| 197 | + |
| 207 | ++ |

TABLE 2-continued

| # cpds | 5-LO(IC$_{50}$, uM) |
|---|---|
| 208 | ++ |
| 211 | ++ |
| 217 | ++ |
| 219 | +++ |
| 223 | ++ |
| 224 | +++ |
| 225 | +++ |
| 227 | ++ |
| 228 | ++ |
| 231 | ++ |
| 232 | +++ |
| 243 | +++ |
| 260 | + |
| 265 | +++ |
| 266 | +++ |
| 295 | + |
| 298 | ++ |
| 299 | +++ |
| 304 | ++ |
| 309 | ++ |
| 310 | ++ |
| 311 | +++ |
| 312 | +++ |
| 313 | ++ |
| 314 | ++ |
| 330 | + |
| 379 | ++ |
| 380 | +++ |
| 381 | ++ |
| 382 | ++ |
| 383 | + |
| 384 | ++ |
| 385 | + |
| 386 | ++ |
| 387 | + |
| 388 | + |
| 389 | + |
| 390 | ++ |
| 391 | ++ |
| 392 | ++ |
| 393 | +++ |
| 394 | +++ |
| 395 | +++ |
| 396 | +++ |
| 397 | + |
| 398 | +++ |
| 399 | +++ |
| 400 | +++ |
| 401 | +++ |
| 402 | +++ |
| 403 | +++ |

Activity range:
+++ indicates <1 uM,
++ indicates between 1-20 uM,
+ indicates >20 uM

TABLE 3

| compounds | LTB4 secretion assay (EC$_{50}$, uM) |
|---|---|
| 127 | +++ |
| 187 | ++ |
| 311 | ++ |
| 312 | +++ |
| 313 | +++ |
| 314 | +++ |

Activity range:
+++ indicates <1 uM,
++ indicates between 1-20 uM,
+ indicates >20 uM

TABLE 4

| | Log₁₀CFU | SEM | n |
|---|---|---|---|
| 127 (50 mg/kg) | 6.47 | 0.16 | 5/5 |
| INH (25 mg/kg) | 5.0 | 0.11 | 5/5 |
| Untreated | 7.24 | 0.17 | 5/5 |

The invention claimed is:

1. A method for treating an inflammatory disease, comprising the application or administration, to a patient in need of such treatment, of an effective amount of a compound having the general formula I:

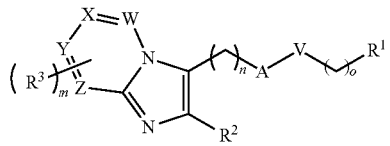

wherein n is 0, 1, 2, or 3;

m is 0, 1, 2, or 3;

o is 0, 1, 2, or 3;

W, X, Y and Z are independently selected from CH, N or N-oxide;

A is $NR^4$, C=O, C=S, OP(O), P=O, $CH_2$, or a heteroaryl selected from the group consisting of

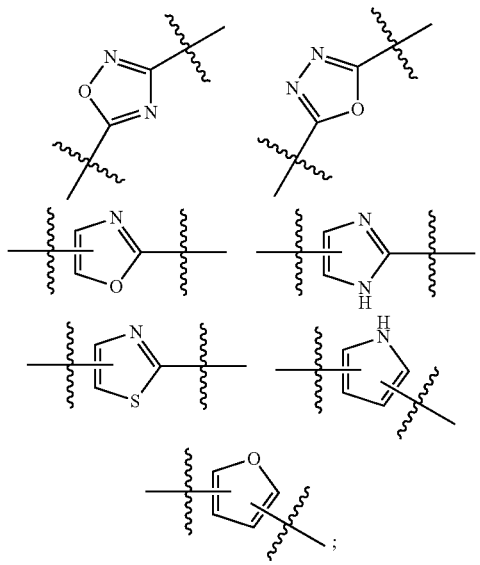

V is C=O, O, S, $CH_2$ or $NR^5$;

$R^1$ is a moiety selected from the group consisting of

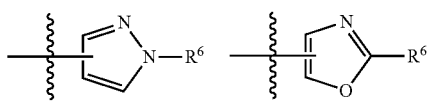

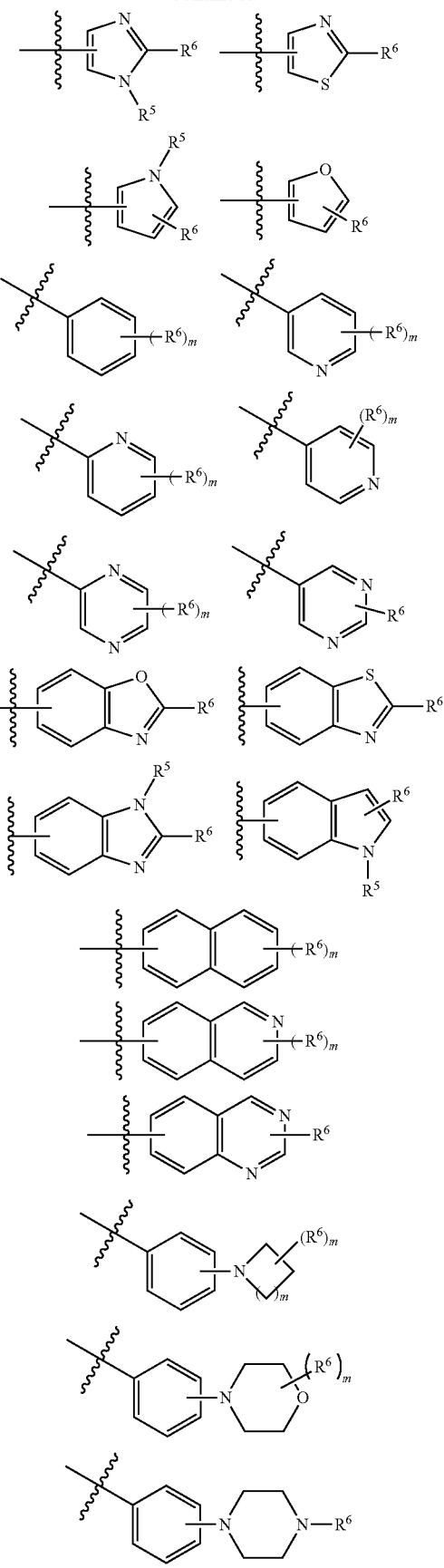

-continued

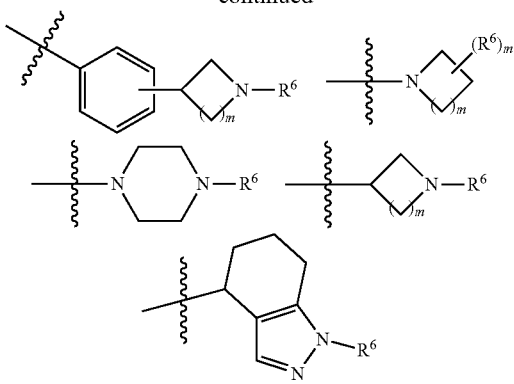

m and n being, independently at each occurrence, selected from 0, 1, 2 or 3;

$R^2$ is, at each occurrence, independently, selected from the group consisting of hydrogen, halogen, $C_1$-$C_{10}$ alkyl, $C_3$-$C_{10}$cycloalkyl, $C_2$-$C_{10}$ alkenyl, $C_3$-$C_{10}$cycloalkenyl, $C_2$-$C_{10}$alkynyl, $C_1$-$C_{10}$haloalkyl, —OH, —OR$^5$, $C_1$-$C_{10}$ alkoxy, $C_3$-$C_{10}$cycloalkoxy, $C_3$-$C_{15}$cycloalkylalkoxy, $C_3$-$C_{15}$cycloalkylalkyl, —CN, —NO$_2$, —NH$_2$, —N(R$^5$)$_2$, —C(O)R$^5$, —C(O)OR$^5$, —C(O)N(R$^5$)$_2$, —P(O)OR$^5$, —P(O)OR$^5$N(R$^5$)$_2$, —SR$^5$, —S(O)R$^5$, —S(O)$_2$R$^5$, —S(O)$_2$N(R$^5$)$_2$, and heterocyclyl, any of which is optionally substituted;

$R^3$ is, at each occurrence, independently selected from the group consisting of hydrogen, halogen, $C_1$-$C_{10}$ alkyl, $C_3$-$C_{10}$cycloalkyl, $C_1$-$C_3$ haloalkyl, hydroxyl, —OR$^6$, —CN, —NO$_2$, —NH$_2$, —N(R$^6$)C(O)R$^6$, —C(O)R$^6$, —C(O)OR$^6$, —C(O)N(R$^6$)$_2$, —S(O)R$^6$, —S(O)$_2$R$^6$, —S(O)$_2$N(R$^6$)$_2$, aryl, and heterocyclyl, any of which is optionally substituted, or two groups of R$^3$ are connected to each other to make a five or six membered cyclic or heterocyclic ring, any of which is optionally substituted;

$R^4$ and $R^5$ are, at each occurrence, independently selected from the group consisting of hydrogen, $C_1$-$C_{10}$ alkyl, $C_3$-$C_{10}$cycloalkyl, $C_2$-$C_{10}$ alkenyl, $C_3$-$C_{10}$ cycloalkenyl, $C_2$-$C_{10}$alkynyl, $C_1$-$C_{10}$haloalkyl, —OH, —OR$^7$, $C_1$-$C_{10}$alkoxy, $C_3$-$C_{10}$cycloalkoxy, $C_3$-$C_{15}$cycloalkylalkoxy, $C_3$-$C_{15}$cycloalkylalkyl, —NH$_2$, —N(R$^7$)$_2$, —C(O)R$^7$, —C(O)OR$^7$, —C(O)N(R$^7$)$_2$, —S(O)R$^7$, —S(O)$_2$R$^7$, —S(O)$_2$N(R$^7$)$_2$, aryl, and heterocyclyl, any of which is optionally substituted;

$R^6$ is, at each occurrence, independently selected from the group consisting of hydrogen, $C_1$-$C_{10}$ alkyl, $C_3$-$C_{10}$cyclo alkyl, $C_2$-$C_{10}$ alkenyl, $C_3$-$C_{10}$ cycloalkenyl, $C_2$-$C_{10}$alkynyl, $C_1$-$C_{10}$haloalkyl, hydroxyl, —OR$^8$, —C(O)R$^8$, —R$^8$(R$^8$)C(O)R$^8$, —C(O)OR$^8$, —R$^8$(R$^8$)C(O)OR$^8$, —CN, —NO$_2$, —NH$_2$, —N(R$^8$)$_2$, —C(O)N(R$^8$)$_2$, —R$^8$(R$^8$)C(O)N(R$^8$)$_2$, —S(O)R$^8$, —S(O)$_2$R$^8$, —S(O)$_2$N(R$^8$)$_2$, aryl, and heterocyclyl, any of which is optionally substituted;

$R^7$ is, at each occurrence, independently selected from the group consisting of hydrogen, $C_1$-$C_{10}$ alkyl, $C_3$-$C_{10}$cycloalkyl, $C_2$-$C_{10}$ alkenyl, $C_3$-$C_{10}$cycloalkenyl, $C_2$-$C_{10}$alkynyl, $C_1$-$C_{10}$haloalkyl, aryl, and heterocyclyl, any of which is optionally substituted; and $R^8$ is, at each occurrence, independently selected from the group consisting of hydrogen, $C_1$-$C_8$ alkyl optionally substituted with at least one hydroxyl or halogen; $C_3$-$C_7$cycloalkyl, $C_2$-$C_{10}$alkenyl, $C_3$-$C_{10}$ cycloalkenyl, $C_2$-$C_{10}$alkynyl, $C_1$-$C_{10}$haloalkyl, aryl, and heterocyclyl, any of which is optionally substituted, or a pharmaceutically acceptable salt thereof.

2. The method use according to claim 1, wherein said compound has an inhibitory activity on an enzyme involved in an inflammatory pathway, at a concentration of said compound between 0.01-30 µM, having an IC$_{50}$ on arachidonate 5-lipoxygenase of less than 1 µM and/or having an EC$_{50}$ of less than 1 µM on the production of leukotriene B4 (LTB4) in peripheral blood mononuclear cells (PBMC).

3. The method according to claim 1, wherein said compound has a formula selected from:

Ethyl 2-methylimidazo[1,2-a]pyridine-3-carboxylate (1)

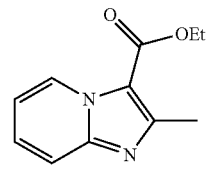

2-Methylimidazo[1,2-a]pyridine-3-carboxylic acid (2)

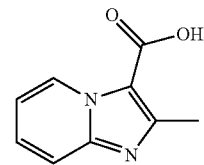

N-Benzyl-2-methylimidazo[1,2-a]pyridine-3-carboxamide (3)

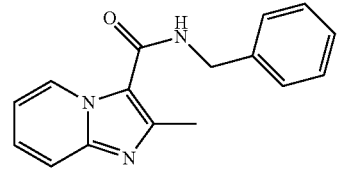 [SMILES: Cc1nc2ccccn2c1C(=O)NCc1ccccc1]

N-(4-Fluorobenzyl)-2-methylimidazo[1,2-a]pyridine-3-carboxamide (4)

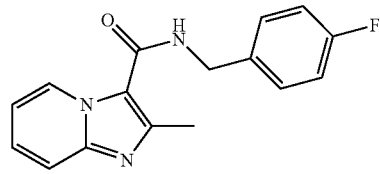 [SMILES: Cc1nc2ccccn2c1C(=O)NCc1ccc(F)cc1]

2-Methyl-N-(pyridin-3-ylmethyl)imidazo[1,2-a]pyridine-3-carboxamide (5)

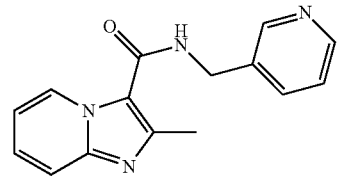 [SMILES: Cc1nc2ccccn2c1C(=O)NCc1cccnc1]

2-Methyl-N-(4-phenoxybenzyl)imidazo[1,2-a]pyridine-3-carboxamide (6)

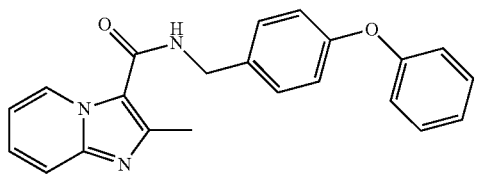

N-(4-Methoxybenzyl)-2-methylimidazo[1,2-a]pyridine-3-carboxamide (7)

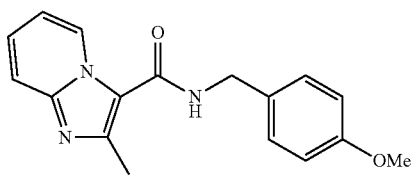 [SMILES: COc1ccc(CNC(=O)c2c(C)nc3ccccn23)cc1]

N-(4-Methoxyphenethyl)-2-methylimidazo[1,2-a]pyridine-3-carboxamide (8)

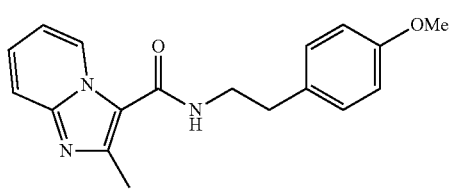 [SMILES: COc1ccc(CCNC(=O)c2c(C)nc3ccccn23)cc1]

N-(Cyclohexylmethyl)-2-methylimidazo[1,2-a]pyridine-3-carboxamide (9)

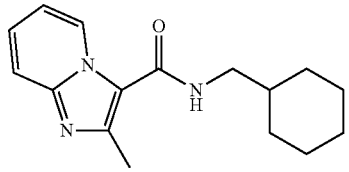 [SMILES: Cc1nc2ccccn2c1C(=O)NCC1CCCCC1]

tert-Butyl 4-((2-methylimidazo[1,2-a]pyridine-3-carboxamido)methyl)piperidine-1-carboxylate (10)

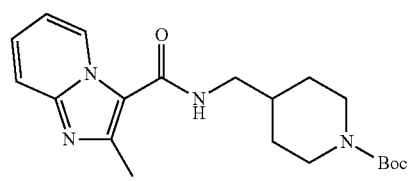 [SMILES: Cc1nc2ccccn2c1C(=O)NCC1CCN(C(=O)OC(C)(C)C)CC1]

2-Methyl-N-(pyridin-4-yl)imidazo[1,2-a]pyridine-3-carboxamide (11)

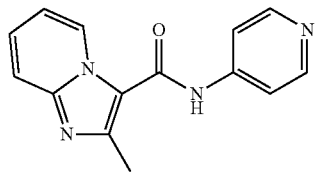 [SMILES: Cc1nc2ccccn2c1C(=O)Nc1ccncc1]

2-Methyl-N-phenethylimidazo[1,2-a]pyridine-3-carboxamide (12)

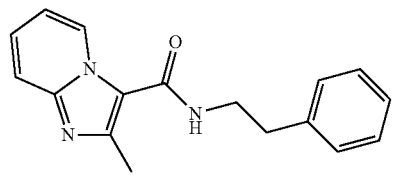 [SMILES: Cc1nc2ccccn2c1C(=O)NCCc1ccccc1]

2-Methyl-N-(4-phenoxyphenyl)imidazo[1,2-a]pyridine-3-carboxamide (13)

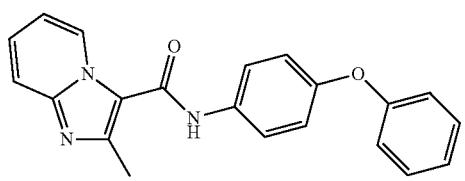 [SMILES: Cc1nc2ccccn2c1C(=O)Nc1ccc(Oc2ccccc2)cc1]

N-(4-Benzyloxy)phenyl)-2-methylimidazo[1,2-a]pyridine-3-carboxamide (14)

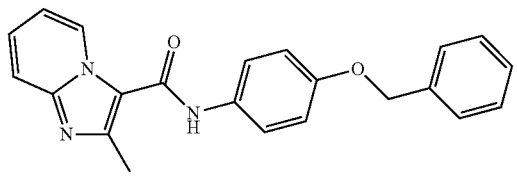 [SMILES: Cc1nc2ccccn2c1C(=O)Nc1ccc(OCc2ccccc2)cc1]

N-Benzyl-8-chloro-2-methylimidazo[1,2-a]pyridine-3-carboxamide (15)

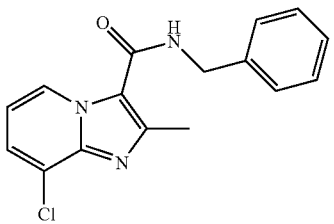 [SMILES: Cc1nc2c(Cl)cccn2c1C(=O)NCc1ccccc1]

N-Benzyl-7-chloro-2-methylimidazo[1,2-a]pyridine-3-carboxamide (16)

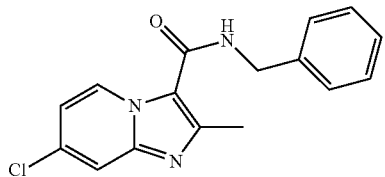 [SMILES: Cc1nc2cc(Cl)ccn2c1C(=O)NCc1ccccc1]

N-Benzyl-6-chloro-2-methylimidazo[1,2-a]pyridine-3-carboxamide (17)

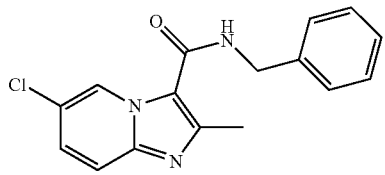 [SMILES: Cc1nc2ccc(Cl)cn2c1C(=O)NCc1ccccc1]

Ethyl 2-methyl-7-phenylimidazo[1,2-a]pyridine-3-carboxylate (18)

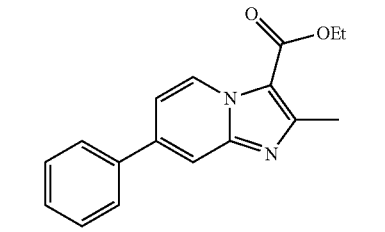 [SMILES: CCOC(=O)c1c(C)nc2cc(-c3ccccc3)ccn12]

2-Methyl-7-phenylimidazo[1,2-a]pyridine-3-carboxylic acid (19)

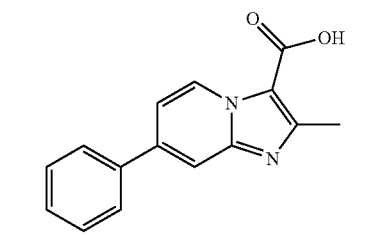 [SMILES: Cc1nc2cc(-c3ccccc3)ccn2c1C(=O)O]

N-(Biphenyl-4-ylmethyl)-2-methylimidazo[1,2-a]pyridine-3-carboxamide (20)

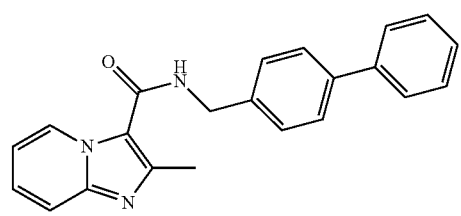 [SMILES: Cc1nc2ccccn2c1C(=O)NCc1ccc(-c2ccccc2)cc1]

N-((1H-Indol-5-yl)methyl)-2-methylimidazo[1,2-a]pyridine-3-carboxamide (21)

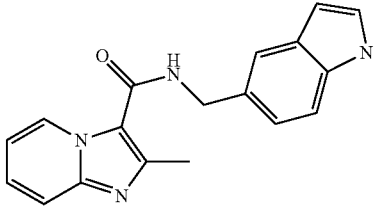 [SMILES: Cc1nc2ccccn2c1C(=O)NCc1ccc2[nH]ccc2c1]

N-Benzyl-2-methyl-7-phenylimidazo[1,2-a]pyridine-3-carboxamide (22)

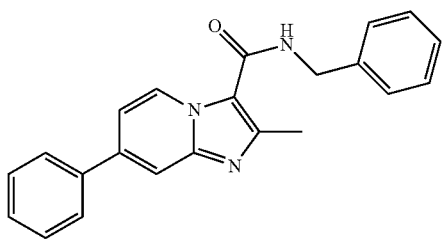 [SMILES: Cc1nc2cc(-c3ccccc3)ccn2c1C(=O)NCc1ccccc1]

(S)-Methyl 2-(2-methylimidazo[1,2-a]pyridine-3-carboxamido)-3-phenylpropanoate (23)

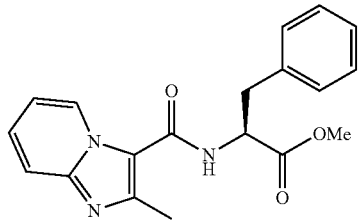 [SMILES: COC(=O)[C@H](Cc1ccccc1)NC(=O)c1c(C)nc2ccccn12]

2-Methyl-N-(piperidin-4-ylmethyl)imidazo[1,2-a]pyridine-3-carboxamide (24)

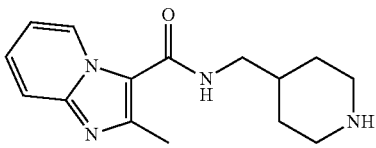 [SMILES: Cc1nc2ccccn2c1C(=O)NCC1CCNCC1]

Methyl 4-((2-methylimidazo[1,2-a]pyridine-3-carboxamido)methyl)benzoate (25)

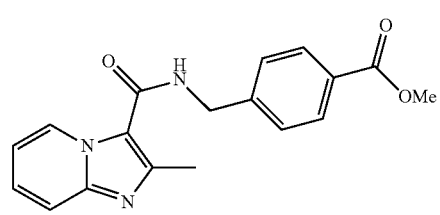 [SMILES: COC(=O)c1ccc(CNC(=O)c2c(C)nc3ccccn23)cc1]

4-((2-Methylimidazo[1,2-a]pyridine-3-carboxamido)methyl)benzoic acid (26)

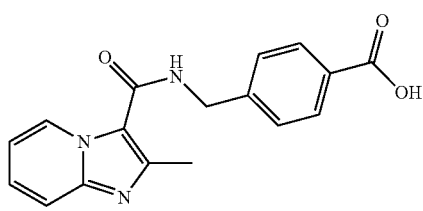 [SMILES: Cc1nc2ccccn2c1C(=O)NCc1ccc(C(=O)O)cc1]

Ethyl 2-methyl-6-phenylimidazo[1,2-a]pyridine-3-carboxylate (27)

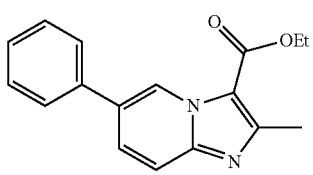 [SMILES: CCOC(=O)c1c(C)nc2ccc(-c3ccccc3)cn12]

2-Methyl-N-(2-phenoxyethyl)imidazo[1,2-a]pyridine-3-carboxamide (28)

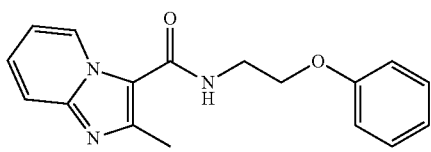 [SMILES: Cc1nc2ccccn2c1C(=O)NCCOc1ccccc1]

N-(2-(Benzyloxy)ethyl)-2-methylimidazo[1,2-a]pyridine-3-carboxamide (29)

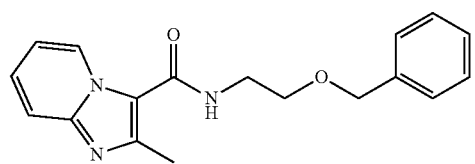 [SMILES: Cc1nc2ccccn2c1C(=O)NCCOCc1ccccc1]

N-Benzyl-6-cyano-2-methylimidazo[1,2-a]pyridine-3-carboxamide (30)

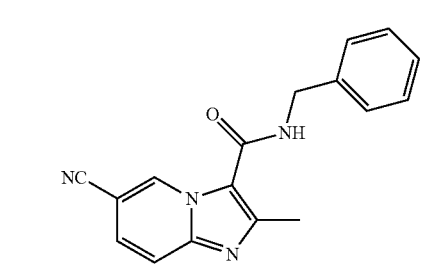 [SMILES: Cc1nc2ccc(C#N)cn2c1C(=O)NCc1ccccc1]

N-Benzyl-2,8-dimethylimidazo[1,2-a]pyridine-3-carboxamide (31)

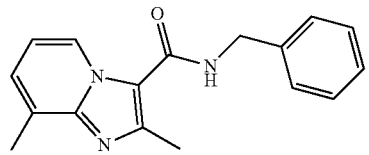 [SMILES: Cc1nc2c(C)cccn2c1C(=O)NCc1ccccc1]

N-Benzyl-2,7-dimethylimidazo[1,2-a]pyridine-3-carboxamide (32)

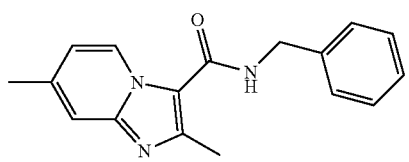 [SMILES: Cc1ccn2c(C(=O)NCc3ccccc3)c(C)nc2c1]

N-Benzyl-2,6-dimethylimidazo[1,2-a]pyridine-3-carboxamide (33)

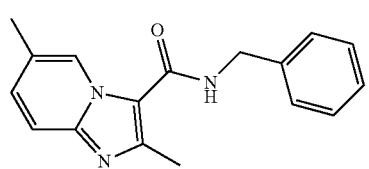 [SMILES: Cc1ccc2nc(C)c(C(=O)NCc3ccccc3)n2c1]

N-Benzyl-2,5-dimethylimidazo[1,2-a]pyridine-3-carboxamide (34)

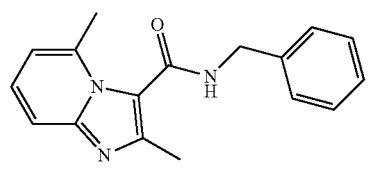

N-Benzyl-8-fluoro-2-methylimidazo[1,2-a]pyridine-3-carboxamide (35)

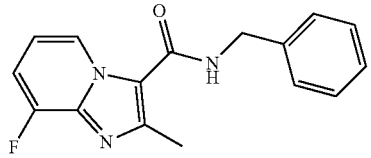 [SMILES: Cc1nc2c(F)cccn2c1C(=O)NCc1ccccc1]

N-Benzyl-2-methyl-8-(trifluromethyl)imidazo[1,2-a]pyridine-3-carboxamide (36)

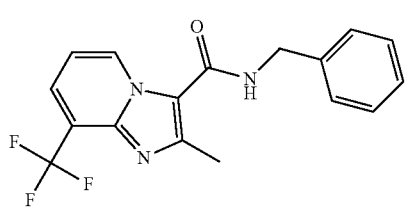 [SMILES: Cc1nc2c(C(F)(F)F)cccn2c1C(=O)NCc1ccccc1]

N-Benzyl-2-propylimidazo[1,2-a]pyridine-3-carboxamide (37)

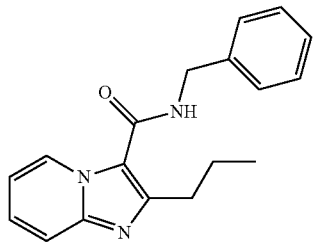 [SMILES: CCCc1nc2ccccn2c1C(=O)NCc1ccccc1]

N-Benzyl-2-cyclopropylimidazo[1,2-a]pyridine-3-carboxamide (38)

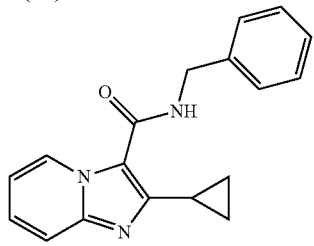

N-Benzyl-2-methyl-6-phenylimidazo[1,2-a]pyridine-3-carboxamide (39)

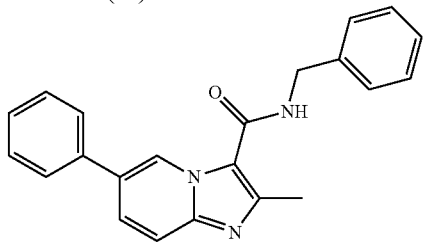

N-Benzyl-6-fluoro-2-methylimidazo[1,2-a]pyridine-3-carboxamide (40)

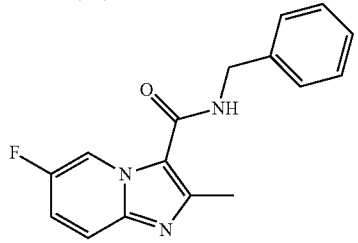 [SMILES: Cc1nc2ccc(F)cn2c1C(=O)NCc1ccccc1]

N-(2-Methylimidazo[1,2-a]pyridin-3-yl)-2-phenylacetamide (41)

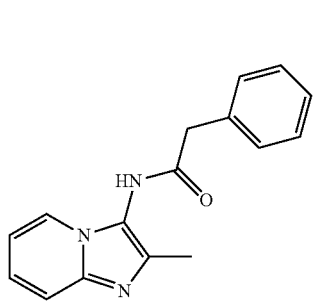 [SMILES: Cc1nc2ccccn2c1NC(=O)Cc1ccccc1]

N-Benzyl-7-cyano-2-methylimidazo[1,2-a]pyridine-3-carboxamide (42)

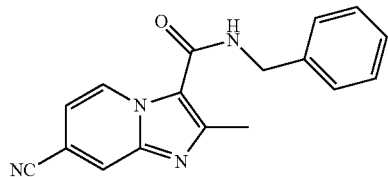 [SMILES: Cc1nc2cc(C#N)ccn2c1C(=O)NCc1ccccc1]

N-(Biphenyl-4-ylmethyl)-6-chloro-2-methylimidazo[1,2-a]pyridine-3-carboxamide (43)

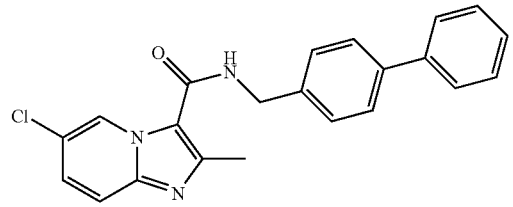 [SMILES: Cc1nc2ccc(Cl)cn2c1C(=O)NCc1ccc(-c2ccccc2)cc1]

N-(Biphenyl-4-ylmethyl)-7-chloro-2-methylimidazo[1,2-a]pyridine-3-carboxamide (44)

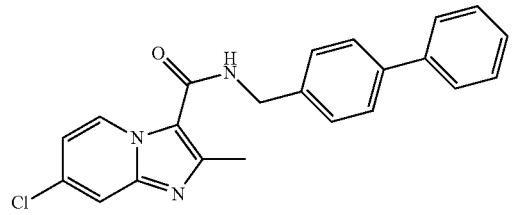 [SMILES: Cc1nc2cc(Cl)ccn2c1C(=O)NCc1ccc(-c2ccccc2)cc1]

2-Ethyl-N-(4-phenoxybenzyl)imidazo[1,2-a]pyridine-3-carboxamide (45)

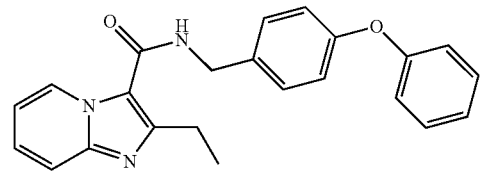 [SMILES: CCc1nc2ccccn2c1C(=O)NCc1ccc(Oc2ccccc2)cc1]

N-(Biphenyl-4-ylmethyl)-2-propylimidazo[1,2-a]pyridine-3-carboxamide (46)

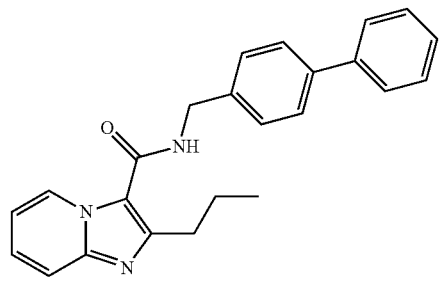 [SMILES: CCCc1nc2ccccn2c1C(=O)NCc1ccc(-c2ccccc2)cc1]

N-Benzyl-8-cyano-2-methylimidazo[1,2-a]pyridine-3-carboxamide (47)

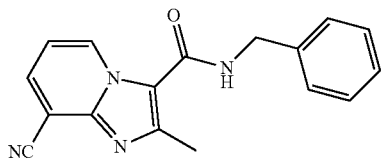 [SMILES: Cc1nc2c(C#N)cccn2c1C(=O)NCc1ccccc1]

N-Benzyl-8-hydroxy-2-methylimidazo[1,2-a]pyridine-3-carboxamide (48)

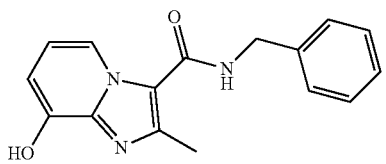

N-(4-tert-Butylbenzyl)-2-ethylimidazo[1,2-a]pyridine-3-carboxamide (49)

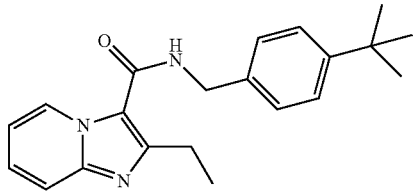 [SMILES: CCc1nc2ccccn2c1C(=O)NCc1ccc(C(C)(C)C)cc1]

2-Ethyl-N-((1-methyl-1H-indol-5-yl)methyl)imidazo[1,2-a]pyridine-3-carboxamide (50)

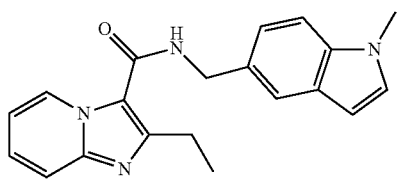 [SMILES: CCc1nc2ccccn2c1C(=O)NCc1ccc2c(ccn2C)c1]

2-Ethyl-N-(4-(trifluoromethoxy)benzyl)imidazo[1,2-a]pyridine-3-carboxamide (51)

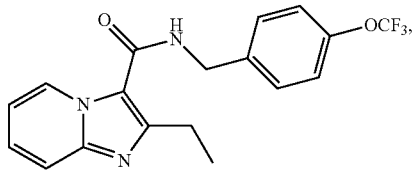 [SMILES: CCc1nc2ccccn2c1C(=O)NCc1ccc(OC(F)(F)F)cc1]

2-Ethyl-N-(4-trifluoromethoxy)benzyl)imidazo[1,2-a]pyridine-3-carboxamide (52)

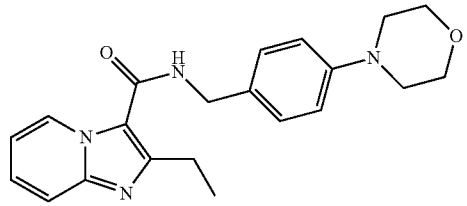 [SMILES: CCc1nc2ccccn2c1C(=O)NCc1ccc(N2CCOCC2)cc1]

2-Ethyl-N-(4-isopropoxybenzyl)imidazo[1,2-a]pyridine-3-carboxamide (53)

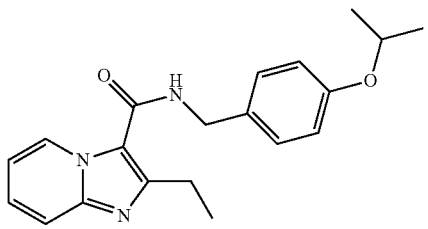 [SMILES: CCc1nc2ccccn2c1C(=O)NCc1ccc(OC(C)C)cc1]

2-Ethyl-N-(4-isobutoxybenzyl)imidazo[1,2-a]pyridine-3-carboxamide (54)

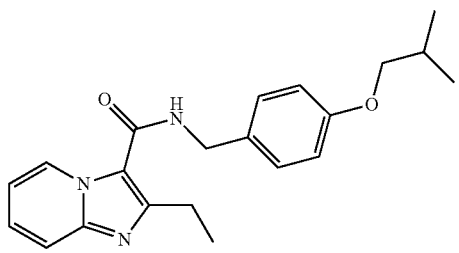 [SMILES: CCc1nc2ccccn2c1C(=O)NCc1ccc(OCC(C)C)cc1]

6-Chloro-2-ethyl-N-(4-(trifluoromethoxy)benzyl)imidazo[1,2-a]pyridine-3-carboxamide (55)

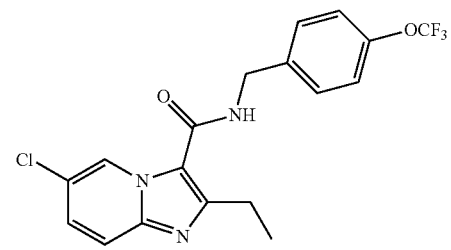 [SMILES: CCc1nc2ccc(Cl)cn2c1C(=O)NCc1ccc(OC(F)(F)F)cc1]

7-Chloro-2-ethyl-N-((4'-fluorobiphenyl-4-yl)methyl)imidazo[1,2-a]pyridine-3-carboxamide (56)

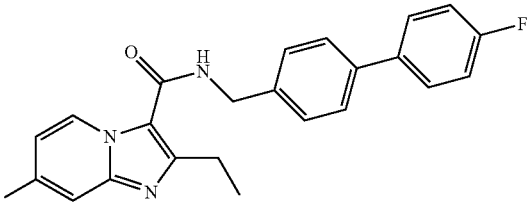

N-(Biphenyl-4-ylmethyl)-2-ethyl-6-methylimidazo[1,2-a]pyridine-3-carboxamide (57)

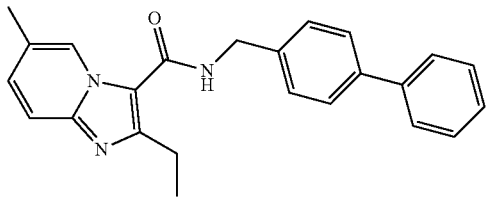 [SMILES: CCc1nc2ccc(C)cn2c1C(=O)NCc1ccc(-c2ccccc2)cc1]

2-Ethyl-6-methyl-N-(4-phenoxybenzyl)imidazo[1,2-a]pyridine-3-carboxamide (58)

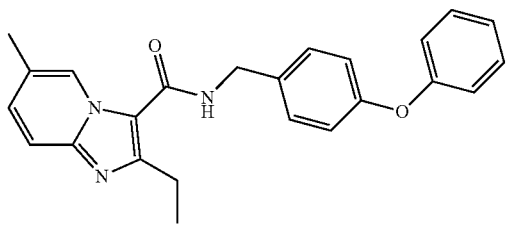 [SMILES: CCc1nc2ccc(C)cn2c1C(=O)NCc1ccc(Oc2ccccc2)cc1]

2-Ethyl-6-methyl-N-(4-(trifluoromethoxy)benzyl)imidazo[1,2-a]pyridine-3-carboxamide (59)

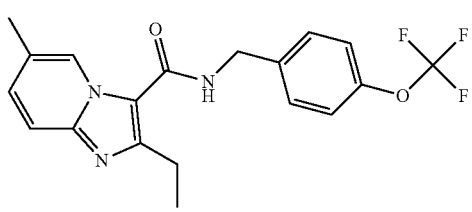 [SMILES: CCc1nc2ccc(C)cn2c1C(=O)NCc1ccc(OC(F)(F)F)cc1]

2-Ethyl-6-methyl-N-((1-methyl-1H-indol-6-yl)methyl)imidazo[1,2-a]pyridine-3-carboxamide (60)

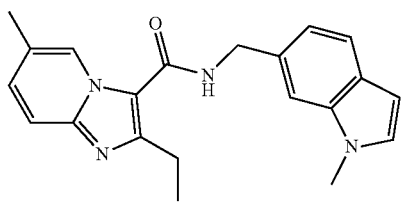 [SMILES: CCc1nc2ccc(C)cn2c1C(=O)NCc1ccc2ccn(C)c2c1]

N-(Biphenyl-4-ylmethyl)-6-chloro-2-methylimidazo[1,2-a]pyridine-3-carboxamide (61)

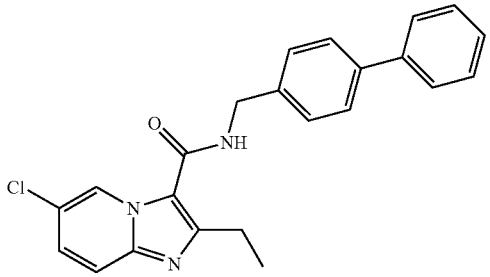 [SMILES: CCc1nc2ccc(Cl)cn2c1C(=O)NCc1ccc(-c2ccccc2)cc1]

6-Chloro-2-methyl-N-(4-phenoxybenzyl)imidazo[1,2-a]pyridine-3-carboxamide (62)

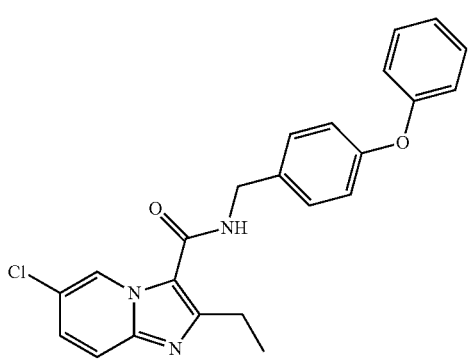 [SMILES: CCc1nc2ccc(Cl)cn2c1C(=O)NCc1ccc(Oc2ccccc2)cc1]

N-(4-tert-Butylbenzyl)-6-chloro-2-methylimidazo[1,2-a]pyridine-3-carboxamide (63)

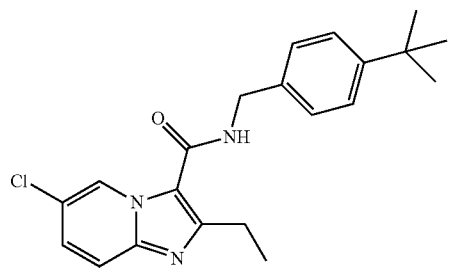 [SMILES: CCc1nc2ccc(Cl)cn2c1C(=O)NCc1ccc(C(C)(C)C)cc1]

6-Chloro-2-methyl-N-(4-morpholinobenzyl)imidazo[1,2-a]pyridine-3-carboxamide (64)

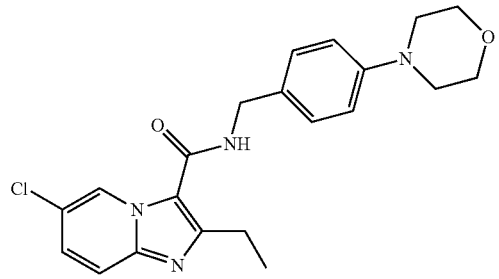 [SMILES: CCc1nc2ccc(Cl)cn2c1C(=O)NCc1ccc(N2CCOCC2)cc1]

6-Chloro-N-(4-isopropoxybenzyl)-2-methylimidazo[1,2-a]pyridine-3-carboxamide (65)

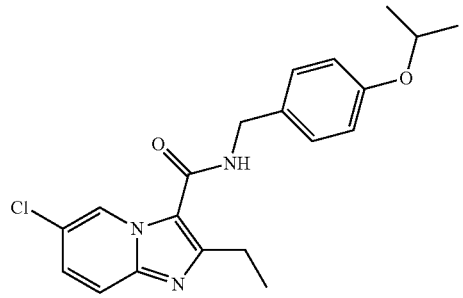 [SMILES: CCc1nc2ccc(Cl)cn2c1C(=O)NCc1ccc(OC(C)C)cc1]

6-Chloro-N-(4-isobutoxybenzyl)-2-methylimidazo[1,2-a]pyridine-3-carboxamide (66)

7-Chloro-2-ethyl-N-(4-(4-(4-fluorophenoxy)piperidin-1-yl)benzyl)imidazo[1,2-a]pyridine-3-carboxamide (70)

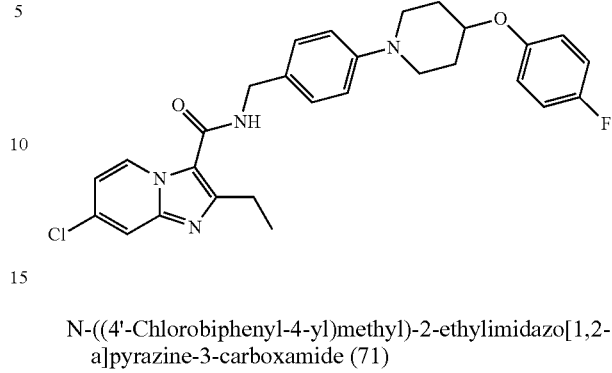

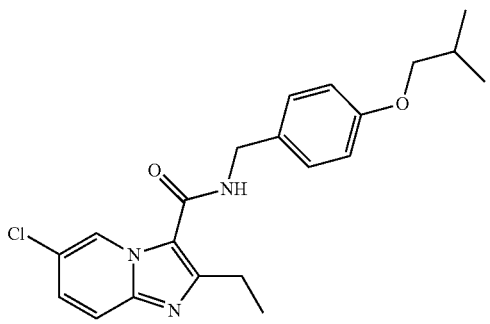 [SMILES: CCc1nc2ccc(Cl)cn2c1C(=O)NCc1ccc(OCC(C)C)cc1]

N-((4'-Chlorobiphenyl-4-yl)methyl)-2-ethylimidazo[1,2-a]pyrazine-3-carboxamide (71)

6-Chloro-2-methyl-N-((1-methyl-1H-indol-5-yl)methyl)imidazo[1,2-a]pyridine-3-carboxamide (67)

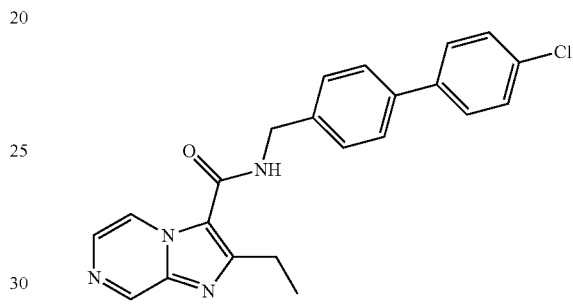

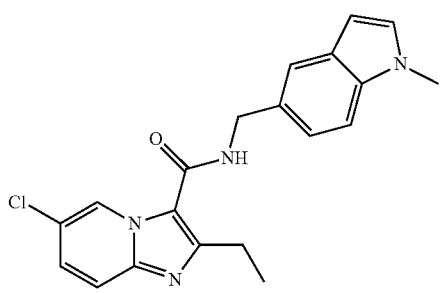 [SMILES: CCc1nc2ccc(Cl)cn2c1C(=O)NCc1ccc2c(ccn2C)c1]

6-Chloro-N-((2'-chlorobiphenyl-4-yl)methyl)-2-ethylimidazo[1,2-a]pyridine-3-carboxamide (72)

6-Chloro-2-methyl-N-((1-methyl-1H-indol-6-yl)methyl)imidazo[1,2-a]pyridine-3-carboxamide (68)

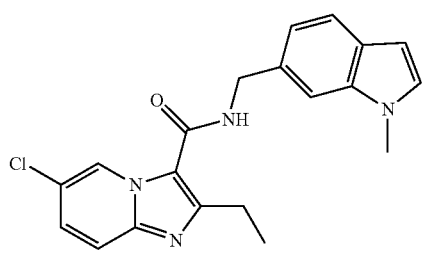 [SMILES: CCc1nc2ccc(Cl)cn2c1C(=O)NCc1ccc2ccn(C)c2c1]

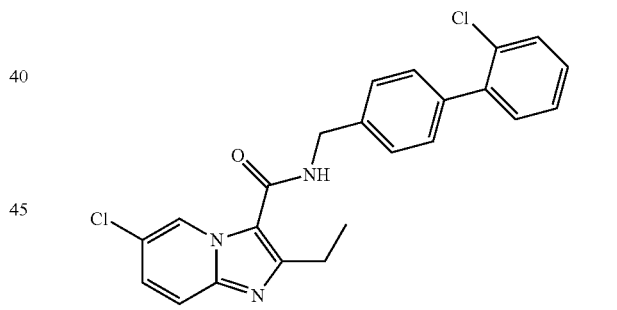

6-Chloro-N-((4'-chlorobiphenyl-4-yl)methyl)-2-ethylimidazo[1,2-a]pyridine-3-carboxamide (73)

2-Ethyl-6-nitro-N-(4-(trifluoromethoxy)benzyl)imidazo[1,2-a]pyridine-3-carboxamide (69)

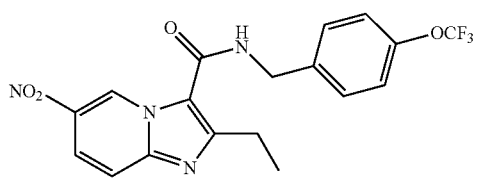 [SMILES: CCc1nc2ccc([N+](=O)[O-])cn2c1C(=O)NCc1ccc(OC(F)(F)F)cc1]

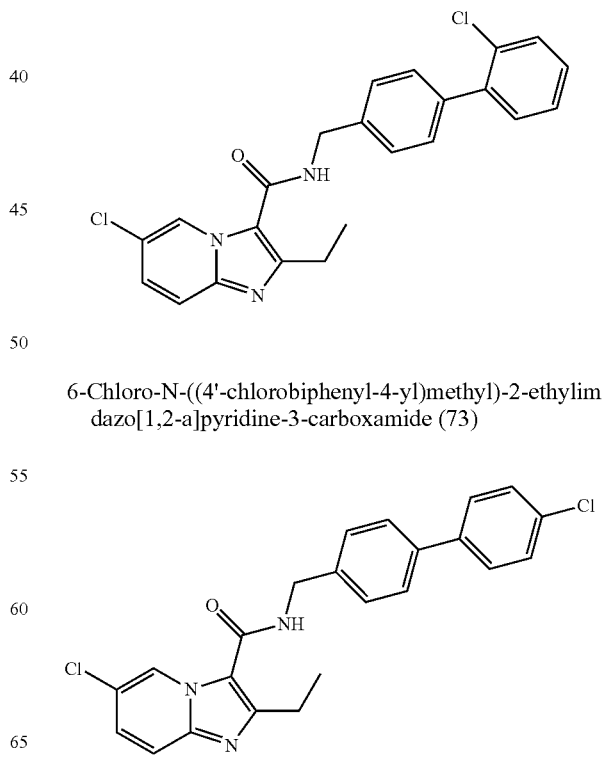

6-Chloro-2-ethyl-N-(4-(piperidin-1-yl)benzyl)imidazo[1,2-a]pyridine-3-carboxamide (74)

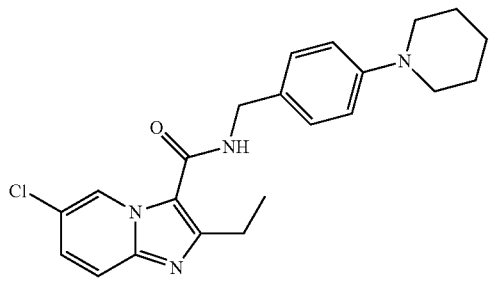 [SMILES: CCc1nc2ccc(Cl)cn2c1C(=O)NCc1ccc(N2CCCCC2)cc1]

6-Chloro-2-ethyl-N-((2'-methylbiphenyl-4-yl)methyl)imidazo[1,2-a]pyridine-3-carboxamide (75)

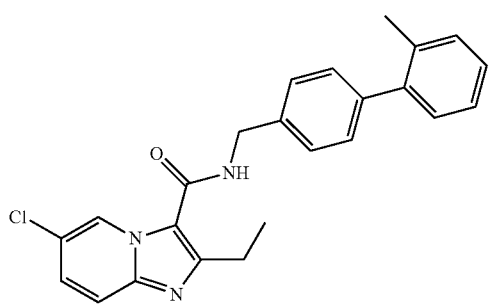 [SMILES: CCc1nc2ccc(Cl)cn2c1C(=O)NCc1ccc(-c2ccccc2C)cc1]

6-Chloro-2-ethyl-N-((3'-methylbiphenyl-4-yl)methyl)imidazo[1,2-a]pyridine-3-carboxamide (76)

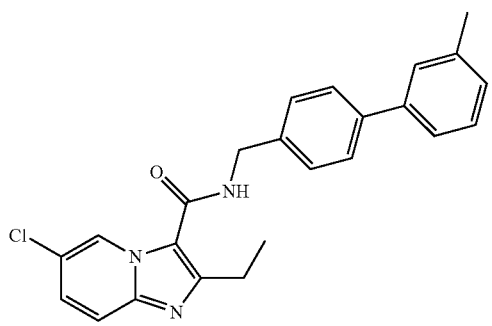 [SMILES: CCc1nc2ccc(Cl)cn2c1C(=O)NCc1ccc(-c2cccc(C)c2)cc1]

6-Chloro-2-ethyl-N-((4'-methylbiphenyl-4-methyl)imidazo[1,2-a]pyridine-3-carboxamide (77)

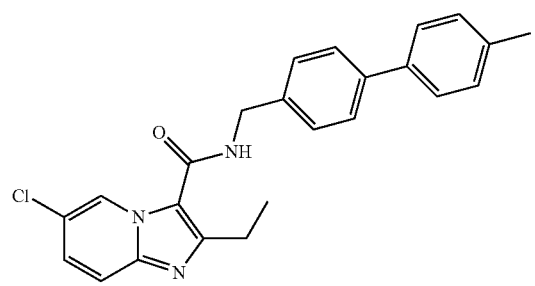 [SMILES: CCc1nc2ccc(Cl)cn2c1C(=O)NCc1ccc(-c2ccc(C)cc2)cc1]

6-Chloro-N-(4-chlorobenzyl)-2-ethylimidazo[1,2-a]pyridine-3-carboxamide (78)

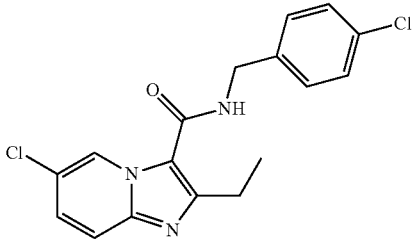 [SMILES: CCc1nc2ccc(Cl)cn2c1C(=O)NCc1ccc(Cl)cc1]

6-Chloro-2-ethyl-N-(naphthalen-2-ylmethyl)imidazo[1,2-a]pyridine-3-carboxamide (79)

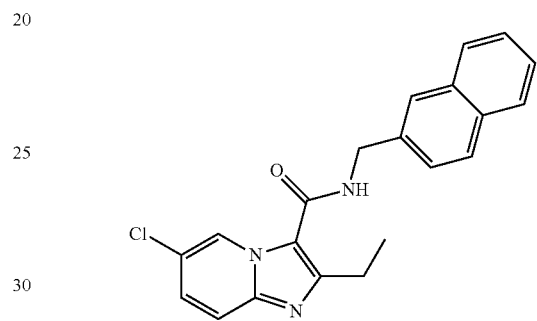

N-(Biphenyl-4-ylmethyl)-6-chloro-2-(trifluoromethyl)imidazo[1,2-a]pyridine-3-carboxamide (80)

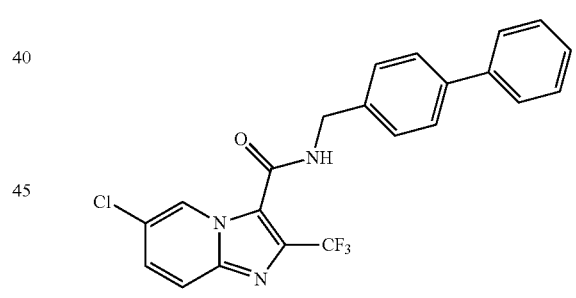

N-(4-tert-Butylbenzyl)-6-chloro-2-(trifluoromethyl)imidazo[1,2-a]pyridine-3-carboxamide (81)

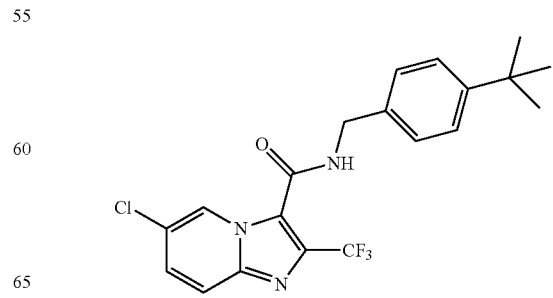

7-Chloro-N-((2'-chlorobiphenyl-4-yl)methyl)-2-ethylimidazo[1,2-a]pyridine-3-carboxamide (82)

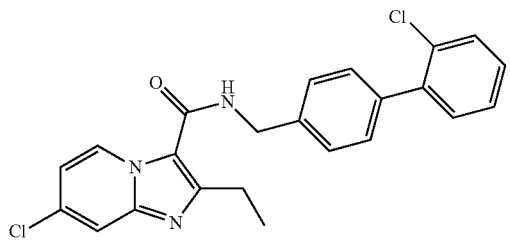 [SMILES: CCc1nc2cc(Cl)ccn2c1C(=O)NCc1ccc(-c2ccccc2Cl)cc1]

7-Chloro-N-((4'-chlorobiphenyl-4-yl)methyl)-2-ethylimidazo[1,2-a]pyridine-3-carboxamide (83)

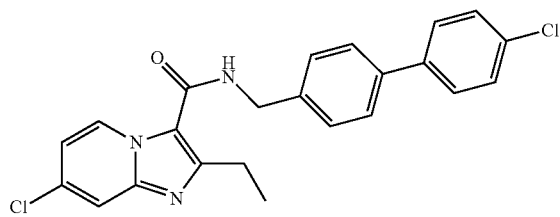 [SMILES: CCc1nc2cc(Cl)ccn2c1C(=O)NCc1ccc(-c2ccc(Cl)cc2)cc1]

7-Chloro-N-(4-chlorobenzyl)-2-ethylimidazo[1,2-a]pyridine-3-carboxamide (84)

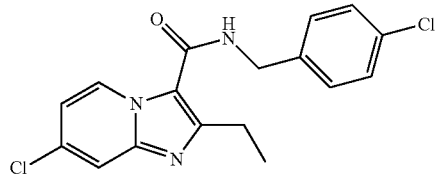 [SMILES: CCc1nc2cc(Cl)ccn2c1C(=O)NCc1ccc(Cl)cc1]

7-Chloro-2-ethyl-N-((2'-methylbiphenyl-4-yl)methyl)imidazo[1,2-a]pyridine-3-carboxamide (85)

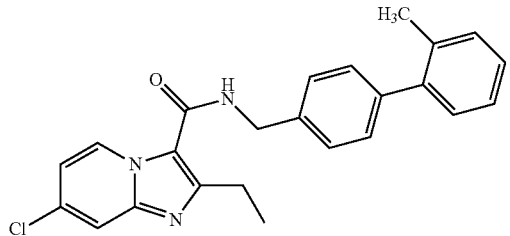

7-Chloro-2-ethyl-N-((3'-methylbiphenyl-4-yl)methyl)imidazo[1,2-a]pyridine-3-carboxamide (86)

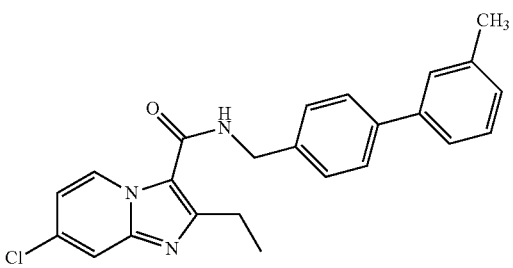 [SMILES: CCc1nc2cc(Cl)ccn2c1C(=O)NCc1ccc(-c2cccc(C)c2)cc1]

7-Chloro-2-ethyl-N-((4'-methylbiphenyl-4-yl)methyl)imidazo[1,2-a]pyridine-3-carboxamide (87)

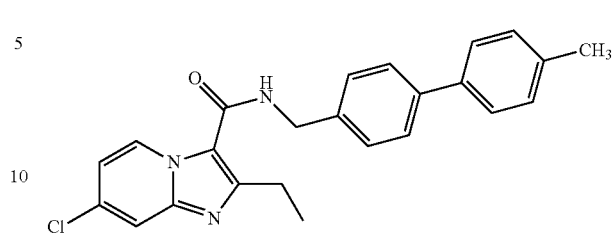

7-Chloro-2-ethyl-N-(4-hydroxybenzyl)imidazo[1,2-a]pyridine-3-carboxamide (88)

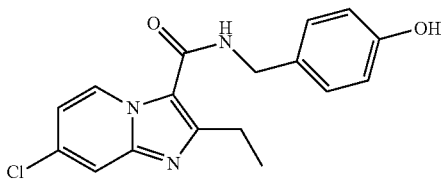 [SMILES: CCc1nc2cc(Cl)ccn2c1C(=O)NCc1ccc(O)cc1]

7-Chloro-2-ethyl-N-(4-piperidin-1-yl)benzyl)imidazo[1,2-a]pyridine-3-carboxamide (89)

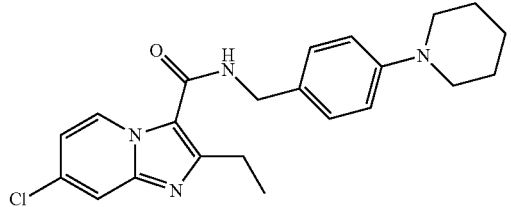 [SMILES: CCc1nc2cc(Cl)ccn2c1C(=O)NCc1ccc(N2CCCCC2)cc1]

7-Chloro-2-ethyl-N-(naphthalen-2-ylmethyl)imidazo[1,2-a]pyridine-3-carboxamide (90)

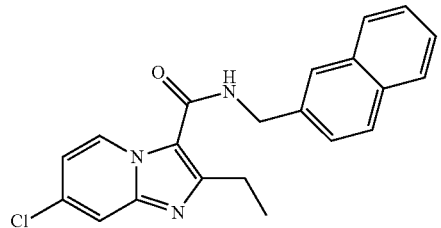 [SMILES: CCc1nc2cc(Cl)ccn2c1C(=O)NCc1ccc2ccccc2c1]

N-(Biphenyl-4-ylmethyl)-7-chloro-2-ethylimidazo[1,2-a]pyridine-3-carboxamide (91)

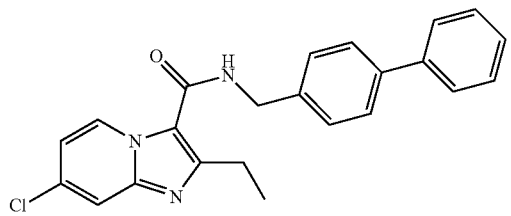 [SMILES: CCc1nc2cc(Cl)ccn2c1C(=O)NCc1ccc(-c2ccccc2)cc1]

N-(4-tert-Butylbenzyl)-7-chloro-2-ethylimidazo[1,2-a]pyridine-3-carboxamide (92)

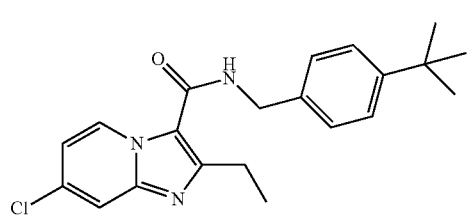 [SMILES: CCc1nc2cc(Cl)ccn2c1C(=O)NCc1ccc(C(C)(C)C)cc1]

7-Chloro-2-ethyl-N-(4-morpholinobenzyl)imidazo[1,2-a]pyridine-3-carboxamide (93)

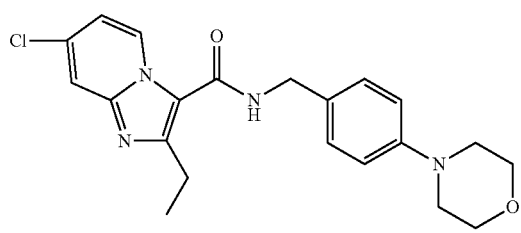 [SMILES: CCc1nc2cc(Cl)ccn2c1C(=O)NCc1ccc(N2CCOCC2)cc1]

2-Ethyl-7-methyl-N-(4-morpholinobenzyl)imidazo[1,2-a]pyridine-3-carboxamide (94)

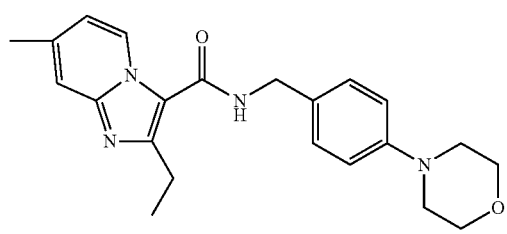 [SMILES: CCc1nc2cc(C)ccn2c1C(=O)NCc1ccc(N2CCOCC2)cc1]

2-Ethyl-7-methyl-N-(napthalen-2-ylmethyl)imidazo[1,2-a]pyridine-3-carboxamide (95)

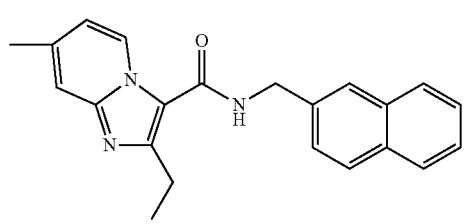 [SMILES: CCc1nc2cc(C)ccn2c1C(=O)NCc1ccc2ccccc2c1]

N-(4-Bromobenzyl)-7-chloro-2-ethylimidazo[1,2-a]pyridine-3-carboxamide (96)

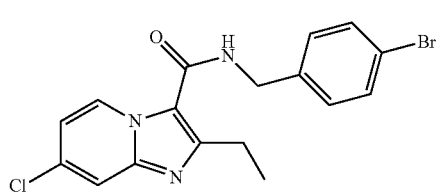 [SMILES: CCc1nc2cc(Cl)ccn2c1C(=O)NCc1ccc(Br)cc1]

6-Chloro-N-((4'-cyanobiphenyl-4-yl)methyl)-2-ethylimidazo[1,2-a]pyridine-3-carboxamide (97)

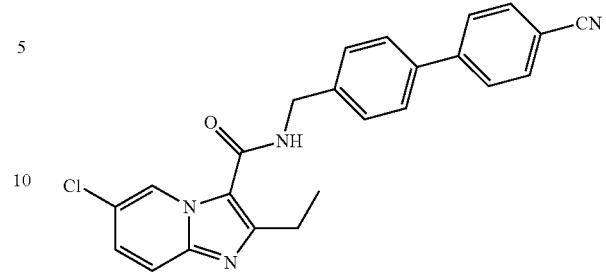

6-Chloro-2-ethyl-N-((2'-(trifluoromethyl)biphenyl-4-yl)methyl)imidazo[1,2-a]pyridine-3-carboxamide (98)

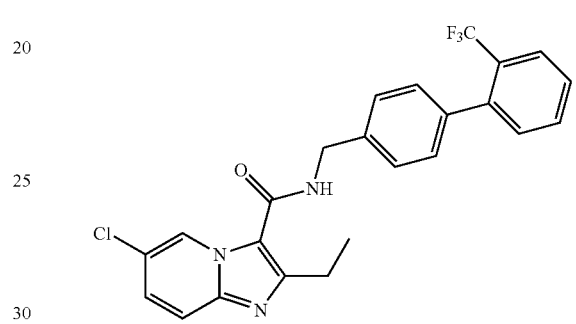

6-Chloro-N-((3'-cyanobiphenyl-4-yl)methyl)-2-ethylimidazo[1,2-a]pyridine-3-carboxamide (99)

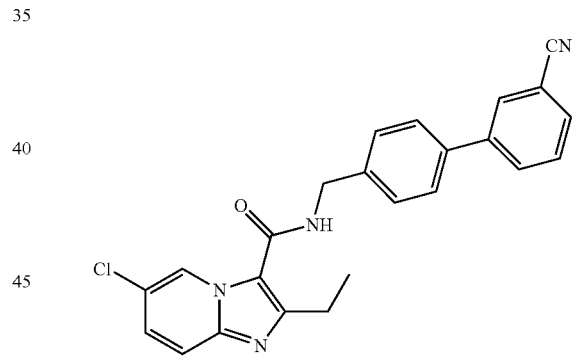

6-Chloro-N-((4'-chloro-2'-(trifluoromethyl)biphenyl-4-yl)methyl)-2-ethylimidazo[1,2-a]pyridine-3-carboxamide (100)

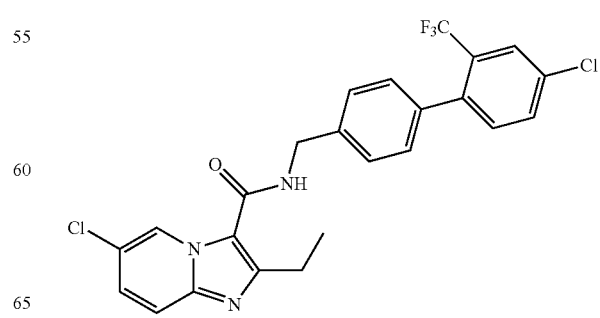

7-Chloro-N-((3'-cyanobiphenyl-4-yl)methyl)-2-ethylimidazo[1,2-a]pyridine-3-carboxamide (101)

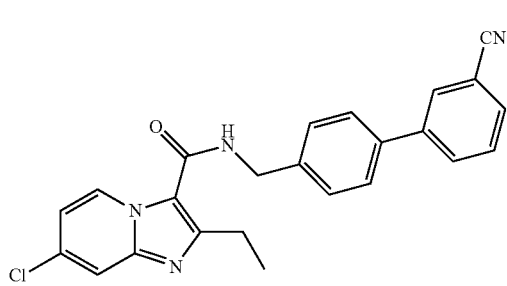 [SMILES: CCc1nc2cc(Cl)ccn2c1C(=O)NCc1ccc(-c2cccc(C#N)c2)cc1]

7-Chloro-2-ethyl-N-((2'-(trifluoromethyl)biphenyl-4-yl)methyl)imidazo[1,2-a]pyridine-3-carboxamide (102)

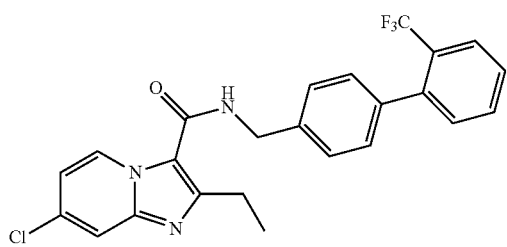 [SMILES: CCc1nc2cc(Cl)ccn2c1C(=O)NCc1ccc(-c2ccccc2C(F)(F)F)cc1]

7-Chloro-N-((4'-chloro-2'-(trifluoromethyl)biphenyl-4-yl)methyl)-2-ethylimidazo[1,2-a]pyridine-3-carboxamide (103)

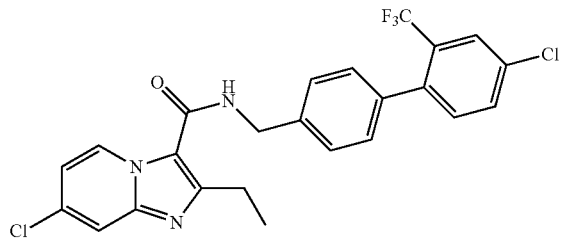 [SMILES: CCc1nc2cc(Cl)ccn2c1C(=O)NCc1ccc(-c2ccc(Cl)cc2C(F)(F)F)cc1]

6-Chloro-N-((4'-cyano-2'-methylbiphenyl-4-yl)methyl)-2-ethylimidazo[1,2-a]pyridine-3-carboxamide (104)

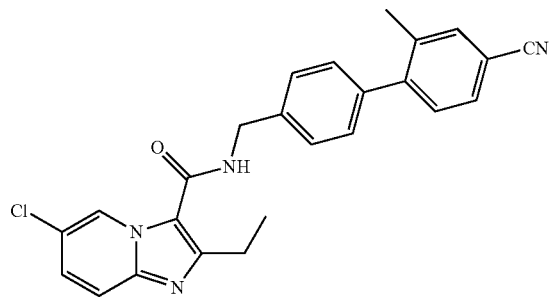 [SMILES: CCc1nc2ccc(Cl)cn2c1C(=O)NCc1ccc(-c2ccc(C#N)cc2C)cc1]

6-Chloro-2-ethyl-N-(4-(4-methylpiperazin-1-yl)benzyl)imidazo[1,2-a]pyridine-3-carboxamide (105)

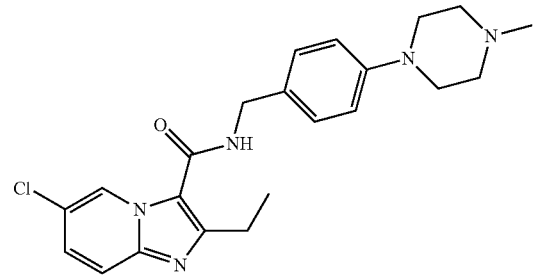 [SMILES: CCc1nc2ccc(Cl)cn2c1C(=O)NCc1ccc(N2CCN(C)CC2)cc1]

7-Chloro-N-((2'-cyanobiphenyl-4-yl)methyl)-2-ethylimidazo[1,2-a]pyridine-3-carboxamide (106)

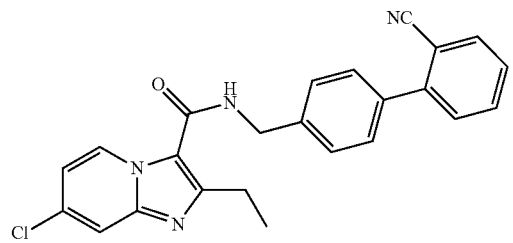

7-Chloro-2-ethyl-N-(4-(trifluoromethoxy)benzyl)imidazo[1,2-a]pyridine-3-carboxamide (107)

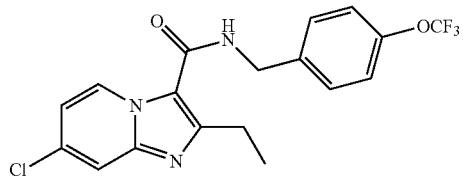 [SMILES: CCc1nc2cc(Cl)ccn2c1C(=O)NCc1ccc(OC(F)(F)F)cc1]

7-Chloro-2-ethyl-(4-(4-methylpiperazin-1-yl)benzyl)imidazo[1,2-a]pyridine-3-carboxamide (108)

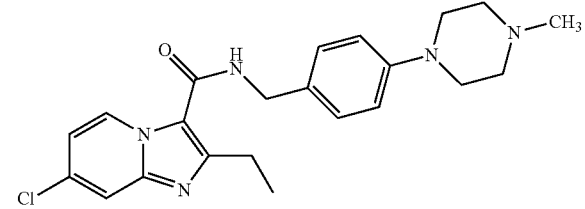 [SMILES: CCc1nc2cc(Cl)ccn2c1C(=O)NCc1ccc(N2CCN(C)CC2)cc1]

7-Chloro-N-((4'-cyano-2'-methylbiphenyl-4-yl)methyl)-2-ethylimidazo[1,2-a]pyridine-3-carboxamide (109)

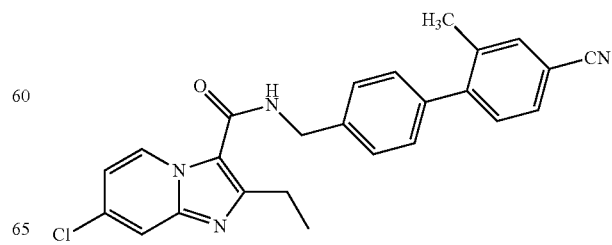

7-Chloro-2-ethyl-N-(4-pentylamino)benzyl)imidazo[1,2-a]pyridine-3-carboxamide (110)

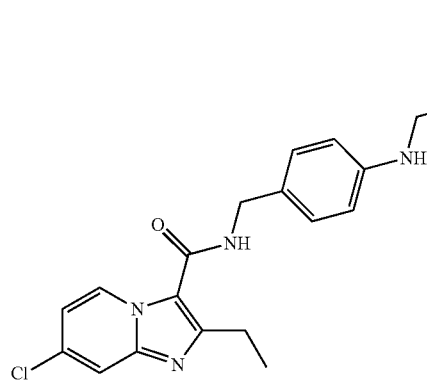

7-Chloro-2-ethyl-N-((4'-(trifluoromethyl)biphenyl-4-yl)methyl)imidazo[1,2-a]pyridine-3-carboxamide (111)

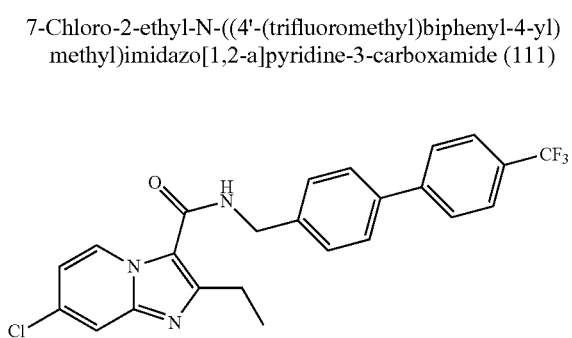

7-Chloro-2-ethyl-N-((4'-(trifluoromethoxy)biphenyl-4-yl)methyl)imidazo[1,2-a]pyridine-3-carboxamide (112)

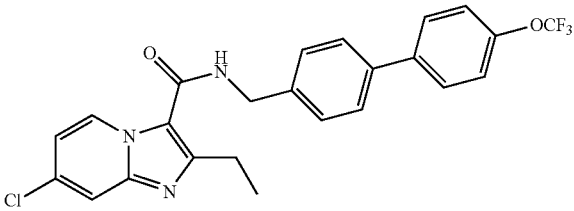 [SMILES: CCc1nc2cc(Cl)ccn2c1C(=O)NCc1ccc(-c2ccc(OC(F)(F)F)cc2)cc1]

7-Chloro-2-ethyl-N-((4'-methoxybiphenyl-4-yl)methyl)imidazo[1,2-a]pyridine-3-carboxamide (113)

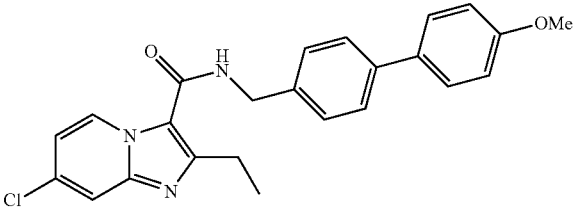

N-((4'-tert-Butylbiphenyl-4-yl)methyl)-7-chloro-2-ethylimidazo[1,2-a]pyridine-3-carboxamide (114)

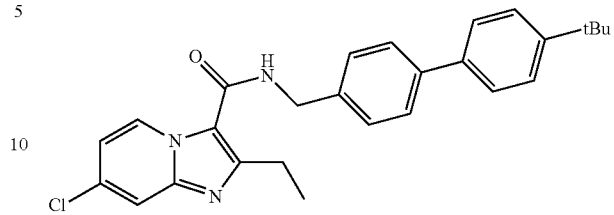

N-(7-Chloro-2-ethylimidazo[1,2-a]pyridine-3-yl)biphenyl-4-carboxamide (115)

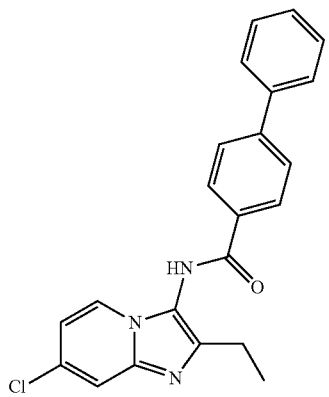 [SMILES: CCc1nc2cc(Cl)ccn2c1NC(=O)c1ccc(-c2ccccc2)cc1]

2-(Biphenyl-4-yl)-N-(7-chloro-2-ethylimidazo[1,2-a]pyridine-3-yl)acetamide (116)

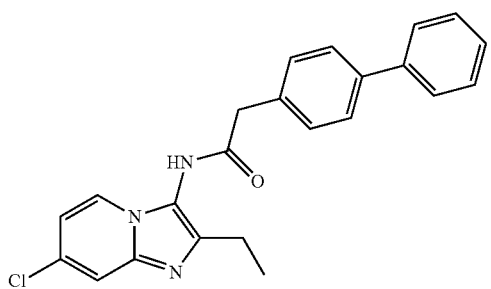 [SMILES: CCc1nc2cc(Cl)ccn2c1NC(=O)Cc1ccc(-c2ccccc2)cc1]

N-(4-(1H-Pyrrol-1-yl)benzyl-7-chloro-2-ethylimidazo[1,2-a]pyridine-3-carboxamide (117)

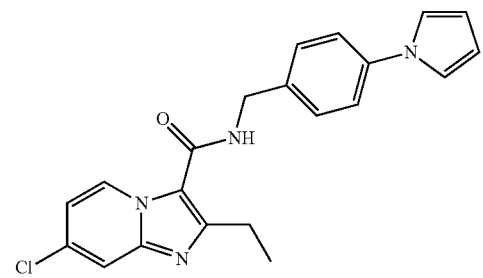 [SMILES: CCc1nc2cc(Cl)ccn2c1C(=O)NCc1ccc(-n2cccc2)cc1]

209

2-Ethyl-7-methoxy-N-(4-(trifluoromethoxy)benzyl)imidazo[1,2-a]pyridine-3-carboxamide (118)

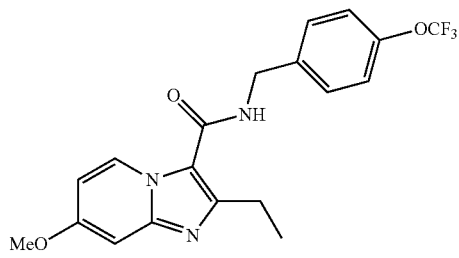 [SMILES: CCc1nc2cc(OC)ccn2c1C(=O)NCc1ccc(OC(F)(F)F)cc1]

7-Chloro-2-ethyl-N-(4-(5-methoxypyridin-2-yl)benzyl)imidazo[1,2-a]pyridine-3-carboxamide (119)

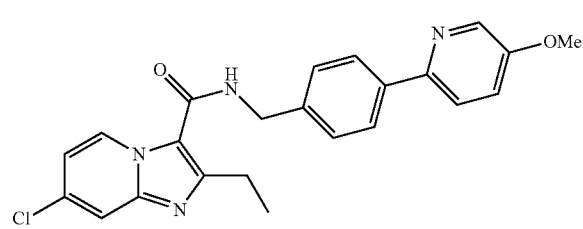 [SMILES: CCc1nc2cc(Cl)ccn2c1C(=O)NCc1ccc(-c2ccc(OC)cn2)cc1]

2-Ethyl-6-fluoro-N-(4-(trifluoromethoxy)benzyl)imidazo[1,2-a]pyridine-3-carboxamide (120)

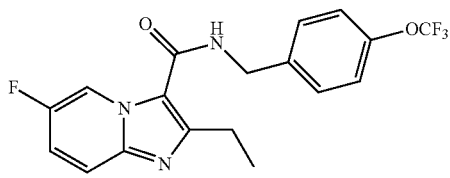 [SMILES: CCc1nc2ccc(F)cn2c1C(=O)NCc1ccc(OC(F)(F)F)cc1]

2-Ethyl-N-(4-(trifluoromethoxy)benzyl)-6-(trifluoromethyl)imidazo[1,2-a]pyridine-3-carboxamide (121)

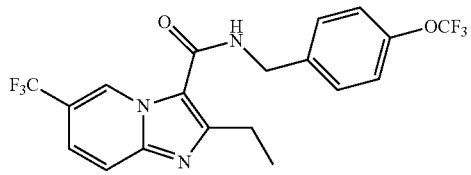 [SMILES: CCc1nc2ccc(C(F)(F)F)cn2c1C(=O)NCc1ccc(OC(F)(F)F)cc1]

210

6-Chloro-2-ethyl-N-(4-(4-(4-(trifluoromethoxy)phenoxy)piperidin-1-yl)benzyl)imidazo-[1,2-a]pyridine-3-carboxamide (127)

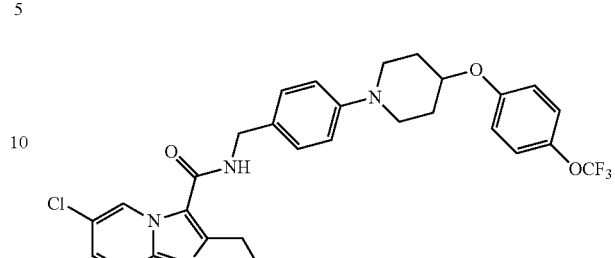

7-Chloro-2-ethyl-N-(4-(4-(4-(trifluoromethoxy)phenoxy)piperidin)-1-yl)benzyl)imidazo-[1,2-a]pyridine-3-carboxamide (123)

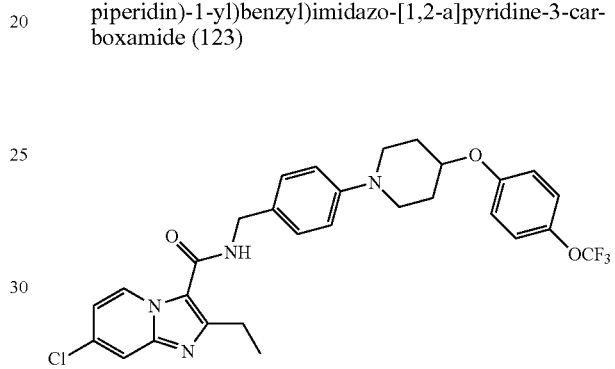

2-Ethyl-N-(4-(4-(4-(trifluoromethoxy)phenoxy)piperidin-1-yl)benzyl)-6-(trifluoromethyl)imidazo[1,2-a]pyridine-3-carboxamide (124)

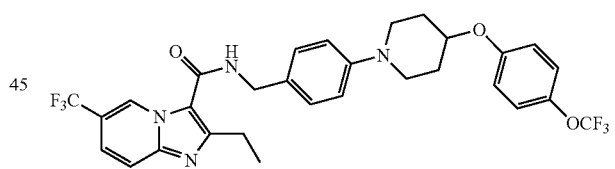

N-(4-(4-(4-(Butramidomethyl)phenyl)piperazin-1-yl)benzyl)-7-chloro-2-ethylimidazo[1,2-a]pyridine-3-carboxamide (125)

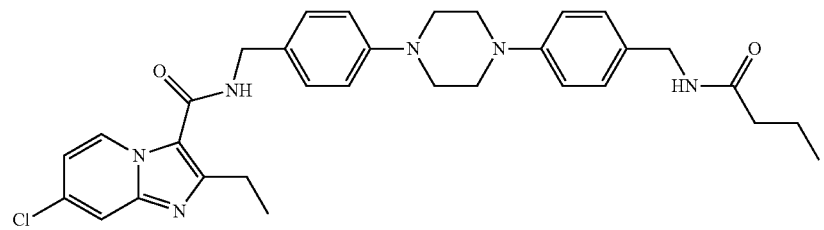 [SMILES: CCCC(=O)NCc1ccc(N2CCN(c3ccc(CNC(=O)c4c(CC)nc5cc(Cl)ccn45)cc3)CC2)cc1]

211

7-Chloro-2-ethyl-N-(4-(4-(4-fluorobenzyl)piperazin-1-yl)benzyl)imidazo[1,2-a]pyridine-3-carboxamide (126)

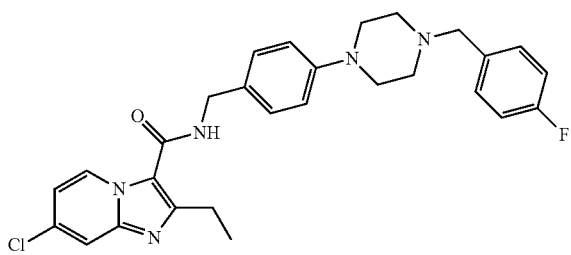 [SMILES: CCc1nc2cc(Cl)ccn2c1C(=O)NCc1ccc(N2CCN(Cc3ccc(F)cc3)CC2)cc1]

7-Chloro-2-ethyl-N-(4-(4-(4-fluorophenyl)piperazin-1-yl)benzyl)imidazo[1,2-a]pyridine-3-carboxamide (127)

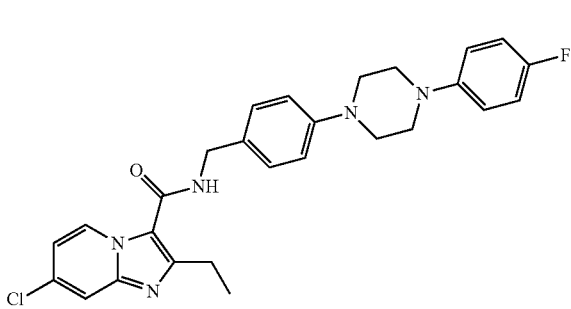

7-Chloro-2-ethyl-N-(4-(4-(trifluoromethoxy)phenoxy)benzyl)imidazo[1,2-a]pyridine-3-carboxamide (128)

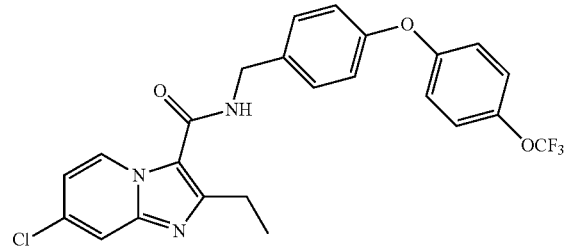 [SMILES: CCc1nc2cc(Cl)ccn2c1C(=O)NCc1ccc(Oc2ccc(OC(F)(F)F)cc2)cc1]

7-Chloro-2-ethyl-N-(4-(4-fluorophenoxy)benzyl)imidazo[1,2-a]pyridine-3-carboxamide (129)

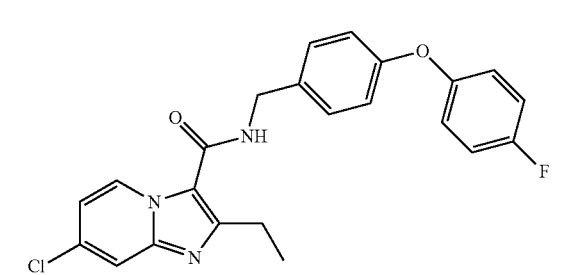 [SMILES: CCc1nc2cc(Cl)ccn2c1C(=O)NCc1ccc(Oc2ccc(F)cc2)cc1]

212

6-Chloro-2-ethyl-N-(4-(4-(4-fluorobenzyl)piperazin-1-yl)benzyl)imidazo[1,2-a]pyridine-3-carboxamide (130)

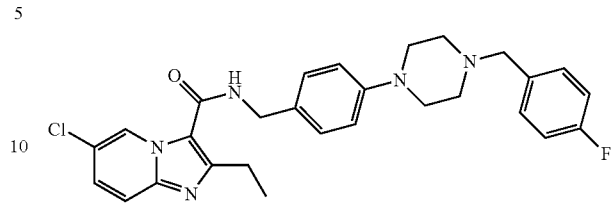

6-Chloro-2-ethyl-N-(4-(4-(trifluoromethoxy)phenoxy)benzyl)imidazo[1,2-a]pyridine-3-carboxamide (131)

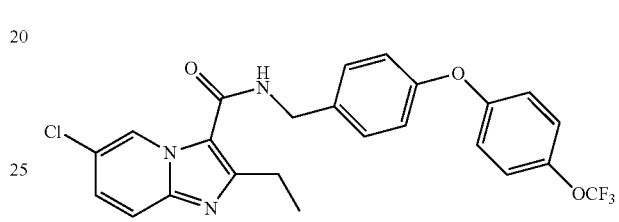

6-Chloro-2-ethyl-N-((1-(4-(trifluoromethoxy)phenyl)-1H-pyrazol-3-yl)methyl)imidazo[1,2-a]pyridine-3-carboxamide (132)

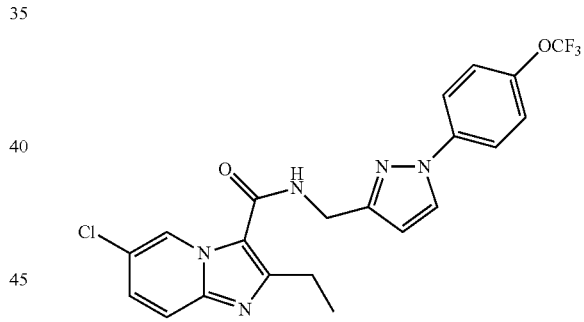

7-Chloro-2-ethyl-N-((1-(4-(trifluoromethoxy)phenyl)-1H-pyrazol-3-yl)methyl)imidazo[1,2-a]pyridine-3-carboxamide (133)

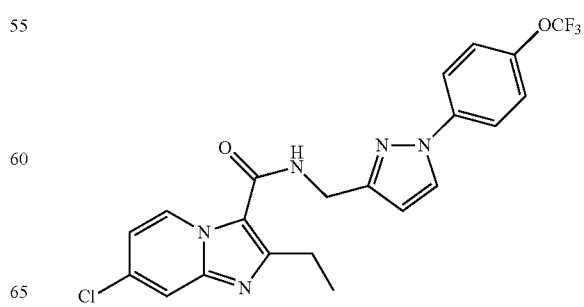

6-Chloro-N-(4-cyanobenzyl)-2-ethylimidazo[1,2-a]pyridine-3-carboxamide (134)

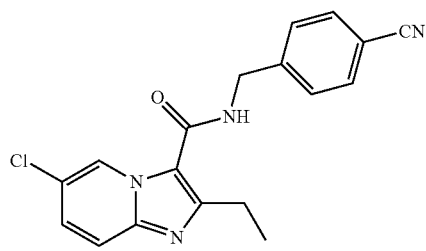 [SMILES: CCc1nc2ccc(Cl)cn2c1C(=O)NCc1ccc(C#N)cc1]

6-Chloro-2-ethyl-N-(4-(trifluoromethyl)benzyl)imidazo[1,2-a]pyridine-3-carboxamide (135)

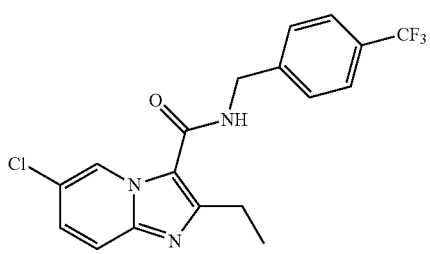 [SMILES: CCc1nc2ccc(Cl)cn2c1C(=O)NCc1ccc(C(F)(F)F)cc1]

6-Chloro-2-ethyl-N-(4-methoxyphenethyl)imidazo[1,2-a]pyridine-3-carboxamide (136)

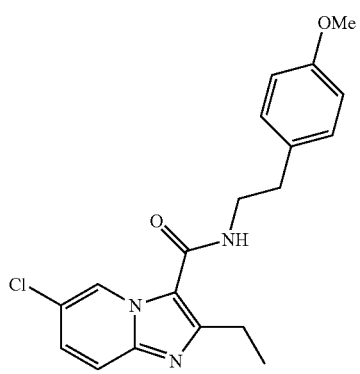 [SMILES: CCc1nc2ccc(Cl)cn2c1C(=O)NCCc1ccc(OC)cc1]

6-Chloro-N-(4-chlorophenethyl)-2-ethylimidazo[1,2-a]pyridine-3-carboxamide (137)

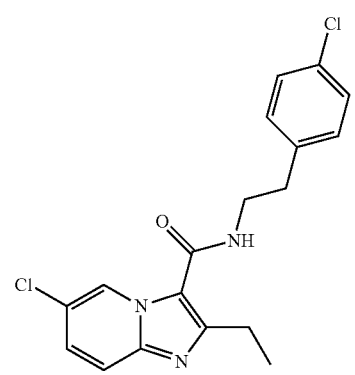 [SMILES: CCc1nc2ccc(Cl)cn2c1C(=O)NCCc1ccc(Cl)cc1]

6-Chloro-2-ethyl-N-((1-(4-(trifluoromethoxy)benzyl)piperidin-4-yl)methyl)imidazo[1,2-a]pyridine-3-carboxamide (138)

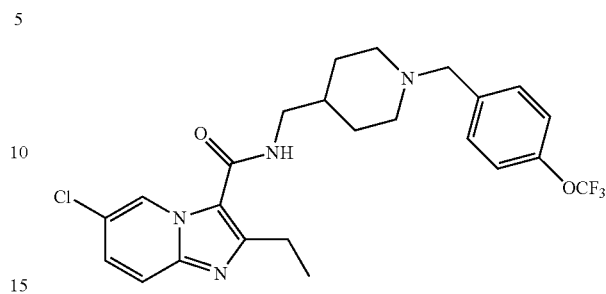

6-Chloro-2-ethyl-N-((1-(4-fluorobenzyl)piperidin-4-yl)methyl)imidazo[1,2-a]pyridine-3-carboxamide (139)

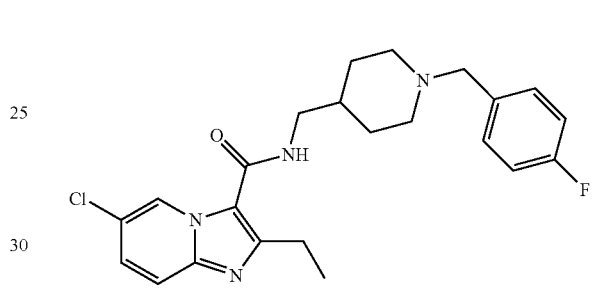

7-Chloro-2-ethyl-N-((1-(4-(trifluoromethoxy)benzyl)piperidin-4-yl)methyl)imidazo[1,2-a]pyridine-3-carboxamide (140)

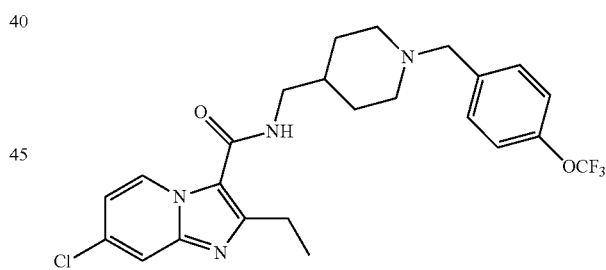

2-Ethyl-N-(4-trifluoromethoxy)benzyl)imidazo[1,2-a]pyrazine-3-carboxamide (141)

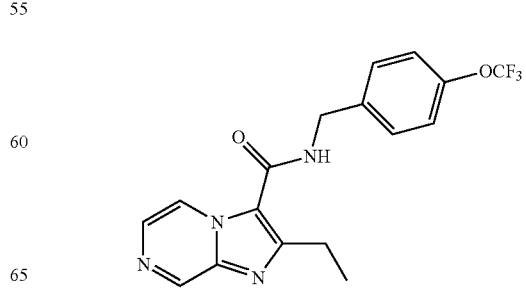

2-Ethyl-3-((4-(trifluoromethoxy)benzyl)carbamoyl)imidazo[1,2-a]pyridine 7-oxide (142)

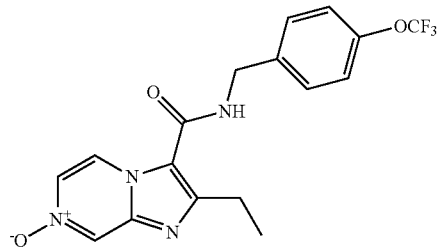

6-Chloro-2-ethyl-3-((4-(trifluoromethoxy)phenoxy)methyl)imidazo[1,2-a]pyridine (143)

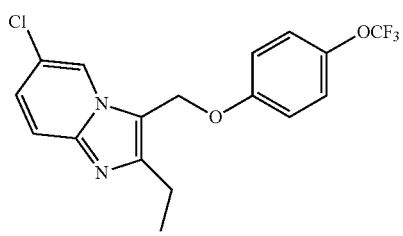 [SMILES: CCc1nc2ccc(Cl)cn2c1COc1ccc(OC(F)(F)F)cc1]

N-((6-Chloro-2-ethylimidazo[1,2-a]pyridin-3-yl)methyl)-4-(trifluoromethoxy)aniline (144)

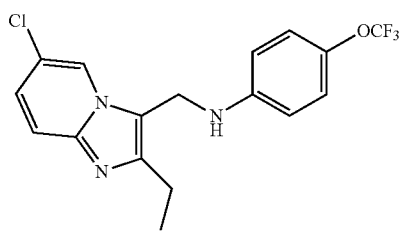 [SMILES: CCc1nc2ccc(Cl)cn2c1CNc1ccc(OC(F)(F)F)cc1]

6-Chloro-2-ethylimidazo[1,2-a]pyridine-3-carbaldehyde (145)

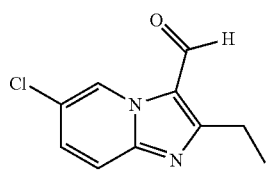

(6-Chloro-2-ethylimidazo[1,2-a]pyridin-3-yl)methanol (146)

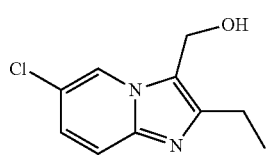

6-Chloro-2-ethyl-N-((1-(4-(trifluoromethoxy)phenyl)-4,5,6,7-tetrahydro-1H-indazol-4-yl)methyl)imidazo[1,2-a]pyridine-3-carboxamide (147)

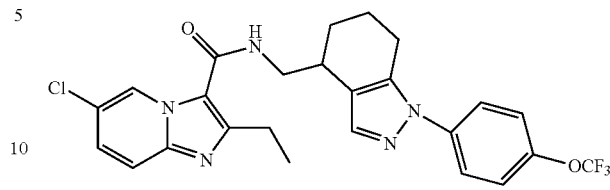

\6-Chloro-2-ethyl-N-(4-(4-(4-fluorophenyl)piperazin-1-yl)benzyl)imidazo[1,2-a]pyridine-3-carboxamide (148)

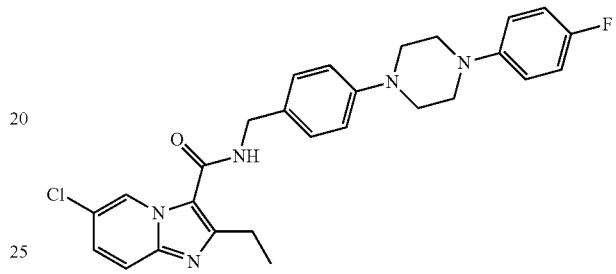

6-Chloro-2-ethyl-N-((1-(4-fluorophenyl)-4,5,6,7-tetrahydro-1H-indazol-4-yl)methyl)imidazo[1,2-a]pyridine-3-carboxamide (149)

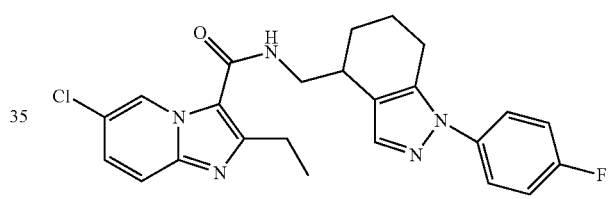

2-Ethyl-7-nitro-N-(4-(trifluoromethoxy)benzyl)imidazo[1,2-a]pyridine-3-carboxamide (150)

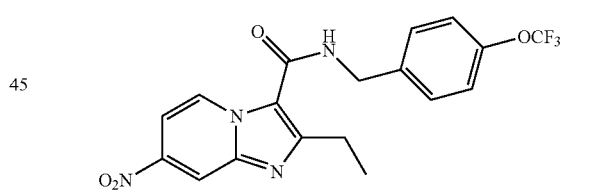

6-Chloro-2-ethyl-N-((1-(4-(trifluoromethyl)phenyl)-1H-pyrazol-3-yl)methyl)imidazo[1,2-a]pyridine-3-carboxamide (151)

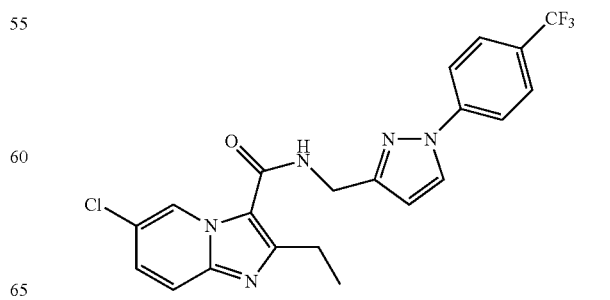

217

7-Chloro-2-ethyl-N-((1-(4-(trifluoromethyl)phenyl)-1H-pyrazol-3-yl)methyl)imidazo[1,2-a]pyridine-3-carboxamide (152)

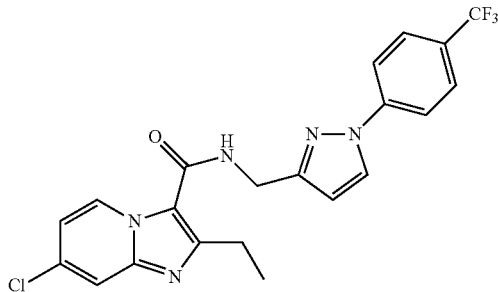 [SMILES: CCc1nc2cc(Cl)ccn2c1C(=O)NCc1ccn(-c2ccc(C(F)(F)F)cc2)n1]

6-Chloro-2-ethyl-N-((1-(4-fluorophenyl)-1H-pyrazol-3-yl)methyl)imidazo[1,2-a]pyridine-3-carboxamide (153)

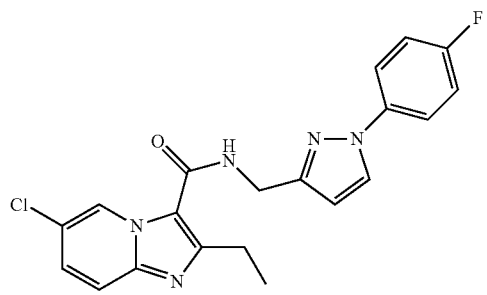 [SMILES: CCc1nc2ccc(Cl)cn2c1C(=O)NCc1ccn(-c2ccc(F)cc2)n1]

7-Chloro-2-ethyl-N-((1-(4-fluorphenyl)-1H-pyrazol-3-yl)methyl)imidazo[1,2-a]pyridine-3-carboxamide (154)

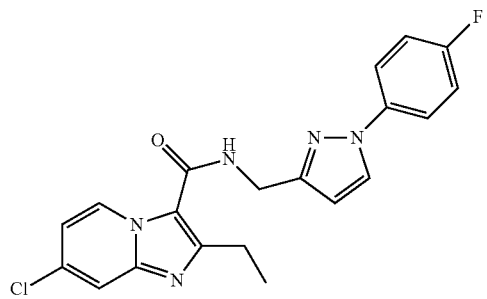 [SMILES: CCc1nc2cc(Cl)ccn2c1C(=O)NCc1ccn(-c2ccc(F)cc2)n1]

7-Chloro-2-ethyl-N-(4-(trifluoromethyl)benzyl)imidazo[1,2a]pyridine-3-carboxamide (155)

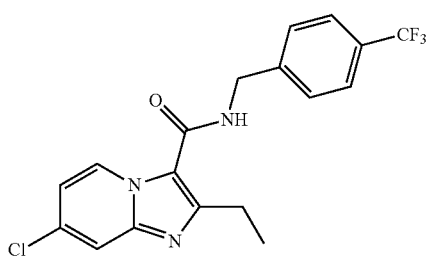 [SMILES: CCc1nc2cc(Cl)ccn2c1C(=O)NCc1ccc(C(F)(F)F)cc1]

218

6-Chloro-2-ethyl-N-(4-(4-(4-(trifluoromethoxy)benzyl)piperazin-1-yl)benzyl)imidazo[1,2-a]pyridine-3-carboxamide (156)

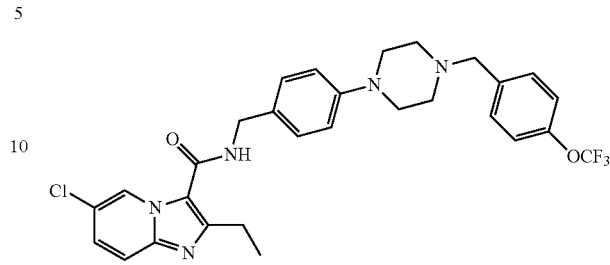

7-Chloro-2-ethyl-N-(4-(4-(4-(trifluoromethoxy)benzyl)piperazin-1-yl)benzyl)imidazo[1,2-a]pyridine-3-carboxamide (157))

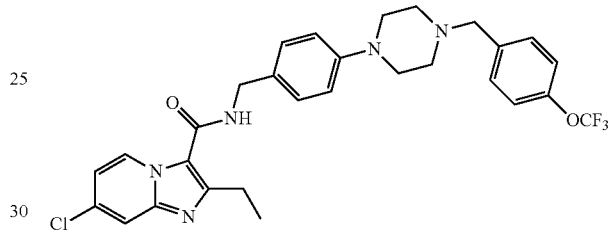

6-Chloro-2-ethyl-N-(4-(4-(4-(trifluoromethoxy)phenyl)piperazin-1-yl)benzyl)imidazo[1,2-a]pyridine-3-carboxamide (158)

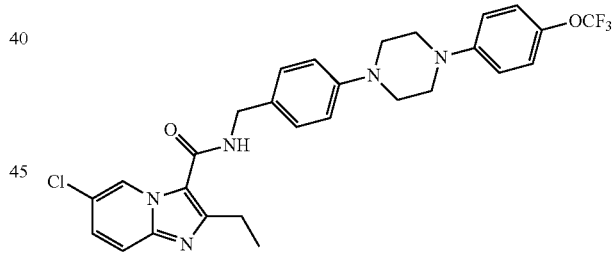

7-Chloro-2-ethyl-N-(4-(4(4-(trifluoromethoxy)phenyl)piperazin-1-yl)benzyl)imidazo[1,2-a]pyridine-3-carboxamide (159)

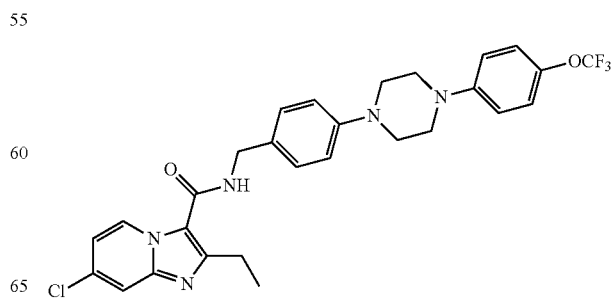

6-Chloro-N-(4-(4-chlorophenoxy)benzyl-2-ethylimidazo[1,2-a]pyridine-3-carboxamide (160)

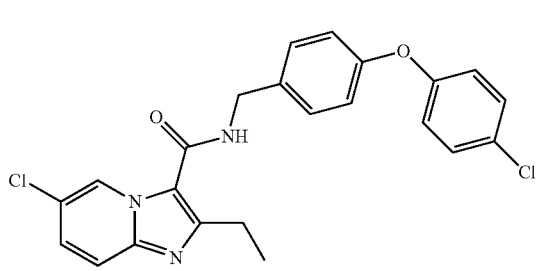 [SMILES: CCc1nc2ccc(Cl)cn2c1C(=O)NCc1ccc(Oc2ccc(Cl)cc2)cc1]

7-Chloro-N-(4-(4-chlorophenoxy)benzyl)-2-ethylimidazo[1,2-a]pyridine-3-carboxamide

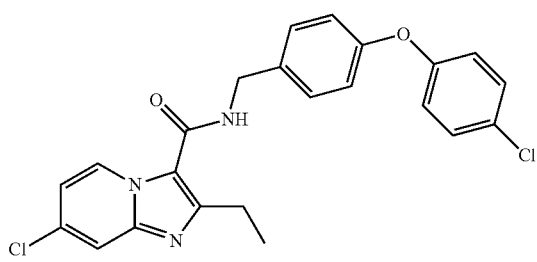 [SMILES: CCc1nc2cc(Cl)ccn2c1C(=O)NCc1ccc(Oc2ccc(Cl)cc2)cc1]

[1,1'-Biphenyl]-4-ylmethyl 6-chloro-2-ethylimidazo[1,2-a]pyridine-3-carboxylate (162)

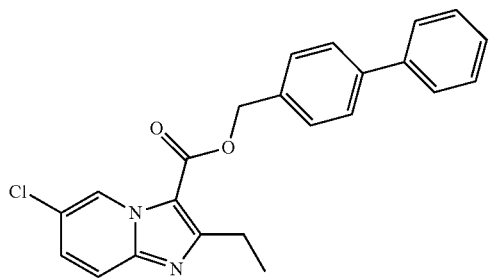 [SMILES: CCc1nc2ccc(Cl)cn2c1C(=O)OCc1ccc(-c2ccccc2)cc1]

4-Phenoxybenzyl 6-chloro-2-ethylimidazo[1,2-a]pyridine-3-carboxylate (163)

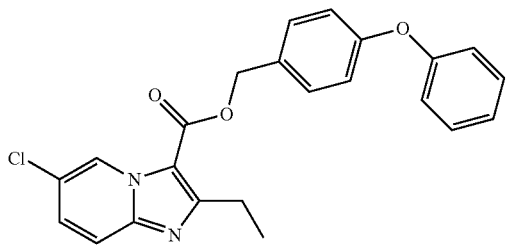 [SMILES: CCc1nc2ccc(Cl)cn2c1C(=O)OCc1ccc(Oc2ccccc2)cc1]

6-Chloro-2-ethyl-N-(4-(4-fluorophenoxy)benzyl)-N-methylimidazo[1,2-a]pyridine-3-carboxamide (164)

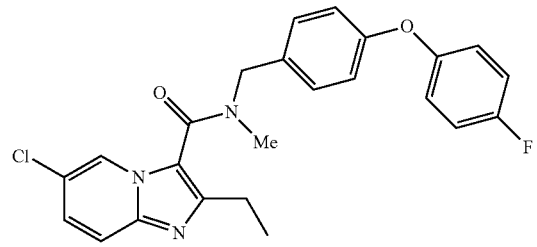 [SMILES: CCc1nc2ccc(Cl)cn2c1C(=O)N(C)Cc1ccc(Oc2ccc(F)cc2)cc1]

5-(6-Chloro-2-ethylimidazo[1,2-a]pyridin-3-yl)-3-(4-(trifluoromethoxy)benzyl)-1,2,4-oxadiazole (165)

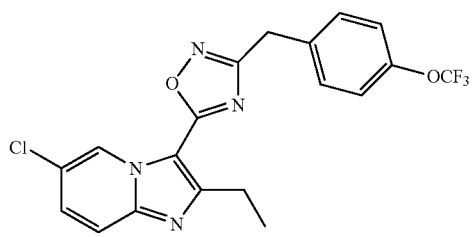 [SMILES: CCc1nc2ccc(Cl)cn2c1-c1nc(Cc2ccc(OC(F)(F)F)cc2)no1]

6-Chloro-N-(4-(4-(4-chlorophenoxy)piperidin-1-yl)benzyl)-2-ethylimidazo[1,2-a]pyridine-3-carboxamide (166)

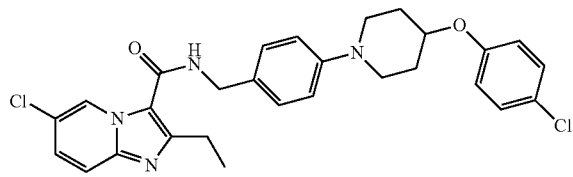 [SMILES: CCc1nc2ccc(Cl)cn2c1C(=O)NCc1ccc(N2CCC(Oc3ccc(Cl)cc3)CC2)cc1]

7-Chloro-N-(4-(4-(4-chlorophenoxy)piperidin-1-yl)benzyl)-2-ethylimidazo[1,2-a]pyridine-3-carboxamide (167)

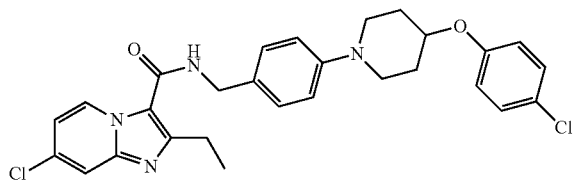 [SMILES: CCc1nc2cc(Cl)ccn2c1C(=O)NCc1ccc(N2CCC(Oc3ccc(Cl)cc3)CC2)cc1]

6-Chloro-2-ethyl-N-(4-(4-(4-((trifluoromethoxy))phenoxy)piperidin-1-yl)benzyl)imidazo[1,2-a]pyridine-3-carboxamide (168)

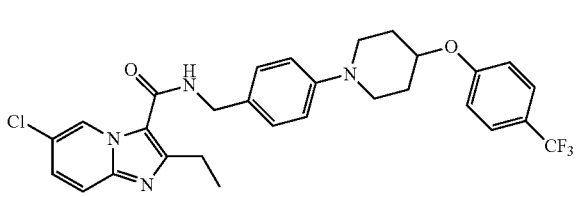 [SMILES: CCc1nc2ccc(Cl)cn2c1C(=O)NCc1ccc(N2CCC(Oc3ccc(C(F)(F)F)cc3)CC2)cc1]

221

7-Chloro-2-ethyl-N-(4-(4-(4-(trifluoromethoxy)phenoxy)
piperidin-1-yl)benzyl)imidazo[1,2-a]pyridine-3-car-
boxamide (169)

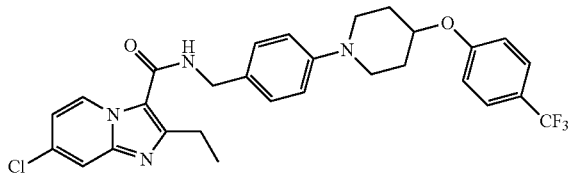 [SMILES: CCc1nc2cc(Cl)ccn2c1C(=O)NCc1ccc(N2CCC(Oc3ccc(C(F)(F)F)cc3)CC2)cc1]

6-Chloro-2-ethyl-N-(4-(4-(trifluormethyl)benzyloxy)
benzyl)imidazo[1,2-a]pyridine-3-carboxamide (170)

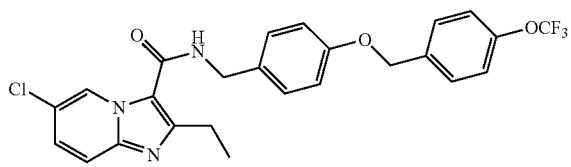 [SMILES: CCc1nc2ccc(Cl)cn2c1C(=O)NCc1ccc(OCc2ccc(OC(F)(F)F)cc2)cc1]

7-Chloro-2-ethyl-N-(4-(4-(trifluoromethyl)benzyloxy)
benzyl)imidazo[1,2-a]pyridine-3-carboxamide (171)

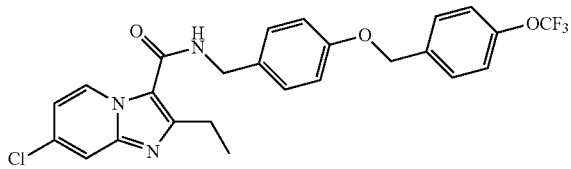 [SMILES: CCc1nc2cc(Cl)ccn2c1C(=O)NCc1ccc(OCc2ccc(OC(F)(F)F)cc2)cc1]

6-Chloro-2-ethyl-N-(4-(4-fluorobenzyloxy)benzyl)imi-
dazo[1,2-a]pyridine-3-carboxamide (172)

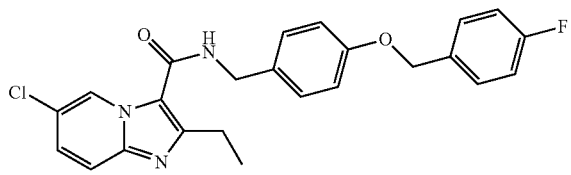 [SMILES: CCc1nc2ccc(Cl)cn2c1C(=O)NCc1ccc(OCc2ccc(F)cc2)cc1]

7-Chloro-2-ethyl-N-(4-(4-fluorobenzyloxy)imidazo[1,2-
a]pyridine-3-carboxamide (173)

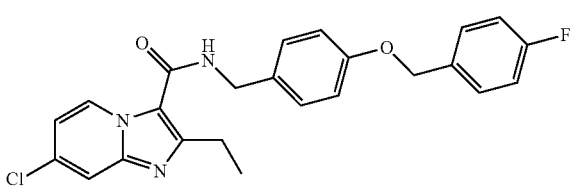 [SMILES: CCc1nc2cc(Cl)ccn2c1C(=O)NCc1ccc(OCc2ccc(F)cc2)cc1]

222

6-Chloro-2-ethyl-N-(4-(4-(trifluoromethoxy)pheny-
lamino)benzyl)imidazo[1,2-a]pyridine-3-carboxamide
(174)

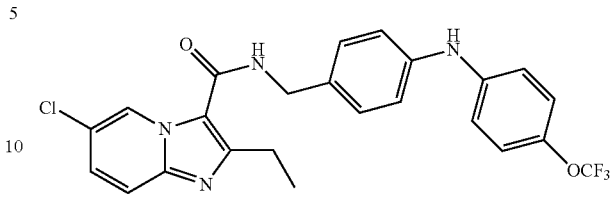

7-Chloro-2-ethyl-N-(4-(4-(trifluoromethoxy)pheny-
lamino)benzyl)imidazo[1,2-a]carboxamide (175)

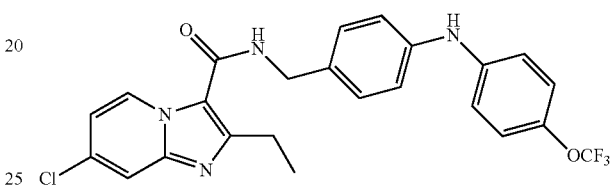

6-Bromo-2-ethyl-N-(4-(trifluoromethoxy)benzyl)imi-
dazo[1,2-a]pyridine-3-carboxamide (176)

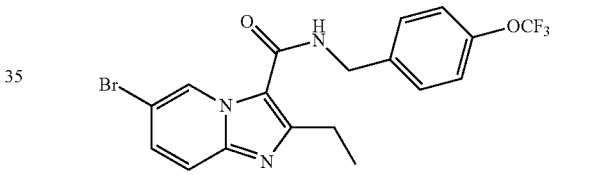

6-Bromo-2-ethyl-N-(4-(4-fluorophenoxy)benzyl)imidazo
[1,2-a]pyridine-3-carboxamide (177)

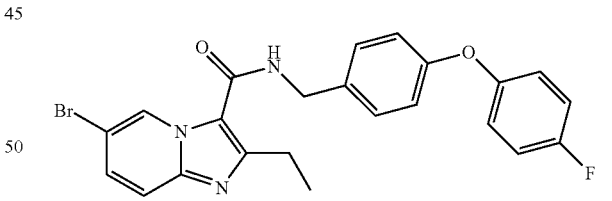

6,7-Dichloro-2-ethyl-N-(4-(trifluoromethoxy)benzyl)
imidazo[1,2-a]pyridine-3-carboxamide (178)

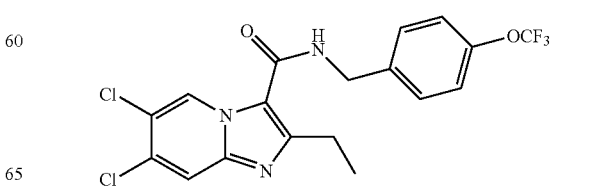

223

6,7-Dichloro-2-ethyl-N-(4-(4-(4-fluorobenzyl)piperazin-1-yl)benzyl)imidazo[1,2-a]pyridine-3-carboxamide (179)

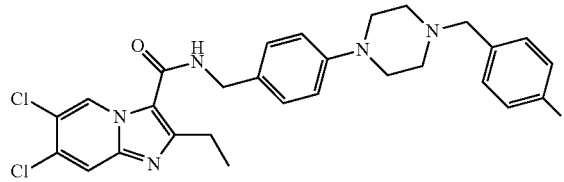

6,7-Dichloro-2-ethyl-N-(4-(4-(4-(fluorophenyl)piperazin-1-yl)benzyl)imidazo[1,2-a]pyridine-3-carboxamide (180)

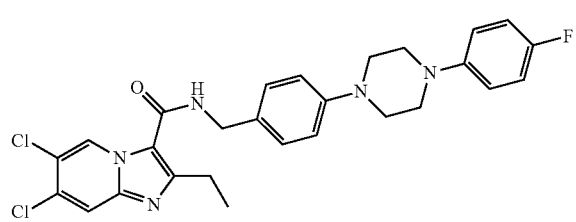 [SMILES: CCc1nc2cc(Cl)c(Cl)cn2c1C(=O)NCc1ccc(N2CCN(c3ccc(F)cc3)CC2)cc1]

2-Ethyl-N-(4-(4-(4-(trifluoromethoxy)phenyl)piperazin-1-yl)benzyl)imidazo[1,2-a]pyridine-3-carboxamide (181)

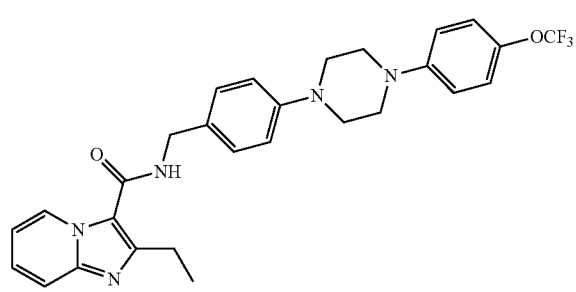

6-Chloro-N-(4-(2,6-dimethylmorpholino)benzyl)-2-ethylimidazo[1,2-a]pyridine-3-carboxamide (182)

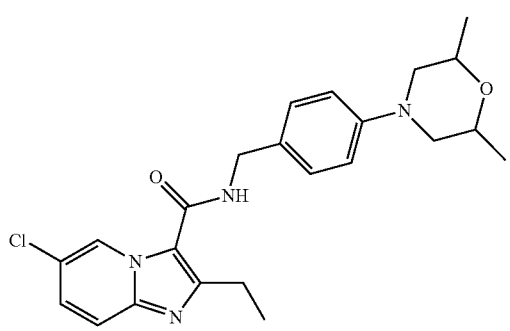 [SMILES: CCc1nc2ccc(Cl)cn2c1C(=O)NCc1ccc(N2CC(C)OC(C)C2)cc1]

224

7-Chloro-N-(4-(2,6-dimethylmorpholino)benzyl)-2-ethylimidazo[1,2-a]pyridine-3-carboxamide (183)

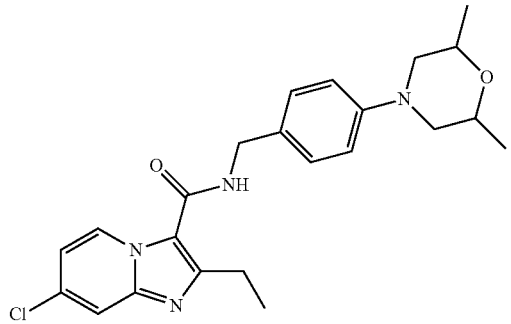 [SMILES: CCc1nc2cc(Cl)ccn2c1C(=O)NCc1ccc(N2CC(C)OC(C)C2)cc1]

6-Chloro-2-methyl-N-(4-(trifluoromethoxy)benzyl)imidazo[1,2-a]pyridine-3-carboxamide (184)

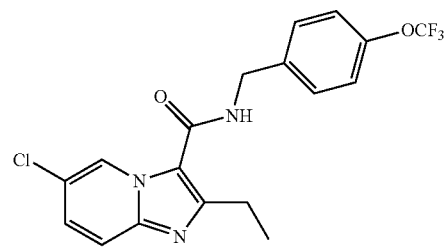 [SMILES: CCc1nc2ccc(Cl)cn2c1C(=O)NCc1ccc(OC(F)(F)F)cc1]

6-Chloro-2-ethyl-N-((2-(4-(trifluoromethoxy)phenyl)-1H-benzo[d]imidazol-5-yl)methyl) imidazo[1,2-a]pyridine-3-carboxamide (185)

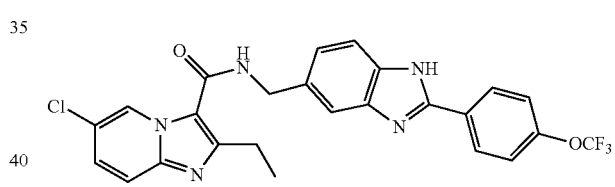

7-Chloro-2-ethyl-N-((2-(4-(trifluoromethoxy)phenyl)-1H-benzo[d]imidazol-5-yl)methyl) imidazo[1,2-a]pyridine-3-carboxamide (186)

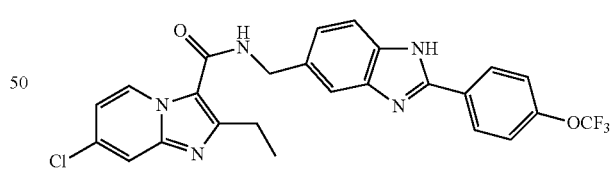

7-Chloro-2-ethyl-N-((2-(4-(trifluoromethoxy)phenyl)benzo[d]oxazol-5-yl)methyl)imidazo[1,2-a]pyridine-3-carboxamide (187)

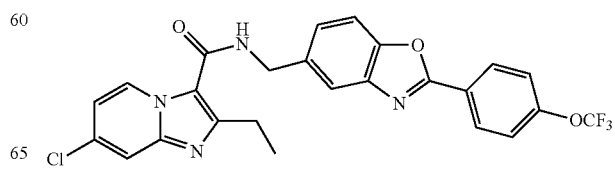

7-Chloro-2-ethyl-N-((6-(4-fluorophenoxy-3-yl)methyl)imidazo[1,2-a]pyridine-3-carboxamide (188)

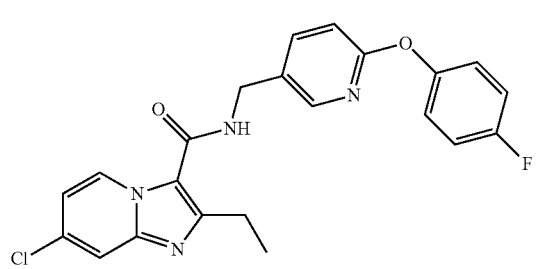

6-Chloro-2-ethyl-N-((6-(4-(trifluoromethoxy)phenoxy)pyridin-3-yl)methyl)imidazo[1,2-a]pyridine-3-carboxamide (189)

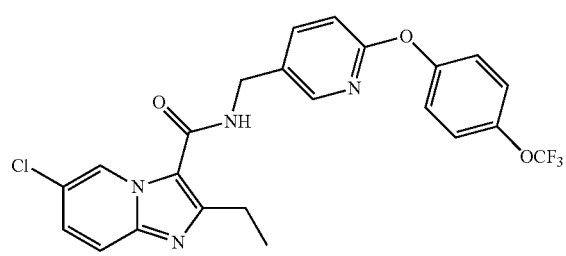 [SMILES: CCc1nc2ccc(Cl)cn2c1C(=O)NCc1ccc(Oc2ccc(OC(F)(F)F)cc2)nc1]

7-Chloro-2-ethyl-N-((6-(4-(trifluoromethoxy)phenoxy)pyridin-3-yl)methyl)imidazo[1,2-a]pyridine-3-carboxamide (190)

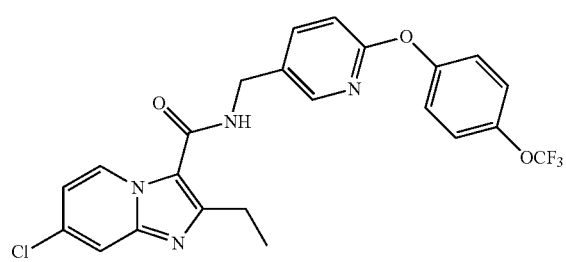

6-Chloro-2-ethyl-N-(4-(pyrrolidin-1-yl)benzyl)imidazo[1,2-a]pyridine-3-carboxamide (91)

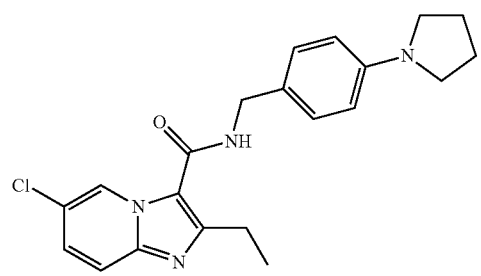 [SMILES: CCc1nc2ccc(Cl)cn2c1C(=O)NCc1ccc(N2CCCC2)cc1]

N-(4-(Azepan-1-yl)benzyl)-6-chloro-2-ethylimidazo[1,2-a]pyridine-3-carboxamide (192)

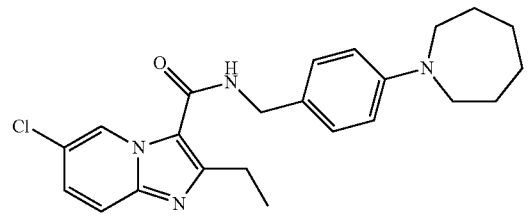 [SMILES: CCc1nc2ccc(Cl)cn2c1C(=O)NCc1ccc(N2CCCCCC2)cc1]

N-(4-(Azepan-1-yl)benzyl)-7-chloro-2-ethylimidazo[1,2-a]pyridine-3-carboxamide (193)

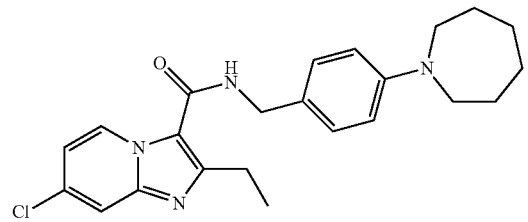 [SMILES: CCc1nc2cc(Cl)ccn2c1C(=O)NCc1ccc(N2CCCCCC2)cc1]

7-Chloro-N-(4-(5,6-dihydropyridin-1(2H)-yl)benzyl)-2-ethylimidazo[1,2-a]pyridine-3-carboxamide (194)

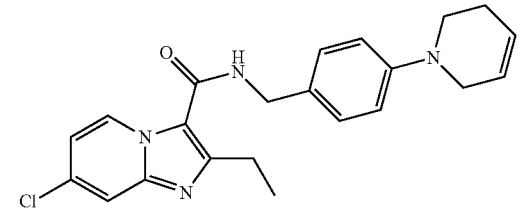 [SMILES: CCc1nc2cc(Cl)ccn2c1C(=O)NCc1ccc(N2CC=CCC2)cc1]

7-Chloro-2-ethyl-N-(4-(4-methylpiperidin-1-yl)benzyl)imidazo[1,2-a]pyridine-3-carboxamide (195)

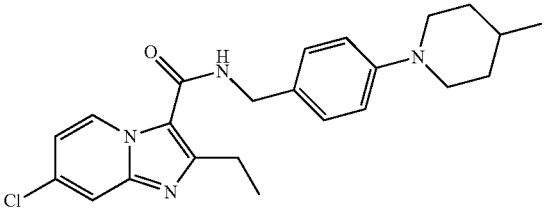 [SMILES: CCc1nc2cc(Cl)ccn2c1C(=O)NCc1ccc(N2CCC(C)CC2)cc1]

7-Chloro-2-ethyl-N-((2-(morpholinomethyl)-1H-benzo[d]imidazol-5-yl)methyl)imidazo[1,2-a]pyridine-3-carboxamide (196)

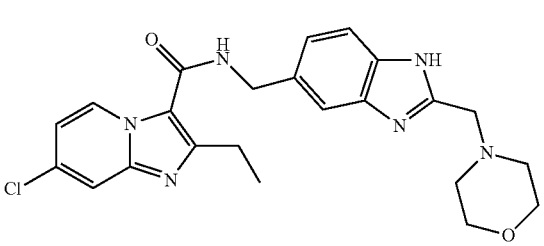 [SMILES: CCc1nc2cc(Cl)ccn2c1C(=O)NCc1ccc2[nH]c(CN3CCOCC3)nc2c1]

227

6-Chloro-N-(4-(3,5-dimethylpiperidin-1-yl)benzyl)-2-ethylimidazo[1,2-a]pyridine-3-carboxamide (197)

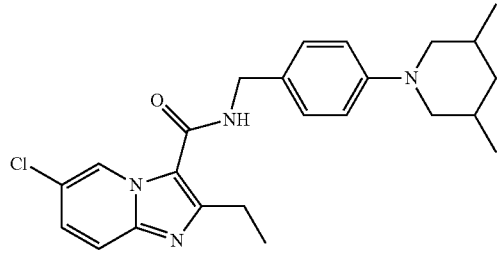 [SMILES: CCc1nc2ccc(Cl)cn2c1C(=O)NCc1ccc(N2CC(C)CC(C)C2)cc1]

7-Chloro-N-(4-(3,5-dimethylpiperidin-1-yl)benzyl)-2-ethylimidazo[1,2-a]pyridine-3-carboxamide (198)

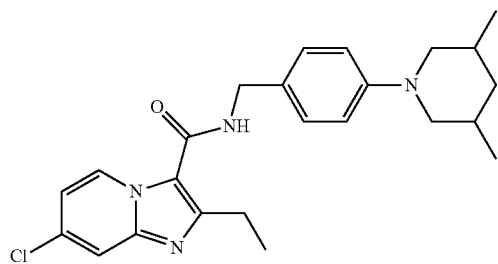 [SMILES: CCc1nc2cc(Cl)ccn2c1C(=O)NCc1ccc(N2CC(C)CC(C)C2)cc1]

7-Chloro-2-ethyl-N-(4-(4-hydroxypiperidin-1-yl)benzyl)imidazo[1,2-a]pyridine-3 (199)

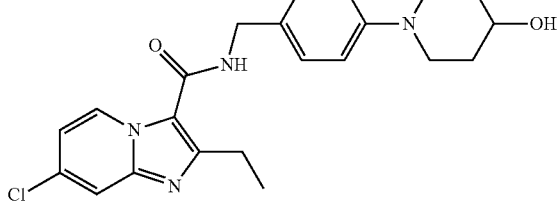

7-Chloro-2-ethyl-N-(4-(4-oxopiperidin-1-yl)benzyl)imidazo[1,2-a]pyridine-3-carboxamide (200)

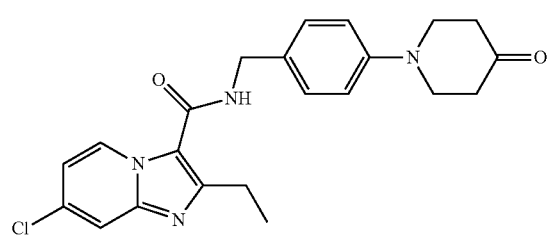 [SMILES: CCc1nc2cc(Cl)ccn2c1C(=O)NCc1ccc(N2C=CC(=O)CC2)cc1]

228

7-Chloro-2-ethyl-N-(4-(4-oxo-3,4-dihydropyridin-1(2H)-yl)benzyl)imidazo[1,2-a]pyridine-3-carboxamide (201)

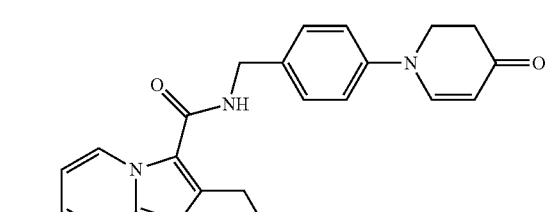

7-Chloro-N-(4-(3a,4-dihydro-1H-isoindol-2(3H,7H,7aH)-yl)benzyl-2-ethylimidazo[1,2-a]pyridine-3-carboxamide (202)

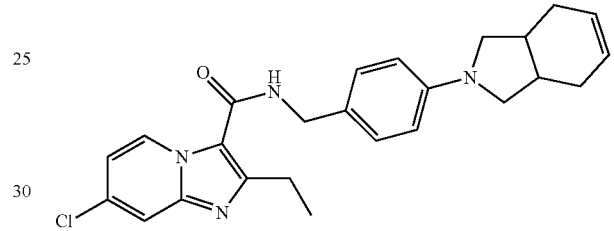

7-Chloro-2-ethyl-N-(4-(4-fluorophenoxy)benzyl)imidazo[1,2-a]pyridine-3-carboxamide (203)

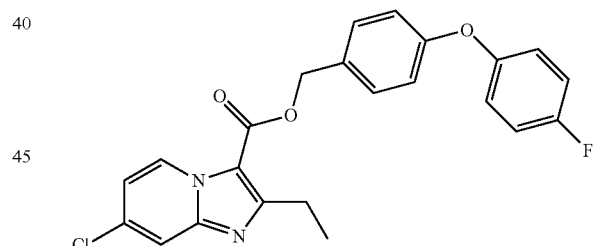

7-Chloro-2-ethyl-N-((4'-(trifluoromethoxy)biphenyl-3-yl)methyl)imidazo[1,2-a]pyridine-3-carboxamide (204)

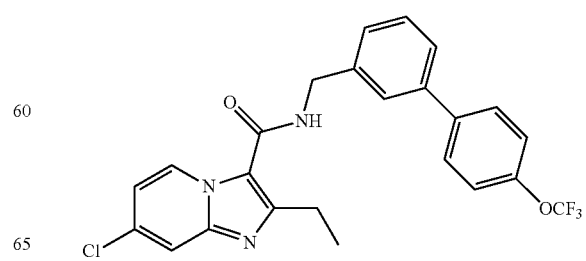

229

2-Ethyl-6-fluoro-N-(4-(4-(trifluoromethoxy)benzyloxyl)
benzyl)imidazo[1,2-a]pyridine-3-carboxamide (205)

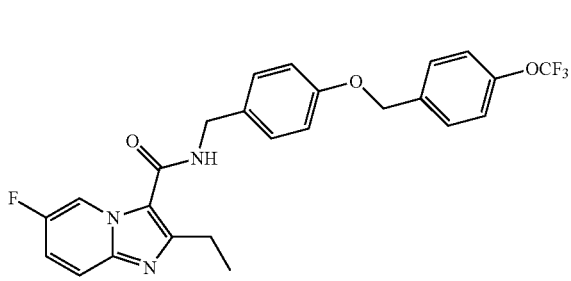 [SMILES: CCc1nc2ccc(F)cn2c1C(=O)NCc1ccc(OCc2ccc(OC(F)(F)F)cc2)cc1]

6-Bromo-2-ethyl-N-(4-(4-(trifluoromethoxy)benzyloxy)
imidazo[1,2-a]pyridine-3-carboxamide (206)

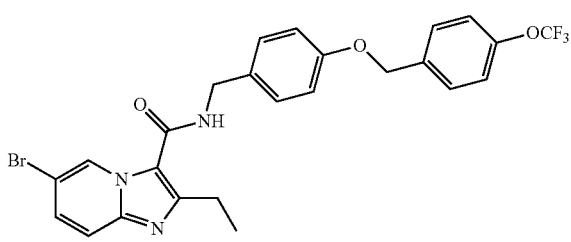 [SMILES: CCc1nc2ccc(Br)cn2c1C(=O)NCc1ccc(OCc2ccc(OC(F)(F)F)cc2)cc1]

2-Ethyl-N-(4-(4-(trifluoromethoxy)benzyloxy)benzyl)
imidazo[1,2-a]pyridine-3-carboxamide (207)

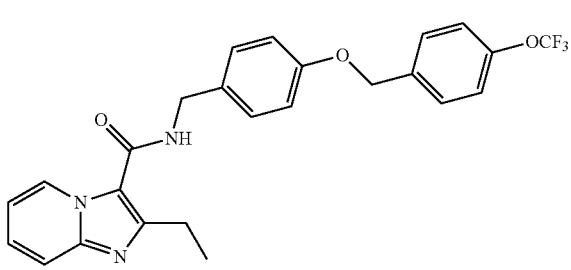 [SMILES: CCc1nc2ccccn2c1C(=O)NCc1ccc(OCc2ccc(OC(F)(F)F)cc2)cc1]

N-(4-(4-Benzylpiperidin-1-yl)benzyl)-7-chloro-2-eth-
ylimidazo[1,2-a]pyridine-3-carboxamide (208)

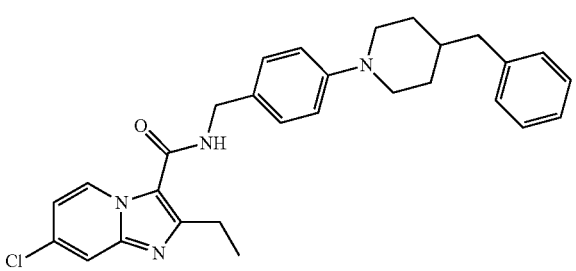 [SMILES: CCc1nc2cc(Cl)ccn2c1C(=O)NCc1ccc(N2CCC(Cc3ccccc3)CC2)cc1]

230

7-Chloro-2-ethyl-N-(4-(4-phenylpiperidin-1-yl)benzyl)
imidazo[1,2-a]pyridine-3-carboxamide (209)

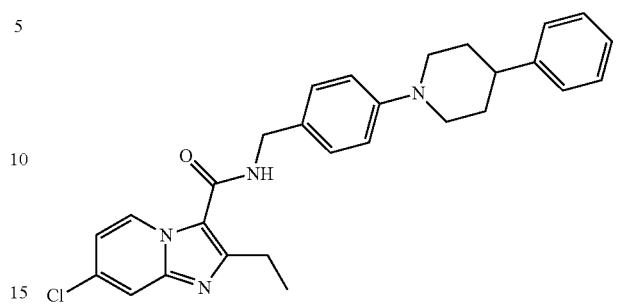

6-Chloro-2-ethyl-N-(4-(4-phenylpiperidin-1-yl)benzyl)
imidazo[1,2-a]pyridine-3-carboxamide (210)

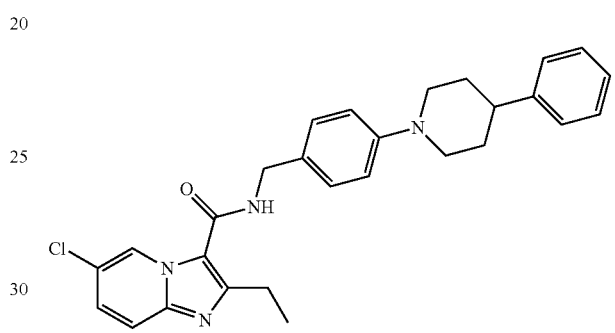

7-Chloro-N-(4-(4,4-dimethylpiperidin-1-yl)benzyl)-2-
ethyl-1,8a-dihydroimidazo[1,2-a]pyridine-3-carboxa-
mide (211)

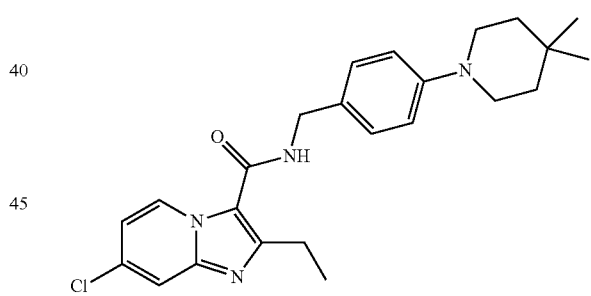

7-Chloro-2-ethyl-N-(4-(4-(hydroxymethyl)piperidin-1-
yl)benzyl)imidazo[1,2-a]pyridine-3-carboxamide (212)

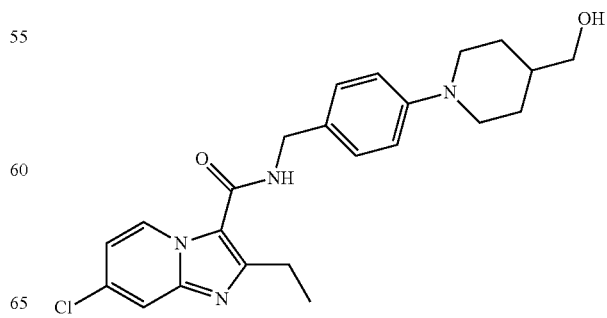

6-chloro-2-ethyl-N-(4-(4-((4-(trifluoromethoxy)phenoxy)methyl)piperidin-1-yl)benzyl)imidazo[1,2-a]pyridine-3-carboxamide (213)

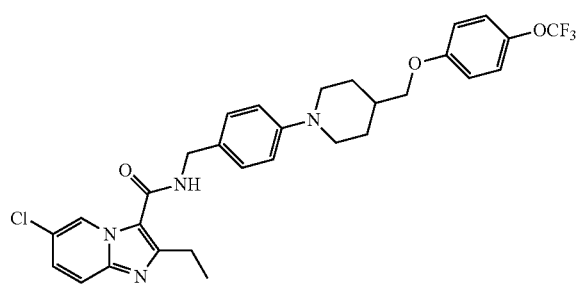 [SMILES: CCc1nc2ccc(Cl)cn2c1C(=O)NCc1ccc(N2CCC(COc3ccc(OC(F)(F)F)cc3)CC2)cc1]

7-Chloro-2-ethyl-N-(4-(4-((4-(trifluoromethoxy)phenoxy)methyl)piperidin-1-yl)benzyl)imidazo[1,2-a]pyridine-3-carboxamide (214)

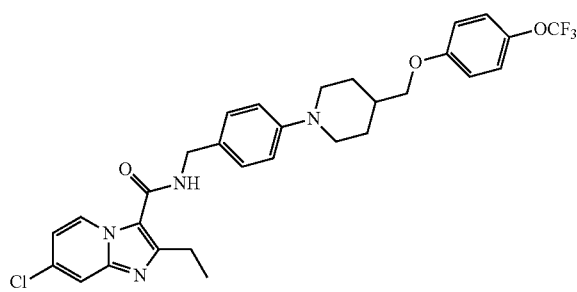 [SMILES: CCc1nc2cc(Cl)ccn2c1C(=O)NCc1ccc(N2CCC(COc3ccc(OC(F)(F)F)cc3)CC2)cc1]

7-Chloro-2-ethyl-N-(4-((4-(trifluoromethoxy)benzyl)amino)benzyl)imidazo[1,2-a]pyridine-3-carboxamide (215)

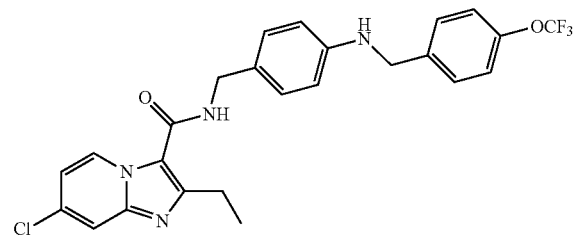 [SMILES: CCc1nc2cc(Cl)ccn2c1C(=O)NCc1ccc(NCc2ccc(OC(F)(F)F)cc2)cc1]

N-(4-(1H-isoindol-2(3H,3aH,4H,5H,6H,7H,7aH)-yl)benzyl)-7-chloro-2-ethylimidazo[1,2-a]pyridine-3-carboxamide (216)

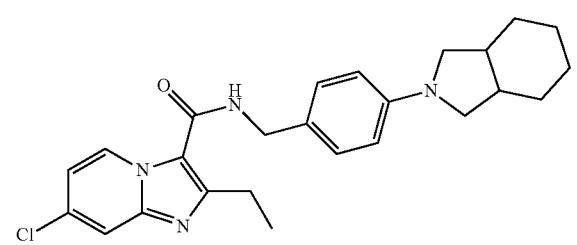

7-Chloro-2-ethyl-N-(4-(4,5,6,7-tetrahydro-2H-isoindol-2-yl)benzyl)imidazo[1,2-a]pyridine-3-carboxamide (217)

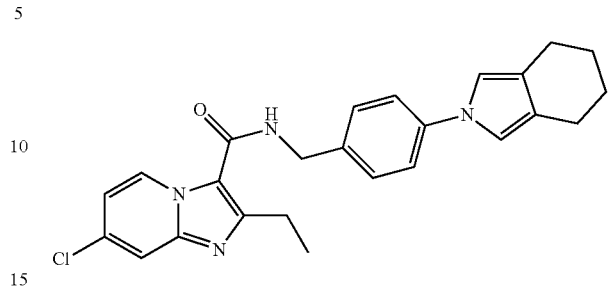

7-Chloro-2-ethyl-N-(4-(4-methylenepiperidin-1-yl)benzyl)imidazo[1,2-a]pyridine-3-carboxamide (218)

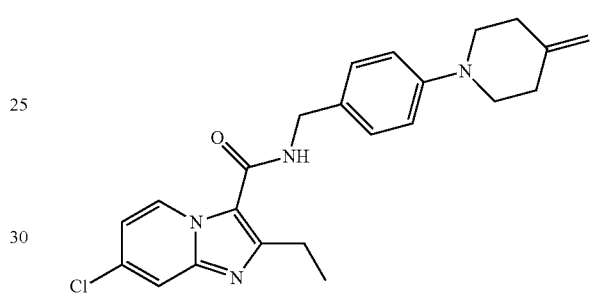

2-Ethyl-7-methyl-N-(4-(4-(trifluoromethoxy)phenoxy)benzyl)imidazo[1,2-a]pyridine-3-carboxamide (219)

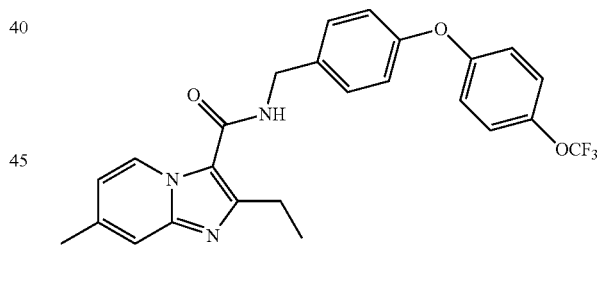

2-Ethyl-N-(4-(4-(4-fluorophenyl)piperazin-1yl)benzyl)-7-methylimidazo[1,2-a]pyridine-3-carboxamide (220)

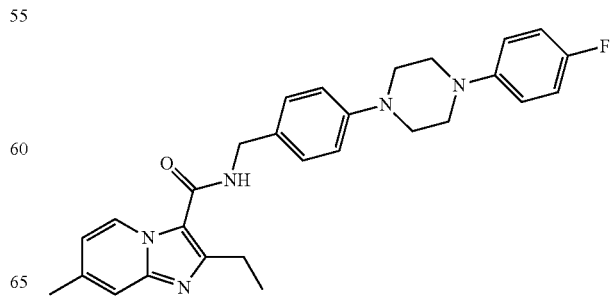

233

6-Chloro-2-ethyl-N-(4-(octahydroisoquinolin-2(1H)-yl)benzyl)imidazo[1,2-a]pyridine-3-carboxamide (221)

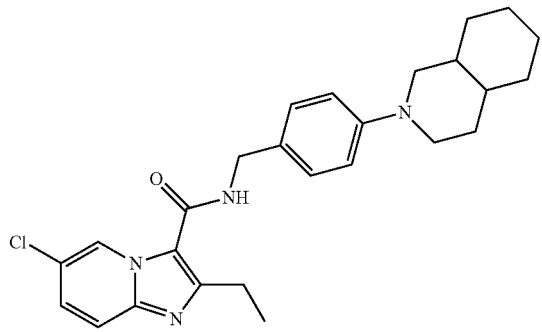 [SMILES: CCc1nc2ccc(Cl)cn2c1C(=O)NCc1ccc(N2CCC3CCCCC3C2)cc1]

7-chloro-2-ethyl-N-(4-(octahydroisoquinolin-2(1H)-yl)benzyl)imidazo[1,2-a]pyridine-3-carboxamide (222)

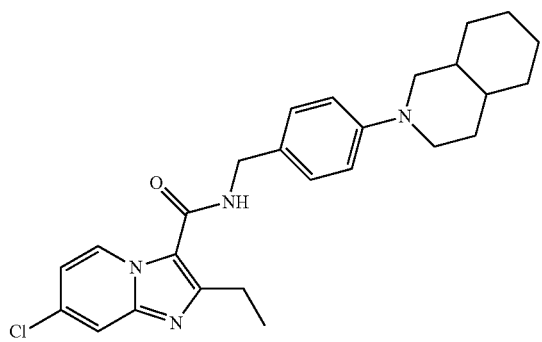 [SMILES: CCc1nc2cc(Cl)ccn2c1C(=O)NCc1ccc(N2CCC3CCCCC3C2)cc1]

2-Ethyl-8-fluoro-N-(4-(4-(4-fluorophenyl)piperazin-1-yl)benzyl)imidazo[1,2-a]pyridine-3-carboxamide (223)

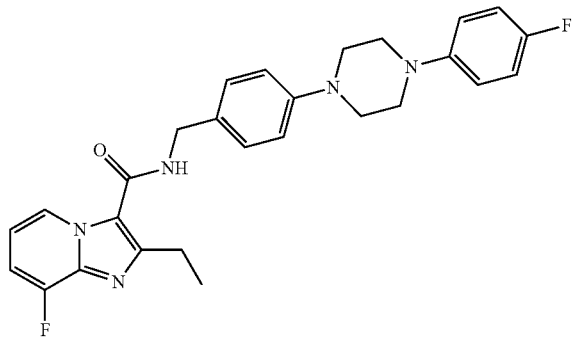 [SMILES: CCc1nc2c(F)cccn2c1C(=O)NCc1ccc(N2CCN(c3ccc(F)cc3)CC2)cc1]

2-Ethyl-8-fluoro-N-(4-(4-(trifluoromethoxy)phenyl)benzyl)imidazo[1,2-a]pyridine-3-carboxamide (224)

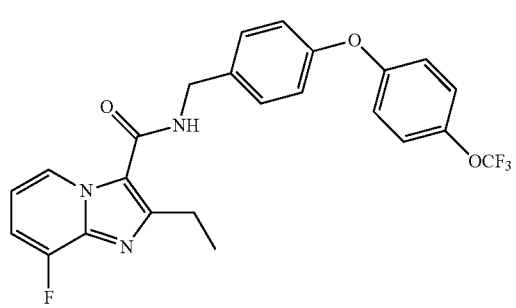 [SMILES: CCc1nc2c(F)cccn2c1C(=O)NCc1ccc(Oc2ccc(OC(F)(F)F)cc2)cc1]

234

2-Ethyl-6-fluoro-N-(4-(4-(trifluoromethoxy)phenyl)benzyl)imidazo[1,2-a]pyridine-3-carboxamide (225)

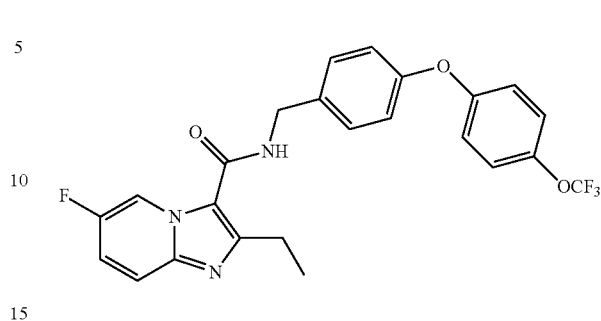

6-Bromo-2-ethyl-N-(4-(4-(trifluoromethoxy)phenyl)benzyl)imidazo[1,2-a]pyridine-3-carboxamide (226)

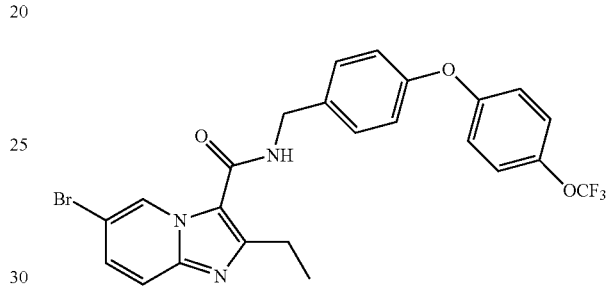

2-Ethyl-N-(4-(4-(4-fluorophenyl)piperazin-1-yl)benzyl)imidazo[1,2-a]pyridine-3-carboxamide (227)

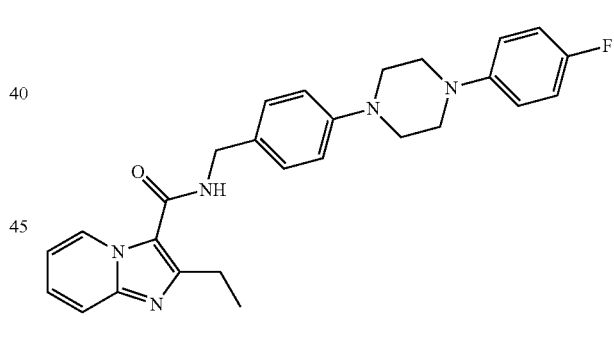

2-Ethyl-6-fluoro-N-(4-(4-(4-fluorophenyl)piperazin-1-yl)benzyl)imidazo[1,2-a]pyridine-3-carboxamide (228)

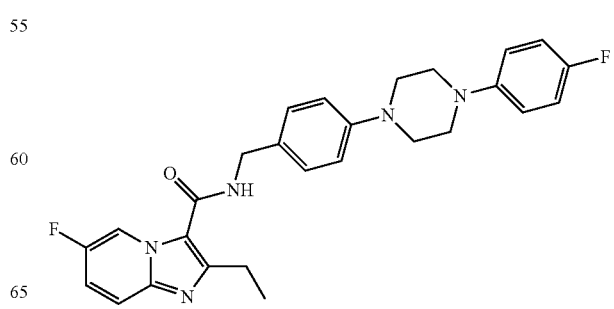

235

6-Bromo-2-ethyl-N-(4-(4-(4-fluorophenyl)piperazin-1-yl)benzyl)imidazo[1,2-a]pyridine-3-carboxamide (229)

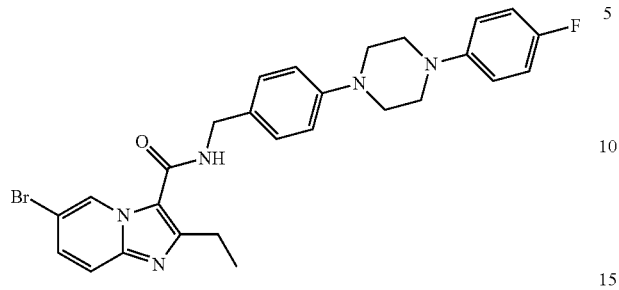

6-Chloro-2-ethyl-N-(4-(4-(hydroxymethyl)piperidin-1-yl)benzyl)imidazo[1,2-a]pyridine-3-carboxamide (230)

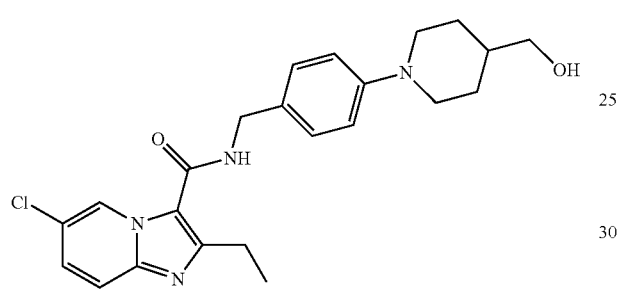

2-Ethyl-N-(4-(4-(4-fluorophenyl)piperazin-1-yl)benzyl)-6-methylimidazo[1,2-a]pyridine-carboxamide (231)

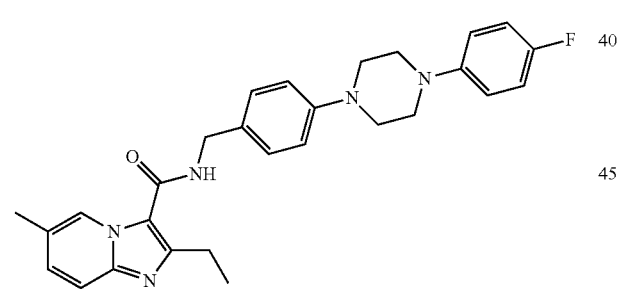

2-Ethyl-6-methyl-N-(4-(4-(trifluoromethoxy)phenyl)benzyl)imidazo[1,2-a]pyridine-carboxamide (232)

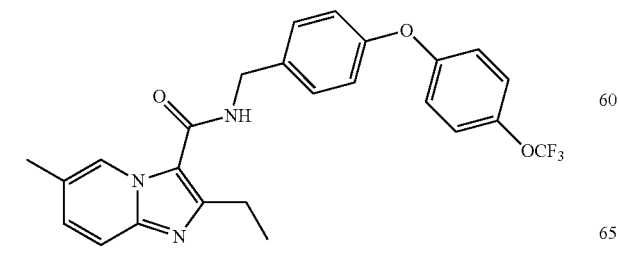

236

6-Chloro-2-ethyl-N-(4-(4-(trifluoromethyl)piperidin-1-yl)benzyl)imidazo[1,2-a]pyridine-3-carboxamide (233)

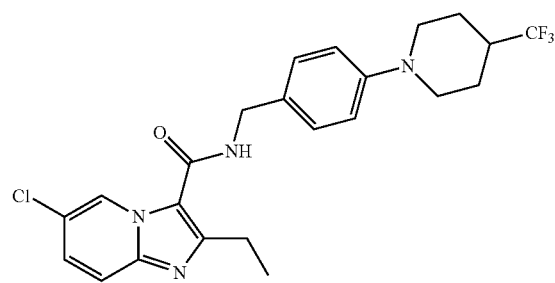 [SMILES: CCc1nc2ccc(Cl)cn2c1C(=O)NCc1ccc(N2CCC(C(F)(F)F)CC2)cc1]

7-Chloro-2-ethyl-N-(4-(4-(trifluoromethyl)piperidin-1-yl)benzyl)imidazo[1,2-a]pyridine-3-carboxamide (234)

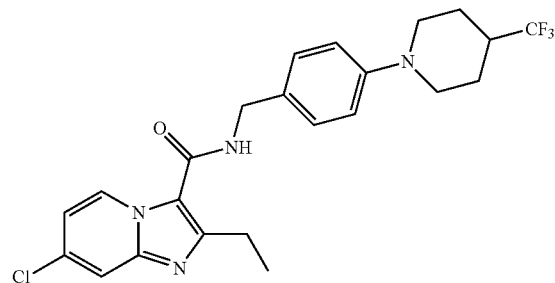 [SMILES: CCc1nc2cc(Cl)ccn2c1C(=O)NCc1ccc(N2CCC(C(F)(F)F)CC2)cc1]

6-chloro-N-(4-(4,4-difluoropiperidin-1-benzyl)-2-ethylimidazo[1,2-a]pyridine-3-carboxamide (235)

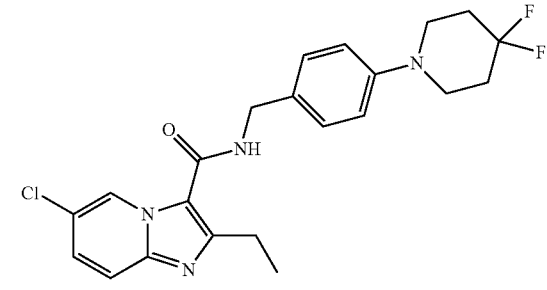 [SMILES: CCc1nc2ccc(Cl)cn2c1C(=O)NCc1ccc(N2CCC(F)(F)CC2)cc1]

7-Chloro-N-(4-(4,4-difluoropiperidin-1-yl)benzyl)-2-ethylimidazo[1,2-a]pyridine-3-carboxamide (236)

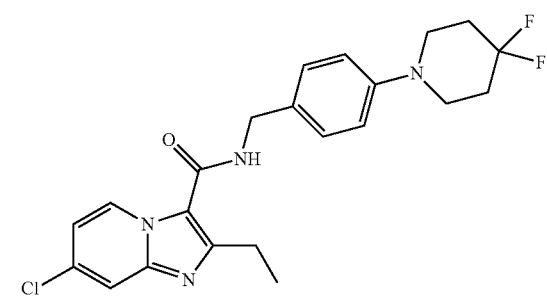 [SMILES: CCc1nc2cc(Cl)ccn2c1C(=O)NCc1ccc(N2CCC(F)(F)CC2)cc1]

6-Chloro-2-ethyl-N-(4-(hexahydropyrrolo[1,2-a]pyrazin-2(1H)-yl)benzyl)imidazo[1,2-a]pyridine-3-carboxamide (237)

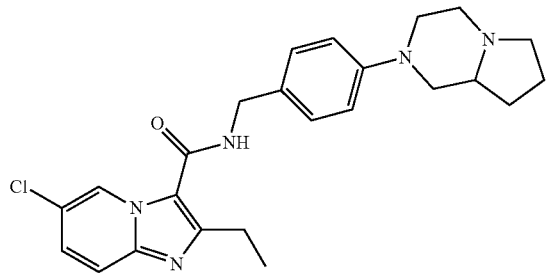 [SMILES: CCc1nc2ccc(Cl)cn2c1C(=O)NCc1ccc(N2CCN3CCCC3C2)cc1]

6-Chloro-N,2-diethylimidazo[1,2-a]pyridine-3-carboxamide

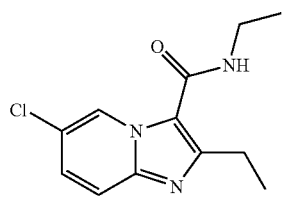 [SMILES: CCNC(=O)c1c(CC)nc2ccc(Cl)cn12]

6-Chloro-2-ethyl-N-isobutylimidazo[1,2-a]pyridine-3-carboxamide (239)

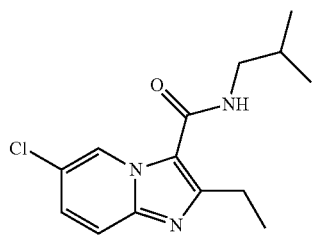 [SMILES: CCc1nc2ccc(Cl)cn2c1C(=O)NCC(C)C]

6-Bromo-2-ethyl-N-(4-morpholinobenzyl)imidazo[1,2-a]pyridine-3-carboxamide (240)

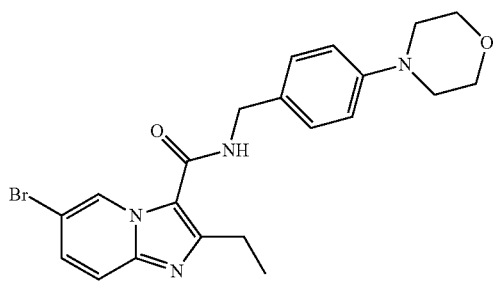

2-Ethyl-6-fluoro-N-(4-morpholinobenzyl)imidazo[1,2-a]pyridine-3-carboxamide (241)

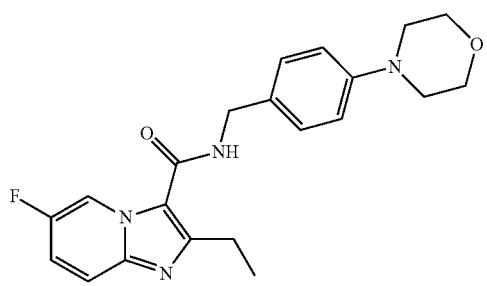 [SMILES: CCc1nc2ccc(F)cn2c1C(=O)NCc1ccc(N2CCOCC2)cc1]

2-Ethyl-8-fluoro-N-(4-morpholinobenzyl)imidazo[1,2-a]pyridine-3-carboxamide (242)

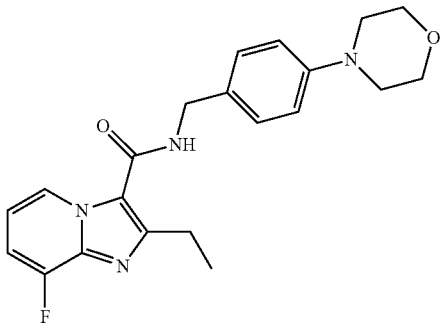 [SMILES: CCc1nc2c(F)cccn2c1C(=O)NCc1ccc(N2CCOCC2)cc1]

2-Ethyl-N-(4-(4-((4-fluorophenoxy)methyl)piperidin-1-yl)benzyl)imidazo[1,2-a]pyridine-3-carboxamide (243)

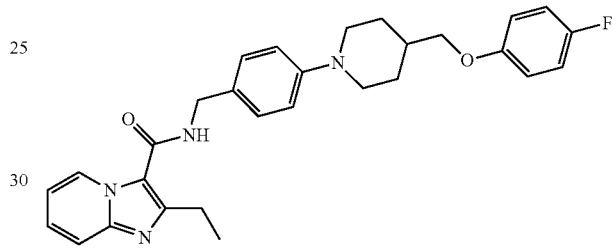

6-Chloro-2-ethyl-N-(4-(4-((4-fluorophenoxy)methyl)piperidin-1-yl)benzyl)imidazo[1,2-a]pyridine-3-carboxamide (244)

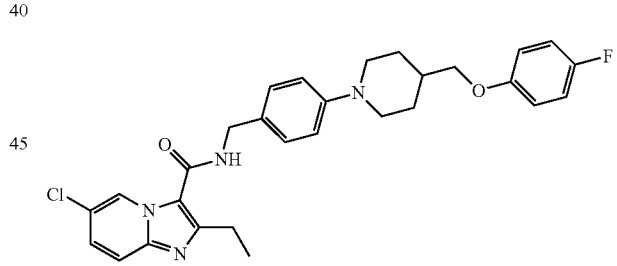

7-Chloro-2-ethyl-N-(4-(4-((4-fluorophenoxy)methyl)piperidin-1-yl)benzyl)imidazo[1,2-a]pyridine-3-carboxamide (245)

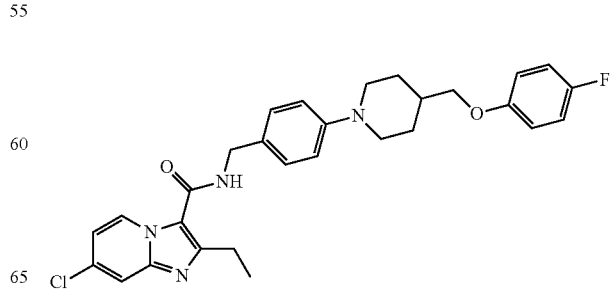

239

2-Ethyl-7-(4-phenylpiperazin-1-yl)-N-(4-(trifluoromethyl)benzyl)imidazo[1,2-a]pyridine-3-carboxamide (246)

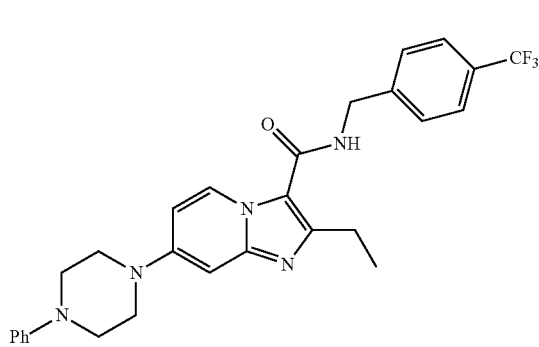 [SMILES: CCc1nc2cc(N3CCN(c4ccccc4)CC3)ccn2c1C(=O)NCc1ccc(C(F)(F)F)cc1]

6-Chloro-2-ethyl-N-(4-(4-(methoxymethyl)piperidin-1-yl)benzyl)imidazo[1,2-a]pyridine-3-carboxamide (247)

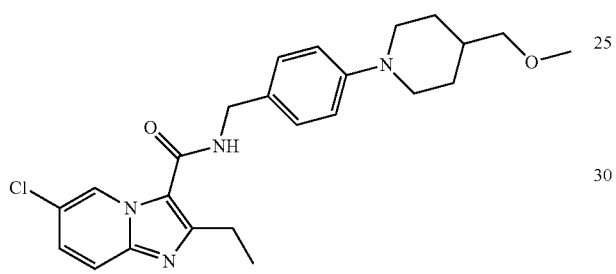

7-Chloro-2-ethyl-N-(4-(4-(methoxymethyl)piperidin-1-yl)benzyl)imidazo[1,2-a]pyridine-3-carboxamide (248)

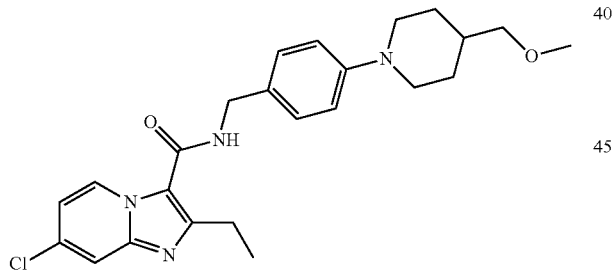

6-Chloro-2-ethyl-N-(4-(4-(4-(fluorophenyl)piperidin-1-yl)benzyl)imidazo[1,2-a]pyridine-3-carboxamide (249)

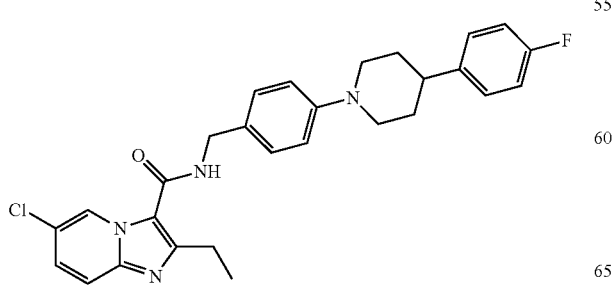

240

7-Chloro-2-ethyl-(4-(4-(4-(fluorophenyl)piperidin-1-yl)benzyl)imidazo[1,2-a]pyridine-3-carboxamide (250)

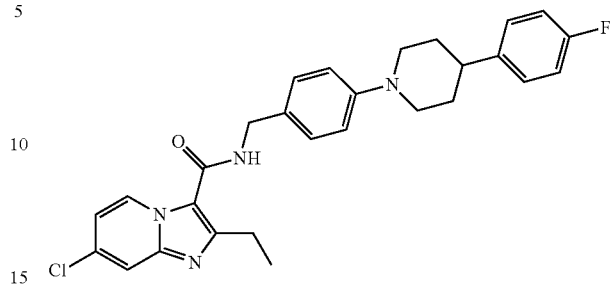

6-chloro-2-ethyl-N-(4-(2-methylpiperidin-1-yl)benzyl)imidazo[1,2-a]pyridine-3-carboxamide (251)

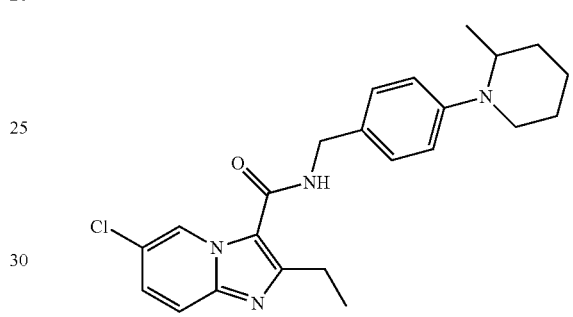

7-chloro-2-ethyl-N-(4-(2-methylpiperidin-1-yl)benzyl)imidazo[1,2-a]pyridine-3-carboxamide (252)

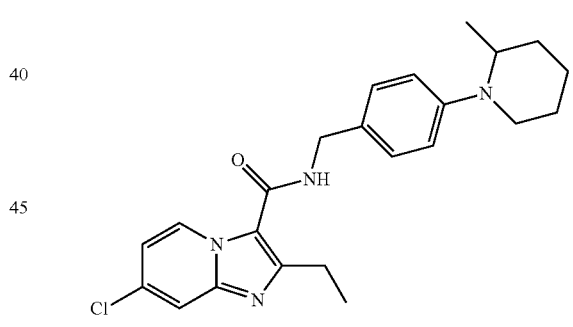

7-Bromo-2-ethyl-N-(4-morpholinobenzyl)imidazo[1,2-a]pyridine-3-carboxamide (253)

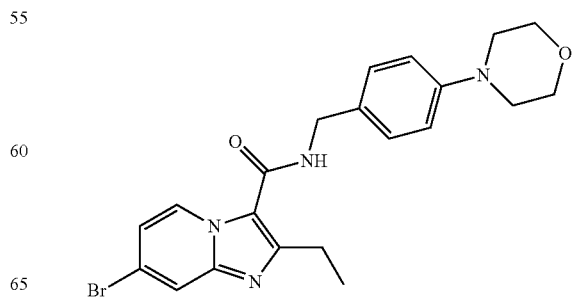

241

2-Ethyl-7-(4-methylpiperazin-1-yl)-N-(4-morpholinobenzyl)imidazo[1,2-a]pyridine-3-carboxamide (254)

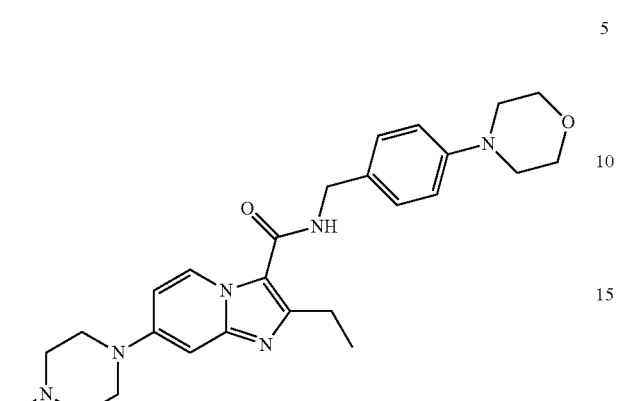

2-Ethyl-N-(4-morpholinobenzyl)-7-(pyridin-4-yl)imidazo[1,2-a]pyridine-3-carboxamide (255)

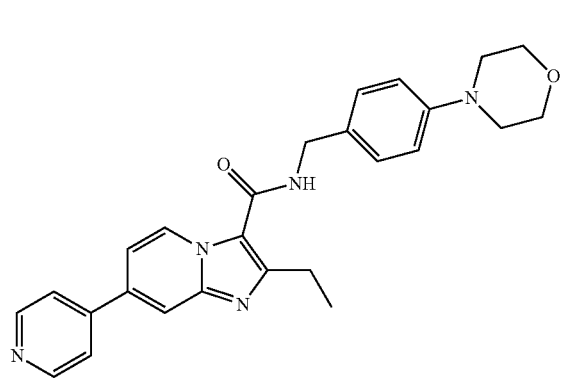 [SMILES: CCc1nc2cc(-c3ccncc3)ccn2c1C(=O)NCc1ccc(N2CCOCC2)cc1]

2-Ethyl-7-(4-(4-fluorophenyl)piperazin-1-yl)-N-(4-morpholinobenzyl)imidazo[1,2-a]pyridine-3-carboxamide (256)

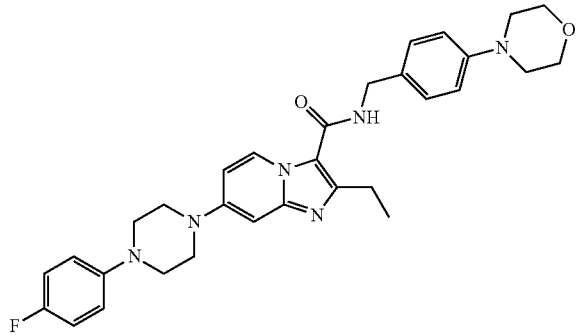 [SMILES: CCc1nc2cc(N3CCN(c4ccc(F)cc4)CC3)ccn2c1C(=O)NCc1ccc(N2CCOCC2)cc1]

242

2-Ethyl-7-(4-(4-fluorobenzyl)piperazin-1-yl)-N-(4-morpholinobenzyl)imidazo[1,2-a]pyridine-3-carboxamide (257)

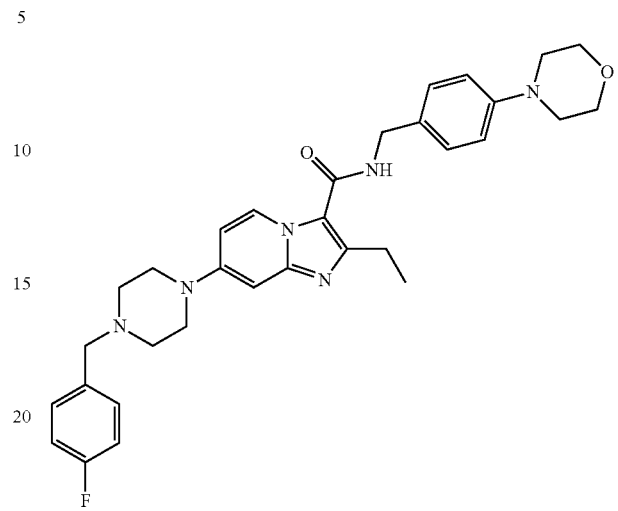

6-Chloro-2-ethyl-N-((2-(4-fluorophenyl)benzo[d]oxazol-5-yl)methyl)imidazo[1,2-a]pyridine-3-carboxamide (258)

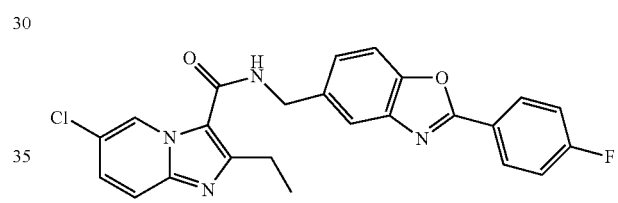

7-Chloro-2-ethyl-N-((2-(4-fluorophenyl)benzo[d]oxazol-5-yl)methyl)imidazo[1,2-a]pyridine-3-carboxamide (259)

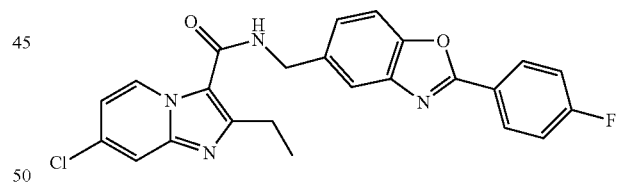

8-Bromo-2-ethyl-N-(4-(4-(4-fluorophenyl)piperazin-1-yl)benzyl)imidazo[1,2-a]pyridine-3-carboxamide (260)

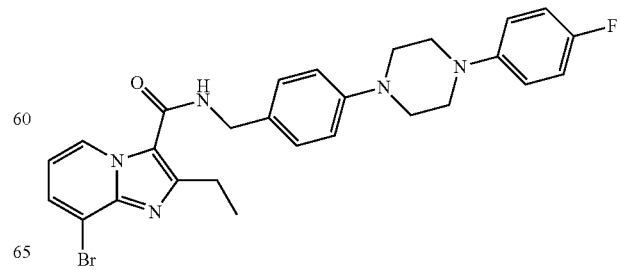

243

2-Ethyl-7-methoxy-N-(4-morpholinobenzyl)imidazo[1,2-a]pyridine-3-carboxamide (261)

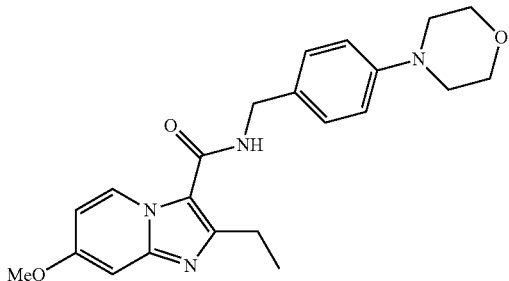 [SMILES: CCc1nc2cc(OC)ccn2c1C(=O)NCc1ccc(N2CCOCC2)cc1]

2-Ethyl-8-methoxy-N-(4-morpholinobenzyl)imidazo[1,2-a]pyridine-3-carboxamide 262)

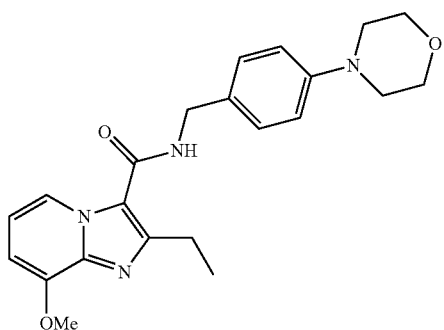 [SMILES: CCc1nc2c(OC)cccn2c1C(=O)NCc1ccc(N2CCOCC2)cc1]

2-Ethyl-N-(4-(4-(4-fluorophenyl)piperazin-1-yl)-8-methoxyimidazo[1,2-a]pyridine-3-carboxamide (263)

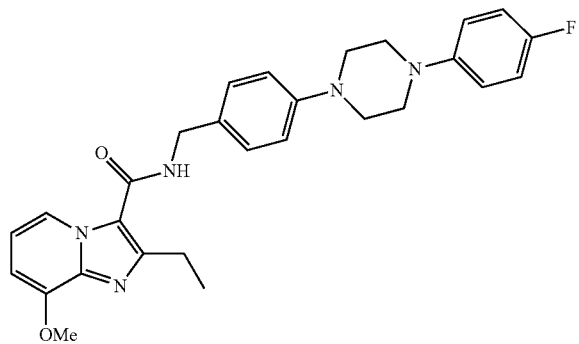 [SMILES: CCc1nc2c(OC)cccn2c1C(=O)NCc1ccc(N2CCN(c3ccc(F)cc3)CC2)cc1]

2-Ethyl-N-(4-(4-(4-fluorophenyl)piperazin-1-yl)benzyl)-7-methoxyimidazo[1,2-a]pyridine-3-carboxamide (264)

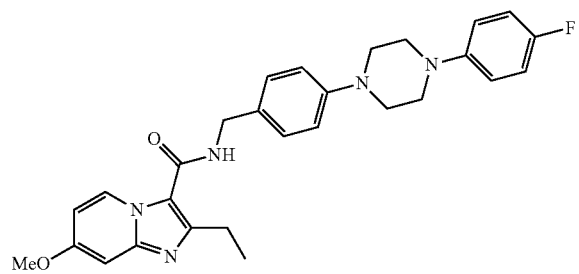 [SMILES: CCc1nc2cc(OC)ccn2c1C(=O)NCc1ccc(N2CCN(c3ccc(F)cc3)CC2)cc1]

244

2-Ethyl-N-(4-(4-(4-fluorophenyl)piperidin-1-yl)benzyl)imidazo[1,2-a]pyridine-3-carboxamide (265)

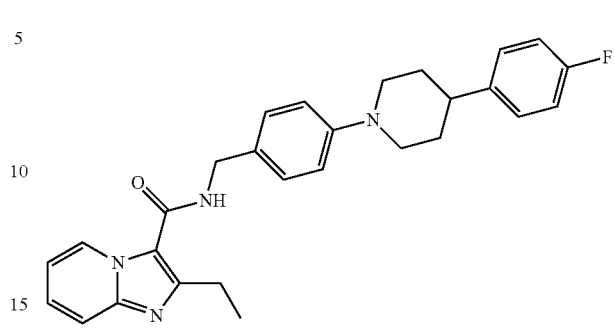

2-Ethyl-N-(4-(4-(4-trifluoromethoxy)phenyl)piperidin-1-yl)benzyl)imidazo[1,2-a]pyridine-3-carboxamide (266)

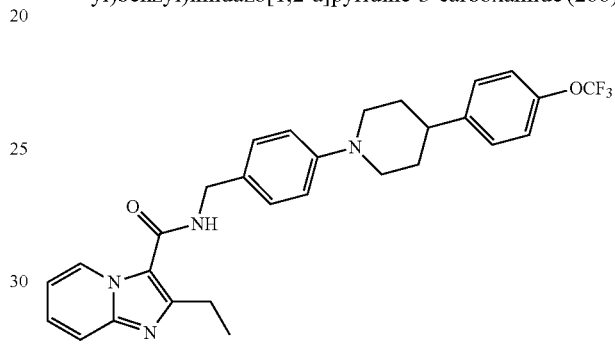

6-Chloro-2-ethyl-N-(4-(4-(4-(trifluoromethoxy)phenyl)piperidin-1-yl)benzyl)imidazo[1,2-a]pyridine-3-carboxamide (267)

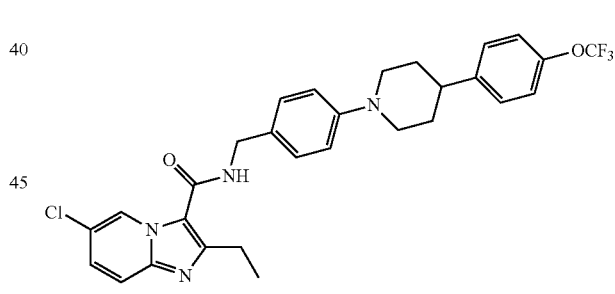

7-Chloro-2-ethyl-N-(4-(4-(4-(trifluoromethoxy)phenyl)piperidin-1-yl)benzyl)imidazo[1,2-a]pyridine-3-carboxamide (268)

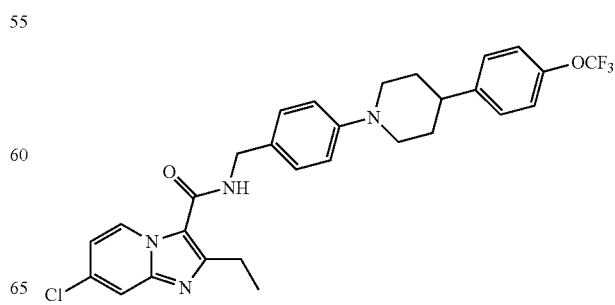

Ethyl 4-(4-((6-chloro-2-ethylimidazo[1,2-a]pyridine-3-carboxamido)methyl)phenyl)piperidine-4-carboxylate (269)

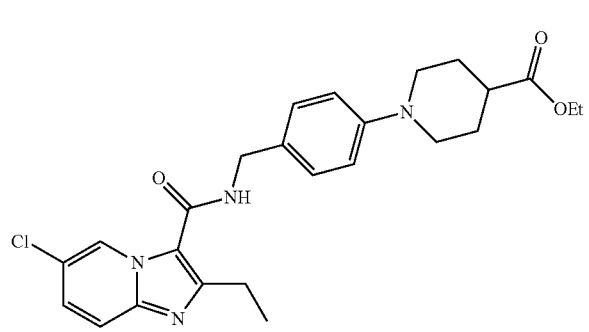 [SMILES: CCOC(=O)C1CCN(c2ccc(CNC(=O)c3c(CC)nc4ccc(Cl)cn34)cc2)CC1]

Ethyl 1-(4-((7-chloro-2-ethylimidazo[1,2-a]pyridine-3-carboxamido)methyl)phenyl)piperidine-4-carboxylate (270)

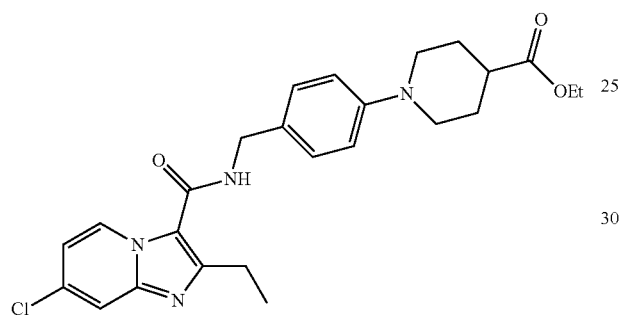

2-Ethyl-N-(4-(4-(4-fluorophenyl)piperazin-1-yl)benzyl)-6-methoxyimidazo[1,2-a]pyridine-3-carboxamide (271)

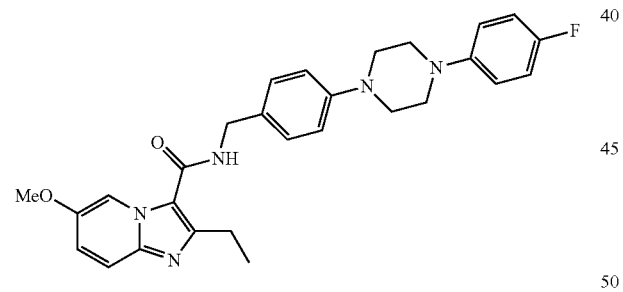

2-Ethyl-6-fluoro-N-(4-morpholinobenzyl)imidazo[1,2-a]pyridine-3-carboxamide (272)

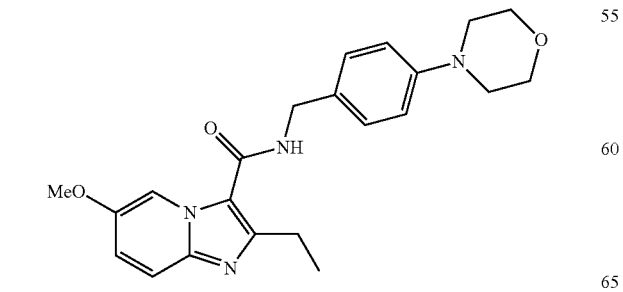

2-Ethyl-N-(4-morpholinobenzyl)-6-(trifluoromethyl)imidazo[1,2-a]pyridine-3-carboxamide (273)

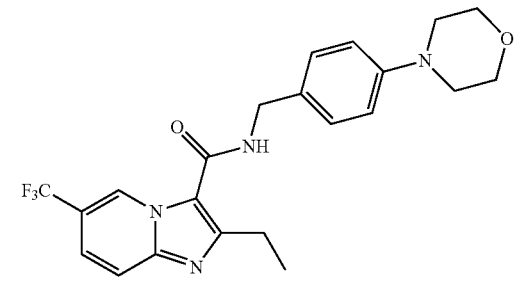 [SMILES: CCc1nc2ccc(C(F)(F)F)cn2c1C(=O)NCc1ccc(N2CCOCC2)cc1]

2-Ethyl-N-(4-morpholinobenzyl)-8-(trifluoromethyl)imidazo[1,2-a]pyridine-3-carboxamide (274)

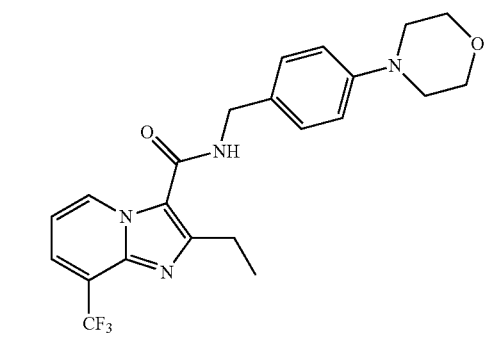 [SMILES: CCc1nc2c(C(F)(F)F)cccn2c1C(=O)NCc1ccc(N2CCOCC2)cc1]

1-(4-((7-Chloro-2-ethylimidazo[1,2-a]pyridine-3-carboxamido)methyl)phenyl)piperidine-4-carboxylic acid (275)

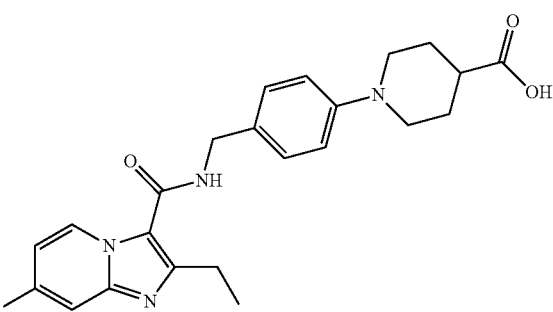

6-Chloro-2-ethyl-N-(4-(4-(isopropoxymethyl)piperidin-1-yl)benzyl)imidazo[1,2-a]pyridine-3-carboxamide (276)

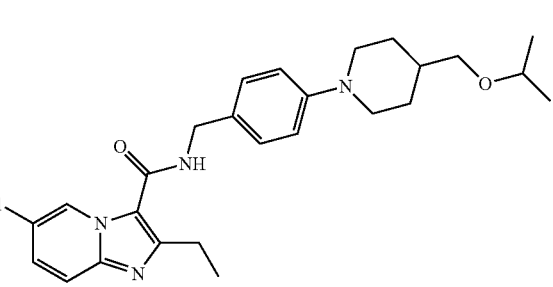

247

7-Chloro-2-ethyl-N-(4-(4-(isopropoxymethyl)piperidin-1-yl)benzyl)imidazo[1,2-a]pyridine-3-carboxamide (277)

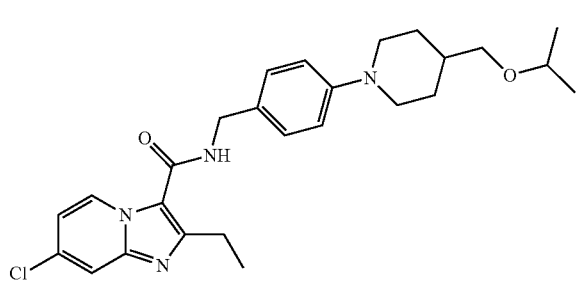 [SMILES: CCc1nc2cc(Cl)ccn2c1C(=O)NCc1ccc(N2CCC(COC(C)C)CC2)cc1]

8-(Difluoromethoxy)-2-ethyl-N-(4-(4-(4-(fluorophenyl)piperazin-1-yl)benzyl)imidazo[1,2-a]pyridine-3-carboxamide (278)

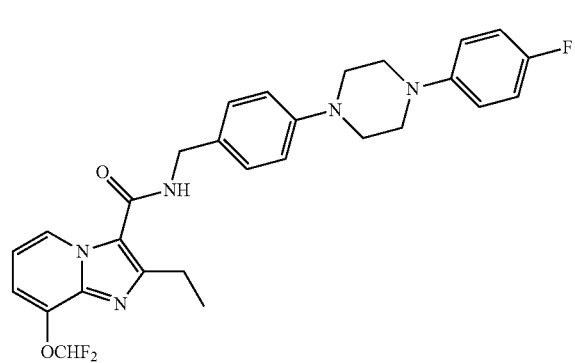 [SMILES: CCc1nc2c(OC(F)F)cccn2c1C(=O)NCc1ccc(N2CCN(c3ccc(F)cc3)CC2)cc1]

8-(Difluoromethoxy)-2-ethyl-N-(4-morpholinobenzyl)imidazo[1,2-a]pyridine-3-carboxamide (279)

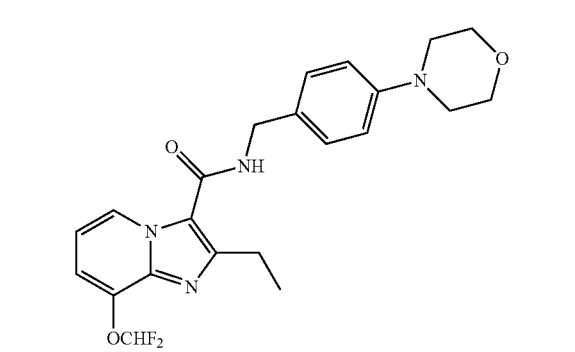 [SMILES: CCc1nc2c(OC(F)F)cccn2c1C(=O)NCc1ccc(N2CCOCC2)cc1]

2-Ethyl-7-methyl-N-(4-(trifluoromethoxy)benzyl)imidazo[1,2-a]pyridine-3-carboxamide (280)

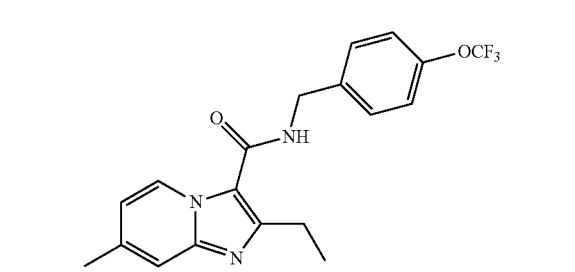 [SMILES: CCc1nc2cc(C)ccn2c1C(=O)NCc1ccc(OC(F)(F)F)cc1]

248

7-Bromo-2-ethyl-N-(4-(trifluoromethoxy)benzyl)imidazo[1,2-a]pyridine-3-carboxamide (281)

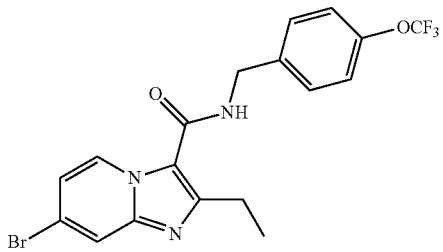 [SMILES: CCc1nc2cc(Br)ccn2c1C(=O)NCc1ccc(OC(F)(F)F)cc1]

2-Ethyl-8-fluoro-N-(4-(trifluoromethoxy)benzyl)imidazo[1,2-a]pyridine-3-carboxamide (282)

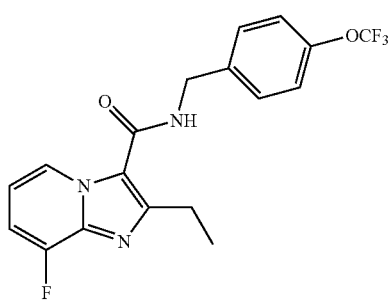 [SMILES: CCc1nc2c(F)cccn2c1C(=O)NCc1ccc(OC(F)(F)F)cc1]

2-Ethyl-N-(4-(4-(4-(fluorophenyl)piperazin-1-yl)benzyl)-8-(pyridin-4-yl)imidazo[1,2-a]pyridine-3-carboxamide (283)

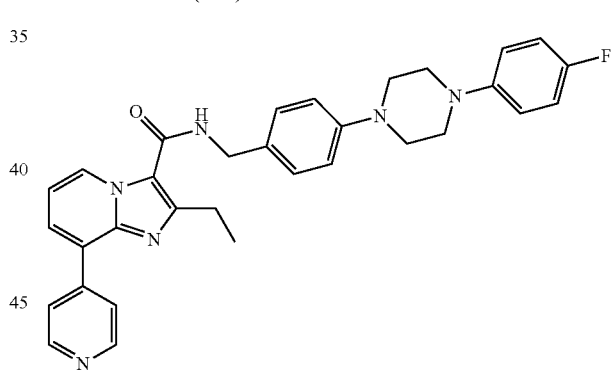

2-Ethyl-N-(4-morpholinobenzyl)-8-(pyridin-4-yl)imidazo[1,2-a]pyridine-3-carboxamide (284)

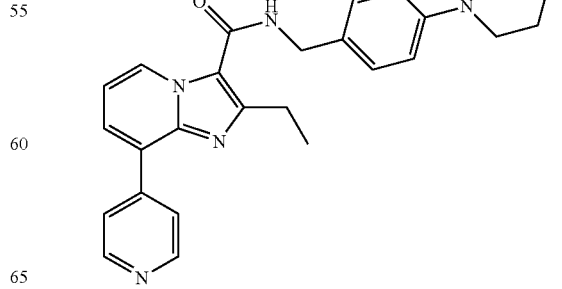

6-Chloro-N-(4-(4-(cyclopentyloxymethyl)piperidin-1-yl)
benzyl)-2-ethylimidazo[1,2-a]pyridine-3-carboxamide
(285)

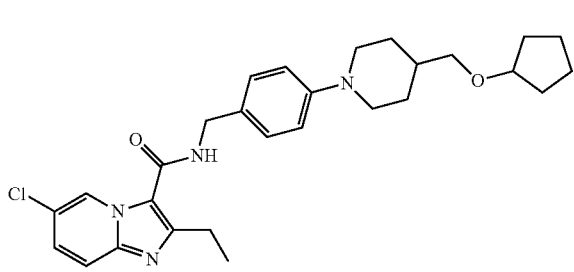 [SMILES: CCc1nc2ccc(Cl)cn2c1C(=O)NCc1ccc(N2CCC(COC3CCCC3)CC2)cc1]

7-Chloro-N-(4-(4-(cyclopentyloxymethyl)piperidin-1-yl)
benzyl)-2-ethylimidazo[1,2-a]pyridine-3-carboxamide
(286)

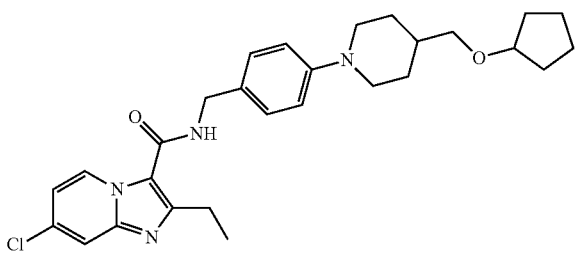 [SMILES: CCc1nc2cc(Cl)ccn2c1C(=O)NCc1ccc(N2CCC(COC3CCCC3)CC2)cc1]

7-Chloro-2-ethyl-N-(4'-formylbiphenyl-4-yl)methyl)imi-
dazo[1,2-a]pyridine-3-carboxamide (287)

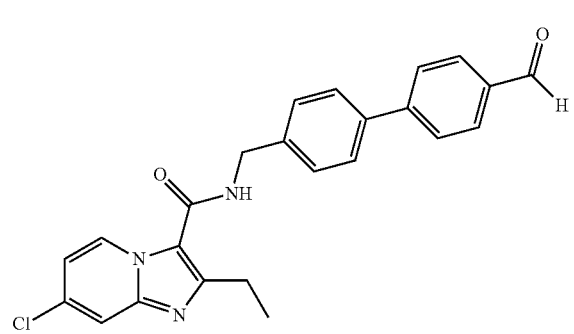 [SMILES: CCc1nc2cc(Cl)ccn2c1C(=O)NCc1ccc(-c2ccc(C=O)cc2)cc1]

7-Chloro-2-ethyl-N-(4-(morpholine-4-carbonyl)benzyl)
imidazo[1,2-a]pyridine-3-carboxamide (288)

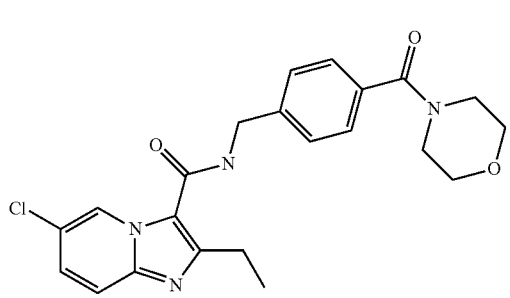 [SMILES: CCc1nc2ccc(Cl)cn2c1C(=O)NCc1ccc(C(=O)N2CCOCC2)cc1]

5-(6-Chloro-2-ethylimidazo[1,2-a]pyridin-3-yl)-3-(4-(4-
(fluorophenoxy)benzyl)-1,2,4-oxadiazole (289)

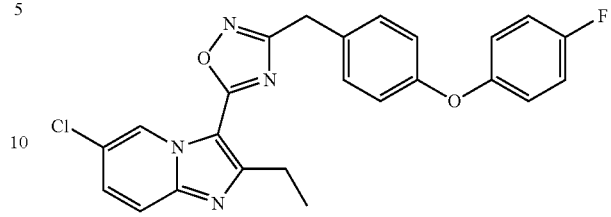

2-Ethyl-N-(4-morpholinobenzyl)-7-(trifluoromethyl)imi-
dazo[1,2-a]pyridine-3-carboxamide (290)

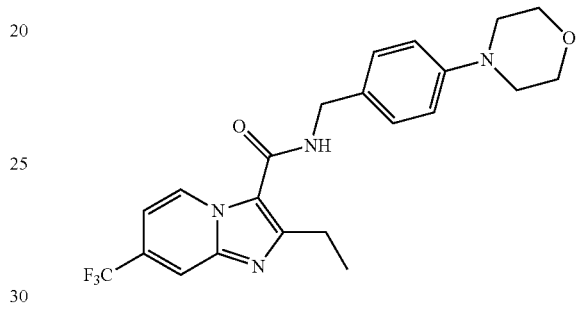

N-(4-(4-Carbamoylpiperidin-1-yl)benzyl)-6-chloro-2-
ethylimidazo[1,2-a]pyridine-3-carboxamide (291)

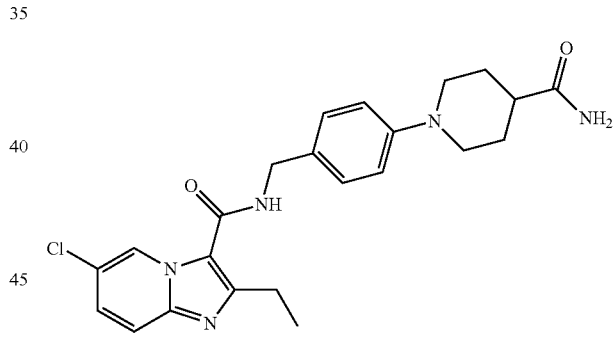

N-(4-(4-Carbamoylpiperidin-1-yl)benzyl)-7-chloro-2-
ethylimidazo[1,2-a]pyridine-3-carboxamide (292)

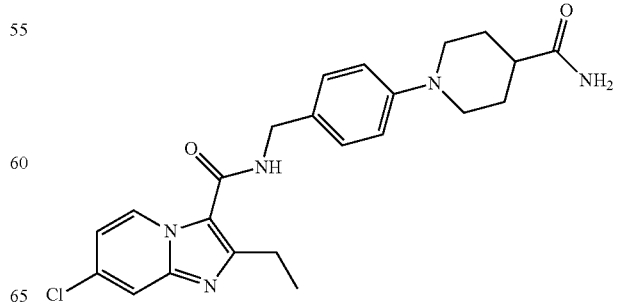

6-Chloro-N-(4-(4-(dimethylcarbamoyl)piperidin-1-yl)benzyl)-2-ethylimidazo[1,2-a]pyridine-3-carboxamide (293)

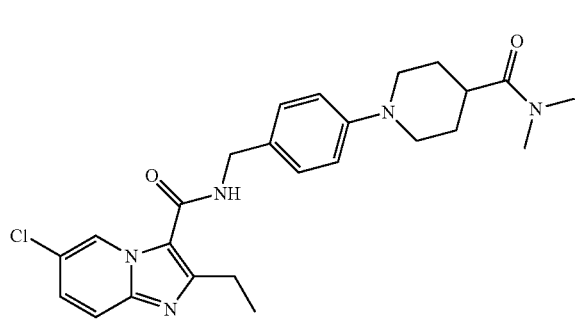 [SMILES: CCc1nc2ccc(Cl)cn2c1C(=O)NCc1ccc(N2CCC(C(=O)N(C)C)CC2)cc1]

7-Chloro-N-(4-(4-(dimethylcarbamoyl)piperidin-1-yl)benzyl-2-ethylimidazo[1,2-a]pyridine-3-carboxamide (294)

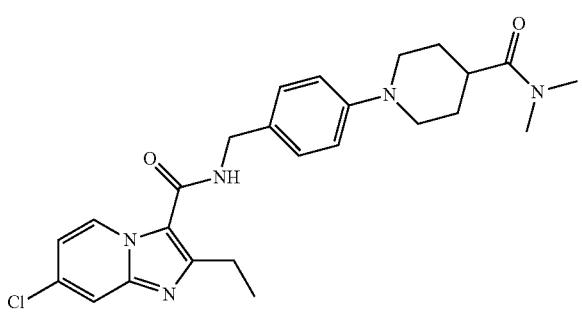 [SMILES: CCc1nc2cc(Cl)ccn2c1C(=O)NCc1ccc(N2CCC(C(=O)N(C)C)CC2)cc1]

7-Chloro-N-(4-(4-((difluoromethoxy)methyl)piperidin-1-yl)benzyl)-2-ethylimidazo[1,2-a]pyridine-3-carboxamide (295)

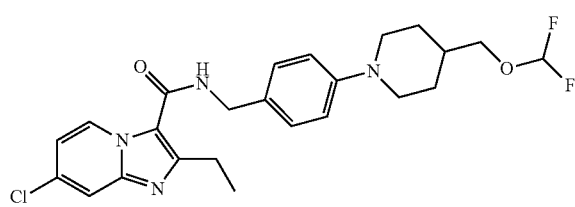 [SMILES: CCc1nc2cc(Cl)ccn2c1C(=O)NCc1ccc(N2CCC(COC(F)F)CC2)cc1]

6-Chloro-N-(4-(4-(4-chlorophenyl)piperidin-1-yl)benzyl)-2-ethylimidazo[1,2-a]pyridine-3-carboxamide (296)

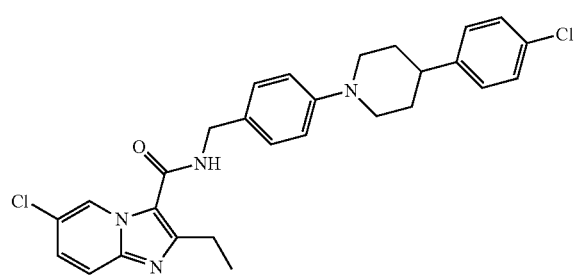 [SMILES: CCc1nc2ccc(Cl)cn2c1C(=O)NCc1ccc(N2CCC(c3ccc(Cl)cc3)CC2)cc1]

7-Chloro-N-(4-(4-(4-chlorophenyl)piperidin-1-yl)benzyl)-2-ethylimidazo[1,2-a]pyridine-3-carboxamide (297)

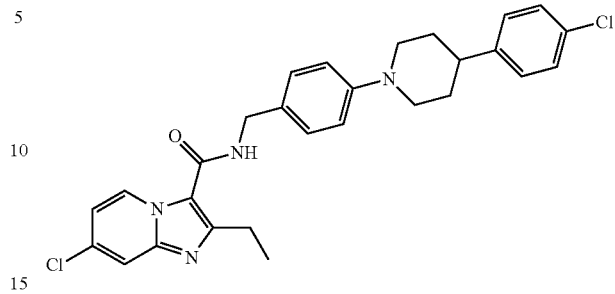

6-Chloro-N-((2-cyclohexylbenzo[d]oxazol-5-yl)methyl)-2-ethylimidazo[1,2-a]pyridine-3-carboxamide (298)

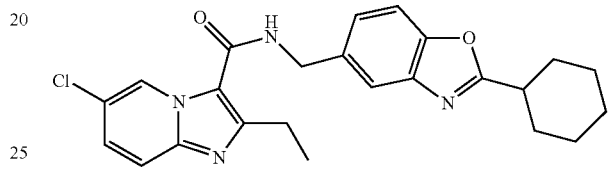

7-Chloro-N-((2-cyclohexylbenzo[d]oxazol-5-yl)methyl)-2-ethylimidazo[1,2-a]pyridine-3-carboxamide (299)

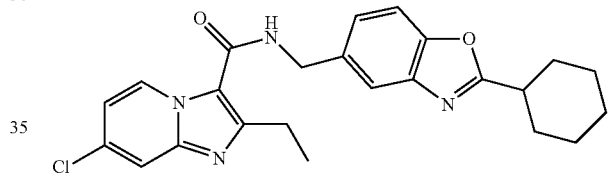

6-Chloro-2-ethyl-N-(4-(4-(4-fluorobenzyloxy)piperidin-1-yl)benzyl)imidazo[1,2-a]pyridine-3-carboxamide (300)

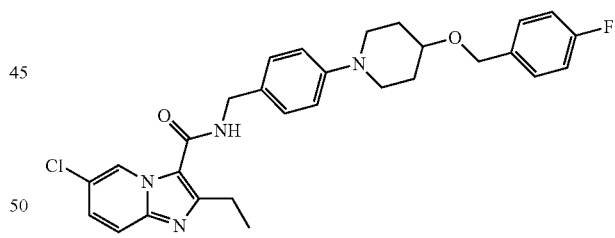

7-Chloro-2-ethyl-N-(4-(4-(4-fluorobenzyloxy)piperidin-1-yl)benzyl) imidazo[1,2-a]pyridine-3-carboxamide (301)

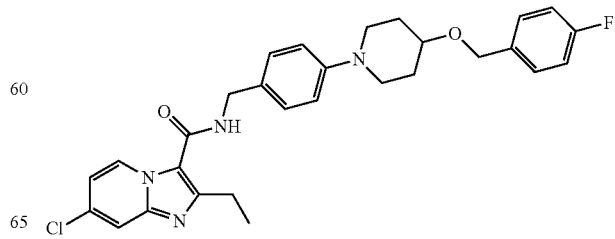

6-Chloro-N-(3-chloro-4-morpholinobenzyl)-2-ethylimidazo[1,2-a]pyridine-3-carboxamide (302)

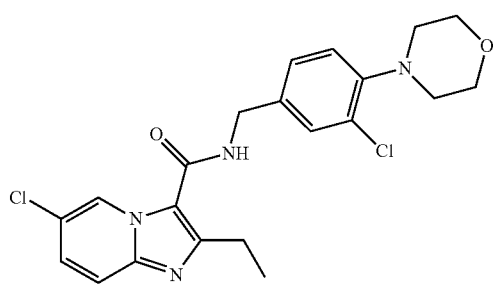 [SMILES: CCc1nc2ccc(Cl)cn2c1C(=O)NCc1ccc(N2CCOCC2)c(Cl)c1]

7-Chloro-N-(3-chloro-4-morpholinobenzyl)-2-ethylimidazo[1,2-a]pyridine-3-carboxamide (303)

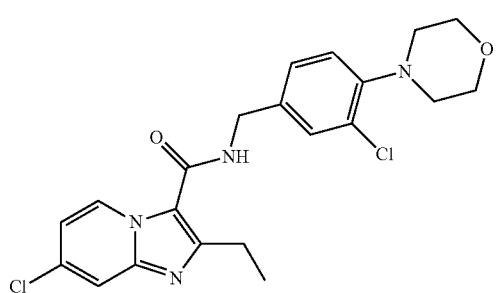 [SMILES: CCc1nc2cc(Cl)ccn2c1C(=O)NCc1ccc(N2CCOCC2)c(Cl)c1]

7-Bromo-2-ethyl-N-(4-(4-(4-fluorophenyl)piperazin-1-yl)benzyl)imidazo[1,2-a]pyridine-3-carboxamide (304)

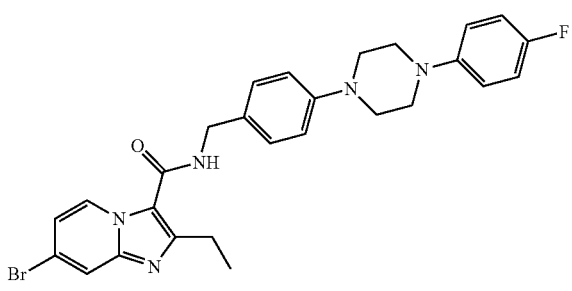

2-Ethyl-N-(4-morpholinobenzyl)-7-(pyridin-3-yl)imidazo[1,2-a]pyridine-3-carboxamide (305)

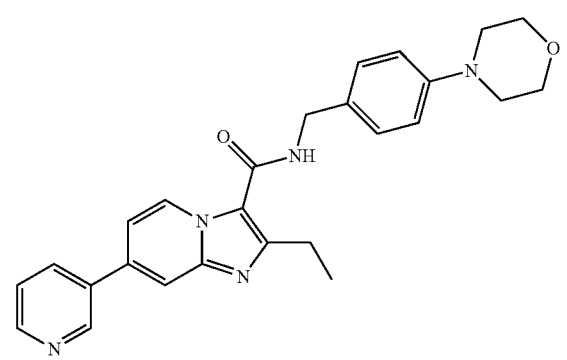 [SMILES: CCc1nc2cc(-c3cccnc3)ccn2c1C(=O)NCc1ccc(N2CCOCC2)cc1]

6-Chloro-2-ethyl-N-(4-(4-(4-fluorophenyl)-4-hydroxypiperidin-1-yl)benzyl)imidazo[1,2-a]pyridine-3-carboxamide (306)

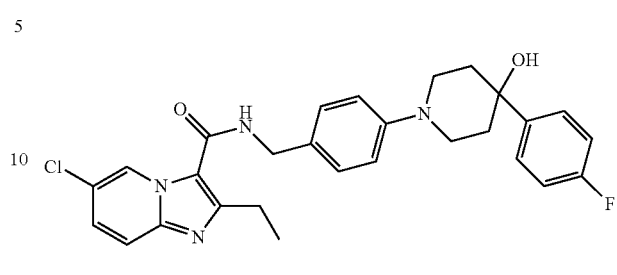

1-(4-((6-Chloro-2-ethylimidazo[1,2-a]pyridine-3-carboxamido)methyl)phenyl)piperidine-4-carboxylic acid (307)

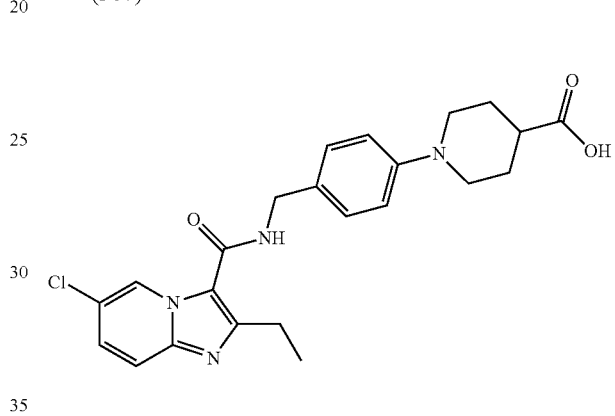

6-Chloro-2-ethyl-N-(4-(4-(4-fluorophenoxy)piperidin-1-yl)benzyl)imidazo[1,2-a]pyridine-3-carboxamide (308)

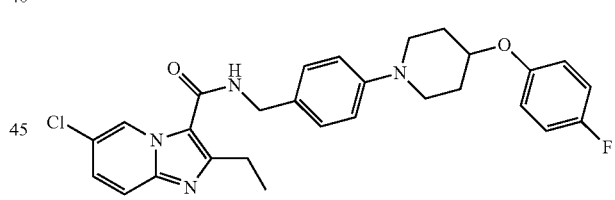

6-Chloro-2-ethyl-N-(1-(4-((trifluoromethoxy)benzyl)piperidin-4-yl)imidazo[1,2-a]pyridine-3-carboxamide (309)

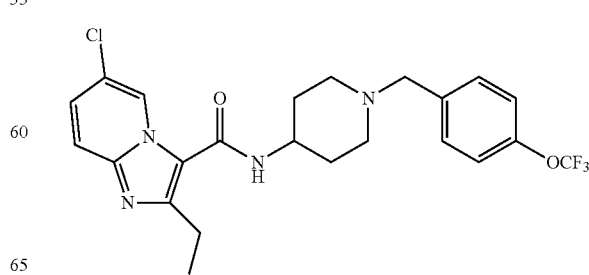

3-(((4'-Chloro-[1,1'-biphenyl]-4-yl)methyl)carbamoyl)-2-ethylimidazo[1,2-a]pyrazine 7-oxide (310)

6-Chloro-2-ethyl-N-(4-(4-(4-fluorophenyl)piperazin-1-yl)benzyl)-N-methylimidazo[1,2-a]pyridine-3-carboxamide (314)

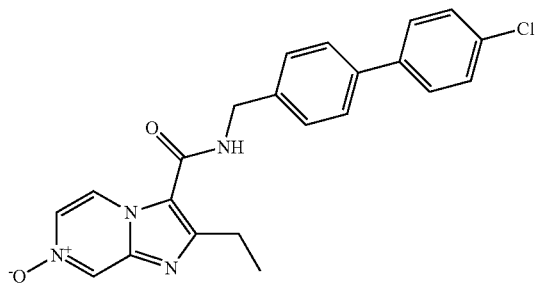

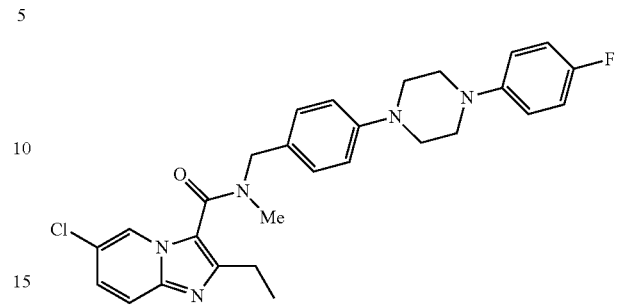

N-((6-Chloro-2-ethylimidazo[1,2-a]pyridin-3-yl)methyl)-4-(4-(4-fluorophenyl)piperazin-1-yl)aniline (311)

2-ethyl-6-methyl-N-(4-morpholinobenzyl)imidazo[1,2-a]pyridine-3-carboxamide (315)

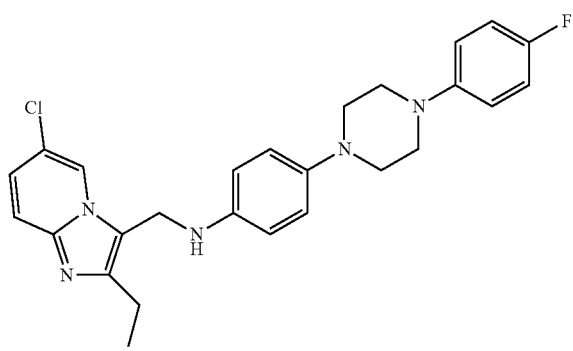 [SMILES: CCc1nc2ccc(Cl)cn2c1CNc1ccc(N2CCN(c3ccc(F)cc3)CC2)cc1]

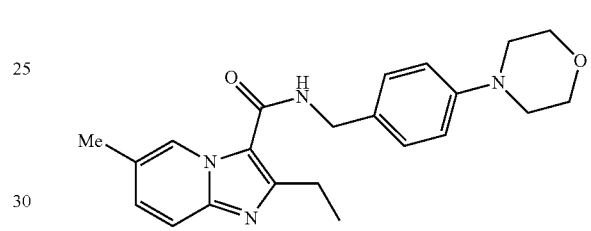

6-chloro-2-ethyl-N-(4-(4-(2-(4-fluorophenyl)acetamido)piperidin-1-yl)benzyl)imidazo[1,2-a]pyridine-3-carboxamide (316)

2-Ethyl-7-nitro-N-(4-(4-(4-(trifluoromethoxy)phenoxy)piperidin-1-yl)benzyl)imidazo[1,2-a]pyridine-3-carboxamide (312)

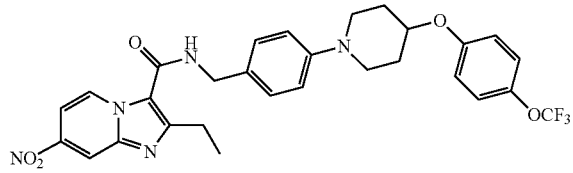 [SMILES: CCc1nc2cc([N+](=O)[O-])ccn2c1C(=O)NCc1ccc(N2CCC(Oc3ccc(OC(F)(F)F)cc3)CC2)cc1]

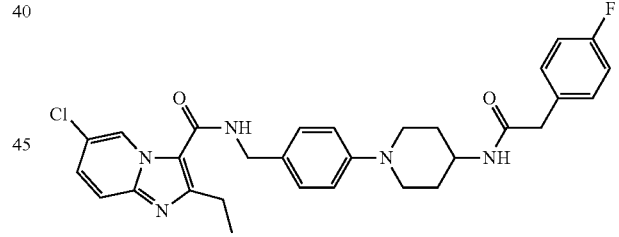

N-(4-(4-(benzyloxy)piperidin-1-yl)benzyl)-6-chloro-2-ethylimidazo[1,2-a]pyridine-3-carboxamide (317)

6-Chloro-2-ethylimidazo[1,2-a]pyridin-3-yl)(4-(4-(trifluoromethoxy)benzyloxy)piperidin-1-yl)methanone (313)

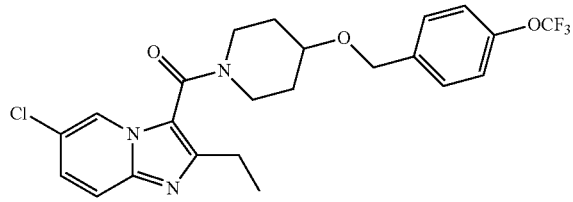 [SMILES: CCc1nc2ccc(Cl)cn2c1C(=O)N1CCC(OCc2ccc(OC(F)(F)F)cc2)CC1]

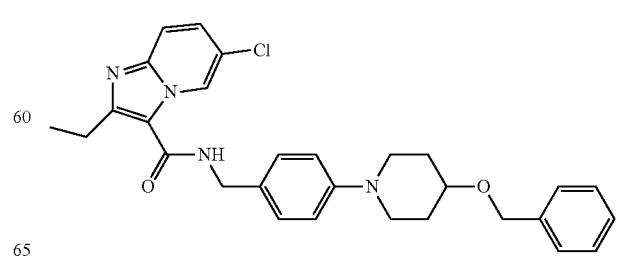

257

6-chloro-2-ethyl-N-(4-(4-(4-fluorobenzamido)piperidin-1-yl)benzyl)imidazo[1,2-a]pyridine-3-carboxamide (318)

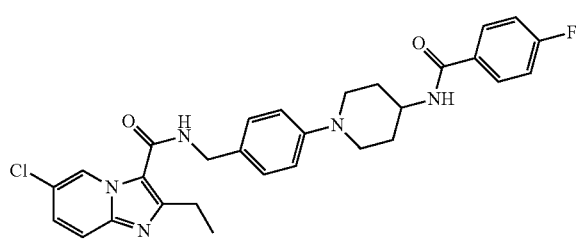 [SMILES: CCc1nc2ccc(Cl)cn2c1C(=O)NCc1ccc(N2CCC(NC(=O)c3ccc(F)cc3)CC2)cc1]

6-chloro-2-ethyl-N-(4-(4-(4-fluorobenzoyl)piperazin-1-yl)benzyl)imidazo[1,2-a]pyridine-3-carboxamide (319)

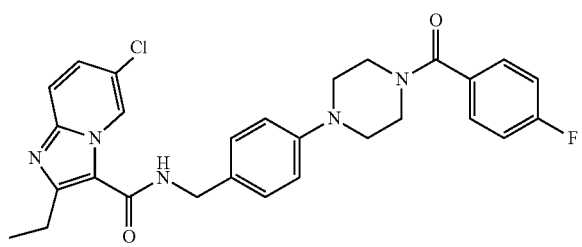 [SMILES: CCc1nc2ccc(Cl)cn2c1C(=O)NCc1ccc(N2CCN(C(=O)c3ccc(F)cc3)CC2)cc1]

6-chloro-2-ethyl-N-(4-(4-(4-fluorophenyl)acetyl)piperazin-1-yl)benzyl)imidazo[1,2-a]pyridine-3-carboxamide (320)

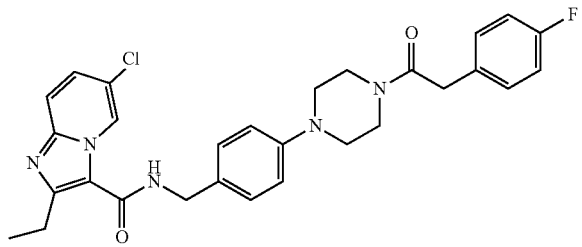 [SMILES: CCc1nc2ccc(Cl)cn2c1C(=O)NCc1ccc(N2CCN(C(=O)Cc3ccc(F)cc3)CC2)cc1]

6-chloro-2-ethyl-N-(4-(4-hydroxy-4-methylpiperidin-1-yl)benzyl)imidazo[1,2-a]pyridine-3-carboxamide (321)

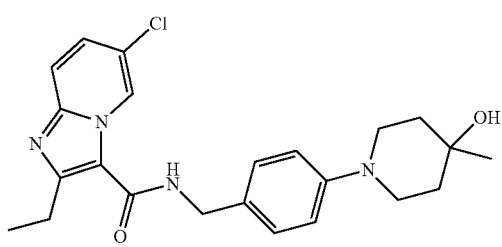 [SMILES: CCc1nc2ccc(Cl)cn2c1C(=O)NCc1ccc(N2CCC(C)(O)CC2)cc1]

258

N-(4-(4-tert-butyl)-4-hydroxypiperidin-1-yl)benzyl)-6-chloro-2-ethylimidazo[1,2-a]pyridine-3-carboxamide (322)

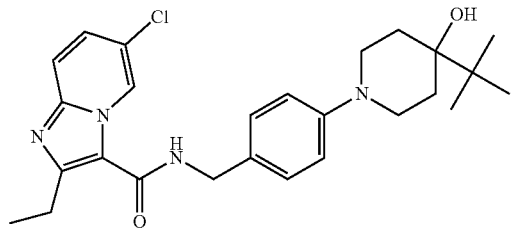 [SMILES: CCc1nc2ccc(Cl)cn2c1C(=O)NCc1ccc(N2CCC(O)(C(C)(C)C)CC2)cc1]

6-chloro-2-ethyl-N-(4-(4-(4-fluorobenzoyl)piperidin-yl)benzyl)imidazo[1,2-a]pyridine-3-carboxamide (323)

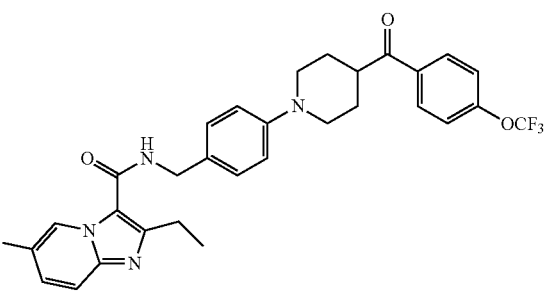

6-chloro-2-ethyl-N-(4-(4-(4-(trifluoromethoxy)benzoyl)piperidin-1-yl)imidazo[1,2-a]pyridine-3-carboxamide (324)

6-chloro-2-ethyl-N-(4-(4-(2-(4-fluorophenyl) acetyl)piperidin-1-yl)benzyl)imidazo[1,2-a]pyridine-carboxamide (325)

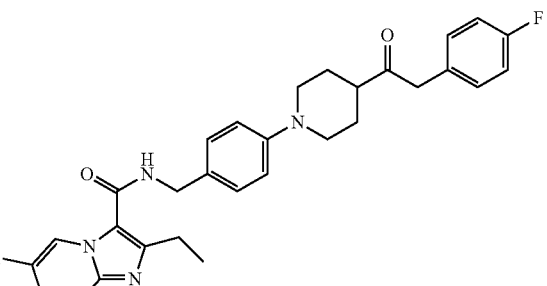

6-chloro-2-ethyl-N-(4-(1-(4-fluorobenzoyl)-4-yl)benzyl)imidazo[1,2-a]pyridine-3-carboxamide (326)

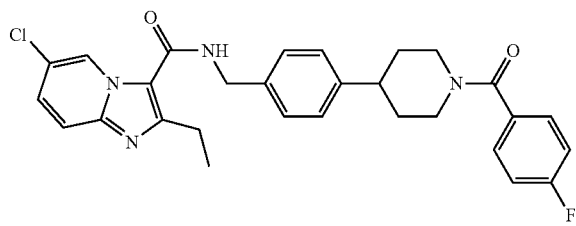 [SMILES: CCc1nc2ccc(Cl)cn2c1C(=O)NCc1ccc(C2CCN(C(=O)c3ccc(F)cc3)CC2)cc1]

6-chloro-2-ethyl-N-(4-(1-(2-(4-fluorophenyl)acetyl)piperidin-4-yl)benzyl)imidazo[1,2-a]pyridine-3-carboxamide (327)

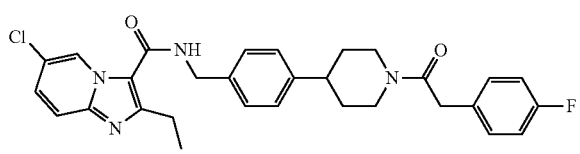 [SMILES: CCc1nc2ccc(Cl)cn2c1C(=O)NCc1ccc(C2CCN(C(=O)Cc3ccc(F)cc3)CC2)cc1]

6-chloro-2-ethyl-N-(4-(4-hydroxy-4-phenylpiperidin-1-yl)benzyl)imidazo[1,2-a]pyridine-3-carboxamide (328)

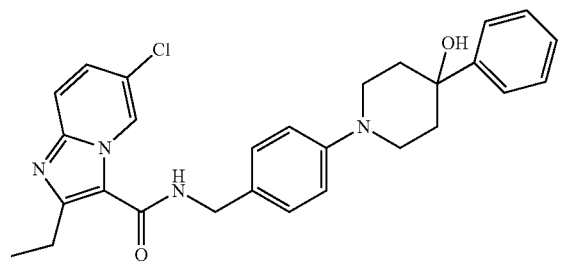 [SMILES: CCc1nc2ccc(Cl)cn2c1C(=O)NCc1ccc(N2CCC(O)(c3ccccc3)CC2)cc1]

(E)-6-chloro-2-ethyl-N-(4-(4-fluorostyryl)benzyl)imidazo[1,2-a]pyridine-3-carboxamide (329)

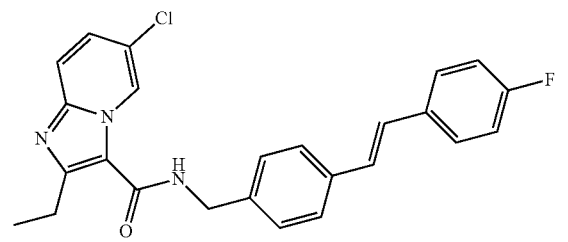 [SMILES: CCc1nc2ccc(Cl)cn2c1C(=O)NCc1ccc(/C=C/c2ccc(F)cc2)cc1]

(4-(benzyloxy)piperidin-1-yl)(6-chloro-2-ethylimidazo[1,2-a]pyridin-3-yl)methanone (330)

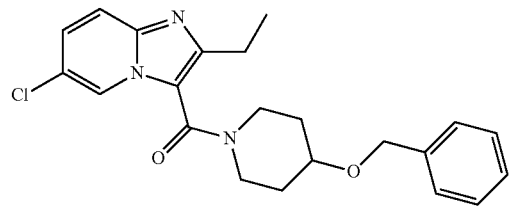 [SMILES: CCc1nc2ccc(Cl)cn2c1C(=O)N1CCC(OCc2ccccc2)CC1]

(6-chloro-2-ethylimidazo[1,2-a]pyridin-3-yl)(4-((4-methylbenzyl)oxy)piperidin-1-yl)methanone (331)

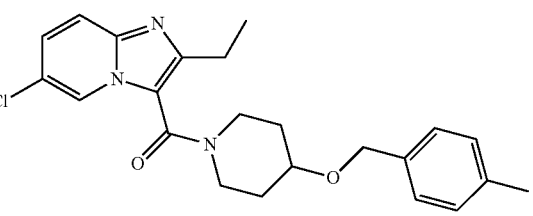

(6-chloro-2-ethylimidazo[1,2-a]pyridin-3-yl)(4-((4-chlorobenzyl)oxy)piperidin-1-yl)methanone (332)

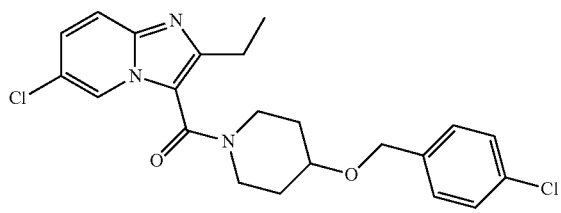 [SMILES: CCc1nc2ccc(Cl)cn2c1C(=O)N1CCC(OCc2ccc(Cl)cc2)CC1]

(6-chloro-2-ethylimidazo[1,2-a]pyridin-3-yl)(4-((4-fluorobenzyl)oxy)piperidin-1-yl)methanone (333)

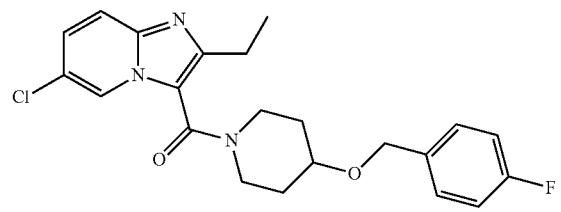 [SMILES: CCc1nc2ccc(Cl)cn2c1C(=O)N1CCC(OCc2ccc(F)cc2)CC1]

(6-chloro-2-ethylimidazo[1,2-a]pyridin-3-yl)(4-((4-(trifluoromethyl)benzyl)oxy)piperidin-1-yl)methanone (334)

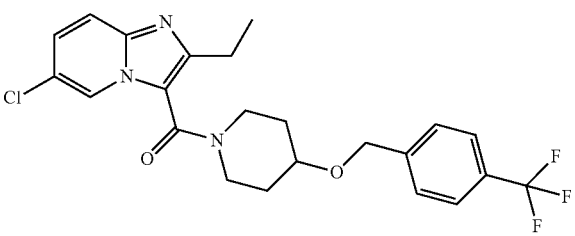 [SMILES: CCc1nc2ccc(Cl)cn2c1C(=O)N1CCC(OCc2ccc(C(F)(F)F)cc2)CC1]

261

(6-chloro-2-ethylimidazo[1,2-a]pyridin-3-yl)(4-((4-methoxybenzyl)oxy)piperidin-1-yl)methanone (335)

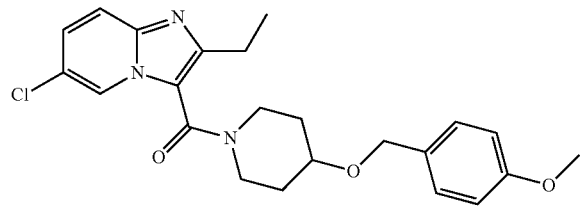 [SMILES: CCc1nc2ccc(Cl)cn2c1C(=O)N1CCC(OCc2ccc(OC)cc2)CC1]

(6-chloro-2-ethylimidazo[1,2-a]pyridin-3-yl)(4-((3-fluorobenzyl)oxy)piperidin-1-yl)methanone (336)

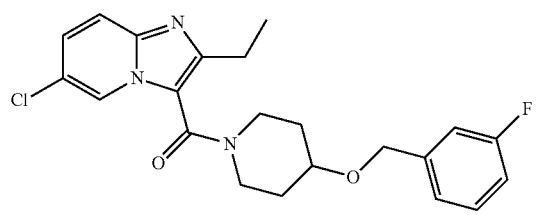 [SMILES: CCc1nc2ccc(Cl)cn2c1C(=O)N1CCC(OCc2cccc(F)c2)CC1]

(6-chloro-2-ethylimidazo[1,2-a]pyridin-3-yl)(4-((2-fluorobenzyl)oxy)piperidin-1-yl)methanone (337)

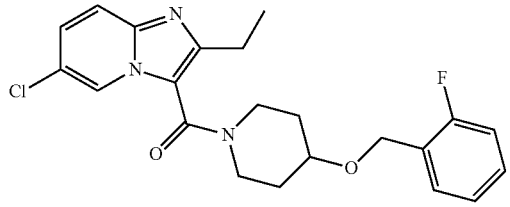 [SMILES: CCc1nc2ccc(Cl)cn2c1C(=O)N1CCC(OCc2ccccc2F)CC1]

1-(6-chloro-2-ethylimidazo[1,2-a]pyridin-3-yl)-N-(4-fluorobenzyl)methanamine (338)

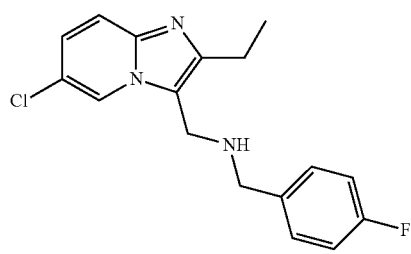 [SMILES: CCc1nc2ccc(Cl)cn2c1CNCc1ccc(F)cc1]

262

4-(((((6-chloro-2-ethylimidazo[1,2-a]pyridin-3-yl)methyl)amino)methyl)-N,N-dimethylaniline (339)

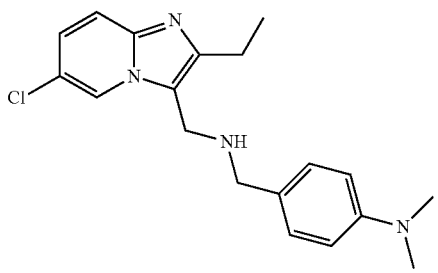 [SMILES: CCc1nc2ccc(Cl)cn2c1CNCc1ccc(N(C)C)cc1]

1-(4-(((((6-chloro-2-ethylimidazo[1,2-a]pyridin-3-yl)methyl)amino)methyl)phenyl)piperidin-4-ol (340)

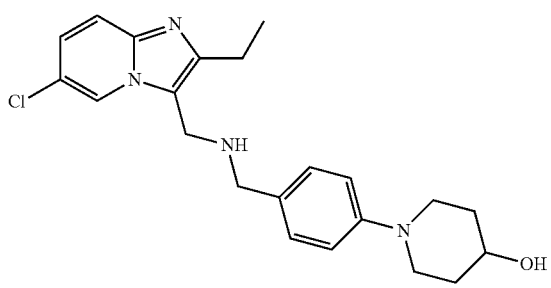 [SMILES: CCc1nc2ccc(Cl)cn2c1CNCc1ccc(N2CCC(O)CC2)cc1]

N-(4-(4-(benzyloxy)piperidin-1-yl)benzyl)-1-(6-chloro-2-ethylimidazo[1,2-a]pyridin-3-yl)methanamine (341)

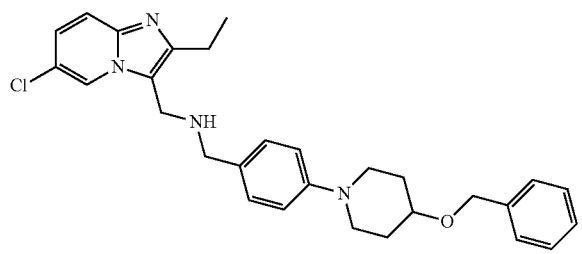 [SMILES: CCc1nc2ccc(Cl)cn2c1CNCc1ccc(N2CCC(OCc3ccccc3)CC2)cc1]

N-((6-chloro-2-ethylimidazo[1,2-a]pyridin-3-yl)methyl)-2-(pyridin-2-yl)ethanamine (342)

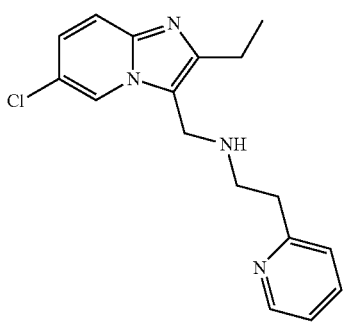 [SMILES: CCc1nc2ccc(Cl)cn2c1CNCCc1ccccn1]

N-((6-chloro-2-ethylimidazo[1,2-a]pyridin-3-yl)methyl-2-(pyridin-3-yl)ethanamine (343)

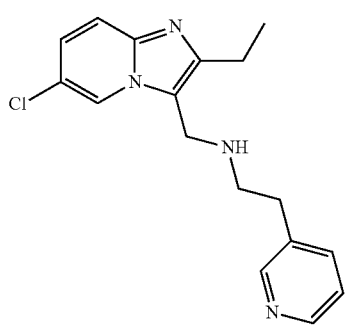 [SMILES: CCc1nc2ccc(Cl)cn2c1CNCCc1cccnc1]

N-((6-chloro-2-ethylimidazo[1,2-a]pyridin-3-yl)methyl)-2-(pyridin-4-yl)ethanamine (344)

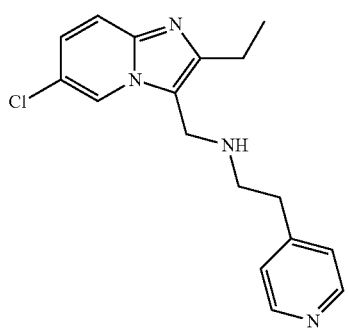 [SMILES: CCc1nc2ccc(Cl)cn2c1CNCCc1ccncc1]

1-Benzyl-N-((6-chloro-2-ethylimidazo[1,2-a]pyridin-3-yl)methyl)pyrrolidin-3-amine (345)

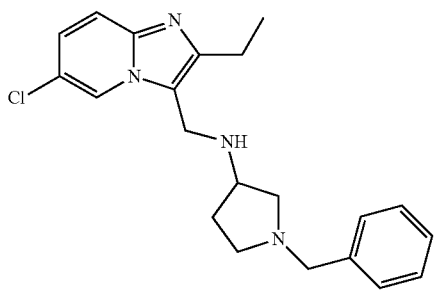 [SMILES: CCc1nc2ccc(Cl)cn2c1CNC1CCN(Cc2ccccc2)C1]

N-(4-(1,4-dioxa-8-azaspiro[4.5]decan-8-yl)benzyl)-1-(6-chloro-2-ethylimidazo[1,2-a]pyridin-3-yl)methanamine (346)

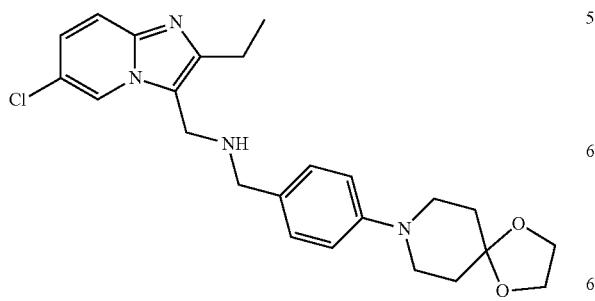

6-chloro-2-ethyl-3-((4-((4-(trifluoromethoxy)benzyl)oxy)piperidin-1-yl)methyl)imidazo[1,2-a]pyridine (347)

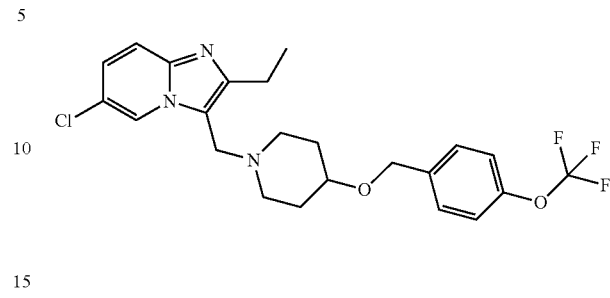

2-(7-chloro-2-ethylimidazo[1,2-a]pyridin-3-yl)-5-(4-fluorobenzyl)-1,3,4-oxadiazole (348)

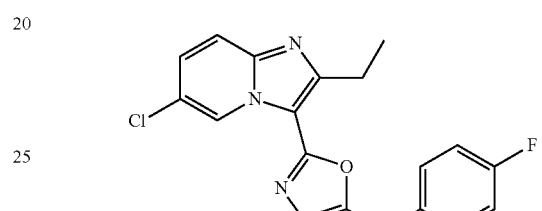

6-chloro-2-ethyl-3-((4-(4-fluorophenethyl)piperidin-1-yl)methyl)imidazo[1,2-a]pyridine (349)

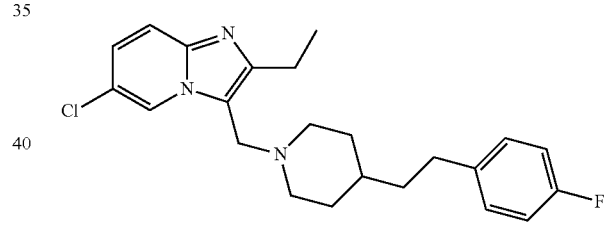

(6-chloro-2-ethylimidazo[1,2-a]pyridin-3-yl)(4-((4-(1,1,1-trifluoro-2-hydroxybutan-2-yl)-1H-1,2,3-triazol-1-yl)methyl)piperidin-1-yl)methanone (350)

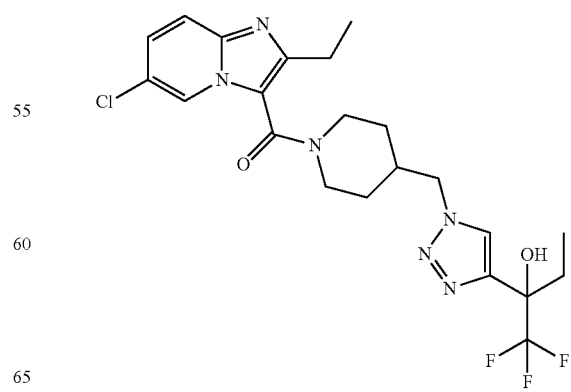

2-(1-(((1-((2-ethylimidazo[1,2-a]pyridin-3-yl)methyl)piperidin-4-yl)methyl)-1H-1,2,3-triazol-4-yl)-1,1,1-trifluorobutan-2-ol (351)

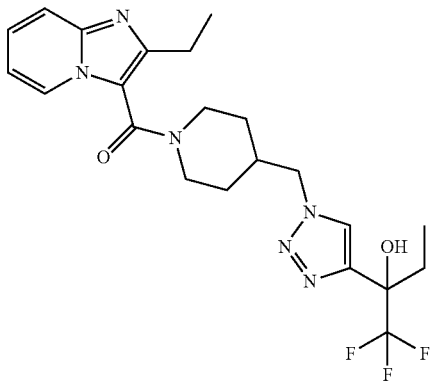 [SMILES: CCc1nc2ccccn2c1C(=O)N1CCC(Cn2cc(C(O)(CC)C(F)(F)F)nn2)CC1]

6-chloro-2-ethyl-N-(3-methyl(4-(trifluoromethoxy)benzyl)amino)benzyl)imidazo[1,2-a]pyridine-3-carboxamide (352)

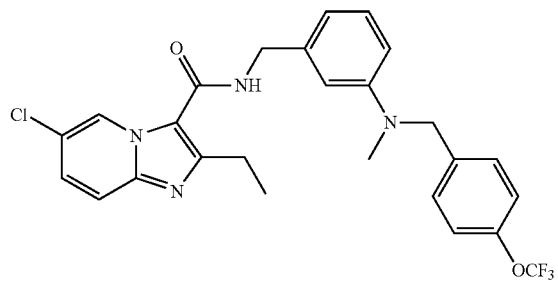

6-chloro-2-ethyl-N-(3-((4-(trifluoromethoxy)benzyl)oxy)benzyl)imidazo[1,2-a]pyridine-3-carboxamide (353)

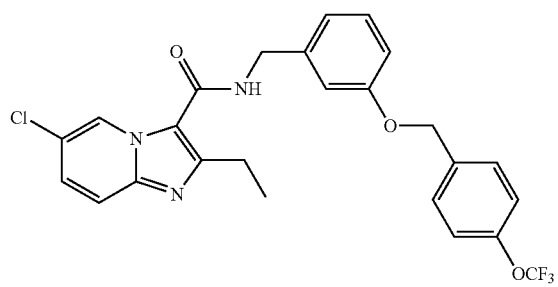

6-chloro-2-ethyl-N-(3-(4-(4-(trifluoromethoxy)phenyl)piperidin-1-yl)benzyl)imidazo[1,2-a]pyridine-3-carboxamide (354)

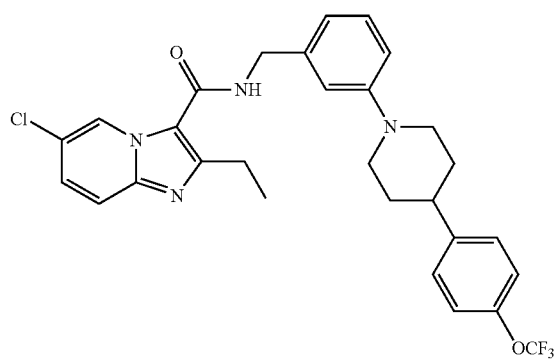 [SMILES: CCc1nc2ccc(Cl)cn2c1C(=O)NCc1cccc(N2CCC(c3ccc(OC(F)(F)F)cc3)CC2)c1]

6-chloro-2-ethyl-N-(3-(2-((4-fluorophenyl)amino)-2-oxoethyl)benzyl)imidazo[1,2-a]pyridine-3-carboxamide (355)

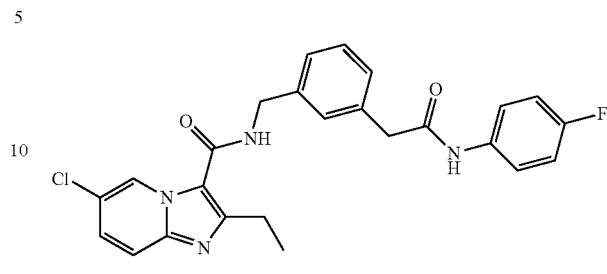

6-chloro-2-ethyl-N-(3-(4-(4-(trifluoromethoxy)phenyl)piperazin-1-yl)benzyl)imidazo[1,2-a]pyridine-3-carboxamide (356)

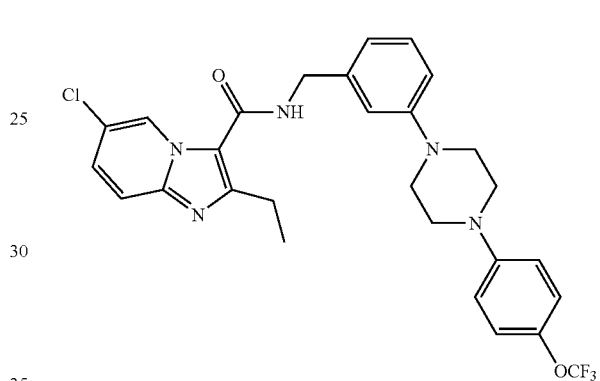

2-ethyl-N-(4-((tetrahydro-2H-pyran-4-yl)methyl)benzyl)imidazo[1,2-a]pyridine-3-carboxamide (357)

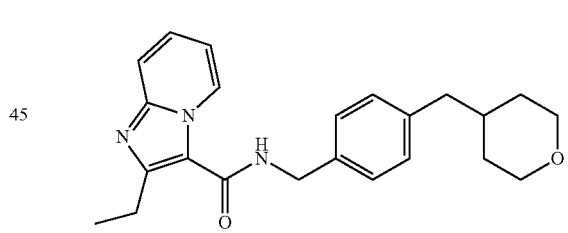

6-chloro-2-ethyl-N-(4-((tetrahydro-2H-pyran-4-yl)methyl)benzyl)imidazo[1,2-a]pyridine-3-carboxamide (358)

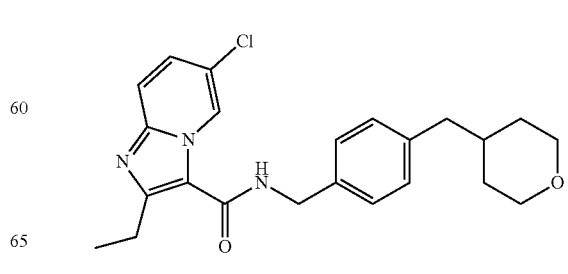

7-chloro-2-ethyl-N-(4-((tetrahydro-2H-pyran-4-yl)me-
thyl)benzyl)imidazo[1,2-a]pyridine-3-carboxamide
(359)

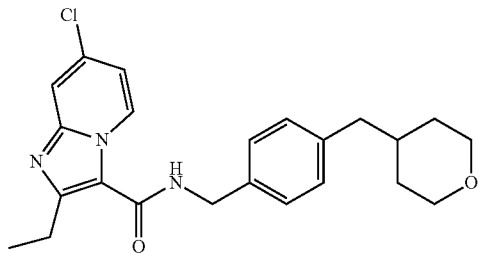 [SMILES: CCc1nc2cc(Cl)ccn2c1C(=O)NCc1ccc(CC2CCOCC2)cc1]

6-chloro-2-ethyl-N-(3-(4-(4-(trifluoromethoxy)phenoxy)
piperidin-1-yl)benzyl)imidazo[1,2-a]pyridine-3-car-
boxamide (360)

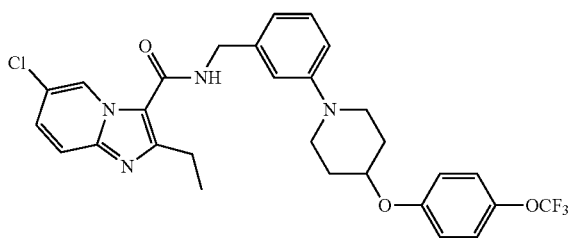 [SMILES: CCc1nc2ccc(Cl)cn2c1C(=O)NCc1cccc(N2CCC(Oc3ccc(OC(F)(F)F)cc3)CC2)c1]

6-chloro-N-((5-chlorobenzo[b]thiophen-2-yl)methyl)-2-
ethylimidazo[1,2-a]pyridine-3-carboxamide (361)

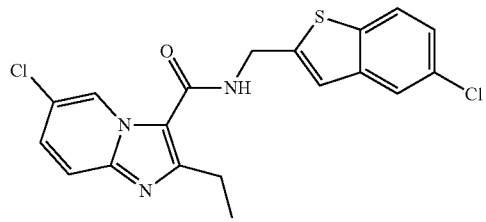 [SMILES: CCc1nc2ccc(Cl)cn2c1C(=O)NCc1cc2cc(Cl)ccc2s1]

2-ethyl-N-(4-(tetrahydro-2H-pyran-4-yl)benzyl)imidazo
[1,2-a]pyridine-3-carboxamide (362)

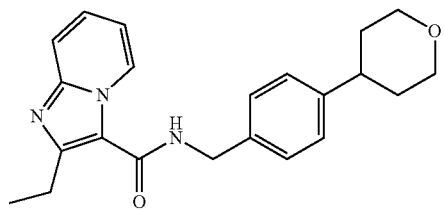 [SMILES: CCc1nc2ccccn2c1C(=O)NCc1ccc(C2CCOCC2)cc1]

6-chloro-2-ethyl-N-(4-(tetrahydro-2H-pyran-4-yl)benzyl)
imidazo[1,2-a]pyridine-3-carboxamide (363)

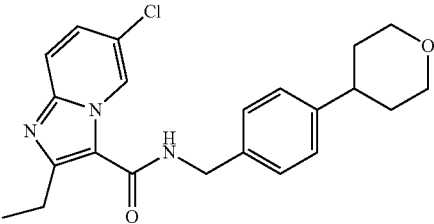 [SMILES: CCc1nc2ccc(Cl)cn2c1C(=O)NCc1ccc(C2CCOCC2)cc1]

7-chloro-2-ethyl-N-(4-(4-(tetrahydro-2H-pyran-4-yl)ben-
zyl)imidazo[1,2-a]pyridine-3-carboxamide (364)

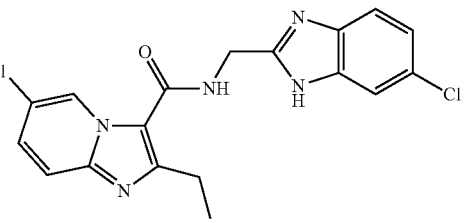

6-chloro-N-((6-chloro-1H-benzo[d]imidazol-2-yl)me-
thyl)-2-ethylimidazo[1,2-a]pyridine-3-carboxamide
(365)

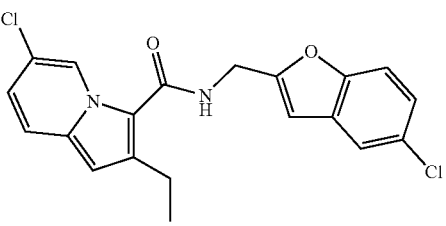 [SMILES: CCc1cc2ccc(Cl)cn2c1C(=O)NCc1cc2cc(Cl)ccc2o1]

6-chloro-N-((5-chlorobenzofuran-2-yl)methyl)-2-eth-
ylimidazo[1,2-a]pyridine-3-carboxamide (366)

6-chloro-N-((6-chloro-1-methyl-1H-benzo[d]imidazol-2-yl)methyl)-2-ethylimidazo[1,2-a]pyridine-3-carboxamide (367)

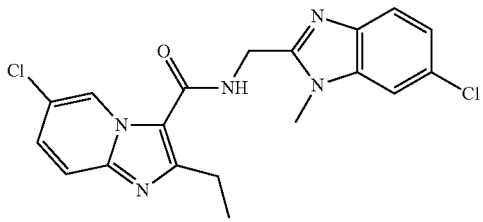 [SMILES: CCc1nc2ccc(Cl)cn2c1C(=O)NCc1nc2ccc(Cl)cc2n1C]

6-chloro-N-((5-chloro-1-methyl-1H-benzo[d]imidazol-2-yl)methyl)-2-ethylimidazo[1,2-a]pyridine-3-carboxamide (368)

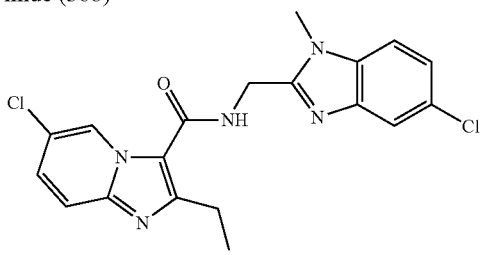

6-chloro-N-((6-chlorobenzo[d]oxazol-2-yl)methyl)-2-ethylimidazo[1,2-a]pyridine-3-carboxamide (369)

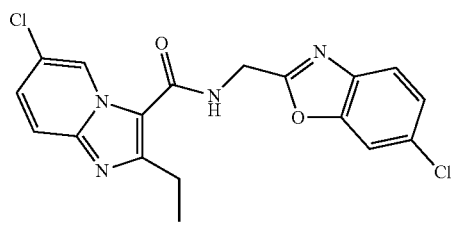 [SMILES: CCc1nc2ccc(Cl)cn2c1C(=O)NCc1nc2ccc(Cl)cc2o1]

7-chloro-2-ethyl-N-((5-(4-(trifluoromethoxy)phenyl)benzo[d]oxazol-2-yl)methyl)imidazo[1,2-a]pyridine-3-carboxamide (370)

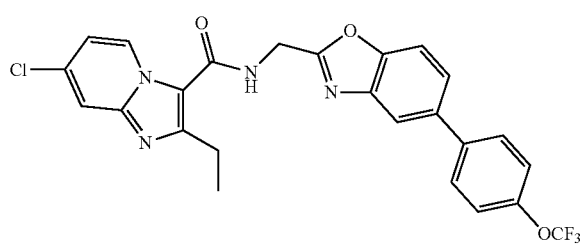 [SMILES: CCc1nc2cc(Cl)ccn2c1C(=O)NCc1nc2cc(-c3ccc(OC(F)(F)F)cc3)ccc2o1]

6-chloro-N-((6-chlorobenzo[d]thiazol-2-yl)methyl)-2-ethylimidazo[1,2-a]pyridine-3-carboxamide (371)

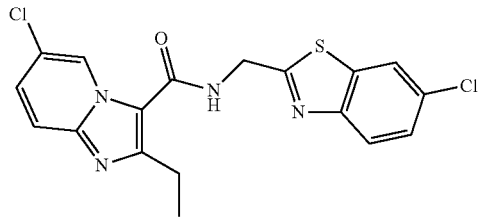 [SMILES: CCc1nc2ccc(Cl)cn2c1C(=O)NCc1nc2ccc(Cl)cc2s1]

2-ethyl-6-fluoro-N-(4-(4-(4-(trifluoromethoxy)phenyl)piperidin-1-yl)benzyl)imidazo[1,2-a]pyridine-3-carboxamide (372)

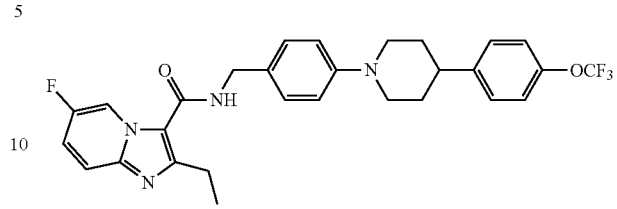

2-ethyl-8-fluoro-N-(4-(4-(4-(trifluoromethoxy)phenyl)piperidin-1-yl)benzyl)imidazo[1,2-a]pyridine-3-carboxamide (373)

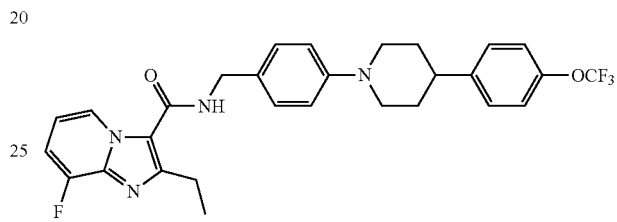

7-chloro-2-ethyl-N-((6-(4-(trifluoromethoxy)phenyl)benzo[d]oxazol-2-yl)methyl)imidazo[1,2-a]pyridine-3-carboxamide (374)

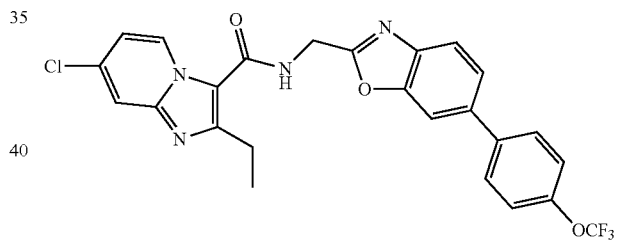

N1-((7-chloro-2-ethylimidazo[1,2-a]pyridin-3-yl)methyl)-N4-(4-(fluorophenyl)piperidin-4-yl)benzene-1,4-diamine (375)

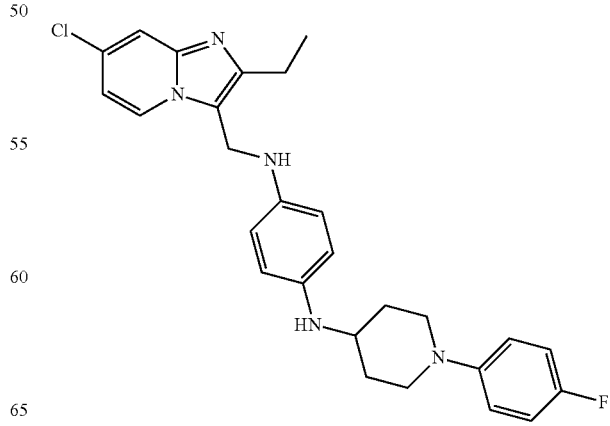

271

N-((7-chloro-2-ethylimidazo[1,2-a]pyridin-3-yl)methyl)-4-(4-(4-(trifluoromethoxy)phenyl)piperidin-1-yl)aniline (376)

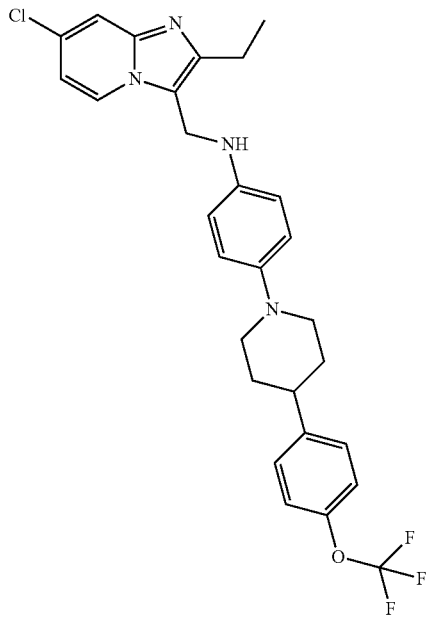 [SMILES: CCc1nc2cc(Cl)ccn2c1CNc1ccc(N2CCC(c3ccc(OC(F)(F)F)cc3)CC2)cc1]

7-chloro-2-ethyl-N-(4-(5-(4-fluorobenzyl)-2-oxooxazolidin-3-yl)benzyl)imidazo[1,2-a]pyridine-3-carboxamide (377)

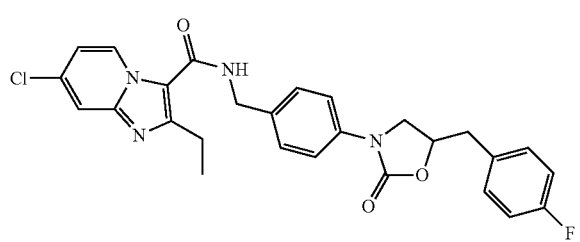 [SMILES: CCc1nc2cc(Cl)ccn2c1C(=O)NCc1ccc(N2CC(Cc3ccc(F)cc3)OC2=O)cc1]

7-chloro-2-ethyl-N-(4-(5-((4-fluorophenoxy)methyl)-2-oxooxazolidin-3-yl)benzyl)imidazo[1,2-a]pyridine-3-carboxamide (378)

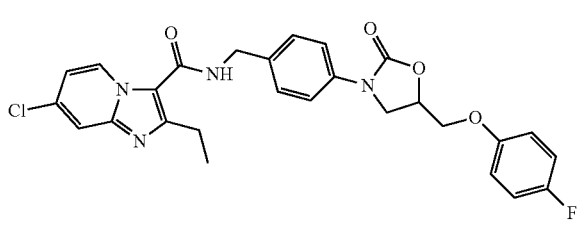 [SMILES: CCc1nc2cc(Cl)ccn2c1C(=O)NCc1ccc(N2CC(COc3ccc(F)cc3)OC2=O)cc1]

272

N-((6-Chloro-2-ethylimidazo[1,2-a]pyridin-3-yl)methyl)-4-(4-fluorophenoxy)aniline (379)

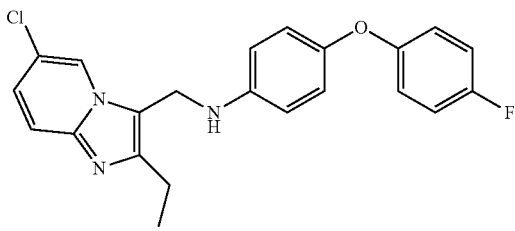 [SMILES: CCc1nc2ccc(Cl)cn2c1CNc1ccc(Oc2ccc(F)cc2)cc1]

(7-Chloro-2-ethylimidazo[1,2-a]pyridin-3-yl)(4-(4-(trifluoromethoxy)phenoxy)piperidin-1-yl)methanone (380)

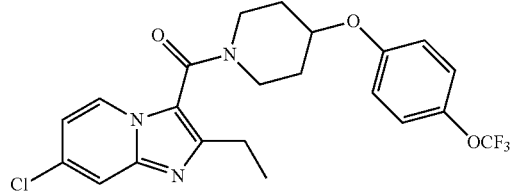 [SMILES: CCc1nc2cc(Cl)ccn2c1C(=O)N1CCC(Oc2ccc(OC(F)(F)F)cc2)CC1]

1-(6-chloro-2-ethylimidazo[1,2-a]pyridin-3-yl)-N-(4-(4-(4-fluorophenyl)piperazin-1-yl)benzyl)methanamine (381)

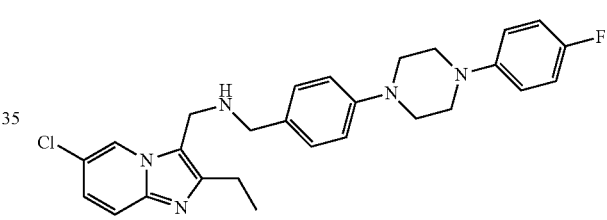

(6-chloro-2-ethylimidazo[1,2-a]pyridin-3-yl)(3-(4-(trifluoromethoxy)benzyloxy)-piperidin-1-yl)methanone (382)

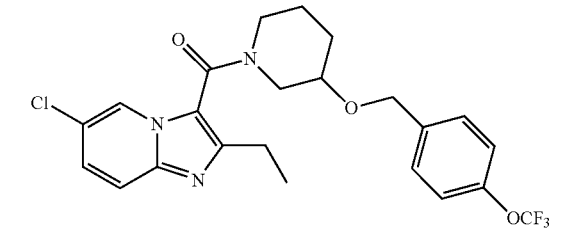 [SMILES: CCc1nc2ccc(Cl)cn2c1C(=O)N1CCCC(OCc2ccc(OC(F)(F)F)cc2)C1]

N-((6-chloro-2-ethylimidazo[1,2-a]pyridin-3-yl)methyl)-4'-(trifluoromethoxy)biphenyl-4-amine (383)

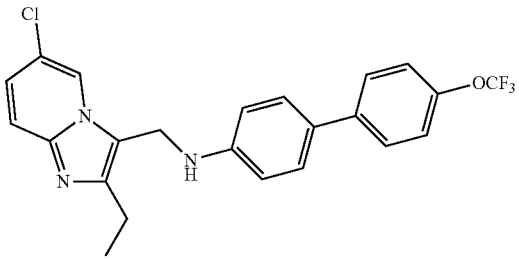 [SMILES: CCc1nc2ccc(Cl)cn2c1CNc1ccc(-c2ccc(OC(F)(F)F)cc2)cc1]

(6-Chloro-2-ethylimidazo[1,2-a]pyridin-3-yl)(4-(4-(trifluoromethoxy)phenoxy)piperidin-1-ethanone (384)

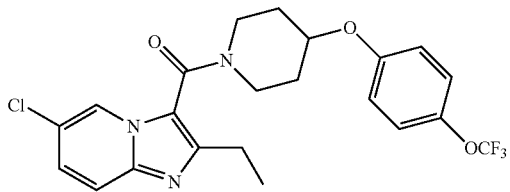 [SMILES: CCc1nc2ccc(Cl)cn2c1C(=O)N1CCC(Oc2ccc(OC(F)(F)F)cc2)CC1]

(2-Ethylimidazo[1,2-a]pyrimidin-3-yl)(4-((4-(trifluoromethoxy)benzyl)oxy)piperidin-1-yl)methanone (385)

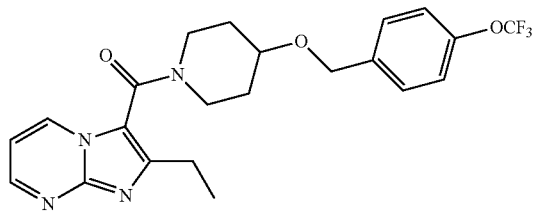 [SMILES: CCc1nc2ncccn2c1C(=O)N1CCC(OCc2ccc(OC(F)(F)F)cc2)CC1]

N-((4'-Chloro-[1,1'-biphenyl]4-yl)methyl)-2-ethylimidazo[1,2-a]pyrimidine-3-carboxamide (386)

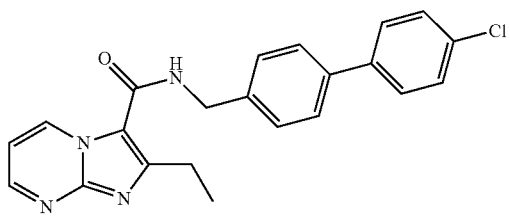 [SMILES: CCc1nc2ncccn2c1C(=O)NCc1ccc(-c2ccc(Cl)cc2)cc1]

(2-Ethylimidazo[1,2-a]pyridazin-3-yl)(4-((4-(trifluoromethoxy)benzyl)oxy)piperidin-1-yl)methanone (387)

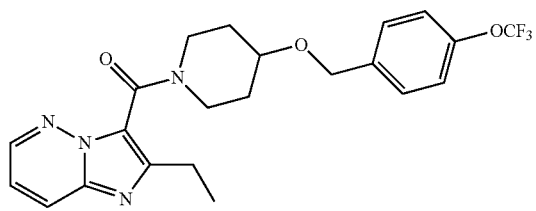 [SMILES: CCc1nc2cccnn2c1C(=O)N1CCC(OCc2ccc(OC(F)(F)F)cc2)CC1]

N-((4'-Chloro-[1,1'-biphenyl]-4-yl)methyl)-2-ethylimidazo[1,2-b]pyridazine-3-carboxamide (388)

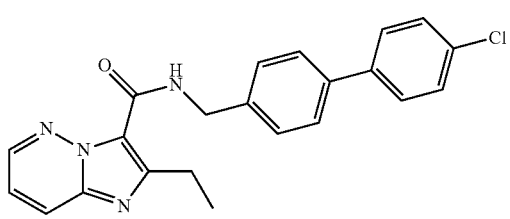 [SMILES: CCc1nc2cccnn2c1C(=O)NCc1ccc(-c2ccc(Cl)cc2)cc1]

(2-Ethylimidazo[1,2-a]pyrazin-3-yl)(4-((4-(trifluoromethoxy)benzyl)oxy)piperidin-1-yl)methanone (389)

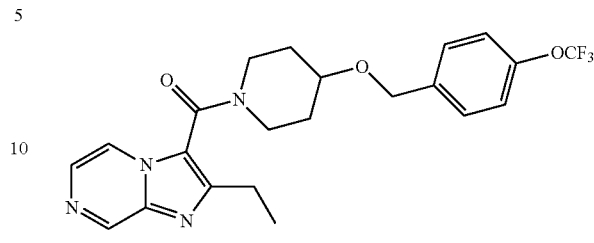

(S)-(6-chloro-2-ethylimidazo[1,2-a]pyridin-3-yl)(3-(4-(trifluoromethoxy)benzyloxy)-pyrrolidin-1-yl)methanone (390)

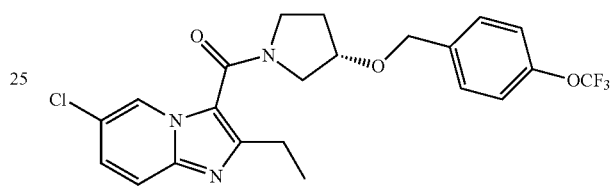

(R)-(6-chloro-2-ethylimidazo[1,2-a]pyridin-3-yl)(3-(4-(trifluoromethoxy)benzyloxy)-pyrrolidin-1-yl)methanone (39)

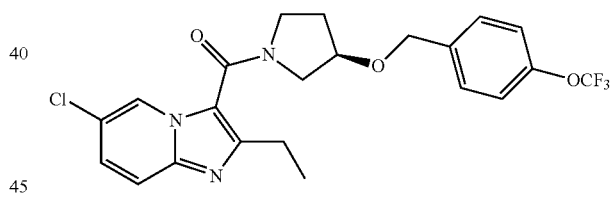

N-(((6-chloro-2-ethylimidazo[1,2-a]pyridin-3-yl)methyl)-4-(4-(4-chlorophenyl)piperidin-1-yl)aniline (392)

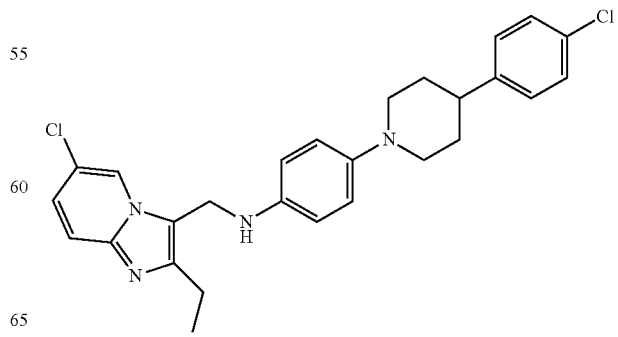

(7-chloro-2-ethylimidazo[1,2-a]pyridin-3-yl)(4-(4-(trifluoromethoxy)benzyloxy)piperidin-1-yl)methanone (393)

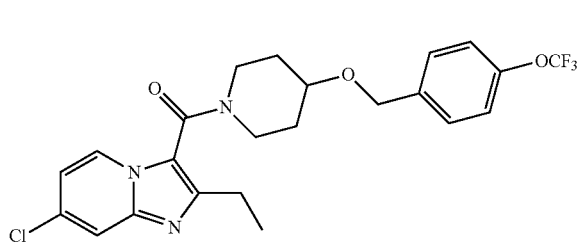 [SMILES: CCc1nc2cc(Cl)ccn2c1C(=O)N1CCC(OCc2ccc(OC(F)(F)F)cc2)CC1]

N-((6-chloro-2-ethylimidazo[1,2-a]pyridin-3-yl)methyl)-4-(4-(trifluoromethoxy)-phenoxy)aniline (394)

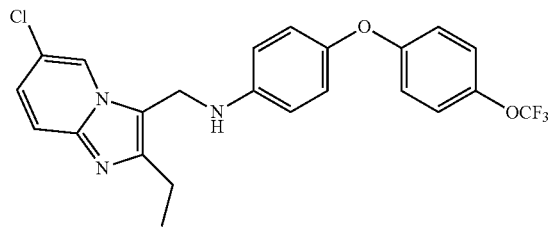 [SMILES: CCc1nc2ccc(Cl)cn2c1CNc1ccc(Oc2ccc(OC(F)(F)F)cc2)cc1]

N-((2-Ethylimidazo[1,2-a]pyrimidin-3-yl)methyl)-4-(4-(4-fluorophenyl)piperazin-1-yl)aniline (395)

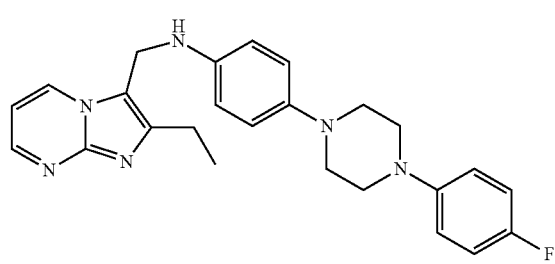 [SMILES: CCc1nc2ncccn2c1CNc1ccc(N2CCN(c3ccc(F)cc3)CC2)cc1]

N-((2-Ethylimidazo[1,2-b]pyridazin-3-yl)methyl)-4-(4-(4-fluorophenyl)piperazin-1-yl)aniline (396)

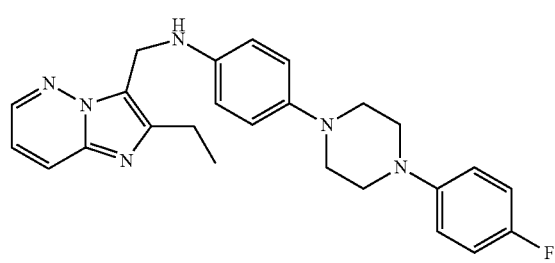 [SMILES: CCc1nc2cccnn2c1CNc1ccc(N2CCN(c3ccc(F)cc3)CC2)cc1]

6-chloro-2-ethyl-3-((4-(4-fluorophenyl)piperazin-1-yl)methyl)imidazo[1,2-a]pyridine (397)

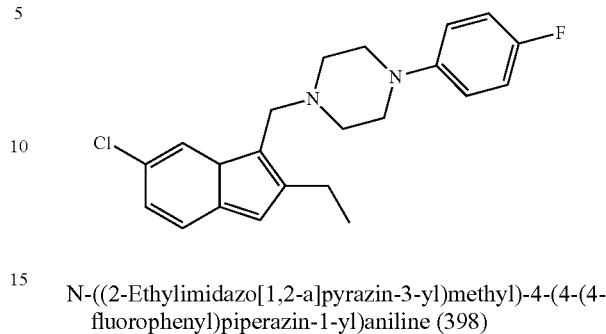

N-((2-Ethylimidazo[1,2-a]pyrazin-3-yl)methyl)-4-(4-(4-fluorophenyl)piperazin-1-yl)aniline (398)

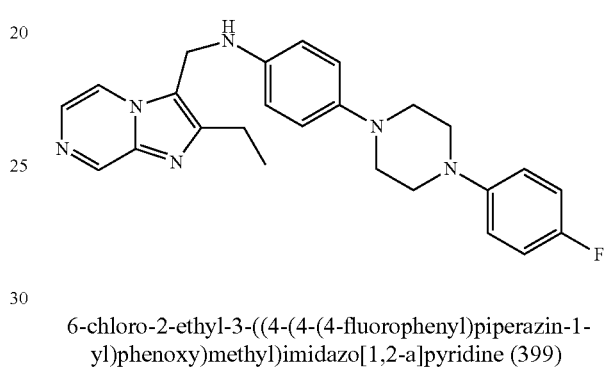

6-chloro-2-ethyl-3-((4-(4-(4-fluorophenyl)piperazin-1-yl)phenoxy)methyl)imidazo[1,2-a]pyridine (399)

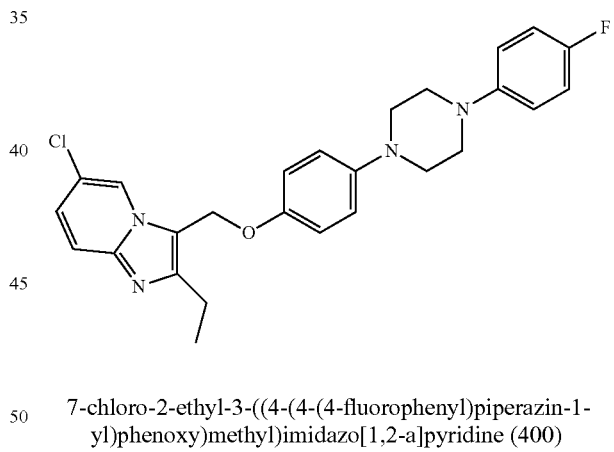

7-chloro-2-ethyl-3-((4-(4-(4-fluorophenyl)piperazin-1-yl)phenoxy)methyl)imidazo[1,2-a]pyridine (400)

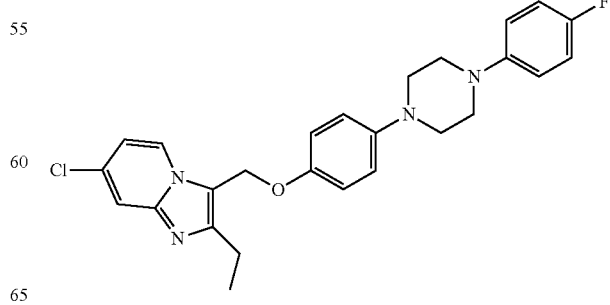

277

N-((2,5-dimethylimidazo[1,2-a]pyridin-3-yl)methyl)-4-(4-(4-fluorophenyl)piperidin-1-yl)aniline (401)

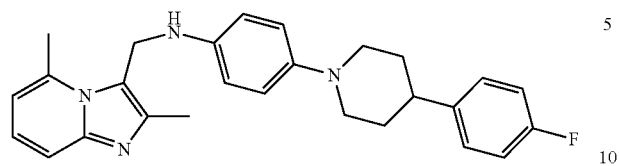

N-((2,5-dimethylimidazo[1,2-a]pyridin-3-yl)methyl)-4-(4-(4-fluorophenyl)piperazin-1-yl) aniline (402)

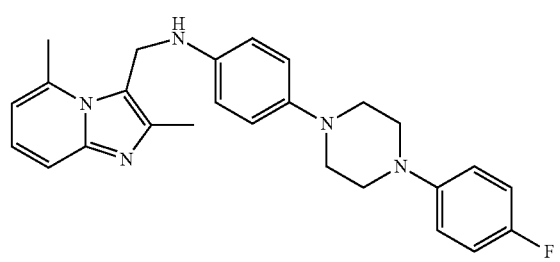 [SMILES: Cc1nc2cccc(C)n2c1CNc1ccc(N2CCN(c3ccc(F)cc3)CC2)cc1]

2-Ethyl-6-fluoro-N-(1-(4-(phenylamino)phenyl)pyrrolidin-3-yl)imidazo[1,2-a]pyridine-3-carboxamide (403)

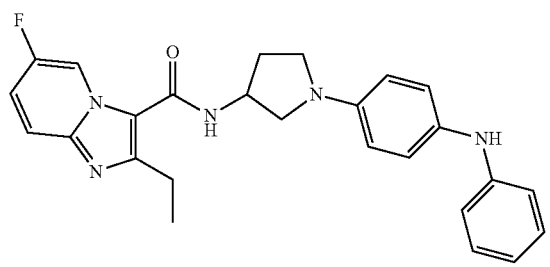 [SMILES: CCc1nc2ccc(F)cn2c1C(=O)NC1CCN(c2ccc(Nc3ccccc3)cc2)C1]

and pharmaceutically acceptable salts thereof.

4. The method according to claim 1, wherein said compound has a formulae selected from:

7-Chloro-2-ethyl-N-(4-(4-(4-fluorophenyl)piperazin-1-yl)benzyl)imidazo[1,2-a]pyridine-3-carboxamide (127)

278

7-Chloro-2-ethyl-N-(4-(4-(trifluoromethoxy)phenoxy)benzyl)imidazo[1,2-a]pyridine-3-carboxamide (128)

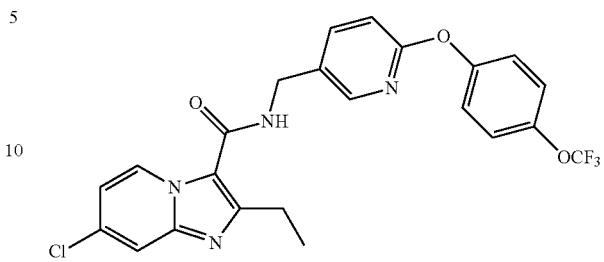

6-Chloro-2-ethyl-N-((6-(4-(trifluoromethoxy)phenoxy)pyridin-3-yl)methyl)imidazo[1,2-a]pyridine-3-carboxamide (189)

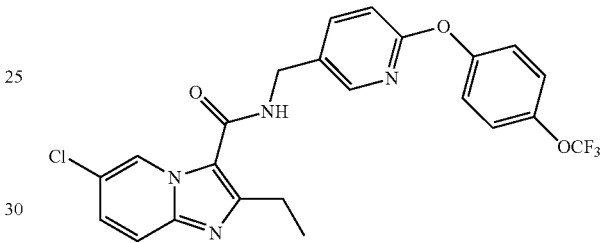

2-Ethyl-7-methyl-N-(4-(4-(trifluoromethoxy)phenoxy)benzyl)imidazo[1,2-a]pyridine-3-carboxamide (219)

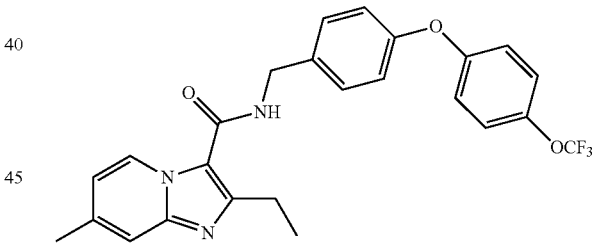

2-Ethyl-8-fluoro-N-(4-(4-(trifluoromethoxy)phenoxy)benzyl)imidazo[1,2-a]pyridine-3-carboxamide (224)

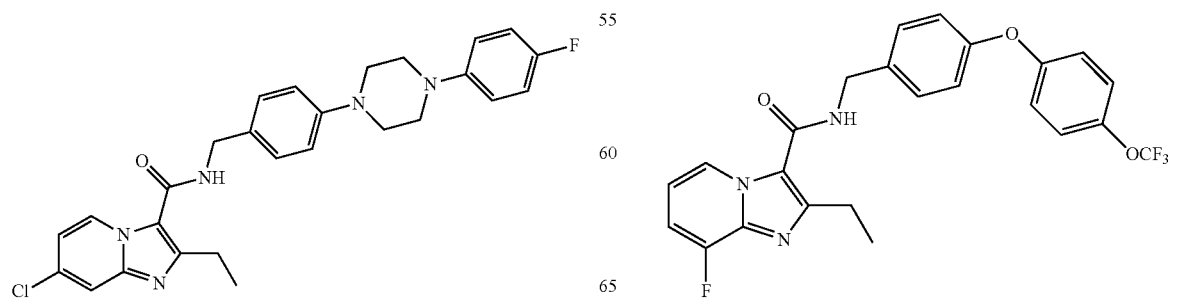

2-Ethyl-6-fluoro-N-(4-(4-(trifluoromethoxy)phenoxy)
benzyl)imidazo[1,2-a]pyridine-3-carboxamide (225)

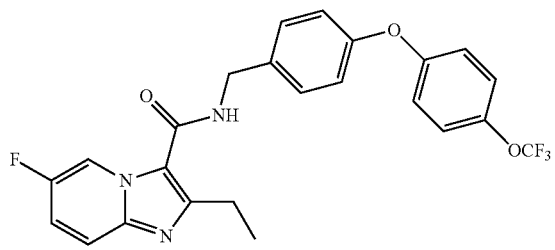 [SMILES: CCc1nc2ccc(F)cn2c1C(=O)NCc1ccc(Oc2ccc(OC(F)(F)F)cc2)cc1]

2-Ethyl-N-(4-(4-(4-(trifluoromethoxy)phenyl)piperidin-
1-yl)benzyl)imidazo[1,2-a]pyridine-3-carboxamide
(266)

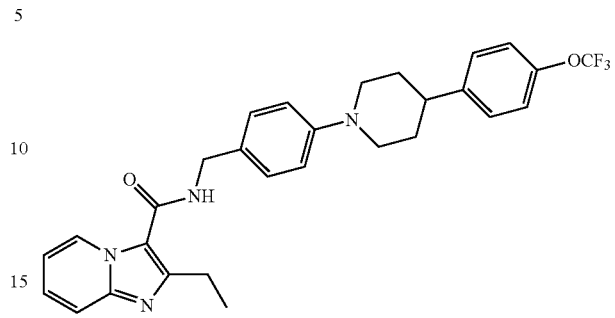

2-Ethyl-6-methyl-N-(4-(4-(trifluoromethoxy)phenoxy)
benzyl)imidazo[1,2-a]pyridine-3-carboxamide (232)

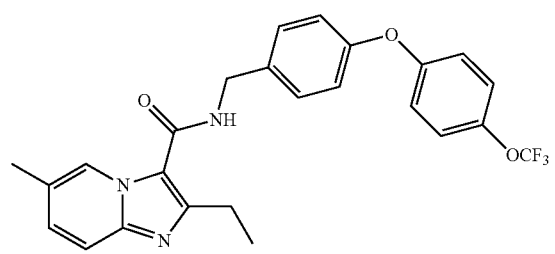 [SMILES: CCc1nc2ccc(C)cn2c1C(=O)NCc1ccc(Oc2ccc(OC(F)(F)F)cc2)cc1]

7-Chloro-N-((2-cyclohexylbenzo[d]oxazol-5-yl)methyl)-
2-ethylimidazo[1,2-a]pyridine-3-carboxamide (299)

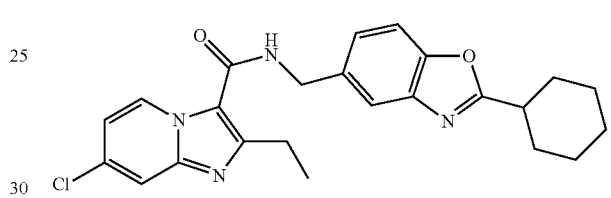

2-Ethyl-N-(4-(4-((4-fluorophenoxy)methyl)piperidin-1-
yl)benzyl)imidazo[1,2-a]pyridine-3-carboxamide (243)

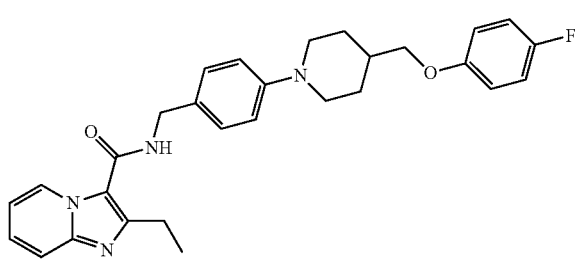 [SMILES: CCc1nc2ccccn2c1C(=O)NCc1ccc(N2CCC(COc3ccc(F)cc3)CC2)cc1]

N-((6-Chloro-2-ethylimidazo[1,2-a]pyridin-3-yl)methyl)-
4-(4-(4-fluorophenyl)piperazin-1-yl)aniline (311)

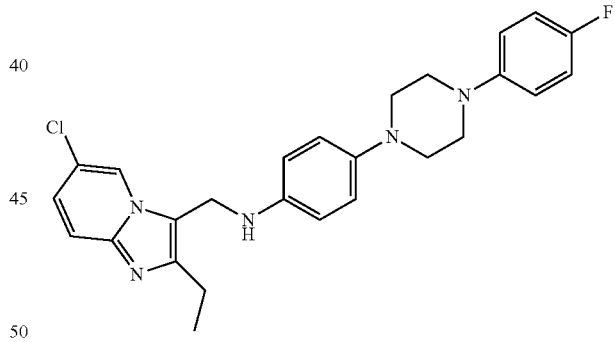

2-Ethyl-N-(4-(4-(4-fluorophenyl)piperidin-1-yl)benzyl)
imidazo[1,2-a]pyridine-3-carboxamide (265)

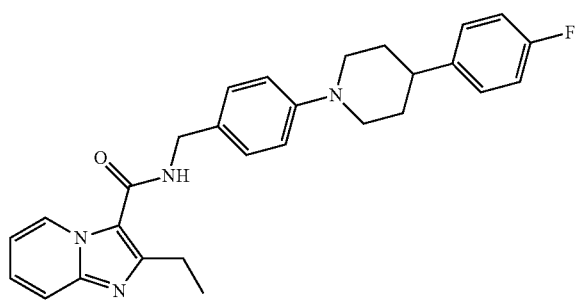 [SMILES: CCc1nc2ccccn2c1C(=O)NCc1ccc(N2CCC(c3ccc(F)cc3)CC2)cc1]

2-Ethyl-7-nitro-N-(4-(4-(4-(trifluoromethoxy)phenoxy)
piperidin-1-yl)benzyl)imidazo[1,2-a]pyridine-3-car-
boxamide (312)

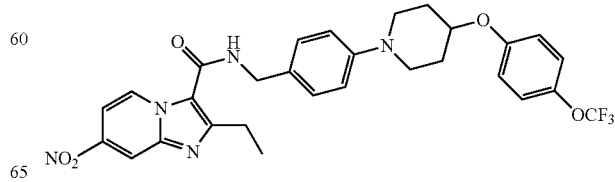

(6-Chloro-2-ethylimidazo[1,2-a]pyridin-3-yl)(4-(4-(trifluoromethoxy)benzyloxy) piperidin-1-yl)methanone (313)

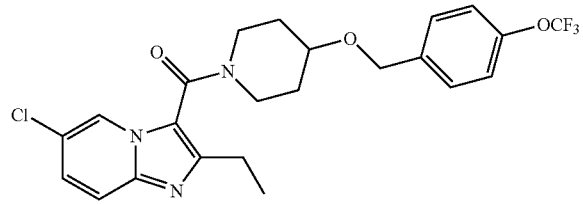 [SMILES: CCc1nc2ccc(Cl)cn2c1C(=O)N1CCC(OCc2ccc(OC(F)(F)F)cc2)CC1]

6-Chloro-2-ethyl-N-(4-(4-(4-fluorophenyl)piperazin-1-yl)benzyl)-N-methylimidazo[1,2-a]pyridine-3-carboxamide (314)

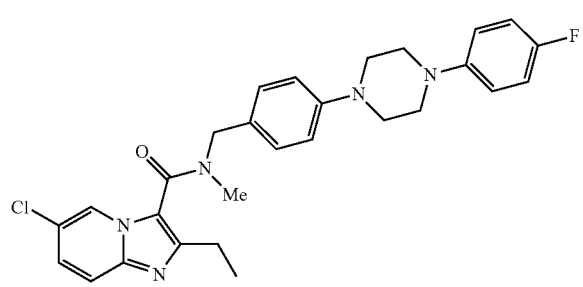 [SMILES: CCc1nc2ccc(Cl)cn2c1C(=O)N(C)Cc1ccc(N2CCN(c3ccc(F)cc3)CC2)cc1]

(7-Chloro-2-ethylimidazo[1,2-a]pyridin-3-yl)(4-(4-(trifluoromethoxy)phenoxy)piperidin-1-yl)methanone (380)

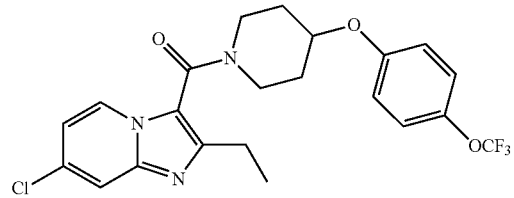 [SMILES: CCc1nc2cc(Cl)ccn2c1C(=O)N1CCC(Oc2ccc(OC(F)(F)F)cc2)CC1]

7-chloro-2-ethylimidazo[1,2-a]pyridin-3-yl)(4-(4-(trifluoromethoxy)benzyloxy)piperidin-1-yl)methanone (393)

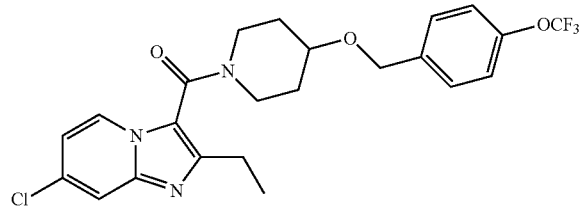 [SMILES: CCc1nc2cc(Cl)ccn2c1C(=O)N1CCC(OCc2ccc(OC(F)(F)F)cc2)CC1]

N-((6-chloro-2-ethylimidazo[1,2-a]pyridin-3-yl)methyl)-4-(4-(trifluoromethoxy)-phenoxy)aniline (394)

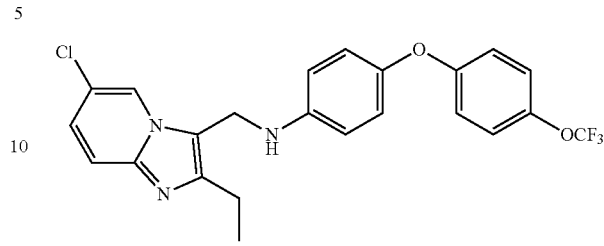

N-((2-Ethylimidazo[1,2-a]pyridazin-3-yl)methyl)-4-(4-(4-fluorophenyl)piperazin-1-yl)aniline (395)

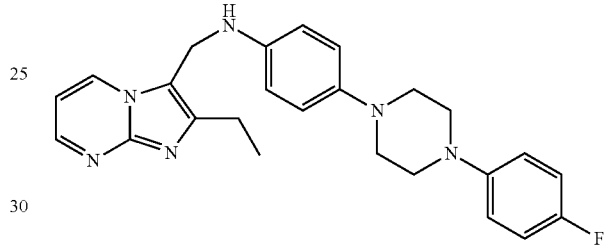

N-((2-Ethylimidazo[1,2-b]pyridazin-3-yl)methyl)-4-(4-(4-fluorophenyl)piperazin-1-yl)aniline (396)

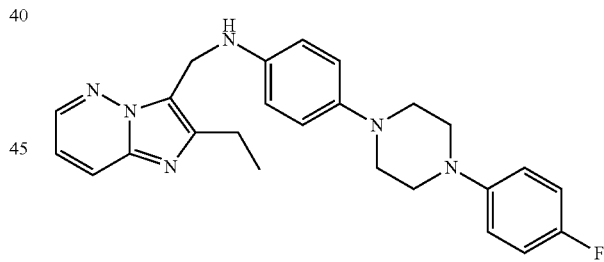

N-((2-Ethylimidazo[1,2-a]pyrazin-3-yl)methyl)-4-(4-(4-fluorophenyl)piperazin-1-yl)aniline (398)

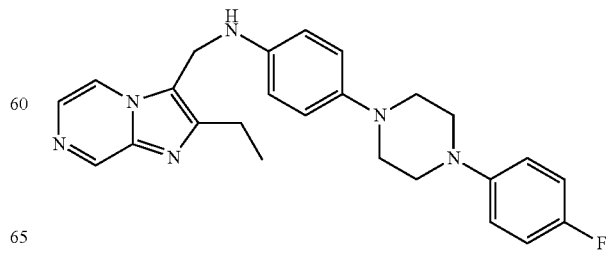

6-chloro-2-ethyl-3-((4-(4-(4-fluorophenyl)piperazin-1-yl)phenoxy)methyl)imidazo[1,2-a]pyridine (399)

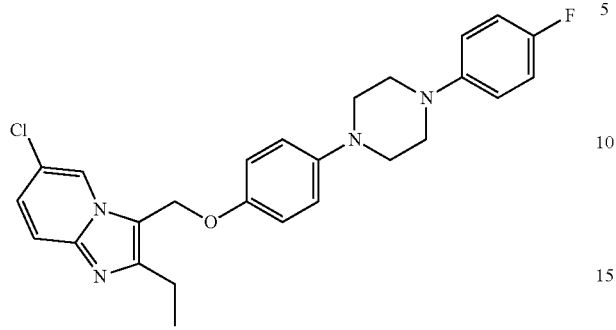

7-chloro-2-ethyl-3-((4-(4-(4-fluorophenyl)piperazin-1-yl)phenoxy)methyl)imidazo[1,2-a]pyridine (400)

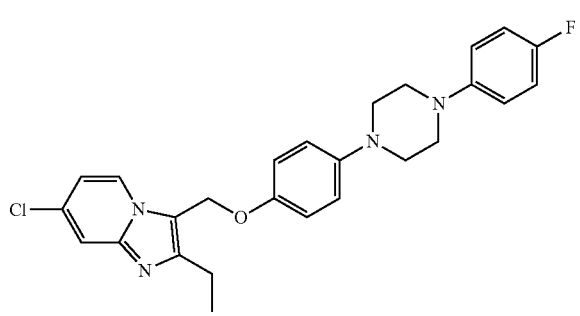 [SMILES: CCc1nc2cc(Cl)ccn2c1COc1ccc(N2CCN(c3ccc(F)cc3)CC2)cc1]

N-((2,5-dimethylimidazo[1,2-a]pyridin-3-yl)methyl)-4-(4-(4-fluorophenyl)piperidin-1-yl)aniline (401)

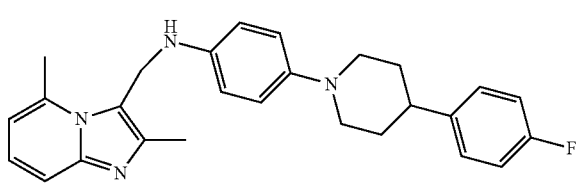 [SMILES: Cc1nc2cccc(C)n2c1CNc1ccc(N2CCC(c3ccc(F)cc3)CC2)cc1]

N-((2,5-dimethylimidazo[1,2-a]pyridin-3-yl)methyl)-4-(4-(4-fluorophenyl)piperazin-1-yl)aniline (402)

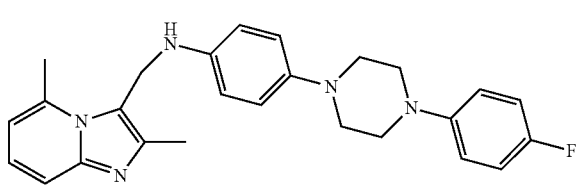

2-Ethyl-6-fluoro-N-(1-(4-(phenylamino)phenyl)pyrrolidin-3-yl)imidazo[1,2-a]pyridine-3-carboxamide (403)

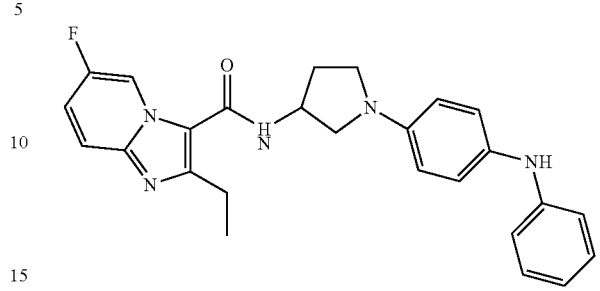

and pharmaceutically acceptable salts thereof.

5. The method according to claim 1, wherein said compound is in a composition that also comprises a pharmaceutically acceptable carrier.

6. The method according to claim 1, wherein said inflammatory disease is asthma, or arthritis, or dermatitis, or chronic obstructive pulmonary disease (COPD), or inflammation post infection, or atherosclerosis, or pain.

7. The method according to claim 1, wherein said effective amount is an amount in the range of 0.01 mg/kg body weight to 1 g/kg body weight of said patient.

8. A compound that competitively inhibits the specific binding of a compound as defined in claim 1 to arachidonate 5-lipoxygenase (5-lipoxygenase, 5-LO, Alox5).

9. A method for treating an inflammatory disease comprising administering or applying, to a patient in need of such treatment, an effective amount of a compound according to claim 8.

10. The method of treatment according to claim 9, wherein said patient is a patient suffering from asthma, atherosclerosis, pain, chronic obstructive pulmonary disease (COPD), inflammation post infection, arthritis and/or dermatitis.

11. The method, according to claim 1, wherein the inflammatory disease is asthma.

12. The method, according to claim 2, wherein said enzyme is arachidonate 5 lipoxygenase.

13. The method, according to claim 3, wherein said compound has a formulae selected from:

2-Ethyl-6-methyl-N-(4-phenoxybenzyl)imidazo[1,2-a]pyridine-3-carboxamide (58)

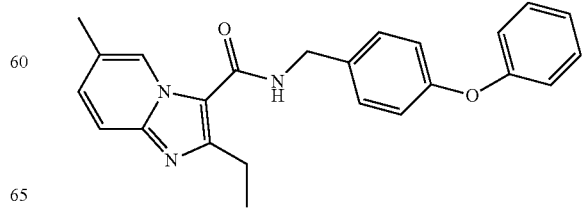

7-Chloro-2-ethyl-N-(4-(4-(4-fluorophenoxy)piperidin-1-yl)benzyl)imidazo[1,2-a]pyridine-3-carboxamide (70)

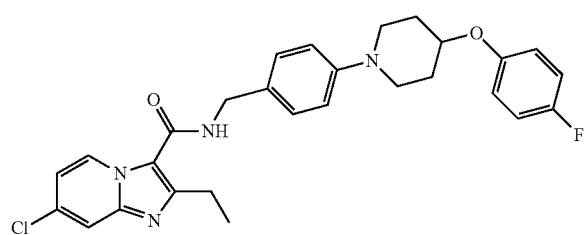 [SMILES: CCc1nc2cc(Cl)ccn2c1C(=O)NCc1ccc(N2CCC(Oc3ccc(F)cc3)CC2)cc1]

7-Chloro-2-ethyl-N-((2'-methylbiphenyl-4-yl)methyl)imidazo[1,2-a]pyridine-3-carboxamide (85)

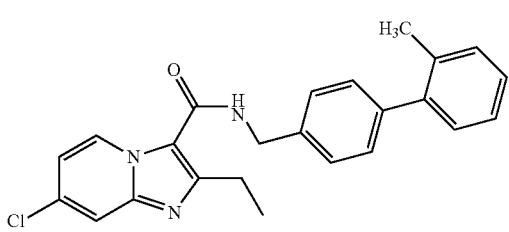 [SMILES: CCc1nc2cc(Cl)ccn2c1C(=O)NCc1ccc(-c2ccccc2C)cc1]

7-Chloro-2-ethyl-N-((3'-methylbiphenyl-4-yl)methyl)imidazo[1,2-a]pyridine-3-carboxamide (86)

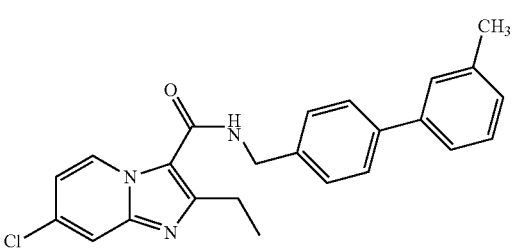 [SMILES: CCc1nc2cc(Cl)ccn2c1C(=O)NCc1ccc(-c2cccc(C)c2)cc1]

6-Chloro-N-((4'-chloro-2'-(trifluoromethyl)biphenyl-4-yl)methyl)-2-ethylimidazo[1,2-a]pyridine-3-carboxamide (100)

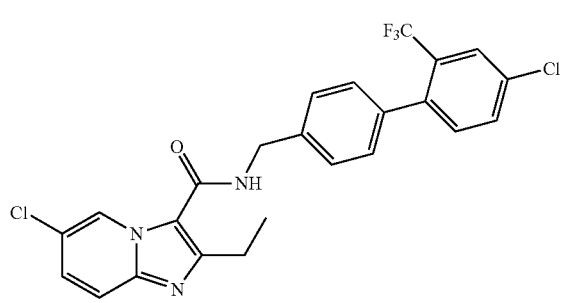 [SMILES: CCc1nc2ccc(Cl)cn2c1C(=O)NCc1ccc(-c2ccc(Cl)cc2C(F)(F)F)cc1]

7-Chloro-N-((4'-chloro-2'-(trifluoromethyl)biphenyl-4-yl)methyl)-2-ethylimidazo[1,2-a]pyridine-3-carboxamide (103)

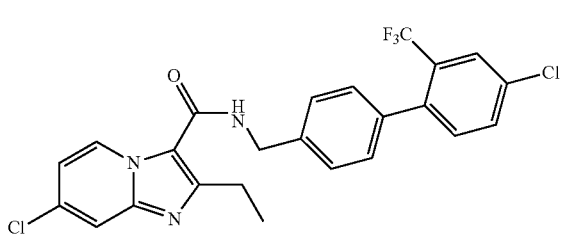 [SMILES: CCc1nc2cc(Cl)ccn2c1C(=O)NCc1ccc(-c2ccc(Cl)cc2C(F)(F)F)cc1]

7-Chloro-2-ethyl-N-(4-(pentylamino)benzyl)imidazo[1,2-a]pyridine-3-carboxamide (110)

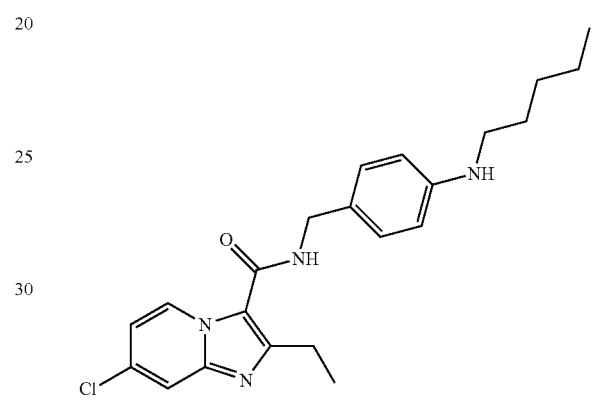

7-Chloro-2-ethyl-N-(4-(4-(4-(trifluoromethoxy)phenoxy)piperidin-1-yl)benzyl)imidazo-[1,2-a]pyridine-3-carboxamide (123)

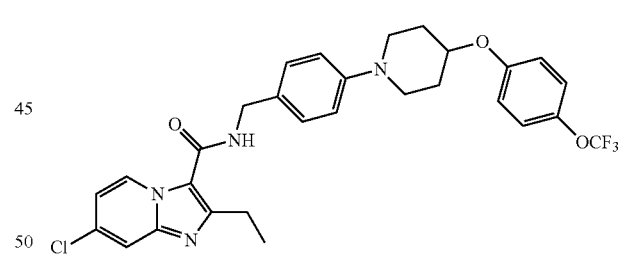

2-Ethyl-N-(4-(4-(4-(trifluoromethoxy)phenoxy)piperidin-1-yl)benzyl)-6-(trifluoromethoxy)imidazo[1,2-a]pyridine-3-carboxamide (124)

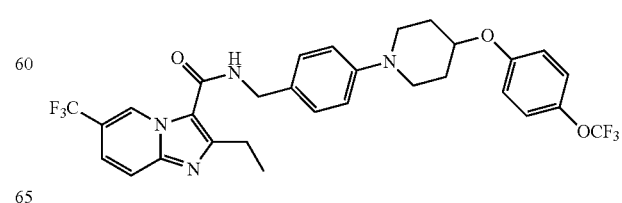

287

7-Chloro-2-ethyl-N-(4-(4-(4-fluorobenzyl)piperazin-1-yl)benzyl)imidazo[1,2-a]pyridine-3-carboxamide (126)

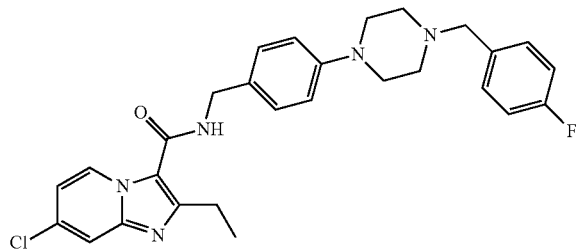 [SMILES: CCc1nc2cc(Cl)ccn2c1C(=O)NCc1ccc(N2CCN(Cc3ccc(F)cc3)CC2)cc1]

7-Chloro-2-ethyl-N-(4-(4-(4-fluorophenyl)piperazin-1-yl)benzyl)imidazo[1,2-a]pyridine-3-carboxamide (127)

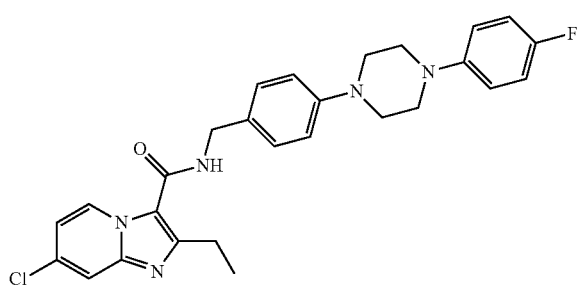 [SMILES: CCc1nc2cc(Cl)ccn2c1C(=O)NCc1ccc(N2CCN(c3ccc(F)cc3)CC2)cc1]

7-Chloro-2-ethyl-N-(4-(4-(trifluoromethoxy)phenoxy)benzyl)imidazo[1,2-a]pyridine-3-carboxamide (128)

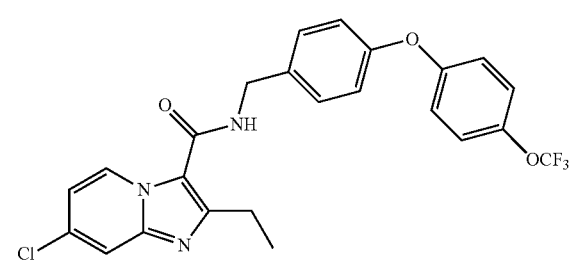 [SMILES: CCc1nc2cc(Cl)ccn2c1C(=O)NCc1ccc(Oc2ccc(OC(F)(F)F)cc2)cc1]

6-Chloro-2-ethyl-N-(4-(4-(4-fluorobenzyl)piperazin-1-yl)benzyl)imidazo[1,2-a]pyridine-3-carboxamide (130)

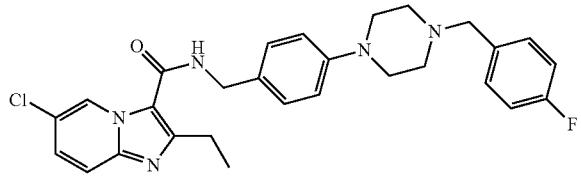

6-Chloro-2-ethyl-3-((4-(trifluoromethoxy)phenoxy)methyl)imidazo[1,2-a]pyridine (143)

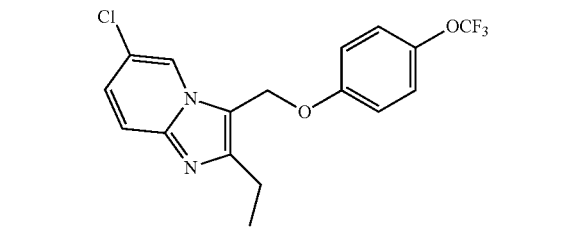 [SMILES: CCc1nc2ccc(Cl)cn2c1COc1ccc(OC(F)(F)F)cc1]

288

7-Chloro-2-ethyl-N-(4-(4-(4-(trifluoromethoxy)benzyl)piperazin-1-yl)benzyl)imidazo[1,2-a]pyridine-3-carboxamide (157)

7-Chloro-N-(4-(4-chlorophenoxy)benzyl)-2-ethylimidazo[1,2-a]pyridine-3-carboxamide (161)

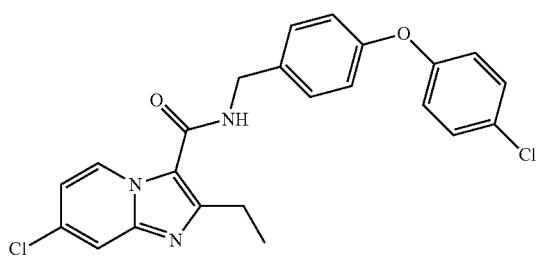 [SMILES: CCc1nc2cc(Cl)ccn2c1C(=O)NCc1ccc(Oc2ccc(Cl)cc2)cc1]

6-Chloro-2-ethyl-N-(4-(4-fluorophenoxy)benzyl)-N-methylimidazo[1,2-a]pyridine-3-carboxamide (164)

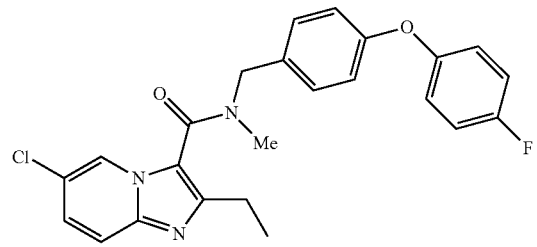 [SMILES: CCc1nc2ccc(Cl)cn2c1C(=O)N(C)Cc1ccc(Oc2ccc(F)cc2)cc1]

6-Chloro-2-ethyl-N-(4-(4-(trifluoromethoxy)phenylamino)benzyl)imidazo[1,2-a]pyridine-3-carboxamide (174)

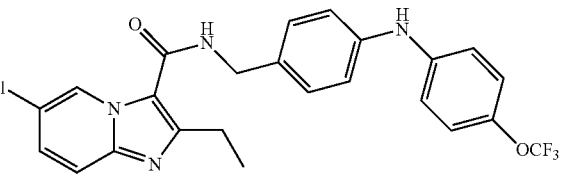

7-Chloro-2-ethyl-N-(4-(4-(trifluoromethoxy)phenylamino)benzyl)imidazo[1,2-a]pyridine-3-carboxamide (175)

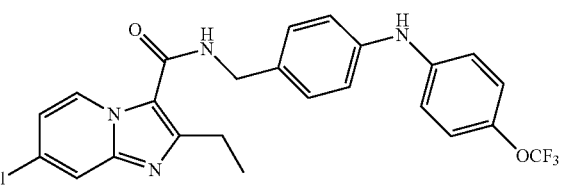

289

2-Ethyl-N-(4-(4-(4-(trifluoromethoxy)phenyl)piperazin-1-yl)benzyl)imidazo[1,2-a]pyridine-3-carboxamide (181)

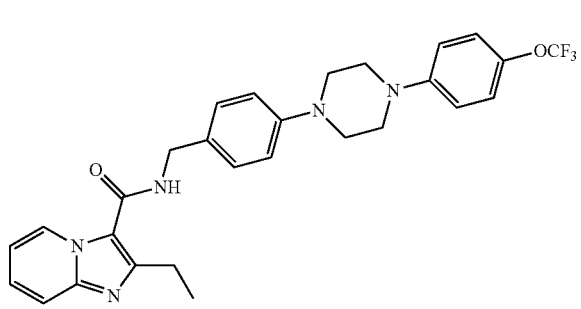 [SMILES: CCc1nc2ccccn2c1C(=O)NCc1ccc(N2CCN(c3ccc(OC(F)(F)F)cc3)CC2)cc1]

6-chloro-2-ethyl-N-((6-(4-(trifluoromethoxy)phenoxy)pyridin-3-yl)methyl)imidazo[1,2-a]pyridine-3-carboxamide (189)

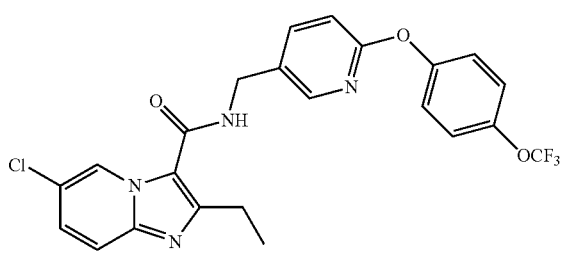 [SMILES: CCc1nc2ccc(Cl)cn2c1C(=O)NCc1ccc(Oc2ccc(OC(F)(F)F)cc2)nc1]

7-Chloro-2-ethyl-N-((6-(4-(trifluoromethoxy)phenoxy)pyridin-3-yl)methyl)imidazo[1,2-a]pyridine-3-carboxamide (190)

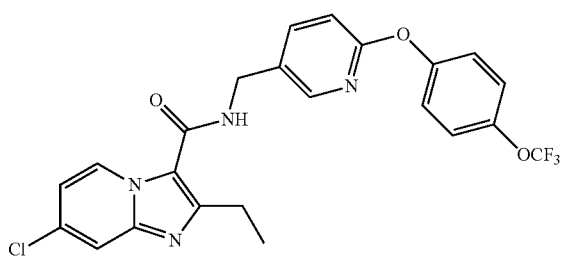

N-(4-(Azepan-1-yl)benzyl)-7-chloro-2-ethylimidazo[1,2-a]pyridine-3-carboxamide (193)

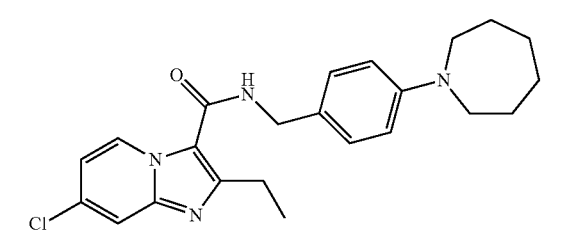 [SMILES: CCc1nc2cc(Cl)ccn2c1C(=O)NCc1ccc(N2CCCCCC2)cc1]

290

7-Chloro-N-(4-(5,6-dihydropyridin-1(2H)-yl)benzyl)-2-ethylimidazo[1,2-a]pyridine-3-carboxamide (194)

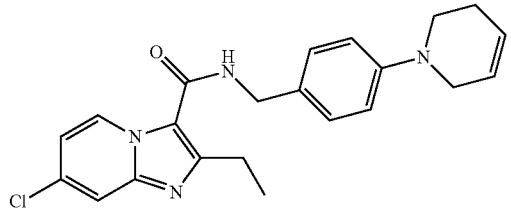 [SMILES: CCc1nc2cc(Cl)ccn2c1C(=O)NCc1ccc(N2CC=CCC2)cc1]

6-Chloro-N-(4-(3,5-dimethylpiperidin-1-yl)benzyl)-2-ethylimidazo[1,2-a]pyridine-3-carboxamide (197)

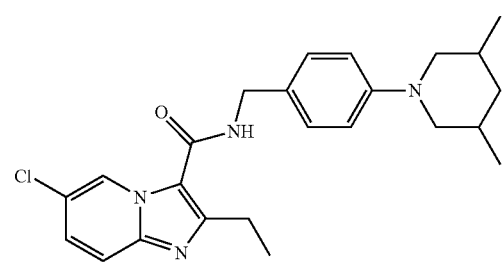 [SMILES: CCc1nc2ccc(Cl)cn2c1C(=O)NCc1ccc(N2CC(C)CC(C)C2)cc1]

2-Ethyl-N-(4-(4-(trifluoromethoxy)benzoyloxy)benzyl)imidazo[1,2-a]pyridine-3-carboxamide (207)

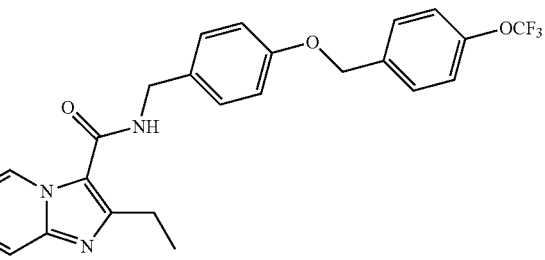

N-(4-(4-Benzylpiperidin-1-yl)benzyl)-7-chloro-2-ethylimidazo[1,2-a]pyridine-3-carboxamide (208)

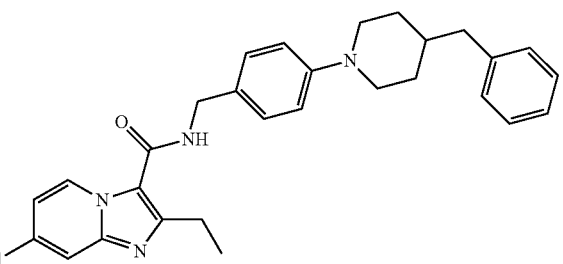

7-Chloro-2-ethyl-N-(4-(4-phenylpiperidin-1-yl)benzyl)
imidazo[1,2-a]pyridine-3-carboxamide (209)

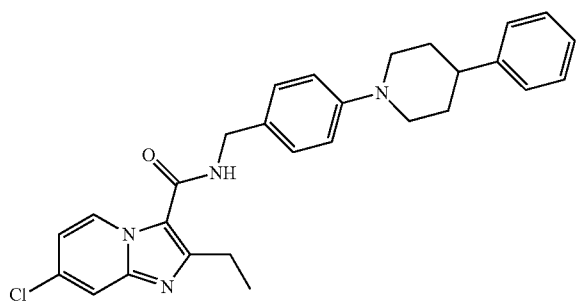 [SMILES: CCc1nc2cc(Cl)ccn2c1C(=O)NCc1ccc(N2CCC(c3ccccc3)CC2)cc1]

7-Chloro-N-(4-(4,4-dimethylpiperidin-1-yl)benzyl)-2-
ethyl-1,8a-dihydroimidazo[1,2-a]pyridine-3-carboxa-
mide (211)

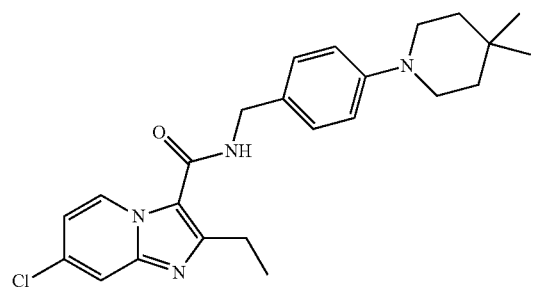 [SMILES: CCc1nc2cc(Cl)ccn2c1C(=O)NCc1ccc(N2CCC(C)(C)CC2)cc1]

7-Chloro-2-ethyl-N-(4-(4,5,6,7-tetrahydro-2H-isoindol-
2-yl)benzyl)imidazo[1,2-a]pyridin-3-carboxamide
(217)

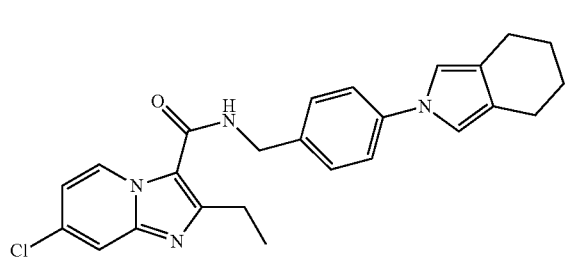 [SMILES: CCc1nc2cc(Cl)ccn2c1C(=O)NCc1ccc(-n2cc3c(c2)CCCC3)cc1]

2-Ethyl-7-methyl-N-(4-(4-(trifluoromethoxy)phenoxy)
benzyl) imidazo[1,2-a]pyridine-3-carboxamide (219)

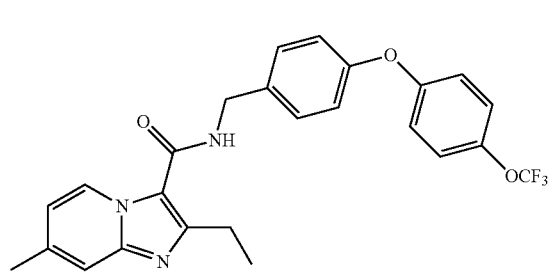 [SMILES: CCc1nc2cc(C)ccn2c1C(=O)NCc1ccc(Oc2ccc(OC(F)(F)F)cc2)cc1]

2-Ethyl-8-fluoro-N-(4-(4-(4-fluorophenyl)piperazin-1-yl)
benzyl)imidazo[1,2-a]pyridine-3-carboxamide (223)

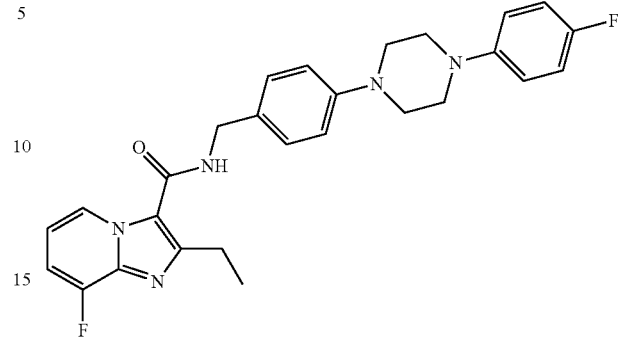

2-Ethyl-8-fluoro-N-(4-(4-(trifluoromethoxy)phenoxy)
benzyl)imidazo[1,2-a]pyridine-3-carboxamide (224)

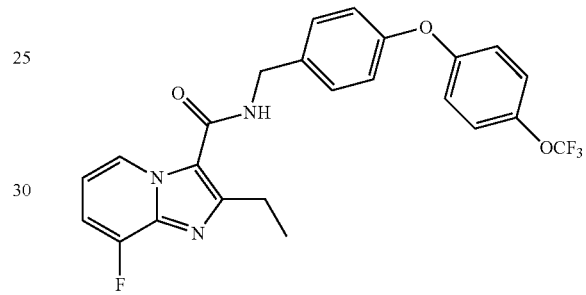

2-Ethyl-6-fluoro-N-(4-(4-(trifluoromethoxy)phenoxy)
benzyl)imidazo[1,2-a]pyridine-3-carboxamide (225)

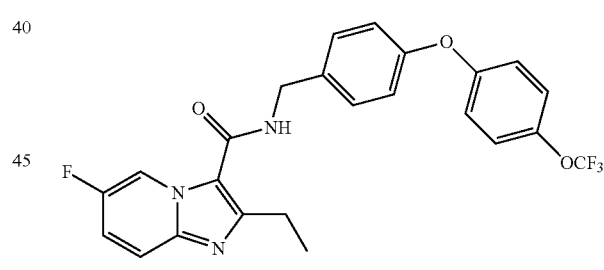

2-Ethyl-N-(4-(4-(4-fluorophenyl)piperazin-1-yl)benzyl)
imidazo[1,2-a]pyridine-3-carboxamide (227)

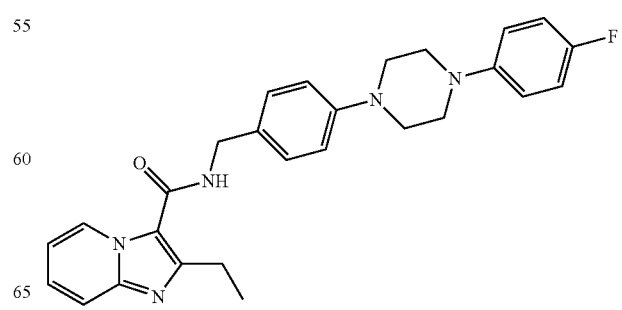

293

2-Ethyl-6-fluoro-N-(4-(4-(4-fluorophenyl)piperazin-1-yl)
benzyl)imidazo[1,2-a]pyridine-3-carboxamide (228)

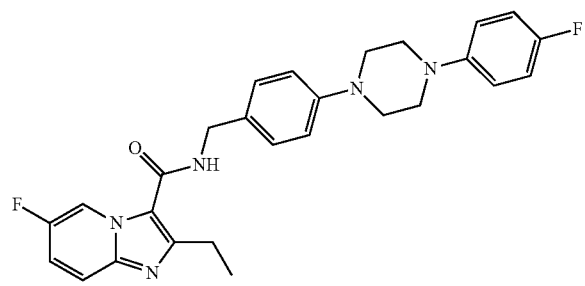 [SMILES: CCc1nc2ccc(F)cn2c1C(=O)NCc1ccc(N2CCN(c3ccc(F)cc3)CC2)cc1]

2-Ethyl-N-(4-(4-(4-fluorophenyl)piperazin-1-yl)benzyl)-
6-methylimidazo[1,2-a]pyridine-3-carboxamide (231)

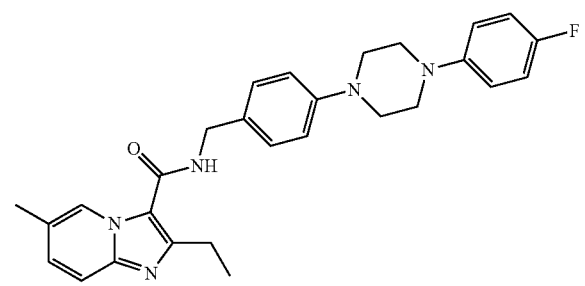 [SMILES: CCc1nc2ccc(C)cn2c1C(=O)NCc1ccc(N2CCN(c3ccc(F)cc3)CC2)cc1]

2-Ethyl-6-methyl-N-(4-(4-(trifluoromethoxy)phenoxy)
benzyl)imidazo[1,2-a]pyridine-3-carboxamide (232)

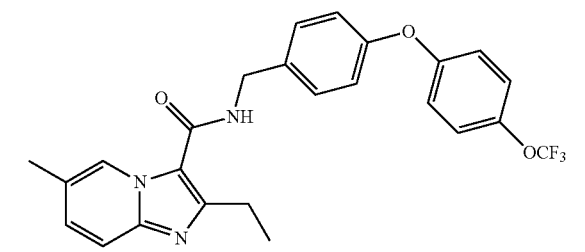 [SMILES: CCc1nc2ccc(C)cn2c1C(=O)NCc1ccc(Oc2ccc(OC(F)(F)F)cc2)cc1]

2-Ethyl-N-(4-(4-((4-fluorophenoxy)methyl)piperidin-1-
yl)benzyl)imidazo[1,2-a]pyridine-3-carboxamide (243)

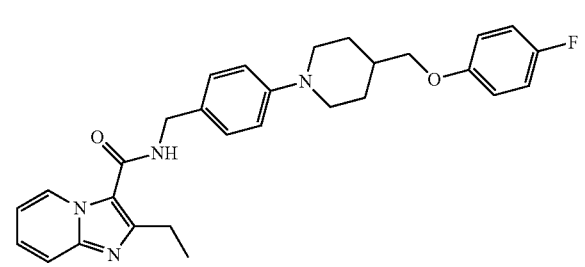 [SMILES: CCc1nc2ccccn2c1C(=O)NCc1ccc(N2CCC(COc3ccc(F)cc3)CC2)cc1]

294

8-Bromo-2-ethyl-N-(4-(4-(4-fluorophenyl)piperazin-1-
yl)benzyl)imidazo[1,2-a]pyridine-3-carboxamide (260)

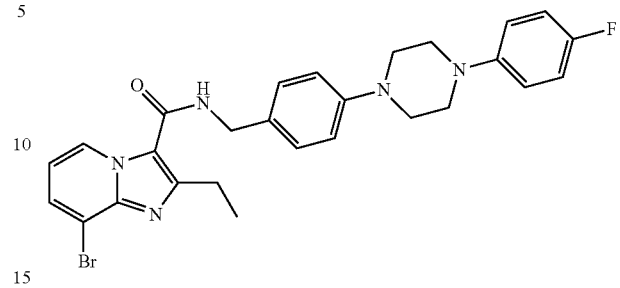

2-Ethyl-N-(4-(4-(4-fluorphenyl)piperidin-1-yl)benzyl)
imidazo[1,2-a]pyridine-3-carboxamide (265)

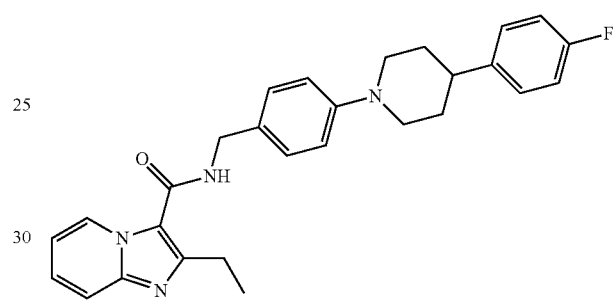

2-Ethyl-N-(4-(4-(4-(trifluoromethoxy)phenyl)piperidin-
1-yl)benzyl)imidazo[1,2-a]pyridine-3-carboxamide
(266)

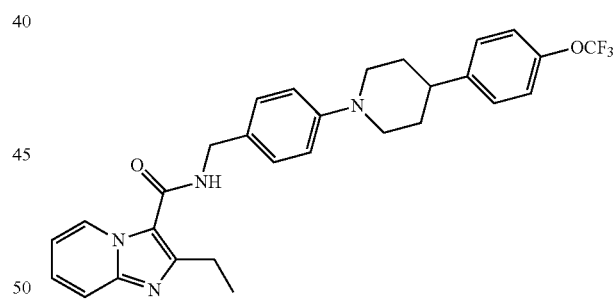

7-Chloro-N-(4-(4-((difluoromethoxy)methyl)piperidin-1-
yl)benzyl)-2-ethylimidazo[1,2-a]pyridine-3-carboxam-
ide (295)

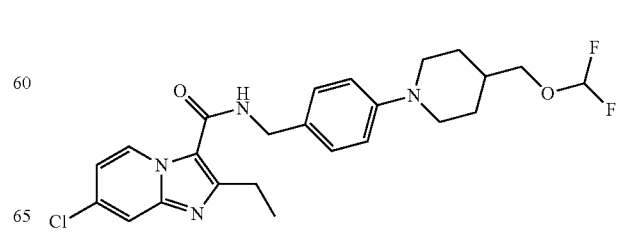

6-Chloro-N-(4-(4-(4-chlorophenyl)piperidin-1-yl)benzyl)-2-ethylimidazo[1,2-a]pyridine-3-carboxamide (296)

N-((6-Chloro-2-ethylimidazo[1,2-a]pyridin-3-yl)methyl)-4-(4-(4-fluorphenyl)piperazin-1-yl)aniline (311)

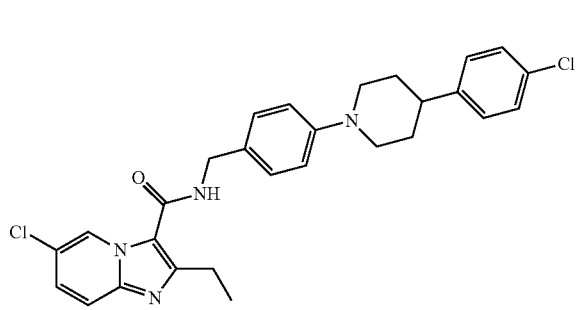 [SMILES: CCc1nc2ccc(Cl)cn2c1C(=O)NCc1ccc(N2CCC(c3ccc(Cl)cc3)CC2)cc1]
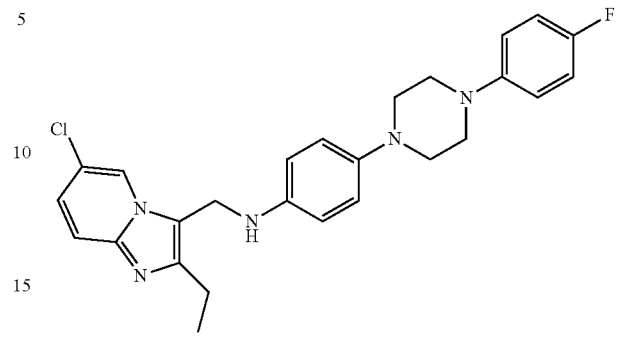

6-Chloro-N-((2-cyclohexylbenzo[d]oxazol-5-yl)methyl)-2-ethylimidazo[1,2-a]pyridine-3-carboxamide (298)

2-Ethyl-7-nitro-N-(4-(4-(4-(trifluoromethoxy)phenoxy)piperidin-1-yl)benzyl)imidazo[1,2-a]pyridine-3-carboxamide (312)

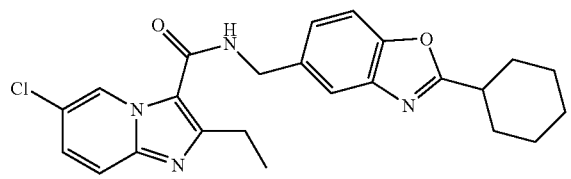 [SMILES: CCc1nc2ccc(Cl)cn2c1C(=O)NCc1ccc2oc(C3CCCCC3)nc2c1]
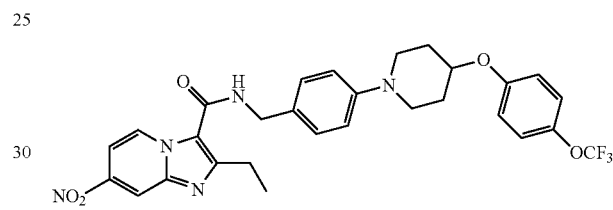

7-Chloro-N-((2-cyclohexylbenzo[d]oxazol-5-yl)methyl)-2-ethylimidazo[1,2-a]pyridine-3-carboxamide (299)

6-Chloro-2-ethylimidazo[2-a]pyridin-3-yl)(4-(4-(trifluoromethoxy)benzyloxy)piperidin-1-yl)methanone (313)

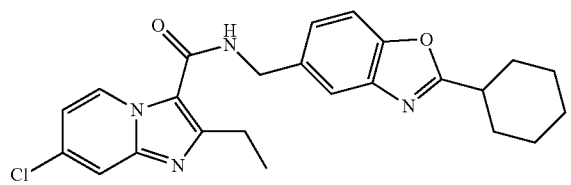 [SMILES: CCc1nc2cc(Cl)ccn2c1C(=O)NCc1ccc2oc(C3CCCCC3)nc2c1]
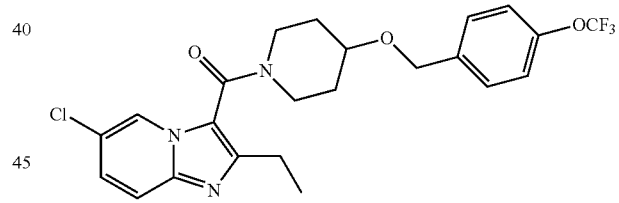

7-Bromo-2-ethyl-N-(4-(4-(4-fluorophenyl)piperazin-1-yl)benzyl)imidazo[1,2-a]pyridine-3-carboxamide (304)

6-Chloro-2-ethyl-N-(4-(4-(4-fluorophenyl)piperazin-1-yl)benzyl)-N-methylimidazo[1,2-a]pyridine-3-carboxamide (314)

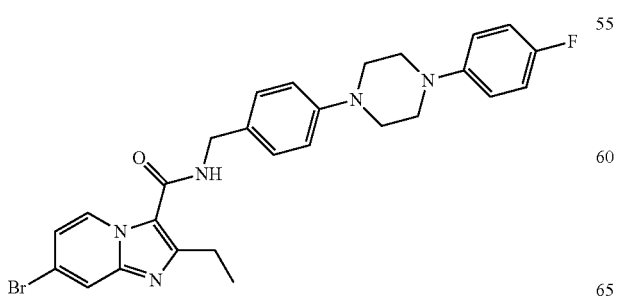
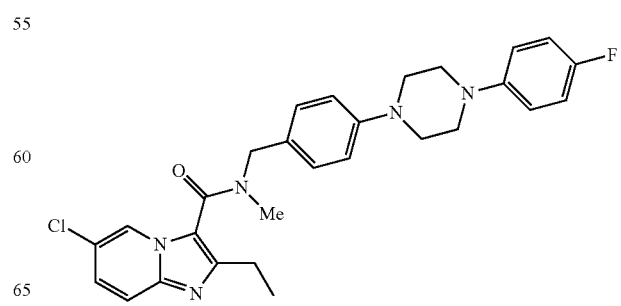

6-chloro-2-ethyl-N-(4-(4-(4-(trifluoromethoxy)benzoyl)
piperidin-1-yl)benzyl)imidazo[1,2-a]pyridine-3-car-
boxamide (324)

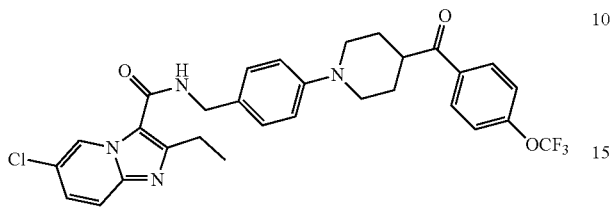

6-chloro-2-ethyl-3-((4-(((4-(trifluoromethoxy)benzyl)
oxy)piperidin-1-yl)methyl)imidazo[1,2-a]pyridine
(347)

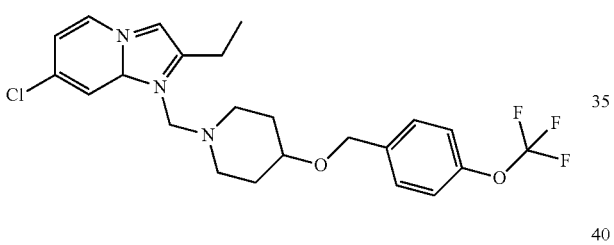

N1-((7-chloro-2-ethylimidazo[1,2-a]pyridin-3-yl)me-
thyl)-N4-(1-(4-fluorophenyl)piperidin-4-yl)benzene-1,
4-diamine (375)

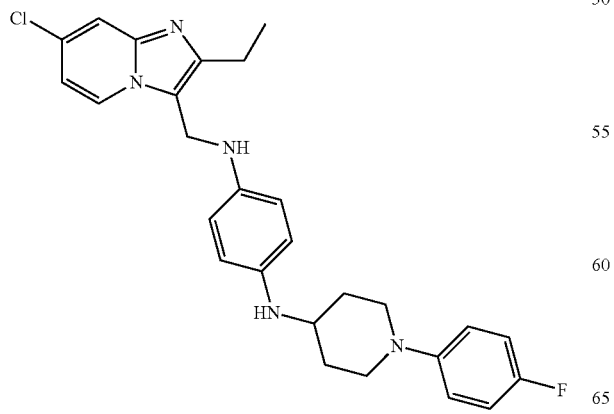

N-((7-chloro-2-ethylimidazo[1,2-a]pyridin-3-yl)methyl)-
4-(4-(4-(trifluoromethoxy)phenyl)piperidin-1-yl)
aniline 376

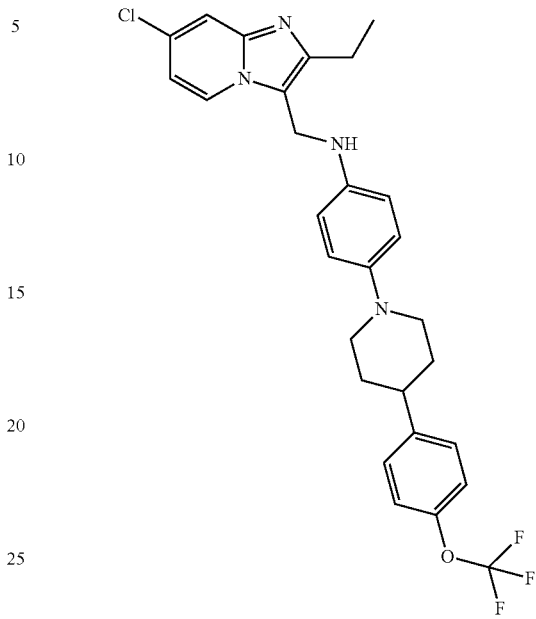

7-Chloro-2-ethylimidazo[1,2-a]pyridin-3-yl)(4-(4-(trif-
luoromethoxy)phenoxy)piperidin-1-yl)methanone
(380)

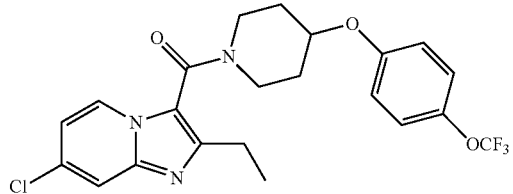 [SMILES: CCc1nc2cc(Cl)ccn2c1C(=O)N1CCC(Oc2ccc(OC(F)(F)F)cc2)CC1]

(7-chloro-2-ethylimidazo[1,2-a]pyridin-3-yl)(4-(4-(trif-
luoromethoxy)benzyloxy)piperidin-1-yl)methanone
(393)

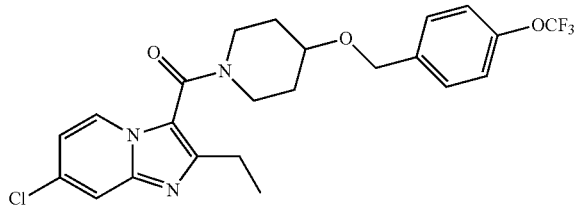 [SMILES: CCc1nc2cc(Cl)ccn2c1C(=O)N1CCC(OCc2ccc(OC(F)(F)F)cc2)CC1]

N-((6-chloro-2-ethylimidazo[1,2-a]pyridin-3-yl)methyl)-
4-(4-(trifluoromethoxy)-phenoxy)aniline (394)

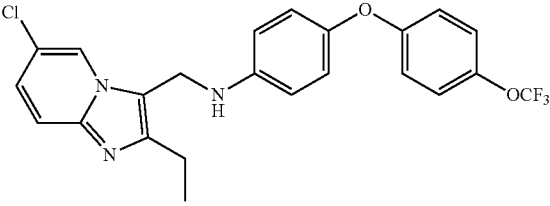 [SMILES: CCc1nc2ccc(Cl)cn2c1CNc1ccc(Oc2ccc(OC(F)(F)F)cc2)cc1]

N-((2-Ethylimidazo[1,2-a]pyrimidin-3-yl)methyl)-4-(4-(4-fluorophenyl)piperazin-1-yl)aniline (395)

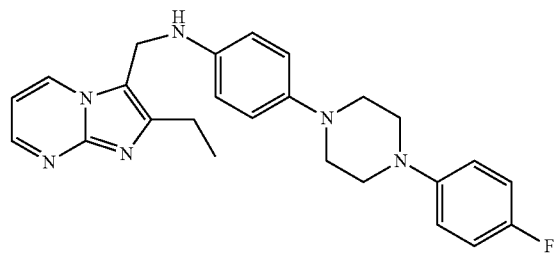 [SMILES: CCc1nc2ncccn2c1CNc1ccc(N2CCN(c3ccc(F)cc3)CC2)cc1]

N-((2-Ethylimidazo[1,2-b]pyridazin-3-yl)methyl)-4-(4-(4-fluorophenyl)piperazin-1-yl)aniline (396)

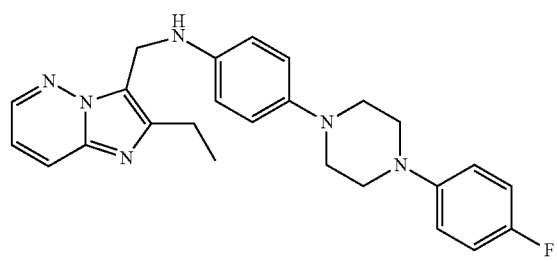 [SMILES: CCc1nc2cccnn2c1CNc1ccc(N2CCN(c3ccc(F)cc3)CC2)cc1]

N-((2-Ethylimidazo[1,2-a]pyrazin-3-yl)methyl)-4-(4-(4-fluorophenyl)piperazin-1-yl)aniline (398)

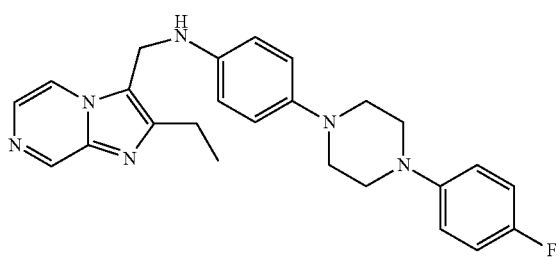 [SMILES: CCc1nc2cnccn2c1CNc1ccc(N2CCN(c3ccc(F)cc3)CC2)cc1]

6-chloro-2-ethyl-3-((4-(4-(4-fluorophenyl)piperazin-1-yl)phenoxy)methyl)imidazo[1,2-a]pyridine (399)

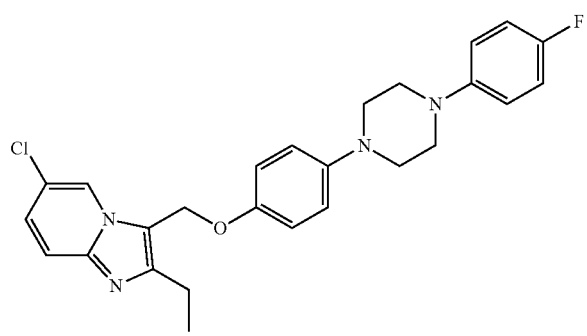 [SMILES: CCc1nc2ccc(Cl)cn2c1COc1ccc(N2CCN(c3ccc(F)cc3)CC2)cc1]

7-chloro-2-ethyl-3-(4-(4-(4-fluorophenyl)piperazin-1-yl)phenoxy)methyl)imidazo[1,2-a]pyridine (400)

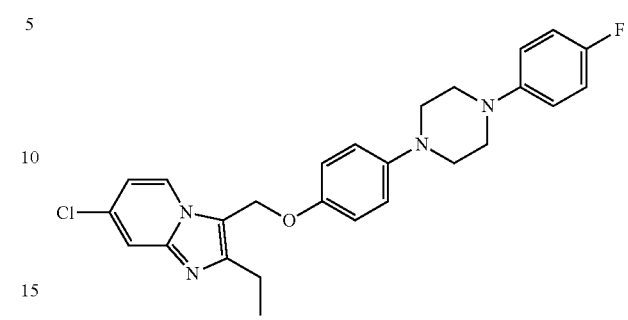

N-((2,5-dimethylimidazo[1,2-a]pyridin-3-yl)methyl)-4-(4-(4-fluorophenyl)piperidin-1-yl)aniline (401)

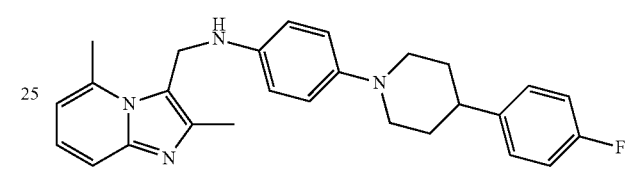

N-((2,5-dimethylimidazo[1,2-a]pyridin-3-yl)methyl)-4-(4-(4-fluorophenyl)piperazin-1-yl(aniline (402)

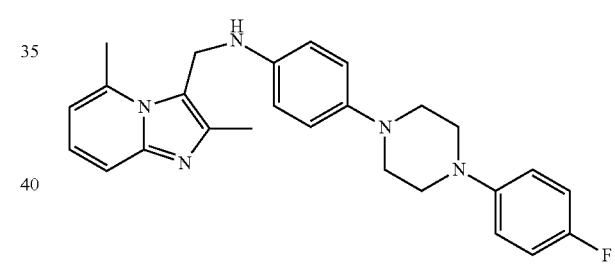

2-Ethyl-6-fluoro-N-(1-(4-(phenylamino)phenyl)pyrrolidin-3-yl)imidazo[1,2-a]pyridine-3-carboxamide (403)

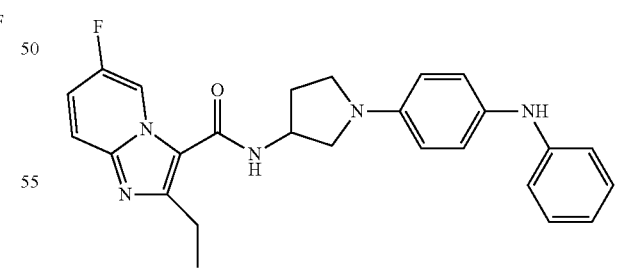

and pharmaceutically acceptable salts thereof.

* * * * *

UNITED STATES PATENT AND TRADEMARK OFFICE
CERTIFICATE OF CORRECTION

| | | |
|---|---|---|
| PATENT NO. | : 9,029,389 B2 | Page 1 of 5 |
| APPLICATION NO. | : 14/112933 | |
| DATED | : May 12, 2015 | |
| INVENTOR(S) | : Zaesung No et al. | |

It is certified that error appears in the above-identified patent and that said Letters Patent is hereby corrected as shown below:

In the Specification

Column 8,
Line 21, "0.01-30M," should read --0.01-30μM,--

Column 15,
Line 14, "5% CO2" should read --5% $CO_2$--

Column 20,
Line 4, "appropriatethylboronic acid" should read --appropriate arylboronic acid--

Column 45,
Line 3, "7.46 (s, L H)," should read --7.46(s, lH),--

Column 50,
Line 48, "-3-carboxamide" should read -- -3-carboxamide (55)--

Column 54,
Line 6, "-3-carboxamide" should read -- -3-carboxamide (65)--

Column 58,
Line 29, "-3-carboxamide" should read -- -3-carboxamide (78)--

Column 58,
Line 49, "-3-carboxamide" should read -- -3-carboxamide (79)--

Column 60,
Line 8, "-2-ethlimidazo" should read -- -2-ethylimidazo--

Signed and Sealed this
Twenty-sixth Day of April, 2016

Michelle K. Lee
*Director of the United States Patent and Trademark Office*

Column 99,
Line 40, "(M+H)$^{425}$, 427" should read --(M+H)$^+$ 425, 427--

Column 100,
Line 49, "-2(3H7H," should read -- -2(3H, 7H,--

Column 103,
Line 38, "CDCl$_3$)$_8$." should read --CDCl$_3$)δ.--

Column 111,
Line 56, "δ ☐ 1.23-1.41" should read --δ 1.23-1.41--

Column 113,
Line 66, "δ ☐ 1.34" should read --δ 1.34--

Column 134,
Line 49, "(M+H)." should read --(M+H)$^+$.--

Column 139,
Line 37, "(Br isotope" should read --(Br$^-$ isotope--

Column 145,
Line 1, "Avance" should read --Advance--

Column 148,
Line 31, "methanone" should read --methanone (330)--

Column 149,
Line 2, "[M+H]." should read --[M+H]$^+$.--

Column 149,
Line 65, "(CDC13," should read --(CDCl$_3$,--

Column 170,
Line 44, "Yellow oil; NMR" should read --Yellow oil; $^1$H NMR--

Column 170,
Line 44, "J = PG 7.2" should read --J = 7.2--

Column 170,
Line 45, "(d439, J = 2.0" should read --(d, J = 2.0--

Column 210,
Line 3, "(127)" should read --(122)--

CERTIFICATE OF CORRECTION (continued)
U.S. Pat. No. 9,029,389 B2

Column 210,
Line 52, "(Butramidomethyl)" should read --(Butyramidomethyl)--

Column 216,
Line 13, "\6-Chloro-" should read --6-Chloro- --

Column 217,
Line 36, "-(4-fluorphenyl)-" should read -- -(4-fluorophenyl)- --

Column 219,
Line 18, "3-carboxamide" should read --3-carboxamide (161)--

Column 221,
Line 16, "-(trifluormethyl)" should read -- -(trifluoromethyl)--

Column 222,
Line 16, "[1,2-a]carboxamide" should read --[1,2-a]pyridine-3-carboxamide--

Column 225,
Line 1, "fluorophenoxy-3-yl" should read --fluorophenoxy)pyridin-3-yl)--

Column 225,
Line 53, "(91)" should read --(191)--

Column 227,
Line 38, "-3 (199)" should read -- -3-carboxamide (199)--

Column 232,
Line 52, "piperazin-lyl)" should read --piperazin-1-yl)--

Column 233,
Line 51, "phenyl)" should read --phenoxy)--

Column 234,
Line 1, "phenyl)" should read --phenoxy)--

Column 234,
Line 17, "phenyl)" should read --phenoxy)--

Column 235,
Line 37, "pyridine-carboxamide" should read --pyridine-3-carboxamide--

Column 235,
Lines 53-54, "phenyl)benzyl)imidazo[1,2-a]pyridine-carboxamide" should read --phenoxy)benzyl)imidazo[1,2-a]pyridine-3-carboxamide--

Column 236,
Line 34, "-1-benzyl)-" should read -- -1-yl) benzyl)- --

Column 237,
Lines 16-17, "-3-carboxamide" should read -- -3-carboxamide (238)--

Column 245,
Line 1, "Ethyl 4-(4-" should read --Ethyl 1-(4- --

Column 251,
Line 51, "-N-(4-(4-(4-(4-" should read -- -N-(4-(4-(4- --

Column 257,
Line 35, "-N-(4-(4-" should read -- -N-(4-(4-(2-(4- --

Column 258,
Line 16, "piperidin-y1)" should read --piperidin-1-y1)--

Column 258,
Line 34, "-1-y1)imidazo" should read -- -1-yl)benzyl)imidazo--

Column 258,
Lines 51-52, "-carboxamide (325)" should read -- -3-carboxamide (325)--

Column 259,
Line 1, "-fluorobenzoyl)-4-" should read -- -fluorobenzoyl)piperidin-4- --

Column 263,
Lines 1-2, "methyl-2-" should read --methyl)-2--

Column 268,
Line 18, "-N-(4-(4-(tetrahydro-" should read -- -N-(4-(tetrahydro- --

Column 270,
Line 47, "-N4-(4-" should read -- -N4-(1-(4- --

Column 273,
Line 2, "-1-ethanone" should read -- -1-yl)methanone--

Column 273,
Line 27, "[1.1'-biphenyl]4-y1)" should read --[1,1'-biphenyl]-4-y1)--

Column 274,
Lines 35-36, "methanone (39)" should read --methanone (391)--

Column 282,
Line 17, "pyridazin-3-" should read --pyrimidin-3- --

Column 296,
Line 2, "-fluorphenyl)" should read -- -fluorophenyl)--

Column 296,
Line 35, "[2-a]" should read --[1,2-a]--

Column 300,
Line 1, "-3-(4-" should read -- -3-((4- --